US010723699B2

(12) United States Patent
Yang et al.

(10) Patent No.: US 10,723,699 B2
(45) Date of Patent: *Jul. 28, 2020

(54) CYCLOHEXENE DERIVATIVE, PREPARATION METHOD THEREOF, AND PHARMACEUTICAL COMPOSITION FOR PREVENTING OR TREATING METABOLIC DISEASE COMPRISING THE SAME AS ACTIVE INGREDIENT

(71) Applicant: Hyundai Pharm Co., Ltd., Cheonan-si, Chungcheongnam-do (KR)

(72) Inventors: Jin Yang, Yongin-si (KR); Jin Woong Kim, Suwon-si (KR); Han Kyu Lee, Hwaseong-si (KR); Jae Hyun Kim, Yongin-si (KR); Chang Mo Son, Suwon-si (KR); Kyu Hwan Lee, Ansan-si (KR); Jeong Un Hwang, Suwon-si (KR); Hyung Ho Choi, Suwon-si (KR); Dae Hoon Kim, Seoul (KR); Jae Keol Rhee, Hwaseong-si (KR)

(73) Assignee: HYUNDAI PHARM CO., LTD., Chungcheongnam-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/771,909

(22) PCT Filed: Oct. 31, 2016

(86) PCT No.: PCT/KR2016/012391
§ 371 (c)(1),
(2) Date: Apr. 27, 2018

(87) PCT Pub. No.: WO2017/078352
PCT Pub. Date: May 11, 2017

(65) Prior Publication Data
US 2018/0318274 A1    Nov. 8, 2018

(30) Foreign Application Priority Data

Nov. 4, 2015    (KR) .................. 10-2015-0154473

(51) Int. Cl.
| | |
|---|---|
| C07D 211/22 | (2006.01) |
| C07D 405/12 | (2006.01) |
| C07D 401/14 | (2006.01) |
| C07D 491/113 | (2006.01) |
| C07D 401/04 | (2006.01) |
| C07D 413/14 | (2006.01) |
| C07D 413/04 | (2006.01) |
| C07D 401/12 | (2006.01) |
| C07D 487/10 | (2006.01) |
| A61P 3/06 | (2006.01) |
| A61P 3/04 | (2006.01) |

(52) U.S. Cl.
CPC .............. *C07D 211/22* (2013.01); *A61P 3/04* (2018.01); *A61P 3/06* (2018.01); *C07D 401/04* (2013.01); *C07D 401/12* (2013.01); *C07D 401/14* (2013.01); *C07D 405/12* (2013.01); *C07D 413/04* (2013.01); *C07D 413/14* (2013.01); *C07D 487/10* (2013.01); *C07D 491/113* (2013.01)

(58) Field of Classification Search
CPC .. C07D 211/22; C07D 405/12; C07D 401/14; C07D 491/113; C07D 401/04; C07D 413/14; C07D 413/04; C07D 401/12; C07D 487/10
See application file for complete search history.

(56) References Cited

U.S. PATENT DOCUMENTS 9,758,527 B2 *  9/2017  Yang .................... C07D 405/12

FOREIGN PATENT DOCUMENTS

| KR | 20150126564 A | 11/2015 |
|---|---|---|
| KR | 101651505 B1 | 8/2016 |
| WO | 2004065380 A1 | 8/2004 |
| WO | 2005007647 A1 | 1/2005 |
| WO | 2005007658 A2 | 1/2005 |
| WO | 2008025798 A1 | 3/2008 |
| WO | 2008070692 A2 | 6/2008 |

(Continued)

OTHER PUBLICATIONS

Extended European Search Report dated Jun. 28, 2018 in EP 16862368.4.

*Primary Examiner* — Matthew P Coughlin
(74) *Attorney, Agent, or Firm* — Panitch Schwarze Belisario & Nadel LLP

(57) ABSTRACT

The present invention relates to a cyclohexene derivative, a preparation method thereof, and a pharmaceutical composition for preventing or treating metabolic disease containing the cyclohexene derivative as an active ingredient. The cyclohexene derivative according to the present invention increases the intracellular activity of cyclic adenosine monophosphate (cAMP) by activating G protein-coupled receptor 119 (GPR-119) and simultaneously exhibits weight loss and hypoglycemic effects by inducing the release of glucagon-like peptide-1 (GLP-1), which is a neuroendocrine protein, and thus can be useful as a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia and syndrome X.

13 Claims, 6 Drawing Sheets

(56) References Cited

FOREIGN PATENT DOCUMENTS

| | | |
|---|---|---|
| WO | 2008083238 A2 | 7/2008 |
| WO | 2009106565 A1 | 9/2009 |
| WO | 2013187646 A1 | 12/2013 |
| WO | 2015167309 A1 | 11/2015 |

* cited by examiner

[Fig. 1]
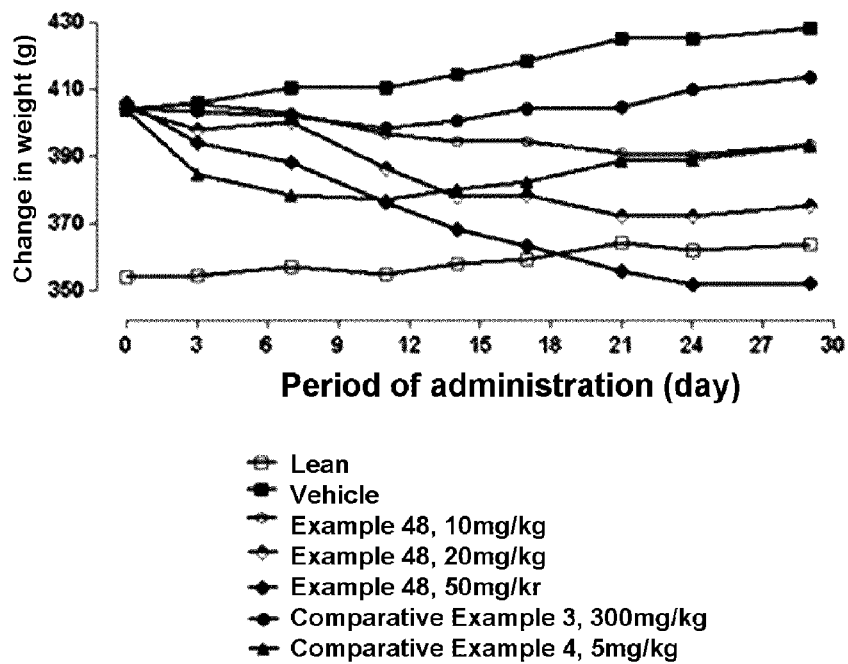
[Fig. 2a]
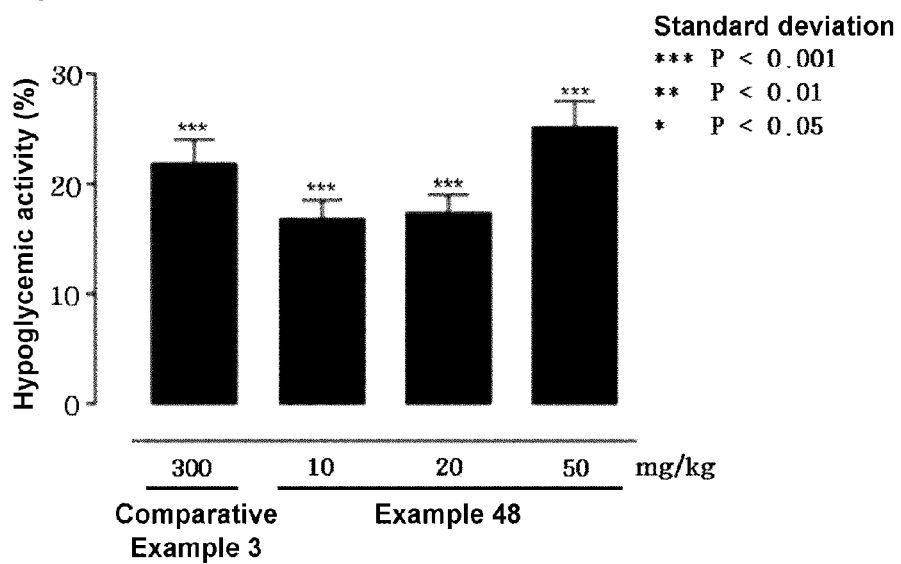

[Fig. 2b]
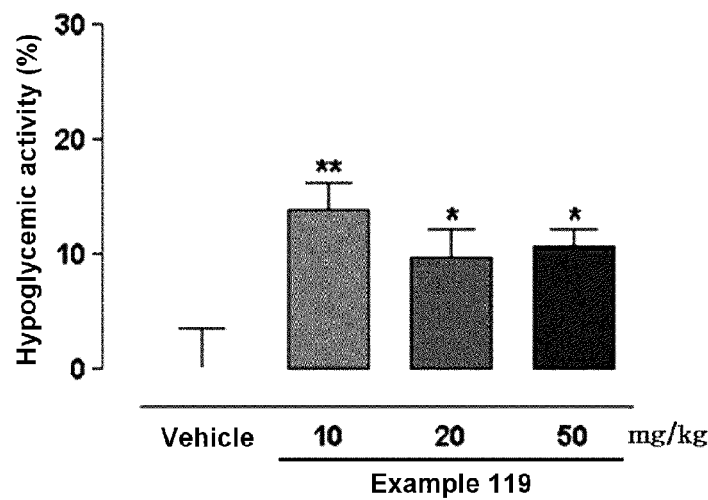
[Fig. 3a]
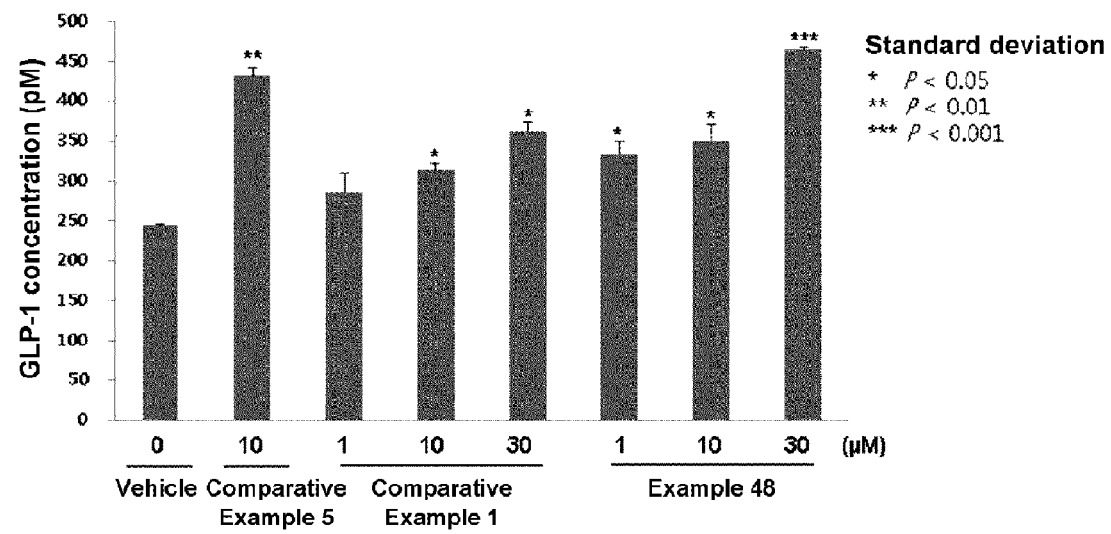

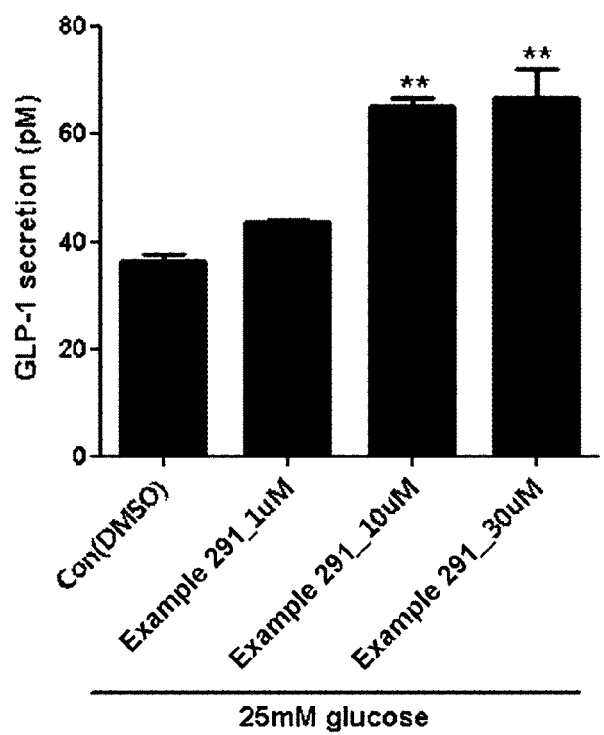
[Fig. 3b]
data shown are mean ± SEM
* $P < 0.05$ vs Con(DMSO) by ANOVA(Turkey's test)
** $P < 0.01$ vs Con(DMSO) by ANOVA(Turkey's test)

[Fig. 4]
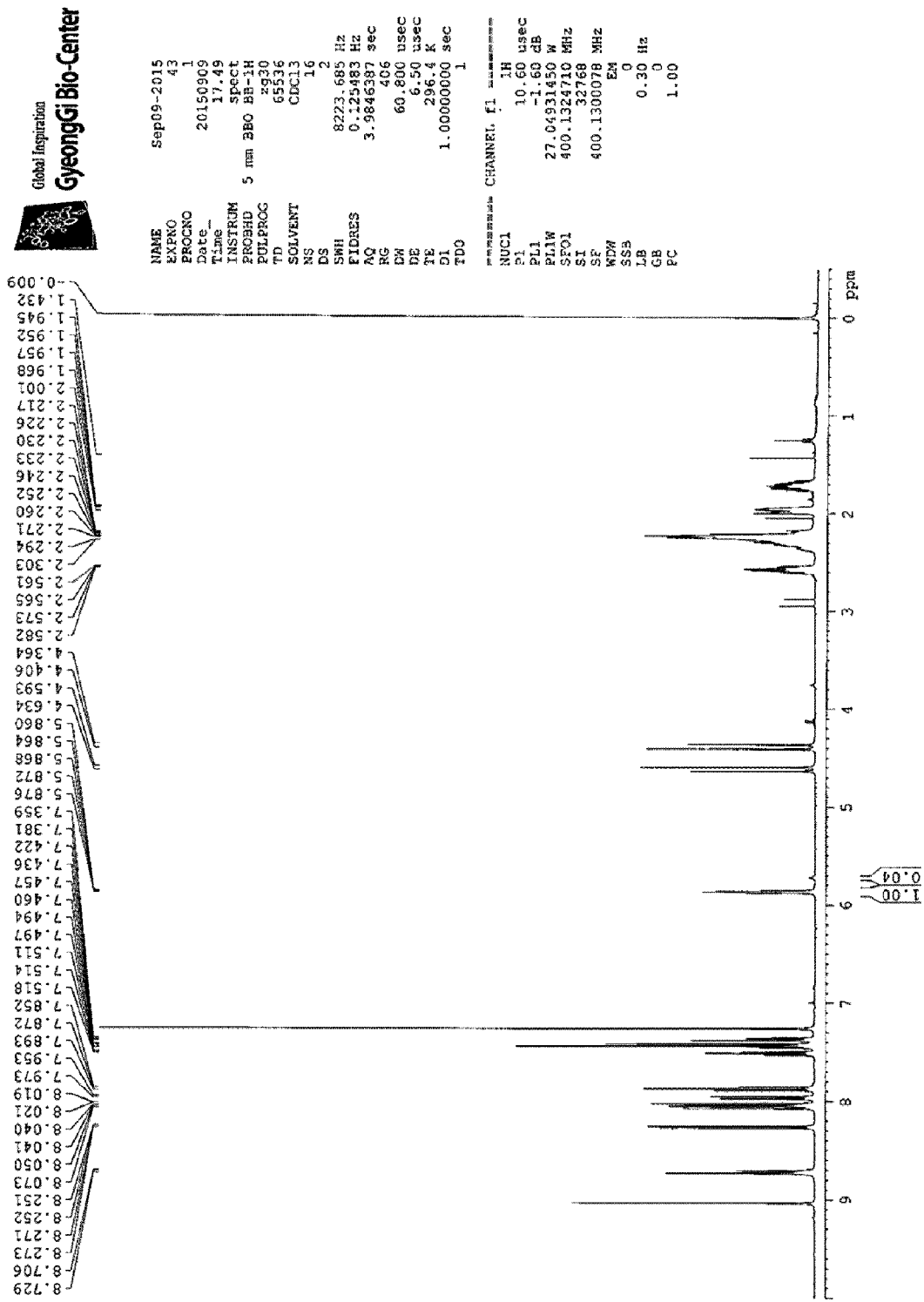

[Fig. 5]
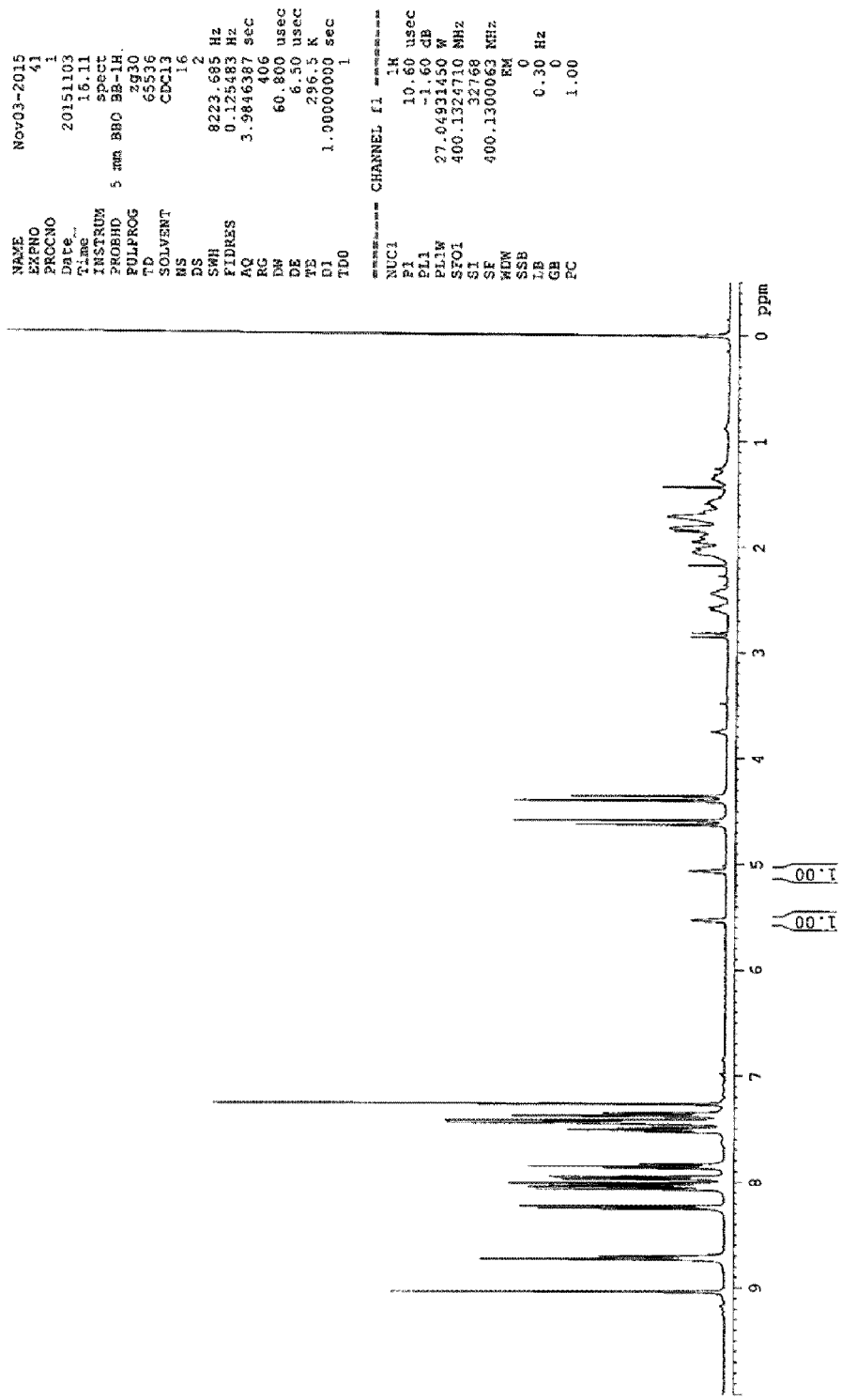

[Fig. 6]
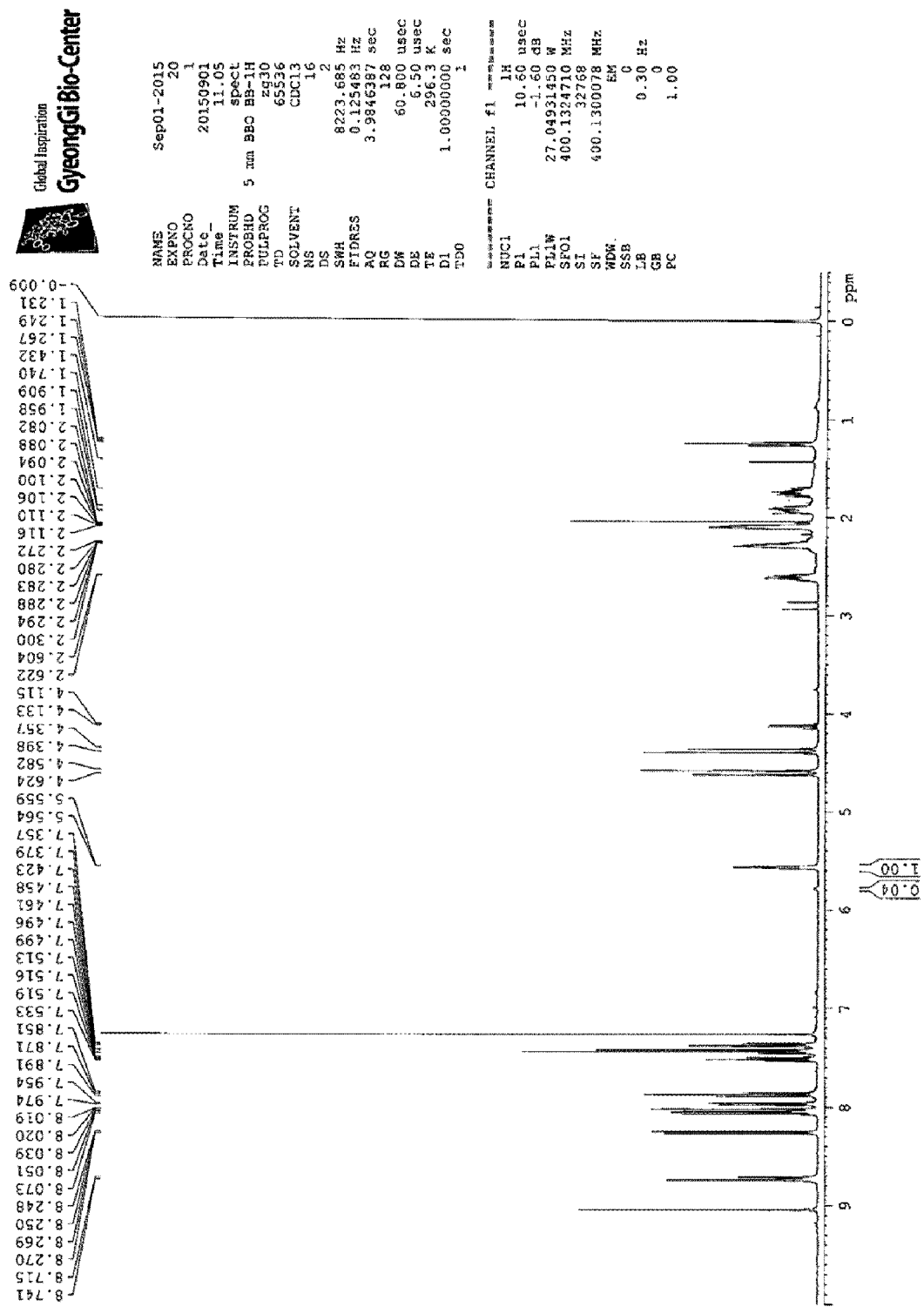

CYCLOHEXENE DERIVATIVE, PREPARATION METHOD THEREOF, AND PHARMACEUTICAL COMPOSITION FOR PREVENTING OR TREATING METABOLIC DISEASE COMPRISING THE SAME AS ACTIVE INGREDIENT

CROSS-REFERENCE TO RELATED APPLICATION

This application is a Section 371 of International Application No. PCT/KR2016/012391, filed Oct. 31, 2016, which was published in the English language on May 11, 2017, under International Publication No. WO 2017/078352 A1, which claims priority to Korean Patent Application No. 10-2015-0154473, filed on Nov. 4, 2015.

STATEMENT OF GOVERNMENT INTEREST

The present invention was supported by a grant under Korean Government R&D Program as Project ID No.: 10042208 2 with the Ministry of Trade, Industry and Energy Government Department with the Korea Evaluation Institute of Industrial Technology Program Management Institution. The Program Name is Industrial Technology Innovation Technology Development Program and the Project Name is New Drug Study Based on Novel Diabetes Mellitus Target (GPR119, etc.) with the Supervision Institution being HYUNDAI PHARM CO., LTD. having a Project Period of Jun. 1, 2012-May 31, 2014.

TECHNICAL FIELD

The present invention relates to a cyclohexene derivative, or an optical isomer or pharmaceutically acceptable salt thereof, a preparation method thereof, and a pharmaceutical composition for preventing or treating metabolic disease comprising the same as an active ingredient.

BACKGROUND ART

Metabolic diseases are disorders that are caused due to the abnormal metabolisms in separate organs from the human body, and thus include generic types of diseases caused by impaired metabolisms resulting from the in vivo imbalance of saccharides, lipids, proteins, vitamins, minerals, moisture, etc. In particular, metabolic diseases caused due to the weakening of immunity and the lack of nutrition supply account for over 99% of the adult diseases. Most adult diseases are caused by the nutritional imbalance caused by inadequate food intake, the lack of exercise, etc.

Representative examples of the metabolic diseases include obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc. When the metabolic diseases cause fat accumulation in the body, insulin resistance occurs in which insulin that is a hormone which moves glucose from the blood into the liver and muscles is not normally produced or its functions decline, thereby causing an increase in blood glucose level and arteriosclerosis, which leads to the onset of the adult diseases.

As a representative example of the metabolic diseases, diabetes mellitus is a serious metabolic disease from which over one hundred million people suffer all over the world. There are over 12,000,000 diabetic patients in the U.S., and approximately 600,000 new patients have been diagnosed with the diabetes mellitus each year. All people who do not have the same cause of diabetes but have suffered from the diabetes mellitus commonly produce an excessive amount of glucose in the liver, and have no activity to move glucose into cells in which the glucose is used as a main fuel for the body. People who do not suffer from diabetes mellitus depend on insulin hormones produced in the pancreas so that the glucose moves from the blood into cells of the body. However, people suffering from the diabetes neither produce insulin nor efficiently use the insulin produced thereby, and thus cannot move the glucose into their cells. Therefore, residual glucose that does not move into the cells may accumulate in blood, causing a disease referred to as hyperglycemia and leading to serious health problems over time.

Also, diabetes mellitus is a metabolic or vascular syndrome, or a syndrome associated with neuropathic factors. In general, the metabolic syndrome characterized by hyperglycemia include changes in carbohydrate, fat and protein metabolisms caused since insulin secretion is lacking or significantly decreased, or insulin exists but has no effects. The vascular syndrome results from abnormal blood vessels which cause cardiovascular, retinal and renal complications. Dysfunction in the peripheral and autonomic nervous systems is also a part of the diabetic syndrome. In addition, diabetes has been reported to be associated with the onset of renal disease, ocular disease and neurologic problems. The renal disease (nephropathy) develops when a "filtration mechanism" in the kidney is damaged, and an excessive amount of proteins leak into the urine, resulting in impaired kidney function. Also, diabetes mellitus is a provoking cause of inducing damage to the posterior retina of an eye, and increases the risk of developing cataract and glaucoma.

More specifically, the diabetes mellitus may be classified into two clinical syndromes; type 1 and 2 diabetes mellitus. Type 1 diabetes mellitus known as insulin-dependent diabetes mellitus (IDDM) is caused by autoimmune destruction of pancreatic β-cells producing insulin, and requires regular administration of exogenous insulin. Type 2 diabetes mellitus known as non-insulin-dependent diabetes mellitus (NIDDM) appears to develop due to its loss of an ability to properly regulate a blood glucose level. The type 2 diabetes mellitus is characterized by a disorder developed in people suffering from the type 2 diabetes mellitus who are deficient in insulin secretion or exhibit insulin resistance, that is, hardly have insulin or cannot effectively take use of insulin.

In the prior art, the current therapy against diabetes mellitus encompasses insulin, insulin secretagogues, glucose-lowering effectors, peroxisome proliferator-activated receptor (PPAR) activators, etc. However, there are problems associated with currently available therapies, including hypoglycemia, weight gain, a decreased responsiveness to treatment over time, gastrointestinal dysfunction, and edema.

Accordingly, research has been conducted in various fields to introduce a more effective new therapy into the market. One specific target is G protein-coupled receptor 119 (GPR-119).

GPR-119 is one of G-protein-coupled receptors (GPCRs) that are mainly expressed in pancreatic, small intestinal, rectal and adipose tissues. When a ligand or agonist binds to the receptor, the receptor is structurally changed, and coupled to G-protein to catalyze reactions of secondary messengers in cells or organs.

GPR-119 receptors and isoforms thereof are found in mammalian species including humans, rats, mice, hamsters, chimpanzees, rhesus monkeys, cattle, and dogs. In particular, it is known that the expression of GPR-119 in pancreatic β-cells indicates that the GPR-119 receptors exert an effect on the insulin secretion. The activation of GPR-119 stimulates a cyclic adenosine monophosphate (cAMP) single pathway in which the intracellular activity of cAMP as a secondary messenger is enhanced in these cells. The stimulation of cAMP is involved in a variety of cellular reactions, such as expression of enzymes or genes, etc., and the stimulation of cAMP in the β-cells is induced through the activation of GPR-119. Also, gastric inhibitory polypeptides (GIPs), glucagon-like peptide-1 (GLP-1), peptide YY (PYY), and the like cause an insulin secretion action through the G-protein-coupled receptor in the β-cells. Incretins such as the GIP and GLP-1 are gut hormones that strongly stimulate the insulin secretion in a blood glucose level-dependent manner after meals.

GPR-119 activators are effective in improvements in β-cell functions and β-cell groups. The activation of GPR-119 stimulates the insulin secretion in vitro and in vivo (rodents) in a glucose-dependent manner. The finding of potent GPR-119 activators may reduce a level of plasma glucose to promote blood glucose control without the risk of developing hypoglycemia.

In recent years, it was shown that the GPR-119 activators efficiently reduce a blood glucose level in diabetic rodents without the risk of developing hypoglycemia. It was confirmed that the secretion of both insulin and incretin induced by the GPR-119 activators is dependent on the GPR-119 receptors in GPR-119-knockout animals. Also, it was shown that the GPR-119 activators induce weight loss in Sprague Dawley rats by reducing the food intake.

T. Soga et al. discloses that the activation of GPR-119 induce cAMP to induce secretion of glucose-dependent glucagon-like peptide-1 (GLP-1) and insulin (T. Soga et al., Biochem. Biophy. Res. Commu. 326, (2005), 744-751). It was found that GLP-1 mediates its action through GLP-1R that is a certain G protein-coupled receptor (GPCR), regulates glucose homeostasis, stimulates glucose-dependent insulin secretion, and increases a mass of pancreatic β-cells. Also, it was found that GLP-1 slows down a gastric emptying rate and improves satiety.

However, the existing GLP-1 peptide activators have a negative effect on effectiveness due to deficiency in bioavailability when administered orally. Therefore, there is a demand for development of GPR-119 activators that exhibit excellent oral bioavailability and induce the secretion of GLP-1 into the blood as well.

As one example of the research results, it was proven that the GPR-119 activators disclosed in WO 2005/007647, WO 2005/007658 and the article by Overton, H. A. et al. (Overton, H. A. et al., Cell metabolism, 3 (2006), 167-175) cause an acute decline in food intake after chronic administration, resulting in reduced body weight in rats. Also, WO 2004/065380 discloses the therapeutic agents for treating metabolic diseases using trisubstituted pyrimidine derivatives with the growing interest in trisubstituted heteroaryl derivatives. Further, WO 2008/083238 discloses the therapeutic agents for treating diabetes mellitus using aryl, heteroaryl or heterocyclyl derivatives, characterized in that the therapeutic agents activate IC-GPCR2 or GPR-119 as therapeutic agents for type 1 diabetes mellitus associated with insulin resistance. However, there are no known compounds having a cyclohexene backbone and use thereof for treating metabolic diseases.

Accordingly, the present inventors have conducted research on activators of GPR-119, and found that a cyclohexene derivative according to the present invention, or an optical isomer or pharmaceutically acceptable salt thereof activates G protein-coupled receptor 119 (GPR-119) to enhance the intracellular activity of cyclic adenosine monophosphate (cAMP), and induces the release of glucagon-like peptide-1 (GLP-1), which is a neuroendocrine protein, to simultaneously exhibit weight-loss and hypoglycemic effects, and thus is useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia and syndrome X. Therefore, the present invention has been completed based on these facts.

DISCLOSURE

Technical Problem

An aspect of the present invention may provide a cyclohexene derivative, or an optical isomer or pharmaceutically acceptable salt thereof.

Another aspect of the present invention may provide a method for preparing the cyclohexene derivative.

Still another aspect of the present invention may provide a pharmaceutical composition for preventing or treating metabolic diseases, which includes the cyclohexene derivative as an active ingredient.

Yet another aspect of the present invention may provide a G protein-coupled receptor 119 (GPR-119) activator including the cyclohexene derivative as an active ingredient.

*23 Yet another aspect of the present invention may provide a health functional food for preventing or improving metabolic diseases, which includes the cyclohexene derivative as an active ingredient.

Technical Solution

To solve the above problems, the present invention provides a compound represented by the following Formula 1, or an optical isomer or pharmaceutically acceptable salt thereof.

[Formula 1]

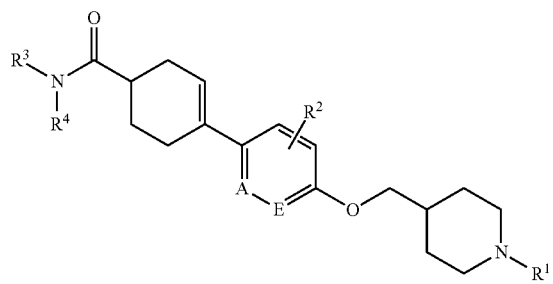

In Formula 1, $R^1$ is —H, —OH, a $C_{1-10}$ linear or branched alkyl, a $C_{1-10}$ linear or branched alkoxy, a $C_{1-10}$ linear or branched alkoxycarbonyl, or an unsubstituted or substituted 5- to 10-membered heteroaryl containing one or more heteroatoms selected from the group consisting of N, O, and S, wherein:

the substituted 5- to 10-membered heteroaryl is a 5- to 10-membered heteroaryl substituted with one or more $C_{1-10}$ linear or branched alkyl;

$R^2$ is —H, —OH, a halogen, a $C_{1-10}$ linear or branched alkyl, or a $C_{1-10}$ linear or branched alkoxy;

R³ is —H, a C₁₋₁₀ linear or branched alkyl which is not substituted or substituted with one or more —OH or a halogen, a C₁₋₁₀ linear or branched alkoxy, a C₁₋₁₀ linear or branched alkoxy C₁₋₁₀ linear or branched alkyl, an unsubstituted C₃₋₁₀ cycloalkyl, an unsubstituted 5- to 10-membered heteroaryl C₁₋₁₀ linear or branched alkyl containing one or more heteroatoms selected from the group consisting of N, O, and S, —(CH₂)ₙNR⁵R⁶, —(CH₂)ₘC(=O)OR⁷, or —(CH₂)ₚC(=O)NR⁸R⁹, wherein:

R⁵ and R⁶ are each independently —H, -Boc

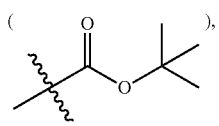

or a C₁₋₅ linear or branched alkyl,

R⁷ is —H, or a C₁₋₅ linear or branched alkyl, and

R⁸ and R⁹ may be taken together with a nitrogen atom to which they are attached to form an unsubstituted or substituted 5- to 10-membered heterocycloalkyl containing one or more heteroatoms selected from the group consisting of N, O, and S, wherein:

the substituted 5- to 10-membered heterocycloalkyl is a 5- to 10-membered heterocycloalkyl substituted with one or more substituents selected from the group consisting of —CN, a C₁₋₅ linear or branched alkyl, a C₁₋₅ linear or branched alkoxy, and —C(=O)NR¹⁰R¹¹, wherein R¹⁰ and R¹¹ are each independently —H, or a C₁₋₅ linear or branched alkyl;

n, m, and p are each independently an integer ranging from 1 to 10;

R⁴ is —H, a C₁₋₁₀ linear or branched alkyl which is not substituted or substituted with one or more —OH, or a C₁₋₁₀ linear or branched alkoxy;

provided that R³ and R⁴ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:

the substituted 3- to 10-membered heterocycloalkyl is a 3- to 10-membered heterocycloalkyl substituted with one or more substituents selected from the group consisting of —OH, —CN, =O, a halogen, a C₁₋₅ linear or branched alkyl which is not substituted or substituted with one or more —OH, a C₁₋₅ linear or branched alkoxy, an unsubstituted C₃₋₁₀ cycloalkyl C₁₋₅ linear or branched alkyl, an unsubstituted C₃₋₁₀ cycloalkyl, an unsubstituted 3- to 10-membered heterocycloalkyl containing one or more heteroatoms selected from the group consisting of N, O, and S, —C(=O)NR¹²R¹³, —NR¹⁴R¹⁵, and =NR¹⁶; or substituted in a spiro fashion with a C₅₋₁₀ cycloakenyl fused with an unsubstituted C₆₋₁₀ aryl, or a 3- to 10-membered heterocycloalkyl which is not substituted or substituted with one or more -Boc

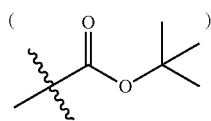

and contains one or more heteroatoms selected from the group consisting of N, O, and S, R¹², R¹³, R¹⁴, and R¹⁵ are each independently —H, or a C₁₋₅ linear or branched alkyl, and R¹⁶ is —H, —OH, or a C₁₋₅ linear or branched alkoxy, provided that the fused 3- to 10-membered heterocycloalkyl is a 3- to 10-membered heterocycloalkyl fused with an unsubstituted C₆₋₁₀ aryl, and the substitution and fusion may occur at the same time in the case of the unsubstituted, substituted or fused 3- to 10-membered heterocycloalkyl; and A and E are each independently —CH=, or —N=.

The compound of Formula 1 according to the present invention has a chiral center. In this case, any stereoselectivity in (+) and (−) directions from the corresponding chiral center may be introduced. According to one exemplary embodiment of the present invention, the compound of Formula 1 according to the present invention may have a chiral center at a position indicated as follows.

[Formula 1]

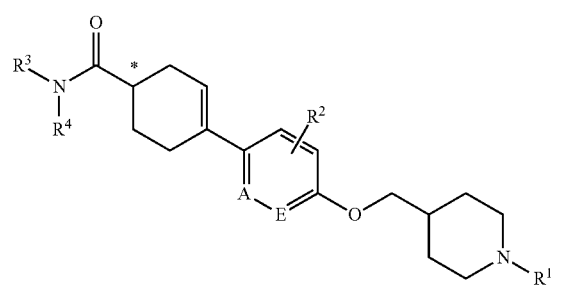

In Formula 1, the symbol "*" represents a chiral center.

Also, as shown in the following Scheme 1, the present invention provides a method for preparing the compound represented by Formula 1, which includes:

reacting a compound represented by Formula 2 with a compound represented by Formula 3 to prepare a compound represented by Formula 4 (Step 1);

reacting the compound represented by Formula 4 prepared in Step 1 with a compound represented by Formula 5 to prepare a compound represented by Formula 6 (Step 2);

reacting the compound represented by Formula 6 prepared in Step 2 with a base to prepare a compound represented by Formula 7 (Step 3); and reacting the compound represented by Formula 7 prepared in Step 3 with a compound represented by Formula 8 to obtain the compound represented by Formula 1 (Step 4).

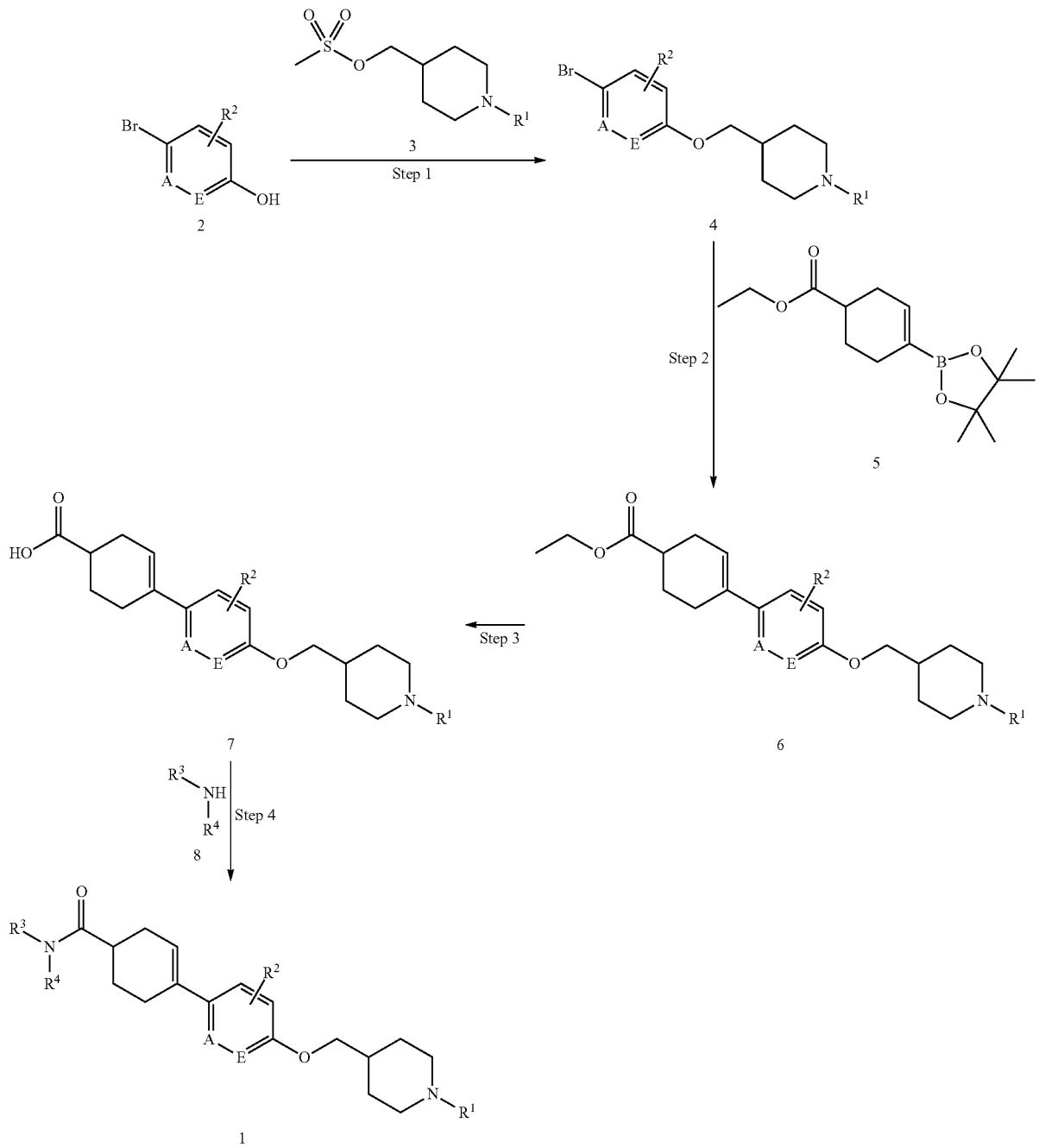

[Scheme 1]

In Scheme 1, $R^1$, $R^2$, $R^3$, $R^4$, A, and E are as defined in Formula 1.

In addition, the present invention provides a pharmaceutical composition for preventing or treating metabolic diseases, which includes the compound represented by Formula 1, or an optical isomer or pharmaceutically acceptable salt thereof as an active ingredient.

Also, the present invention provides a G protein-coupled receptor 119 (GPR-119) activator including the compound represented by Formula 1, or the optical isomer or pharmaceutically acceptable salt thereof as an active ingredient.

Further, the present invention provides a health functional food for preventing or improving metabolic diseases, which includes the compound represented by Formula 1, or the optical isomer or pharmaceutically acceptable salt thereof as an active ingredient.

Advantageous Effects

The cyclohexene derivative according to the present invention, or the optical isomer or pharmaceutically acceptable salt thereof activates G protein-coupled receptor 119 (GPR-119) to enhance the intracellular activity of cyclic adenosine monophosphate (cAMP), and simultaneously induces the release of glucagon-like peptide-1 (GLP-1), which is a neuroendocrine protein, to simultaneously exhibit weight-loss and hypoglycemic effects, and thus can be useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

DESCRIPTION OF DRAWINGS

FIG. 1 is a graph determining the changes in weights of rats after compounds of Example 48 and Comparative Examples 3 and 4 according to the present invention are administered to a diet-induced obesity (DIO) rat model for 4 weeks (In FIG. 1, the term "untreated group (Vehicle)" represents an untreated group in a high-fat DIO rat model; and the term "Lean" represents an untreated group in a normal SD rat model rather than a disease model).

FIG. 2A is a graph for evaluating hypoglycemic effects over time when glucose is administered at the end of the 4-week period of administration of the compounds of Example 48 and Comparative Example 3 according to the present invention in the DIO rat model, and after 30 minutes of administration of the compounds of Example 48 and Comparative Example 3.

FIG. 2B is a graph for evaluating hypoglycemic effects over time when glucose is administered at the end of the 4-week period of administration of the compound of Example 119 according to the present invention in the DIO rat model, and after 30 minutes of administration of the compound of Example 119.

FIGS. 3A and 3B are graphs plotted for amounts of secreted glucagon-like peptide-1 (GLP-1) when NCI-H716 cells that are human enterocytes are treated with the compounds of Comparative Examples 1 and 5 and Examples 48 and 291 according to the present invention.

FIG. 4 shows $^1$H NMR (400, CDCl$_3$) data of the (-)-4-bromocyclohex-3-enecarboxylic acid prepared in Preparative Example 35 using Chirabite-AR.

FIG. 5 shows $^1$H NMR (400, CDCl$_3$) data of the (±)HBA (4-bromocyclohex-3-ene-1-carboxylic acid) using Chirabite-AR.

FIG. 6 shows $^1$H NMR (400, CDCl$_3$) data of the (-)-4-bromocyclohex-3-enecarboxylic acid prepared in Preparative Example 36 using Chirabite-AR.

BEST MODE

Hereinafter, the present invention will be described in detail.

The present invention provides a compound represented by the following Formula 1, or an optical isomer or pharmaceutically acceptable salt thereof.

[Formula 1]

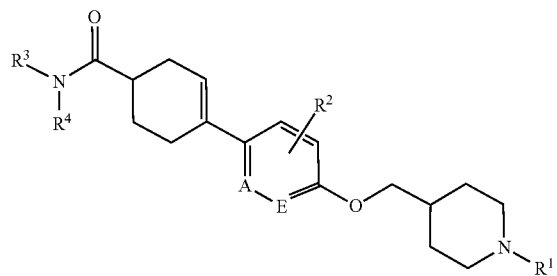

*70

In Formula 1, $R^1$ is —H, —OH, a $C_{1-10}$ linear or branched alkyl, a $C_{1-10}$ linear or branched alkoxy, a $C_{1-10}$ linear or branched alkoxycarbonyl, or an unsubstituted or substituted 5- to 10-membered heteroaryl containing one or more heteroatoms selected from the group consisting of N, O, and S, wherein:

the substituted 5- to 10-membered heteroaryl is a 5- to 10-membered heteroaryl substituted with one or more $C_{1-10}$ linear or branched alkyl;

$R^2$ is —H, —OH, a halogen, a $C_{1-10}$ linear or branched alkyl, or a $C_{1-10}$ linear or branched alkoxy;

$R^3$ is —H, a $C_{1-10}$ linear or branched alkyl which is not substituted or substituted with one or more —OH or a halogen, a $C_{1-10}$ linear or branched alkoxy, a $C_{1-10}$ linear or branched alkoxy $C_{1-10}$ linear or branched alkyl, an unsubstituted $C_{3-10}$ cycloalkyl, an unsubstituted 5- to 10-membered heteroaryl $C_{1-10}$ linear or branched alkyl containing one or more heteroatoms selected from the group consisting of N, O, and S, —(CH$_2$)$_n$NR$^5$R$^6$, —(CH$_2$)$_m$C(=O)OR$^7$, or —(CH$_2$)$_p$C(=O)NR$^8$R$^9$, wherein:

$R^5$ and $R^6$ are each independently —H, -Boc

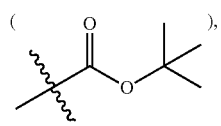

or a $C_{1-5}$ linear or branched alkyl, $R^7$ is —H, or a $C_{1-5}$ linear or branched alkyl, and $R^8$ and $R^9$ may be taken together with a nitrogen atom to which they are attached to form an unsubstituted or substituted 5- to 10-membered heterocycloalkyl containing one or more heteroatoms selected from the group consisting of N, O, and S, wherein:

the substituted 5- to 10-membered heterocycloalkyl is a 5- to 10-membered heterocycloalkyl substituted with one or more substituents selected from the group consisting of —CN, a $C_{1-5}$ linear or branched alkyl, a $C_{1-5}$ linear or branched alkoxy, and —C(=O)NR$^{10}$R$^{11}$, and R$^{10}$ and R$^{11}$ are each independently —H, or a $C_{1-5}$ linear or branched alkyl, n, m, and p are each independently an integer ranging from 1 to 10;

$R^4$ is —H, a $C_{1-10}$ linear or branched alkyl which is not substituted or substituted with one or more —OH, or a $C_{1-10}$ linear or branched alkoxy;

provided that $R^3$ and $R^4$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:

the substituted 3- to 10-membered heterocycloalkyl is a 3- to 10-membered heterocycloalkyl substituted with one or more substituents selected from the group consisting of —OH, —CN, =O, a halogen, a $C_{1-5}$ linear or branched alkyl which is not substituted or substituted with one or more —OH, a $C_{1-5}$ linear or branched alkoxy, an unsubstituted $C_{3-10}$ cycloalkyl $C_{1-5}$ linear or branched alkyl, an unsubstituted $C_{3-10}$ cycloalkyl, an unsubstituted 3- to 10-membered heterocycloalkyl containing one or more heteroatoms selected from the group consisting of N, O, and S, —C(=O)NR$^{12}$R$^{13}$, —NR$^{14}$R$^{15}$, and =NR$^{16}$; or substituted in a spiro fashion with a $C_{5-10}$ cycloakenyl fused with an unsubstituted $C_{6-10}$ aryl, or a 3- to 10-membered heterocycloalkyl which is not substituted or substituted with one or more -Boc

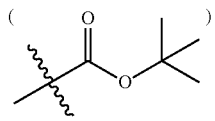

and contains one or more heteroatoms selected from the group consisting of N, O, and S, R$^{12}$, R$^{13}$, R$^{14}$, and R$^{15}$ are each independently —H, or a $C_{1-5}$ linear or branched alkyl, and R$^{16}$ is —H, —OH, or a $C_{1-5}$ linear or branched alkoxy, provided that the fused 3- to 10-membered heterocycloalkyl is a 3- to 10-membered heterocycloalkyl fused with an unsubstituted $C_{6-10}$ aryl, and the substitution and fusion may occur at the same time in the case of the unsubstituted, substituted or fused 3- to 10-membered heterocycloalkyl; and A and E are each independently —CH=, or —N=.

The compound of Formula 1 according to the present invention has a chiral center. In this case, any stereoselectivity in (+) and (−) directions from the corresponding chiral center may be introduced. According to one exemplary embodiment of the present invention, the compound of Formula 1 according to the present invention may have a chiral center at a position indicated as follows.

[Formula 1]

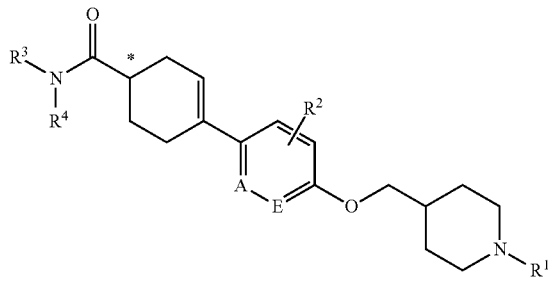

In Formula 1, the symbol "*" represents a chiral center.

Preferably, R$^{1}$ is a $C_{1-10}$ linear or branched alkoxycarbonyl, or an unsubstituted or substituted 5- to 10-membered heteroaryl containing one or more heteroatoms selected from the group consisting of N, O, and S, wherein:

the substituted 5- to 10-membered heteroaryl is a 5- to 10-membered heteroaryl substituted with one or more $C_{1-10}$ linear or branched alkyl;

R$^{2}$ is —H or a halogen;

R$^{3}$ is a $C_{1-10}$ linear or branched alkyl which is not substituted or substituted with one or more —OH or a halogen, a $C_{1-10}$ linear or branched alkoxy, a $C_{1-10}$ linear or branched alkoxy $C_{1-10}$ linear or branched alkyl, an unsubstituted $C_{3-10}$ cycloalkyl, an unsubstituted 5- to 10-membered heteroaryl $C_{1-10}$ linear or branched alkyl containing one or more heteroatoms selected from the group consisting of N, O, and S, —(CH$_{2}$)$_{n}$NR$^{5}$R$^{6}$, —(CH$_{2}$)$_{m}$C(=O)OR$^{7}$, or —(CH$_{2}$)$_{p}$C(=O)NR$^{8}$R$^{9}$, wherein:

R$^{5}$ and R$^{6}$ are each independently —H or -Boc

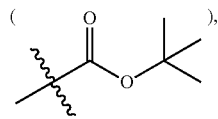

R$^{7}$ is —H, or a $C_{1-5}$ linear or branched alkyl, and

R$^{8}$ and R$^{9}$ may be taken together with a nitrogen atom to which they are attached to form an unsubstituted or substituted 5- to 10-membered heterocycloalkyl containing one or more heteroatoms selected from the group consisting of N, O, and S, wherein:

the substituted 5- to 10-membered heterocycloalkyl is a 5- to 10-membered heterocycloalkyl substituted with one or more substituents selected from the group consisting of —CN and —C(=O)NR$^{10}$R$^{11}$, and R$^{10}$ and R$^{11}$ are each independently —H, n, m, and p is each independently an integer ranging from 1 to 5;

R$^{4}$ is —H, or a $C_{1-10}$ linear or branched alkyl which is not substituted or substituted with one or more —OH;

provided that R$^{3}$ and R$^{4}$ may be taken together with a nitrogen atom to which they are attached to form an unsubstituted 3- to 10-membered heterocycloakenyl containing one or more heteroatoms selected from the group consisting of N, O, and S, or an unsubstituted, substituted or fused 3- to 10-membered heterocycloalkyl containing one or more heteroatoms selected from the group consisting of N, O, and S, wherein:

the substituted 3- to 10-membered heterocycloalkyl is a 3- to 10-membered heterocycloalkyl substituted with one or more substituents selected from the group consisting of —OH, —CN, =O, a halogen, a $C_{1-5}$ linear or branched alkyl which is not substituted or substituted with one or more —OH, an unsubstituted $C_{3-10}$ cycloalkyl $C_{1-5}$ linear or branched alkyl, an unsubstituted $C_{3-10}$ cycloalkyl, an unsubstituted 3- to 10-membered heterocycloalkyl containing one or more heteroatoms selected from the group consisting of N, O, and S, —C(=O)NR$^{12}$R$^{13}$, —NR$^{14}$R$^{15}$, and =NR$^{16}$; or substituted in a spiro fashion with a $C_{5-10}$ cycloakenyl fused with an unsubstituted $C_{6-10}$ aryl, or a 3- to 10-membered heterocycloalkyl which is not substituted or substituted with one or more -Boc

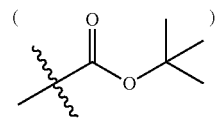

and contains one or more heteroatoms selected from the group consisting of N, O, and S, R$^{12}$, R$^{13}$, R$^{14}$, and R$^{15}$ are each independently —H, or a $C_{1-5}$ linear or branched alkyl, and R$^{16}$ is —OH, or a $C_{1-5}$ linear or branched alkoxy, provided that the fused 3- to 10-membered heterocycloalkyl is a 3- to 10-membered heterocycloalkyl fused with an unsubstituted $C_{6-10}$ aryl, and the substitution and fusion may occur at the same time in the case of the unsubstituted, substituted or fused 3- to 10-membered heterocycloalkyl; and A and E are each independently —CH═, or —N═.
More preferably,
R¹ is
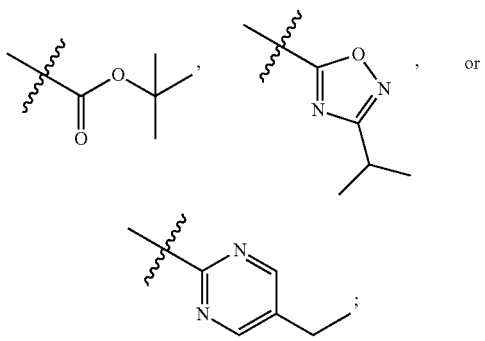
*109R² is —H or —F;
R³ is
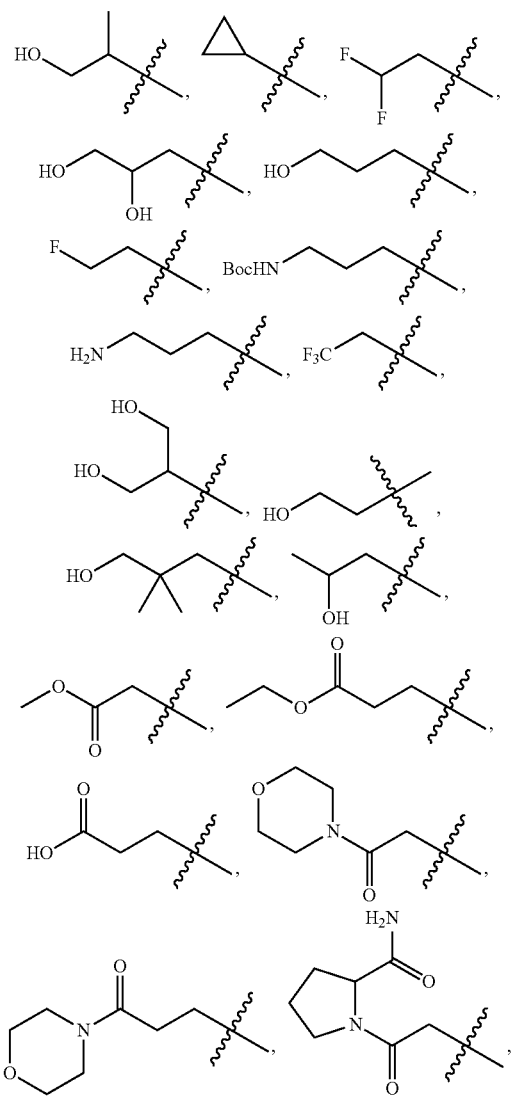
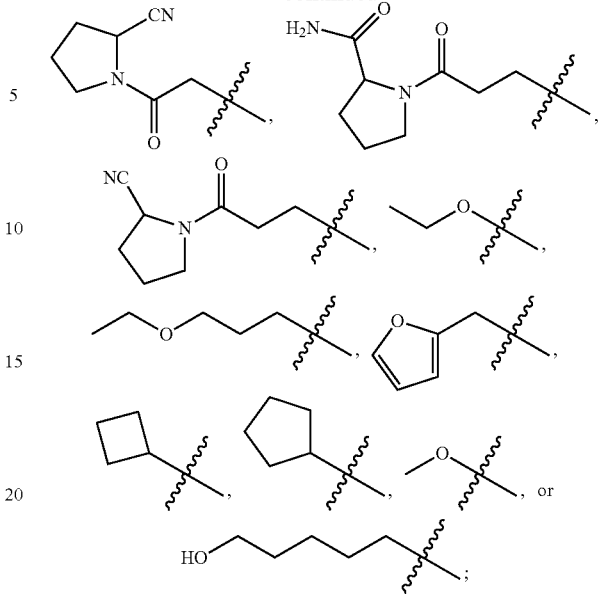
R⁴ is —H, methyl, ethyl, or
provided that R³ and R⁴ may be taken together with a nitrogen atom to which they are attached to form
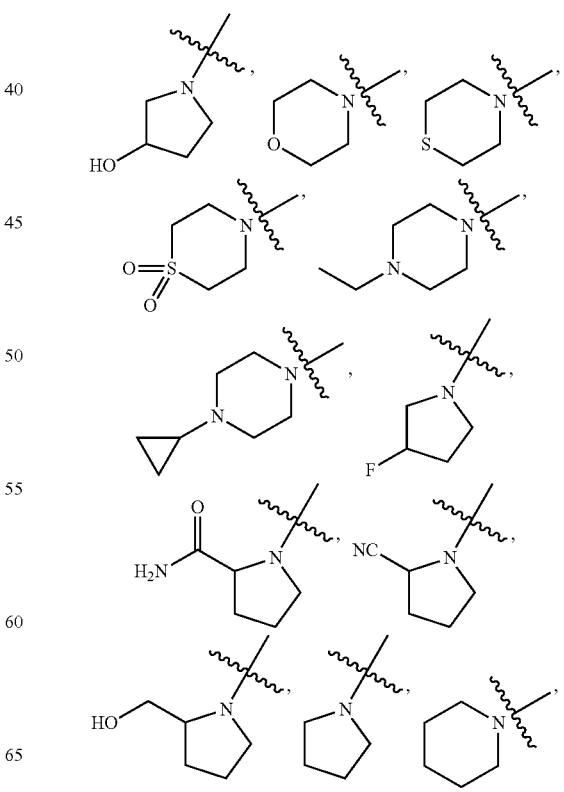

-continued

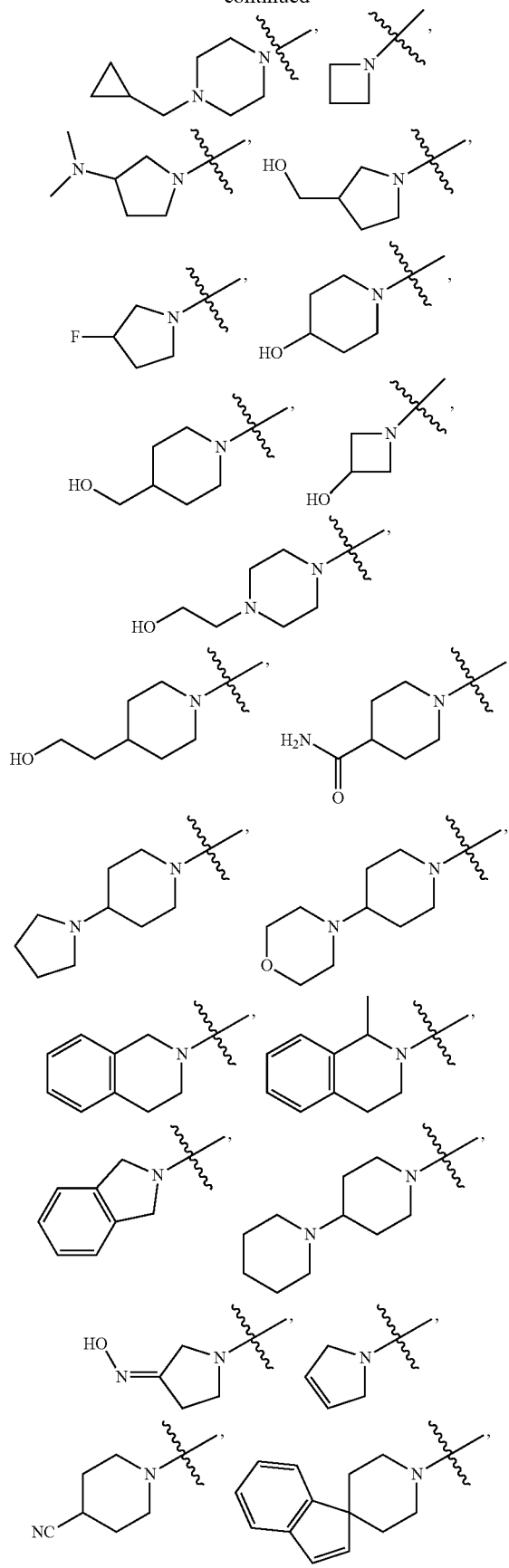
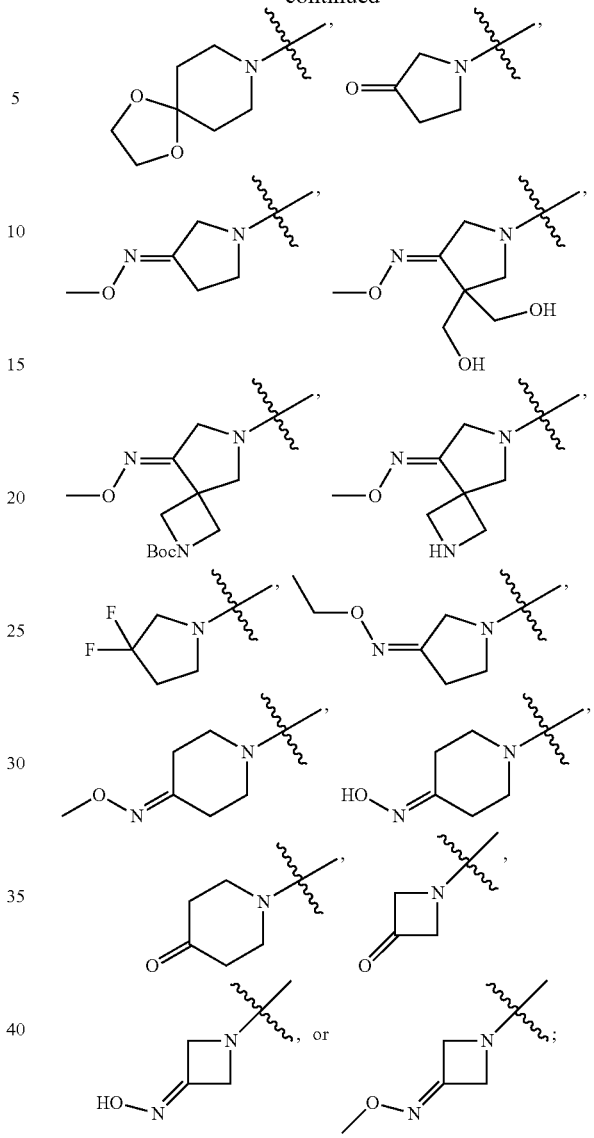

and

A and E are each independently —CH═, or —N═.

Preferred examples of the compound represented by Formula 1 according to the present invention may include the following compounds, but the present invention is not limited thereto.

(1) tert-butyl 4-((4-(4-((R)-1-hydroxypropan-2-ylcarbamoyl)cyclohex-1-enyl)phenoxy)methyl)piperidine-1-carboxylate;
(2) tert-buty 4-((4-(4-(cyclopropylcarbamoyl)cyclohex-1-enyl)phenoxy)methyl)piperidine-1-carboxylate;
(3) tert-butyl 4-((4-(4-(2,2-difluoroethylcarbamoyl)cyclohex-1-enyl)phenoxy)methyl)piperidine-1-carboxylate;
(4) tert-butyl 4-((4-(4-((R)-2,3-dihydroxypropylcarbamoyl)cyclohex-1-enyl)phenoxy)methyl)piperidine-1-carboxylate;
(5) tert-butyl 4-((4-(4-((R)-3-hydroxypyrrolidine-1-carbonyl)cyclohex-1-enyl)phenoxy)methyl)piperidine-1-carboxylate;
(6) tert-butyl 4-((4-(4-((3-hydroxypropyl)(methyl)carbamoyl)cyclohex-1-enyl)phenoxy)methyl)piperidine-1-carboxylate;

(7) tert-butyl 4-((4-(4-(morpholine-4-carbonyl)cyclohex-1-enyl)phenoxy)methyl)piperidine-1-carboxylate;
(8) 4-(4-((1-(5-ethylpyrimidin-2-yl)piperidin-4-yl)methoxy)phenyl)-N—((R)-1-hydroxypropan-2-yl)cyclohex-3-enecarboxamide;
(9) 4-(4-((1-(5-ethylpyrimidin-2-yl)piperidin-4-yl)methoxy)phenyl)-N-(3-hydroxypropyl)cyclohex-3-enecarboxamide;
(10) tert-butyl 4-((6-(4-((R)-2,3-dihydroxypropylcarbamoyl)cyclohex-1-enyl)pyridin-3-yloxy)methyl)piperidine-1-carboxylate;
(11) tert-butyl 4-((6-(4-((S)-1-hydroxypropan-2-ylcarbamoyl)cyclohex-1-enyl)pyridin-3-yloxy)methyl)piperidine-1-carboxylate;
(12) N—((R)-2,3-dihydroxypropyl)-4-(4-((1-(5-ethylpyrimidin-2-yl)piperidin-4-yl)methoxy)phenyl)cyclohex-3-enecarboxamide;
(13) (4-(4-((1-(5-ethylpyrimidin-2-yl)piperidin-4-yl)methoxy)phenyl)cyclohex-3-enyl)(morpholino)methanone;
(14) tert-butyl 4-((6-(4-(1,3-dihydroxypropan-2-ylcarbamoyl)cyclohex-1-enyl)pyridin-3-yloxy)methyl)piperidine-1-carboxylate;
(15) N-(1,3-dihydroxypropan-2-yl)-4-(4-((1-(5-ethylpyrimidin-2-yl)piperidin-4-yl)methoxy)phenyl)cyclohex-3-enecarboxamide;
(16) (4-(4-((1-(5-ethylpyrimidin-2-yl)piperidin-4-yl)methoxy)phenyl)cyclohex-3-enyl)((R)-3-hydroxypyrrolidin-1-yl)methanone;
(17) N—((R)-2,3-dihydroxypropyl)-4-(4-((1-(3-isopropyl-1,2,4-oxadiazol-5-yl)piperidin-4-yl)methoxy)phenyl)cyclohex-3-enecarboxamide;
(18) N—((S)-2,3-dihydroxypropyl)-4-(4-((1-(3-isopropyl-1,2,4-oxadiazol-5-yl)piperidin-4-yl)methoxy)phenyl)cyclohex-3-enecarboxamide;
(19) N—((S)-1-hydroxypropan-2-yl)-4-(4-((1-(3-isopropyl-1,2,4-oxadiazol-5-yl)piperidin-4-yl)methoxy)phenyl)cyclohex-3-enecarboxamide;
(20) N—((R)-1-hydroxypropan-2-yl)-4-(4-((1-(3-isopropyl-1,2,4-oxadiazol-5-yl)piperidin-4-yl)methoxy)phenyl)cyclohex-3-enecarboxamide;
(21) 4-(4-((1-(5-ethylpyrimidin-2-yl)piperidin-4-yl)methoxy)phenyl)-N-(2-hydroxyethyl)-N-methylcyclohex-3-enecarboxamide;
(22) N-(3-hydroxy-2,2-dimethylpropyl)-4-(4-((1-(3-isopropyl-1,2,4-oxadiazol-5-yl)piperidin-4-yl)methoxy)phenyl)cyclohex-3-enecarboxamide;
(23) N-(1,3-dihydroxypropan-2-yl)-4-(4-((1-(3-isopropyl-1,2,4-oxadiazol-5-yl)piperidin-4-yl)methoxy)phenyl)cyclohex-3-enecarboxamide;
(24) tert-butyl 4-((5-(4-((S)-1-hydroxypropan-2-ylcarbamoyl)cyclohex-1-enyl)pyridin-2-yloxy)methyl)piperidine-1-carboxylate;
(25) tert-butyl 4-((5-(4-((R)-1-hydroxypropan-2-ylcarbamoyl)cyclohex-1-enyl)pyridin-2-yloxy)methyl)piperidine-1-carboxylate;
(26) tert-butyl 4-((5-(4-((S)-2-hydroxypropylcarbamoyl)cyclohex-1-enyl)pyridin-2-yloxy)methyl)piperidine-1-carboxylate;
(27) tert-butyl 4-((5-(4-((R)-2-hydroxypropylcarbamoyl)cyclohex-1-enyl)pyridin-2-yloxy)methyl)piperidine-1-carboxylate;
(28) N—((R)-2-hydroxypropyl)-4-(4-((1-(3-isopropyl-1,2,4-oxadiazol-5-yl)piperidin-4-yl)methoxy)phenyl)cyclohex-3-enecarboxamide;
(29) N—((S)-2-hydroxypropyl)-4-(4-((1-(3-isopropyl-1,2,4-oxadiazol-5-yl)piperidin-4-yl)methoxy)phenyl)cyclohex-3-enecarboxamide;
(30) 4-(4-((1-(5-ethylpyrimidin-2-yl)piperidin-4-yl)methoxy)phenyl)-N—((R)-2-hydroxypropyl)cyclohex-3-enecarboxamide;
(31) N-(2-hydroxyethyl)-4-(4-((1-(3-isopropyl-1,2,4-oxadiazol-5-yl)piperidin-4-yl)methoxy)phenyl)cyclohex-3-enecarboxamide;
(32) tert-butyl 4-((5-(4-((R)-2,3-dihydroxypropylcarbamoyl)cyclohex-1-enyl)pyridin-2-yloxy)methyl)piperidine-1-carboxylate;
(33) tert-butyl 4-((5-(4-((S)-2,3-dihydroxypropylcarbamoyl)cyclohex-1-enyl)pyridin-2-yloxy)methyl)piperidine-1-carboxylate;
(34) N-(2-hydroxyethyl)-4-(4-((1-(3-isopropyl-1,2,4-oxadiazol-5-yl)piperidin-4-yl)methoxy)phenyl)-N-methylcyclohex-3-enecarboxamide;
(35) N-ethyl-N-(2-hydroxyethyl)-4-(4-((1-(3-isopropyl-1,2,4-oxadiazol-5-yl)piperidin-4-yl)methoxy)phenyl)cyclohex-3-enecarboxamide;
(36) N—((R)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(37) N—((S)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(38) N—((R)-2-hydroxypropyl)-4-(5-((1-(3-isopropyl-1,2,4-oxadiazol-5-yl)piperidin-4-yl)methoxy)pyridin-2-yl)cyclohex-3-enecarboxamide;
(39) N—((S)-2-hydroxypropyl)-4-(5-((1-(3-isopropyl-1,2,4-oxadiazol-5-yl)piperidin-4-yl)methoxy)pyridin-2-yl)cyclohex-3-enecarboxamide;
(40) N—((R)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide;
(41) N—((S)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide;
(42) tert-butyl 4-((5-(4-((S)-3-hydroxypyrrolidine-1-carbonyl)cyclohex-1-enyl)pyridin-2-yloxy)methyl)piperidine-1-carboxylate;
(43) tert-butyl 4-((5-(4-((R)-3-hydroxypyrrolidine-1-carbonyl)cyclohex-1-enyl)pyridin-2-yloxy)methyl)piperidine-1-carboxylate;
(44) tert-butyl 4-((2-fluoro-4-(4-((S)-3-hydroxypyrrolidine-1-carbonyl)cyclohex-1-enyl)phenoxy)methyl)piperidine-1-carboxylate;
(45) tert-butyl 4-((2-fluoro-4-(4-((R)-3-hydroxypyrrolidine-1-carbonyl)cyclohex-1-enyl)phenoxy)methyl)piperidine-1-carboxylate;
(46) N-(1,3-dihydroxypropan-2-yl)-4-(5-((1-(3-isopropyl-1,2,4-oxadiazol-5-yl)piperidin-4-yl)methoxy)pyridin-2-yl)cyclohex-3-enecarboxamide;
(47) N-(3-hydroxy-2,2-dimethylpropyl)-4-(5-((1-(3-isopropyl-1,2,4-oxadiazol-5-yl)piperidin-4-yl)methoxy)pyridin-2-yl)cyclohex-3-enecarboxamide;
(48) ((R)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone;
(49) ((S)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone;
(50) N-(2,2-difluoroethyl)-4-(4-((1-(5-ethylpyrimidin-2-yl)piperidin-4-yl)methoxy)phenyl)cyclohex-3-enecarboxamide;

(51) N-(2,2-difluoroethyl)-4-(4-((1-(3-isopropyl-1,2,4-oxadiazol-5-yl)piperidin-4-yl)methoxy)phenyl)cyclohex-3-enecarboxamide;

(52) (4-(4-((1-(3-isopropyl-1,2,4-oxadiazol-5-yl)piperidin-4-yl)methoxy)phenyl)cyclohex-3-enyl)(pyrrolidin-1-yl)methanone;

(53) ((S)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone;

(54) ((R)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone;

(55) (4-ethylpiperazin-1-yl)(4-(4-((1-(5-ethylpyrimidin-2-yl)piperidin-4-yl)methoxy)phenyl)cyclohex-3-enyl)methanone;

(56) (4-(4-((1-(3-isopropyl-1,2,4-oxadiazol-5-yl)piperidin-4-yl)methoxy)phenyl)cyclohex-3-enyl)(piperidin-1-yl)methanone;

(57) tert-butyl 4-((2-fluoro-4-(4-((S)-3-fluoropyrrolidine-1-carbonyl)cyclohex-1-enyl)phenoxy)methyl)piperidine-1-carboxylate;

(58) tert-butyl 4-((2-fluoro-4-(4-((R)-3-fluoropyrrolidine-1-carbonyl)cyclohex-1-enyl)phenoxy)methyl)piperidine-1-carboxylate;

(59) tert-butyl 4-((2-fluoro-4-(4-((S)-1-hydroxypropan-2-ylcarbamoyl)cyclohex-1-enyl)phenoxy)methyl)piperidine-1-carboxylate;

(60) tert-butyl 4-((2-fluoro-4-(4-((R)-1-hydroxypropan-2-ylcarbamoyl)cyclohex-1-enyl)phenoxy)methyl)piperidine-1-carboxylate;

(61) tert-butyl 4-((2-fluoro-4-(4-((S)-2-hydroxypropylcarbamoyl)cyclohex-1-enyl)phenoxy)methyl)piperidine-1-carboxylate;

(62) tert-butyl 4-((2-fluoro-4-(4-((R)-2-hydroxypropylcarbamoyl)cyclohex-1-enyl)phenoxy)methyl)piperidine-1-carboxylate;

(63) tert-butyl 4-((4-(4-((S)-2,3-dihydroxypropylcarbamoyl)cyclohex-1-enyl)-2-fluorophenoxy)methyl)piperidine-1-carboxylate;

(64) tert-butyl 4-((4-(4-((R)-2,3-dihydroxypropylcarbamoyl)cyclohex-1-enyl)-2-fluorophenoxy)methyl)piperidine-1-carboxylate;

(65) azetidin-1-yl(4-(4-((1-(3-isopropyl-1,2,4-oxadiazol-5-yl)piperidin-4-yl)methoxy)phenyl)cyclohex-3-enyl)methanone;

(66) (4-(4-((1-(3-isopropyl-1,2,4-oxadiazol-5-yl)piperidin-4-yl)methoxy)phenyl)cyclohex-3-enyl)(morpholino)methanone;

(67) tert-butyl 4-((4-(4-(1,3-dihydroxypropan-2-ylcarbamoyl)cyclohex-1-enyl)-2-fluorophenoxy)methyl)piperidine-1-carboxylate;

(68) tert-butyl 4-((5-(4-(1,3-dihydroxypropan-2-ylcarbamoyl)cyclohex-1-enyl)pyridin-2-yloxy)methyl)piperidine-1-carboxylate;

(69) tert-butyl 4-((2-fluoro-4-(4-(morpholine-4-carbonyl)cyclohex-1-enyl)phenoxy)methyl)piperidine-1-carboxylate;

(70) tert-butyl 4-((5-(4-(morpholine-4-carbonyl)cyclohex-1-enyl)pyridin-2-yloxy)methyl)piperidine-1-carboxylate;

(71) tert-butyl 4-((2-fluoro-4-(4-(thiomorpholine-4-carbonyl)cyclohex-1-enyl)phenoxy)methyl)piperidine-1-carboxylate;

(72) tert-butyl 4-((5-(4-(thiomorpholine-4-carbonyl)cyclohex-1-enyl)pyridin-2-yloxy)methyl)piperidine-1-carboxylate;

(73) tert-butyl 4-((2-fluoro-4-(4-(thiomorpholine-1,1-dioxide-4-carbonyl)cyclohex-1-enyl)phenoxy)methyl)piperidine-1-carboxylate;

(74) (4-(4-((1-(3-isopropyl-1,2,4-oxadiazol-5-yl)piperidin-4-yl)methoxy)phenyl)cyclohex-3-enyl)(thiomorpholino)methanone;

(75) N-(2-fluoroethyl)-4-(4-((1-(3-isopropyl-1,2,4-oxadiazol-5-yl)piperidin-4-yl)methoxy)phenyl)cyclohex-3-enecarboxamide;

(76) tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate;

(77) N-(3-aminopropyl)-4-(4-((1-(3-isopropyl-1,2,4-oxadiazol-5-yl)piperidin-4-yl)methoxy)phenyl)-N-methylcyclohex-3-enecarboxamide;

(78) 4-(4-((1-(3-isopropyl-1,2,4-oxadiazol-5-yl)piperidin-4-yl)methoxy)phenyl)-N-(2,2,2-trifluoroethyl)cyclohex-3-enecarboxamide;

(79) (4-ethylpiperazin-1-yl)(4-(4-((1-(3-isopropyl-1,2,4-oxadiazol-5-yl)piperidin-4-yl)methoxy)phenyl)cyclohex-3-enyl)methanone;

(80) N-(1,3-dihydroxypropan-2-yl)-4-(3-fluoro-4-((1-(3-isopropyl-1,2,4-oxadiazol-5-yl)piperidin-4-yl)methoxy)phenyl)cyclohex-3-enecarboxamide;

(81) 4-(3-fluoro-4-((1-(3-isopropyl-1,2,4-oxadiazol-5-yl)piperidin-4-yl)methoxy)phenyl)-N-(2-hydroxyethyl)-N-methylcyclohex-3-enecarboxamide;

(82) tert-butyl 4-((2-fluoro-4-(4-(3-hydroxy-2,2-dimethylpropylcarbamoyl)cyclohex-1-enyl)phenoxy)methyl)piperidine-1-carboxylate;

(83) 4-(3-fluoro-4-((1-(3-isopropyl-1,2,4-oxadiazol-5-yl)piperidin-4-yl)methoxy)phenyl)-N—((S)-1-hydroxypropan-2-yl)cyclohex-3-enecarboxamide;

(84) 4-(3-fluoro-4-((1-(3-isopropyl-1,2,4-oxadiazol-5-yl)piperidin-4-yl)methoxy)phenyl)-N—((R)-1-hydroxypropan-2-yl)cyclohex-3-enecarboxamide;

(85) tert-butyl 4-((4-(4-(2,2-difluoroethylcarbamoyl)cyclohex-1-enyl)-2-fluorophenoxy)methyl)piperidine-1-carboxylate;

(86) tert-butyl 4-((5-(4-(2,2,2-trifluoroethylcarbamoyl)cyclohex-1-enyl)pyridin-2-yloxy)methyl)piperidine-1-carboxylate;

(87) tert-butyl 4-((5-(4-(2,2-difluoroethylcarbamoyl)cyclohex-1-enyl)pyridin-2-yloxy)methyl)piperidine-1-carboxylate;

(88) tert-butyl 4-((5-(4-(2-fluoroethylcarbamoyl)cyclohex-1-enyl)pyridin-2-yloxy)methyl)piperidine-1-carboxylate;

(89) (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone;

(90) tert-butyl 4-((5-(4-((R)-3-fluoropyrrolidine-1-carbonyl)cyclohex-1-enyl)pyridin-2-yloxy)methyl)piperidine-1-carboxylate;

(91) tert-butyl 4-((5-(4-((S)-3-fluoropyrrolidine-1-carbonyl)cyclohex-1-enyl)pyridin-2-yloxy)methyl)piperidine-1-carboxylate;

(92) 4-(3-fluoro-4-((1-(3-isopropyl-1,2,4-oxadiazol-5-yl)piperidin-4-yl)methoxy)phenyl)-N-(2,2,2-trifluoroethyl)cyclohex-3-enecarboxamide;

(93) N-(2,2-difluoroethyl)-4-(3-fluoro-4-((1-(3-isopropyl-1,2,4-oxadiazol-5-yl)piperidin-4-yl)methoxy)phenyl)cyclohex-3-enecarboxamide;

(94) 4-(3-fluoro-4-((1-(3-isopropyl-1,2,4-oxadiazol-5-yl)piperidin-4-yl)methoxy)phenyl)-N-(2-fluoroethyl)cyclohex-3-enecarboxamide;

(95) (4-(3-fluoro-4-((1-(3-isopropyl-1,2,4-oxadiazol-5-yl)piperidin-4-yl)methoxy)phenyl)cyclohex-3-enyl)((S)-3-fluoropyrrolidin-1-yl)methanone;
(96) (4-(3-fluoro-4-((1-(3-isopropyl-1,2,4-oxadiazol-5-yl)piperidin-4-yl)methoxy)phenyl)cyclohex-3-enyl)((R)-3-fluoropyrrolidin-1-yl)methanone;
(97) (4-(3-fluoro-4-((1-(3-isopropyl-1,2,4-oxadiazol-5-yl)piperidin-4-yl)methoxy)phenyl)cyclohex-3-enyl)(morpholino)methanone;
(98) (4-(3-fluoro-4-((1-(3-isopropyl-1,2,4-oxadiazol-5-yl)piperidin-4-yl)methoxy)phenyl)cyclohex-3-enyl)(thiomorpholino)methanone;
(99) N-(2,2-difluoroethyl)-4-(5-((1-(3-isopropyl-1,2,4-oxadiazol-5-yl)piperidin-4-yl)methoxyl)pyridin-2-yl)cyclohex-3-enecarboxamide;
(100) (4-(5-((1-(3-isopropyl-1,2,4-oxadiazol-5-yl)piperidin-4-yl)methoxy)pyridin-2-yl)cyclohex-3-enyl)(morpholino)methanone;
(101) ((R)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone;
(102) ((S)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone;
(103) 4-(4-((1-(5-ethylpyrimidin-2-yl)piperidin-4-yl)methoxy)phenyl)-N-(2,2,2-trifluoroethyl)cyclohex-3-enecarboxamide;
(104) 4-(4-((1-(5-ethylpyrimidin-2-yl)piperidin-4-yl)methoxy)phenyl)-N-(2-fluoroethyl)cyclohex-3-enecarboxamide;
(105) (2S)-1-(4-(4-((1-(5-ethylpyrimidin-2-yl)piperidin-4-yl)methoxy)phenyl)cyclohex-3-enecarbonyl)pyrrolidine-2-carboxamide;
(106) (2S)-1-(4-(4-((1-(5-ethylpyrimidin-2-yl)piperidin-4-yl)methoxy)phenyl)cyclohex-3-enecarbonyl)pyrrolidine-2-carbonitrile;
(107) tert-butyl 4-((4-(4-((S)-2-carbamoylpyrrolidine-1-carbonyl)cyclohex-1-enyl)-2-fluorophenoxy)methyl)piperidine-1-carboxylate;
(108) (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide;
(109) (methyl 2-(4-(3-fluoro-4-((1-(3-isopropyl-1,2,4-oxadiazol-5-yl)piperidin-4-yl)methoxy)phenyl)cyclohex-3-enecarboxamido)acetate;
(110) ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate;
(111) 3-(4-(3-fluoro-4-((1-(3-isopropyl-1,2,4-oxadiazol-5-yl)piperidin-4-yl)methoxy)phenyl)cyclohex-3-enecarboxamido)propanoic acid;
(112) 4-(3-fluoro-4-((1-(3-isopropyl-1,2,4-oxadiazol-5-yl)piperidin-4-yl)methoxy)phenyl)-N-(2-morpholino-2-oxoethyl)cyclohex-3-enecarboxamide;
(113) 4-(3-fluoro-4-((1-(3-isopropyl-1,2,4-oxadiazol-5-yl)piperidin-4-yl)methoxy)phenyl)-N-(3-morpholino-3-oxopropyl)cyclohex-3-enecarboxamide;
(114) tert-butyl 4-((4-(4-((S)-2-cyanopyrrolidine-1-carbonyl)cyclohex-1-enyl)-2-fluorophenoxy)methyl)piperidine-1-carboxylate;
(115) (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile;
(116) (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide;
(117) (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile;
(118) (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;
(119) (4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone;
(120) 4-(3-fluoro-4-((1-(3-isopropyl-1,2,4-oxadiazol-5-yl)piperidin-4-yl)methoxy)phenyl)-N-(2-hydroxyethyl)cyclohex-3-enecarboxamide;
(121) (2R)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide;
(122) N-(2-((R)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide;
(123) (4-cyclopropylpiperazin-1-yl)(4-(4-((1-(5-ethylpyrimidin-2-yl)piperidin-4-yl)methoxy)phenyl)cyclohex-3-enyl)methanone;
(124) (4-(cyclopropylmethyl)piperazin-1-yl)(4-(4-((1-(5-ethylpyrimidin-2-yl)piperidin-4-yl)methoxy)phenyl)cyclohex-3-enyl)methanone;
(125) tert-butyl 4-((3-fluoro-4-(4-((S)-2-hydroxypropylcarbamoyl)cyclohex-1-enyl)phenoxy)methyl)piperidine-1-carboxy late;
(126) tert-butyl 4-((3-fluoro-4-(4-((R)-2-hydroxypropylcarbamoyl)cyclohex-1-enyl)phenoxy)methyl)piperidine-1-carboxylate;
(127) 4-(4-((1-(5-ethylpyrimidin-2-yl)piperidin-4-yl)methoxy)phenyl)-N—((S)-1-hydroxypropan-2-yl)cyclohex-3-enecarboxamide;
(128) N—((S)-2,3-dihydroxypropyl)-4-(4-((1-(5-ethylpyrimidin-2-yl)piperidin-4-yl)methoxy)phenyl)cyclohex-3-enecarboxamide;
(129) tert-butyl 4-((3-fluoro-4-(4-((R)-1-hydroxypropan-2-ylcarbamoyl)cyclohex-1-enyl)phenoxy)methyl)piperidine-1-carboxylate;
(130) tert-butyl 4-((3-fluoro-4-(4-((S)-1-hydroxypropan-2-ylcarbamoyl)cyclohex-1-enyl)phenoxy)methyl)piperidine-1-carboxylate;
(131) tert-butyl 4-((4-(4-((R)-2,3-dihydroxypropylcarbamoyl)cyclohex-1-enyl)-3-fluorophenoxy)methyl)piperidine-1-carboxylate;
(132) tert-butyl 4-((4-(4-((S)-2,3-dihydroxypropylcarbamoyl)cyclohex-1-enyl)-3-fluorophenoxy)methyl)piperidine-1-carboxylate;
(133) (2S)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide;
(134) (2S)-1-(3-(4-(3-fluoro-4-((1-(3-isopropyl-1,2,4-oxadiazol-5-yl)piperidin-4-yl)methoxy)phenyl)cyclohex-3-enecarboxamido)propanoyl)pyrrolidine-2-carboxamide;
(135) (4-(4-((1-(5-ethylpyrimidin-2-yl)piperidin-4-yl)methoxy)phenyl)cyclohex-3-enyl)((S)-3-hydroxypyrrolidin-1-yl)methanone;
(136) 4-(4-((1-(5-ethylpyrimidin-2-yl)piperidin-4-yl)methoxy)phenyl)-N—((S)-2-hydroxypropyl)cyclohex-3-enecarboxamide;
(137) tert-butyl 4-((4-(4-(cyclopropylcarbamoyl)cyclohex-1-enyl)-3-fluorophenoxy)methyl)piperidine-1-carboxylate;
(138) tert-butyl 4-((3-fluoro-4-(4-(2-fluoroethylcarbamoyl)cyclohex-1-enyl)phenoxy)methyl)piperidine-1-carboxylate;

(139) N-(2-((S)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide;
(140) N-(3-((S)-2-cyanopyrrolidin-1-yl)-3-oxopropyl)-4-(3-fluoro-4-((1-(3-isopropyl-1,2,4-oxadiazol-5-yl)piperidin-4-yl)methoxy)phenyl)cyclohex-3-enecarboxamide;
(141) tert-butyl 4-((4-(4-(2,2-difluoroethylcarbamoyl)cyclohex-1-enyl)-3-fluorophenoxy)methyl)piperidine-1-carboxylate;
(142) tert-butyl 4-((3-fluoro-4-(4-(2,2,2-trifluoroethylcarbamoyl)cyclohex-1-enyl)phenoxy)methyl)piperidine-1-carboxylate;
(143) ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone;
(144) ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone;
(145) ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride;
(146) ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride;
(147) ((R)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;
(148) ((S)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;
(149) ((R)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;
(150) ((S)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone;
(151) (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone hydrochloride;
(152) (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone;
(153) (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone;
(154) ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone;
(155) ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone;
(156) ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride;
(157) ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride;
(158) (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone hydrochloride;
(159) (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone hydrochloride;
(160) (4-(4-((1-(5-ethylpyrimidin-2-yl)piperidin-4-yl)methoxy)phenyl)cyclohex-3-enyl)((S)-3-fluoropyrrolidin-1-yl)methanone;
(161) (4-(4-((1-(5-ethylpyrimidin-2-yl)piperidin-4-yl)methoxy)phenyl)cyclohex-3-enyl)((S)-3-fluoropyrrolidin-1-yl)methanone hydrochloride;
(162) (4-(4-((1-(5-ethylpyrimidin-2-yl)piperidin-4-yl)methoxy)phenyl)cyclohex-3-enyl)(pyrrolidin-1-yl)methanone;
(163) (4-(4-((1-(5-ethylpyrimidin-2-yl)piperidin-4-yl)methoxy)phenyl)cyclohex-3-enyl)(piperidin-1-yl)methanone;
(164) (4-(4-((1-(5-ethylpyrimidin-2-yl)piperidin-4-yl)methoxy)phenyl)cyclohex-3-enyl)(4-hydroxypiperidin-1-yl)methanone;
(165) (4-(4-((1-(5-ethylpyrimidin-2-yl)piperidin-4-yl)methoxy)phenyl)cyclohex-3-enyl)(4-(hydroxymethyl)piperidin-1-yl)methanone;
(166) (4-(4-((1-(5-ethylpyrimidin-2-yl)piperidin-4-yl)methoxy)phenyl)cyclohex-3-enyl)(pyrrolidin-1-yl)methanone hydrochloride;
(167) (4-(4-((1-(5-ethylpyrimidin-2-yl)piperidin-4-yl)methoxy)phenyl)cyclohex-3-enyl)(piperidin-1-yl)methanone hydrochloride;
(168) (4-(4-((1-(5-ethylpyrimidin-2-yl)piperidin-4-yl)methoxy)phenyl)cyclohex-3-enyl)(4-hydroxypiperidin-1-yl)methanone hydrochloride;
(169) (4-(4-((1-(5-ethylpyrimidin-2-yl)piperidin-4-yl)methoxy)phenyl)cyclohex-3-enyl)(4-(hydroxymethyl)piperidin-1-yl)methanone hydrochloride;
(170) azetidin-1-yl(4-(4-((1-(5-ethylpyrimidin-2-yl)piperidin-4-yl)methoxy)phenyl)cyclohex-3-enyl)methanone;
(171) (4-(4-((1-(5-ethylpyrimidin-2-yl)piperidin-4-yl)methoxy)phenyl)cyclohex-3-enyl)(3-hydroxyazetidin-1-yl)methanone;
(172) (4-(4-((1-(5-ethylpyrimidin-2-yl)piperidin-4-yl)methoxy)phenyl)cyclohex-3-enyl)(4-(2-hydroxyethyl)piperazin-1-yl)methanone;
(173) (4-(4-((1-(5-ethylpyrimidin-2-yl)piperidin-4-yl)methoxy)phenyl)cyclohex-3-enyl)(4-(2-hydroxyethyl)piperidin-1-yl)methanone;
(174) N-ethoxy-4-(4-((1-(5-ethylpyrimidin-2-yl)piperidin-4-yl)methoxy)phenyl)cyclohex-3-enecarboxamide;
(175) N-ethyl-4-(4-((1-(5-ethylpyrimidin-2-yl)piperidin-4-yl)methoxy)phenyl)-N-(2-hydroxyethyl)cyclohex-3-enecarboxamide;
(176) 4-(4-((1-(5-ethylpyrimidin-2-yl)piperidin-4-yl)methoxy)phenyl)-N-(2-hydroxyethyl)cyclohex-3-enecarboxamide;
(177) 4-(4-((1-(5-ethylpyrimidin-2-yl)piperidin-4-yl)methoxy)phenyl)-N-(3-hydroxy-2,2-dimethylpropyl)cyclohex-3-enecarboxamide;
(178) 1-(4-(4-((1-(5-ethylpyrimidin-2-yl)piperidin-4-yl)methoxy)phenyl)cyclohex-3-enecarbonyl)piperidine-4-carboxamide;
(179) 4-(4-((1-(5-ethylpyrimidin-2-yl)piperidin-4-yl)methoxy)phenyl)-N-(3-methoxypropyl)cyclohex-3-enecarboxamide;
(180) 4-(4-((1-(5-ethylpyrimidin-2-yl)piperidin-4-yl)methoxy)phenyl)-N-(furan-2-ylmethyl)cyclohex-3-enecarboxamide;
(181) 4-(4-((1-(5-ethylpyrimidin-2-yl)piperidin-4-yl)methoxy)phenyl)-N,N-bis(2-hydroxyethyl)cyclohex-3-enecarboxamide;
(182) (4-hydroxypiperidin-1-yl)(4-(4-((1-(3-isopropyl-1,2,4-oxadiazol-5-yl)piperidin-4-yl)methoxy)phenyl)cyclohex-3-enyl)methanone;
(183) (4-(hydroxymethyl)piperidin-1-yl)(4-(4-((1-(3-isopropyl-1,2,4-oxadiazol-5-yl)piperidin-4-yl)methoxy)phenyl)cyclohex-3-enyl)methanone;

(184) N-cyclopropyl-4-(4-((1-(3-isopropyl-1,2,4-oxadiazol-5-yl)piperidin-4-yl)methoxy)phenyl)cyclohex-3-enecarboxamide;

(185) N-(3-hydroxypropyl)-4-(4-((1-(3-isopropyl-1,2,4-oxadiazol-5-yl)piperidin-4-yl)methoxy)phenyl)cyclohex-3-enecarboxamide;

(186) (4-(2-hydroxyethyl)piperidin-1-yl)(4-(4-((1-(3-isopropyl-1,2,4-oxadiazol-5-yl)piperidin-4-yl)methoxy)phenyl)cyclohex-3-enyl)methanone;

(187) (4-(2-hydroxyethyl)piperazin-1-yl)(4-(4-((1-(3-isopropyl-1,2,4-oxadiazol-5-yl)piperidin-4-yl)methoxy)phenyl)cyclohex-3-enyl)methanone;

(188) 4-(4-((1-(3-isopropyl-1,2,4-oxadiazol-5-yl)piperidin-4-yl)methoxy)phenyl)-N-(methoxymethyl)cyclohex-3-enecarboxamide;

(189) N-cyclopropyl-4-(4-((1-(5-ethylpyrimidin-2-yl)piperidin-4-yl)methoxy)phenyl)cyclohex-3-enecarboxamide;

(190) tert-butyl 4-((4-(4-(2-hydroxyethylcarbamoyl)cyclohex-1-enyl)phenoxy)methyl)piperidine-1-carboxylate;

(191) tert-butyl 4-((4-(4-(3-hydroxy-2,2-dimethylpropylcarbamoyl)cyclohex-1-enyl)phenoxy)methyl)piperidine-1-carboxylate;

(192) tert-butyl 4-((4-(4-(methoxymethylcarbamoyl)cyclohex-1-enyl)phenoxy)methyl)piperidine-1-carboxylate;

(193) tert-butyl 4-((4-(4-(4-(pyrrolidin-1-yl)piperidine-1-carbonyl)cyclohex-1-enyl)phenoxy)methyl)piperidine-1-carboxylate;

(194) tert-butyl 4-((4-(4-(cyclobutylcarbamoyl)cyclohex-1-enyl)phenoxy)methyl)piperidine-1-carboxylate;

(195) tert-butyl 4-((4-(4-(cyclopentylcarbamoyl)cyclohex-1-enyl)phenoxy)methyl)piperidine-1-carboxylate;

(196) tert-butyl 4-((4-(4-(4-morpholinopiperidine-1-carbonyl)cyclohex-1-enyl)phenoxy)methyl)piperidine-1-carboxylate;

(197) 4-(4-((1-(5-ethylpyrimidin-2-yl)piperidin-4-yl)methoxy)phenyl)-N-methoxy-N-methylcyclohex-3-enecarboxamide;

(198) 4-(4-((1-(5-ethylpyrimidin-2-yl)piperidin-4-yl)methoxy)phenyl)-N-methoxycyclohex-3-enecarboxamide;

(199) tert-butyl 4-((4-(4-(ethyl(2-hydroxyethyl)carbamoyl)cyclohex-1-enyl)phenoxy)methyl)piperidine-1-carboxylate;

(200) tert-butyl 4-((4-(4-(4-(2-hydroxyethyl)piperidine-1-carbonyl)cyclohex-1-enyl)phenoxy)methyl)piperidine-1-carboxylate;

(201) tert-butyl 4-((4-(4-(4-(2-hydroxyethyl)piperazine-1-carbonyl)cyclohex-1-enyl)phenoxy)methyl)piperidine-1-carboxylate;

(202) tert-butyl 4-((4-(4-(pyrrolidine-1-carbonyl)cyclohex-1-enyl)phenoxy)methyl)piperidine-1-carboxylate;

(203) tert-butyl 4-((4-(4-(4-ethylpiperazine-1-carbonyl)cyclohex-1-enyl)phenoxy)methyl)piperidine-1-carboxylate;

(204) tert-butyl 4-((4-(4-(piperidine-1-carbonyl)cyclohex-1-enyl)phenoxy)methyl)piperidine-1-carboxylate;

(205) tert-butyl 4-((4-(4-(3-ethoxypropylcarbamoyl)cyclohex-1-enyl)phenoxy)methyl)piperidine-1-carboxylate;

(206) tert-butyl 4-((4-(4-(bis(2-hydroxyethyl)carbamoyl)cyclohex-1-enyl)phenoxy)methyl)piperidine-1-carboxylate;

(207) 1-(4-(4-((1-(3-isopropyl-1,2,4-oxadiazol-5-yl)piperidin-4-yl)methoxy)phenyl)cyclohex-3-enecarbonyl)piperidine-4-carboxamide;

(208) (4-(4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone;

(209) (4-(4-((1-(3-isopropyl-1,2,4-oxadiazol-5-yl)piperidin-4-yl)methoxy)phenyl)cyclohex-3-enyl)(4-morpholinopiperidin-1-yl)methanone;

(210) N-cyclopentyl-4-(4-((1-(3-isopropyl-1,2,4-oxadiazol-5-yl)piperidin-4-yl)methoxy)phenyl)cyclohex-3-enecarboxamide;

(211) N-cyclobutyl-4-(4-((1-(3-isopropyl-1,2,4-oxadiazol-5-yl)piperidin-4-yl)methoxy)phenyl)cyclohex-3-enecarboxamide;

(212) (3,4-dihydroisoquinolin-2(1H)-yl)(4-(4-((1-(3-isopropyl-1,2,4-oxadiazol-5-yl)piperidin-4-yl)methoxy)phenyl)cyclohex-3-enyl)methanone;

(213) (4-(4-((1-(3-isopropyl-1,2,4-oxadiazol-5-yl)piperidin-4-yl)methoxy)phenyl)cyclohex-3-enyl)(1-methyl-3,4-dihydroisoquinolin-2(1H)-yl)methanone;

(214) isoindolin-2-yl(4-(4-((1-(3-isopropyl-1,2,4-oxadiazol-5-yl)piperidin-4-yl)methoxy)phenyl)cyclohex-3-enyl)methanone;

(215) 1,4'-bipiperidin-1'-yl(4-(4-((1-(3-isopropyl-1,2,4-oxadiazol-5-yl)piperidin-4-yl)methoxy)phenyl)cyclohex-3-enyl)methanone;

(216) tert-butyl 4-((4-(4-(1,4'-bipiperidine-1'-carbonyl)cyclohex-1-enyl)phenoxy)methyl)piperidine-1-carboxylate;

(217) (4-(4-((1-(5-ethylpyrimidin-2-yl)piperidin-4-yl)methoxy)phenyl)cyclohex-3-enyl)(3-(hydroxyimino)pyrrolidin-1-yl)methanone;

(218) (4-(4-((1-(5-ethylpyrimidin-2-yl)piperidin-4-yl)methoxy)phenyl)cyclohex-3-enyl)(4-(pyrrolidin-1-yl)piperidin-1-yl)methanone;

(219) 1,4'-bipiperidin-1'-yl(4-(4-((1-(5-ethylpyrimidin-2-yl)piperidin-4-yl)methoxy)phenyl)cyclohex-3-enyl)methanone;

(220) (4-(4-((1-(5-ethylpyrimidin-2-yl)piperidin-4-yl)methoxy)phenyl)cyclohex-3-enyl)(4-morpholinopiperidin-1-yl)methanone;

(221) tert-butyl 4-((4-(4-(furan-2-ylmethylcarbamoyl)cyclohex-1-enyl)phenoxy)methyl)piperidine-1-carboxylate;

(222) tert-butyl 4-((4-(4-(methoxycarbamoyl)cyclohex-1-enyl)phenoxy)methyl)piperidine-1-carboxylate;

(223) tert-butyl 4-((4-(4-(methoxy(methyl)carbamoyl)cyclohex-1-enyl)phenoxy)methyl)piperidine-1-carboxylate;

(224) tert-butyl 4-((4-(4-(2,5-dihydro-1H-pyrrole-1-carbonyl)cyclohex-1-enyl)phenoxy)methyl)piperidine-1-carboxylate;

(225) tert-butyl 4-((4-(4-(4-hydroxypiperidine-1-carbonyl)cyclohex-1-enyl)phenoxy)methyl)piperidine-1-carboxylate;

(226) tert-butyl 4-((4-(4-(4-(hydroxymethyl)piperidine-1-carbonyl)cyclohex-1-enyl)phenoxy)methyl)piperidine-1-carboxylate;

(227) 1-(4-(4-((1-(5-ethylpyrimidin-2-yl)piperidin-4-yl)methoxy)phenyl)cyclohex-3-enecarbonyl)piperidine-4-carbonitrile;

(228) (4-(4-((1-(5-ethylpyrimidin-2-yl)piperidin-4-yl)methoxy)phenyl)cyclohex-3-enyl)(spiro[indene-1,4'-piperidin]-1'-yl)methanone;

*343 (229) (4-(4-((1-(5-ethylpyrimidin-2-yl)piperidin-4-yl)methoxy)phenyl)cyclohex-3-enyl)(1,4-dioxa-8-azaspiro[4.5]decan-8-yl)methanone;

(230) N-cyclopentyl-4-(4-((1-(5-ethylpyrimidin-2-yl)piperidin-4-yl)methoxy)phenyl)cyclohex-3-enecarboxamide;

(231) N-cyclobutyl-4-(4-((1-(5-ethylpyrimidin-2-yl)piperidin-4-yl)methoxy)phenyl)cyclohex-3-enecarboxamide;

(232) (3,4-dihydroisoquinolin-2(1H)-yl)(4-(4-((1-(5-ethylpyrimidin-2-yl)piperidin-4-yl)methoxy)phenyl)cyclohex-3-enyl)methanone;

(233) tert-butyl 4-((4-(4-(5-hydroxypentylcarbamoyl)cyclohex-1-enyl)phenoxy)methyl)piperidine-1-carboxylate;
(234) 4-(4-((1-(5-ethylpyrimidin-2-yl)piperidin-4-yl)methoxy)phenyl)-N-(5-hydroxypentyl)cyclohex-3-enecarboxamide;
(235) (2,5-dihydro-1H-pyrrol-1-yl)(4-(4-((1-(5-ethylpyrimidin-2-yl)piperidin-4-yl)methoxy)phenyl)cyclohex-3-enyl)methanone;
(236) tert-butyl 4-((4-(4-((2-hydroxyethyl)(methyl)carbamoyl)cyclohex-1-enyl)phenoxy)methyl)piperidine-1-carboxylate;
(237) tert-butyl 4-((4-(4-(1,3-dihydroxypropan-2-ylcarbamoyl)cyclohex-1-enyl)phenoxy)methyl)piperidine-1-carboxylate;
(238) tert-butyl 4-((4-(4-(3-hydroxypropylcarbamoyl)cyclohex-1-enyl)phenoxy)methyl)piperidine-1-carboxylate;
(239) tert-butyl 4-((4-(4-(1,2,3,4-tetrahydroisoquinoline-2-carbonyl)cyclohex-1-enyl)phenoxy)methyl)piperidine-1-carboxylate;
(240) tert-butyl 4-((4-(4-(isoindoline-2-carbonyl)cyclohex-1-enyl)phenoxy)methyl)piperidine-1-carboxylate;
(241) (4-(4-((1-(5-ethylpyrimidin-2-yl)piperidin-4-yl)methoxy)phenyl)cyclohex-3-enyl)(isoindolin-2-yl)methanone;
(242) 4-(4-((1-(5-ethylpyrimidin-2-yl)piperidin-4-yl)methoxy)phenyl)-N-(3-hydroxypropyl)-N-methylcyclohex-3-enecarboxamide;
(243) N-(3-hydroxypropyl)-4-(4-((1-(3-isopropyl-1,2,4-oxadiazol-5-yl)piperidin-4-yl)methoxy)phenyl)-N-methylcyclohex-3-enecarboxamide;
(244) N-(furan-2-ylmethyl)-4-(4-((1-(3-isopropyl-1,2,4-oxadiazol-5-yl)piperidin-4-yl)methoxy)phenyl)cyclohex-3-enecarboxamide;
(245) N-(3-ethoxypropyl)-4-(4-((1-(3-isopropyl-1,2,4-oxadiazol-5-yl)piperidin-4-yl)methoxy)phenyl)cyclohex-3-enecarboxamide;
(246) 4-(4-((1-(3-isopropyl-1,2,4-oxadiazol-5-yl)piperidin-4-yl)methoxy)phenyl)-N-methoxycyclohex-3-enecarboxamide;
(247) 4-(4-((1-(3-isopropyl-1,2,4-oxadiazol-5-yl)piperidin-4-yl)methoxy)phenyl)-N-methoxy-N-methylcyclohex-3-enecarboxamide;
(248) N,N-bis(2-hydroxyethyl)-4-(4-((1-(3-isopropyl-1,2,4-oxadiazol-5-yl)piperidin-4-yl)methoxy)phenyl)cyclohex-3-enecarboxamide;
(249) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(250) 1-(4-(4-((1-(5-ethylpyrimidin-2-yl)piperidin-4-yl)methoxy)phenyl)cyclohex-3-enecarbonyl)pyrrolidin-3-one;
(251) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(252) 1-(4-(4-((1-(3-isopropyl-1,2,4-oxadiazol-5-yl)piperidin-4-yl)methoxy)phenyl)cyclohex-3-enecarbonyl)piperidine-4-carboxamide;
(253) (Z)-(3,3-bis(hydroxymethyl)-4-(methoxyimino)pyrrolidin-1-yl)(4-(4-((1-(5-ethylpyrimidin-2-yl)piperidin-4-yl)methoxy)phenyl)cyclohex-3-enyl)methanone;
(254) (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate;
(255) (Z)-(4-(4-((1-(5-ethylpyrimidin-2-yl)piperidin-4-yl)methoxy)phenyl)cyclohex-3-enyl)(8-(methoxyimino)-2,6-diazaspiro[3.4]octan-6-yl)methanone hydrochloride;
(256) tert-butyl 4-((4-(4-(4-(cyclopropylmethyl)piperazine-1-carbonyl)cyclohex-1-enyl)phenoxy)methyl)piperidine-1-carboxylate;
(257) tert-butyl 4-((4-(4-(3,3-difluoropyrrolidine-1-carbonyl)cyclohex-1-enyl)phenoxy)methyl)piperidine-1-carboxylate;
(258) (3,3-difluoropyrrolidin-1-yl)(4-(4-((1-(5-ethylpyrimidin-2-yl)piperidin-4-yl)methoxy)phenyl)cyclohex-3-enyl)methanone;
(259) (3,3-difluoropyrrolidin-1-yl)(4-(4-((1-(3-isopropyl-1,2,4-oxadiazol-5-yl)piperidin-4-yl)methoxy)phenyl)cyclohex-3-enyl)methanone;
(260) N-(5-hydroxypentyl)-4-(4-((1-(3-isopropyl-1,2,4-oxadiazol-5-yl)piperidin-4-yl)methoxy)phenyl)cyclohex-3-enecarboxamide;
(261) tert-butyl 4-((4-(4-(2,2,2-trifluoroethylcarbamoyl)cyclohex-1-enyl)phenoxy)methyl)piperidine-1-carboxylate;
(262) tert-butyl 4-((4-(4-(4-cyanocyclohexanecarbonyl)cyclohex-1-enyl)phenoxy)methyl)piperidine-1-carboxylate;
(263) tert-butyl 4-((4-(4-(1,4-dioxa-8-azaspiro[4.5]decane-8-carbonyl)cyclohex-1-enyl)phenoxy)methyl)piperidine-1-carboxylate;
(264) tert-butyl 4-((4-(4-(spiro[indene-1,4'-piperidin]-1'-yl-carbonyl)cyclohex-1-enyl)phenoxy)methyl)piperidine-1-carboxylate;
(265) tert-butyl 4-((4-(4-(3-oxopyrrolidine-1-carbonyl)cyclohex-1-enyl)phenoxy)methyl)piperidine-1-carboxylate;
(266) 1-(4-(4-((1-(3-isopropyl-1,2,4-oxadiazol-5-yl)piperidin-4-yl)methoxy)phenyl)cyclohex-3-enecarbonyl)piperidine-4-carbonitrile;
(267) (4-(4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone;
(268) (2,3-dihydrospiro[indene-1,4'-piperidin]-1'-yl)(4-(4-((1-(3-isopropyl-1,2,4-oxadiazol-5-yl)piperidin-4-yl)methoxy)phenyl)cyclohex-3-enyl)methanone;
(269) (3-(ethoxyimino)pyrrolidin-1-yl)(4-(4-((1-(5-ethylpyrimidin-2-yl)piperidin-4-yl)methoxy)phenyl)cyclohex-3-enyl)methanone;
(270) tert-butyl 4-((4-(4-(4-(methoxyimino)piperidine-1-carbonyl)cyclohex-1-enyl)phenoxy)methyl)piperidine-1-carboxylate;
(271) tert-butyl 4-((4-(4-(4-(hydroxyimino)piperidine-1-carbonyl)cyclohex-1-enyl)phenoxy)methyl)piperidine-1-carboxylate;
(272) tert-butyl 4-((4-(4-(4-oxopiperidine-1-carbonyl)cyclohex-1-enyl)phenoxy)methyl)piperidine-1-carboxylate;
(273) tert-butyl 4-((4-(4-(3-(methoxyimino)pyrrolidine-1-carbonyl)cyclohex-1-enyl)phenoxy)methyl)piperidine-1-carboxylate;
(274) 1-(4-(4-((1-(5-ethylpyrimidin-2-yl)piperidin-4-yl)methoxy)phenyl)cyclohex-3-enecarbonyl)piperidin-4-one;
(275) 1-(4-(4-((1-(3-isopropyl-1,2,4-oxadiazol-5-yl)piperidin-4-yl)methoxy)phenyl)cyclohex-3-enecarbonyl)piperidin-4-one;
(276) (4-(hydroxyimino)piperidin-1-yl)(4-(4-((1-(3-isopropyl-1,2,4-oxadiazol-5-yl)piperidin-4-yl)methoxy)phenyl)cyclohex-3-enyl)methanone;
(277) (4-(4-((1-(5-ethylpyrimidin-2-yl)piperidin-4-yl)methoxy)phenyl)cyclohex-3-enyl)(4-(hydroxyimino)piperidin-1-yl)methanone;
(278) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;

(279) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;

(280) tert-butyl 4-((4-(4-(3-oxoazetidine-1-carbonyl)cyclohex-1-enyl)phenoxy)methyl)piperidine-1-carboxylate;

(281) tert-butyl 4-((4-(4-(3-(hydroxyimino)azetidine-1-carbonyl)cyclohex-1-enyl)phenoxy)methyl)piperidine-1-carboxylate;

(282) tert-butyl 4-((4-(4-(3-(methoxyimino)azetidine-1-carbonyl)cyclohex-1-enyl)phenoxy)methyl)piperidine-1-carboxylate;

(283) 1-(4-(4-((1-(5-ethylpyrimidin-2-yl)piperidin-4-yl)methoxy)phenyl)cyclohex-3-enecarbonyl)azetidin-3-one;

(284) 1-(4-(4-((1-(3-isopropyl-1,2,4-oxadiazol-5-yl)piperidin-4-yl)methoxy)phenyl)cyclohex-3-enecarbonyl)azetidin-3-one;

(285) (3-(hydroxyimino)azetidin-1-yl)(4-(4-((1-(3-isopropyl-1,2,4-oxadiazol-5-yl)piperidin-4-yl)methoxy)phenyl)cyclohex-3-enyl)methanone;

(286) (4-(4-((1-(3-isopropyl-1,2,4-oxadiazol-5-yl)piperidin-4-yl)methoxy)phenyl)cyclohex-3-enyl)(3-(methoxyimino)azetidin-1-yl)methanone;

(287) (4-(4-((1-(5-ethylpyrimidin-2-yl)piperidin-4-yl)methoxy)phenyl)cyclohex-3-enyl)(3-(methoxyimino)azetidin-1-yl)methanone;

(288) tert-butyl 4-((4-(4-(3-hydroxyazetidine-1-carbonyl)cyclohex-1-enyl)phenoxy)methyl)piperidine-1-carboxylate;

(289) (3-hydroxyazetidin-1-yl)(4-(4-((1-(3-isopropyl-1,2,4-oxadiazol-5-yl)piperidin-4-yl)methoxy)phenyl)cyclohex-3-enyl)methanone;

(290) (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;

(291) (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;

(292) (4-(4-((1-(5-ethylpyrimidin-2-yl)piperidin-4-yl)methoxy)-3-fluorophenyl)cyclohex-3-enyl)(piperidin-1-yl)methanone;

(293) (4-(4-((1-(5-ethylpyrimidin-2-yl)piperidin-4-yl)methoxy)-3-fluorophenyl)cyclohex-3-enyl)(pyrrolidin-1-yl)methanone;

(294) (4-(4-((1-(5-ethylpyrimidin-2-yl)piperidin-4-yl)methoxy)-3-fluorophenyl)cyclohex-3-enyl)(4-hydroxypiperidin-1-yl)methanone;

(295) 1-(4-(4-((1-(5-ethylpyrimidin-2-yl)piperidin-4-yl)methoxy)-3-fluorophenyl)cyclohex-3-enecarbonyl)azetidin-3-one;

(296) (4-(4-((1-(5-ethylpyrimidin-2-yl)piperidin-4-yl)methoxy)-3-fluorophenyl)cyclohex-3-enyl)(4-(2-hydroxyethyl)piperidin-1-yl)methanone;

(297) 1,4'-bipiperidin-1'-yl(4-(4-((1-(5-ethylpyrimidin-2-yl)piperidin-4-yl)methoxy)-3-fluorophenyl)cyclohex-3-enyl)methanone;

(298) (4-(4-((1-(5-ethylpyrimidin-2-yl)piperidin-4-yl)methoxy)-3-fluorophenyl)cyclohex-3-enyl)(4-(pyrrolidin-1-yl)piperidin-1-yl)methanone;

(299) (4-(4-((1-(5-ethylpyrimidin-2-yl)piperidin-4-yl)methoxy)-3-fluorophenyl)cyclohex-3-enyl)(morpholino)methanone;

(300) (4-(4-((1-(5-ethylpyrimidin-2-yl)piperidin-4-yl)methoxy)-3-fluorophenyl)cyclohex-3-enyl)(thiomorpholino)methanone;

(301) azetidin-1-yl(4-(4-((1-(5-ethylpyrimidin-2-yl)piperidin-4-yl)methoxy)-3-fluorophenyl)cyclohex-3-enyl)methanone;

(302) N-cyclopropyl-4-(4-((1-(5-ethylpyrimidin-2-yl)piperidin-4-yl)methoxy)-3-fluorophenyl)cyclohex-3-enecarboxamide;

(303) N-cyclobutyl-4-(4-((1-(5-ethylpyrimidin-2-yl)piperidin-4-yl)methoxy)-3-fluorophenyl)cyclohex-3-enecarboxamide;

(304) N-cyclopentyl-4-(4-((1-(5-ethylpyrimidin-2-yl)piperidin-4-yl)methoxy)-3-fluorophenyl)cyclohex-3-enecarboxamide;

(305) N-cyclohexyl-4-(4-((1-(5-ethylpyrimidin-2-yl)piperidin-4-yl)methoxy)-3-fluorophenyl)cyclohex-3-enecarboxamide;

(306) (4-(4-((1-(5-ethylpyrimidin-2-yl)piperidin-4-yl)methoxy)-3-fluorophenyl)cyclohex-3-enyl)(1,4-dioxa-8-azaspiro[4.5]decan-8-yl)methanone;

(307) 4-(4-((1-(5-ethylpyrimidin-2-yl)piperidin-4-yl)methoxy)-3-fluorophenyl)-N-(2,2,2-trifluoroethyl)cyclohex-3-enecarboxamide;

(308) 1-(4-(4-((1-(5-ethylpyrimidin-2-yl)piperidin-4-yl)methoxy)-3-fluorophenyl)cyclohex-3-enecarbonyl)piperidin-4-one;

(309) (4-(4-((1-(5-ethylpyrimidin-2-yl)piperidin-4-yl)methoxy)-3-fluorophenyl)cyclohex-3-enyl)(3-hydroxyazetidin-1-yl)methanone;

(310) tert-butyl 4-((6-(4-(4-hydroxypiperidine-1-carbonyl)cyclohex-1-enyl)pyridin-3-yloxy)methyl)piperidine-1-carboxylate;

(311) tert-butyl 4-((6-(4-(piperidine-1-carbonyl)cyclohex-1-enyl)pyridin-3-yloxy)methyl)piperidine-1-carboxylate;

(312) tert-butyl 4-((6-(4-(pyrrolidine-1-carbonyl)cyclohex-1-enyl)pyridin-3-yloxy)methyl)piperidine-1-carboxylate;

(313) 4-(4-((1-(5-ethylpyrimidin-2-yl)piperidin-4-yl)methoxy)-3-fluorophenyl)-N-(2-hydroxyethyl)cyclohex-3-enecarboxamide;

(314) N-(2,2-difluoroethyl)-4-(4-((1-(5-ethylpyrimidin-2-yl)piperidin-4-yl)methoxy)-3-fluorophenyl)cyclohex-3-enecarboxamide;

(315) (4-(6-((1-(3-isopropyl-1,2,4-oxadiazol-5-yl)piperidin-4-yl)methoxy)pyridin-3-yl)cyclohex-3-enyl)(pyrrolidin-1-yl)methanone;

(316) (4-(6-((1-(3-isopropyl-1,2,4-oxadiazol-5-yl)piperidin-4-yl)methoxy)pyridin-3-yl)cyclohex-3-enyl)(piperidin-1-yl)methanone;

(317) (4-(6-((1-(3-isopropyl-1,2,4-oxadiazol-5-yl)piperidin-4-yl)methoxy)pyridin-3-yl)cyclohex-3-enyl)(morpholino)methanone;

(318) (4-(6-((1-(3-isopropyl-1,2,4-oxadiazol-5-yl)piperidin-4-yl)methoxy)pyridin-3-yl)cyclohex-3-enyl)(thiomorpholino)methanone;

(319) 1-(4-(6-((1-(3-isopropyl-1,2,4-oxadiazol-5-yl)piperidin-4-yl)methoxy)pyridin-3-yl)cyclohex-3-enecarbonyl)piperidine-4-carbonitrile;

(320) (4-(2-hydroxyethyl)piperidin-1-yl)(4-(6-((1-(3-isopropyl-1,2,4-oxadiazol-5-yl)piperidin-4-yl)methoxy)pyridin-3-yl)cyclohex-3-enyl)methanone;

(321) 1-(4-(4-((1-(5-ethylpyrimidin-2-yl)piperidin-4-yl)methoxy)-3-fluorophenyl)cyclohex-3-enecarbonyl)piperidine-4-carbonitrile;

(322) 4-(4-((1-(5-ethylpyrimidin-2-yl)piperidin-4-yl)methoxy)-3-fluorophenyl)-N-(2-fluoroethyl)cyclohex-3-enecarboxamide;

(323) 4-(4-((1-(5-ethylpyrimidin-2-yl)piperidin-4-yl)methoxy)-3-fluorophenyl)-N,N-bis(2-hydroxyethyl)cyclohex-3-enecarboxamide;

(324) 1-(4-(4-((1-(5-ethylpyrimidin-2-yl)piperidin-4-yl)methoxy)-3-fluorophenyl)cyclohex-3-enecarbonyl)piperidine-4-carboxamide;

(325) tert-butyl 4-((6-(4-(4-(hydroxymethyl)piperidine-1-carbonyl)cyclohex-1-enyl)pyridin-3-yloxy)methyl)piperidine-1-carboxylate;
(326) tert-butyl 4-((6-(4-(4-(2-hydroxyethyl)piperidine-1-carbonyl)cyclohex-1-enyl)pyridin-3-yloxy)methyl)piperidine-1-carboxylate;
(327) tert-butyl 4-((6-(4-(morpholine-4-carbonyl)cyclohex-1-enyl)pyridin-3-yloxy)methyl)piperidine-1-carboxylate;
(328) tert-butyl 4-((6-(4-(thiomorpholine-4-carbonyl)cyclohex-1-enyl)pyridin-3-yloxy)methyl)piperidine-1-carboxylate;
(329) (4-(hydroxymethyl)piperidin-1-yl)(4-(5-((1-(3-isopropyl-1,2,4-oxadiazol-5-yl)piperidin-4-yl)methoxy)pyridin-2-yl)cyclohex-3-enyl)methanone;
(330) azetidin-1-yl(4-(3-fluoro-4-((1-(3-isopropyl-1,2,4-oxadiazol-5-yl)piperidin-4-yl)methoxy)phenyl)cyclohex-3-enyl)methanone;
(331) (4-(3-fluoro-4-((1-(3-isopropyl-1,2,4-oxadiazol-5-yl)piperidin-4-yl)methoxy)phenyl)cyclohex-3-enyl)(pyrrolidin-1-yl)methanone;
(332) (4-(3-fluoro-4-((1-(3-isopropyl-1,2,4-oxadiazol-5-yl)piperidin-4-yl)methoxy)phenyl)cyclohex-3-enyl)(piperidin-1-yl)methanone;
(333) (4-(3-fluoro-4-((1-(3-isopropyl-1,2,4-oxadiazol-5-yl)piperidin-4-yl)methoxy)phenyl)cyclohex-3-enyl)(4-(hydroxymethyl)piperidin-1-yl)methanone;
(334) (4-(3-fluoro-4-((1-(3-isopropyl-1,2,4-oxadiazol-5-yl)piperidin-4-yl)methoxy)phenyl)cyclohex-3-enyl)(3-hydroxyazetidin-1-yl)methanone;
(335) (4-(3-fluoro-4-((1-(3-isopropyl-1,2,4-oxadiazol-5-yl)piperidin-4-yl)methoxy)phenyl)cyclohex-3-enyl)(4-(2-hydroxyethyl)piperidin-1-yl)methanone;
(336) (4-(3-fluoro-4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone;
(337) (3-(hydroxyimino)azetidin-1-yl)(4-(6-((1-(3-isopropyl-1,2,4-oxadiazol-5-yl)piperidin-4-yl)methoxy)pyridin-3-yl)cyclohex-3-enyl)methanone;
(338) 1-(4-(6-((1-(3-isopropyl-1,2,4-oxadiazol-5-yl)piperidin-4-yl)methoxy)pyridin-3-yl)cyclohex-3-enecarbonyl)piperidine-4-carbonitrile;
(339) azetidin-1-yl(4-(6-((1-(3-isopropyl-1,2,4-oxadiazol-5-yl)piperidin-4-yl)methoxy)pyridin-3-yl)cyclohex-3-enyl)methanone;
(340) tert-butyl 4-((6-(4-(4-cyanopiperidine-1-carbonyl)cyclohex-1-enyl)pyridin-3-yloxy)methyl)piperidine-1-carboxylate;
(341) tert-butyl 4-((6-(4-((2-hydroxyethyl)(methyl)carbamoyl)cyclohex-1-enyl)pyridin-3-yloxy)methyl)piperidine-1-carboxylate;
(342) tert-butyl 4-((6-(4-(4-oxopiperidine-1-carbonyl)cyclohex-1-enyl)pyridin-3-yloxy)methyl)piperidine-1-carboxylate;
(343) tert-butyl 4-((6-(4-(4-cyanopiperazine-1-carbonyl)cyclohex-1-enyl)pyridin-3-yloxy)methyl)piperidine-1-carboxylate;
(344) tert-butyl 4-((6-(4-(4-(hydroxyimino)piperidine-1-carbonyl)cyclohex-1-enyl)pyridin-3-yloxy)methyl)piperidine-1-carboxylate;
(345) 1-(4-(3-fluoro-4-((1-(3-isopropyl-1,2,4-oxadiazol-5-yl)piperidin-4-yl)methoxy)phenyl)cyclohex-3-enecarbonyl)piperidin-4-one;
(346) (4-ethylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;
(347) (4-(3-fluoro-4-((1-(3-isopropyl-1,2,4-oxadiazol-5-yl)piperidin-4-yl)methoxy)phenyl)cyclohex-3-enyl)(4-(3-hydroxypropyl)piperazin-1-yl)methanone;
(348) (4-cyclopropylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;
(349) (4-(6-((1-(5-ethylpyrimidin-2-yl)piperidin-4-yl)methoxy)pyridin-3-yl)cyclohex-3-enyl)(pyrrolidin-1-yl)methanone;
(350) (4-(6-((1-(5-ethylpyrimidin-2-yl)piperidin-4-yl)methoxy)pyridin-3-yl)cyclohex-3-enyl)(piperidin-1-yl)methanone;
(351) (4-(6-((1-(5-ethylpyrimidin-2-yl)piperidin-4-yl)methoxy)pyridin-3-yl)cyclohex-3-enyl)(morpholino)methanone;
*466 (352) (4-(6-((1-(5-ethylpyrimidin-2-yl)piperidin-4-yl)methoxy)pyridin-3-yl)cyclohex-3-enyl)(thiomorpholino)methanone;
(353) (4-(6-((1-(5-ethylpyrimidin-2-yl)piperidin-4-yl)methoxy)pyridin-3-yl)cyclohex-3-enyl)(4-hydroxypiperidin-1-yl)methanone;
(354) (4-(6-((1-(5-ethylpyrimidin-2-yl)piperidin-4-yl)methoxy)pyridin-3-yl)cyclohex-3-enyl)(4-(hydroxymethyl)piperidin-1-yl)methanone;
(355) (4-cyclopropylpiperazin-1-yl)(4-(6-((1-(3-isopropyl-1,2,4-oxadiazol-5-yl)piperidin-4-yl)methoxy)pyridin-3-yl)cyclohex-3-enyl)methanone;
(356) 4-(4-((1-(5-bromopyridin-2-yl)piperidin-4-yl)methoxy)phenyl)-N-(2-hydroxyethyl)cyclohex-3-enecarboxamide;
(357) 4-(4-((1-(5-bromopyrimidin-2-yl)piperidin-4-yl)methoxy)phenyl)-N-(2-hydroxyethyl)cyclohex-3-enecarboxamide;
(358) N-(2-hydroxyethyl)-4-(4-((1-(pyridin-2-yl)piperidin-4-yl)methoxy)phenyl)cyclohex-3-enecarboxamide;
(359) 4-(4-((1-(5-ethylpyrimidin-2-yl)piperidin-4-yl)methoxy)-3-fluorophenyl)-N-(2-hydroxyethyl)-N-methylcyclohex-3-enecarboxamide;
(360) N-ethyl-4-(4-((1-(5-ethylpyrimidin-2-yl)piperidin-4-yl)methoxy)-3-fluorophenyl)-N-(2-hydroxyethyl)cyclohex-3-enecarboxamide;
(361) 1-(4-(3-fluoro-4-((1-(3-isopropyl-1,2,4-oxadiazol-5-yl)piperidin-4-yl)methoxy)phenyl)cyclohex-3-enecarbonyl)piperidine-4-carboxamide;
(362) 1,4'-bipiperidin-1'-yl(4-(3-fluoro-4-((1-(3-isopropyl-1,2,4-oxadiazol-5-yl)piperidin-4-yl)methoxy)phenyl)cyclohex-3-enyl)methanone;
(363) N-cyclopropyl-4-(3-fluoro-4-((1-(3-isopropyl-1,2,4-oxadiazol-5-yl)piperidin-4-yl)methoxy)phenyl)cyclohex-3-enecarboxamide;
(364) N-cyclobutyl-4-(3-fluoro-4-((1-(3-isopropyl-1,2,4-oxadiazol-5-yl)piperidin-4-yl)methoxy)phenyl)cyclohex-3-enecarboxamide;
(365) N-cyclopentyl-4-(3-fluoro-4-((1-(3-isopropyl-1,2,4-oxadiazol-5-yl)piperidin-4-yl)methoxy)phenyl)cyclohex-3-enecarboxamide;
(366) N-cyclohexyl-4-(3-fluoro-4-((1-(3-isopropyl-1,2,4-oxadiazol-5-yl)piperidin-4-yl)methoxy)phenyl)cyclohex-3-enecarboxamide;
(367) (4-ethylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;
(368) (4-(3-fluoro-4-((1-(3-isopropyl-1,2,4-oxadiazol-5-yl)piperidin-4-yl)methoxy)phenyl)cyclohex-3-enyl)(4-(3-hydroxypropyl)piperazin-1-yl)methanone;

(369) (4-cyclopropylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;

(370) (4-(3-fluoro-4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone;

(371) 4-(3-fluoro-4-((1-(3-isopropyl-1,2,4-oxadiazol-5-yl)piperidin-4-yl)methoxy)phenyl)-N-(3-hydroxy-2,2-dimethylpropyl)cyclohex-3-enecarboxamide;

(372) 4-(3-fluoro-4-((1-(3-isopropyl-1,2,4-oxadiazol-5-yl)piperidin-4-yl)methoxy)phenyl)-N,N-bis(2-hydroxyethyl)cyclohex-3-enecarboxamide;

(373) azetidin-1-yl(4-(4-((1-(3-isopropyl-1,2,4-oxadiazol-5-yl)piperidin-4-yl)methoxy)-3-(trifluoromethyl)phenyl)cyclohex-3-enyl)methanone;

(374) (4-(4-((1-(3-isopropyl-1,2,4-oxadiazol-5-yl)piperidin-4-yl)methoxy)-3-(trifluoromethyl)phenyl)cyclohex-3-enyl)(pyrrolidin-1-yl)methanone;

(375) (4-(4-((1-(5-ethylpyrimidin-2-yl)piperidin-4-yl)methoxy)-3-(trifluoromethyl)phenyl)cyclohex-3-enyl)(piperidin-1-yl)methanone;

(376) 4-(4-((1-(5-ethylpyrimidin-2-yl)piperidin-4-yl)methoxy)-3-fluorophenyl)-N-(3-hydroxypropyl)-N-methylcyclohex-3-enecarboxamide;

(377) (4-(4-((1-(5-ethylpyrimidin-2-yl)piperidin-4-yl)methoxy)-3-fluorophenyl)cyclohex-3-enyl)(4-(hydroxyimino)piperidin-1-yl)methanone;

(378) 4-(4-((1-(5-ethylpyrimidin-2-yl)piperidin-4-yl)methoxy)-3-fluorophenyl)-N-(3-hydroxy-2,2-dimethylpropyl)cyclohex-3-enecarboxamide;

(379) (4-(4-((1-(5-ethylpyrimidin-2-yl)piperidin-4-yl)methoxy)-3-fluorophenyl)cyclohex-3-enyl)(4-methylpiperazin-1-yl)methanone;

(380) (4-(4-((1-(5-ethylpyrimidin-2-yl)piperidin-4-yl)methoxy)phenyl)cyclohex-3-enyl)(4-(3-hydroxypropyl)piperazin-1-yl)methanone;

(381) (4-(3-fluoro-4-((1-(3-isopropyl-1,2,4-oxadiazol-5-yl)piperidin-4-yl)methoxy)phenyl)cyclohex-3-enyl)(piperazin-1-yl)methanone;

(382) (4-(3-fluoro-4-((1-(3-isopropyl-1,2,4-oxadiazol-5-yl)piperidin-4-yl)methoxy)phenyl)cyclohex-3-enyl)(4-methylpiperazin-1-yl)methanone;

(383) tert-butyl 4-(4-(4-((1-(5-ethylpyrimidin-2-yl)piperidin-4-yl)methoxy)-3-fluorophenyl)cyclohex-3-enecarbonyl)piperazine-1-carboxylate;

(384) (4-(4-((1-(5-ethylpyrimidin-2-yl)piperidin-4-yl)methoxy)-3-fluorophenyl)cyclohex-3-enyl)(4-methylpiperazin-1-yl)methanone;

(385) 2-((1-(5-ethylpyrimidin-2-yl)piperidin-4-yl)methoxy)-5-(4-(piperidine-1-carbonyl)cyclohex-1-enyl)benzonitrile;

(386) 2-((1-(5-ethylpyrimidin-2-yl)piperidin-4-yl)methoxy)-5-(4-(pyrrolidine-1-carbonyl)cyclohex-1-enyl)benzonitrile;

(387) 5-(4-(azetidine-1-carbonyl)cyclohex-1-enyl)-2-((1-(5-ethylpyrimidin-2-yl)piperidin-4-yl)methoxy)benzonitrile;

(388) 2-((1-(5-ethylpyrimidin-2-yl)piperidin-4-yl)methoxy)-5-(4-(morpholine-4-carbonyl)cyclohex-1-enyl)benzonitrile;

(389) 2-((1-(5-ethylpyrimidin-2-yl)piperidin-4-yl)methoxy)-5-(4-(thiomorpholine-4-carbonyl)cyclohex-1-enyl)benzonitrile;

(390) 2-((1-(5-ethylpyrimidin-2-yl)piperidin-4-yl)methoxy)-5-(4-(4-hydroxypiperidine-1-carbonyl)cyclohex-1-enyl)benzonitrile;

(391) 2-((1-(5-ethylpyrimidin-2-yl)piperidin-4-yl)methoxy)-5-(4-(4-(hydroxymethyl)piperidine-1-carbonyl)cyclohex-1-enyl)benzonitrile;

(392) tert-butyl 4-((2-fluoro-4-(4-(pyrrolidine-1-carbonyl)cyclohex-1-enyl)phenoxy)methyl)piperidine-1-carboxylate;

(393) (4-(3-amino-4-((1-(5-ethylpyrimidin-2-yl)piperidin-4-yl)methoxy)phenyl)cyclohex-3-enyl)(pyrrolidin-1-yl)methanone;

(394) 2-((1-(5-ethylpyrimidin-2-yl)piperidin-4-yl)methoxy)-5-(4-(4-(2-hydroxyethyl)piperidine-1-carbonyl)cyclohex-1-enyl)benzonitrile;

(395) (4-cyclopropylpiperazin-1-yl)(4-((4-((1-(5-ethylpyrimidin-2-yl)piperidin-4-yl)methoxy)phenyl)cyclohex-3-enyl)methanone;

(396) (4-(4-((1-(5-ethylpyrimidin-2-yl)piperidin-4-yl)methoxy)-3-(trifluoromethyl)phenyl)cyclohex-3-enyl)(4-hydroxypiperidin-1-yl)methanone;

(397) (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone;

(398) 1-(4-(4-((1-(5-ethylpyrimidin-2-yl)piperidin-4-yl)methoxy)-3-(trifluoromethyl)phenyl)cyclohex-3-enecarbonyl)piperidine-4-carbonitrile;

(399) 1-(4-(4-((1-(5-ethylpyrimidin-2-yl)piperidin-4-yl)methoxy)-3-(trifluoromethyl)phenyl)cyclohex-3-enecarbonyl)piperidine-4-carboxamide;

(400) (4-(4-((1-(5-ethylpyrimidin-2-yl)piperidin-4-yl)methoxy)-3-(trifluoromethyl)phenyl)cyclohex-3-enyl)(morpholino)methanone;

(401) isopropyl 4-((2-fluoro-4-(4-(pyrrolidine-1-carbonyl)cyclohex-1-enyl)phenoxy)methyl)piperidine-1-carboxylate;

(402) trichloromethyl 4-((2-fluoro-4-(4-(pyrrolidine-1-carbonyl)cyclohex-1-enyl)phenoxy)methyl)piperidine-1-carboxylate;

(403) phenyl 4-((2-fluoro-4-(4-(pyrrolidine-1-carbonyl)cyclohex-1-enyl)phenoxy)methyl)piperidine-1-carboxylate;

(404) 4-nitrophenyl 4-((2-fluoro-4-(4-(pyrrolidine-1-carbonyl)cyclohex-1-enyl)phenoxy)methyl)piperidine-1-carboxylate;

(405) 1,1,1,3,3,3-hexafluoropropan-2-yl 4-((2-fluoro-4-(4-(pyrrolidine-1-carbonyl)cyclohex-1-enyl)phenoxy)methyl)piperidine-1-carboxylate;

(406) 1,1,1-trifluoropropan-2-yl 4-((2-fluoro-4-(4-(pyrrolidine-1-carbonyl)cyclohex-1-enyl)phenoxy)methyl)piperidine-1-carboxylate;

(407) 1,3-difluoropropan-2-yl 4-((2-fluoro-4-(4-(pyrrolidine-1-carbonyl)cyclohex-1-enyl)phenoxy)methyl)piperidine-1-carboxylate;

(408) 1-methylcyclopropyl 14-((2-fluoro-4-(4-(pyrrolidine-1-carbonyl)cyclohex-1-enyl)phenoxy)methyl)piperidine-1-carboxylate;

(409) (4-(3-fluoro-4-((1-(1-(trifluoromethyl)cyclopentanecarbonyl)piperidin-4-yl)methoxy)phenyl)cyclohex-3-enyl)(pyrrolidin-1-yl)methanone;

(410) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;

(411) (4-(3-fluoro-4-((1-(3-isopropyl-1,2,4-oxadiazol-5-yl)piperidin-4-yl)methoxy)phenyl)cyclohex-3-enyl)(4-(hydroxyimino)piperidin-1-yl)methanone;

(412) 4-(4-(4-((1-(5-ethylpyrimidin-2-yl)piperidin-4-yl)methoxy)phenyl)cyclohex-3-enecarbonyl)-N-propylpiperazine-1-carboxamide;

(413) 4-(4-(4-((1-(5-ethylpyrimidin-2-yl)piperidin-4-yl)methoxy)phenyl)cyclohex-3-enecarbonyl)-N-isopropylpiperazine-1-carboxamide;

(414) 1-(4-(4-(4-((1-(5-ethylpyrimidin-2-yl)piperidin-4-yl)methoxy)phenyl)cyclohex-3-enecarbonyl)piperazin-1-yl)-3-methylbut-2-en-1-one;

(415) (4-(4-((1-(5-ethylpyrimidin-2-yl)piperidin-4-yl)methoxy)-3-methylphenyl)cyclohex-3-enyl)(piperidin-1-yl)methanone;

(416) (4-(4-((1-(5-ethylpyrimidin-2-yl)piperidin-4-yl)methoxy)-3-methylphenyl)cyclohex-3-enyl)(pyrrolidin-1-yl)methanone;

(417) (4-(4-((1-(5-ethylpyrimidin-2-yl)piperidin-4-yl)methoxy)-3-methylphenyl)cyclohex-3-enyl)(morpholino)methanone;

(418) (4-(4-((1-(5-ethylpyrimidin-2-yl)piperidin-4-yl)methoxy)-3-methylphenyl)cyclohex-3-enyl)(thiomorpholino)methanone;

(419) (4-(3-fluoro-4-((1-(2-fluoro-2-methylpropyl)piperidin-4-yl)methoxy)phenyl)cyclohex-3-enyl)(pyrrolidin-1-yl)methanone;

(420) (4-(3-fluoro-4-((1-(1-methyl-1H-tetrazol-5-yl)piperidin-4-yl)methoxy)phenyl)cyclohex-3-enyl)(pyrrolidin-1-yl)methanone;

(421) (4-(3-fluoro-4-((1-(1-(trifluoromethyl)cyclopropanecarbonyl)piperidin-4-yl)methoxy)phenyl)cyclohex-3-enyl)(pyrrolidin-1-yl)methanone;

(422) (4-(4-((1-(5-ethylpyrimidin-2-yl)piperidin-4-yl)methoxy)-2-fluorophenyl)cyclohex-3-enyl)(morpholino)methanone;

(423) (4-(4-((1-(5-ethylpyrimidin-2-yl)piperidin-4-yl)methoxy)-2-fluorophenyl)cyclohex-3-enyl)(thiomorpholino)methanone;

(424) 1-(4-(4-((1-(5-ethylpyrimidin-2-yl)piperidin-4-yl)methoxy)-2-fluorophenyl)cyclohex-3-enecarbonyl)piperidine-4-carbonitrile;

(425) azetidin-1-yl(4-(4-((1-(5-ethylpyrimidin-2-yl)piperidin-4-yl)methoxy)-2-fluorophenyl)cyclohex-3-enyl)methanone;

(426) (4-(4-((1-(5-ethylpyrimidin-2-yl)piperidin-4-yl)methoxy)-2-fluorophenyl)cyclohex-3-enyl)(piperidin-1-yl)methanone;

(427) (4-(4-((1-(5-ethylpyrimidin-2-yl)piperidin-4-yl)methoxy)-2-fluorophenyl)cyclohex-3-enyl)((R)-2-(hydroxymethyl)pyrrolidin-1-yl)methanone;

(428) (4-(4-((1-(5-ethylpyrimidin-2-yl)piperidin-4-yl)methoxy)-3-fluorophenyl)cyclohex-3-enyl)(4-methylpiperazin-1-yl)methanone;

(429) (−)-(4-(4-((1-(5-ethylpyrimidin-2-yl)piperidin-4-yl)methoxy)-3-fluorophenyl)cyclohex-3-enyl)(pyrrolidin-1-yl)methanone;

(430) (−)-(4-(4-((1-(5-ethylpyrimidin-2-yl)piperidin-4-yl)methoxy)-3-fluorophenyl)cyclohex-3-enyl)(4-(2-hydroxyethyl)piperidin-1-yl)methanone;

(431) (4-(4-((1-(5-ethylpyrimidin-2-yl)piperidin-4-yl)methoxy)-2-fluorophenyl)cyclohex-3-enyl)(4-hydroxypiperidin-1-yl)methanone;

(432) (4-(4-((1-(5-ethylpyrimidin-2-yl)piperidin-4-yl)methoxy)-2-fluorophenyl)cyclohex-3-enyl)(4-(hydroxymethyl)piperidin-1-yl)methanone;

(433) (4-(4-((1-(5-ethylpyrimidin-2-yl)piperidin-4-yl)methoxy)-2-fluorophenyl)cyclohex-3-enyl)(4-hydroxypiperidin-1-yl)methanone;

(434) (4-(4-((1-(5-ethylpyrimidin-2-yl)piperidin-4-yl)methoxy)-3-fluorophenyl)cyclohex-3-enyl)(piperazin-1-yl)methanone;

*549 (435) (4-(3-fluoro-4-((1-(3-(trifluoromethyl)-1,2,4-oxadiazol-5-yl)piperidin-4-yl)methoxy)phenyl)cyclohex-3-enyl)(pyrrolidin-1-yl)methanone;

(436) 2,2-difluoro-1-(4-((2-fluoro-4-(4-(pyrrolidine-1-carbonyl)cyclohex-1-enyl)phenoxy)methyl)piperidin-1-yl)butan-1-one;

(437) 4-(4-((1-(5-ethylpyrimidin-2-yl)piperidin-4-yl)methoxy)-2-fluorophenyl)-N,N-bis(2-hydroxyethyl)cyclohex-3-enecarboxamide;

(438) N-ethyl-4-(4-((1-(5-ethylpyrimidin-2-yl)piperidin-4-yl)methoxy)-2-fluorophenyl)-N-(2-hydroxyethyl)cyclohex-3-enecarboxamide;

(439) 2,2-difluoro-1-(4-((2-fluoro-4-(4-(morpholine-4-carbonyl)cyclohex-1-enyl)phenoxy)methyl)piperidin-1-yl)butan-1-one;

(440) 1,1,1-trifluoropropan-2-yl 4-((2-fluoro-4-(4-(morpholine-4-carbonyl)cyclohex-1-enyl)phenoxy)methyl)piperidine-1-carboxylate;

(441) (−)-4-(4-((1-(5-ethylpyrimidin-2-yl)piperidin-4-yl)methoxy)-3-fluorophenyl)-N-(2-hydroxyethyl)cyclohex-3-enecarboxamide;

(442) (+)-tert-butyl 4-((2-fluoro-4-(4-(morpholine-4-carbonyl)cyclohex-1-enyl)phenoxy)methyl)piperidine-1-carboxylate;

(443) (−)-tert-butyl 4-((2-fluoro-4-(4-(morpholine-4-carbonyl)cyclohex-1-enyl)phenoxy)methyl)piperidine-1-carboxylate;

(444) isopropyl 4-((2-fluoro-4-(4-(morpholine-4-carbonyl)cyclohex-1-enyl)phenoxy)methyl)piperidine-1-carboxylate;

(445) phenyl 4-((2-fluoro-4-(4-(morpholine-4-carbonyl)cyclohex-1-enyl)phenoxy)methyl)piperidine-1-carboxylate;

(446) 1,1,1,3,3,3-hexafluoropropan-2-yl 4-((2-fluoro-4-(4-(morpholine-4-carbonyl)cyclohex-1-enyl)phenoxy)methyl)piperidine-1-carboxylate;

(447) 1,3-difluoropropan-2-yl 14-((2-fluoro-4-(4-(morpholine-4-carbonyl)cyclohex-1-enyl)phenoxy)methyl)piperidine-1-carboxy late;

(448) (4-(2-fluoro-4-((1-(3-isopropyl-1,2,4-oxadiazol-5-yl)piperidin-4-yl)methoxy)phenyl)cyclohex-3-enyl)(morpholino)methanone;

(449) (4-(2-fluoro-4-((1-(3-isopropyl-1,2,4-oxadiazol-5-yl)piperidin-4-yl)methoxy)phenyl)cyclohex-3-enyl)(thiomorpholino)methanone;

(450) (4-(3-fluoro-4-((1-(1-(trifluoromethyl)cyclopentanecarbonyl)piperidin-4-yl)methoxy)phenyl)cyclohex-3-enyl)(morpholino)methanone;

(451) 1-(4-((2-fluoro-4-(4-(morpholine-4-carbonyl)cyclohex-1-enyl)phenoxy)methyl)piperidin-1-yl)-3-methylbut-2-en-1-one;

(452) (4-(4-((1-(5-ethylpyrimidin-2-yl)piperidin-4-yl)methoxy)-2-fluorophenyl)cyclohex-3-enyl)(4-(trifluoromethyl)piperidin-1-yl)methanone;

(453) (4,4-difluoropiperidin-1-yl)(4-(4-((1-(5-ethylpyrimidin-2-yl)piperidin-4-yl)methoxy)-2-fluorophenyl)cyclohex-3-enyl)methanone;

(454) (3,3-difluoropyrrolidin-1-yl)(4-(4-((1-(5-ethylpyrimidin-2-yl)piperidin-4-yl)methoxy)-2-fluorophenyl)cyclohex-3-enyl)methanone;

(455) (4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone;

(456) (4-(4-((1-(5-ethylpyrimidin-2-yl)piperidin-4-yl)methoxy)-3-fluorophenyl)cyclohex-3-enyl)(4-(trifluoromethyl)piperidin-1-yl)methanone;

(457) (4,4-difluoropiperidin-1-yl)(4-(4-((1-(5-ethylpyrimidin-2-yl)piperidin-4-yl)methoxy)-3-fluorophenyl)cyclohex-3-enyl)methanone;
(458) ((−)-4-(4-((1-(5-ethylpyrimidin-2-yl)piperidin-4-yl)methoxy)phenyl)cyclohex-3-enyl)((S)-3-fluoropyrrolidin-1-yl)methanone;
(459) (3,3-difluoropyrrolidin-1-yl)(4-(4-((1-(5-ethylpyrimidin-2-yl)piperidin-4-yl)methoxy)-3-fluorophenyl)cyclohex-3-enyl)methanone;
(460) (4-(4-((1-(5-ethylpyrimidin-2-yl)piperidin-4-yl)methoxy)-3-fluorophenyl)cyclohex-3-enyl)(3,3,4,4-tetrafluoropyrrolidin-1-yl)methanone;
(461) (−)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone;
(462) (+)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone;
(463) (−)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone;
(464) (+)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone;
(465) ((−)-4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone; and
(466) ((+)-4-(4-(((1-(5-ethylpyrimidin-2-yl)piperidin-4-yl)methoxy)phenyl)cyclohex-3-enyl)((S)-2-(hydroxymethyl)pyrrolidin-1-yl)methanone.

The compound represented by Formula 1 according to the present invention may be used in the form of a pharmaceutically acceptable salt, and an acid addition salt formed by a pharmaceutically acceptable free acid is useful as the salt. The acid addition salt may be obtained from inorganic acids such as hydrochloric acid, nitric acid, phosphoric acid, sulfuric acid, hydrobromic acid, hydriodic acid, nitrous acid, or phosphorous acid, non-toxic organic acids such as aliphatic mono- and di-carboxylates, phenyl-substituted alkanoates, hydroxy alkanoates, and alkandioates, aromatic acids, aliphatic and aromatic sulfonic acids, and organic acids such as acetic acid, benzoic acid, citric acid, lactic acid, maleic acid, gluconic acid, methanesulfonic acid, 4-toluenesulfonic acid, tartaric acid, and fumaric acid. Such a pharmaceutically innocuous salt includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 3-hydroxybutyrate, glycolate, malate, tartrate, methanesulfonate, propanesulfonate, naphthalene-1-sulfonate, naphthalene-2-sulfonate, or mandelate.

The acid addition salt according to the present invention may be prepared using a conventional method, for example, prepared by dissolving the compound represented by Formula 1 in an organic solvent, for example, methanol, ethanol, acetone, methylenechloride, acetonitrile, etc., adding an organic or inorganic acid and filtering and drying the resulting precipitate, or by distilling a solvent and an excessive amount of an acid under reduced pressure and drying the resulting distillate, or prepared under an organic solvent.

In addition to the compound represented by Formula 1 and the pharmaceutically acceptable salt thereof, the present invention also encompasses all types of solvates, hydrates, optical isomers and the like which may be prepared from the compound of Formula 1 and the pharmaceutically acceptable salt thereof.

In this specification, the term "isomer" is used as a meaning encompassing stereoisomers generally used without limitation, as apparent to those skilled in the related art. The stereoisomers generally refer to isomers formed as the spatial positioning of atoms in a molecule differs, and may include enantiomers and diastereomers, but the present invention is not limited thereto. Definitions of the enantiomers and the diastereomers are apparent to those skilled in the related art. The enantiomers refer to isomers that are non-superimposable mirror images of each other like the relationship between right and left hands, and thus are referred to as optical isomers. The diastereomers generally refer to stereoisomers which are not mirror images of each other, and thus may be classified into diastereomers in which the spatial positioning of constituent atoms differs, and cis-trans isomers formed as the spatial positioning of atoms differs due to the restricted rotation of carbon-carbon bonds in cycloalkane and alkene compounds.

According to one exemplary embodiment of the present invention, the compounds (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone and (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone disclosed in Examples 290 and 291 of the present invention; the compounds (+)-tert-butyl 4-((2-fluoro-4-(4-(morpholine-4-carbonyl)cyclohex-1-enyl)phenoxy)methyl)piperidine-1-carboxylate and (−)-tert-butyl 4-((2-fluoro-4-(4-(morpholine-4-carbonyl)cyclohex-1-enyl)phenoxy)methyl)piperidine-1-carboxylate disclosed in Examples 442 and 443; the compounds (−)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone and (462) (+)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone disclosed in Examples 461 and 462; the compounds (−)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone and (+)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone disclosed in Examples 463 and 464; and the compounds ((−)-4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone and ((+)-4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone disclosed in Examples 465 and 466 are diastereomers of each other.

In addition, as shown in the following Scheme 1, the present invention provides a method for preparing the compound represented by Formula 1, which includes:

reacting a compound represented by Formula 2 with a compound represented by Formula 3 to prepare a compound represented by Formula 4 (Step 1);

reacting the compound represented by Formula 4 prepared in Step 1 with a compound represented by Formula 5 to prepare a compound represented by Formula 6 (Step 2);

reacting the compound represented by Formula 6 prepared in Step 2 with a base to prepare a compound represented by Formula 7 (Step 3); and reacting the compound represented by Formula 7 prepared in Step 3 with a compound represented by Formula 8 to obtain the compound represented by Formula 1 (Step 4).

Hereinafter, respective steps of the method for preparing the compound represented by Formula 1 according to the present invention will be described in detail.

In the method for preparing the compound represented by Formula 1 according to the present invention, Step 1 includes performing a coupling reaction between a compound represented by Formula 2 and a compound represented by Formula 3 to obtain a compound represented by Formula 4.

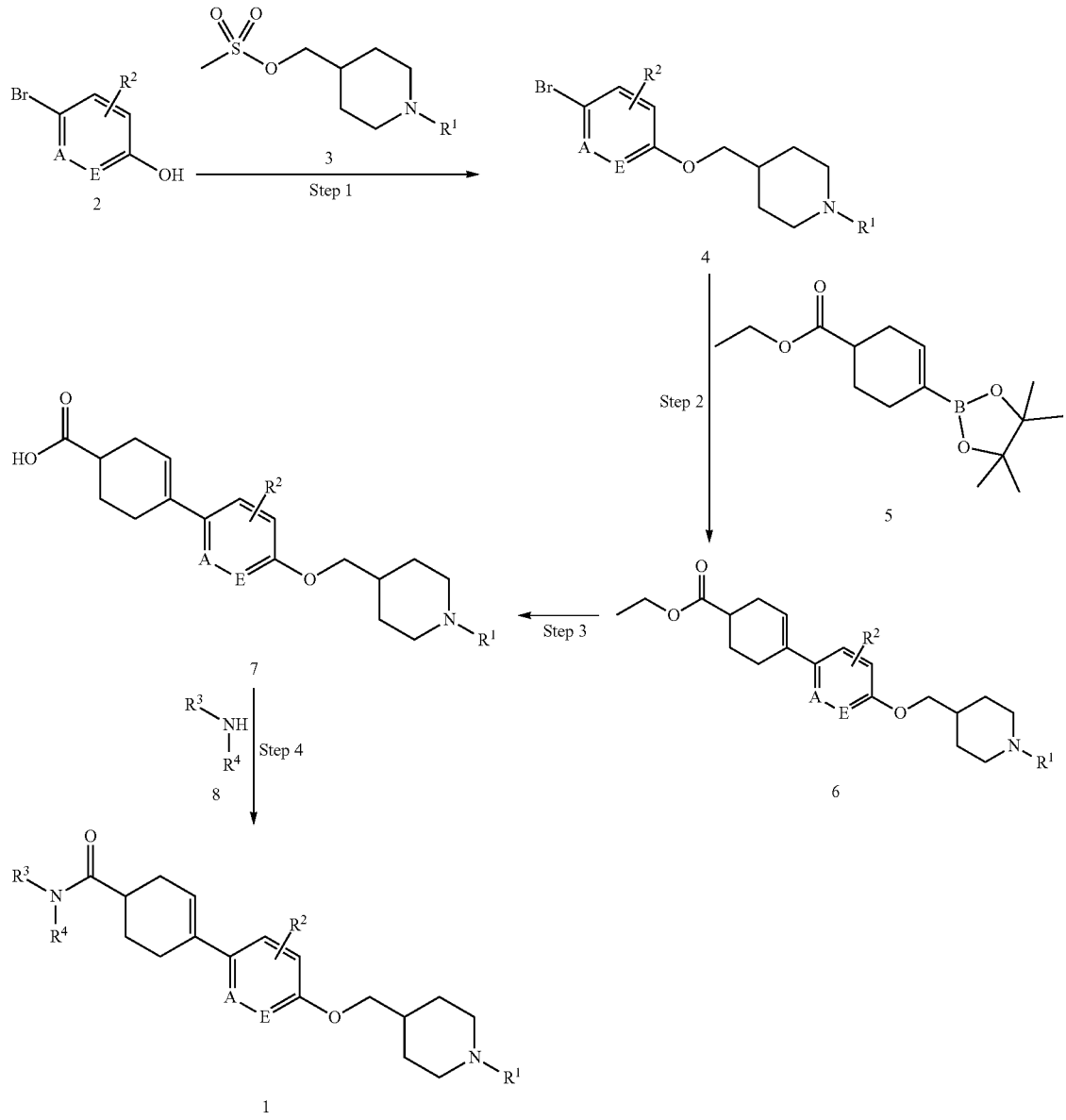

[Scheme 1]

In Scheme 1, $R^1$, $R^2$, $R^3$, $R^4$, A, and E are as defined in Formula 1.

According to one exemplary embodiment of the present invention, the compound of Formula 5 is a compound having a chiral center. In this case, any stereoselectivity in (+) and (−) directions from the corresponding chiral center may be introduced. The introduction of the corresponding stereoselectivity causes formation of a compound having the corresponding stereoselectivity as the compound of Formula 1 that is a final product.

In this case, dimethylformamide (DMF), tetrahydrofuran (THF), dichloromethane (DCM), toluene, acetonitrile, and the like may be used as the reaction solvent. Preferably, dimethylformamide (DMF) may be used. Also, cesium carbonate ($Cs_2CO_3$), potassium hydroxide (KOH), sodium hydroxide (NaOH), lithium hydroxide (LiOH), and the like may be used as the base. Preferably, cesium carbonate ($Cs_2CO_3$) may be used. In addition, the reaction is preferably carried out at a reaction temperature ranging from 0° C. to a boiling point of a solvent, and the reaction time is not particularly limited, but the reaction is preferably carried out for 0.5 to 10 hours.

In the method for preparing the compound represented by Formula 1 according to the present invention, Step 2 includes reacting the compound represented by Formula 4 prepared in Step 1 with a compound represented by Formula 5 in the presence of a base to obtain a compound represented by Formula 6. More specifically, Step 2 includes performing a Suzuki coupling reaction between the compound represented by Formula 4 prepared in Step 1 and a boronate compound represented by Formula 5 to obtain a compound represented by Formula 6. As described above, the compound of Formula 5 is a compound having a chiral center. In this case, any stereoselectivity in (+) and (−) directions from the corresponding chiral center may be introduced.

In this case, at least one organic solvent selected from the group consisting of dioxane, ethanol, tetrahydrofuran (THF), diethylether, diphenylether, diisopropylether (DIPE), dimethylformamide (DMF), dimethylacetamide (DMA), dimethyl sulfoxide (DMSO), dichloromethane (DCM), chlorobenzene, toluene, and benzene may be mixed with water to form a solvent mixture, which may be used as the reaction solvent. Also, cesium carbonate ($Cs_2CO_3$), potassium hydroxide (KOH), sodium hydroxide (NaOH), lithium hydroxide (LiOH), and the like may be used as the base. Preferably, cesium carbonate ($Cs_2CO_3$) may be used. In addition, the reaction is preferably carried out at a reaction temperature ranging from 0° C. to a boiling point of the solvent, and a reaction time is not particularly limited, but the reaction is preferably carried out for 0.5 to 10 hours.

In the method for preparing the compound represented by Formula 1 according to the present invention, Step 3 includes reacting the compound represented by Formula 6 prepared in Step 2 with a base to prepare a compound represented by Formula 7.

In this case, at least one organic solvent selected from the group consisting of dioxane, ethanol, tetrahydrofuran (THF), diethylether, diphenylether, diisopropylether (DIPE), dimethylformamide (DMF), dimethylacetamide (DMA), dimethyl sulfoxide (DMSO), dichloromethane (DCM), chlorobenzene, toluene, and benzene may be mixed with water to form a solvent mixture, which may be used as the reaction solvent. Also, cesium carbonate ($Cs_2CO_3$), potassium hydroxide (KOH), sodium hydroxide (NaOH), lithium hydroxide (LiOH), and the like may be used as the base. Preferably, lithium hydroxide (LiOH) may be used. In addition, the reaction is preferably carried out at a reaction temperature ranging from 0° C. to a boiling point of the solvent, and the reaction time is not particularly limited, but the reaction is preferably carried out for 0.5 to 10 hours.

In the method for preparing the compound represented by Formula 1 according to the present invention, Step 4 includes reacting the compound represented by Formula 7 prepared in Step 3 with a compound represented by Formula 8 to obtain the compound represented by Formula 1.

In this case, at least one organic solvent selected from the group consisting of dioxane, ethanol, tetrahydrofuran (THF), diethylether, diphenylether, diisopropylether (DIPE), dimethylformamide (DMF), dimethylacetamide (DMA), dimethyl sulfoxide (DMSO), dichloromethane (DCM), chlorobenzene, toluene, and benzene may be mixed with water to form a solvent mixture, which may be used as the reaction solvent. Also, the reaction is preferably carried out at a reaction temperature ranging from 0° C. to a boiling point of the solvent, and the reaction time is not particularly limited, but the reaction is preferably carried out for 0.5 to 10 hours.

Also, as shown in the following Scheme 2, the present invention provides a method for preparing the compound of (−)-4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone or (+)-4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone, which includes:

preparing (−)-4-bromocyclohex-3-enecarboxylic acid of the intermediate compound 4 or (+)-4-bromocyclohex-3-enecarboxylic acid of the intermediate compound 5 from (±)HBA (Step 1);

preparing ((−)-4-bromocyclohex-3-enyl)((R)-2-(hydroxymethyl)pyrrolidin-1-yl)methanone of the intermediate compound 6 or ((+)-4-bromocyclohex-3-enyl)((R)-2-(hydroxymethyl)pyrrolidin-1-yl)methanone of the intermediate compound 7 from the intermediate compound 4 or 5 prepared in Step 1 (Step 2); and reacting the intermediate compound 6 or 7 prepared in Step 2 with 5-ethyl-2-(4-((4-(4,4,5,5-tetramethyl-1,3,2-dioxaborolan-2-yl)phenoxy)methyl)piperidin-1-yl)pyrimidine of the intermediate compound 3 (Step 3).

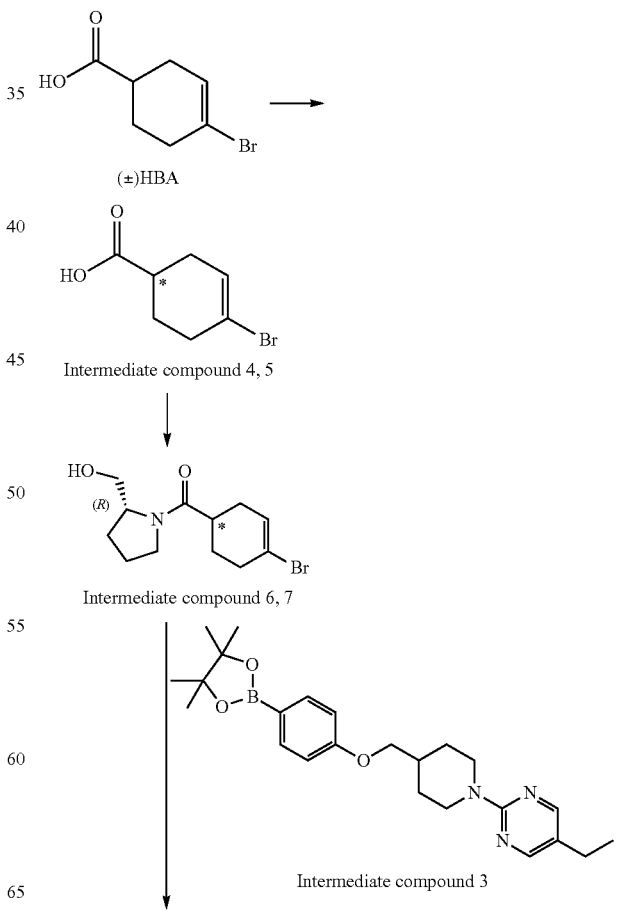

-continued

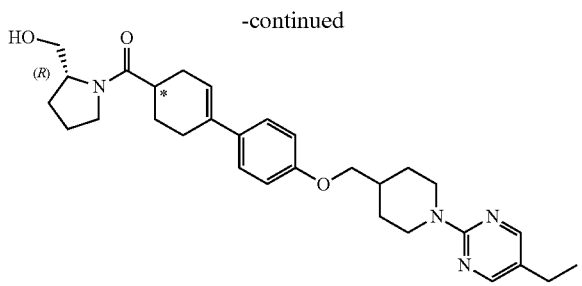

Example 290, Example 291

Example 290, Example 291

In the chemical formula, the symbol "*" represents a chiral center.

Also, the present invention provides a pharmaceutical composition for preventing or treating metabolic diseases, which includes the compound represented by Formula 1 or the optical isomer or pharmaceutically acceptable salt thereof as an active ingredient.

The pharmaceutical composition according to the present invention activates G protein-coupled receptor 119 (GPR-119) to enhance the intracellular activity of cyclic adenosine monophosphate (cAMP), and induces the release of glucagon-like peptide-1 (GLP-1) that is a neuroendocrine protein. In this case, the GPR-119 is a G-protein-coupled receptor (GPCR) mainly expressed in insulin-secreting cells of the pancreas. Thus, a GPR-119 expression profile has potential usefulness in treating various metabolic diseases including obesity and diabetes.

Further, the present invention provides a GPR-119 activator including the compound represented by Formula 1 or the optical isomer or pharmaceutically acceptable salt thereof as an active ingredient.

In this regard, an experiment is performed to evaluate a level of cAMP activation in response to stimulation of the GPR-119 receptor by the compound according to the present invention. As a result, it is confirmed that almost all the example compounds according to the present invention activate cAMP by 50% ($EC_{50}$) when present at a low concentration of 200 nM or less, indicating that the example compounds has an excellent effect of activation (see Table 2 for Experimental Example 1).

Also, an oral glucose tolerance test (OGTT) is performed on the compound according to the present invention. As a result, it is revealed that all the example compounds according to the present invention have a superior hypoglycemic effect, compared to GPR-119 activators (Comparative Examples 1 and 2) known in the prior art, and thus have a remarkably effective effect of activating GPR-119 in vivo (see Table 3 for Experimental Example 2).

In addition, an experiment is performed to simultaneously evaluate the weight-loss and hypoglycemic effects of the compound represented by Formula 1 according to the present invention or the optical isomer or pharmaceutically acceptable salt thereof. As a result, it is confirmed that the compound according to the present invention has a steady weight-loss effect for a 4-week period of oral administration (see FIG. 1 for Experimental Example 3). At the end of the 4-week administration, the compound according to the present invention is administered, and 2 g/kg of glucose is orally administered after 30 minutes so as to evaluate a hypoglycemic effect. As a result, it is revealed that the compound according to the present invention exhibits a remarkably excellent hypoglycemic effect (see FIG. 2 for Experimental Example 3). Accordingly, it can be seen that the compound according to the present invention simultaneously exhibits the weight-loss and hypoglycemic effects during the period of administration.

Additionally, an experiment is performed to evaluate an ability of the compound according to the present invention to induce secretion of GLP-1. As a result, it is revealed that the compound according to the present invention has an excellent effect of inducing the GLP-1 secretion (see FIG. 3 for Experimental Example 4).

Further, an acute toxicity test is performed on the compound according to the present invention in rats with cataract (Ihara's cataract rats; ICRs). As a result, it can be seen that the compound of the present invention has an $LD_{50}$ value of 2 g/kg or more in female ICR rats, indicating that the compound exhibits very low toxicity (see Experimental Example 5).

Therefore, the cyclohexene derivative according to the present invention, or the optical isomer or pharmaceutically acceptable salt thereof has a very excellent effect of activating cAMP as a GPR-119 activator, and also simultaneously exhibits the weight-loss and hypoglycemic effects, and thus may be useful for a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

For clinical administration, the compound represented by Formula 1 according to the present invention may be administered in the form of various oral and parenteral formulations. When the compound is prepared into formulations, the formulations are prepared using a filler, an extender, a binder, a wetting agent, a disintegrating agent, a diluent or vehicle (e.g., a surfactant), etc.

Solid formulations for oral administration include tablets, pills, powders, granules, capsules, troche, and the like. In this case, the solid formulations are prepared by mixing one or more of the compounds of the present invention with one or more vehicles such as starch, calcium carbonate, sucrose, lactose, gelatin, etc. In addition to simple vehicles, lubricants such as magnesium stearate and talc may also be used herein. Liquid formulations for oral administration include suspensions, solutions for internal use, emulsions, or syrups. In addition to simple diluents generally used herein, for example, water and liquid paraffin, the liquid formulations may include various vehicles, for example, wetting agents, sweetening agents, aromatics, preservatives, etc.

Preparations for parenteral administration include sterile aqueous solutions, non-aqueous solvents, suspensions, emulsions, lyophilized formulations, suppositories, etc. Propylene glycol, polyethylene glycol, vegetable oils such as olive oil, injectable esters such as ethylolate, and the like may be used as the non-aqueous solvents and suspensions. Witepsol, macrogol, Tween 61, cacao butter, laurin butter, glycerol, gelatin, and the like may be used as base materials for suppositories.

Also, the effective dose of the compound according to the present invention administered into the human body may vary according to the age, weight and sex of a patient, a mode of administration, the general physical conditions, and the severity of a disease. In general, the daily dose of the compound is in a range of approximately 0.001 to 100 mg/kg, preferably in a range of 0.01 to 35 mg/kg. In the case of an adult patient weighing 70 kg, the dose of the compound according to the present invention is generally in a range of 0.07 to 7,000 mg/day, preferably in a range of 0.7 to 2,500 mg/day, and may also administered once a day or multiple times in divided doses at certain intervals by a medical judgment of a general physician or pharmacist.

Further, the present invention provides a health functional food for preventing or improving metabolic diseases, which includes the compound represented by Formula 1 or the optical isomer or pharmaceutically acceptable salt thereof as an active ingredient.

Also, the present invention provides a compound (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone, or a pharmaceutically acceptable salt thereof.

In addition, the present invention provides a compound (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone, or a pharmaceutically acceptable salt thereof.

Additionally, the present invention provides a pharmaceutical composition for preventing or treating metabolic diseases, which includes, as an active ingredient, the compound (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone or (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone, or the pharmaceutically acceptable salt thereof.

According to one exemplary embodiment of the present invention, the compounds may activate GPR-119 to enhance the intracellular activity of cAMP, and may induce the release of GLP-1 that is a neuroendocrine protein.

According to another exemplary embodiment of the present invention, the metabolic diseases may be selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X, but the present invention is not limited thereto.

Also, the present invention provides a GPR-119 activator including, as an active ingredient, the compound (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone or (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone, or the pharmaceutically acceptable salt thereof.

Further, the present invention provides a health functional food for preventing or improving metabolic diseases, which includes, as an active ingredient, the compound (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone or (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone, or the pharmaceutically acceptable salt thereof.

According to one exemplary embodiment of the present invention, the metabolic diseases may be selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X, but the present invention is not limited thereto.

MODE FOR INVENTION

Hereinafter, the present invention will be described in detail with reference to examples and experimental examples thereof.

However, it should be understood that the examples and experimental examples are given by way of illustration of the present invention only, and are not intended to limit the scope of the present invention.

Preparative Example 1: Preparation of ethyl 4-(trifluoromethylsulfonyloxy)cyclohex-3-enecarboxylate

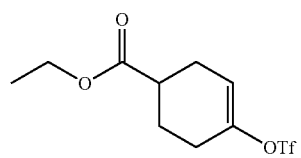 [SMILES: CCOC(=O)C1CC=C(OS(=O)(=O)C(F)(F)F)CC1]

136 ml of lithium hexamethyldisilazide (LiHMDS) was dissolved in 100 ml of THF in a 1,000 ml flask while stirring under nitrogen. After the resulting mixture was cooled to a temperature of 5° C., 17.8 g of ethyl 4-oxocyclohexanecarboxylate was slowly added dropwise, and the mixture was then stirred for 5 minutes. 41 g of 1,1,1-trifluoro-N-phenyl-N-(trifluoromethylsulfonyl)methanesulfonamide was slowly added dropwise, and then stirred for 2 hours. After the reaction was terminated, 300 ml of distilled water was slowly added, and the resulting mixture was extracted with 500 ml of ethyl acetate, washed with 100 ml of brine, dried with anhydrous magnesium sulfate, concentrated, and then isolated by silica column chromatography to obtain the title compound.

$^1$H NMR (400, CDCl$_3$): 3.69 (3H, s), 3.40 (4H, m), 3.20 (1H, m), 2.57 (2H, d), 2.48 (3H, m), 2.27 (2H, d), 1.47 (9H, s), 1.06 (3H, d)

Preparative Example 2: Preparation of ethyl 4-(4,4,5,5-tetramethyl-1,3,2-dioxaborolan-2-yl)cyclohex-3-enecarboxylate

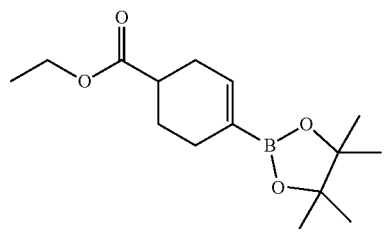 [SMILES: CCOC(=O)C1CC=C(B2OC(C)(C)C(C)(C)O2)CC1]

48.9 g of ethyl 4-(trifluoromethylsulfonyloxy)cyclohex-3-enecarboxylate was dissolved in 300 ml of 1.4-dioxane in a 1,000 ml flask while stirring under nitrogen. 41 g of bis(pinacolate)diboron, 9 g of tetrakis(triphenylphosphine)palladium, and 32 g of potassium acetate were sequentially added dropwise thereto, and the resulting mixture was then stirred for 5 minutes. The mixture was gradually heated to a temperature of 90° C., and then stirred for 4 hours. After the reaction was terminated, the reaction mixture was cooled to room temperature. Then, 300 ml of hexane was added thereto, and filtered through celite. 300 ml of distilled water was slowly added thereto, and the reaction mixture was extracted with 500 ml of ethyl acetate, washed with 100 ml of brine, dried with anhydrous magnesium sulfate, concentrated, and then isolated by silica column chromatography to obtain the title compound.

¹H NMR (400, CDCl₃): 6.56 (1H, s), 4.16(3H, q), 2.52 (1H, m), 2.40 (6H, m), 1.63 (2H, m), 1.29 (15H, m)

Preparative Example 3: Preparation of (1-(5-ethylpyrimidin-2-yl)piperidin-4-yl)methanol

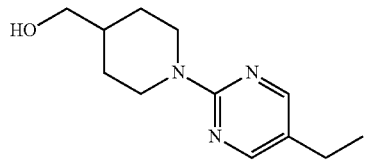 [SMILES: CCc1cnc(N2CCC(CO)CC2)nc1]

6.3 g of Piperidin-4-yl methanol was dissolved in 100 ml of DMF in a 250 ml flask, and then stirred under nitrogen. 10 ml of N,N-diisopropylethylamine was added dropwise thereto, and 5.2 g of 2-chloro-5-ethylpyrimidine was then added dropwise. The resulting mixture was gradually heated to a temperature of 60° C., and then stirred for 4 hours. After the reaction was terminated, the reaction mixture was slowly cooled to room temperature. Then, 100 ml of distilled water was slowly added thereto, and the reaction mixture was extracted with 300 ml of ethyl acetate, washed with 50 ml of brine, dried with anhydrous magnesium sulfate, and then concentrated to prepare the title compound.

¹H NMR (400, CDCl₃): 8.21 (2H, s), 4.80 (2H, d), 3.54 (2H, d), 2.94 (2H, m), 2.48 (2H, m), 1.86 (2H, m), 1.81 (1H, s), 1.26 (2H, m), 1.20 (3H, m)

Preparative Example 4: Preparation of (1-(5-ethylpyrimidin-2-yl)piperidin-4-yl)methyl methanesulfonate

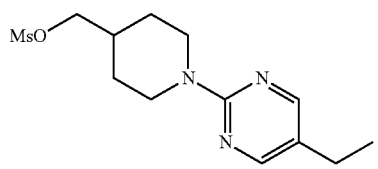 [SMILES: CCc1cnc(N2CCC(COS(C)(=O)=O)CC2)nc1]

11.4 g of (1-(5-ethylpyrimidin-2-yl)piperidin-4-yl)methanol was dissolved in 100 ml of dichloromethane in a 250 ml flask, and then stirred under nitrogen. 10 ml of triethylamine was added dropwise thereto, 4.2 ml of methanesulfonyl chloride was slowly added dropwise at 5° C., and the resulting mixture was then stirred for 30 minutes. When the reaction was terminated, 50 ml of distilled water was slowly added, and the reaction mixture was extracted with 20 ml of dichloromethane, washed with 100 ml of brine, dried with anhydrous magnesium sulfate, and then concentrated to obtain the title compound as a solid from diethyl ether.

¹H NMR (400, CDCl₃): 8.18 (2H, s), 4.77 (2H, d), 4.10 (2H, d), 3.04 (3H, m), 2.84 (2H, m), 2.46 (2H, m), 2.07 (1H, m), 1.86 (2H, d), 1.27 (2H, m), 1.19 (3H, m)

Preparative Example 5: Preparation of (1-(3-isopropyl-1,2,4-oxadiazol-5-yl)piperidin-4-yl)methanol

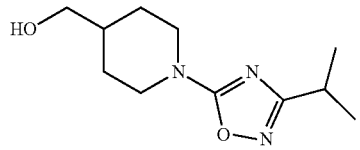 [SMILES: CC(C)c1noc(N2CCC(CO)CC2)n1]

300 g of piperidin-4-yl methanol was added to an acetonitrile/water mixture (400 m/1400 ml), and dissolved in a 1,000 ml flask while stirring under nitrogen. 330 g of sodium bicarbonate and 302 g of cyanogen bromide were added thereto, and then heated at reflux for 12 hours or more. When the reaction was completed, 100 ml of distilled water was slowly added thereto, and the resulting reaction mixture was extracted three times with 100 ml of dichloromethane, dried with anhydrous magnesium sulfate, and then concentrated. Residues were added to 2,000 ml of ethyl acetate, dissolved while stirring. Then, 175 g of N-hydroxyisobutyramide was added thereto, and 1,700 ml of a 1 M zinc chloride solution was slowly added dropwise, and the resulting mixture was then stirred for 12 hours or more. When the reaction was terminated, the resulting solids were filtered, and washed with 2,000 ml of diethyl ether. The resulting solids were added to 1,000 ml of ethanol, and dissolved while stirring, and 1,000 ml of a 4 N HCl aqueous solution was added dropwise thereto, and then heated at reflux for 4 hours or more. When the reaction was completed, the resulting reaction mixture was distilled under reduced pressure to remove ethanol, and the pH of the reaction mixture was then made basic with sodium bicarbonate. Then, the mixture was extracted three times with 1,000 ml of ethyl acetate. The extracted solution was dried with anhydrous magnesium sulfate, concentrated, and then isolated by silica column chromatography to obtain the title compound.

¹H NMR (400, CDCl₃): 4.24 (2H, d), 3.86 (2H, d), 3.15 (2H, m), 2.91 (1H, m), 1.91 (2H, m), 1.48 (2H, m), 1.43 (1H, m), 1.32 (6H, d)

Preparative Example 6: Preparation of (1-(3-isopropyl-1,2,4-oxadiazol-5-yl)piperidin-4-yl)methyl methanesulfonate

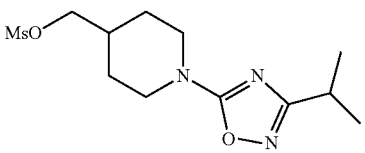 [SMILES: CC(C)c1noc(N2CCC(COS(C)(=O)=O)CC2)n1]

The title compound was prepared in the same manner as in <Preparative Example 4>, except that (1-(3-isopropyl-1,2,4-oxadiazol-5-yl)piperidin-4-yl)methanol was used instead of the (1-(5-ethylpyrimidin-2-yl)piperidin-4-yl) methyl methanesulfonate.

¹H NMR (400, CDCl₃): 4.24 (2H, d), 3.86 (2H, d), 3.15 (2H, m), 3.04 (3H, m), 2.91 (1H, m), 1.91 (2H, m), 1.48 (2H, m), 1.32 (6H, d)

Preparative Example 7: Preparation of tert-butyl 4-((methylsulfonyloxy)methyl)piperidine-1-carboxylate

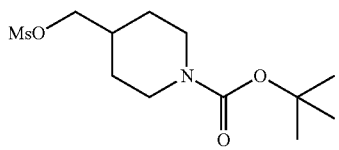 [SMILES: CC(C)(C)OC(=O)N1CCC(COS(C)(=O)=O)CC1]

The title compound was prepared in the same manner as in <Preparative Example 4>, except that tert-butyl 4-(hydroxymethyl)piperidine-1-carboxylate was used instead of the (1-(5-ethylpyrimidin-2-yl)piperidin-4-yl)methyl methanesulfonate.

$^1$H NMR (400, CDCl$_3$): 4.20 (2H, m), 4.04 (2H, d), 2.99 (3H, s), 2.70 (2H, m), 1.90 (1H, m), 1.70 (2H, m), 1.43 (9H, s), 1.10 (2H, m)

Preparative Example 8: Preparation of 2-(4-((4-bromophenoxy)methyl)piperidin-1-yl)-5-ethylpyrimidine

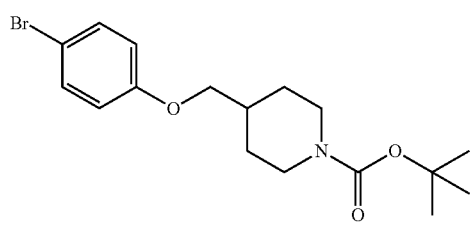

50 g of (1-(5-ethylpyrimidin-2-yl)piperidin-4-yl)methyl methanesulfonate was dissolved in 300 ml of DMF in a 1,000 ml flask, and then stirred under nitrogen. 110 g of cesium carbonate was added dropwise thereto, and 30 g of 4-bromophenol was also added dropwise. The resulting mixture was stirred at 60° C. for 5 hours. When the reaction was terminated, the mixture was slowly cooled to room temperature. Solids formed by slowly adding 500 ml of distilled water at 0° C. were filtered, and then dried to obtain the title compound as a solid.

$^1$H NMR (400, CDCl$_3$): 8.21 (2H, s), 7.32 (2H, d), 6.85 (2H, d), 4.80 (2H, d), 3.54 (2H, m), 2.48 (2H, m), 1.86 (2H, d), 1.81 (1H, m), 1.26 (2H, m), 1.20 (3H, m)

Preparative Example 9: Preparation of 5-(4-((4-bromophenoxy)methyl)piperidin-1-yl)-3-isopropyl-1,2,4-oxadiazole

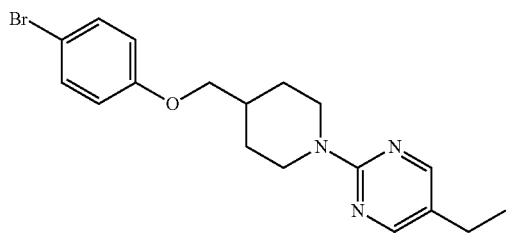 [SMILES: CCc1cnc(N2CCC(COc3ccc(Br)cc3)CC2)nc1]

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate.

$^1$H NMR (400, CDCl$_3$): 7.32 (2H, d), 6.85 (2H, d), 4.24 (2H, d), 3.86 (2H, d), 3.15 (1H, m), 1.91 (2H, m), 1.48 (2H, m), 1.32 (6H, d)

Preparative Example 10: Preparation of tert-butyl 4-((4-bromophenoxy)methyl)piperidine-1-carboxylate

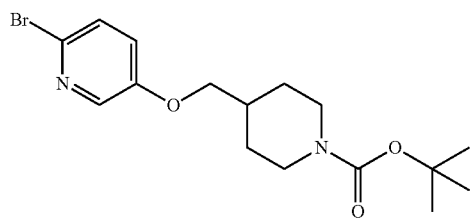

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate.

$^1$H NMR (400, CDCl$_3$): 7.32 (2H, d), 6.85 (2H, d), 4.15 (2H, d), 3.86 (2H, d), 2.78 (2H, m), 2.12 (1H, m), 1.87 (9H, s), 1.32 (2H, m)

Preparative Example 11: Preparation of tert-butyl 4-((6-bromopyridin-3-yloxy)methyl)piperidine-1-carboxylate

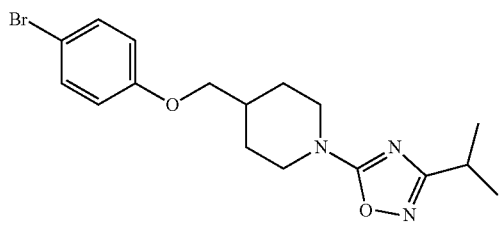 [SMILES: CC(C)c1noc(N2CCC(COc3ccc(Br)cc3)CC2)n1]

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate, and 2-bromo-5-hydroxypyridine was used instead of the 4-bromophenol.

$^1$H NMR (400, CDCl$_3$): 8.21 (1H, s), 7.38 (1H, d), 7.15 (1H, d), 4.15 (2H, d), 3.85 (2H, d), 2.78 (2H, m), 2.12 (1H, m), 1.87 (2H, m), 1.48 (9H, s), 1.32 (2H, m)

Preparative Example 12: Preparation of tert-butyl 4-((5-bromopyridin-2-yloxy)methyl)piperidine-1-carboxylate

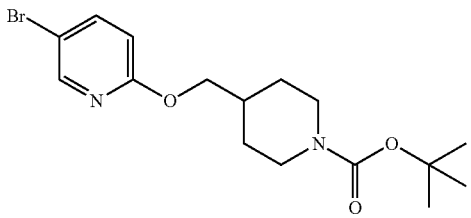 [SMILES: CC(C)(C)OC(=O)N1CCC(COc2ccc(Br)cn2)CC1]

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate, and 5-bromo-2-hydroxypyridine was used instead of the 4-bromophenol.

$^1$H NMR (400, CDCl$_3$): 8.14 (1H, s), 7.63 (1H, d), 6.71 (1H, d), 4.15 (2H, d), 3.85 (2H, d), 2.78 (2H, m), 2.12 (1H, m), 1.87 (2H, m), 1.48 (9H, s), 1.32 (2H, m)

Preparative Example 13: Preparation of 5-(4-((6-chloropyridin-3-yloxy)methyl)piperidin-1-yl)-3-isopropyl-1,2,4-oxadiazole

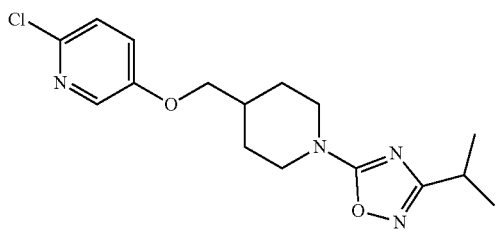 [SMILES: CC(C)c1noc(N2CCC(COc3ccc(Cl)nc3)CC2)n1]

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate, and 2-chloro-5-hydroxypyridine was used instead of the 4-bromophenol.

$^1$H NMR (400, CDCl$_3$): 8.21 (1H, s), 7.38 (1H, d), 7.15 (1H, d), 4.24 (2H, d), 3.86 (2H, d), 3.15 (2H, m), 2.91 (1H, m), 1.48 (2H, m), 1.32 (6H, d)

Preparative Example 14: Preparation of tert-butyl 4-((4-bromo-2-fluorophenoxy)methyl)piperidine-1-carboxylate

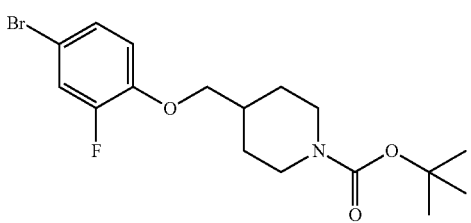 [SMILES: CC(C)(C)OC(=O)N1CCC(COc2ccc(Br)cc2F)CC1]

The title compound was prepared in the same manner as in <Preparative Example 8>, except that tert-butyl 4-((methylsulfonyloxy)methyl)piperidine-1-carboxylate was used instead of the (i-(5-ethylpyrimidin-2-yl)piperidin-4-yl)methyl methanesulfonate, and 2-fluoro-4-bromophenol was used instead of the 4-bromophenol.

$^1$H NMR (400, CDCl$_3$): 7.13 (1H, s), 7.08 (1H, d), 6.89 (1H, m), 4.15 (2H, d), 3.85 (2H, d), 2.78 (2H, m), 2.12 (1H, m), 1.87 (2H, m), 1.48 (9H, s), 1.32 (2H, m)

Preparative Example 15: Preparation of tert-butyl 4-((4-bromo-3-fluorophenoxy)methyl)piperidine-1-carboxylate

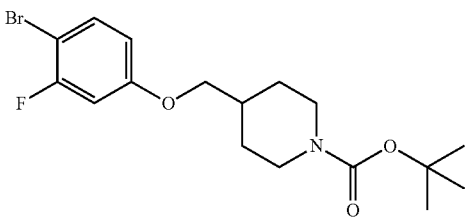 [SMILES: CC(C)(C)OC(=O)N1CCC(COc2ccc(Br)c(F)c2)CC1]

The title compound was prepared in the same manner as in <Preparative Example 8>, except that tert-butyl 4-((methylsulfonyloxy)methyl)piperidine-1-carboxylate was used instead of the (1-(5-ethylpyrimidin-2-yl)piperidin-4-yl)methyl methanesulfonate, and 3-fluoro-4-bromophenol was used instead of the 4-bromophenol.

$^1$H NMR (400, CDCl$_3$): 7.13 (1H, s), 6.65 (1H, d), 6.59 (1H, m), 4.15 (2H, d), 3.85 (2H, d), 2.78 (2H, m), 2.12 (1H, m), 1.87 (2H, m), 1.48 (9H, s), 1.32 (2H, m)

Preparative Example 16: Preparation of 5-(4-((4-bromo-2-fluorophenoxy)methyl)piperidin-1-yl)-3-isopropyl-1,2,4-oxadiazole

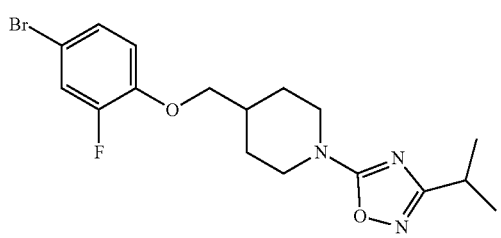

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate, and 2-fluoro-4-bromophenol was used instead of the 4-bromophenol.

$^1$H NMR (400, CDCl$_3$): 7.13 (1H, s), 7.08 (1H, d), 6.89 (1H, m), 4.24 (2H, d), 3.86 (2H, d), 3.15 (2H, m), 2.91 (1H, m), 1.91 (2H, m), 1.48 (2H, s), 1.32 (6H, d)

Preparative Example 17: Preparation of tert-butyl 4-((4-(4-(ethoxycarbonyl)cyclohex-1-enyl)phenoxy)methyl)piperidine-1-carboxylate

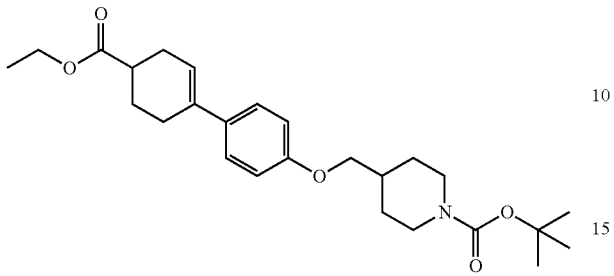

5 g of tert-butyl 4-((4-bromophenoxy)methyl)piperidine-1-carboxylate was dissolved in a tetrahydrofuran/water/ethanol mixture (100 ml/20 ml/10 ml) in a 500 ml flask, and stirred under nitrogen. 550 mg of (1,1'-bis(diphenylphosphino)ferrocene)palladium(II) dichloride, 11 g of cesium carbonate, and 4.2 g of ethyl 4-(4,4,5,5-tetramethyl-1,3,2-dioxaborolan-2-yl)cyclohex-3-enecarboxylate were sequentially added dropwise thereto. The resulting mixture was gradually heated to a temperature of 80° C., and then stirred for 5 hours. After the reaction was terminated, the reaction mixture was slowly cooled to room temperature, 100 ml of distilled water was slowly added thereto, and the reaction mixture was filtered through celite. The filtrate was extracted with 300 ml of ethyl acetate, washed with 100 ml of brine, dried with anhydrous magnesium sulfate, concentrated, and then isolated by silica column chromatography to prepare the title compound.

$^1$H NMR (400, CDCl$_3$): 7.32 (2H, d), 6.85 (2H, d), 6.02 (1H, s), 4.10 (2H, m), 4.15 (2H, d), 3.85 (2H, d), 2.61 (1H, m), 2.47 (4H, m), 2.21 (2H, m), 1.98 (1H, m), 1.86 (2H, m), 1.61 (9H, s), 1.31 (2H, m), 1.20 (3H, m)

Preparative Example 18: Preparation of 4-(4-((1-(tert-butoxycarbonyl)piperidin-4-yl)methoxy)phenyl)cyclohex-3-enecarboxylic Acid

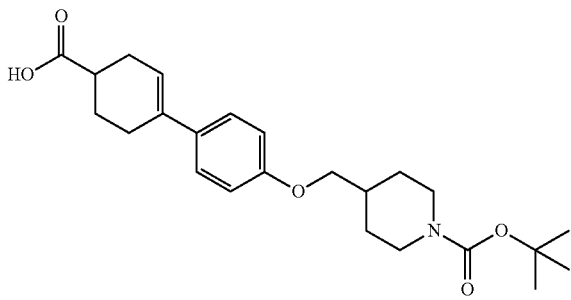

3.2 g of tert-butyl 4-((4-(4-(ethoxycarbonyl)cyclohex-1-enyl)phenoxy)methyl)piperidine-1-carboxylate was dissolved in a tetrahydrofuran/water/ethanol mixture (100 ml/50 ml/10 ml) in a 250 ml flask, and stirred under nitrogen. 2.4 g of lithium hydroxide monohydrate was added dropwise thereto, and then reacted at room temperature for 18 hours. After the reaction was terminated, the pH of the resulting reaction mixture was adjusted to pH 1 to 2 using concentrated HCl. The resulting solids were filtered, and dried to prepare the desired title compound.

$^1$H NMR (400, CDCl$_3$): 7.32 (2H, d), 6.85 (2H, d), 6.02 (1H, s), 4.15 (2H, m), 3.85 (2H, d), 2.61 (1H, m), 2.47 (4H, m), 2.21 (2H, m), 1.98 (1H, m), 1.86 (2H, m), 1.61 (9H, s), 1.31 (2H, m)

Preparative Example 19: Preparation of ethyl 4-(4-((1-(5-ethylpyrimidin-2-yl)piperidin-4-yl)methoxy)phenyl)cyclohex-3-enecarboxylate

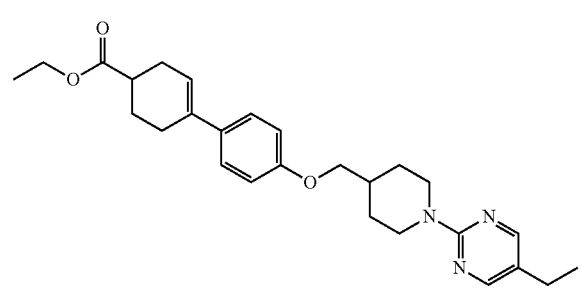 [SMILES: CCOC(=O)C1CC=C(c2ccc(OCC3CCN(c4ncc(CC)cn4)CC3)cc2)CC1]

The title compound was prepared in the same manner as in <Preparative Example 17>, except that 2-(4-((4-bromophenoxy)methyl)piperidin-1-yl)-5-ethylpyrimidine was used instead of the tert-butyl 4-((4-bromophenoxy)methyl)piperidine-1-carboxy late.

$^1$H NMR (400, CDCl$_3$): 8.21 (2H, s), 7.32 (2H, d), 6.85 (2H, d), 6.02 (1H, s), 4.80 (2H, d), 4.19 (2H, m), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 20: Preparation of 4-(4-((1-(5-ethylpyrimidin-2-yl)piperidin-4-yl)methoxy)phenyl)cyclohex-3-enecarboxylic Acid

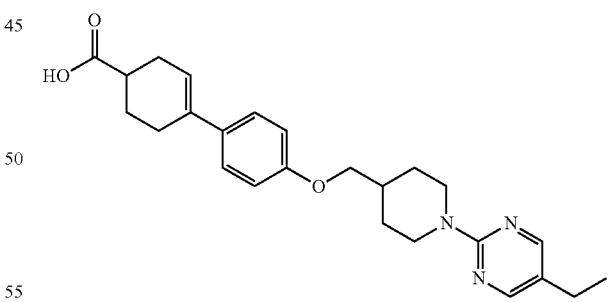

The title compound was prepared in the same manner as in <Preparative Example 18>, except that ethyl 4-(4-((1-(5-ethylpyrimidin-2-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 7.32 (2H, d), 6.85 (2H, d), 6.02 (1H, s), 4.80 (2H, d), 3.54 (2H, m), 2.94 (2H, m), 2.61 (1H, m), 2.48 (2H, m), 2.47 (4H, m), 2.21 (2H, m), 1.86 (2H, d), 1.81 (1H, m), 1.26 (2H, m), 1.20 (3H, m)

Preparative Example 21: Preparation of ethyl 4-(4-((1-(3-isopropyl-1,2,4-oxadiazol-5-yl)piperidin-4-yl)methoxy)phenyl)cyclohex-3-enecarboxylate

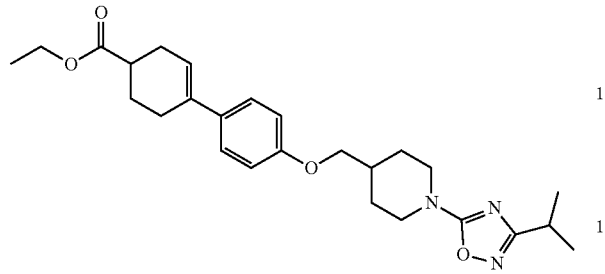

The title compound was prepared in the same manner as in <Preparative Example 17>, except that 5-(4-((4-bromophenoxy)methyl)piperidin-1-yl)-3-isopropyl-1,2,4-oxadiazole was used instead of the tert-butyl 4-((4-bromophenoxy)methyl)piperidine-1-carboxylate.

$^1$H NMR (400, CDCl$_3$): 7.32 (2H, d), 6.85 (2H, d), 6.02 (1H, s), 4.24 (2H, d), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 22: Preparation of 4-(4-((1-(3-isopropyl-1,2,4-oxadiazol-5-yl)piperidin-4-yl)methoxy)phenyl)cyclohex-3-enecarboxylic Acid

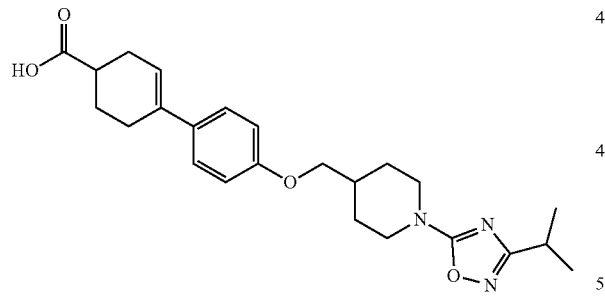

The title compound was prepared in the same manner as in <Preparative Example 18>, except that ethyl 4-(4-((1-(3-isopropyl-1,2,4-oxadiazol-5-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.32 (2H, d), 6.85 (2H, d), 6.02 (1H, s), 4.24 (2H, d), 3.86 (2H, m), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 23: Preparation of tert-butyl 4-((6-(4-(ethoxycarbonyl)cyclohex-1-enyl)pyridin-3-yloxy)methyl)piperidine-1-carboxylate

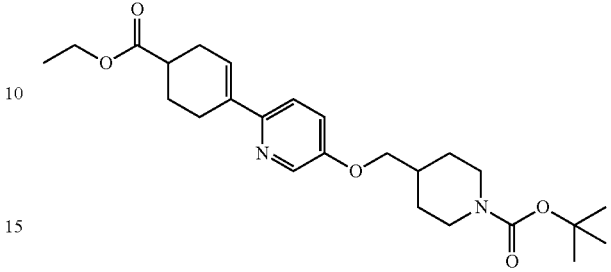

The title compound was prepared in the same manner as in <Preparative Example 17>, except that tert-butyl 4-((6-bromopyridin-3-yloxy)methyl)piperidine-1-carboxylate was used instead of the tert-butyl 4-((4-bromophenoxy)methyl)piperidine-1-carboxylate.

$^1$H NMR (400, CDCl$_3$): 8.21 (1H, s), 7.38 (1H, d), 7.15 (1H, d), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 24: Preparation of 4-(5-((1-(tert-butoxycarbonyl)piperidin-4-yl)methoxy)pyridin-2-yl)cyclohex-3-enecarboxylic Acid

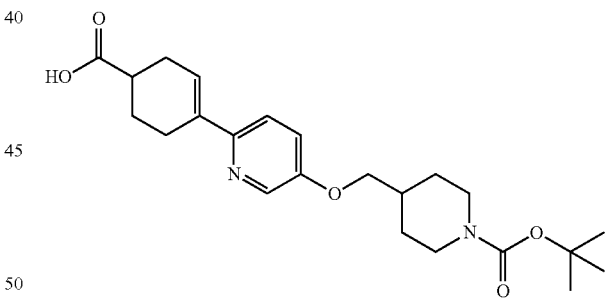

The title compound was prepared in the same manner as in <Preparative Example 18>, except that tert-butyl 4-((6-(4-(ethoxycarbonyl)cyclohex-1-enyl)pyridin-3-yloxy)methyl)piperidine-1-carboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (1H, s), 7.38 (1H, d), 7.15 (1H, d), 6.02 (1H, s), 4.15 (2H, m), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 25: Preparation of ethyl 4-(5-((1-(3-isopropyl-1,2,4-oxadiazol-5-yl)piperidin-4-yl)methoxy)pyridin-2-yl)cyclohex-3-enecarboxylate

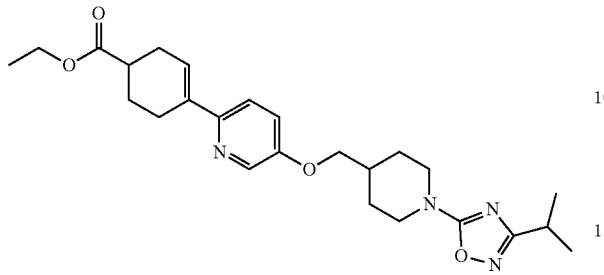

The title compound was prepared in the same manner as in <Preparative Example 17>, except that 5-(4-((6-chloropyridin-3-yloxy)methyl)piperidin-1-yl)-3-isopropyl-1,2,4-oxadiazole was used instead of the tert-butyl 4-((4-bromophenoxy)methyl)piperidine-1-carboxylate.

$^1$H NMR (400, CDCl$_3$): 8.21 (1H, s), 7.38 (1H, d), 7.15 (1H, d), 6.02 (1H, s), 4.24 (2H, m), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 26: Preparation of 4-(5-((1-(3-isopropyl-1,2,4-oxadiazol-5-yl)piperidin-4-yl)methoxy)pyridin-2-yl)cyclohex-3-enecarboxylic Acid

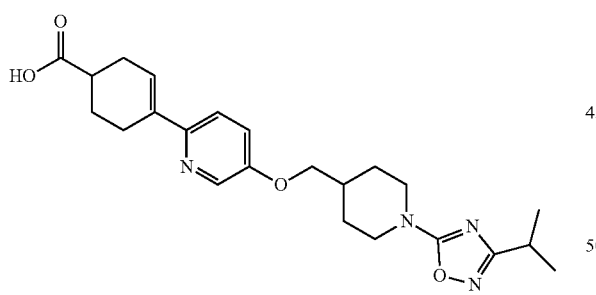

The title compound was prepared in the same manner as in <Preparative Example 18>, except that 4-(5-((1-(3-isopropyl-1,2,4-oxadiazol-5-yl)piperidin-4-yl)methoxy)pyridin-2-yl)cyclohex-3-enecarboxylic acid was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (1H, s), 7.38 (1H, d), 7.15 (1H, d), 6.02 (1H, s), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 27: Preparation of tert-butyl 4-((5-(4-(ethoxycarbonyl)cyclohex-1-enyl)pyridin-2-yloxy)methyl)piperidine-1-carboxylate

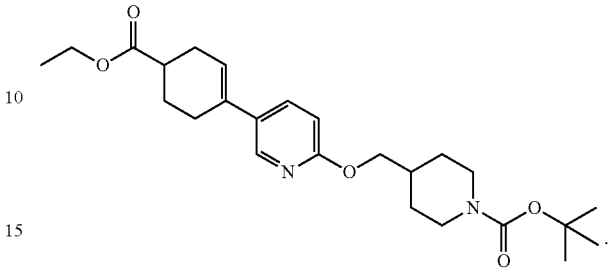

The title compound was prepared in the same manner as in <Preparative Example 17>, except that tert-butyl 4-((5-bromopyridin-2-yloxy)methyl)piperidine-1-carboxylate was used instead of the tert-butyl 4-((4-bromophenoxy)methyl)piperidine-1-carboxylate.

$^1$H NMR (400, CDCl$_3$): 8.14 (1H, s), 7.63 (1H, d), 6.71 (1H, d), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 28: Preparation of 4-(6-((1-(tert-butoxycarbonyl)piperidin-4-yl)methoxy)pyridin-3-yl)cyclohex-3-enecarboxylic Acid

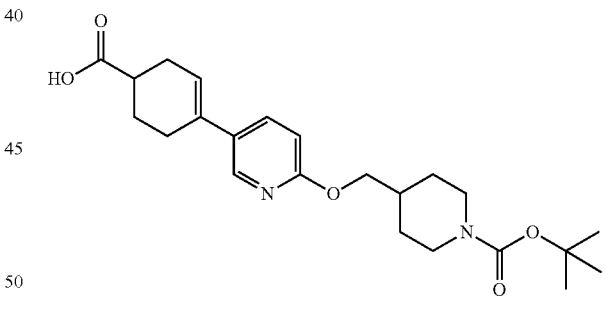

The title compound was prepared in the same manner as in <Preparative Example 18>, except that tert-butyl 4-((5-(4-(ethoxycarbonyl)cyclohex-1-enyl)pyridin-2-yloxy)methyl)piperidine-1-carboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.14 (1H, s), 7.63 (1H, d), 6.71 (1H, d), 6.02 (1H, s), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 29: Preparation of tert-butyl 4-((4-(4-(ethoxycarbonyl)cyclohex-1-enyl)-2-fluorophenoxy)methyl)piperidine-1-carboxylate

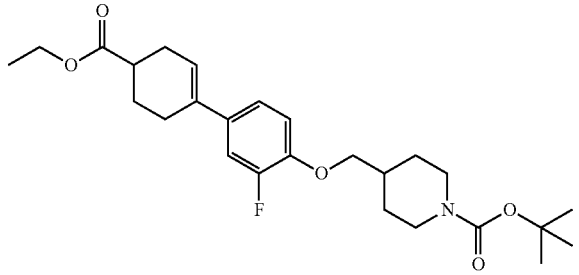 [SMILES: CCOC(=O)C1CC=C(c2ccc(OCC3CCN(C(=O)OC(C)(C)C)CC3)c(F)c2)CC1]

The title compound was prepared in the same manner as in <Preparative Example 17>, except that tert-butyl 4-((4-bromo-2-fluorophenoxy)methyl)piperidine-1-carboxylate was used instead of the tert-butyl 4-((4-bromophenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 30: Preparation of 4-(4-((1-(tert-butoxycarbonyl)piperidin-4-yl)methoxy)-3-fluorophenyl)cyclohex-3-enecarboxylic Acid

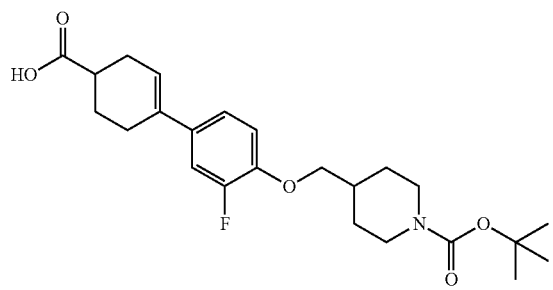 [SMILES: CC(C)(C)OC(=O)N1CCC(COc2ccc(C3=CCC(C(=O)O)CC3)cc2F)CC1]

The title compound was prepared in the same manner as in <Preparative Example 18>, except that tert-butyl 4-((4-(4-(ethoxycarbonyl)cyclohex-1-enyl)-2-fluorophenoxy)methyl)piperidine-1-carboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.15 (2H, m), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 31: Preparation of ethyl 4-(3-fluoro-4-((1-(3-isopropyl-1,2,4-oxadiazol-5-yl)piperidin-4-yl)methoxy)phenyl)cyclohex-3-enecarboxylate

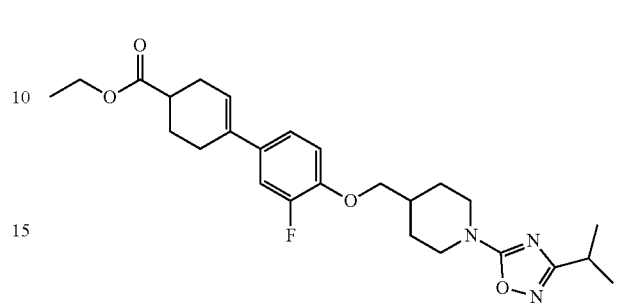

The title compound was prepared in the same manner as in <Preparative Example 17>, except that 5-(4-((4-bromo-2-fluorophenoxy)methyl)piperidin-1-yl)-3-isopropyl-1,2,4-oxadiazole was used instead of the tert-butyl 4-((4-bromophenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.24 (2H, d), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 32: Preparation of 4-(3-fluoro-4-((1-(3-isopropyl-1,2,4-oxadiazol-5-yl)piperidin-4-yl)methoxy)phenyl)cyclohex-3-enecarboxylic Acid

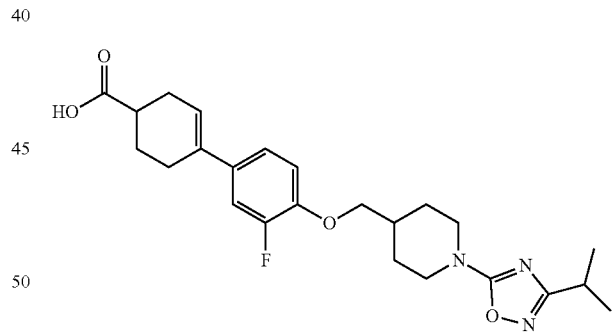

The title compound was prepared in the same manner as in <Preparative Example 18>, except that ethyl 4-(3-fluoro-4-((1-(3-isopropyl-1,2,4-oxadiazol-5-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, d), 7.08 (1H, d), 6.89 (1H, m), 6.02 (1H, s), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 33: Preparation of tert-butyl 4-((4-(4-(ethoxycarbonyl)cyclohex-1-enyl)-3-fluorophenoxy)methyl)piperidine-1-carboxylate

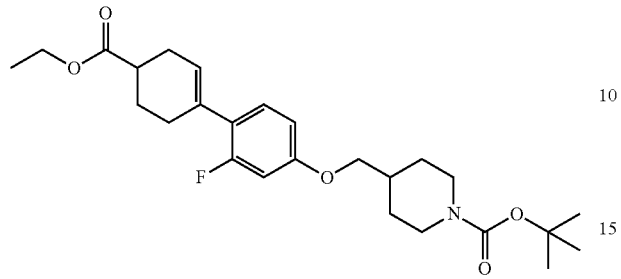

The title compound was prepared in the same manner as in <Preparative Example 17>, except that tert-butyl 4-((4-bromo-3-fluorophenoxy)methyl)piperidine-1-carboxylate was used instead of the tert-butyl 4-((4-bromophenoxy)methyl)piperidine-1-carboxylate.

$^1$H NMR (400, CDCl$_3$): 7.13 (1H, m), 6.65 (1H, d), 6.59 (1H, d), 6.02 (1H, s), 4.19 (2H, m), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m), 1.29 (3H, m)

Preparative Example 34: Preparation of 4-(4-((1-(tert-butoxycarbonyl)piperidin-4-yl)methoxy)-2-fluorophenyl)cyclohex-3-enecarboxylic Acid

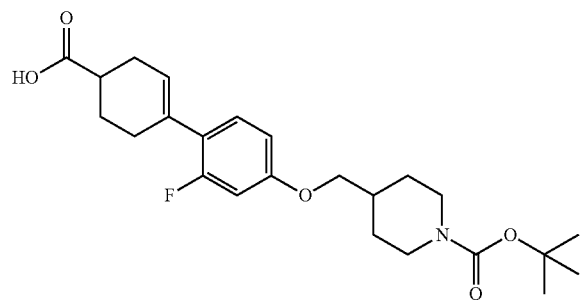 [SMILES: CC(C)(C)OC(=O)N1CCC(COc2ccc(C3=CCC(C(=O)O)CC3)c(F)c2)CC1]

The title compound was prepared in the same manner as in <Preparative Example 18>, except that tert-butyl 4-((4-(4-(ethoxycarbonyl)cyclohex-1-enyl)-3-fluorophenoxy)methyl)piperidine-1-carboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, m), 6.65 (1H, d), 6.59 (1H, d), 6.02 (1H, s), 4.15 (2H, d), 3.85 (2H, d), 2.78 (2H, m), 2.61 (1H, m), 2.47 (4H, m), 2.21 (2H, m), 2.12 (1H, m), 1.87 (2H, m), 1.48 (9H, s), 1.32 (2H, m)

Preparative Example 35: Preparation of (−)-4-bromocyclohex-3-enecarboxylic Acid

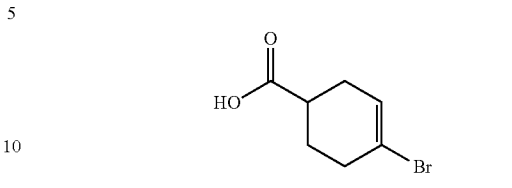

Step 1: Formation of Salt 170 g of (±)HBA was put into a 5,000 ml flask under a nitrogen atmosphere, 2,550 ml of acetone and 850 ml of methanol were added thereto, and the resulting mixture was then dissolved while stirring. 49 g of (1S,2S)-(+)-amino-2-indanol was dissolved in 340 ml of methanol, and added dropwise to the flask. The resulting mixture was stirred at 20° C. for 30 minutes, cooled to a temperature of −5° C., and then additionally stirred for another 30 minutes. The resulting solids were filtered, and then dried to obtain the solid compound.

Step 2: Recrystallization of Salt 80.26 g of the formed salt was put into a 3,000 ml flask under a nitrogen atmosphere, 1,600 ml of acetone and 104 ml of methanol were added thereto, and the resulting mixture was dissolved while stirring at 55° C. for 30 minutes. The temperature of the mixture was lowered to −5° C. by 1° C. per minute, and the mixture was then additionally stirred for another 30 minutes. The resulting solids were again filtered, and then dried to obtain the solid compound.

The same procedure as described above was further repeated four times.

Step 3: Decomposition of Salt 24.3 g of the formed salt was put into a 1,000 ml flask under a nitrogen atmosphere, 500 ml of distilled water and 30 ml of ethyl acetate were added thereto, and the resulting mixture was then stirred. The pH of the mixture was adjusted to pH 1.5 by adding a 1 M HCl aqueous solution at 20° C., and the mixture was separated from ethyl acetate, dried with anhydrous magnesium sulfate, and concentrated. Then, solids were formed from ethyl acetate/hexane, and then filtered to obtain the title compound.

The resulting title compound was mixed with Chirabite-AR (TCI, C2184) at a ratio of 1:1, and subjected to NMR to determine an excessive amount of enantiomers.

$^1$H NMR (400, CDCl$_3$): 6.05 (1H, t), 2.67 (1H, m), 2.56 (2H, m), 2.38 (2H, m), 2.12 (1H, m), 1.91 (2H, m)

$^1$H NMR (400, CDCl$_3$) data of the title compound using Chirabite-AR was shown in FIG. 4. As shown in FIG. 4, when the same amount of Chirabate-AR was used, the title compound showed chemical shift of specific peak at 5.87.

(−)-4-Bromocyclohex-3-enecarboxylic acid+Chirabite-AR NMR $^1$H NMR (400, CDCl$_3$): 10.21 (1H, s), 9.02 (1H, s), 8.27 (1H, s), 8.27 (1H, d), 8.05 (2H, t), 7.95 (1H, d), 7.87 (1H, t), 7.51 (1H, t), 7.26 (1H, t), 7.36 (1H, d), 5.88 (0.6H, m), 5.32 (0.4H, m), 4.59 (1H, d), 4.31 (1H, d), 2.61 (2H, m), 2.30 (9H, m), 1.96 (2H, m), 1.74 (3H, m)

Preparative Example 36: Preparation of (+)-4-bromocyclohex-3-enecarboxylic Acid

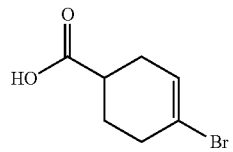

Step 1: Formation of Salt 170 g of (±)HBA was put into a 5,000 ml flask under a nitrogen atmosphere, 2,550 ml of acetone and 850 ml of methanol were added thereto, and the resulting mixture was then dissolved while stirring. 49 g of (1R,2R)-(−)-amino-2-indanol was dissolved in 340 ml of methanol, and added dropwise to the flask. The resulting mixture was stirred at 20° C. for 30 minutes, cooled to a temperature of −5° C., and then additionally stirred for another 30 minutes. The resulting solids were filtered, and then dried to obtain the solid compound. $^1$H NMR (400, $CDCl_3$) data of the (±)HBA using Chirabite-AR was shown in FIG. 5.

Step 2: Recrystallization of Salt 80.26 g of the formed salt was put into a 3,000 ml flask under a nitrogen atmosphere, 1,600 ml of acetone and 104 ml of methanol were added thereto, and the resulting mixture was dissolved while stirring at 55° C. for 30 minutes. The temperature of the mixture was lowered to −5° C. by 1° C. per minute, and the mixture was then additionally stirred for another 30 minutes. The resulting solids were again filtered, and then dried to obtain the solid compound.

The same procedure as described above was further repeated four times.

Step 3: Decomposition of Salt 24.3 g of the formed salt was put into a 1,000 ml flask under a nitrogen atmosphere, 500 ml of distilled water and 30 ml of ethyl acetate were added thereto, and the resulting mixture was then stirred. The pH of the mixture was adjusted to pH 1.5 by adding a 1 M HCl aqueous solution at 20° C., and the mixture was separated from ethyl acetate, dried with anhydrous magnesium sulfate, and concentrated. Then, solids were formed from ethyl acetate/hexane, and then filtered to obtain the title compound.

The resulting title compound was mixed with Chirabite-AR (TCI, C2184) at a ratio of 1:1, and subjected to NMR to determine an excessive amount of enantiomers. $^1$H NMR (400, $CDCl_3$) data of the title compound was shown in FIG. 6. As shown in FIG. 6, when the same amount of Chirabite-AR was used, the title compound showed chemical shift of specific peak at 5.70.

$^1$H NMR (400, $CDCl_3$): 6.05 (1H, t), 2.67 (1H, m), 2.56 (2H, m), 2.38 (2H, m), 2.12 (1H, m), 1.91 (2H, m)

Preparative Example 37: Preparation of ((−)-4-bromocyclohex-3-enyl)((R)-2-(hydroxymethyl)pyrrolidin-1-yl)methanone

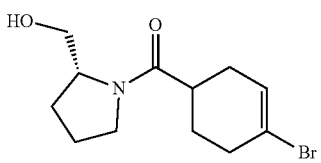 [SMILES: O=C(C1CC=C(Br)CC1)N1CCC[C@@H]1CO]

13.3 g of (−)-4-bromocyclohex-3-enecarboxylic acid was put into a 500 ml flask under a nitrogen atmosphere, 200 ml of dichloromethane was added thereto, and the resulting mixture was dissolved while stirring. 18 ml of triethylamine, 6.6 ml of D-prolinol, and 27.1 g of 1-[bis(dimethylamino)methylene]-1H-1,2,3-triazole[4,5-b]pyridinium 3-oxide hexafluorophosphate (HATU) were added dropwise thereto. The resulting mixture was stirred at 20° C. for an hour. After the reaction was terminated, 100 ml of dichloromethane was additionally added thereto, and the resulting organic layer was washed with 300 ml of distilled water, dried with anhydrous magnesium sulfate, and then concentrated to obtain the title compound.

$^1$H NMR (400, $CDCl_3$): 6.06 (1H, m), 4.91 (1H, dd), 4.21 (1H, q), 3.60 (4H, m), 2.61 (1H, m), 2.51 (2H, m), 2.39 (1H, m), 2.25 (1H, m), 2.19 (1H, m), 2.06 (2H, m), 1.89 (2H, m), 1.60 (1H, m)

Preparative Example 38: Preparation of ((+)-4-bromocyclohex-3-enyl)((R)-2-(hydroxymethyl)pyrrolidin-1-yl)methanone

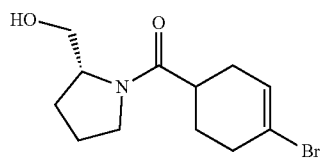 [SMILES: O=C(C1CC=C(Br)CC1)N1CCC[C@@H]1CO]

13.3 g of (−)-4-bromocyclohex-3-enecarboxylic acid was put into a 500 ml flask under a nitrogen atmosphere, 200 ml of dichloromethane was added thereto, and the resulting mixture was dissolved while stirring. 18 ml of triethylamine, 6.6 ml of D-prolinol, and 27.1 g of HATU were added dropwise thereto. The resulting mixture was stirred at 20° C. for an hour. After the reaction was terminated, 100 ml of dichloromethane was additionally added thereto, and the resulting organic layer was washed with 300 ml of distilled water, dried with anhydrous magnesium sulfate, and then concentrated to obtain the title compound.

$^1$H NMR (400, $CDCl_3$): 6.06 (1H, m), 4.91 (1H, dd), 4.21 (1H, q), 3.60 (4H, m), 2.61 (1H, m), 2.51 (2H, m), 2.39 (1H, m), 2.25 (1H, m), 2.19 (1H, m), 2.06 (2H, m), 1.89 (2H, m), 1.60 (1H, m)

Preparative Example 39: Preparation of 5-ethyl-2-(4-((4-(4,4,5,5-tetramethyl-1,3,2-dioxaborolan-2-yl)phenoxy)methyl)piperidin-1-yl)pyrimidine

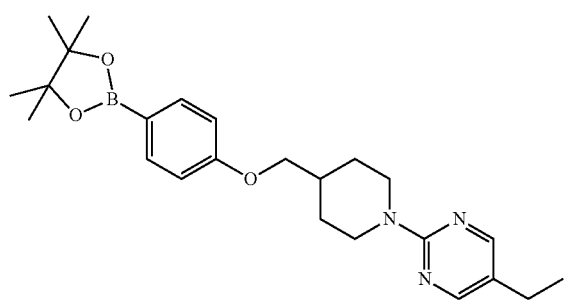 [SMILES: CCc1cnc(N2CCC(COc3ccc(B4OC(C)(C)C(C)(C)O4)cc3)CC2)nc1]

The title compound was prepared in the same manner as in <Preparative Example 8>, except that 4-(4,4,5,5-tetramethyl-1,3,2-dioxaborolan-2-yl)phenol was used instead of the 4-bromophenol.

$^1$H NMR (400, CDCl$_3$): 8.16 (2H, s), 7.73 (2H, d), 6.80 (2H, d), 4.76 (2H, d), 3.84 (2H, d), 2.90 (2H, t), 2.42 (2H, d), 2.09 (1H, m), 1.94 (2H, d), 1.45-1.25 (15H, m), 1.22 (3H, t)

Preparative Example 40: Preparation of 2-(4-((4-bromo-2-fluorophenoxy)methyl)piperidin-1-yl)-5-ethylpyrimidine

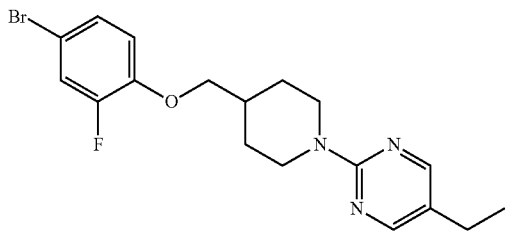

The title compound was prepared in the same manner as in <Preparative Example 8>, except that 2-fluoro-4-bromophenol was used instead of the 4-bromophenol.

$^1$H NMR (400, CDCl$_3$): 8.21 (2H, s), 7.13 (1H, d), 7.08 (1H, d), 6.89 (1H, m), 4.80 (2H, d), 3.54 (2H, m), 2.48 (2H, m), 1.86 (2H, d), 1.81 (1H, m), 1.26 (2H, m), 1.20 (3H, m)

Preparative Example 41: Preparation of ethyl 4-(4-((1-(5-ethylpyrimidin-2-yl)piperidin-4-yl)methoxy)-3-fluorophenyl)cyclohex-3-enecarboxylate

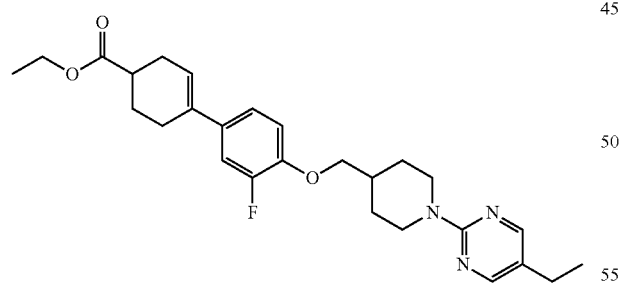

The title compound was prepared in the same manner as in <Preparative Example 17>, except that 2-(4-((4-bromo-2-fluorophenoxy)methyl)piperidin-1-yl)-5-ethylpyrimidine was used instead of the tert-butyl 4-((4-bromophenoxy)methyl)piperidine-1-carboxylate.

$^1$H NMR (400, CDCl$_3$): 8.21 (2H, s), 7.13 (1H, d), 7.08 (1H, d), 6.89 (1H, m), 6.02 (1H, s), 4.80 (2H, d), 4.19 (2H, m), 3.54 (2H, m), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 42: Preparation of 4-(4-((1-(5-ethylpyrimidin-2-yl)piperidin-4-yl)methoxy)-3-fluorophenyl)cyclohex-3-enecarboxylic Acid

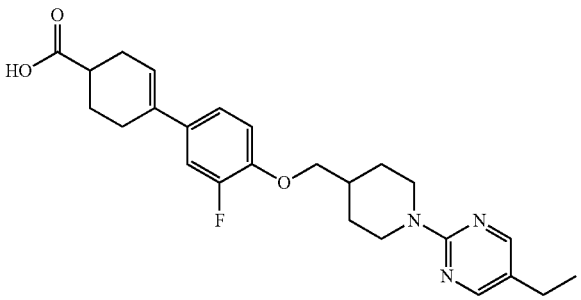

The title compound was prepared in the same manner as in <Preparative Example 18>, except that ethyl 4-(4-((1-(5-ethylpyrimidin-2-yl)piperidin-4-yl)methoxy)-3-fluorophenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 7.13 (1H, d), 7.08 (1H, d), 6.89 (1H, m), 6.02 (1H, s), 4.80 (2H, d), 3.54 (2H, m), 2.94 (2H, m), 2.61 (1H, m), 2.48 (2H, m), 2.47 (4H, m), 2.21 (2H, m), 1.86 (2H, d), 1.81 (1H, m), 1.26 (2H, m), 1.20 (3H, m)

Preparative Example 43: Preparation of 5-(4-((5-bromopyridin-2-yloxy)methyl)piperidin-1-yl)-3-isopropyl-1,2,4-oxadiazole

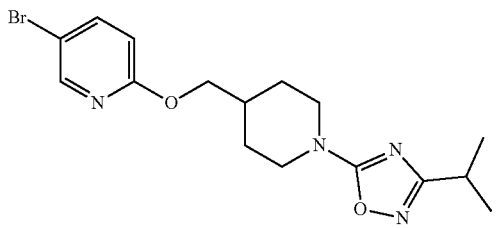 [SMILES: CC(C)c1noc(N2CCC(COc3ccc(Br)cn3)CC2)n1]

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate, and 5-bromo-2-hydroxypyridine was used instead of the 4-bromophenol.

$^1$H NMR (400, CDCl$_3$): 8.21 (1H, s), 7.38 (1H, d), 7.15 (1H, d), 4.24 (2H, d), 3.86 (2H, d), 3.15 (2H, m), 2.91 (1H, m), 1.48 (2H, m), 1.32 (6H, d)

Preparative Example 44: Preparation of ethyl 4-(6-((1-(3-isopropyl-1,2,4-oxadiazol-5-yl)piperidin-4-yl)methoxy)pyridin-3-yl)cyclohex-3-enecarboxylate

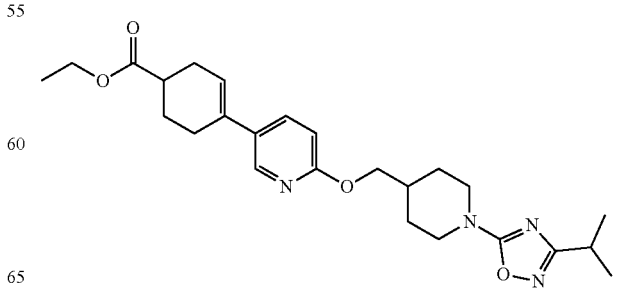

The title compound was prepared in the same manner as in <Preparative Example 17>, except that 5-(4-((5-bromopyridin-2-yloxy)methyl)piperidin-1-yl)-3-isopropyl-1,2,4-oxadiazole was used instead of the tert-butyl 4-((4-bromophenoxy)methyl)piperidine-1-carboxylate.

$^1$H NMR (400, CDCl$_3$): 8.14 (1H, d), 7.61 (1H, dd), 6.68 (1H, d), 6.06 (1H, m), 4.24 (2H, d), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 45: Preparation of 4-(6-((1-(3-isopropyl-1,2,4-oxadiazol-5-yl)piperidin-4-yl)methoxy)pyridin-3-yl)cyclohex-3-enecarboxylic Acid

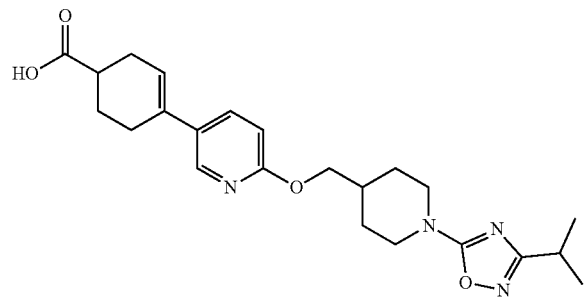 [SMILES: CC(C)c1noc(N2CCC(COc3ccc(C4=CCC(C(=O)O)CC4)cn3)CC2)n1]

The title compound was prepared in the same manner as in <Preparative Example 18>, except that ethyl 4-(6-((1-(3-isopropyl-1,2,4-oxadiazol-5-yl)piperidin-4-yl)methoxy)pyridin-3-yl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.14 (1H, d), 7.61 (1H, dd), 6.68 (1H, d), 6.06 (1H, m), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 46: Preparation of 2-(4-((5-bromopyridin-2-yloxy)methyl)piperidin-1-yl)-5-ethylpyrimidine

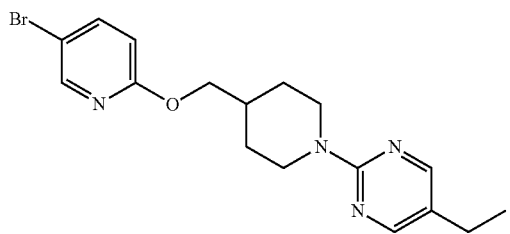 [SMILES: CCc1cnc(N2CCC(COc3ccc(Br)cn3)CC2)nc1]

The title compound was prepared in the same manner as in <Preparative Example 8>, except that 5-bromo-2-hydroxypyridine was used instead of the 4-bromophenol.

$^1$H NMR (400, CDCl$_3$): 8.21 (2H, s), 8.21 (1H, s), 7.38 (1H, d), 7.15 (1H, d), 4.80 (2H, d), 3.54 (2H, m), 2.48 (2H, m), 1.86 (2H, d), 1.81 (1H, m), 1.26 (2H, m), 1.20 (3H, m)

Preparative Example 47: Preparation of ethyl 4-(6-((1-(5-ethylpyrimidin-2-yl)piperidin-4-yl)methoxy)pyridin-3-yl)cyclohex-3-enecarboxylate

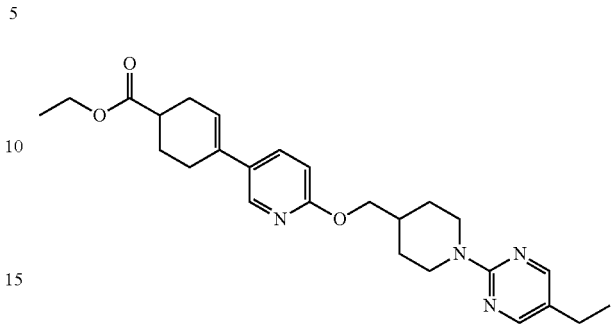

The title compound was prepared in the same manner as in <Preparative Example 17>, except that 2-(4-((5-bromopyridin-2-yloxy)methyl)piperidin-1-yl)-5-ethylpyrimidine was used instead of the tert-butyl 4-((4-bromophenoxy)methyl)piperidine-1-carboxylate.

$^1$H NMR (400, CDCl$_3$): 8.21 (2H, s), 8.15 (1H, d), 7.61 (1H, dd), 6.69 (1H, d), 6.06 (1H, m), 4.80 (2H, d), 4.19 (2H, m), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 48: Preparation of 4-(6-((1-(5-ethylpyrimidin-2-yl)piperidin-4-yl)methoxy)pyridin-3-yl)cyclohex-3-enecarboxylic Acid

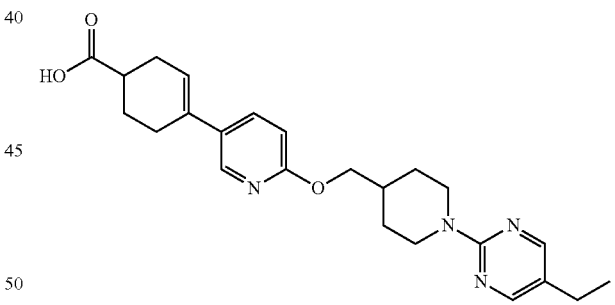

The title compound was prepared in the same manner as in <Preparative Example 18>, except that ethyl 4-(6-((1-(5-ethylpyrimidin-2-yl)piperidin-4-yl)methoxy)pyridin-3-yl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 8.15 (1H, d), 7.61 (1H, dd), 6.69 (1H, d), 6.06 (1H, m), 4.80 (2H, d), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m)

Preparative Example 49: Preparation of 2-(4-((4-bromo-2-(trifluoromethyl)phenoxy)methyl)piperidin-1-yl)-5-ethylpyrimidine

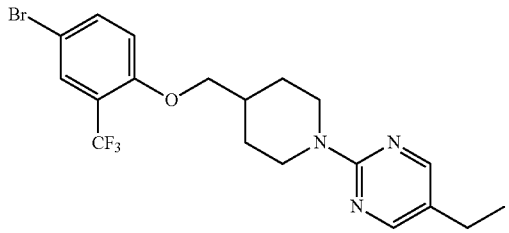

The title compound was prepared in the same manner as in <Preparative Example 8>, except that 4-bromo-2-(trifluoromethyl)phenol was used instead of the 4-bromophenol.

$^1$H NMR (400, CDCl$_3$): 8.21 (2H, s), 7.47 (1H, dd), 6.91 (1H, d), 6.10 (1H, d), 4.80 (2H, d), 3.54 (2H, m), 2.48 (2H, m), 1.86 (2H, d), 1.81 (1H, m), 1.26 (2H, m), 1.20 (3H, m)

Preparative Example 50: Preparation of ethyl 4-(4-((1-(5-ethylpyrimidin-2-yl)piperidin-4-yl)methoxy)-3-(trifluoromethyl)phenyl)cyclohex-3-enecarboxylate

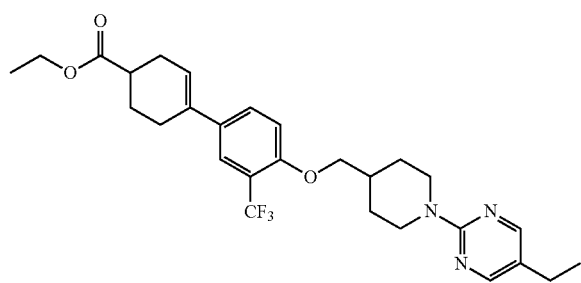 [SMILES: CCOC(=O)C1CC=C(c2ccc(OCC3CCN(c4ncc(CC)cn4)CC3)c(C(F)(F)F)c2)CC1]

The title compound was prepared in the same manner as in <Preparative Example 17>, except that 2-(4-((4-bromo-2-(trifluoromethyl)phenoxy)methyl)piperidin-1-yl)-5-ethylpyrimidine was used instead of the tert-butyl 4-((4-bromophenoxy)methyl)piperidine-1-carboxylate.

$^1$H NMR (400, CDCl$_3$): 8.21 (2H, s), 7.47 (1H, dd), 6.91 (1H, d), 6.10 (1H, d), 6.06 (1H, m), 4.80 (2H, d), 4.19 (2H, m), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 51: Preparation of 4-(4-((1-(5-ethylpyrimidin-2-yl)piperidin-4-yl)methoxy)-3-(trifluoromethyl)phenyl)cyclohex-3-enecarboxylic Acid

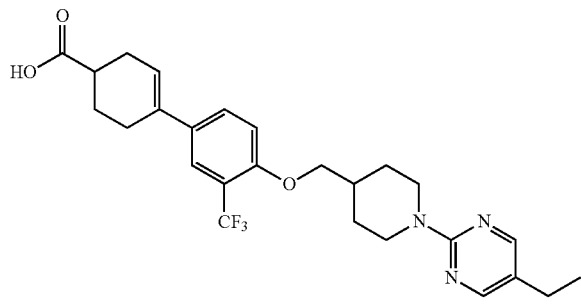 [SMILES: CCc1cnc(N2CCC(COc3ccc(C4=CCC(C(=O)O)CC4)cc3C(F)(F)F)CC2)nc1]

The title compound was prepared in the same manner as in <Preparative Example 18>, except that ethyl 4-(4-((1-(5-ethylpyrimidin-2-yl)piperidin-4-yl)methoxy)-3-(trifluoromethyl)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 7.47 (1H, dd), 6.91 (1H, d), 6.10 (1H, d), 6.06 (1H, m), 4.80 (2H, d), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m)

Preparative Example 52: Preparation of 5-bromo-2-((1-(5-ethylpyrimidin-2-yl)piperidin-4-yl)methoxy)benzonitrile

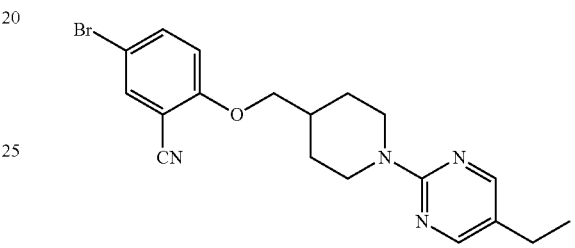

The title compound was prepared in the same manner as in <Preparative Example 8>, except that 5-bromo-2-hydroxybenzonitrile was used instead of the 4-bromophenol.

$^1$H NMR (400, CDCl$_3$): 8.21 (2H, s), 7.53 (2H, m), 6.87 (1H, d), 4.80 (2H, d), 3.54 (2H, m), 2.48 (2H, m), 1.86 (2H, d), 1.81 (1H, m), 1.26 (2H, m), 1.20 (3H, m)

Preparative Example 53: Preparation of ethyl 4-(3-cyano-4-((1-(5-ethylpyrimidin-2-yl) piperidin-4-yl)methoxy)phenyl)cyclohex-3-enecarboxylate

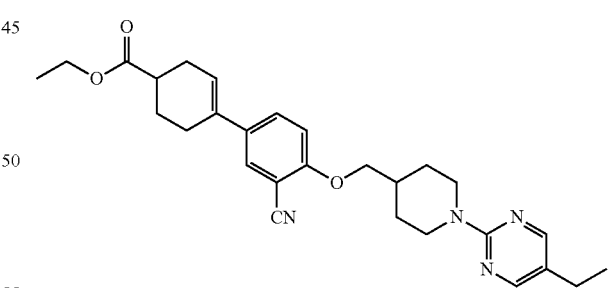

The title compound was prepared in the same manner as in <Preparative Example 17>, except that 5-bromo-2-((1-(5-ethylpyrimidin-2-yl)piperidin-4-yl)methoxy)benzonitrile was used instead of the tert-butyl 4-((4-bromophenoxy)methyl)piperidine-1-carboxylate.

$^1$H NMR (400, CDCl$_3$): 8.21 (2H, s), 7.53 (2H, m), 6.87 (1H, d), 6.06 (1H, m), 4.80 (2H, d), 4.19 (2H, d), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 54: Preparation of 4-(3-cyano-4-((1-(5-ethylpyrimidin-2-yl)piperidin-4-yl)methoxy)phenyl)cyclohex-3-enecarboxylic Acid

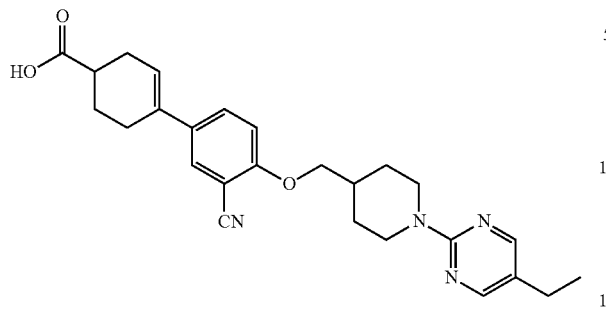

The title compound was prepared in the same manner as in <Preparative Example 18>, except that ethyl 4-(3-cyano-4-((1-(5-ethylpyrimidin-2-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 7.53 (2H, m), 6.87 (1H, d), 6.06 (1H, m), 4.80 (2H, d), 3.54 (2H, d), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m)

Preparative Example 55: Preparation of 2-(4-((4-bromo-2-methylphenoxy)methyl)piperidin-1-yl)-5-ethylpyrimidine

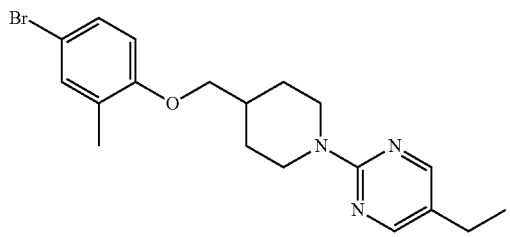 [SMILES: CCc1cnc(N2CCC(COc3ccc(Br)cc3C)CC2)nc1]

The title compound was prepared in the same manner as in <Preparative Example 8>, except that 4-bromo-o-cresol was used instead of the 4-bromophenol.

$^1$H NMR (400, CDCl$_3$): 8.21 (2H, s), 7.18 (2H, m), 6.72 (1H, d), 4.80 (2H, d), 3.54 (2H, m), 2.48 (2H, m), 2.22 (3H, s), 1.86 (2H, d), 1.81 (1H, m), 1.26 (2H, m), 1.20 (3H, m)

Preparative Example 56: Preparation of ethyl 4-(4-((1-(5-ethylpyrimidin-2-yl)piperidin-4-yl)methoxy)-3-methylphenyl)cyclohex-3-enecarboxylate

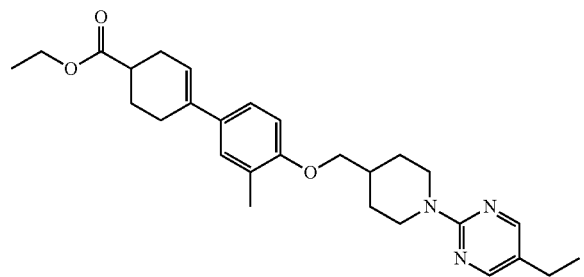

The title compound was prepared in the same manner as in <Preparative Example 17>, except that 2-(4-((4-bromo-2-methylphenoxy)methyl)piperidin-1-yl)-5-ethylpyrimidine was used instead of the tert-butyl 4-((4-bromophenoxy)methyl)piperidine-1-carboxylate.

$^1$H NMR (400, CDCl$_3$): 8.21 (2H, s), 7.18 (2H, m), 6.72 (1H, d), 6.06 (1H, m), 4.80 (2H, d), 4.19 (2H, m), 3.54 (2H, d), 2.94 (2H, m), 2.61 (1H, m), 2.48 (2H, m), 2.47 (4H, m), 2.21 (5H, m), 1.86 (2H, d), 1.81 (1H, m), 1.29 (3H, m), 1.26 (2H, m), 1.20 (3H, m)

Preparative Example 57: Preparation of 4-(4-((1-(5-ethylpyrimidin-2-yl)piperidin-4-yl)methoxy)-3-methylphenyl)cyclohex-3-enecarboxylic Acid

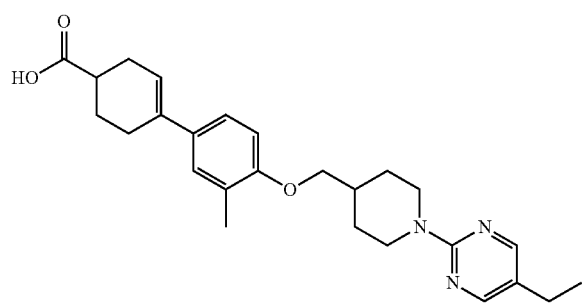

The title compound was prepared in the same manner as in <Preparative Example 18>, except that ethyl 4-(4-((1-(5-ethylpyrimidin-2-yl)piperidin-4-yl)methoxy)-3-methylphenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 7.18 (2H, m), 6.72 (1H, d), 6.06 (1H, m), 4.80 (2H, d), 3.54 (2H, d), 2.94 (2H, m), 2.61 (1H, m), 2.48 (2H, m), 2.47 (4H, m), 2.21 (5H, m), 1.86 (2H, d), 1.81 (1H, m), 1.29 (3H, m), 1.26 (2H, m)

Preparative Example 58: Preparation of 2-(4-((4-bromo-3-fluorophenoxy)methyl)piperidin-1-yl)-5-ethylpyrimidine

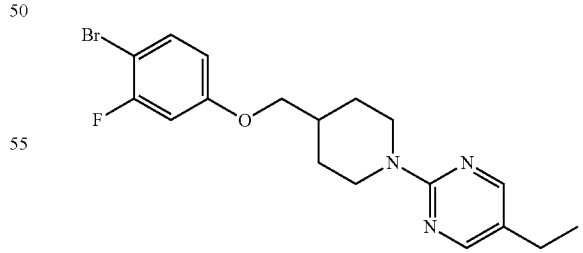

The title compound was prepared in the same manner as in <Preparative Example 8>, except that 4-bromo-3-fluorophenol was used instead of the 4-bromophenol.

$^1$H NMR (400, CDCl$_3$): 8.21 (2H, s), 7.12 (1H, t), 6.63 (1H, dd), 6.56 (2H, m), 4.80 (2H, d), 3.54 (2H, m), 2.48 (2H, m), 1.86 (2H, d), 1.81 (1H, m), 1.26 (2H, m), 1.20 (3H, m)

Preparative Example 59: Preparation of ethyl 4-(4-((1-(5-ethylpyrimidin-2-yl)piperidin-4-yl)methoxy)-2-fluorophenyl)cyclohex-3-enecarboxylate

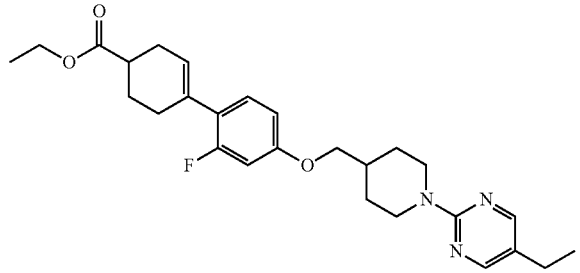 [SMILES: CCOC(=O)C1CC=C(c2ccc(OCC3CCN(c4ncc(CC)cn4)CC3)cc2F)CC1]

The title compound was prepared in the same manner as in <Preparative Example 17>, except that 2-(4-((4-bromo-3-fluorophenoxy)methyl)piperidin-1-yl)-5-ethylpyrimidine was used instead of the tert-butyl 4-((4-bromophenoxy)methyl)piperidine-1-carboxylate.

$^1$H NMR (400, CDCl$_3$): 8.21 (2H, s), 7.12 (1H, t), 6.63 (1H, dd), 6.56 (2H, m), 6.02 (1H, s), 4.80 (2H, d), 4.19 (2H, m), 3.54 (2H, m), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m), 1.20 (3H, m)

Preparative Example 60: Preparation of 4-(4-((1-(5-ethylpyrimidin-2-yl)piperidin-4-yl)methoxy)-2-fluorophenyl)cyclohex-3-enecarboxylic Acid

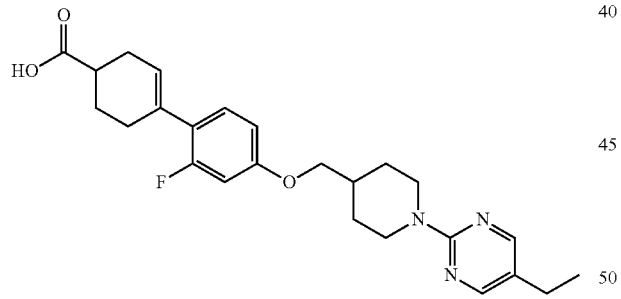

The title compound was prepared in the same manner as in <Preparative Example 18>, except that ethyl 4-(4-((1-(5-ethylpyrimidin-2-yl)piperidin-4-yl)methoxy)-2-fluorophenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 8.21 (2H, s), 7.12 (1H, t), 6.63 (1H, dd), 6.56 (2H, m), 6.02 (1H, s), 4.80 (2H, d), 3.54 (2H, m), 2.94 (2H, m), 2.61 (1H, m), 2.48 (2H, m), 2.47 (4H, m), 2.21 (2H, m), 1.86 (2H, d), 1.81 (1H, m), 1.29 (3H, m), 1.26 (2H, m)

Preparative Example 61: Preparation of 5-(4-((4-bromo-3-fluorophenoxy)methyl)piperidin-1-yl)-3-isopropyl-1,2,4-oxadiazole

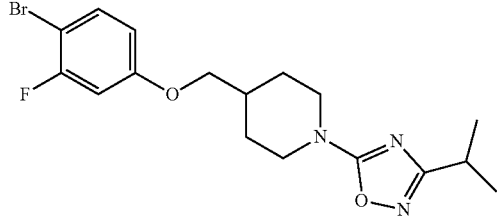 [SMILES: CC(C)c1noc(N2CCC(COc3ccc(Br)c(F)c3)CC2)n1]

The title compound was prepared in the same manner as in <Preparative Example 8>, except that (1-(3-isopropyl-1,2,4-oxadiazol-5-yl)piperidin-4-yl)methyl methanesulfonate was used instead of the (1-(5-ethylpyrimidin-2-yl)piperidin-4-yl)methyl methanesulfonate, and 4-bromo-3-fluorophenol was used instead of the 4-bromophenol.

$^1$H NMR (400, CDCl$_3$): 7.13 (1H, t), 6.63 (1H, dd), 6.55 (1H, dd), 4.24 (2H, d), 3.86 (2H, d), 3.15 (2H, m), 2.91 (1H, m), 1.91 (2H, m), 1.48 (2H, s), 1.32 (6H, d)

Preparative Example 62: Preparation of ethyl 4-(2-fluoro-4-((1-(3-isopropyl-1,2,4-oxadiazol-5-yl)piperidin-4-yl)methoxy)phenyl)cyclohex-3-enecarboxylate

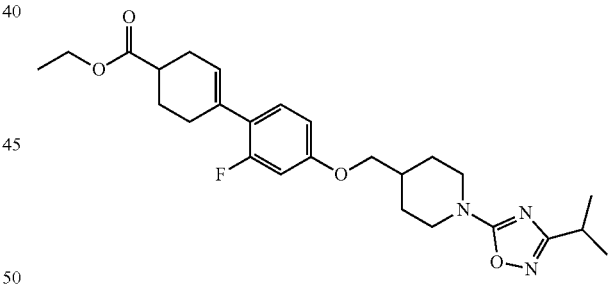

The title compound was prepared in the same manner as in <Preparative Example 17>, except that 5-(4-((4-bromo-3-fluorophenoxy)methyl)piperidin-1-yl)-3-isopropyl-1,2,4-oxadiazole was used instead of the tert-butyl 4-((4-bromophenoxy)methyl)piperidine-1-carboxylate.

$^1$H NMR (400, CDCl$_3$): 7.13 (1H, t), 6.63 (1H, dd), 6.55 (1H, dd), 6.02 (1H, s), 4.24 (2H, d), 4.19 (2H, m), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d), 1.29 (3H, m)

Preparative Example 63: Preparation of 4-(2-fluoro-4-((1-(3-isopropyl-1,2,4-oxadiazol-5-yl)piperidin-4-yl)methoxy)phenyl)cyclohex-3-enecarboxylic Acid

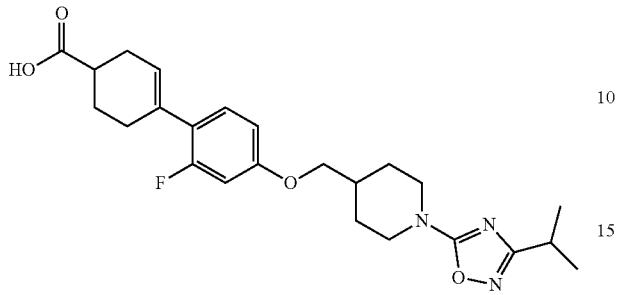

The title compound was prepared in the same manner as in <Preparative Example 18>, except that ethyl 4-(3-fluoro-4-((1-(3-isopropyl-1,2,4-oxadiazol-5-yl)piperidin-4-yl)methoxy)phenyl)cyclohex-3-enecarboxylate was used instead of the tert-butyl 4-((4-(4-(ethoxycarbonyl)cyclohex-1-enyl)phenoxy)methyl)piperidine-1-carboxylate.

$^1$H NMR (400, CDCl$_3$): 7.13 (1H, t), 6.63 (1H, dd), 6.55 (1H, dd), 6.02 (1H, s), 4.24 (2H, d), 3.86 (2H, d), 3.15 (2H, m), 2.91 (1H, m), 2.61 (1H, m), 2.47 (4H, m), 2.21 (2H, m), 1.91 (2H, m), 1.48 (2H, m), 1.32 (6H, d)

Preparative Example 64: Preparation of (−)-(4-bromocyclohex-3-enyl)(3,3-difluoropyrrolidin-1-yl)methanone

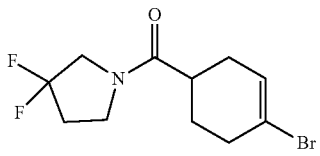 [SMILES: O=C(C1CC=C(Br)CC1)N1CCC(F)(F)C1]

The title compound was prepared in the same manner as in <Preparative Example 37>, except that 3,3-difluoropyrrolidine hydrochloride was used instead of the D-prolinol.

$^1$H NMR (400, CDCl$_3$): 6.06 (1H, m), 4.80 (2H, d), 4.70 (4H, m), 3.80 (2H, m), 2.85 (2H, m), 2.61 (1H, m), 2.30 (2H, m)

Preparative Example 65: Preparation of (+)-(4-bromocyclohex-3-enyl)(3,3-difluoropyrrolidin-1-yl)methanone

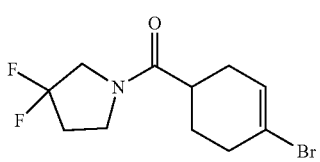 [SMILES: O=C(C1CC=C(Br)CC1)N1CCC(F)(F)C1]

The title compound was prepared in the same manner as in <Preparative Example 38>, except that 3,3-difluoropyrrolidine hydrochloride was used instead of the D-prolinol.

$^1$H NMR (400, CDCl$_3$): 6.06 (1H, m), 4.80 (2H, d), 4.70 (4H, m), 3.80 (2H, m), 2.85 (2H, m), 2.61 (1H, m), 2.30 (2H, m)

Preparative Example 66: Preparation of (−)-(4-bromocyclohex-3-enyl)(3,3,4,4-tetrafluoropyrrolidin-1-yl)methanone

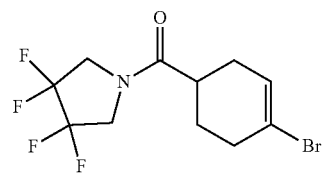 [SMILES: O=C(C1CC=C(Br)CC1)N1CC(F)(F)C(F)(F)C1]

The title compound was prepared in the same manner as in <Preparative Example 37>, except that 3,3,4,4-tetrafluoropyrrolidine hydrochloride was used instead of the D-prolinol.

$^1$H NMR (400, CDCl$_3$): 6.06 (1H, m), 4.02 (4H, m), 3.80 (2H, m), 2.85 (2H, m), 2.61 (1H, m), 2.30 (2H, m)

Preparative Example 67: Preparation of (+)-(4-bromocyclohex-3-enyl)(3,3,4,4-tetrafluoropyrrolidin-1-yl)methanone

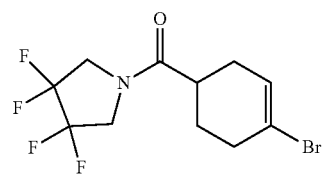 [SMILES: O=C(C1CC=C(Br)CC1)N1CC(F)(F)C(F)(F)C1]

The title compound was prepared in the same manner as in <Preparative Example 38>, except that 3,3,4,4-tetrafluoropyrrolidine hydrochloride was used instead of the D-prolinol.

$^1$H NMR (400, CDCl$_3$): 6.06 (1H, m), 4.02 (4H, m), 3.80 (2H, m), 2.85 (2H, m), 2.61 (1H, m), 2.30 (2H, m)

Preparative Example 68: Preparation of 5-ethyl-2-(4-((3-fluoro-4-(4,4,5,5-tetramethyl-1,3,2-dioxaborolan-2-yl)phenoxy)methyl)piperidin-1-yl)pyrimidine

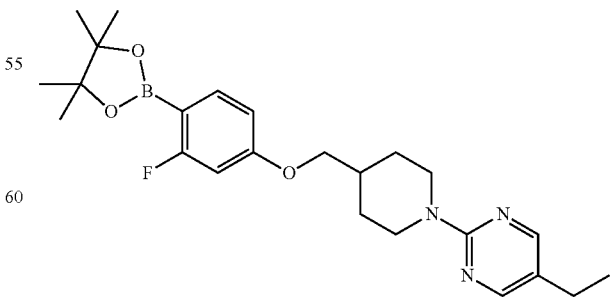

The title compound was prepared in the same manner as in <Preparative Example 8>, except that 3-fluoro-4-(4,4,5, 5-tetramethyl-1,3,2-dioxaborolan-2-yl)phenol was used instead of the 4-bromophenol.

¹H NMR (400, CDCl₃): 8.16 (2H, s), 7.11 (1H, t), 6.62 (1H, dd), 6.56 (1H, dd), 4.76 (2H, d), 3.84 (2H, d), 2.90 (2H, t), 2.42 (2H, d), 2.09 (1H, m), 1.94 (2H, d), 1.45-1.25 (15H, m), 1.22 (3H, t)

Example 1: Preparation of tert-butyl 4-((4-(4-((R)-1-hydroxypropan-2-ylcarbamoyl)cyclohex-1-enyl)phenoxy)methyl)piperidine-1-carboxylate

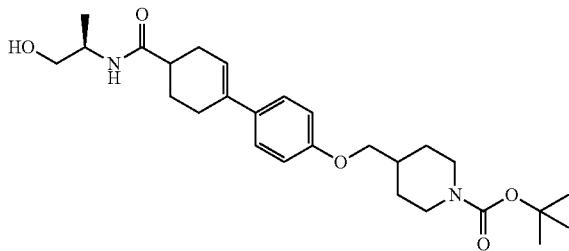

200 mg of 4-(4-((1-(tert-butoxycarbonyl)piperidin-4-yl)methoxy)phenyl)cyclohex-3-enecarboxylic acid was dissolved in 20 Et of DMF in a 100 μl flask, and stirred under nitrogen. 140 mg of EDCI and 110 mg of HOBt were sequentially added dropwise thereto, and the resulting mixture was then additionally stirred for 10 minutes. 72 mg of (R)-2-amino-1-propanol was added dropwise thereto, and the mixture was then stirred at room temperature for 5 hours. After the reaction was terminated, 50 μl of distilled water was slowly added at 0° C., and the resulting solids were filtered, and dried to obtain a desired compound as a white solid (Amount obtained: 167 mg/Yield: 73%).

¹H NMR (400, CDCl₃): 7.31 (2H, d), 6.85 (2H, d), 6.05 (1H, s), 5.75 (1H, d) 4.15 (3H, m), 3.85 (2H, d), 3.72 (1H, m), 3.52 (1H, m), 2.78 (2H, m), 2.50 (5H, m), 2.12 (1H, m), 1.95 (1H, m), 1.88 (2H, m), 1.52 (9H, s), 1.30 (2H, m), 1.25 (3H, d)

Example 2: Preparation of tert-butyl 4-((4-(4-(cyclopropylcarbamoyl)cyclohex-1-enyl)phenoxy)methyl)piperidine-1-carboxylate

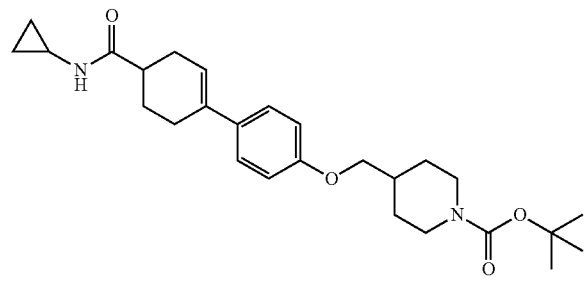 [SMILES: CC(C)(C)OC(=O)N1CCC(COc2ccc(C3=CCC(C(=O)NC4CC4)CC3)cc2)CC1]

The title compound was prepared in the same manner as in <Example 1>, except that cyclopropylamine is used instead of the (R)-2-amino-1-propanol (Amount obtained: 180 mg/Yield: 80%).

¹H NMR (400, CDCl₃): 7.31 (2H, d), 6.86 (2H, d), 6.05 (1H, s), 5.75 (1H, d), 4.15 (3H, m), 3.81 (2H, d), 2.78 (3H, m), 3.45 (5H, m), 2.08 (1H, m), 1.98 (1H, m), 1.82 (2H, m), 1.52 (9H, s), 1.28 (2H, m), 0.78 (2H, d), 0.55 (2H, d)

Example 3: Preparation of tert-butyl 4-((4-(4-(2,2-difluoroethylcarbamoyl)cyclohex-1-enyl)phenoxy)methyl)piperidine-1-carboxylate

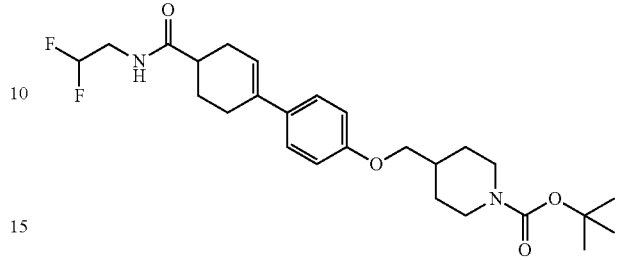

The title compound was prepared in the same manner as in <Example 1>, except that 2,2-difluoroethylamine was used instead of the (R)-2-amino-1-propanol (Amount obtained: 120 mg/Yield: 72%)

¹H NMR (400, CDCl₃): 7.31 (2H, d), 6.85 (2H, d), 6.05 (1H, s), 5.87 (1H, m), 4.15 (2H, m), 3.85 (2H, d), 3.68 (2H, m), 2.78 (2H, m), 2.50 (5H, m), 2.12 (1H, m), 1.85 (4H, m), 1.52 (9H, s), 1.30 (2H, m)

Example 4: Preparation of tert-butyl 4-((4-(4-((R)-2,3-dihydroxypropylcarbamoyl)cyclohex-1-enyl)phenoxy)methyl)piperidine-1-carboxylate

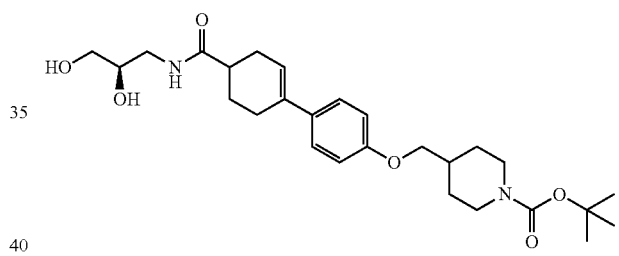

The title compound was prepared in the same manner as in <Example 1>, except that (R)-3-amino-1,2-propanediol was used instead of the (R)-2-amino-1-propanol (Amount obtained: 132 mg/Yield: 68%).

¹H NMR (400, CDCl₃): 7.32 (2H, d), 6.82 (2H, d), 6.04 (2H, s), 4.18 (2H, m), 3.85 (3H, m), 3.52 (4H, m), 2.98 (2H, m), 2.78 (2H, m), 2.52 (5H, m), 2.12 (1H, m), 1.95 (1H, m), 1.88 (2H, m), 1.52 (9H, s), 1.30 (2H, m)

Example 5: Preparation of tert-butyl 4-((4-(4-((R)-3-hydroxypyrrolidine-1-carbonyl)cyclohex-1-enyl)phenoxy)methyl)piperidine-1-carboxylate

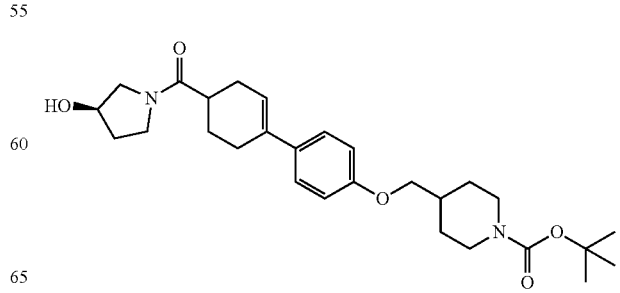

The title compound was prepared in the same manner as in <Example 1>, except that (R)-(+)-3-pyrrolidinol was used instead of the (R)-2-amino-1-propanol (Amount obtained: 130 mg/Yield: 56%).

¹H NMR (400, CDCl₃): 7.31 (2H, d), 6.85 (2H, d), 6.05 (1H, s), 4.60 (1H, d), 4.15 (2H, m), 3.85 (2H, d), 3.62 (4H, m), 2.72 (3H, m), 2.58 (3H, m), 2.34 (1H, m), 1.98 (8H, m), 1.52 (9H, s), 1.30 (2H, m)

Example 6: Preparation of tert-butyl 4-((4-(4-((3-hydroxypropyl)(methyl)carbamoyl)cyclohex-1-enyl) phenoxy)methyl)piperidine-1-carboxylate

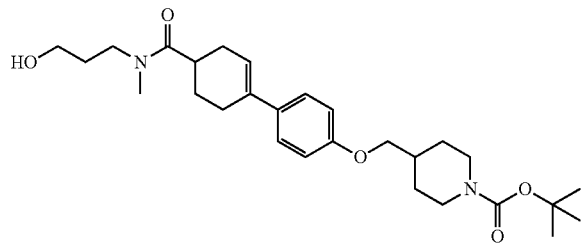 [SMILES: CN(CCCO)C(=O)C1CC=C(c2ccc(OCC3CCN(C(=O)OC(C)(C)C)CC3)cc2)CC1]

The title compound was prepared in the same manner as in <Example 1>, except that 3-(methylamino)-1-propanol was used instead of the (R)-2-amino-1-propanol (Amount obtained: 110 mg/Yield: 58%).

¹H NMR (400, CDCl₃): 7.32 (2H, d), 6.87 (2H, d), 6.05 (1H, s), 4.18 (2H, m), 3.95 (1H, m), 3.82 (2H, m), 3.62 (2H, m), 3.54 (2H, m), 3.12 (3H, s), 2.78 (3H, m), 2.50 (3H, m), 2.32 (1H, m), 1.95 (6H, m), 1.78 (2H, m), 1.52 (9H, s), 1.28 (2H, m)

Example 7: Preparation of tert-butyl 4-((4-(4-(morpholine-4-carbonyl)cyclohex-1-enyl)phenoxy) methyl)piperidine-1-carboxylate

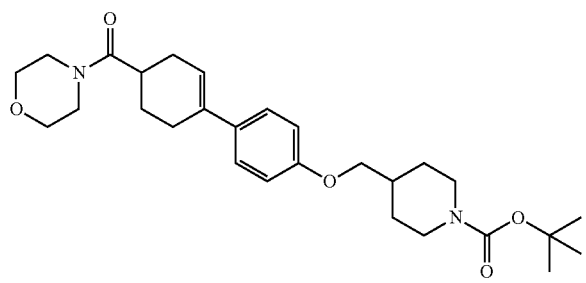 [SMILES: CC(C)(C)OC(=O)N1CCC(COc2ccc(C3=CCC(C(=O)N4CCOCC4)CC3)cc2)CC1]

The title compound was prepared in the same manner as in <Example 1>, except that morpholine was used instead of the (R)-2-amino-1-propanol (Amount obtained: 200 mg/Yield: 80%).

¹H NMR (400, CDCl₃): 7.31 (2H, d), 6.85 (2H, d), 6.05 (1H, s), 4.17 (2H, m), 3.83 (2H, m), 3.72 (4H, m), 3.58 (4H, m), 2.79 (3H, m), 2.59 (3H, m), 2.31 (1H, m), 2.02 (3H, m), 1.89 (2H, m), 1.52 (9H, s), 1.33 (2H, m).

Example 8: Preparation of 4-(4-((1-(5-ethylpyrimidin-2-yl)piperidin-4-yl)methoxy)phenyl)-N—((R)-1-hydroxypropan-2-yl)cyclohex-3-enecarboxamide

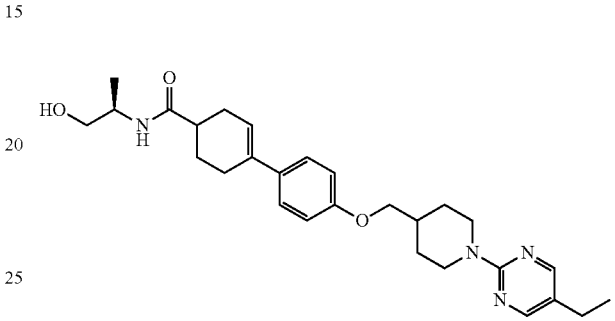

250 mg of 4-(4-((1-(5-ethylpyrimidin-2-yl)piperidin-4-yl) methoxy)phenyl)cyclohex-3-enecarboxylic acid was dissolved in 20 μl of DMF in a 100 μl flask, and stirred under nitrogen. 140 mg of EDCI and 110 mg of HOBt were sequentially added dropwise thereto, and the resulting mixture was additionally stirred for 10 minutes. 0.1 μl of (R)-2-amino-1-propanol was added dropwise thereto, and the mixture was then stirred at room temperature for 5 hours. After the reaction was terminated, 50 μl of distilled water was slowly added at 0° C., and the resulting solids were filtered, and dried to obtain a desired compound as a white solid (Amount obtained: 230 mg/Yield: 82%).

¹H NMR (400, CDCl₃): 8.19 (2H, s), 7.31 (2H, d), 6.85 (2H, d), 6.03 (1H, s), 5.75 (1H, d), 4.79 (2H, d), 4.15 (1H, m), 3.85 (2H, d), 3.72 (1H, m), 3.58 (1H, m), 2.94 (2H, t), 2.82 (1H, m), 2.48 (7H, m), 2.14 (2H, m), 1.88 (3H, m), 1.38 (2H, m), 1.23 (3H, t)

Example 9: Preparation of 4-(4-((1-(5-ethylpyrimidin-2-yl)piperidin-4-yl)methoxy)phenyl)-N-(3-hydroxypropyl)cyclohex-3-enecarboxamide

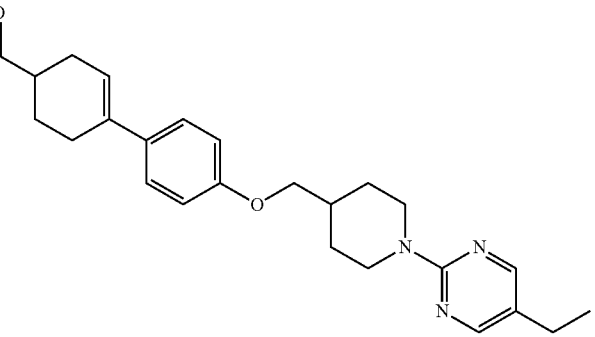

The title compound was prepared in the same manner as in <Example 8>, except that 3-amino-1-propanol was used instead of the (R)-2-amino-1-propanol (Amount obtained: 220 mg/Yield: 79%).

¹H NMR (400, CDCl₃): 8.19 (2H, s), 7.31 (2H, d), 6.85 (2H, d), 6.05 (1H, s), 5.95 (1H, t), 4.75 (2H, d), 3.85 (2H, d), 3.68 (2H, m), 3.48 (2H, m), 3.14 (1H, m), 2.94 (2H, m), 2.42 (7H, m), 2.12 (2H, m), 1.98 (3H, m), 1.72 (2H, m), 1.38 (2H, m), 1.21 (3H, t)

Example 10: Preparation of tert-butyl 4-((6-(4-((R)-2,3-dihydroxypropylcarbamoyl)cyclohex-1-enyl)pyridin-3-yloxy)methyl)piperidine-1-carboxylate

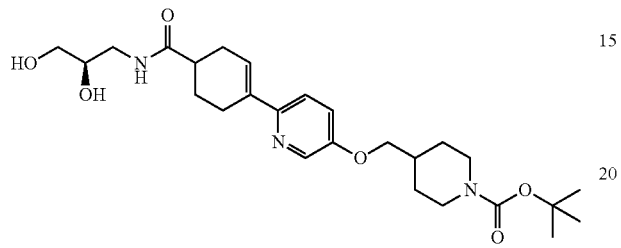

200 mg of 4-(5-((1-(tert-butoxycarbonyl)piperidin-4-yl)methoxy)pyridin-2-yl)cyclohex-3-enecarboxylic acid was dissolved in 25 μl of DMF, and stirred. 140 mg of EDCI and 110 mg of HOBt were sequentially added dropwise thereto, and the resulting mixture was then additionally stirred for 10 minutes. 0.15 μl of (R)-3-amino-1,2-propanediol was added dropwise thereto, and the mixture was stirred at room temperature for 3 hours. When the reaction was terminated, 50 td of distilled water was slowly added at 0° C., and the resulting solids were filtered, and dried to obtain a desired compound as a white solid (Amount obtained: 160 mg/Yield: 68%).

¹H NMR (400, CDCl₃): 8.22 (1H, s), 7.33 (1H, d), 7.18 (1H, d), 6.52 (1H, s), 6.28 (1H, m), 4.18 (2H, m), 3.85 (2H, d), 3.68 (1H, m), 3.72 (3H, m), 2.52 (4H, m), 2.18 (1H, m), 1.92 (4H, m), 1.34 (9H, s), 1.30 (2H, m)

Example 11: Preparation of tert-butyl 4-((6-(4-((S)-1-hydroxypropan-2-ylcarbamoyl)cyclohex-1-enyl)pyridin-3-yloxy)methyl)piperidine-1-carboxylate

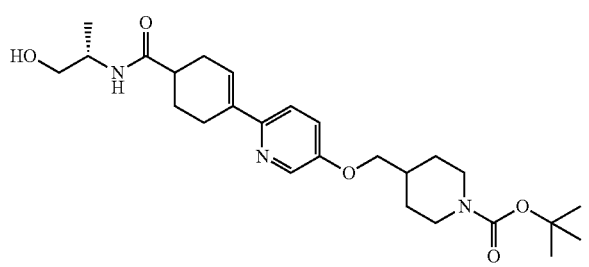 [SMILES: C[C@@H](CO)NC(=O)C1CC=C(c2ccc(OCC3CCN(C(=O)OC(C)(C)C)CC3)cn2)CC1]

The title compound was prepared in the same manner as in <Example 10>, except that (S)-2-amino-1-propanol was used instead of the (R)-3-amino-1,2-propanediol (Amount obtained: 155 mg/Yield: 70%).

¹H NMR (400, CDCl₃): 8.24 (1H, s), 7.33 (1H, d), 7.16 (1H, d), 6.54 (1H, s), 5.78 (1H, m), 4.18 (3H, m), 3.87 (2H, d), 3.64 (2H, m), 2.72 (3H, m), 2.52 (4H, m), 2.14 (1H, m), 1.84 (4H, m), 1.68 (1H, m), 1.48 (9H, s), 1.31 (2H, m), 1.20 (3H, d)

Example 12: Preparation of N—((R)-2,3-dihydroxypropyl)-4-(4-((1-(5-ethylpyrimidin-2-yl)piperidin-4-yl)methoxy)phenyl)cyclohex-3-enecarboxamide

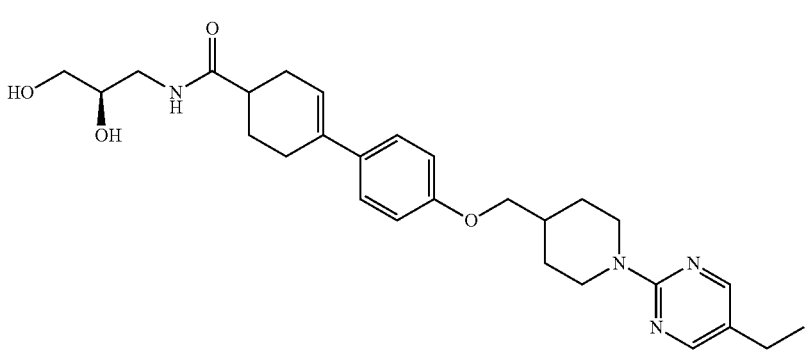 [SMILES: CCc1cnc(N2CCC(COc3ccc(C4=CCC(C(=O)NC[C@@H](O)CO)CC4)cc3)CC2)nc1]

The title compound was prepared in the same manner as in <Example 8>, except that (R)-3-amino-1,2-propanediol was used instead of the (R)-2-amino-1-propanol (Amount obtained: 200 mg/Yield: 85%).

¹H NMR (400, DMSO-_d6_): 8.23 (2H, s), 7.81 (1H, m), 7.33 (2H, d), 6.86 (2H, d), 6.05 (1H, s), 4.73 (1H, m), 4.67 (2H, d), 4.49 (1H, t), 3.85 (2H, d), 3.32 (4H, m), 2.88 (2H, t), 2.42 (7H, m), 1.98 (5H, m), 1.62 (2H, m), 1.18 (4H, m)

Example 13: Preparation of (4-(4-((1-(5-ethylpyrimidin-2-yl)piperidin-4-yl)methoxy)phenyl)cyclohex-3-enyl)(morpholino)methanone

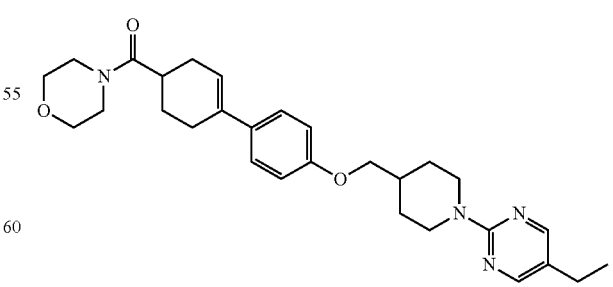

The title compound was prepared in the same manner as in <Example 8>, except that morpholine was used instead of the (R)-2-amino-1-propanol (Amount obtained: 175 mg/Yield: 65%).

¹H NMR (400, CDCl₃): 8.19 (2H, s), 7.33 (2H, d), 6.87 (2H, d), 6.06 (1H, s), 4.80 (2H, d), 3.85 (2H, d), 3.72 (6H, d), 3.58 (2H, m), 2.96 (2H, t), 2.78 (1H, m), 2.52 (7H, m), 2.28 (1H, m), 1.98 (5H, m), 1.38 (2H, m), 1.21 (3H, t)

Example 14: Preparation of tert-butyl 4-((6-(4-(1,3-dihydroxypropan-2-ylcarbamoyl)cyclohex-1-enyl)pyridin-3-yloxy)methyl)piperidine-1-carboxylate

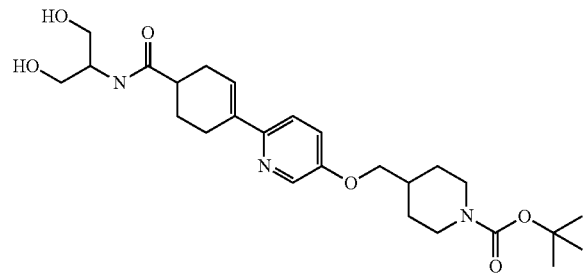 [SMILES: CC(C)(C)OC(=O)N1CCC(COc2ccc(C3=CCC(C(=O)NC(CO)CO)CC3)nc2)CC1]

The title compound was prepared in the same manner as in <Example 10>, except that 2-amino-1.3-propanediol was used instead of the (R)-3-amino-1,2-propanediol (Amount obtained: 195 mg/Yield: 85%).

¹H NMR (400, CDCl₃): 8.22 (1H, s), 7.32 (1H, d), 7.16 (1H, d), 6.49 (2H, m), 4.17 (2H, m), 4.03 (1H, m), 3.89 (6H, m), 2.76 (3H, m), 2.52 (4H, m), 2.15 (1H, m), 1.99 (3H, m), 1.84 (2H, m), 1.67 (1H, m), 1.48 (9H, s), 1.34 (2H, m)

Example 15: Preparation of N-(1,3-dihydroxypropan-2-yl)-4-(4-((1-(5-ethylpyrimidin-2-yl)piperidin-4-yl)methoxy)phenyl)cyclohex-3-enecarboxamide

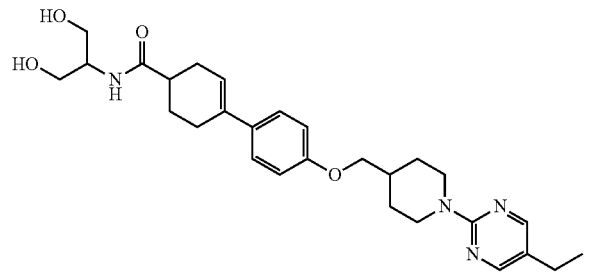 [SMILES: CCc1cnc(N2CCC(COc3ccc(C4=CCC(C(=O)NC(CO)CO)CC4)cc3)CC2)nc1]

The title compound was prepared in the same manner as in <Example 8>, except that 2-amino-1.3-propanediol was used instead of the (R)-2-amino-1-propanol (Amount obtained: 165 mg/Yield: 72%).

¹H NMR (400, DMSO-$d_6$): 8.22 (2H, s), 7.50 (1H, d), 7.33 (2H, d), 6.88 (2H, d), 4.63 (4H, m), 3.84 (2H, d), 3.73 (1H, m), 2.86 (2H, t), 2.43 (2H, m), 2.36 (2H, m), 1.98 (5H, m), 1.21 (7H, m), 1.98 (5H, m)

Example 16: Preparation of (4-(4-((1-(5-ethylpyrimidin-2-yl)piperidin-4-yl)methoxy)phenyl)cyclohex-3-enyl)((R)-3-hydroxypyrrolidin-1-yl)methanone

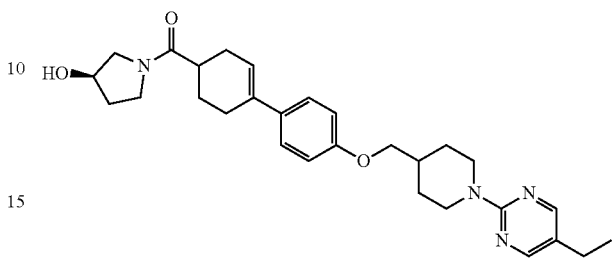

The title compound was prepared in the same manner as in <Example 8>, except that (R)-(+)-3-pyrrolidinol was used instead of the (R)-2-amino-1-propanol (Amount obtained: 165 mg/Yield: 72%).

¹H NMR (400, CDCl₃): 8.19 (2H, s), 7.33 (2H, d), 6.87 (2H, d), 6.07 (1H, s), 4.80 (2H, d), 4.55 (1H, d), 3.85 (2H, d), 4.55 (5H, m), 2.93 (2H, t), 2.48 (8H, m), 2.05 (7H, m), 1.61 (2H, m), 1.38 (2H, m), 1.18 (3H, m)

Example 17: Preparation of N—((R)-2,3-dihydroxypropyl)-4-(4-((1-(3-isopropyl-1,2,4-oxadiazol-5-yl)piperidin-4-yl)methoxy)phenyl)cyclohex-3-enecarboxamide

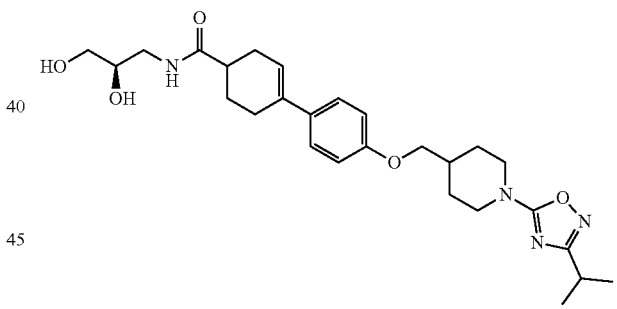

200 mg of 4-(4-((1-(3-isopropyl-1,2,4-oxadiazol-5-yl)piperidin-4-yl)methoxy)phenyl)cyclohex-3-enecarboxylic acid was dissolved in 25 it of DMF, and stirred. 140 mg of EDCI and 110 mg of HOBt were sequentially added dropwise thereto, and the resulting mixture was then additionally stirred for 10 minutes. 0.15 μl of (R)-3-amino-1,2-propanediol was added dropwise thereto, and the mixture was stirred at room temperature for 3 hours. After the reaction was terminated, 50 μl of distilled water was slowly added at 0° C., and the resulting solids were filtered, and dried to obtain a desired compound as a white solid (Amount obtained: 187 mg/Yield: 83%).

¹H NMR (400, CDCl₃): 7.32 (2H, d), 6.86 (2H, d), 6.15 (1H, t), 6.03 (1H, s), 4.23 (2H, d), 3.85 (2H, d), 3.80 (1H, m), 3.58 (2H, m), 3.48 (2H, m), 3.14 (4H, m), 2.92 (1H, m), 2.49 (5H, m), 2.09 (2H, m), 1.94 (3H, m), 1.43 (2H, m), 1.30 (6H, d)

Example 18: Preparation of N—((S)-2,3-dihydroxypropyl)-4-(4-((1-(3-isopropyl-1,2,4-oxadiazol-5-yl)piperidin-4-yl)methoxy)phenyl)cyclohex-3-enecarboxamide

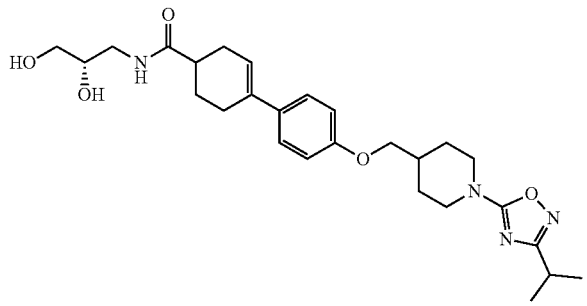 [SMILES: CC(C)c1noc(N2CCC(COc3ccc(C4=CCC(C(=O)NC[C@H](O)CO)CC4)cc3)CC2)n1]

The title compound was prepared in the same manner as in <Example 17>, except that (S)-3-amino-1,2-propanediol was used instead of the (R)-3-amino-1,2-propanediol (Amount obtained: 155 mg/Yield: 70%).

$^1$H NMR (400, CDCl$_3$): 7.32 (2H, d), 6.83 (2H, d), 6.21 (1H, t), 6.03 (1H, s), 4.20 (2H, d), 3.85 (2H, d), 3.80 (1H, m), 3.58 (2H, m), 3.48 (2H, m), 3.14 (4H, m), 2.92 (1H, m), 2.49 (5H, m), 2.09 (2H, m), 1.94 (3H, m), 1.43 (2H, m), 1.30 (6H, d)

Example 19: Preparation of N—((S)-1-hydroxypropan-2-yl)-4-(4-((1-(3-isopropyl-1,2,4-oxadiazol-5-yl)piperidin-4-yl)methoxy)phenyl)cyclohex-3-enecarboxamide

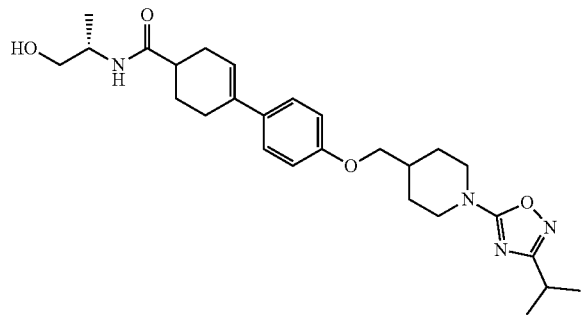

The title compound was prepared in the same manner as in <Example 17>, except that (S)-2-amino-1-propanol was used instead of the (R)-3-amino-1,2-propanediol (Amount obtained: 130 mg/Yield: 62%).

$^1$H NMR (400, CDCl$_3$): 7.33 (2H, d), 6.84 (2H, d), 6.04 (1H, s), 5.74 (1H, s), 4.23 (2H, d), 4.14 (1H, s), 3.84 (2H, d), 3.73 (1H, m), 3.69 (1H, m), 3.14 (2H, m), 2.91 (1H, m), 2.53 (5H, m), 2.08 (3H, m), 1.94 (3H, m), 1.47 (2H, m), 1.30 (6H, d), 1.20 (3H, m)

Example 20: Preparation of N—((R)-1-hydroxypropan-2-yl)-4-(4-((1-(3-isopropyl-1,2,4-oxadiazol-5-yl)piperidin-4-yl)methoxy)phenyl)cyclohex-3-enecarboxamide

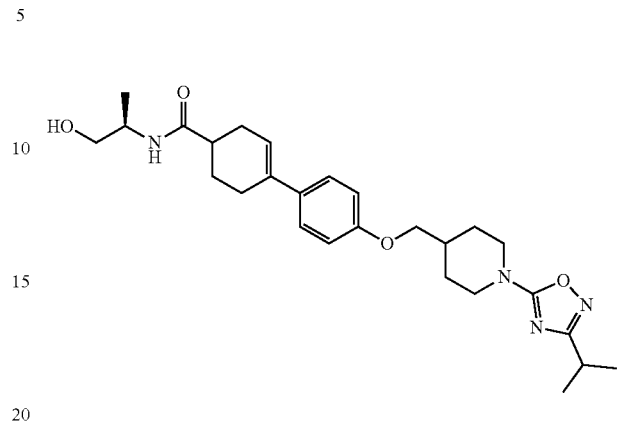

The title compound was prepared in the same manner as in <Example 17>, except that (R)-2-amino-1-propanol was used instead of the (R)-3-amino-1,2-propanediol (Amount obtained: 150 mg/Yield: 71%).

$^1$H NMR (400, CDCl$_3$): 7.33 (2H, d), 6.84 (2H, d), 6.04 (1H, s), 5.74 (1H, s), 4.23 (2H, d), 4.14 (1H, s), 3.84 (2H, d), 3.73 (1H, m), 3.69 (1H, m), 3.14 (2H, m), 2.91 (1H, m), 2.53 (5H, m), 2.08 (3H, m), 1.94 (3H, m), 1.47 (2H, m), 1.30 (6H, d), 1.20 (3H, m)

Example 21: Preparation of 4-(4-((1-(5-ethylpyrimidin-2-yl)piperidin-4-yl)methoxy)phenyl)-N-(2-hydroxyethyl)-N-methylcyclohex-3-enecarboxamide

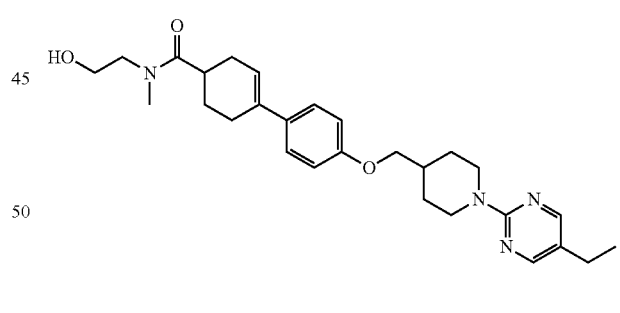

The title compound was prepared in the same manner as in <Example 8>, except that 2-(methylamino)ethanol was used instead of the (R)-2-amino-1-propanol (Amount obtained: 187 mg/Yield: 81%).

$^1$H NMR (400, CDCl$_3$): 8.19 (2H, s), 7.34 (2H, d), 6.87 (2H, d), 6.07 (1H, s), 4.80 (2H, d), 3.85 (4H, m), 3.63 (2H, m), 3.18 (3H, s), 2.96 (2H, t), 2.89 (1H, m), 2.48 (5H, m), 2.06 (5H, m), 1.38 (2H, m), 1.21 (3H, m)

Example 22: Preparation of N-(3-hydroxy-2,2-dimethylpropyl)-4-(4-((1-(3-isopropyl-1,2,4-oxadiazol-5-yl)piperidin-4-yl)methoxy)phenyl)cyclohex-3-enecarboxamide

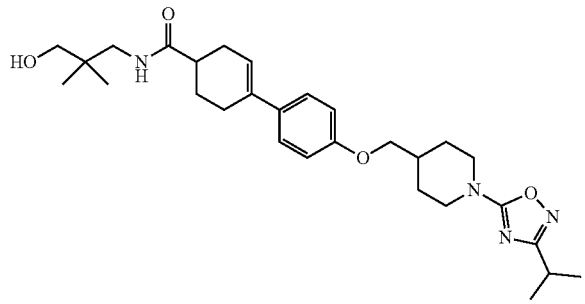 [SMILES: CC(C)c1noc(N2CCC(COc3ccc(C4=CCC(C(=O)NCC(C)(C)CO)CC4)cc3)CC2)n1]

The title compound was prepared in the same manner as in <Example 17>, except that 3-amino-2,2-dimethylpropan-1-ol was used instead of the (R)-3-amino-1,2-propanediol (Amount obtained: 195 mg/Yield: 89%).

$^1$H NMR (400, MeOD): 7.65 (1H, s), 7.31 (2H, d), 6.85 (2H, d), 6.02 (1H, s), 4.18 (2H, d), 3.87 (2H, d), 3.15 (6H, m), 2.86 (1H, m), 2.46 (5H, m), 2.04 (5H, m), 1.48 (2H, m), 1.28 (6H, d), 0.89 (6H, s)

Example 23: Preparation of N-(1,3-dihydroxypropan-2-yl)-4-(4-((1-(3-isopropyl-1,2,4-oxadiazol-5-yl)piperidin-4-yl)methoxy)phenyl)cyclohex-3-enecarboxamide

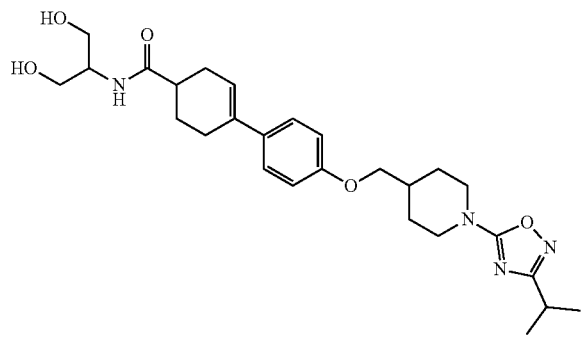 [SMILES: CC(C)c1noc(N2CCC(COc3ccc(C4=CCC(C(=O)NC(CO)CO)CC4)cc3)CC2)n1]

The title compound was prepared in the same manner as in <Example 17>, except that 2-amino-1,3-propanediol was used instead of the (R)-3-amino-1,2-propanediol (Amount obtained: 175 mg/Yield: 79%).

$^1$H NMR (400, MeOD): 7.27 (3H, d), 6.85 (2H, d), 6.02 (1H, s), 4.18 (2H, d), 3.87 (6H, d), 3.18 (3H, m), 2.86 (1H, m), 2.46 (5H, m), 2.04 (5H, m), 1.48 (2H, m), 1.28 (6H, d)

Example 24: Preparation of tert-butyl 4-((5-(4-((S)-1-hydroxypropan-2-ylcarbamoyl)cyclohex-1-enyl)pyridin-2-yloxy)methyl)piperidine-1-carboxylate

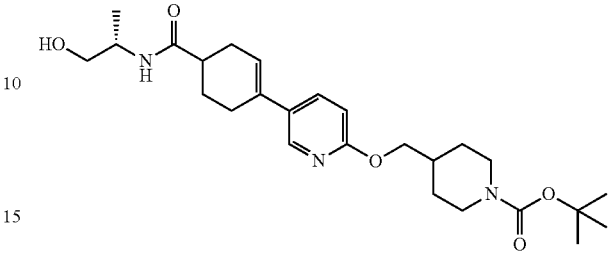

300 mg of 4-(6-((1-(tert-butoxycarbonyl)piperidin-4-yl)methoxy)pyridin-3-yl)cyclohex-3-enecarboxylic acid was dissolved in 25 μl of DMF, and stirred. 210 mg of EDCI and 165 mg of HOBt were sequentially added dropwise thereto, and the resulting mixture was then additionally stirred for 10 minutes. 120 mg of (S)-2-amino-1-propanol was added dropwise thereto, and the mixture was stirred at room temperature for 5 hours. After the reaction was terminated, 50 μl of distilled water was slowly added at 0° C., and the resulting solids were filtered, and dried to obtain a desired compound as a white solid (Amount obtained: 235 mg/Yield: 84%).

$^1$H NMR (400, CDCl$_3$): 8.14 (1H, s), 7.62 (1H, d), 6.70 (1H, d), 6.04 (1H, s), 5.76 (1H, d) 4.16 (5H, m), 4.15 (2H, m), 2.79 (3H, m), 2.50 (5H, m), 2.13 (1H, m), 1.98 (5H, m), 1.48 (9H, s), 1.30 (2H, m), 1.20 (3H, d)

Example 25: Preparation of tert-butyl 4-((5-(4-((R)-1-hydroxypropan-2-ylcarbamoyl)cyclohex-1-enyl)pyridin-2-yloxy)methyl)piperidine-1-carboxylate

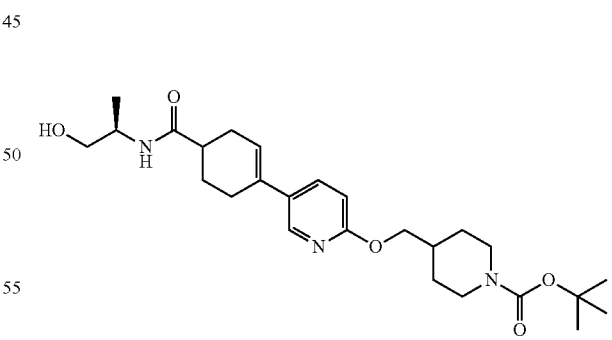

The title compound was prepared in the same manner as in <Example 24>, except that (R)-2-amino-1-propanol was used instead of the (S)-2-amino-1-propanol (Amount obtained: 140 mg/Yield: 62%).

$^1$H NMR (400, CDCl$_3$): 8.14 (1H, s), 7.62 (1H, d), 6.70 (1H, d), 6.04 (1H, s), 5.76 (1H, d) 4.16 (5H, m), 4.15 (2H, m), 2.79 (3H, m), 2.50 (5H, m), 2.13 (1H, m), 1.98 (5H, m), 1.48 (9H, s), 1.30 (2H, m), 1.20 (3H, d)

Example 26: Preparation of tert-butyl 4-((5-(4-((S)-2-hydroxypropylcarbamoyl)cyclohex-1-enyl)pyridin-2-yloxy)methyl)piperidine-1-carboxylate

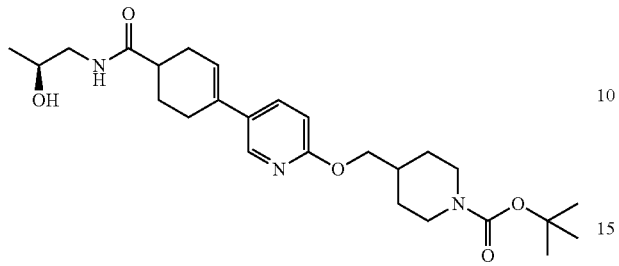

The title compound was prepared in the same manner as in <Example 24>, except that (S)-1-amino-2-propanol was used instead of the (S)-2-amino-1-propanol (Amount obtained: 155 mg/Yield: 67%).

¹H NMR (400, CDCl₃): 8.14 (1H, s), 7.61 (1H, d), 6.70 (1H, d), 6.05 (2H, s), 4.16 (4H, m), 3.97 (1H, m), 3.35 (2H, m), 2.79 (2H, m), 2.51 (6H, m), 2.14 (1H, m), 1.98 (4H, m), 1.48 (9H, s), 1.30 (2H, m), 1.21 (3H, d)

Example 27: Preparation of tert-butyl 4-((5-(4-((R)-2-hydroxypropylcarbamoyl)cyclohex-1-enyl)pyridin-2-yloxy)methyl)piperidine-1-carboxylate

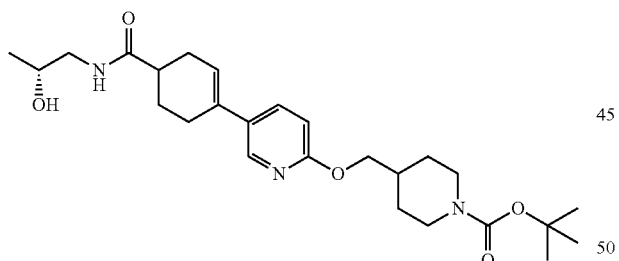

The title compound was prepared in the same manner as in <Example 24>, except that (R)-1-amino-2-propanol was used instead of the (S)-2-amino-1-propanol (Amount obtained: 150 mg/Yield: 65%).

¹H NMR (400, CDCl₃): 8.14 (1H, s), 7.61 (1H, d), 6.70 (1H, d), 6.05 (2H, s), 4.16 (4H, m), 3.97 (1H, m), 3.35 (2H, m), 2.79 (2H, m), 2.51 (6H, m), 2.14 (1H, m), 1.98 (4H, m), 1.48 (9H, s), 1.30 (2H, m), 1.21 (3H, d)

Example 28: Preparation of N—((R)-2-hydroxypropyl)-4-(4-((1-(3-isopropyl-1,2,4-oxadiazol-5-yl)piperidin-4-yl)methoxy)phenyl)cyclohex-3-enecarboxamide

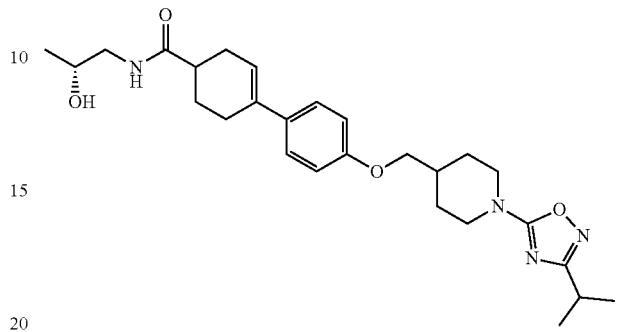

The title compound was prepared in the same manner as in <Example 17>, except that (R)-1-amino-2-propanol was used instead of the (R)-3-amino-1,2-propanediol (Amount obtained: 100 mg/Yield: 43%).

¹H NMR (400, CDCl₃): 7.53 (2H, d), 6.86 (2H, d), 6.04 (2H, s), 4.23 (1H, m), 3.90 (2H, d), 3.50 (1H, m), 3.17 (3H, m), 2.91 (1H, m), 2.14 (2H, m), 1.94 (3H, m), 1.50 (2H, m), 1.32 (6H, d), 1.21 (3H, d)

Example 29: Preparation of N—((S)-2-hydroxypropyl)-4-(4-((1-(3-isopropyl-1,2,4-oxadiazol-5-yl)piperidin-4-yl)methoxy)phenyl)cyclohex-3-enecarboxamide

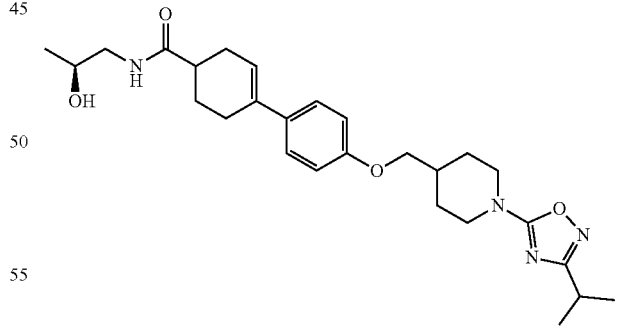

The title compound was prepared in the same manner as in <Example 17>, except that (S)-1-amino-2-propanol was used instead of the (R)-3-amino-1,2-propanediol (Amount obtained: 143 mg/Yield: 62%).

¹H NMR (400, CDCl₃): 7.53 (2H, d), 6.86 (2H, d), 6.04 (2H, s), 4.23 (1H, m), 3.90 (2H, d), 3.50 (1H, m), 3.17 (3H, m), 2.91 (1H, m), 2.14 (2H, m), 1.94 (3H, m), 1.50 (2H, m), 1.32 (6H, d), 1.21 (3H, d)

Example 30: Preparation of 4-(4-((1-(5-ethylpyrimidin-2-yl)piperidin-4-yl)methoxy)phenyl)-N—((R)-2-hydroxypropyl)cyclohex-3-enecarboxamide

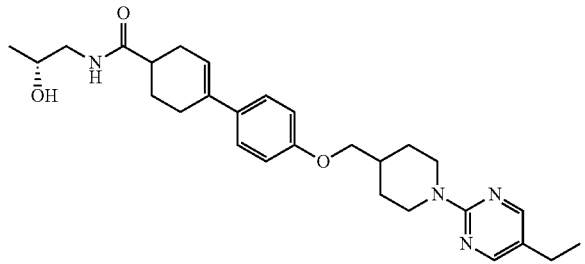 [SMILES: CCc1cnc(N2CCC(COc3ccc(C4=CCC(C(=O)NC[C@@H](C)O)CC4)cc3)CC2)nc1]

The title compound was prepared in the same manner as in <Example 8>, except that (R)-1-amino-2-propanol was used instead of the (R)-2-amino-1-propanol (Amount obtained: 180 mg/Yield: 79%).

$^1$H NMR (400, CDCl$_3$): 8.19 (2H, s), 7.32 (2H, d), 6.87 (2H, d), 6.04 (2H, s), 4.80 (2H, d), 3.96 (1H, m), 3.85 (2H, d), 3.52 (1H, m), 3.20 (1H, m), 2.92 (2H, t), 2.53 (8H, m), 2.13 (2H, m), 1.96 (3H, m), 1.38 (2H, m), 1.28 (6H, m)

Example 31: Preparation of N-(2-hydroxyethyl)-4-(4-((1-(3-isopropyl-1,2,4-oxadiazol-5-yl)piperidin-4-yl)methoxy)phenyl)cyclohex-3-enecarboxamide

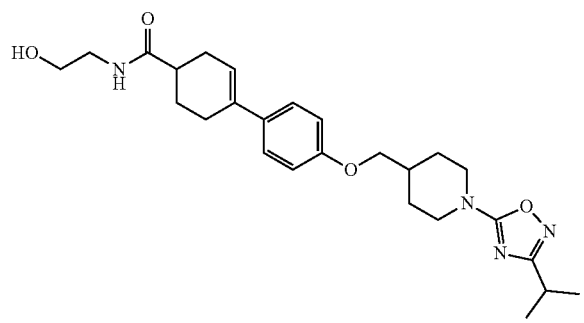 [SMILES: CC(C)c1noc(N2CCC(COc3ccc(C4=CCC(C(=O)NCCO)CC4)cc3)CC2)n1]

The title compound was prepared in the same manner as in <Example 17>, except that 2-aminoethanol was used instead of the (R)-3-amino-1,2-propanediol (Amount obtained: 220 mg/Yield: 94%).

$^1$H NMR (400, CDCl$_3$): 7.33 (2H, d), 6.86 (2H, d), 6.07 (2H, m), 4.23 (2H, m), 3.86 (2H, d), 3.79 (1H, m), 3.51 (1H, m), 3.15 (2H, m), 2.95 (1H, m), 2.51 (1H, m), 2.46 (4H, m), 2.06 (5H, m), 1.50 (2H, m), 1.30 (6H, d)

Example 32: Preparation of tert-butyl 4-((5-(4-((R)-2,3-dihydroxypropylcarbamoyl)cyclohex-1-enyl)pyridin-2-yloxy)methyl)piperidine-1-carboxylate

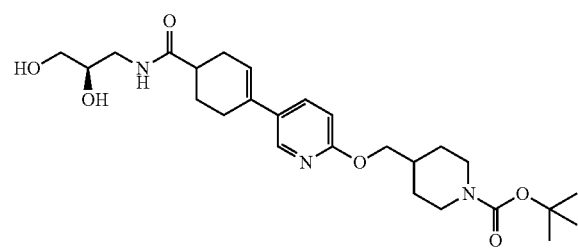 [SMILES: CC(C)(C)OC(=O)N1CCC(COc2ccc(C3=CCC(C(=O)NC[C@@H](O)CO)CC3)cn2)CC1]

The title compound was prepared in the same manner as in <Example 24>, except that (R)-3-amino-1,2-propanediol was used instead of the (S)-2-amino-1-propanol (Amount obtained: 176 mg/Yield: 80%).

$^1$H NMR (400, CDCl$_3$): 8.14 (1H, s), 7.62 (1H, d), 6.71 (1H, d), 6.06 (2H, m), 5.32 (5H, m), 3.80 (1H, m), 3.58 (2H, m), 3.46 (2H, m), 2.93 (1H, m), 2.78 (2H, m), 2.50 (5H, m), 1.98 (5H, s), 1.49 (9H, m), 1.27 (2H, m)

Example 33: Preparation of tert-butyl 4-((5-(4-((S)-2,3-dihydroxypropylcarbamoyl)cyclohex-1-enyl)pyridin-2-yloxy)methyl)piperidine-1-carboxylate

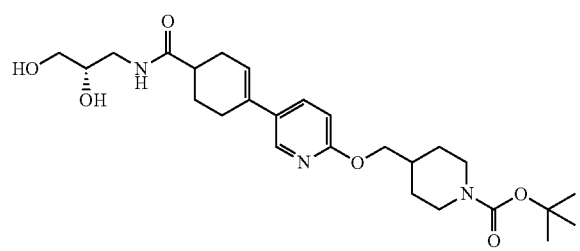 [SMILES: CC(C)(C)OC(=O)N1CCC(COc2ccc(C3=CCC(C(=O)NC[C@H](O)CO)CC3)cn2)CC1]

The title compound was prepared in the same manner as in <Example 24>, except that (S)-3-amino-1,2-propanediol was used instead of the (S)-2-amino-1-propanol (Amount obtained: 200 mg/Yield: 87%).

$^1$H NMR (400, CDCl$_3$): 8.14 (1H, s), 7.62 (1H, d), 6.71 (1H, d), 6.06 (2H, m), 5.32 (5H, m), 3.80 (1H, m), 3.58 (2H, m), 3.46 (2H, m), 2.93 (1H, m), 2.78 (2H, m), 2.50 (5H, m), 1.98 (5H, s), 1.49 (9H, m), 1.27 (2H, m)

Example 34: Preparation of N-(2-hydroxyethyl)-4-(4-((1-(3-isopropyl-1,2,4-oxadiazol-5-yl)piperidin-4-yl)methoxy)phenyl)-N-methylcyclohex-3-enecarboxamide

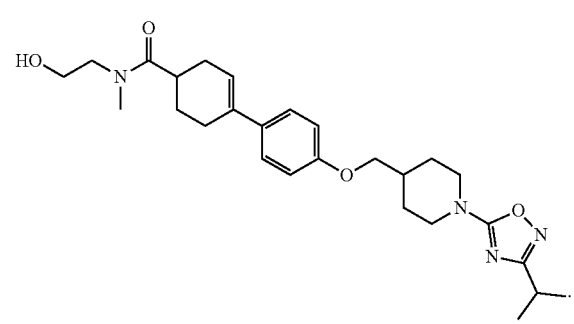

The title compound was prepared in the same manner as in <Example 17>, except that 2-(methylamino)ethanol was used instead of the (R)-3-amino-1,2-propanediol (Amount obtained: 190 mg/Yield: 82%).

$^1$H NMR (400, CDCl$_3$): 7.34 (2H, d), 6.86 (2H, d), 6.07 (2H, m), 4.23 (2H, m), 3.86 (4H, m), 3.63 (2H, m), 3.18 (3H, s), 3.15 (2H, m), 2.92 (2H, m), 2.50 (4H, m), 2.03 (5H, m), 1.92 (2H, m), 1.30 (6H, m)

Example 35: Preparation of N-ethyl-N-(2-hydroxy-ethyl)-4-(4-((1-(3-isopropyl-1,2,4-oxadiazol-5-yl)piperidin-4-yl)methoxy)phenyl)cyclohex-3-enecarboxamide

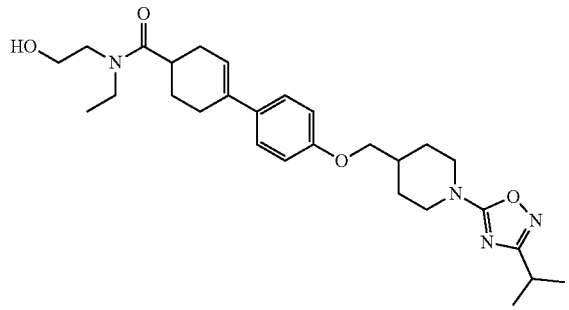 [SMILES: CCN(CCO)C(=O)C1CC=C(c2ccc(OCC3CCN(c4nc(C(C)C)no4)CC3)cc2)CC1]

The title compound was prepared in the same manner as in <Example 17>, except that 2-(ethylamino)ethanol was used instead of the (R)-3-amino-1,2-propanediol (Amount obtained: 184 mg/Yield: 80%).

$^1$H NMR (400, CDCl$_3$): 7.34 (2H, d), 6.87 (2H, d), 6.08 (1H, m), 4.24 (2H, m), 3.86 (4H, m), 3.59 (2H, m), 3.49 (2H, m), 3.11 (2H, m), 2.94 (1H, m), 2.59 (5H, m), 1.98 (5H, m), 1.51 (2H, m), 1.31 (6H, m), 1.14 (3H, m)

Example 36: Preparation of N—((R)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide

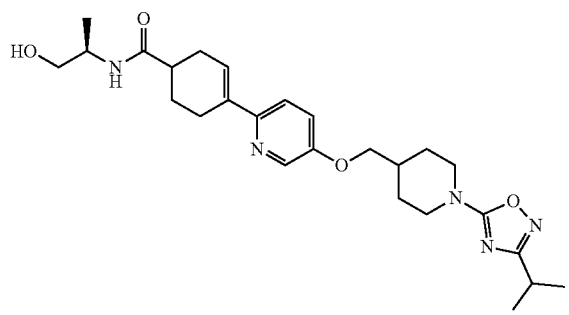

300 mg of 4-(5-((1-(3-isopropyl-1,2,4-oxadiazol-5-yl)piperidin-4-yl)methoxy)pyridin-2-yl)cyclohex-3-enecarboxylic acid was dissolved in 25 μl of DMF, and stirred. 210 mg of EDCI and 165 mg of HOBt were sequentially added dropwise thereto, and the resulting mixture was then additionally stirred for 10 minutes. 120 mg of (R)-2-amino-1-propanol was added dropwise thereto, and the mixture was then stirred at room temperature for 5 hours. After the reaction was terminated, 50 μl of distilled water was slowly added at 0° C., and the resulting solids were filtered, and dried to obtain a desired compound as a white solid (Amount obtained: 280 mg/Yield: 82%).

$^1$H NMR (400, CDCl$_3$): 8.25 (1H, s), 7.35 (1H, d), 7.15 (1H, d), 6.57 (1H, m), 5.82 (1H, m), 4.25 (2H, d), 4.13 (1H, m), 3.90 (2H, d), 3.70 (2H, m), 3.14 (2H, m), 2.94 (1H, m), 2.53 (5H, m), 2.03 (5H, m), 1.50 (2H, m), 1.32 (6H, d), 1.20 (3H, d)

Example 37: Preparation of N—((S)-1-hydroxypropan-2-yl)-4-(5-((1-(3-isopropyl-1,2,4-oxadiazol-5-yl)piperidin-4-yl)methoxy)pyridin-2-yl)cyclohex-3-enecarboxamide

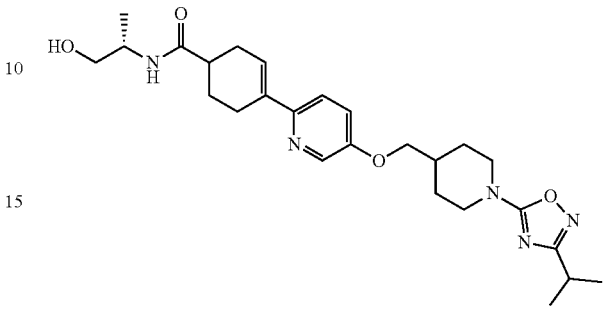

*1062

The title compound was prepared in the same manner as in <Example 36>, except that (S)-2-amino-1-propanol was used instead of the (R)-2-amino-1-propanol (Amount obtained: 160 mg/Yield: 70%).

$^1$H NMR (400, CDCl$_3$): 8.25 (1H, s), 7.35 (1H, d), 7.15 (1H, d), 6.57 (1H, m), 5.82 (1H, m), 4.25 (2H, d), 4.13 (1H, m), 3.90 (2H, d), 3.70 (2H, m), 3.14 (2H, m), 2.94 (1H, m), 2.53 (5H, m), 2.03 (5H, m), 1.50 (2H, m), 1.32 (6H, d), 1.20 (3H, d)

Example 38: Preparation of N—((R)-2-hydroxypropyl)-4-(5-((1-(3-isopropyl-1,2,4-oxadiazol-5-yl)piperidin-4-yl)methoxy)pyridin-2-yl)cyclohex-3-enecarboxamide

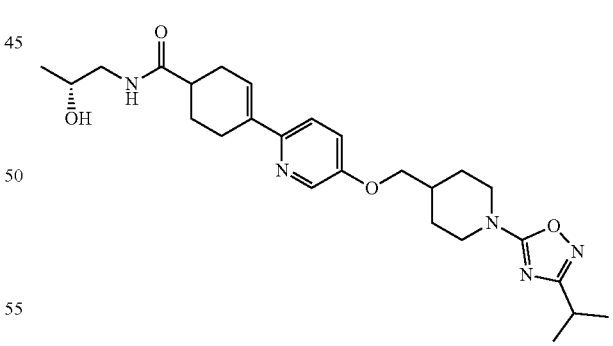

The title compound was prepared in the same manner as in <Example 36>, except that (R)-1-amino-2-propanol was used instead of the (R)-2-amino-1-propanol (Amount obtained: 180 mg/Yield: 81%).

$^1$H NMR (400, CDCl$_3$): 8.24 (1H, s), 7.34 (1H, d), 7.17 (1H, d), 6.54 (1H, m), 6.12 (1H, m), 4.25 (2H, d), 3.96 (1H, m), 3.90 (2H, d), 3.51 (1H, m), 3.16 (3H, m), 2.93 (1H, m), 2.51 (5H, m), 2.03 (5H, m), 1.49 (2H, m), 1.31 (6H, d), 1.21 (3H, d)

Example 39: Preparation of N—((S)-2-hydroxypropyl)-4-(5-((1-(3-isopropyl-1,2,4-oxadiazol-5-yl)piperidin-4-yl)methoxy)pyridin-2-yl)cyclohex-3-enecarboxamide

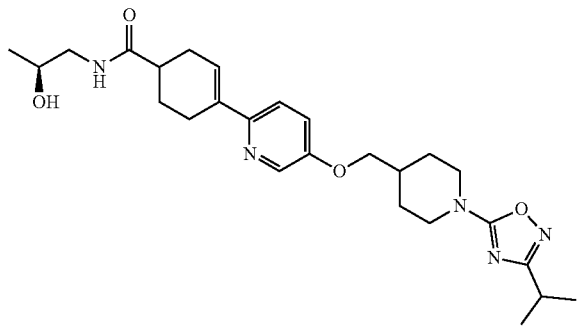

The title compound was prepared in the same manner as in <Example 36>, except that (S)-1-amino-2-propanol was used instead of the (R)-2-amino-1-propanol (Amount obtained: 185 mg/Yield: 76%).

$^1$H NMR (400, CDCl$_3$): 8.24 (1H, s), 7.34 (1H, d), 7.17 (1H, d), 6.54 (1H, m), 6.12 (1H, m), 4.25 (2H, d), 3.96 (1H, m), 3.90 (2H, d), 3.51 (1H, m), 3.16 (3H, m), 2.93 (1H, m), 2.51 (5H, m), 2.03 (5H, m), 1.49 (2H, m), 1.31 (6H, d), 1.21 (3H, d)

Example 40: Preparation of N—((R)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide

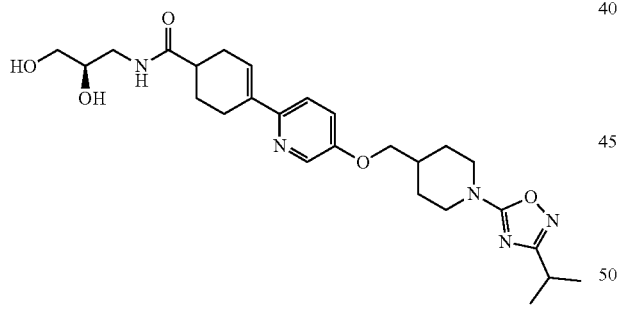

The title compound was prepared in the same manner as in <Example 36>, except that (R)-3-amino-1,2-propanediol was used instead of the (R)-2-amino-1-propanol (Amount obtained: 160 mg/Yield: 71%).

$^1$H NMR (400, CDCl$_3$): 8.24 (1H, s), 7.34 (1H, d), 7.17 (1H, d), 6.52 (1H, m), 6.16 (1H, m), 4.25 (2H, d), 3.90 (2H, d), 3.81 (1H, m), 3.59 (3H, m), 3.15 (3H, m), 2.93 (1H, m), 2.51 (5H, m), 2.09 (5H, m), 1.53 (2H, m), 1.31 (6H, d)

Example 41: Preparation of N—((S)-2,3-dihydroxypropyl)-4-(5-((1-(3-isopropyl-1,2,4-oxadiazol-5-yl)piperidin-4-yl)methoxy)pyridin-2-yl)cyclohex-3-enecarboxamide

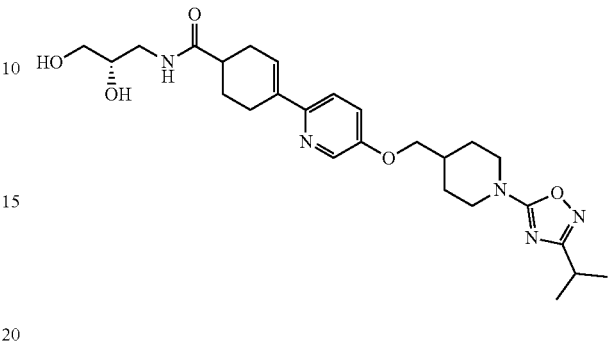

The title compound was prepared in the same manner as in <Example 36>, except that (S)-3-amino-1,2-propanediol was used instead of the (R)-2-amino-1-propanol (Amount obtained: 176 mg/Yield: 77%).

$^1$H NMR (400, CDCl$_3$): 8.24 (1H, s), 7.34 (1H, d), 7.17 (1H, d), 6.52 (1H, m), 6.16 (1H, m), 4.25 (2H, d), 3.90 (2H, d), 3.81 (1H, m), 3.59 (3H, m), 3.15 (3H, m), 2.93 (1H, m), 2.51 (5H, m), 2.09 (5H, m), 1.53 (2H, m), 1.31 (6H, d)

*1081 Example 42: Preparation of tert-butyl 4-((5-(4-((S)-3-hydroxypyrrolidine-1-carbonyl)cyclohex-1-enyl)pyridin-2-yloxy)methyl)piperidine-1-carboxylate

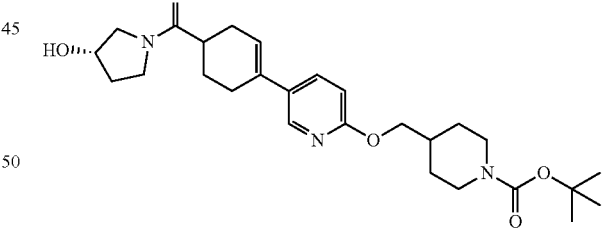

The title compound was prepared in the same manner as in <Example 24>, except that (S)-(−)-3-pyrrolidinol was used instead of the (S)-2-amino-1-propanol (Amount obtained: 145 mg/Yield: 65%).

$^1$H NMR (400, CDCl$_3$): 8.14 (1H, s), 7.63 (1H, d), 6.70 (1H, d), 6.07 (1H, s), 4.58 (1H, d), 4.16 (4H, m), 3.76 (4H, m), 2.75 (7H, m), 1.98 (8H, m), 1.52 (9H, m), 1.29 (2H, m)

Example 43: Preparation of tert-butyl 4-((5-(4-((R)-3-hydroxypyrrolidine-1-carbonyl)cyclohex-1-enyl)pyridin-2-yloxy)methyl)piperidine-1-carboxylate

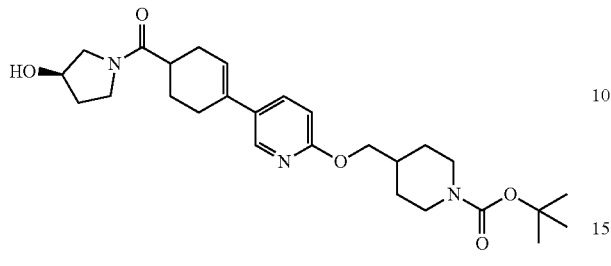

The title compound was prepared in the same manner as in <Example 24>, except that (R)-(+)-3-pyrrolidinol was used instead of the (S)-2-amino-1-propanol (Amount obtained: 162 mg/Yield: 70%).

$^1$H NMR (400, CDCl$_3$): 8.14 (1H, s), 7.63 (1H, d), 6.70 (1H, d), 6.07 (1H, s), 4.58 (1H, d), 4.16 (4H, m), 3.76 (4H, m), 2.75 (7H, m), 1.98 (8H, m), 1.52 (9H, m), 1.29 (2H, m)

Example 44: Preparation of tert-butyl 4-((2-fluoro-4-(4-((S)-3-hydroxypyrrolidine-1-carbonyl)cyclohex-1-enyl)phenoxy)methyl)piperidine-1-carboxylate

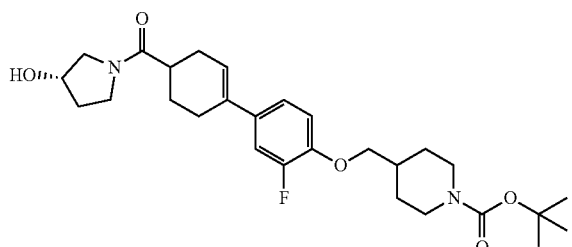

300 mg of 4-(4-((1-(tert-butoxycarbonyl)piperidin-4-yl)methoxy)-3-fluorophenyl)cyclohex-3-enecarboxylic acid was dissolved in 25 j of DMF, and stirred. 210 mg of EDCI and 165 mg of HOBt were sequentially added dropwise thereto, and the resulting mixture was then additionally stirred for 10 minutes. 100 mg of (S)-(−)-3-pyrrolidinol was added dropwise thereto, and the mixture was stirred at room temperature for 12 hours. After the reaction was terminated, 50 td of distilled water was slowly added at 0° C., and the resulting solids were filtered, and dried to obtain a desired compound as a white solid (Amount obtained: 195 mg/Yield: 58%).

$^1$H NMR (400, CDCl$_3$): 7.28 (2H, m), 6.91 (1H, t), 6.10 (1H, s), 4.58 (1H, d), 4.16 (4H, m), 3.88 (2H, d), 3.69 (4H, m), 2.75 (7H, m), 1.98 (8H, m), 1.52 (9H, m), 1.30 (2H, m)

Example 45: Preparation of tert-butyl 4-((2-fluoro-4-(4-((R)-3-hydroxypyrrolidine-1-carbonyl)cyclohex-1-enyl)phenoxy)methyl)piperidine-1-carboxylate

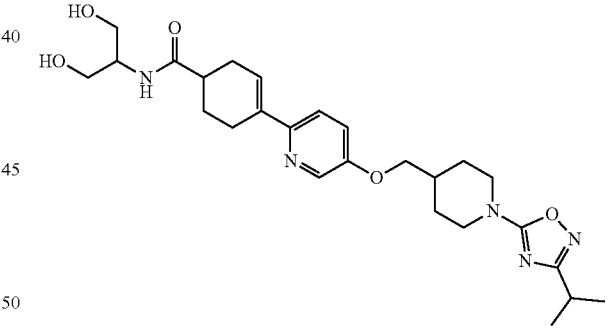

The title compound was prepared in the same manner as in <Example 44>, except that (R)-(+)-3-pyrrolidinol was used instead of the (S)-(−)-3-pyrrolidinol (Amount obtained: 120 mg/Yield: 52%).

$^1$H NMR (400, CDCl$_3$): 7.28 (2H, m), 6.91 (1H, t), 6.10 (1H, s), 4.58 (1H, d), 4.16 (4H, m), 3.88 (2H, d), 3.69 (4H, m), 2.75 (7H, m), 1.98 (8H, m), 1.52 (9H, m), 1.30 (2H, m)

Example 46: Preparation of N-(1,3-dihydroxypropan-2-yl)-4-(5-((1-(3-isopropyl-1,2,4-oxadiazol-5-yl)piperid in-4-yl)methoxy)pyridin-2-yl)cyclohex-3-3-enecarboxamide The title compound was prepared in the same manner as in <Example 36>, except that 2-amino-1,3-propanediol was used instead of the (R)-2-amino-1-propanol (Amount obtained: 185 mg/Yield: 52%).

$^1$H NMR (400, CDCl$_3$): 8.23 (1H, s), 7.34 (1H, d), 7.16 (1H, d), 6.48 (2H, m), 4.25 (2H, d), 4.03 (1H, m), 3.90 (2H, d), 3.81 (4H, m), 3.12 (2H, m), 2.94 (1H, m), 2.56 (1H, m), 2.49 (5H, m), 2.11 (3H, m), 1.98 (2H, m), 1.45 (2H, m), 1.30 (6H, d)

Example 47: Preparation of N-(3-hydroxy-2,2-dimethylpropyl)-4-(5-((1-(3-isopropyl-1,2,4-oxadiazol-5-yl)piperidin-4-yl)methoxy)pyridin-2-yl)cyclohex-3-enecarboxamide

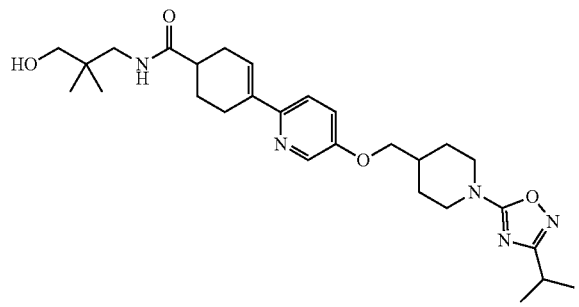 [SMILES: CC(C)c1noc(N2CCC(COc3ccc(C4=CCC(C(=O)NCC(C)(C)CO)CC4)nc3)CC2)n1]

The title compound was prepared in the same manner as in <Example 36>, except that 3-amino-2,2-dimethylpropan-1-ol was used instead of the (R)-2-amino-1-propanol (Amount obtained: 150 mg/Yield: 65%).

$^1$H NMR (400, CDCl$_3$): 8.25 (1H, s), 7.34 (1H, d), 7.17 (1H, d), 6.55 (1H, m), 6.05 (1H, m), 4.25 (2H, d), 3.90 (2H, d), 3.15 (6H, m), 2.93 (1H, m), 2.71 (1H, m), 2.47 (4H, m), 2.14 (2H, m), 1.98 (3H, m), 1.51 (2H, m), 1.31 (6H, m), 0.90 (6H, s)

Example 48: Preparation of ((R)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone

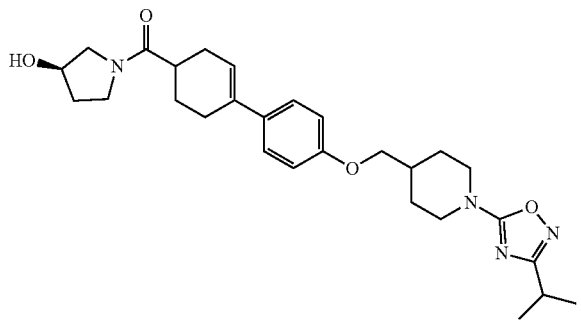 [SMILES: CC(C)c1noc(N2CCC(COc3ccc(C4=CCC(C(=O)N5CC[C@@H](O)C5)CC4)cc3)CC2)n1]

The title compound was prepared in the same manner as in <Example 17>, except that (R)-(+)-3-pyrrolidinol was used instead of the (R)-3-amino-1,2-propanediol (Amount obtained: 175 mg/Yield: 77%).

$^1$H NMR (400, CDCl$_3$): 7.33 (2H, d), 6.86 (2H, d), 6.07 (1H, m), 4.53 (1H, m), 4.23 (2H, d), 3.85 (2H, d), 3.68 (4H, m), 3.11 (2H, m), 2.90 (1H, m), 2.52 (6H, m), 1.99 (7H, m), 1.43 (2H, m), 1.29 (6H, d)

Example 49: Preparation of ((S)-3-hydroxypyrrolidin-1-yl)(4-(4-((1-(3-isopropyl-1,2,4-oxadiazol-5-yl)piperidin-4-yl)methoxy)phenyl)cyclohex-3-enyl)methanone

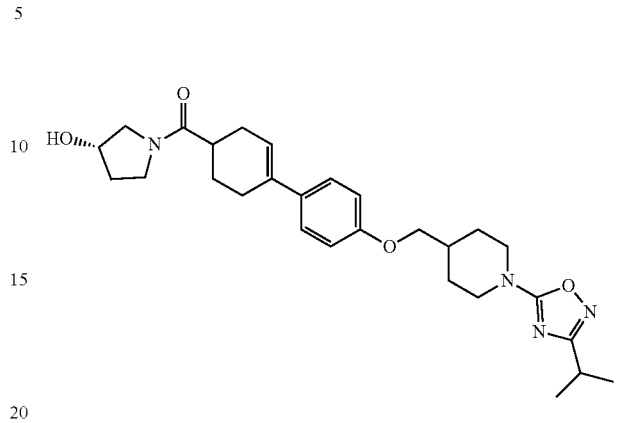

The title compound was prepared in the same manner as in <Example 17>, except that (S)-(−)-3-pyrrolidinol was used instead of the (R)-3-amino-1,2-propanediol (Amount obtained: 120 mg/Yield: 52%).

$^1$H NMR (400, CDCl$_3$): 7.33 (2H, d), 6.86 (2H, d), 6.07 (1H, m), 4.53 (1H, m), 4.23 (2H, d), 3.85 (2H, d), 3.68 (4H, m), 3.11 (2H, m), 2.90 (1H, m), 2.52 (6H, m), 1.99 (7H, m), 1.43 (2H, m), 1.29 (6H, d)

Example 50: Preparation of N-(2,2-difluoroethyl)-4-(4-((1-(5-ethylpyrimidin-2-yl)piperidin-4-yl)methoxy)phenyl)cyclohex-3-enecarboxamide

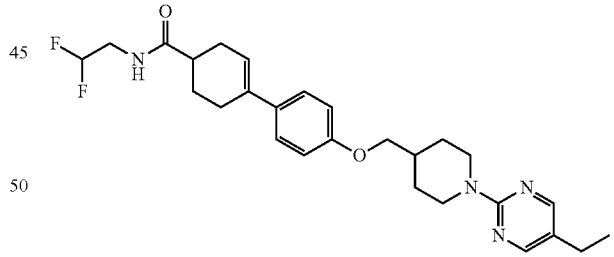

The title compound was prepared in the same manner as in <Example 8>, except that 2,2-difluoroethylamine was used instead of the (R)-2-amino-1-propanol (Amount obtained: 170 mg/Yield: 74%).

$^1$H NMR (400, CDCl$_3$): 8.22 (2H, s), 7.32 (2H, d), 6.87 (2H, d), 6.04 (1H, s), 5.91 (1.5H, m), 5.88 (0.5H, t), 4.80 (2H, d), 3.85 (2H, d), 3.72 (2H, m), 2.98 (2H, t), 2.56 (8H, m), 2.12 (2H, m), 1.94 (3H, m), 1.41 (2H, m), 1.21 (3H, t)

Example 51: Preparation of N-(2,2-difluoroethyl)-4-(4-((1-(3-isopropyl-1,2,4-oxadiazol-5-yl)piperidin-4-yl)methoxy)phenyl)cyclohex-3-enecarboxamide

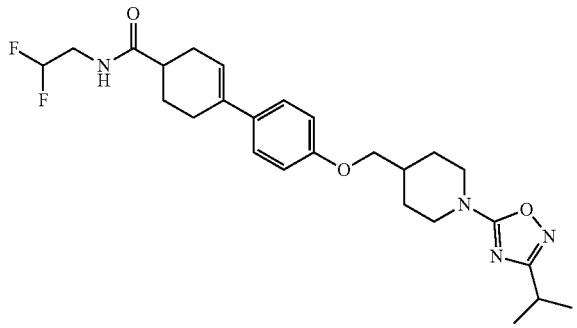 [SMILES: CC(C)c1noc(N2CCC(COc3ccc(C4=CCC(C(=O)NCC(F)F)CC4)cc3)CC2)n1]

The title compound was prepared in the same manner as in <Example 17>, except that 2,2-difluoroethylamine was used instead of the (R)-3-amino-1,2-propanediol (Amount obtained: 175 mg/Yield: 76%).

$^1$H NMR (400, CDCl$_3$): 7.33 (2H, d), 6.86 (2H, d), 6.04 (1H, m), 5.88 (2H, m), 4.23 (2H, d), 3.84 (2H, d), 3.70 (2H, m), 3.14 (2H, t), 2.91 (1H, m), 2.50 (5H, m), 2.10 (2H, m), 2.05 (3H, m), 1.43 (2H, m), 1.30 (6H, d)

Example 52: Preparation of (4-(4-((1-(3-isopropyl-1,2,4-oxadiazol-5-yl)piperidin-4-yl)methoxy)phenyl)cyclohex-3-enyl)(pyrrolidin-1-yl)methanone

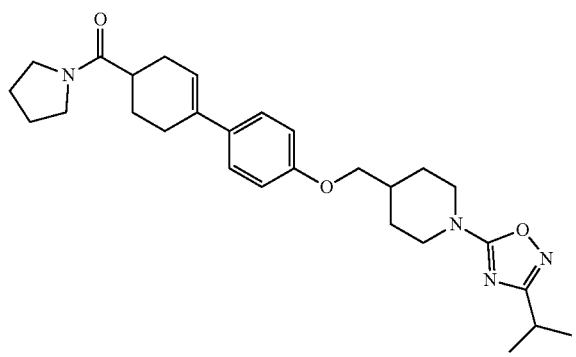 [SMILES: CC(C)c1noc(N2CCC(COc3ccc(C4=CCC(C(=O)N5CCCC5)CC4)cc3)CC2)n1]

The title compound was prepared in the same manner as in <Example 17>, except that pyrrolidine was used instead of the (R)-3-amino-1,2-propanediol (Amount obtained: 200 mg/Yield: 87%).

$^1$H NMR (400, CDCl$_3$): 7.34 (2H, d), 6.86 (2H, d), 6.07 (1H, m), 4.24 (2H, d), 3.84 (2H, d), 3.53 (4H, m), 3.08 (2H, m), 2.91 (1H, m), 2.34 (5H, m), 1.98 (9H, m), 1.47 (2H, m), 1.25 (6H, d)

Example 53: Preparation of ((S)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone

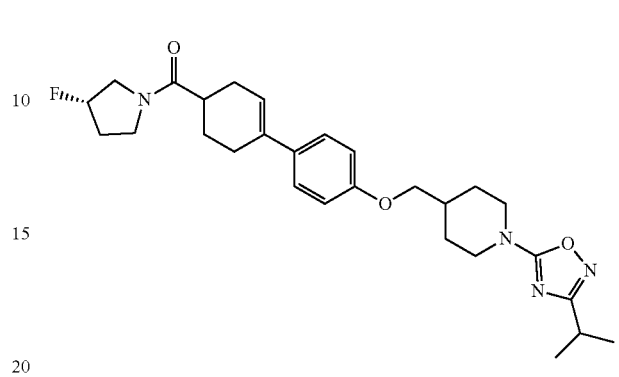

The title compound was prepared in the same manner as in <Example 17>, except that (S)-3-fluoropyrrolidine was used instead of the (R)-3-amino-1,2-propanediol (Amount obtained: 175 mg/Yield: 76%).

$^1$H NMR (400, CDCl$_3$): 7.34 (2H, d), 6.87 (2H, d), 5.36 (1H, m), 4.24 (2H, d), 3.75 (6H, m), 3.14 (2H, t), 2.89 (1H, m), 2.50 (7H, m), 2.00 (5H, m), 1.50 (2H, m), 1.30 (6H, d)

Example 54: Preparation of ((R)-3-fluoropyrrolidin-1-yl)(4-(4-((1-(3-isopropyl-1,2,4-oxadiazol-5-yl)piperidin-4-yl)methoxy)phenyl)cyclohex-3-enyl)methanone

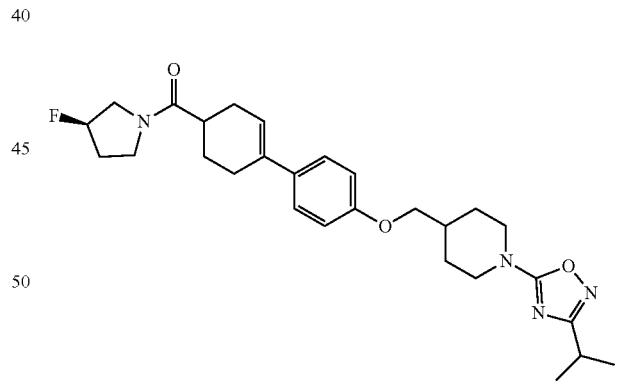

*1130

The title compound was prepared in the same manner as in <Example 17>, except that (R)-3-fluoropyrrolidine was used instead of the (R)-3-amino-1,2-propanediol (Amount obtained: 175 mg/Yield: 77%).

$^1$H NMR (400, CDCl$_3$): 7.34 (2H, d), 6.87 (2H, d), 5.36 (1H, m), 4.24 (2H, d), 3.75 (6H, m), 3.14 (2H, t), 2.89 (1H, m), 2.50 (7H, m), 2.00 (5H, m), 1.50 (2H, m), 1.30 (6H, d)

Example 55: Preparation of (4-ethylpiperazin-1-yl) (4-(4-((1-(5-ethylpyrimidin-2-yl)piperidin-4-yl) methoxy)phenyl)cyclohex-3-enyl)methanone

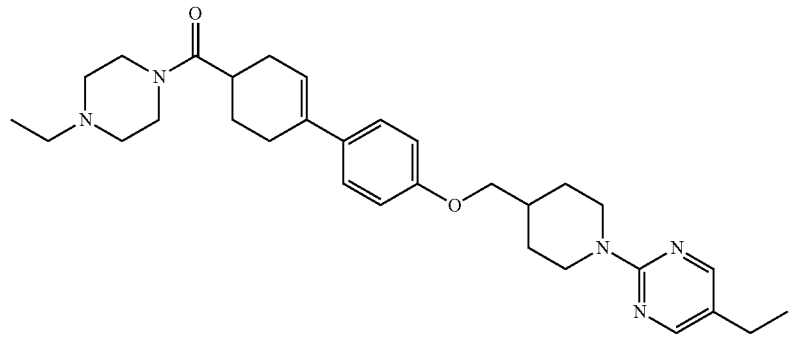 [SMILES: CCc1cnc(N2CCC(COc3ccc(C4=CCC(C(=O)N5CCN(CC)CC5)CC4)cc3)CC2)nc1]

The title compound was prepared in the same manner as in <Example 8>, except that 1-ethyl piperazine was used instead of the (R)-2-amino-1-propanol (Amount obtained: 200 mg/Yield: 87%).

$^1$H NMR (400, CDCl$_3$): 8.19 (2H, s), 7.32 (2H, d), 6.87 (2H, d), 6.05 (1H, s), 4.80 (2H, d), 3.76 (6H, m), 2.50 (13H, m), 1.99 (6H, m), 1.27 (8H, m)

Example 56: Preparation of (4-(4-((1-(3-isopropyl-1,2,4-oxadiazol-5-yl)piperidin-4-yl)methoxy)phenyl) cyclohex-3-enyl)(piperidin-1-yl)methanone

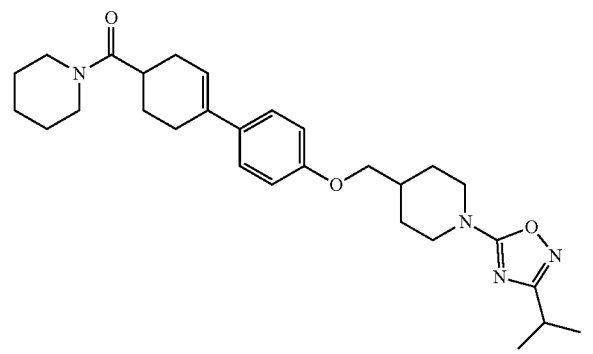 [SMILES: CC(C)c1noc(N2CCC(COc3ccc(C4=CCC(C(=O)N5CCCCC5)CC4)cc3)CC2)n1]

The title compound was prepared in the same manner as in <Example 17>, except that piperidine was used instead of the (R)-3-amino-1,2-propanediol (Amount obtained: 170 mg/Yield: 74%).

$^1$H NMR (400, CDCl$_3$): 7.34 (2H, d), 6.86 (2H, d), 6.07 (1H, m), 4.23 (2H, d), 3.84 (2H, d), 3.59 (4H, m), 3.11 (2H, t), 2.84 (2H, m), 2.49 (3H, m), 2.31 (1H, m), 1.98 (5H, m), 1.67 (6H, m), 1.44 (2H, m), 1.30 (6H, d)

Example 57: Preparation of tert-butyl 4-((2-fluoro-4-(4-((S)-3-fluoropyrrolidine-1-carbonyl)cyclohex-1-enyl)phenoxy)methyl)piperidine-1-carboxylate

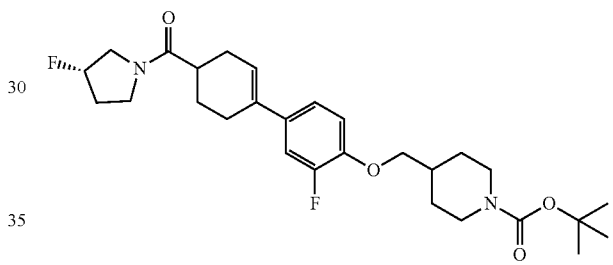

The title compound was prepared in the same manner as in <Example 44>, except that (S)-3-fluoropyrrolidine was used instead of the (S)-(−)-3-pyrrolidinol (Amount obtained: 175 mg/Yield: 76%).

$^1$H NMR (400, CDCl$_3$): 7.15 (2H, m), 6.92 (1H, t), 6.10 (1H, s), 5.23 (1H, m), 4.17 (2H, m), 3.75 (6H, m), 2.73 (3H, m), 2.39 (5H, m), 2.02 (6H, m), 1.48 (9H, m), 1.27 (2H, m)

Example 58: Preparation of tert-butyl 4-((2-fluoro-4-(4-((R)-3-fluoropyrrolidine-1-carbonyl)cyclohex-1-enyl)phenoxy)methyl)piperidine-1-carboxylate

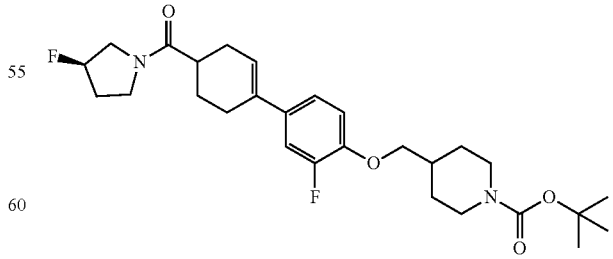

The title compound was prepared in the same manner as in <Example 44>, except that (R)-3-fluoropyrrolidine was used instead of the (S)-(−)-3-pyrrolidinol (Amount obtained: 195 mg/Yield: 85%).

¹H NMR (400, CDCl₃): 7.15 (2H, m), 6.92 (1H, t), 6.10 (1H, s), 5.23 (1H, m), 4.17 (2H, m), 3.75 (6H, m), 2.73 (3H, m), 2.39 (5H, m), 2.02 (6H, m), 1.48 (9H, m), 1.27 (2H, m)

Example 59: Preparation of tert-butyl 4-((2-fluoro-4-(4-((S)-1-hydroxypropan-2-ylcarbamoyl)cyclohex-1-enyl)phenoxy)methyl)piperidine-1-carboxylate

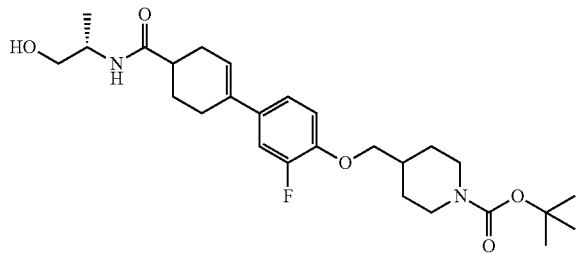 [SMILES: C[C@@H](CO)NC(=O)C1CC=C(c2ccc(OCC3CCN(C(=O)OC(C)(C)C)CC3)c(F)c2)CC1]

The title compound was prepared in the same manner as in <Example 44>, except that (S)-2-amino-1-propanol was used instead of the (S)-(−)-3-pyrrolidinol (Amount obtained: 200 mg/Yield: 87%).

¹H NMR (400, CDCl₃): 7.14 (2H, m), 6.89 (1H, t), 6.06 (1H, s), 5.80 (1H, m), 4.16 (3H, m), 3.88 (2H, d), 2.63 (2H, m), 2.76 (2H, m), 2.41 (6H, m), 2.02 (5H, m), 1.48 (9H, m), 1.26 (5H, m)

Example 60: Preparation of tert-butyl 4-((2-fluoro-4-(4-((R)-1-hydroxypropan-2-ylcarbamoyl)cyclohex-1-enyl)phenoxy)methyl)piperidine-1-carboxylate

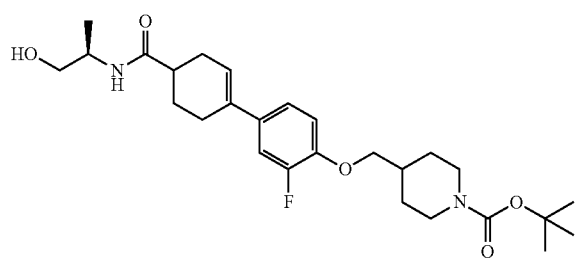 [SMILES: C[C@H](CO)NC(=O)C1CC=C(c2ccc(OCC3CCN(C(=O)OC(C)(C)C)CC3)c(F)c2)CC1]

The title compound was prepared in the same manner as in <Example 44>, except that (R)-2-amino-1-propanol was used instead of the (S)-(−)-3-pyrrolidinol (Amount obtained: 174 mg/Yield: 75%).

¹H NMR (400, CDCl₃): 7.14 (2H, m), 6.89 (1H, t), 6.06 (1H, s), 5.80 (1H, m), 4.16 (3H, m), 3.88 (2H, d), 2.63 (2H, m), 2.76 (2H, m), 2.41 (6H, m), 2.02 (5H, m), 1.48 (9H, m), 1.26 (5H, m)

Example 61: Preparation of tert-butyl 4-((2-fluoro-4-(4-((S)-2-hydroxypropylcarbamoyl)cyclohex-1-enyl)phenoxy)methyl)piperidine-1-carboxylate

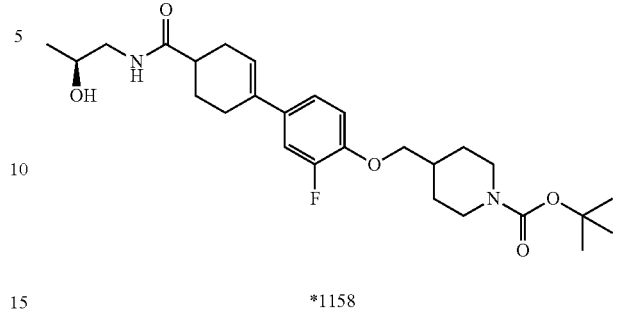

*1158

The title compound was prepared in the same manner as in <Example 44>, except that (S)-1-amino-2-propanol was used instead of the (S)-(−)-3-pyrrolidinol (Amount obtained: 120 mg/Yield: 53%).

¹H NMR (400, CDCl₃): 7.14 (2H, m), 6.89 (1H, t), 6.07 (1H, s), 4.15 (2H, m), 3.96 (1H, m), 3.86 (2H, d), 3.52 (1H, m), 3.17 (1H, m), 2.76 (2H, m), 2.49 (6H, m), 2.02 (5H, m), 1.48 (9H, m), 1.27 (5H, m)

Example 62: Preparation of tert-butyl 4-((2-fluoro-4-(4-((R)-2-hydroxypropylcarbamoyl)cyclohex-1-enyl)phenoxy)methyl)piperidine-1-carboxylate


The title compound was prepared in the same manner as in <Example 44>, except that (R)-1-amino-2-propanol was used instead of the (S)-(−)-3-pyrrolidinol (Amount obtained: 139 mg/Yield: 60%).

¹H NMR (400, CDCl₃): 7.14 (2H, m), 6.89 (1H, t), 6.07 (1H, s), 4.15 (2H, m), 3.96 (1H, m), 3.86 (2H, d), 3.52 (1H, m), 3.17 (1H, m), 2.76 (2H, m), 2.49 (6H, m), 2.02 (5H, m), 1.48 (9H, m), 1.27 (5H, m)

Example 63: Preparation of tert-butyl 4-((4-(4-((S)-2,3-dihydroxypropylcarbamoyl)cyclohex-1-enyl)-2-fluorophenoxy)methyl)piperidine-1-carboxylate

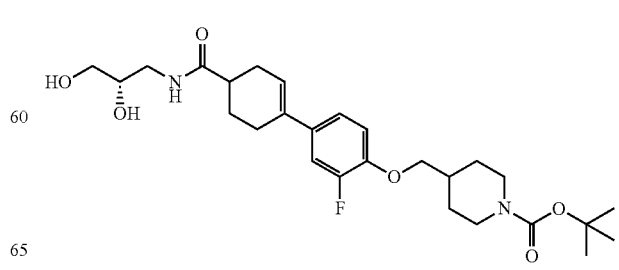

The title compound was prepared in the same manner as in <Example 44>, except that (S)-3-amino-1,2-propanediol was used instead of the (S)-(−)-3-pyrrolidinol (Amount obtained: 185 mg/Yield: 80%).

$^1$H NMR (400, CDCl$_3$): 7.18 (2H, m), 6.93 (1H, t), 6.11 (2H, m), 4.21 (2H, m), 3.91 (3H, m), 3.61 (4H, m), 3.03 (2H, m), 2.83 (2H, m), 2.16 (5H, m), 2.03 (6H, m), 1.50 (9H, m), 1.31 (2H, m)

Example 64: Preparation of tert-butyl 4-((4-(4-(((R)-2,3-dihydroxypropylcarbamoyl)cyclohex-1-enyl)-2-fluorophenoxy)methyl)piperidine-1-carboxylate

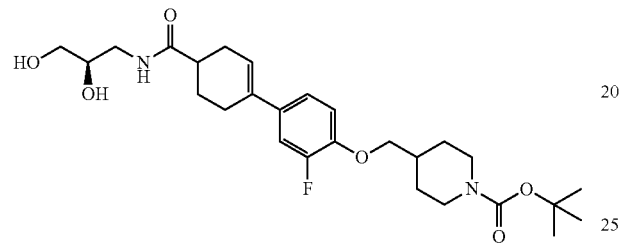

The title compound was prepared in the same manner as in <Example 44>, except that (R)-3-amino-1,2-propanediol was used instead of the (S)-(−)-3-pyrrolidinol (Amount obtained: 177 mg/Yield: 77%).

$^1$H NMR (400, CDCl$_3$): 7.18 (2H, m), 6.93 (1H, t), 6.11 (2H, m), 4.21 (2H, m), 3.91 (3H, m), 3.61 (4H, m), 3.03 (2H, m), 2.83 (2H, m), 2.16 (5H, m), 2.03 (6H, m), 1.50 (9H, m), 1.31 (2H, m)

Example 65: Preparation of azetidin-1-yl(4-(4-((1-(3-isopropyl-1,2,4-oxadiazol-5-yl)piperidin-4-yl)methoxy)phenyl)cyclohex-3-enyl)methanone

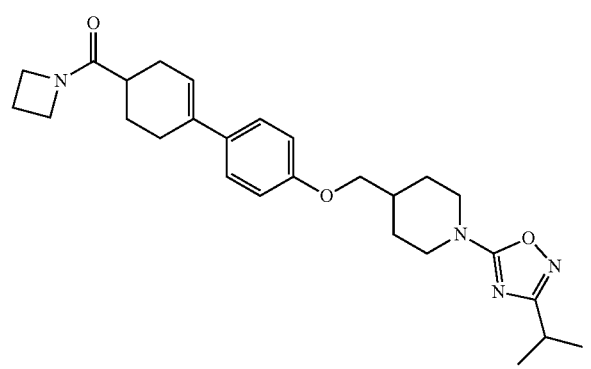 [SMILES: CC(C)c1noc(N2CCC(COc3ccc(C4=CCC(C(=O)N5CCC5)CC4)cc3)CC2)n1]

The title compound was prepared in the same manner as in <Example 17>, except that azetidine was used instead of the (R)-3-amino-1,2-propanediol (Amount obtained: 90 mg/Yield: 40%).

$^1$H NMR (400, CDCl$_3$): 7.34 (2H, d), 6.85 (2H, d), 6.06 (1H, m), 4.24 (4H, m), 4.07 (2H, m), 3.84 (2H, m), 3.11 (2H, t), 2.91 (1H, m), 2.50 (4H, m), 2.31 (3H, m), 1.97 (5H, m), 1.47 (2H, m), 1.31 (6H, m)

Example 66: Preparation of (4-(4-((1-(3-isopropyl-1,2,4-oxadiazol-5-yl)piperidin-4-yl)methoxy)phenyl)cyclohex-3-enyl)(morpholino)methanone

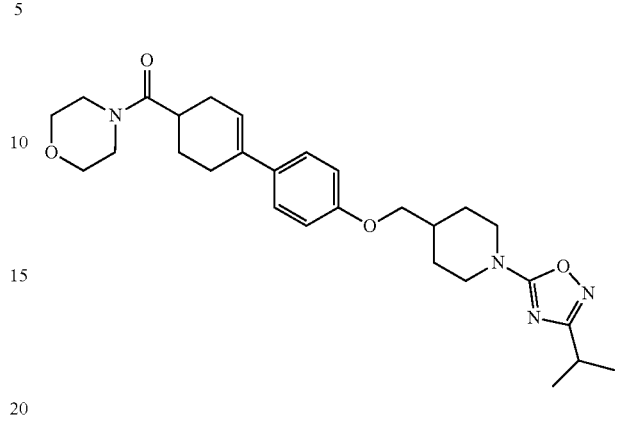

The title compound was prepared in the same manner as in <Example 17>, except that morpholine was used instead of the (R)-3-amino-1,2-propanediol (Amount obtained: 190 mg/Yield: 83%).

$^1$H NMR (400, CDCl$_3$): 7.33 (2H, d), 6.84 (2H, d), 6.06 (1H, m), 4.20 (2H, d), 3.84 (2H, d), 3.72 (8H, m), 3.11 (2H, t), 2.91 (1H, m), 2.77 (1H, m), 2.52 (3H, m), 2.31 (1H, m), 1.98 (5H, m), 1.50 (2H, m), 1.31 (6H, d)

Example 67: Preparation of tert-butyl 4-((4-(4-(1,3-dihydroxypropan-2-ylcarbamoyl)cyclohex-1-enyl)-2-fluorophenoxy)methyl)piperidine-1-carboxylate

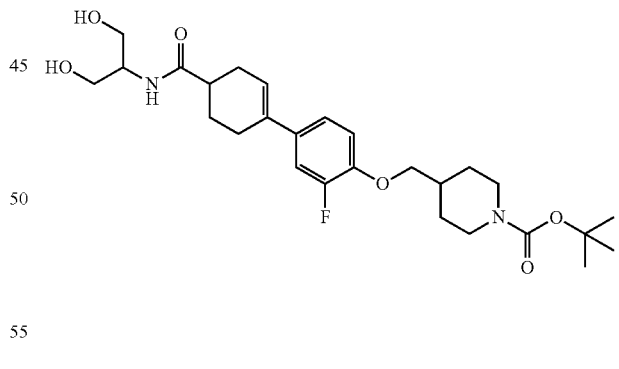

The title compound was prepared in the same manner as in <Example 44>, except that 2-amino-1,3-propanediol was used instead of the (S)-(−)-3-pyrrolidinol (Amount obtained: 115 mg/Yield: 53%).

$^1$H NMR (400, CDCl$_3$): 7.10 (2H, m), 6.88 (1H, t), 6.41 (1H, m), 6.06 (1H, m), 4.15 (2H, m), 3.91 (7H, m), 2.77 (3H, m), 2.45 (6H, m), 2.02 (4H, m), 1.32 (9H, m), 1.26 (2H, m)

Example 68: Preparation of tert-butyl 4-((5-(4-(1,3-dihydroxypropan-2-ylcarbamoyl)cyclohex-1-enyl)pyridin-2-yloxy)methyl)piperidine-1-carboxylate

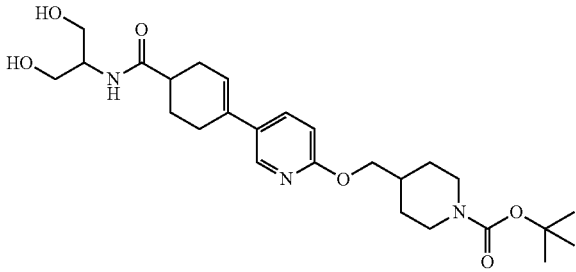 [SMILES: CC(C)(C)OC(=O)N1CCC(COc2ccc(C3=CCC(C(=O)NC(CO)CO)CC3)cn2)CC1]

The title compound was prepared in the same manner as in <Example 24>, except that 2-amino-1,3-propanediol was used instead of the (S)-2-amino-1-propanol (Amount obtained: 142 mg/Yield: 63%).

$^1$H NMR (400, CDCl$_3$): 8.14 (1H, s), 7.61 (1H, d), 6.70 (1H, d), 6.40 (1H, d), 6.04 (1H, s), 4.16 (4H, m), 4.01 (1H, m), 3.90 (4H, m), 2.76 (4H, m), 2.12 (1H, m), 1.93 (2H, m), 1.86 (2H, m), 1.48 (9H, m), 1.26 (2H, m).

Example 69: Preparation of tert-butyl 4-((2-fluoro-4-(4-(morpholine-4-carbonyl)cyclohex-1-enyl)phenoxy)methyl)piperidine-1-carboxylate

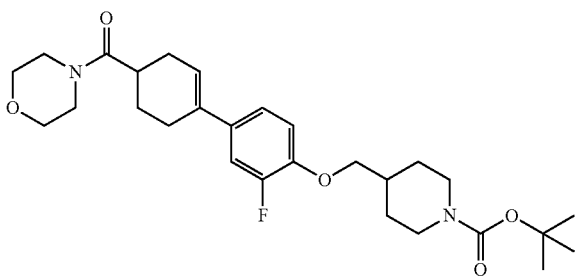

The title compound was prepared in the same manner as in <Example 44>, except that morpholine was used instead of the (S)-(−)-3-pyrrolidinol (Amount obtained: 192 mg/Yield: 83%).

$^1$H NMR (400, CDCl$_3$): 7.14 (2H, m), 6.89 (1H, t), 6.09 (1H, m), 4.16 (2H, m), 3.88 (2H, d), 3.69 (6H, m), 3.58 (2H, m), 2.78 (3H, m), 2.48 (4H, m), 1.91 (5H, m), 1.48 (9H, s), 1.28 (2H, m)

Example 70: Preparation of tert-butyl 4-((5-(4-(morpholine-4-carbonyl)cyclohex-1-enyl)pyridin-2-yloxy)methyl)piperidine-1-carboxylate

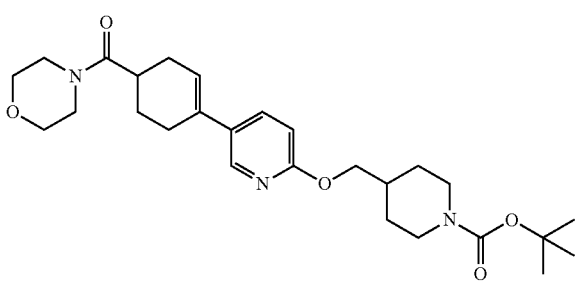

The title compound was prepared in the same manner as in <Example 24>, except that morpholine was used instead of the (S)-2-amino-1-propanol (Amount obtained: 210 mg/Yield: 91%).

$^1$H NMR (400, CDCl$_3$): 8.14 (1H, s), 7.63 (1H, d), 6.68 (1H, d), 6.05 (1H, s), 4.15 (4H, m), 3.71 (6H, m), 3.58 (2H, m), 2.77 (3H, m), 2.52 (3H, m), 2.30 (1H, m), 1.98 (3H, m), 1.84 (2H, d), 1.48 (9H, s), 1.27 (2H, m)

Example 71: Preparation of tert-butyl 4-((2-fluoro-4-(4-(thiomorpholine-4-carbonyl)cyclohex-1-enyl)phenoxy)methyl)piperidine-1-carboxylate

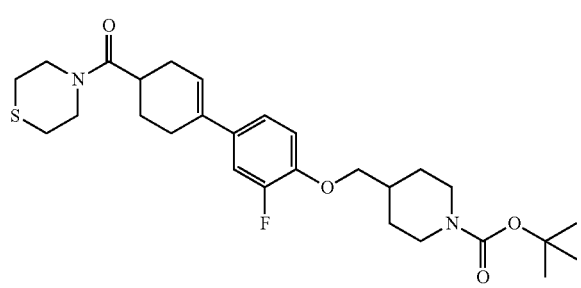 [SMILES: CC(C)(C)OC(=O)N1CCC(COc2ccc(C3=CCC(C(=O)N4CCSCC4)CC3)cc2F)CC1]

The title compound was prepared in the same manner as in <Example 44>, except that thiomorpholine was used instead of the (S)-(−)-3-pyrrolidinol (Amount obtained: 210 mg/Yield: 87%).

$^1$H NMR (400, CDCl$_3$): 7.14 (2H, m), 6.89 (1H, t), 6.07 (1H, m), 4.16 (2H, m), 3.98 (1H, m), 3.88 (5H, d), 2.79 (2H, m), 2.66 (4H, m), 2.31 (3H, m), 2.01 (1H, m), 1.91 (5H, m), 1.48 (9H, s), 1.26 (2H, m)

Example 72: Preparation of tert-butyl 4-((5-(4-(thiomorpholine-4-carbonyl)cyclohex-1-enyl)pyridin-2-yloxy)methyl)piperidine-1-carboxylate

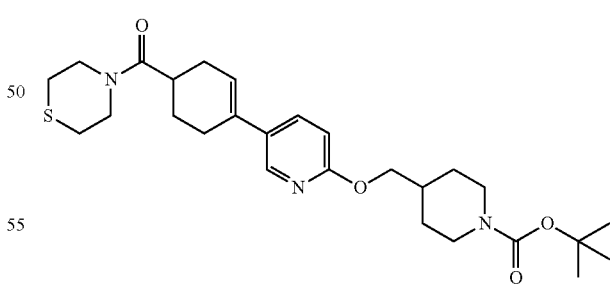

The title compound was prepared in the same manner as in <Example 24>, except that thiomorpholine was used instead of the (S)-2-amino-1-propanol (Amount obtained: 180 mg/Yield: 79%).

$^1$H NMR (400, CDCl$_3$): 8.14 (1H, s), 7.62 (1H, d), 6.71 (1H, d), 6.06 (1H, s), 4.16 (4H, m), 3.85 (4H, m), 2.78 (2H, m), 2.67 (4H, m), 2.55 (3H, m), 2.31 (1H, m), 1.99 (3H, m), 1.84 (2H, d), 1.48 (9H, s), 1.27 (2H, m)

Example 73: Preparation of tert-butyl 4-((2-fluoro-4-(4-(thiomorpholine-1,1-dioxide-4-carbonyl)cyclohex-1-enyl)phenoxy)methyl)piperidine-1-carboxylate

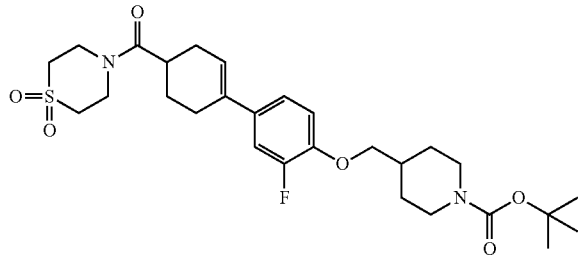 [SMILES: CC(C)(C)OC(=O)N1CCC(COc2ccc(C3=CCC(C(=O)N4CCS(=O)(=O)CC4)CC3)cc2F)CC1]

120 mg of tert-butyl 4-((2-fluoro-4-(4-(thiomorpholine-4-carbonyl)cyclohex-1-enyl)phenoxy)methyl)piperidine-1-carboxylate was dissolved in a THF/water mixture (50 ml/25 ml), and stirred. 360 mg of oxone was added dropwise thereto, and the resulting mixture was stirred for 30 minutes. After the reaction was terminated, the reaction mixture was extracted with 150 it of ethyl acetate, washed with 100 Qt of brine, dried with anhydrous magnesium sulfate, concentrated, and then isolated by silica column chromatography to prepare the title compound (Amount obtained: 100 mg/Yield: 72%).

$^1$H NMR (400, CDCl$_3$): 7.14 (2H, m), 6.90 (1H, t), 6.07 (1H, m), 4.19 (6H, m), 3.89 (2H, d), 3.09 (4H, d), 2.77 (3H, m), 2.54 (3H, m), 2.33 (1H, m), 2.00 (3H, m), 1.87 (2H, m), 1.48 (9H, s), 1.27 (2H, m)

Example 74: Preparation of (4-(4-((1-(3-isopropyl-1,2,4-oxadiazol-5-yl)piperidin-4-yl)methoxy)phenyl)cyclohex-3-enyl)(thiomorpholino)methanone

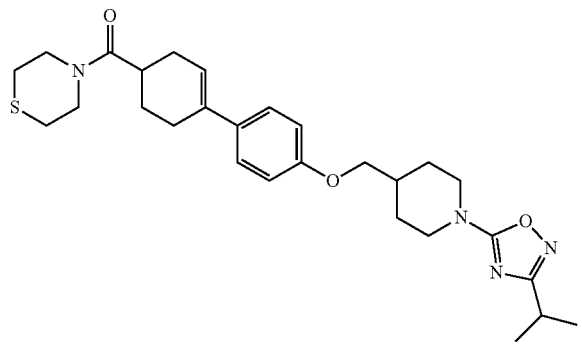 [SMILES: CC(C)c1noc(N2CCC(COc3ccc(C4=CCC(C(=O)N5CCSCC5)CC4)cc3)CC2)n1]

The title compound was prepared in the same manner as in <Example 17>, except that thiomorpholine was used instead of the (R)-3-amino-1,2-propanediol (Amount obtained: 165 mg/Yield: 63%).

$^1$H NMR (400, CDCl$_3$): 7.33 (2H, d), 6.84 (2H, d), 6.05 (1H, s), 4.23 (2H, m), 3.97 (6H, m), 3.08 (2H, t), 2.91 (1H, m), 2.78 (2H, m), 2.66 (4H, m), 2.51 (2H, m), 2.31 (1H, m), 2.03 (5H, m), 1.48 (2H, m), 1.32 (6H, d)

Example 75: Preparation of N-(2-fluoroethyl)-4-(4-((1-(3-isopropyl-1,2,4-oxadiazol-5-yl)piperidin-4-yl)methoxy)phenyl)cyclohex-3-enecarboxamide

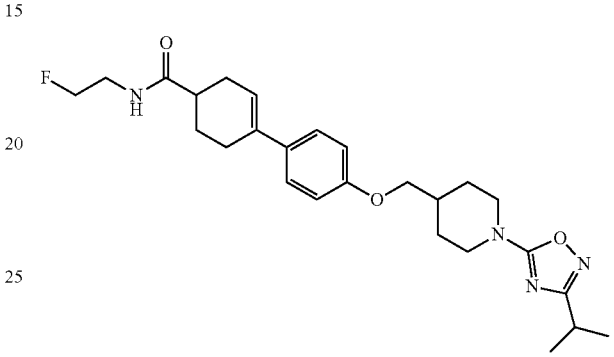

The title compound was prepared in the same manner as in <Example 17>, except that 2-fluoroethylamine was used instead of the (R)-3-amino-1,2-propanediol (Amount obtained: 174 mg/Yield: 75%).

$^1$H NMR (400, CDCl$_3$): 7.33 (2H, d), 6.87 (2H, d), 6.04 (2H, m), 4.53 (1H, m), 4.27 (2H, d), 3.86 (2H, d), 3.66 (2H, m), 3.21 (8H, m), 2.01 (5H, m), 1.45 (1H, m), 1.31 (6H, m)

Example 76: Preparation of tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate

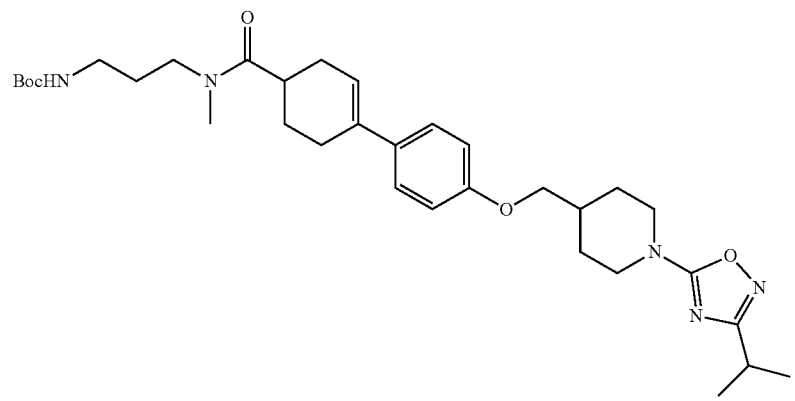 [SMILES: CC(C)c1noc(N2CCC(COc3ccc(C4=CCC(C(=O)N(C)CCCNC(=O)OC(C)(C)C)CC4)cc3)CC2)n1]

The title compound was prepared in the same manner as in <Example 17>, except that tert-butyl 3-(methylamino) propylcarbamate was used instead of the (R)-3-amino-1,2-propanediol (Amount obtained: 160 mg/Yield: 53%).

$^1$H NMR (400, CDCl$_3$): 7.34 (2H, d), 6.86 (2H, d), 6.07 (1H, m), 5.01 (1H, m), 4.21 (2H, d), 3.86 (2H, d), 3.56 (2H, m), 3.33 (2H, m), 3.11 (5H, m), 2.93 (1H, m), 2.80 (1H, m), 2.51 (2H, m), 2.98 (1H, m), 2.01 (5H, m), 1.48 (11H, m), 1.32 (6H, d)

Example 77: Preparation of N-(3-aminopropyl)-4-(4-((1-(3-isopropyl-1,2,4-oxadiazol-5-yl)piperidin-4-yl)methoxy)phenyl)-N-methylcyclohex-3-enecarboxamide

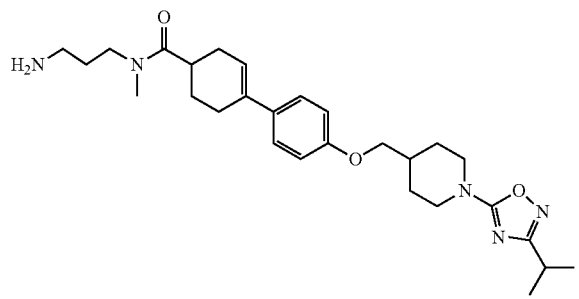 [SMILES: CC(C)c1noc(N2CCC(COc3ccc(C4=CCC(C(=O)N(C)CCCN)CC4)cc3)CC2)n1]

100 mg of tert-butyl 3-(4-(4-((1-(3-isopropyl-1,2,4-oxadiazol-5-yl)piperidin-4-yl)methoxy)phenyl)-N-methylcyclohex-3-enecarboxamido)propylcarbamate was dissolved in 25 at of DCM, and stirred. 4 N HCl dissolved in 2 μl of dioxane was added dropwise thereto, and the resulting mixture was stirred at room temperature for 3 hours. After the reaction was terminated, the resulting solids were filtered, washed with 50 μl of DCM, and then dried to obtain a desired compound as a white solid (Amount obtained: 30 mg/Yield: 34%).

$^1$H NMR (400, DMSO): 7.34 (2H, d), 6.86 (2H, d), 6.07 (1H, m), 5.01 (1H, m), 4.21 (2H, d), 3.86 (2H, d), 3.56 (2H, m), 3.33 (2H, m), 3.11 (5H, m), 2.93 (1H, m), 2.80 (1H, m), 2.51 (2H, m), 2.98 (1H, m), 2.01 (5H, m), 1.48 (2H, m), 1.32 (6H, d)

Example 78: Preparation of 4-(4-((1-(3-isopropyl-1,2,4-oxadiazol-5-yl)piperidin-4-yl)methoxy)phenyl)-N-(2,2,2-trifluoroethyl)cyclohex-3-enecarboxamide

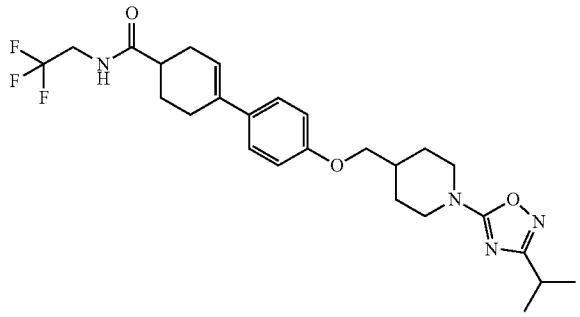 [SMILES: CC(C)c1noc(N2CCC(COc3ccc(C4=CCC(C(=O)NCC(F)(F)F)CC4)cc3)CC2)n1]

The title compound was prepared in the same manner as in <Example 17>, except that 2,2,2-trifluoroethyl amine was used instead of the (R)-3-amino-1,2-propanediol (Amount obtained: 195 mg/Yield: 85%).

$^1$H NMR (400, CDCl$_3$): 7.33 (2H, d), 6.86 (2H, d), 6.04 (1H, m), 5.96 (1H, m), 4.23 (2H, d), 3.99 (2H, m), 3.84 (2H, d), 3.12 (2H, m), 2.92 (1H, m), 2.48 (5H, m), 2.01 (5H, m), 1.46 (2H, m), 1.29 (6H, d)

Example 79: Preparation of (4-ethylpiperazin-1-yl)(4-(4-((1-(3-isopropyl-1,2,4-oxadiazol-5-yl)piperidin-4-yl)methoxy)phenyl)cyclohex-3-enyl)methanone

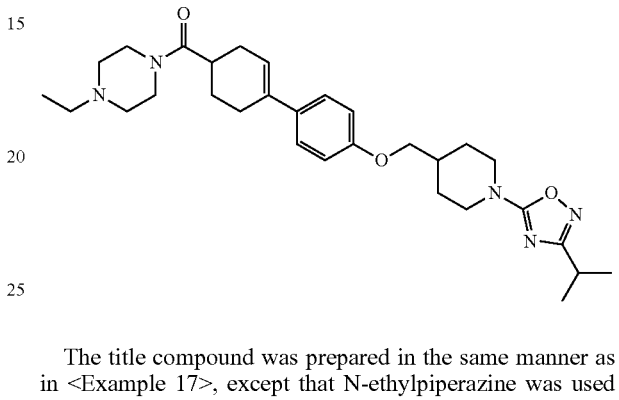

The title compound was prepared in the same manner as in <Example 17>, except that N-ethylpiperazine was used instead of the (R)-3-amino-1,2-propanediol (Amount obtained: 150 mg/Yield: 65%).

$^1$H NMR (400, CDCl$_3$): 7.33 (2H, d), 6.86 (2H, d), 6.05 (1H, m), 4.23 (2H, d), 3.85 (2H, d), 3.70 (2H, m), 3.59 (2H, m), 3.08 (2H, t), 2.92 (1H, m), 2.89 (1H, m), 2.50 (9H, m), 2.24 (1H, m), 1.98 (5H, m), 1.48 (2H, m), 1.31 (6H, d), 1.11 (3H, t)

Example 80: Preparation of N-(1,3-dihydroxypropan-2-yl)-4-(3-fluoro-4-((1-(3-isopropyl-1,2,4-oxadiazol-5-yl)piperidin-4-yl)methoxy)phenyl)cyclohex-3-enecarboxamide

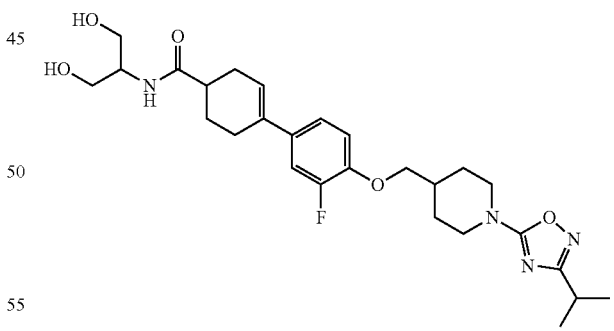

250 mg of 4-(3-fluoro-4-((1-(3-isopropyl-1,2,4-oxadiazol-5-yl)piperidin-4-yl)methoxy)phenyl)cyclohex-3-enecarboxylic acid was dissolved in 25 μl of DMF, and stirred. 200 mg of EDCI and 150 mg of HOBt were sequentially added dropwise thereto, and the resulting mixture was then additionally stirred for 10 minutes. 100 mg of 2-amino-1,3-propanediol was added dropwise thereto, and the mixture was stirred at room temperature for 12 hours. After the reaction was terminated, 50 μl of distilled water was slowly added as 0° C., and the resulting solids were filtered, and

Example 81: Preparation of 4-(3-fluoro-4-((1-(3-isopropyl-1,2,4-oxadiazol-5-yl)piperidin-4-yl)methoxy)phenyl)-N-(2-hydroxyethyl)-N-methylcyclohex-3-enecarboxamide dried to obtain a desired compound as a white solid (Amount obtained: 210 mg/Yield: 71%).

$^1$H NMR (400, CDCl$_3$): 7.14 (2H, m), 6.91 (1H, t), 6.37 (1H, m), 6.07 (1H, m), 4.24 (2H, d), 4.01 (1H, m), 3.91 (2H, m), 3.81 (4H, m), 3.15 (2H, t), 2.94 (1H, m), 2.64 (2H, m), 2.50 (5H, m), 2.14 (2H, m), 1.92 (2H, d), 1.88 (1H, m), 1.45 (2H, m), 1.30 (6H, d)

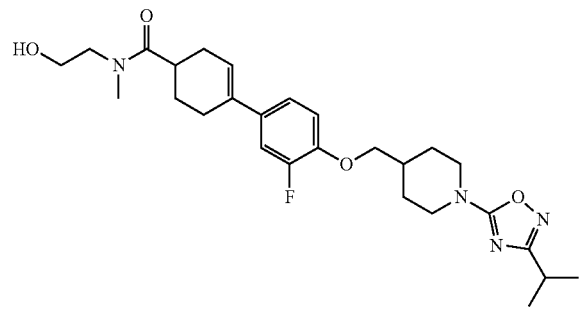 [SMILES: CC(C)c1noc(N2CCC(COc3ccc(C4=CCC(C(=O)N(C)CCO)CC4)cc3F)CC2)n1]

The title compound was prepared in the same manner as in <Example 80>, except that 2-(methylamino)ethanol was used instead of the 2-amino-1,3-propanediol (Amount obtained: 169 mg/Yield: 73%).

$^1$H NMR (400, CDCl$_3$): 7.15 (1H, d), 7.11 (1H, d), 6.91 (1H, m), 6.11 (1H, s), 4.26 (2H, d), 3.94 (2H, d), 3.84 (2H, m), 3.61 (2H, m), 3.21 (3H, s), 3.16 (2H, m), 3.05 (1H, s), 2.91 (1H, m), 2.87 (1H, m), 2.25-2.61 (4H, m), 1.85-2.19 (5H, m), 1.43 (2H, m), 1.30 (6H, d)

Example 82: Preparation of tert-butyl 4-((2-fluoro-4-(4-(3-hydroxy-2,2-dimethylpropylcarbamoyl)cyclohex-1-enyl)phenoxy)methyl)piperidine-1-carboxylate

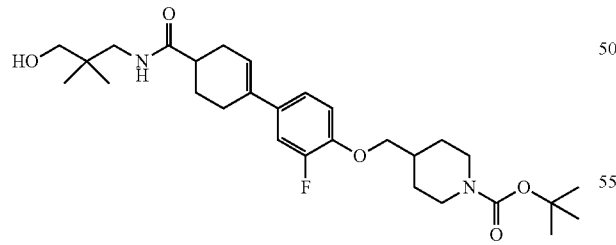

The title compound was prepared in the same manner as in <Example 44>, except that 3-amino-2,2-dimethylpropan-1-ol was used instead of the (S)-(–)-3-pyrrolidinol (Amount obtained: 150 mg/Yield: 65%).

$^1$H NMR (400, CDCl$_3$): 7.15 (1H, d), 7.11 (1H, d), 6.91 (1H, m), 6.11 (1H, s), 6.00 (1H, m), 4.19 (2H, m), 3.89 (3H, m), 3.18 (4H, m), 2.81 (2H, m), 2.45-2.61 (5H, m), 1.85-2.19 (4H, m), 1.48 (9H, s), 1.34 (2H, m), 0.89 (6H, d)

Example 83: Preparation of 4-(3-fluoro-4-((1-(3-isopropyl-1,2,4-oxadiazol-5-yl)piperidin-4-yl)methoxy)phenyl)-N—((S)-1-hydroxypropan-2-yl)cyclohex-3-enecarboxamide

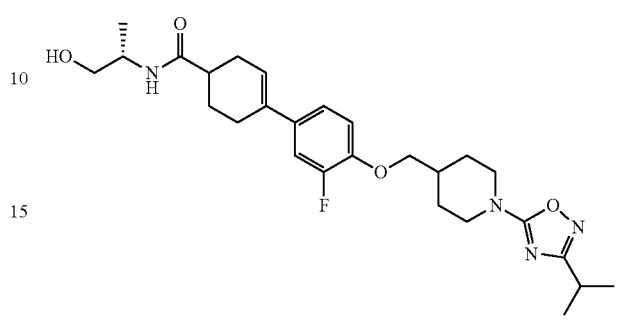

The title compound was prepared in the same manner as in <Example 80>, except that (S)-2-amino-1-propanol was used instead of the 2-amino-1,3-propanediol (Amount obtained: 95 mg/Yield: 48%).

$^1$H NMR (400, CDCl$_3$): 7.15 (1H, d), 7.11 (1H, d), 6.91 (1H, m), 6.11 (1H, s), 5.71 (1H, d), 4.25 (2H, d), 4.16 (1H, m), 3.92 (2H, d), 3.65 (2H, m), 3.16 (2H, m), 2.91 (1H, m), 2.35-2.61 (5H, m), 2.12 (2H, m), 1.98 (2H, d), 1.48 (2H, m), 1.36 (6H, d), 1.21 (3H, d)

Example 84: Preparation of 4-(3-fluoro-4-((1-(3-isopropyl-1,2,4-oxadiazol-5-yl)piperidin-4-yl)methoxy)phenyl)-N—((R)-1-hydroxypropan-2-yl)cyclohex-3-enecarboxamide

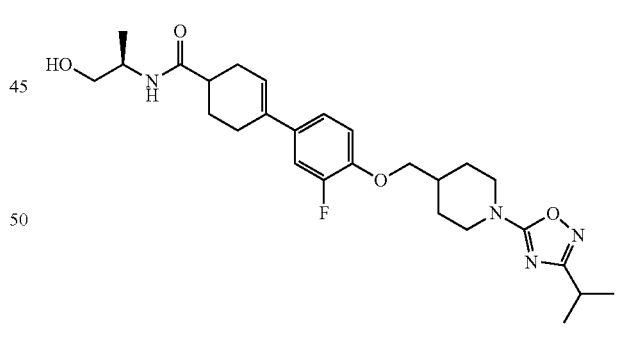

The title compound was prepared in the same manner as in <Example 80>, except that (R)-2-amino-1-propanol was used instead of the 2-amino-1,3-propanediol (Amount obtained: 120 mg/Yield: 53%).

$^1$H NMR (400, CDCl$_3$): 7.15 (1H, d), 7.11 (1H, d), 6.91 (1H, m), 6.11 (1H, s), 5.71 (1H, d), 4.25 (2H, d), 4.16 (1H, m), 3.92 (2H, d), 3.65 (2H, m), 3.16 (2H, m), 2.91 (1H, m), 2.35-2.61 (5H, m), 2.12 (2H, m), 1.98 (2H, d), 1.48 (2H, m), 1.36 (6H, d), 1.21 (3H, d)

Example 85: Preparation of tert-butyl 4-((4-(4-(2,2-difluoroethylcarbamoyl)cyclohex-1-enyl)-2-fluoro-phenoxy)methyl)piperidine-1-carboxylate

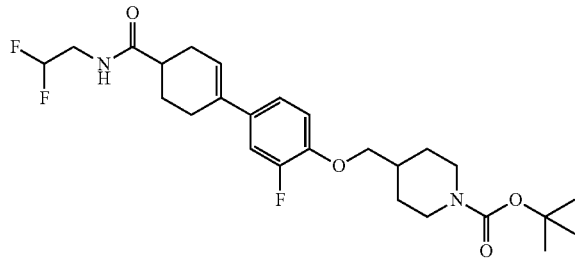 [SMILES: CC(C)(C)OC(=O)N1CCC(COc2ccc(C3=CCC(C(=O)NCC(F)F)CC3)cc2F)CC1]

The title compound was prepared in the same manner as in <Example 44>, except that 2,2-difluoroethylamine was used instead of the (S)-(−)-3-pyrrolidinol (Amount obtained: 150 mg/Yield: 65%).

$^1$H NMR (400, CDCl$_3$): 7.15 (1H, d), 7.11 (1H, d), 6.91 (1H, m), 6.11 (1H, s), 5.88 (1H, m), 5.85 (1H, m), 4.16 (2H, m), 3.87 (2H, d), 3.69 (2H, m), 2.77 (2H, m), 2.35-2.61 (5H, m), 2.12 (2H, m), 2.02 (1H, m), 1.89 (3H, m), 1.46 (9H, s), 1.25 (3H, m)

Example 86: Preparation of tert-butyl 4-((5-(4-(2,2,2-trifluoroethylcarbamoyl)cyclohex-1-enyl)pyridin-2-yloxy)methyl)piperidine-1-carboxylate

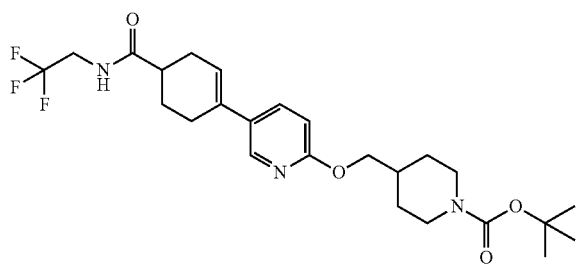 [SMILES: CC(C)(C)OC(=O)N1CCC(COc2ccc(C3=CCC(C(=O)NCC(F)(F)F)CC3)cn2)CC1]

The title compound was prepared in the same manner as in <Example 24>, except that 2,2,2-trifluoroethylamine was used instead of the (S)-2-amino-1-propanol (Amount obtained: 110 mg/Yield: 48%).

$^1$H NMR (400, CDCl$_3$): 8.14 (1H, d), 7.61 (1H, d), 6.70 (1H, d), 6.05 (1H, s), 5.86 (1H, m), 4.16 (4H, d), 3.99 (2H, m), 2.76 (2H, m), 2.35-2.61 (5H, m), 2.12 (1H, m), 1.89 (2H, m), 1.81 (2H, d), 1.48 (9H, s), 1.33 (2H, m)

Example 87: Preparation of tert-butyl 4-((5-(4-(2,2-difluoroethylcarbamoyl)cyclohex-1-enyl)pyridin-2-yloxy)methyl)piperidine-1-carboxylate

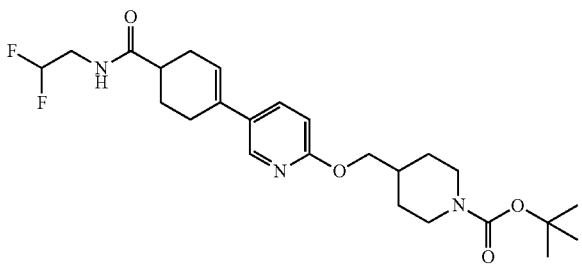 [SMILES: CC(C)(C)OC(=O)N1CCC(COc2ccc(C3=CCC(C(=O)NCC(F)F)CC3)cn2)CC1]

The title compound was prepared in the same manner as in <Example 24>, except that 2,2-difluoroethylamine was used instead of the (S)-2-amino-1-propanol (Amount obtained: 150 mg/Yield: 65%).

$^1$H NMR (400, CDCl$_3$): 8.14 (1H, d), 7.61 (1H, d), 6.70 (1H, d), 6.05 (1H, s), 5.88 (1H, m), 5.85 (1H, m), 4.16 (4H, d), 3.70 (2H, m), 2.76 (2H, m), 2.35-2.61 (5H, m), 2.12 (1H, m), 1.98 (2H, m), 1.82 (2H, d), 1.48 (9H, s), 1.29 (3H, m)

Example 88: Preparation of tert-butyl 4-((5-(4-(2-fluoroethylcarbamoyl)cyclohex-1-enyl)pyridin-2-yloxy)methyl)piperidine-1-carboxylate

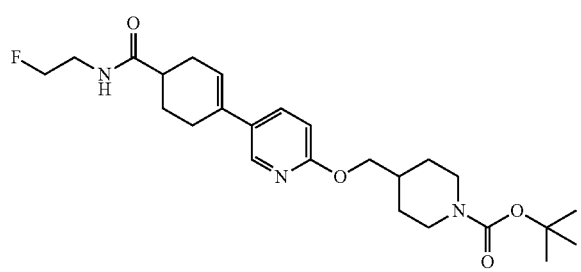 [SMILES: CC(C)(C)OC(=O)N1CCC(COc2ccc(C3=CCC(C(=O)NCCF)CC3)cn2)CC1]

The title compound was prepared in the same manner as in <Example 24>, except that 2-fluoroethylamine was used instead of the (S)-2-amino-1-propanol (Amount obtained: 120 mg/Yield: 52%).

$^1$H NMR (400, CDCl$_3$): 8.14 (1H, d), 7.61 (1H, d), 6.70 (1H, d), 6.05 (1H, s), 5.93 (1H, m), 4.55 (2H, m), 4.16 (4H, d), 3.67 (2H, m), 2.76 (2H, m), 2.35-2.61 (5H, m), 2.12 (1H, m), 1.98 (2H, m), 1.82 (2H, d), 1.48 (9H, s), 1.29 (3H, m)

Example 89: Preparation of (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone

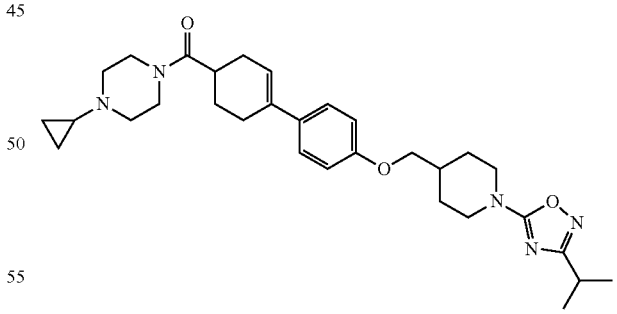

The title compound was prepared in the same manner as in <Example 17>, except that cyclopropylpiperazine was used instead of the (R)-3-amino-1,2-propanediol (Amount obtained: 210 mg/Yield: 87%).

$^1$H NMR (400, CDCl$_3$): 7.32 (2H, d), 6.85 (2H, d), 6.05 (1H, d), 4.22 (2H, d), 3.85 (2H, d), 3.66 (2H, m), 3.53 (2H, m), 3.12 (3H, m), 2.81 (3H, m), 2.35-2.61 (8H, m), 1.91-2.14 (6H, m), 1.68 (1H, m), 1.48 (2H, m), 1.32 (6H, d), 1.15 (1H, m), 0.48 (4H, m)

Example 90: Preparation of tert-butyl 4-((5-(4-((R)-3-fluoropyrrolidine-1-carbonyl)cyclohex-1-enyl)pyridin-2-yloxy)methyl)piperidine-1-carboxylate

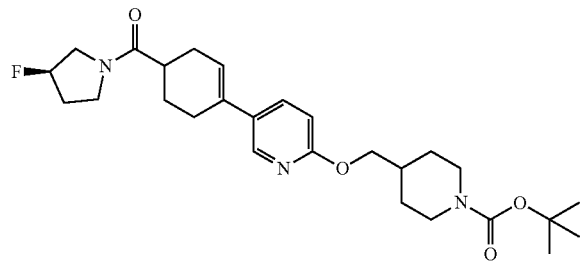

The title compound was prepared in the same manner as in <Example 24>, except that (R)-3-fluoropyrrolidine was used instead of the (S)-2-amino-1-propanol (Amount obtained: 165 mg/Yield: 72%).

$^1$H NMR (400, CDCl$_3$): 8.15 (1H, s), 7.63 (1H, d), 6.70 (1H, d), 6.08 (1H, s), 5.31 (1H, m), 4.16 (4H, m), 3.53-4.01 (2H, m), 2.76 (2H, m), 2.35-2.61 (5H, m), 1.80-2.16 (6H, m), 1.48 (9H, s), 1.29 (3H, m)

Example 91: Preparation of tert-butyl 4-((5-(4-((S)-3-fluoropyrrolidine-1-carbonyl)cyclohex-1-enyl)pyridin-2-yloxy)methyl)piperidine-1-carboxylate

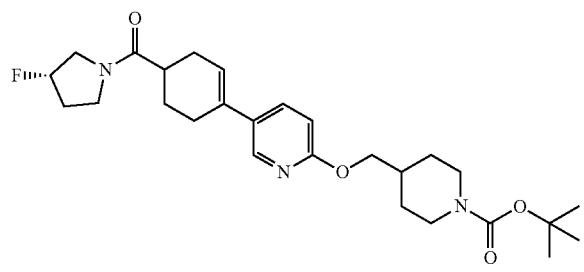 [SMILES: CC(C)(C)OC(=O)N1CCC(COc2ccc(C3=CCC(C(=O)N4CC[C@H](F)C4)CC3)cn2)CC1]

The title compound was prepared in the same manner as in <Example 24>, except that (S)-3-fluoropyrrolidine was used instead of the (S)-2-amino-1-propanol (Amount obtained: 120 mg/Yield: 53%).

$^1$H NMR (400, CDCl$_3$): 8.15 (1H, s), 7.63 (1H, d), 6.70 (1H, d), 6.08 (1H, s), 5.31 (1H, m), 4.16 (4H, m), 3.53-4.01 (2H, m), 2.76 (2H, m), 2.35-2.61 (5H, m), 1.80-2.16 (6H, m), 1.48 (9H, s), 1.29 (3H, m)

Example 92: Preparation of 4-(3-fluoro-4-((1-(3-isopropyl-1,2,4-oxadiazol-5-yl)piperidin-4-yl)methoxy)phenyl)-N-(2,2,2-trifluoroethyl)cyclohex-3-enecarboxamide

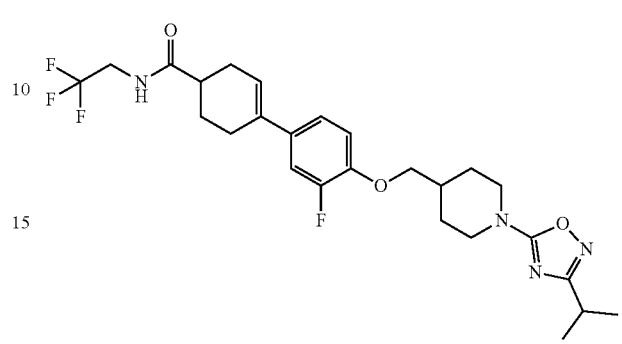

The title compound was prepared in the same manner as in <Example 80>, except that 2,2,2-trifluoroethylamine was used instead of the 2-amino-1,3-propanediol (Amount obtained: 140 mg/Yield: 62%).

$^1$H NMR (400, CDCl$_3$): 7.11 (2H, m), 6.91 (1H, m), 6.07 (1H, d), 5.80 (1H, m), 4.22 (2H, d), 3.99 (1H, m), 3.92 (2H, d), 3.12 (2H, m), 2.92 (1H, m), 2.35-2.61 (5H, m), 1.83-2.21 (5H, m), 1.48 (2H, m), 1.32 (6H, d)

Example 93: Preparation of N-(2,2-difluoroethyl)-4-(3-fluoro-4-((1-(3-isopropyl-1,2,4-oxadiazol-5-yl)piperidin-4-yl)methoxy)phenyl)cyclohex-3-enecarboxamide

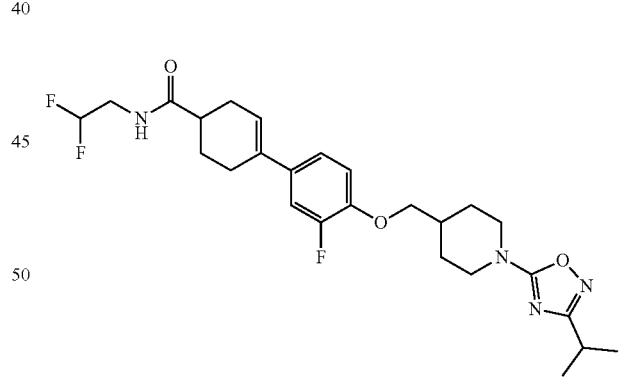

The title compound was prepared in the same manner as in <Example 80>, except that 2,2-difluoroethylamine was used instead of the 2-amino-1,3-propanediol (Amount obtained: 110 mg/Yield: 49%).

$^1$H NMR (400, CDCl$_3$): 7.11 (2H, m), 6.91 (1H, m), 6.07 (1H, d), 5.89 (1H, m), 5.81 (1H, m), 4.22 (2H, d), 3.99 (1H, m), 3.69 (2H, m), 3.12 (2H, m), 2.92 (1H, m), 2.35-2.61 (5H, m), 1.83-2.21 (5H, m), 1.48 (2H, m), 1.32 (6H, d)

Example 94: Preparation of 4-(3-fluoro-4-((1-(3-isopropyl-1,2,4-oxadiazol-5-yl)piperidin-4-yl)methoxy)phenyl)-N-(2-fluoroethyl)cyclohex-3-enecarboxamide

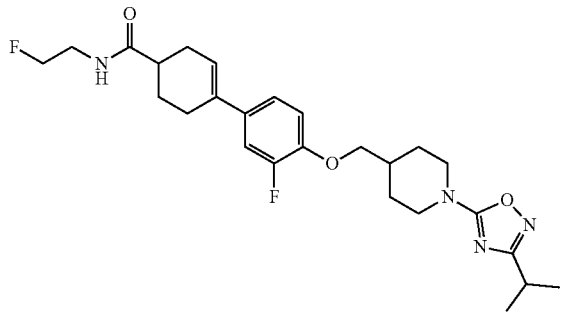 [SMILES: CC(C)c1noc(N2CCC(COc3ccc(C4=CCC(C(=O)NCCF)CC4)cc3F)CC2)n1]

The title compound was prepared in the same manner as in <Example 80>, except that fluoroethylamine was used instead of the 2-amino-1,3-propanediol (Amount obtained: 120 mg/Yield: 53%).

$^1$H NMR (400, CDCl$_3$): 7.11 (2H, m), 6.91 (1H, m), 6.07 (1H, d), 5.94 (1H, s), 4.55 (2H, m), 4.22 (2H, d), 3.99 (1H, m), 3.63 (2H, m), 3.12 (2H, m), 2.92 (1H, m), 2.35-2.61 (5H, m), 1.83-2.21 (5H, m), 1.48 (2H, m), 1.32 (6H, d)

Example 95: Preparation of (4-(3-fluoro-4-((1-(3-isopropyl-1,2,4-oxadiazol-5-yl)piperidin-4-yl)methoxy)phenyl)cyclohex-3-enyl)((S)-3-fluoropyrrolidin-1-yl)methanone

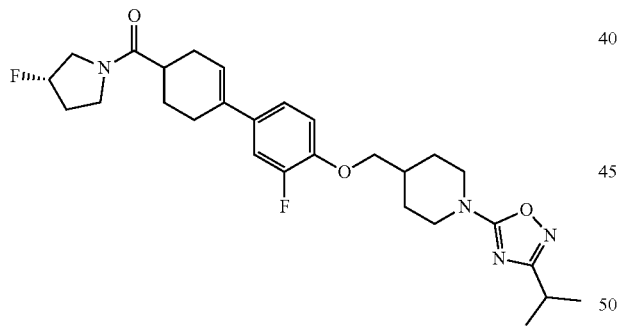

The title compound was prepared in the same manner as in <Example 80>, except that (S)-3-fluoropyrrolidine was used instead of the 2-amino-1,3-propanediol (Amount obtained: 185 mg/Yield: 78%).

$^1$H NMR (400, CDCl$_3$): 7.11 (2H, m), 6.91 (1H, m), 6.10 (1H, s), 5.30 (1H, m), 4.22 (2H, d), 3.95 (2H, d), 3.75 (4H, m), 3.12 (2H, m), 2.92 (1H, m), 2.35-2.61 (5H, m), 1.83-2.21 (5H, m), 1.48 (2H, m), 1.32 (6H, d)

Example 96: Preparation of (4-(3-fluoro-4-((1-(3-isopropyl-1,2,4-oxadiazol-5-yl)piperidin-4-yl)methoxy)phenyl)cyclohex-3-enyl)((R)-3-fluoropyrrolidin-1-yl)methanone

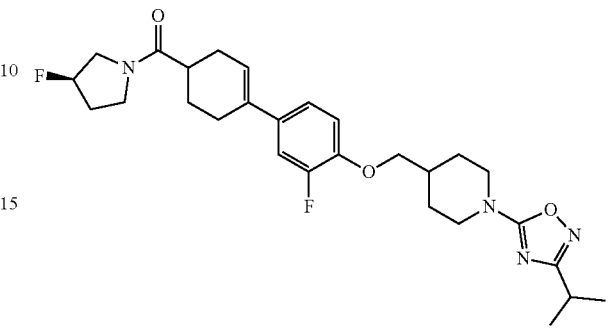

The title compound was prepared in the same manner as in <Example 80>, except that (R)-3-fluoropyrrolidine was used instead of the 2-amino-1,3-propanediol (Amount obtained: 150 mg/Yield: 64%).

$^1$H NMR (400, CDCl$_3$): 7.11 (2H, m), 6.91 (1H, m), 6.10 (1H, s), 5.30 (1H, m), 4.22 (2H, d), 3.95 (2H, d), 3.75 (4H, m), 3.12 (2H, m), 2.92 (1H, m), 2.35-2.61 (5H, m), 1.83-2.21 (5H, m), 1.48 (2H, m), 1.32 (6H, d)

Example 97: Preparation of (4-(3-fluoro-4-((1-(3-isopropyl-1,2,4-oxadiazol-5-yl)piperidin-4-yl)methoxy)phenyl)cyclohex-3-enyl)(morpholino)methanone

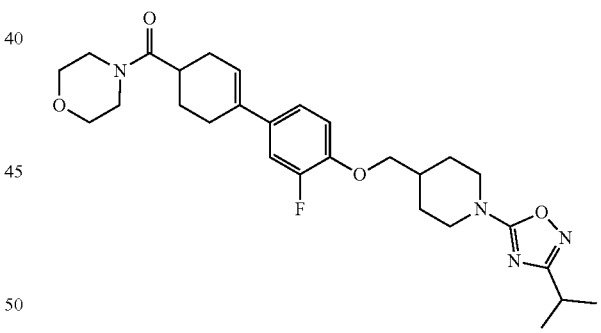

The title compound was prepared in the same manner as in <Example 80>, except that morpholine was used instead of the 2-amino-1,3-propanediol (Amount obtained: 190 mg/Yield: 83%).

$^1$H NMR (400, CDCl$_3$): 7.11 (2H, m), 6.91 (1H, m), 6.09 (1H, s), 4.21 (2H, d), 3.91 (2H, d), 3.72 (6H, m), 3.59 (2H, m), 3.13 (2H, m), 2.92 (1H, m), 2.78 (1H, m), 2.35-2.61 (3H, m), 2.30 (1H, m), 1.83-2.21 (5H, m), 1.48 (2H, m), 1.32 (6H, d)

Example 98: Preparation of (4-(3-fluoro-4-((1-(3-isopropyl-1,2,4-oxadiazol-5-yl)piperidin-4-yl)methoxy)phenyl)cyclohex-3-enyl)(thiomorpholino)methanone

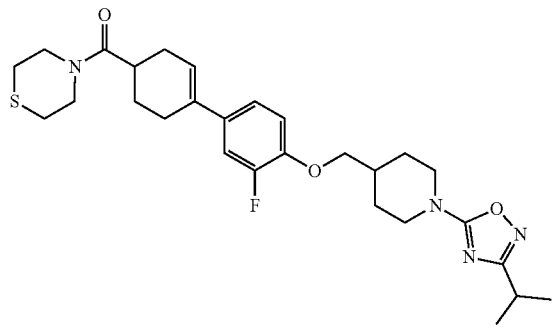 [SMILES: CC(C)c1noc(N2CCC(COc3ccc(C4=CCC(C(=O)N5CCSCC5)CC4)cc3F)CC2)n1]

The title compound was prepared in the same manner as in <Example 80>, except that thiomorpholine was used instead of the 2-amino-1,3-propanediol (Amount obtained: 200 mg/Yield: 78%).

$^1$H NMR (400, CDCl$_3$): 7.11 (2H, m), 6.91 (1H, m), 6.09 (1H, s), 4.21 (2H, d), 3.91 (6H, m), 3.13 (2H, m), 2.92 (1H, m), 2.78 (1H, m), 2.65 (4H, m), 2.35-2.61 (5H, m), 1.83-2.21 (5H, m), 1.48 (2H, m), 1.32 (6H, d)

Example 99: Preparation of N-(2,2-difluoroethyl)-4-(5-((1-(3-isopropyl-1,2,4-oxadiazol-5-yl)piperidin-4-yl)methoxy)pyridin-2-yl)cyclohex-3-enecarboxamide

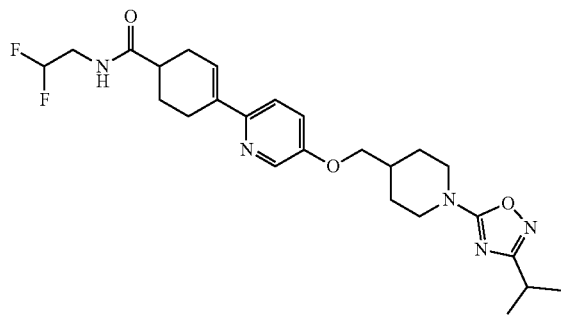 [SMILES: CC(C)c1noc(N2CCC(COc3ccc(C4=CCC(C(=O)NCC(F)F)CC4)nc3)CC2)n1]

The title compound was prepared in the same manner as in <Example 36>, except that 2,2-difluoroethylamine was used instead of the (R)-2-amino-1-propanol (Amount obtained: 165 mg/Yield: 71%).

$^1$H NMR (400, CDCl$_3$): 8.25 (1H, d), 7.34 (1H, d), 7.16 (1H, d), 6.56 (1H, s), 5.89 (1H, m), 5.83 (1H, m), 4.24 (2H, d), 3.89 (2H, d), 3.71 (2H, m), 3.12 (2H, m), 2.92 (1H, m), 2.75 (1H, m), 2.51 (4H, m), 1.83-2.21 (5H, m), 1.49 (2H, m), 1.32 (6H, d)

Example 100: Preparation of (4-(5-((1-(3-isopropyl-1,2,4-oxadiazol-5-yl)piperidin-4-yl)methoxy)pyridin-2-yl)cyclohex-3-enyl)(morpholino)methanone

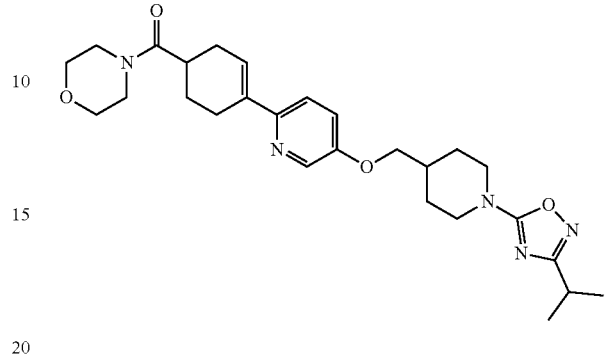

The title compound was prepared in the same manner as in <Example 36>, except that morpholine was used instead of the (R)-2-amino-1-propanol (Amount obtained: 200 mg/Yield: 87%).

$^1$H NMR (400, CDCl$_3$): 8.25 (1H, d), 7.34 (1H, d), 7.16 (1H, d), 6.56 (1H, s), 4.24 (2H, d), 3.90 (2H, d), 3.72 (6H, m), 3.58 (2H, m), 3.12 (2H, m), 2.92 (1H, m), 2.78 (2H, m), 2.57 (2H, m), 2.37 (1H, m), 1.83-2.21 (5H, m), 1.49 (2H, m), 1.32 (6H, d)

Example 101: Preparation of ((R)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl) methanone

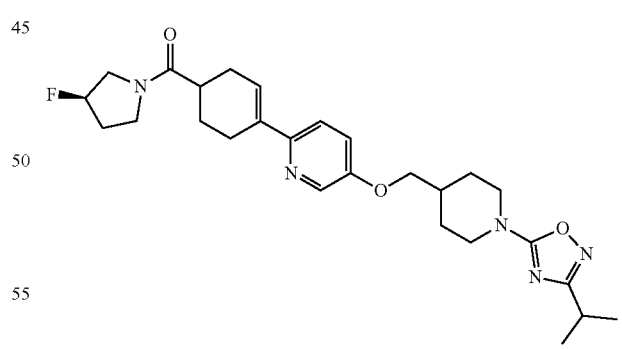

The title compound was prepared in the same manner as in <Example 36>, except that (R)-3-fluoropyrrolidine was used instead of the (R)-2-amino-1-propanol (Amount obtained: 210 mg/Yield: 86%).

$^1$H NMR (400, CDCl$_3$): 8.25 (1H, d), 7.34 (1H, m), 7.16 (1H, m), 6.58 (1H, s), 5.30 (1H, m), 4.23 (2H, d), 3.55-3.99 (6H, m), 3.12 (2H, m), 2.92 (1H, m), 2.25-2.83 (6H, m), 1.83-2.21 (6H, m), 1.49 (2H, m), 1.31 (6H, d)

Example 102: Preparation of ((S)-3-fluoropyrrolidin-1-yl)(4-(5-((1-(3-isopropyl-1,2,4-oxadiazol-5-yl)piperidin-4-yl)methoxy)pyridin-2-yl)cyclohex-3-enyl)methanone

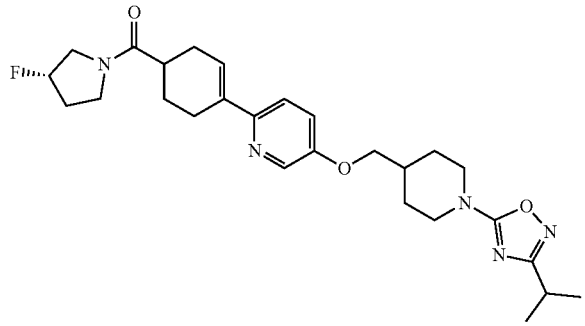 [SMILES: CC(C)c1noc(N2CCC(COc3ccc(C4=CCC(C(=O)N5CC[C@H](F)C5)CC4)nc3)CC2)n1]

The title compound was prepared in the same manner as in <Example 36>, except that (S)-3-fluoropyrrolidine was used instead of the (R)-2-amino-1-propanol (Amount obtained: 220 mg/Yield: 81%).

$^1$H NMR (400, CDCl$_3$): 8.25 (1H, d), 7.34 (1H, m), 7.16 (1H, m), 6.58 (1H, s), 5.30 (1H, m), 4.23 (2H, d), 3.55-3.99 (6H, m), 3.12 (2H, m), 2.92 (1H, m), 2.25-2.83 (6H, m), 1.83-2.21 (6H, m), 1.49 (2H, m), 1.31 (6H, d)

Example 103: Preparation of 4-(4-((1-(5-ethylpyrimidin-2-yl)piperidin-4-yl)methoxy)phenyl)-N-(2,2,2-trifluoroethyl)cyclohex-3-enecarboxamide

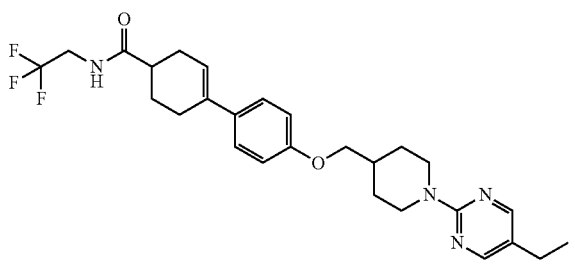 [SMILES: CCc1cnc(N2CCC(COc3ccc(C4=CCC(C(=O)NCC(F)(F)F)CC4)cc3)CC2)nc1]

The title compound was prepared in the same manner as in <Example 8>, except that 2,2,2-trifluoroethylamine was used instead of the (R)-2-amino-1-propanol (Amount obtained: 190 mg/Yield: 77%).

$^1$H NMR (400, CDCl$_3$): 8.19 (2H, s), 7.31 (2H, d), 6.86 (2H, d), 6.03 (1H, s), 4.58 (1H, m), 4.79 (2H, d), 3.99 (2H, m), 3.84 (2H, d), 2.96 (2H, m), 2.51 (7H, m), 1.83-2.21 (5H, m), 1.39 (2H, m), 1.21 (3H, m)

Example 104: Preparation of 4-(4-((1-(5-ethylpyrimidin-2-yl)piperidin-4-yl)methoxy)phenyl)-N-(2-fluoroethyl)cyclohex-3-enecarboxamide

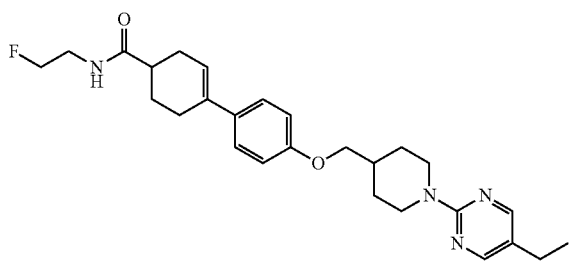 [SMILES: CCc1cnc(N2CCC(COc3ccc(C4=CCC(C(=O)NCCF)CC4)cc3)CC2)nc1]

The title compound was prepared in the same manner as in <Example 8>, except that fluoroethylamine was used instead of the (R)-2-amino-1-propanol (Amount obtained: 180 mg/Yield: 72%).

$^1$H NMR (400, CDCl$_3$): 8.19 (2H, s), 7.31 (2H, d), 6.86 (2H, d), 6.03 (1H, s), 4.58 (1H, m), 4.48 (1H, m), 4.59 (1H, m), 3.85 (2H, d), 3.63 (2H, m), 2.96 (2H, m), 2.51 (7H, m), 1.83-2.21 (5, m), 1.39 (2H, m), 1.21 (3H, m)

Example 105: Preparation of (2S)-1-(4-(4-((1-(5-ethylpyrimidin-2-yl)piperidin-4-yl)methoxy)phenyl)cyclohex-3-enecarbonyl)pyrrolidine-2-carboxamide

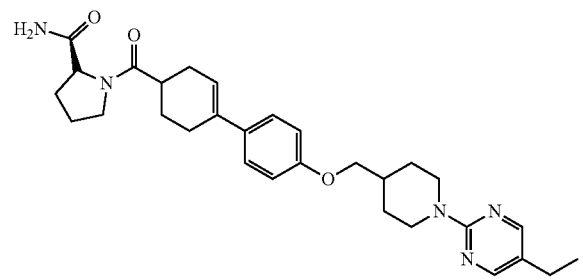

The title compound was prepared in the same manner as in <Example 8>, except that (S)-pyrrolidine-2-carboxamide was used instead of the (R)-2-amino-1-propanol (Amount obtained: 160 mg/Yield: 81%).

$^1$H NMR (400, CDCl$_3$): 8.21 (2H, s), 7.33 (2H, d), 6.86 (2H, d), 6.06 (1H, s), 5.32 (1H, s), 4.79 (2H, d), 4.67 (1H, d), 3.85 (2H, d), 3.68 (1H, m), 3.58 (1H, m), 2.95 (2H, m), 2.74 (1H, m), 2.27-2.62 (7H, m), 1.83-2.21 (10H, m), 1.39 (2H, m), 1.21 (3H, m)

Example 106: Preparation of (2S)-1-(4-(4-((1-(5-ethylpyrimidin-2-yl)piperidin-4-yl)methoxy)phenyl)cyclohex-3-enecarbonyl)pyrrolidine-2-carbonitrile

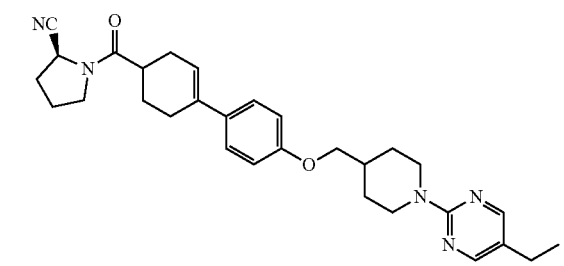 [SMILES: CCc1cnc(N2CCC(COc3ccc(C4=CCC(C(=O)N5CCC[C@H]5C#N)CC4)cc3)CC2)nc1]

The title compound was prepared in the same manner as in <Example 8>, except that (S)-pyrrolidine-2-carbonitrile hydrochloride was used instead of the (R)-2-amino-1-propanol (Amount obtained: 220 mg/Yield: 83%).

$^1$H NMR (400, CDCl$_3$): 8.23 (2H, s), 7.32 (2H, d), 6.86 (2H, d), 6.06 (1H, s), 4.79 (3H, m), 3.85 (2H, d), 3.75 (1H, m), 3.59 (1H, m), 2.99 (2H, m), 2.4-2.71 (7H, m), 1.83-2.38 (10H, m), 1.39 (2H, m), 1.21 (3H, m)

Example 107: Preparation of tert-butyl 4-((4-(4-((S)-2-carbamoylpyrrolidine-1-carbonyl)cyclohex-1-enyl)-2-fluorophenoxy)methyl)piperidine-1-carboxylate

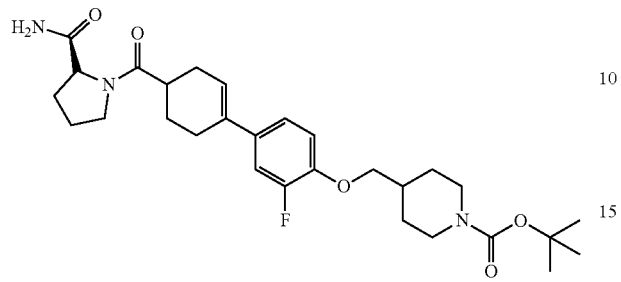

The title compound was prepared in the same manner as in <Example 44>, except that (S)-pyrrolidine-2-carboxamide was used instead of the (S)-(−)-3-pyrrolidinol (Amount obtained: 210 mg/Yield: 82%).

$^1$H NMR (400, CDCl$_3$): 7.11 (3H, m), 6.91 (1H, m), 6.09 (1H, s), 5.32 (1H, s), 4.67 (1H, d), 4.17 (2H, d), 3.88 (2H, d), 3.62 (2H, m), 2.29-2.82 (5H, m), 1.83-2.21 (8H, m), 1.49 (9H, s), 1.29 (2H, m)

Example 108: Preparation of (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide

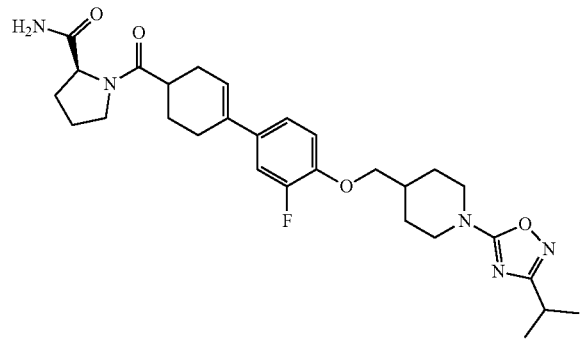 [SMILES: CC(C)c1noc(N2CCC(COc3ccc(C4=CCC(C(=O)N5CCC[C@H]5C(N)=O)CC4)cc3F)CC2)n1]

The title compound was prepared in the same manner as in <Example 80>, except that (S)-pyrrolidine-2-carboxamide was used instead of the 2-amino-1,3-propanediol (Amount obtained: 180 mg/Yield: 79%).

$^1$H NMR (400, CDCl$_3$): 7.11 (3H, m), 6.91 (1H, m), 6.10 (1H, s), 5.32 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 109: Preparation of (methyl 2-(4-(3-fluoro-4-((1-(3-isopropyl-1,2,4-oxadiazol-5-yl)piperidin-4-yl)methoxy)phenyl)cyclohex-3-enecarboxamido)acetate

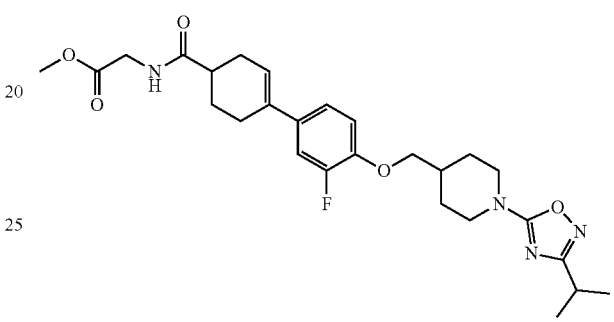

The title compound was prepared in the same manner as in <Example 80>, except that methyl 2-aminoacetate was used instead of the 2-amino-1,3-propanediol (Amount obtained: 850 mg/Yield: 83%).

$^1$H NMR (400, CDCl$_3$): 7.11 (2H, m), 6.90 (1H, m), 6.08 (1H, s), 4.21 (2H, d), 4.11 (2H, d), 3.91 (2H, d), 3.80 (3H, s), 3.12 (2H, m), 2.91 (1H, m), 2.49 (5H, m), 1.83-2.21 (5H, m), 1.49 (2H, m), 1.31 (6H, d)

Example 110: Preparation of ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate

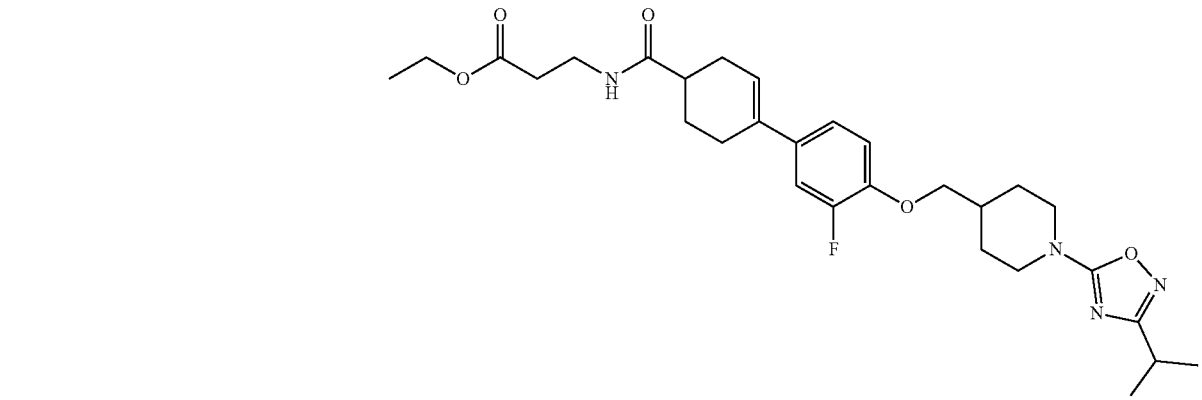 [SMILES: CCOC(=O)CCNC(=O)C1CC=C(c2ccc(OCC3CCN(c4nc(C(C)C)no4)CC3)c(F)c2)CC1]

The title compound was prepared in the same manner as in <Example 80>, except that ethyl 3-aminopropanoate was used instead of the 2-amino-1,3-propanediol (Amount obtained: 940 mg/Yield: 86%).

$^1$H NMR (400, CDCl$_3$): 7.11 (2H, m), 6.90 (1H, m), 6.08 (1H, s), 4.21 (4H, m), 3.91 (2H, d), 3.58 (2H, m), 3.12 (2H, m), 2.91 (1H, m), 2.58 (2H, m), 2.49 (5H, m), 1.83-2.21 (5H, m), 1.49 (2H, m), 1.31 (6H, d), 1.29 (3H, m)

Example 111: Preparation of 3-(4-(3-fluoro-4-((1-(3-isopropyl-1,2,4-oxadiazol-5-yl)piperidin-4-yl)methoxy)phenyl)cyclohex-3-enecarboxamido)propanoic Acid

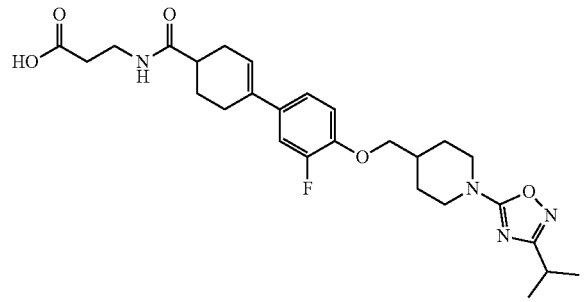 [SMILES: CC(C)c1noc(N2CCC(COc3ccc(C4=CCC(C(=O)NCCC(=O)O)CC4)cc3F)CC2)n1]

2,000 mg of ethyl 3-(4-(3-fluoro-4-((1-(3-isopropyl-1,2,4-oxadiazol-5-yl)piperidin-4-yl)methoxy)phenyl)cyclohex-3-enecarboxamido)propanoate was dissolved in a THF/water/ethanol mixture (100 µl/50 µl/10 µl) in a 500 µl flask, and stirred under nitrogen. 1.4 g of lithium hydroxide monohydrate was added dropwise thereto, and the resulting mixture was reacted at room temperature for 18 hours. After the reaction was terminated, the pH of the resulting reaction mixture was adjusted to pH 1 to 2 using concentrated HCl. The resulting solids were filtered, and dried to prepare the desired title compound (Amount obtained: 660 mg/Yield: 88%).

$^1$H NMR (400, CDCl$_3$): 7.11 (2H, m), 6.90 (1H, m), 6.08 (1H, s), 4.21 (2H, m), 3.91 (2H, d), 3.58 (2H, m), 3.12 (2H, m), 2.91 (1H, m), 2.58 (2H, m), 2.49 (5H, m), 1.83-2.21 (5H, m), 1.49 (2H, m), 1.31 (6H, d)

Example 112: Preparation of 4-(3-fluoro-4-((1-(3-isopropyl-1,2,4-oxadiazol-5-yl)piperidin-4-yl)methoxy)phenyl)-N-(2-morpholino-2-oxoethyl)cyclohex-3-enecarboxamide

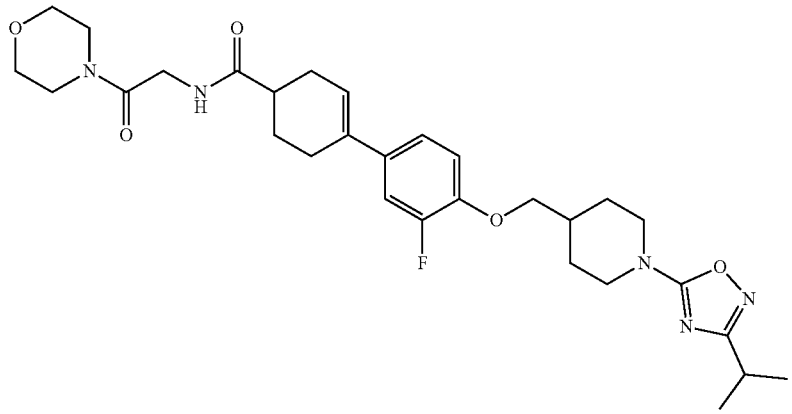 [SMILES: CC(C)c1noc(N2CCC(COc3ccc(C4=CCC(C(=O)NCC(=O)N5CCOCC5)CC4)cc3F)CC2)n1]

250 mg of 2-(4-(3-fluoro-4-((1-(3-isopropyl-1,2,4-oxadiazol-5-yl)piperidin-4-yl)methoxy)phenyl)cyclohex-3-enecarboxamido)acetic acid was dissolved in 20 µl of DMF in a 100 µl flask, and stirred under nitrogen. 140 mg of EDCI and 110 mg of HOBt were sequentially added dropwise thereto, and the resulting mixture was then additionally stirred for 10 minutes. 0.1 µl of morpholine were added dropwise thereof, and the mixture was stirred at room temperature for 5 hours. After the reaction was terminated, 50 µl of distilled water was slowly added at 0° C., and the resulting solids were filtered, and dried to obtain a desired compound as a white solid (Amount obtained: 160 mg/Yield: 72%).

$^1$H NMR (400, CDCl$_3$): 7.11 (2H, m), 6.90 (1H, m), 6.71 (1H, m), 6.07 (1H, s), 4.21 (2H, m), 4.11 (2H, d), 3.91 (2H, d), 3.71 (6H, m), 3.48 (2H, m), 3.12 (2H, m), 2.91 (1H, m), 2.49 (5H, m), 1.83-2.21 (5H, m), 1.49 (2H, m), 1.31 (6H, d)

Example 113: Preparation of 4-(3-fluoro-4-((1-(3-isopropyl-1,2,4-oxadiazol-5-yl)piperidin-4-yl)methoxy)phenyl)-N-(3-morpholino-3-oxopropyl)cyclohex-3-enecarboxamide

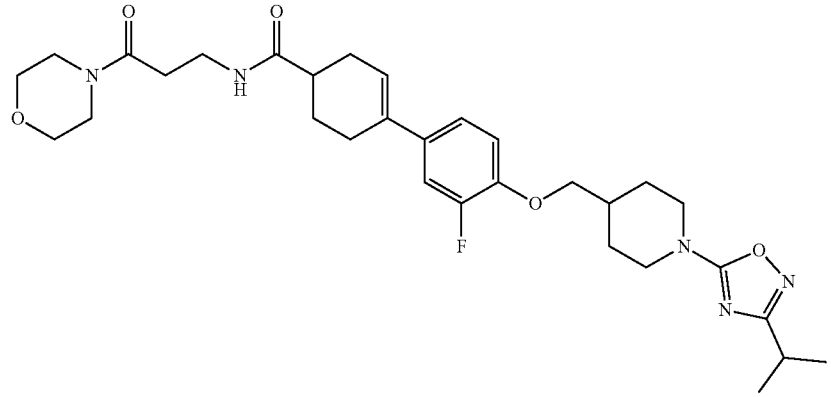 [SMILES: CC(C)c1noc(N2CCC(COc3ccc(C4=CCC(C(=O)NCCC(=O)N5CCOCC5)CC4)cc3F)CC2)n1]

The title compound was prepared in the same manner as in <Example 112>, except that 3-(4-(3-fluoro-4-((1-(3-isopropyl-1,2,4-oxadiazol-5-yl)piperidin-4-yl)methoxy)phenyl)cyclohex-3-enecarboxamido)propanoic acid was used instead of the 2-(4-(3-fluoro-4-((1-(3-isopropyl-1,2,4-oxadiazol-5-yl)piperidin-4-yl)methoxy)phenyl)cyclohex-3-enecarboxamido)acetic acid (Amount obtained: 155 mg/Yield: 74%).

$^1$H NMR (400, CDCl$_3$): 7.11 (2H, m), 6.90 (1H, m), 6.50 (1H, m), 6.06 (1H, s), 4.22 (2H, d), 3.91 (2H, d), 3.71 (6H, m), 3.48 (2H, m), 3.12 (2H, m), 2.91 (1H, m), 2.55 (2H, m), 2.49 (5H, m), 1.83-2.21 (5H, m), 1.49 (2H, m), 1.31 (6H, d)

Example 114: Preparation of tert-butyl 4-((4-(4-((S)-2-cyanopyrrolidine-1-carbonyl)cyclohex-1-enyl)-2-fluorophenoxy)methyl)piperidine-1-carboxylate

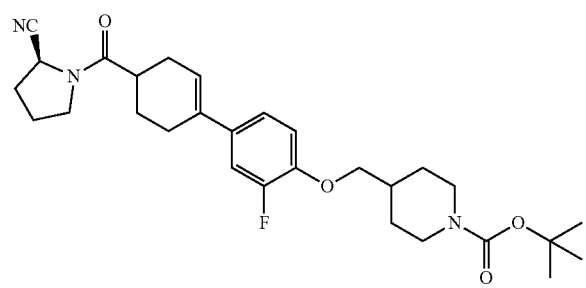 [SMILES: CC(C)(C)OC(=O)N1CCC(COc2ccc(C3=CCC(C(=O)N4CCC[C@H]4C#N)CC3)cc2F)CC1]

The title compound was prepared in the same manner as in <Example 44>, except that (S)-pyrrolidine-2-carbonitrile hydrochloride was used instead of the (S)-(−)-3-pyrrolidinol (Amount obtained: 180 mg/Yield: 76%).

$^1$H NMR (400, CDCl$_3$): 7.11 (3H, m), 6.91 (1H, m), 6.09 (1H, s), 4.67 (1H, d), 4.17 (2H, d), 3.88 (2H, d), 3.62 (2H, m), 2.29-2.82 (5H, m), 1.83-2.21 (8H, m), 1.49 (9H, s), 1.29 (2H, m).

Example 115: Preparation of (2S)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile

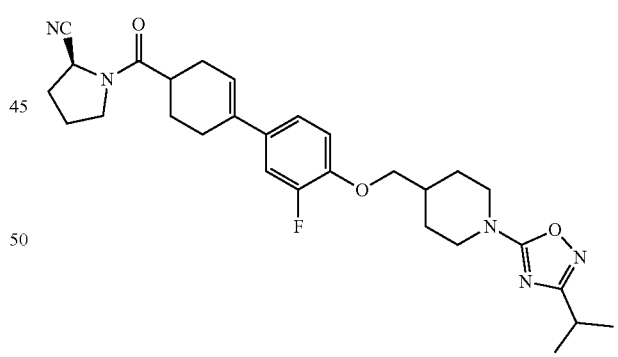

The title compound was prepared in the same manner as in <Example 80>, except that (S)-pyrrolidine-2-carbonitrile hydrochloride was used instead of the 2-amino-1,3-propanediol (Amount obtained: 190 mg/Yield: 82%).

$^1$H NMR (400, CDCl$_3$): 7.11 (3H, m), 6.91 (1H, m), 6.10 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 116: Preparation of (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carboxamide

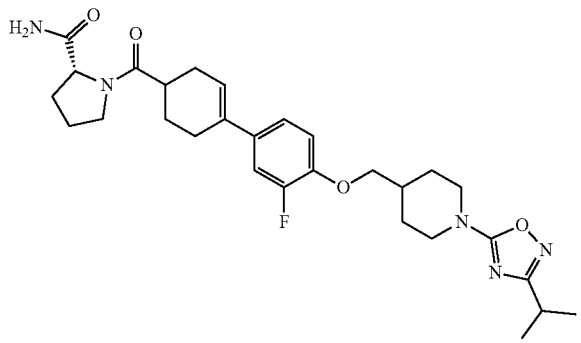 [SMILES: CC(C)c1noc(N2CCC(COc3ccc(C4=CCC(C(=O)N5CCC[C@@H]5C(N)=O)CC4)cc3F)CC2)n1]

The title compound was prepared in the same manner as in <Example 80>, except that (R)-pyrrolidine-2-carboxamide was used instead of the 2-amino-1,3-propanediol (Amount obtained: 210 mg/Yield: 79%).

¹H NMR (400, CDCl₃): 7.11 (3H, m), 6.91 (1H, m), 6.10 (1H, s), 5.32 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 117: Preparation of (2R)-1-(4-(3-fluoro-4-((1-(3-isopropyl-1,2,4-oxadiazol-5-yl)piperidin-4-yl)methoxy)phenyl)cyclohex-3-enecarbonyl)pyrrolidine-2-carbonitrile

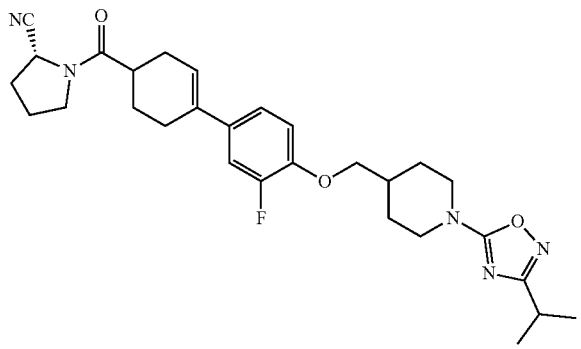 [SMILES: CC(C)c1noc(N2CCC(COc3ccc(C4=CCC(C(=O)N5CCC[C@@H]5C#N)CC4)cc3F)CC2)n1]

The title compound was prepared in the same manner as in <Example 80>, except that (R)-pyrrolidine-2-carbonitrile hydrochloride was used instead of the 2-amino-1,3-propanediol (Amount obtained: 165 mg/Yield: 73%).

¹H NMR (400, CDCl₃): 7.11 (3H, m), 6.91 (1H, m), 6.10 (1H, s), 4.67 (1H, d), 4.22 (2H, d), 3.92 (2H, d), 3.62 (2H, m), 3.12 (2H, m), 2.91 (1H, m), 2.29-2.82 (6H, m), 1.83-2.21 (7H, m), 1.49 (2H, m), 1.31 (6H, d)

Example 118: Preparation of (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone

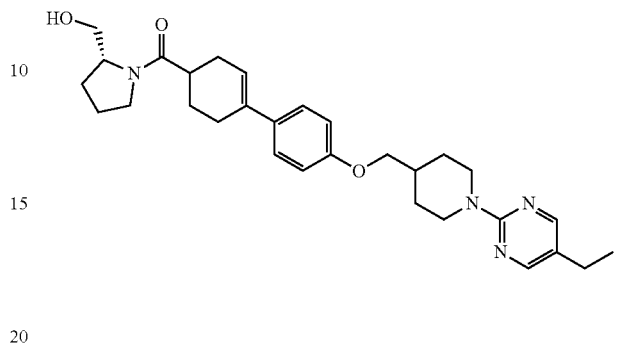

The title compound was prepared in the same manner as in <Example 8>, except that (R)-pyrrolidin-2-yl methanol was used instead of the (R)-2-amino-1-propanol (Amount obtained: 240 mg/Yield: 86%).

¹H NMR (400, CDCl₃): 8.19 (2H, s), 7.32 (1H, d), 6.86 (1H, d), 6.06 (1H, s), 5.19 (1H, m), 4.88 (2H, d), 4.30 (1H, m), 3.85 (2H, d), 3.62 (4H, m), 2.92 (2H, m), 2.25-2.78 (7H, m), 1.83-2.21 (9H, m), 1.61 (1H, m), 1.31 (2H, m), 1.22 (3H, m)

Example 119: Preparation of (4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone

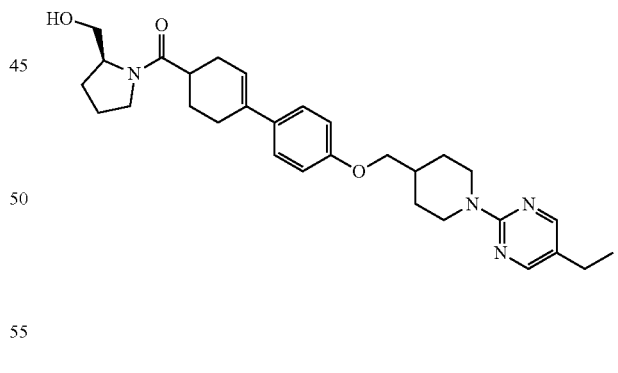

The title compound was prepared in the same manner as in <Example 8>, except that (S)-pyrrolidin-2-yl methanol was used instead of the (R)-2-amino-1-propanol (Amount obtained: 220 mg/Yield: 83%).

¹H NMR (400, CDCl₃): 8.19 (2H, s), 7.32 (1H, d), 6.86 (1H, d), 6.06 (1H, s), 5.19 (1H, m), 4.88 (2H, d), 4.30 (1H, m), 3.85 (2H, d), 3.62 (4H, m), 2.92 (2H, m), 2.25-2.78 (7H, m), 1.83-2.21 (9H, m), 1.61 (1H, m), 1.31 (2H, m), 1.22 (3H, m)

Example 120: Preparation of 4-(3-fluoro-4-((1-(3-isopropyl-1,2,4-oxadiazol-5-yl)piperidin-4-yl)methoxy)phenyl)-N-(2-hydroxyethyl)cyclohex-3-enecarboxamide

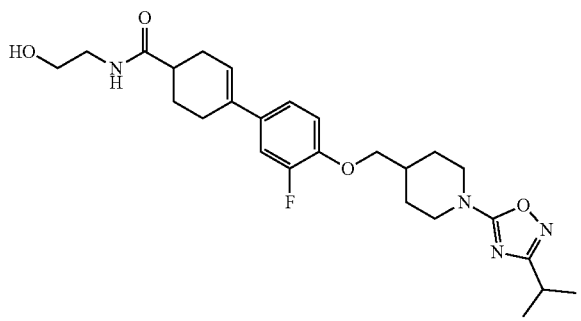 [SMILES: CC(C)c1noc(N2CCC(COc3ccc(C4=CCC(C(=O)NCCO)CC4)cc3F)CC2)n1]

The title compound was prepared in the same manner as in <Example 80>, except that 2-aminoethanol was used instead of the 2-amino-1,3-propanediol (Amount obtained: 180 mg/Yield: 76%).

$^1$H NMR (400, CDCl$_3$): 7.11 (3H, m), 6.91 (1H, m), 6.05 (2H, m), 4.19 (2H, d), 3.91 (2H, d), 3.79 (2H, m), 3.49 (2H, m), 3.12 (2H, m), 2.91 (1H, m), 2.35-2.59 (6H, m), 1.83-2.21 (5H, m), 1.49 (2H, m), 1.31 (6H, d)

Example 121: Preparation of (2R)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide

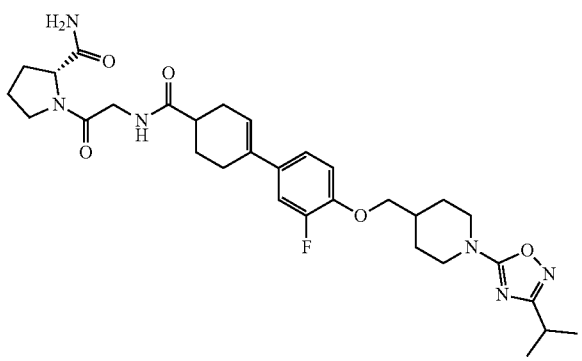 [SMILES: CC(C)c1noc(N2CCC(COc3ccc(C4=CCC(C(=O)NCC(=O)N5CCC[C@@H]5C(N)=O)CC4)cc3F)CC2)n1]

The title compound was prepared in the same manner as in <Example 112>, except that (R)-pyrrolidine-2-carboxamide was used instead of the morpholine (Amount obtained: 160 mg/Yield: 74%).

$^1$H NMR (400, CDCl$_3$): 7.11 (3H, m), 6.91 (1H, m), 6.68 (1H, s), 6.60 (1H, m), 6.07 (2H, m), 5.43 (1H, s), 4.60 (1H, d), 4.22 (2H, d), 4.11 (2H, m), 3.91 (2H, d), 3.65 (1H, m), 3.49 (1H, m), 3.14 (2H, m), 2.91 (1H, m), 2.35-2.59 (6H, m), 1.83-2.21 (8H, m), 1.49 (2H, m), 1.31 (6H, d)

Example 122: Preparation of N-(2-((R)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide

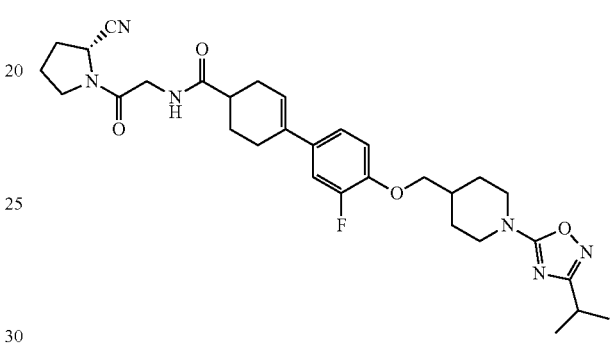

The title compound was prepared in the same manner as in <Example 112>, except that (R)-pyrrolidine-2-carbonitrile hydrochloride was used instead of the morpholine (Amount obtained: 190 mg/Yield: 77%).

$^1$H NMR (400, CDCl$_3$): 7.11 (3H, m), 6.91 (1H, m), 6.60 (1H, m), 6.07 (2H, m), 4.60 (1H, d), 4.22 (2H, d), 4.11 (2H, m), 3.91 (2H, d), 3.65 (1H, m), 3.49 (1H, m), 3.14 (2H, m), 2.91 (1H, m), 2.35-2.59 (6H, m), 1.83-2.21 (8H, m), 1.49 (2H, m), 1.31 (6H, d)

Example 123: Preparation of (4-cyclopropylpiperazin-1-yl)(4-(4-((1-(5-ethylpyrimidin-2-yl)piperidin-4-yl)methoxy)phenyl)cyclohex-3-enyl)methanone

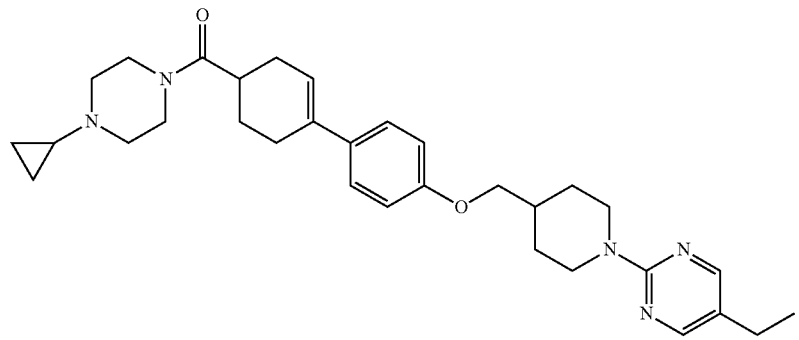 [SMILES: CCc1cnc(N2CCC(COc3ccc(C4=CCC(C(=O)N5CCN(C6CC6)CC5)CC4)cc3)CC2)nc1]

The title compound was prepared in the same manner as in <Example 8>, except that cyclopropylpiperazine was used instead of the (R)-2-amino-1-propanol (Amount obtained: 205 mg/Yield: 79%).

¹H NMR (400, CDCl₃): 8.19 (2H, s), 7.32 (2H, d), 6.86 (2H, d), 6.05 (1H, m), 4.79 (2H, d), 3.85 (2H, d), 3.64 (2H, m), 3.53 (2H, m), 2.93 (2H, m), 2.80 (1H, m), 2.55 (9H, m), 2.30 (1H, m), 2.01 (5H, m), 1.65 (1H, m), 1.33 (2H, m), 1.20 (3H, m), 0.49 (4H, m)

Example 124: Preparation of (4-(cyclopropylmethyl)piperazin-1-yl)(4-(4-((1-(5-ethylpyrimidin-2-yl)piperidin-4-yl)methoxy)phenyl)cyclohex-3-enyl)methanone

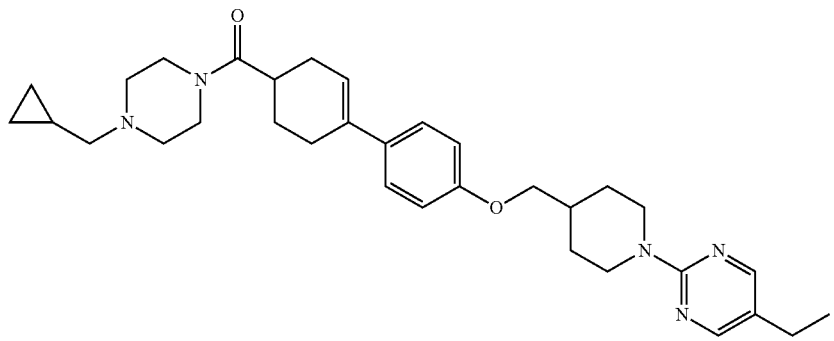 [SMILES: CCc1cnc(N2CCC(COc3ccc(C4=CCC(C(=O)N5CCN(CC6CC6)CC5)CC4)cc3)CC2)nc1]

The title compound was prepared in the same manner as in <Example 8>, except that 1-(cyclopropylmethyl)piperazine was used instead of the (R)-2-amino-1-propanol (Amount obtained: 185 mg/Yield: 77%).

¹H NMR (400, CDCl₃): 8.19 (2H, s), 7.32 (2H, d), 6.86 (2H, d), 6.05 (1H, m), 4.79 (2H, d), 3.85 (2H, d), 3.64 (2H, m), 3.53 (2H, m), 2.93 (2H, m), 2.80 (1H, m), 2.55 (9H, m), 2.30 (3H, m), 2.01 (5H, m), 1.35 (2H, m), 1.20 (3H, m), 0.89 (1H, m), 0.55 (2H, m), 0.14 (2H, m)

Example 125: Preparation of tert-butyl 4-((3-fluoro-4-(4-((S)-2-hydroxypropylcarbamoyl)cyclohex-1-enyl)phenoxy)methyl)piperidine-1-carboxylate

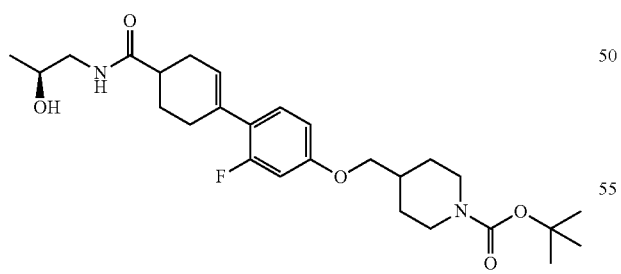

300 mg of 4-(4-((1-(tert-butoxycarbonyl)piperidin-4-yl)methoxy)-2-fluorophenyl)cyclohex-3-enecarboxylic acid was dissolved in 25 µl of DMF, and stirred. 210 mg of EDCI and 165 mg of HOBt were sequentially added dropwise thereto, and the resulting mixture was then additionally stirred for 10 minutes. 120 mg of (S)-1-amino-2-propanol was added dropwise thereto, and the mixture was stirred at room temperature for 5 hours. After the reaction was terminated, 50 µl of distilled water was slowly added at 0° C., and the resulting solids were filtered, and dried to obtain a desired compound as a white solid (Amount obtained: 230 mg/Yield: 82%).

¹H NMR (400, CDCl₃): 7.13 (1H, m), 6.60 (2H, m), 6.11 (1H, s), 5.89 (1H, m), 4.17 (2H, s), 3.96 (1H, s), 3.79 (2H, d), 3.51 (1H, m), 3.19 (1H, m), 2.78 (2H, m), 2.63 (1H, s), 2.48 (5H, m), 2.14 (1H, m), 1.96 (2H, m), 1.81 (2H, m), 1.48 (9H, s), 1.28 (2H, m), 1.21 (3H, d)

Example 126: Preparation of tert-butyl 4-((3-fluoro-4-(4-((R)-2-hydroxypropylcarbamoyl)cyclohex-1-enyl)phenoxy)methyl)piperidine-1-carboxylate

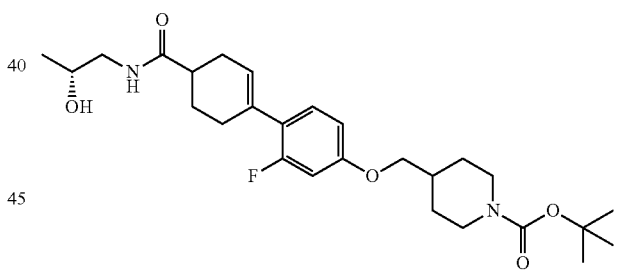

The title compound was prepared in the same manner as in <Example 125>, except that (R)-1-amino-2-propanol was used instead of the (S)-1-amino-2-propanol (Amount obtained: 210 mg/Yield: 80%).

¹H NMR (400, CDCl₃): 7.13 (1H, m), 6.60 (2H, m), 6.11 (1H, s), 5.89 (1H, m), 4.17 (2H, s), 3.96 (1H, s), 3.79 (2H, d), 3.51 (1H, m), 3.19 (1H, m), 2.78 (2H, m), 2.63 (1H, s), 2.48 (5H, m), 2.14 (1H, m), 1.96 (2H, m), 1.81 (2H, m), 1.48 (9H, s), 1.28 (2H, m), 1.21 (3H, d)

Example 127: Preparation of 4-(4-((1-(5-ethylpyrimidin-2-yl)piperidin-4-yl)methoxy)phenyl)-N—((S)-1-hydroxypropan-2-yl)cyclohex-3-enecarboxamide

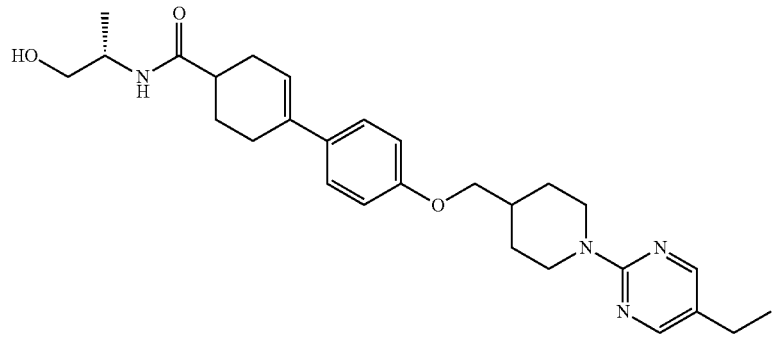 [SMILES: CCc1cnc(N2CCC(COc3ccc(C4=CCC(C(=O)N[C@@H](C)CO)CC4)cc3)CC2)nc1]

The title compound was prepared in the same manner as in <Example 8>, except that (S)-2-amino-1-propanol was used instead of the (R)-2-amino-1-propanol (Amount obtained: 170 mg/Yield: 77%).

$^1$H NMR (400, CDCl$_3$): 8.19 (2H, s), 7.31 (2H, d), 6.86 (2H, d), 6.04 (1H, s), 5.73 (1H, d), 4.79 (2H, d), 4.15 (1H, m), 3.84 (2H, d), 3.72 (1H, m), 3.57 (1H, m), 2.92 (2H, m), 2.80 (1H, s), 2.49 (7H, m), 2.11 (2H, m), 1.91 (3H, m), 1.38 (2H, m), 1.28 (2H, m), 1.21 (3H, d)

Example 128: Preparation of N—((S)-2,3-dihydroxypropyl)-4-(4-((1-(5-ethylpyrimidin-2-yl)piperidin-4-yl)methoxy)phenyl)cyclohex-3-enecarboxamide

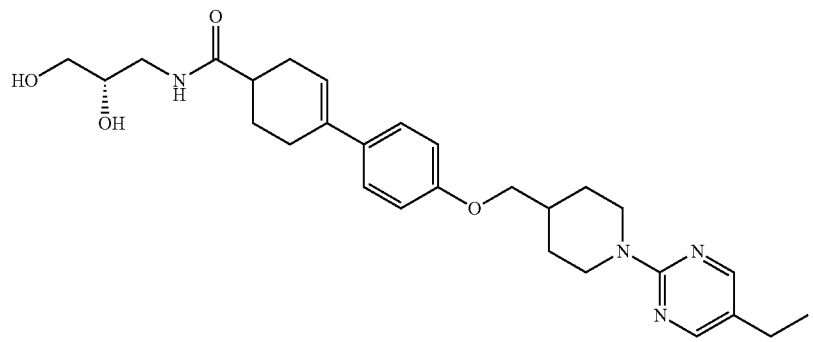 [SMILES: CCc1cnc(N2CCC(COc3ccc(C4=CCC(C(=O)NC[C@H](O)CO)CC4)cc3)CC2)nc1]

The title compound was prepared in the same manner as in <Example 8>, except that (S)-3-amino-1,2-propanediol was used instead of the (R)-2-amino-1-propanol (Amount obtained: 180 mg/Yield: 74%).

$^1$H NMR (400, DMSO-$_{d6}$): 8.23 (2H, s), 7.85 (1H, t), 7.33 (2H, d), 6.88 (2H, d), 6.05 (1H, s), 4.76 (1H, d), 4.68 (2H, d), 4.53 (1H, t), 3.84 (2H, d), 3.49 (1H, m), 3.34 (2H, m), 3.10 (2H, m), 2.89 (2H, m), 2.21 (7H, m), 1.91 (2H, d), 1.65 (1H, m), 1.18 (5H, m)

Example 129: Preparation of tert-butyl 4-((3-fluoro-4-(4-((R)-1-hydroxypropan-2-ylcarbamoyl)cyclohex-1-enyl)phenoxy)methyl)piperidine-1-carboxylate

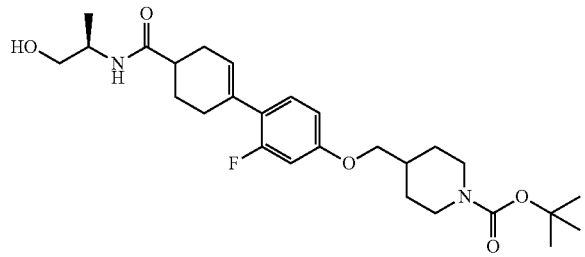 [SMILES: C[C@H](CO)NC(=O)C1CC=C(c2ccc(OCC3CCN(C(=O)OC(C)(C)C)CC3)cc2F)CC1]

The title compound was prepared in the same manner as in <Example 125>, except that (R)-2-amino-1-propanol was used instead of the (S)-1-amino-2-propanol (Amount obtained: 180 mg/Yield: 80%).

$^1$H NMR (400, CDCl$_3$): 7.15 (1H, t), 6.64 (2H, m), 5.89 (1H, s), 5.80 (1H, s), 4.15 (3H, m), 3.79 (2H, d), 3.59 (1H, d), 3.45 (1H, m), 2.87 (1H, s), 2.75 (2H, m), 2.48 (5H, m), 1.94 (5H, m), 1.48 (9H, s), 1.26 (5H, m)

Example 130: Preparation of tert-butyl 4-((3-fluoro-4-(4-((S)-1-hydroxypropan-2-ylcarbamoyl)cyclohex-1-enyl)phenoxy)methyl)piperidine-1-carboxylate

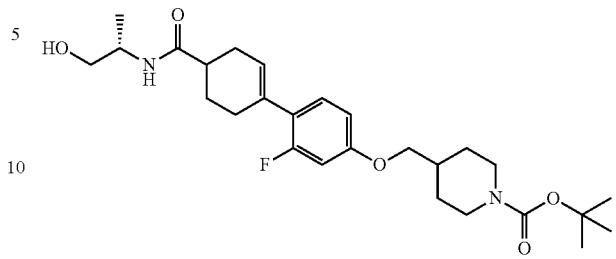

The title compound was prepared in the same manner as in <Example 125>, except that (S)-2-amino-1-propanol was used instead of the (S)-1-amino-2-propanol (Amount obtained: 170 mg/Yield: 74%).

$^1$H NMR (400, CDCl$_3$): 7.15 (1H, t), 6.62 (2H, m), 5.89 (1H, s), 5.83 (1H, s), 4.16 (3H, m), 3.79 (2H, d), 3.69 (1H, d), 2.95 (1H, m), 2.76 (2H, m), 2.49 (5H, m), 1.98 (5H, m), 1.49 (9H, s), 1.26 (5H, m)

Example 131: Preparation of tert-butyl 4-((4-(4-((R)-2,3-dihydroxypropylcarbamoyl)cyclohex-1-enyl)-3-fluorophenoxy)methyl)piperidine-1-carboxylate

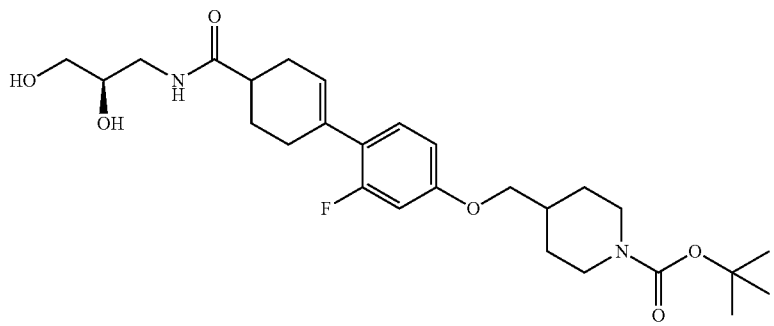 [SMILES: CC(C)(C)OC(=O)N1CCC(COc2ccc(C3=CCC(C(=O)NC[C@@H](O)CO)CC3)c(F)c2)CC1]

The title compound was prepared in the same manner as in <Example 125>, except that (R)-3-amino-1,2-propanediol was used instead of the (S)-1-amino-2-propanol (Amount obtained: 205 mg/Yield: 81%).

$^1$H NMR (400, CDCl$_3$): 7.13 (1H, t), 6.63 (2H, m), 6.55 (1H, m), 5.88 (1H, s), 4.18 (3H, m), 3.81 (3H, m), 3.61 (4H, m), 2.78 (2H, m), 2.45 (5H, m), 1.82 (7H, m), 1.47 (9H, m), 1.25 (2H, m)

Example 132: Preparation of tert-butyl 4-((4-(4-((S)-2,3-dihydroxypropylcarbamoyl)cyclohex-1-enyl)-3-fluorophenoxy)methyl)piperidine-1-carboxylate

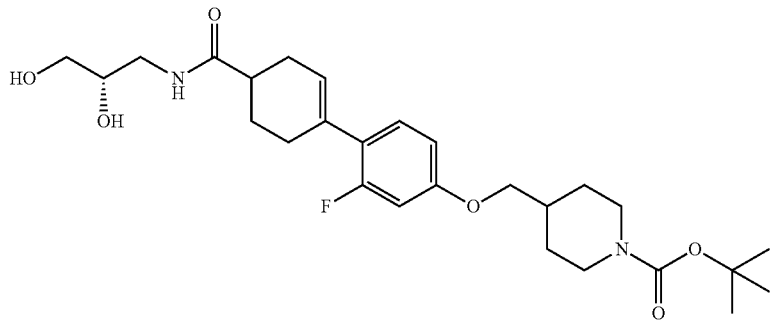 [SMILES: CC(C)(C)OC(=O)N1CCC(COc2ccc(C3=CCC(C(=O)NC[C@H](O)CO)CC3)c(F)c2)CC1]

The title compound was prepared in the same manner as in <Example 125>, except that (S)-3-amino-1,2-propanediol was used instead of the (S)-1-amino-2-propanol (Amount obtained: 165 mg/Yield: 74%).

¹H NMR (400, CDCl₃): 7.13 (1H, t), 6.63 (2H, m), 6.55 (1H, m), 5.88 (1H, s), 4.18 (3H, m), 3.81 (3H, m), 3.61 (4H, m), 2.78 (2H, m), 2.45 (5H, m), 1.82 (7H, m), 1.47 (9H, m), 1.25 (2H, m)

Example 133: Preparation of (2S)-1-(2-(4-(3-fluoro-4-((1-(3-isopropyl-1,2,4-oxadiazol-5-yl)piperidin-4-yl)methoxy)phenyl)cyclohex-3-enecarboxamido)acetyl)pyrrolidine-2-carboxamide

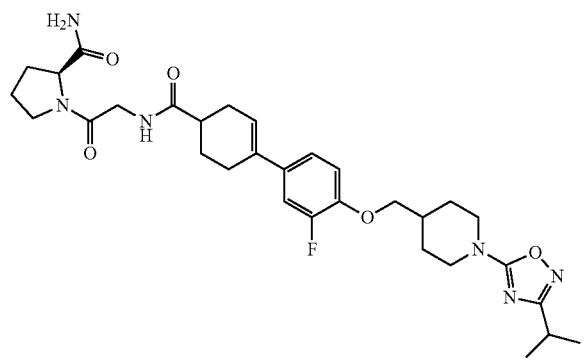 [SMILES: CC(C)c1noc(N2CCC(COc3ccc(C4=CCC(C(=O)NCC(=O)N5CCC[C@H]5C(N)=O)CC4)cc3F)CC2)n1]

The title compound was prepared in the same manner as in <Example 112>, except that (S)-pyrrolidine-2-carboxamide was used instead of the morpholine (Amount obtained: 160 mg/Yield: 71%).

¹H NMR (400, CDCl₃): 7.15 (1H, t), 6.92 (1H, m), 6.67 (1H, m), 6.07 (1H, s), 5.34 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.48 (6H, m), 2.14 (4H, m), 1.91 (3H, m), 1.42 (2H, m), 1.32 (6H, d)

Example 134: Preparation of (2S)-1-(3-(4-(3-fluoro-4-((1-(3-isopropyl-1,2,4-oxadiazol-5-yl)piperidin-4-yl)methoxy)phenyl)cyclohex-3-enecarboxamido)propanoyl)pyrrolidine-2-carboxamide

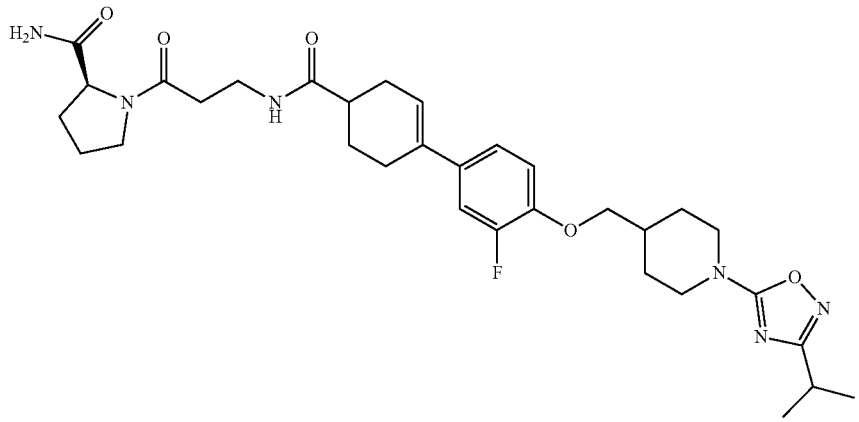 [SMILES: CC(C)c1noc(N2CCC(COc3ccc(C4=CCC(C(=O)NCCC(=O)N5CCC[C@H]5C(N)=O)CC4)cc3F)CC2)n1]

The title compound was prepared in the same manner as in <Example 112> using 3-(4-(3-fluoro-4-((1-(3-isopropyl-1,2,4-oxadiazol-5-yl)piperidin-4-yl)methoxy)phenyl)cyclohex-3-enecarboxamido)propanoic acid and (S)-pyrrolidine-2-carboxamide (Amount obtained: 210 mg/Yield: 80%).

¹H NMR (400, CDCl₃): 7.15 (1H, t), 6.92 (1H, m), 6.67 (1H, m), 6.07 (1H, s), 5.34 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.54 (2H, m), 2.48 (6H, m), 2.14 (4H, m), 1.91 (3H, m), 1.42 (2H, m), 1.32 (6H, d)

Example 135: Preparation of (4-(4-((1-(5-ethylpyrimidin-2-yl)piperidin-4-yl)methoxy)phenyl)cyclohex-3-enyl)((S)-3-hydroxypyrrolidin-1-yl)methanone

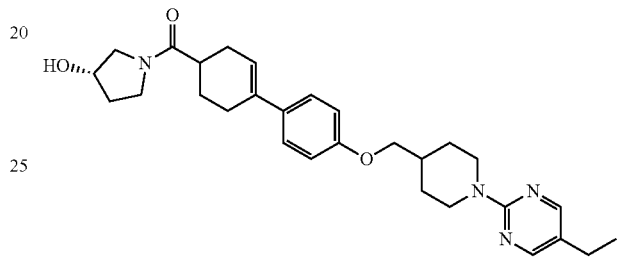

The title compound was prepared in the same manner as in <Example 8>, except that (S)-(+)-3-pyrrolidinol was used instead of the (R)-2-aminopropan-1-ol (Amount obtained: 220 mg/Yield: 81%).

¹H NMR (400, CDCl₃): 8.19 (2H, s), 7.33 (2H, d), 6.87 (2H, d), 6.07 (1H, s), 4.80 (2H, d), 4.55 (1H, d), 3.85 (2H, d), 3.65 (4H, m), 2.94 (2H, t), 2.48 (7H, m), 2.00 (7H, m), 1.40 (2H, m), 1.18 (3H, m)

Example 136: Preparation of 4-(4-((1-(5-ethylpyrimidin-2-yl)piperidin-4-yl) methoxy)phenyl)-N—((S)-2-hydroxypropyl)cyclohex-3-enecarboxamide

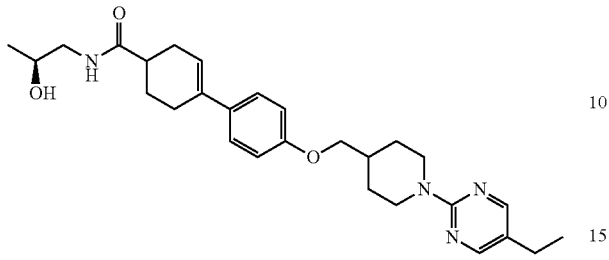

The title compound was prepared in the same manner as in <Example 8>, except that (S)-1-amino-2-propanol was used instead of the (R)-2-amino-1-propanol (Amount obtained: 215 mg/Yield: 82%).

¹H NMR (400, CDCl₃): 8.19 (2H, s), 7.32 (2H, d), 6.87 (2H, d), 6.04 (2H, s), 4.80 (2H, d), 3.96 (1H, m), 3.85 (2H, d), 3.52 (1H, m), 3.14 (1H, m), 2.96 (2H, t), 2.46 (8H, m), 2.18 (2H, m), 1.96 (3H, m), 1.38 (2H, m), 1.24 (6H, m)

Example 137: Preparation of tert-butyl 4-((4-(4-(cyclopropylcarbamoyl)cyclohex-1-enyl)-3-fluorophenoxy)methyl)piperidine-1-carboxylate

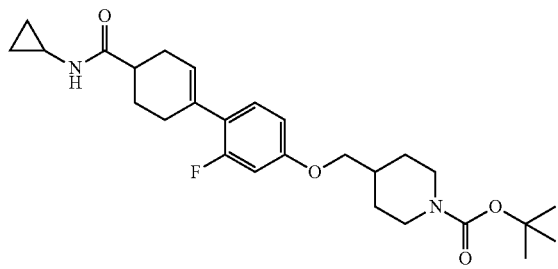 [SMILES: CC(C)(C)OC(=O)N1CCC(COc2ccc(C3=CCC(C(=O)NC4CC4)CC3)c(F)c2)CC1]

The title compound was prepared in the same manner as in <Example 125>, except that cyclopropylamine was used instead of the (S)-1-amino-2-propanol (Amount obtained: 180 mg/Yield: 74%).

¹H NMR (400, CDCl₃): 7.14 (1H, t), 6.64 (2H, m), 5.88 (1H, s), 5.74 (1H, s), 4.17 (2H, m), 3.79 (2H, d), 2.78 (3H, m), 2.46 (5H, m), 1.87 (5H, m), 1.48 (9H, s), 1.28 (2H, m), 0.78 (2H, m), 0.48 (2H, m)

Example 138: Preparation of tert-butyl 4-((3-fluoro-4-(4-(2-fluoroethylcarbamoyl)cyclohex-1-enyl)phenoxy)methyl)piperidine-1-carboxylate

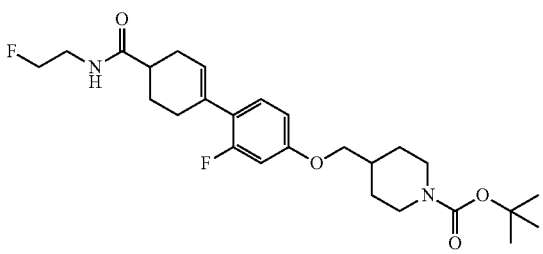 [SMILES: CC(C)(C)OC(=O)N1CCC(COc2ccc(C3=CCC(C(=O)NCCF)CC3)c(F)c2)CC1]

The title compound was prepared in the same manner as in <Example 125>, except that 2-fluoroethylamine was used instead of the (S)-1-amino-2-propanol (Amount obtained: 160 mg/Yield: 71%).

¹H NMR (400, CDCl₃): 7.15 (1H, t), 6.64 (2H, m), 6.04 (1H, m), 5.89 (1H, s), 4.57 (2H, m), 3.79 (2H, d), 3.58 (2H, m), 2.78 (2H, m), 2.54 (5H, m), 1.92 (5H, m), 1.48 (9H, s), 1.28 (2H, m)

Example 139: Preparation of N-(2-((S)-2-cyanopyrrolidin-1-yl)-2-oxoethyl)-4-(3-fluoro-4-((1-(3-isopropyl-1,2,4-oxadiazol-5-yl)piperidin-4-yl)methoxy)phenyl)cyclohex-3-enecarboxamide

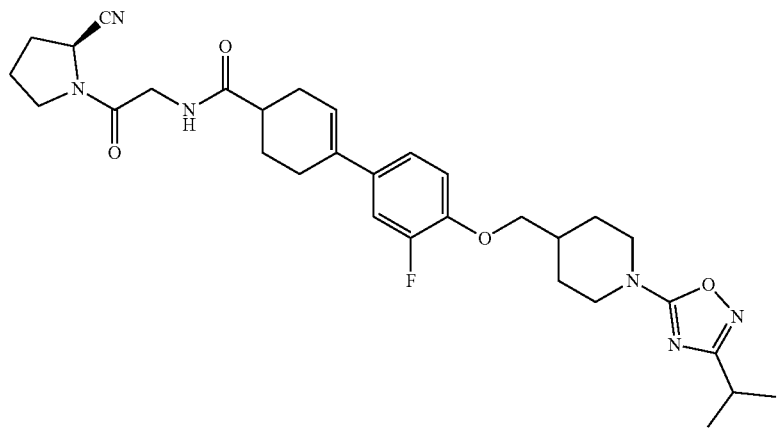 [SMILES: CC(C)c1noc(N2CCC(COc3ccc(C4=CCC(C(=O)NCC(=O)N5CCC[C@H]5C#N)CC4)cc3F)CC2)n1]

The title compound was prepared in the same manner as in <Example 112>, except that (S)-pyrrolidine-2-carbonitrile hydrochloride was used instead of the morpholine (Amount obtained: 190 mg/Yield: 83%).

$^1$H NMR (400, CDCl$_3$): 7.15 (1H, t), 6.92 (1H, m), 6.67 (1H, m), 6.07 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.48 (6H, m), 2.14 (4H, m), 1.91 (3H, m), 1.42 (2H, m), 1.32 (6H, d)

Example 140: Preparation of N-(3-((S)-2-cyanopyrrolidin-1-yl)-3-oxopropyl)-4-(3-fluoro-4-((1-(3-isopropyl-1,2,4-oxadiazol-5-yl)piperidin-4-yl)methoxy)phenyl)cyclohex-3-enecarboxamide

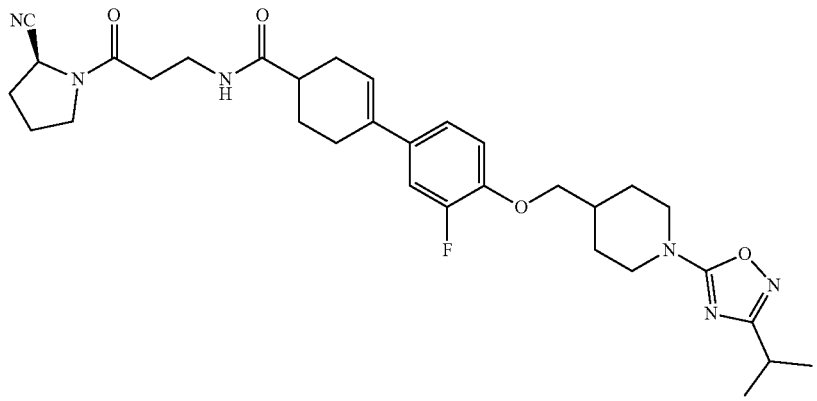 [SMILES: CC(C)c1noc(N2CCC(COc3ccc(C4=CCC(C(=O)NCCC(=O)N5CCC[C@H]5C#N)CC4)cc3F)CC2)n1]

The title compound was prepared in the same manner as in <Example 112> using 3-(4-(3-fluoro-4-((1-(3-isopropyl-1,2,4-oxadiazol-5-yl)piperidin-4-yl)methoxy)phenyl)cyclohex-3-enecarboxamido)propanoic acid and (S)-pyrrolidine-2-carbonitrile hydrochloride (Amount obtained: 145 mg/Yield: 77%).

$^1$H NMR (400, CDCl$_3$): 7.15 (1H, t), 6.92 (1H, m), 6.67 (1H, m), 6.07 (1H, s), 4.61 (1H, m), 4.24 (2H, d), 4.11 (2H, m), 3.92 (2H, d), 3.64 (1H, m), 3.58 (1H, m), 3.14 (2H, t), 2.91 (1H, m), 2.54 (2H, m), 2.48 (6H, m), 2.14 (4H, m), 1.91 (3H, m), 1.42 (2H, m), 1.32 (6H, d)

Example 141: Preparation of tert-butyl 4-((4-(4-(2,2-difluoroethylcarbamoyl)cyclohex-1-enyl)-3-fluorophenoxy)methyl)piperidine-1-carboxylate

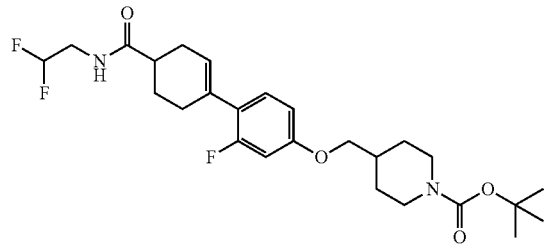 [SMILES: CC(C)(C)OC(=O)N1CCC(COc2ccc(C3=CCC(C(=O)NCC(F)F)CC3)c(F)c2)CC1]

The title compound was prepared in the same manner as in <Example 125>, except that 2,2-difluoroethylamine was used instead of the (S)-1-amino-2-propanol (Amount obtained: 190 mg/Yield: 73%).

$^1$H NMR (400, CDCl$_3$): 7.15 (1H, t), 6.64 (2H, m), 6.04 (1H, m), 5.89 (2H, s), 4.28 (2H, m), 3.79 (2H, d), 3.70 (2H, m), 2.78 (2H, m), 2.54 (5H, m), 1.92 (5H, m), 1.48 (9H, s), 1.28 (2H, m)

Example 142: Preparation of tert-butyl 4-((3-fluoro-4-(4-(2,2,2-trifluoroethylcarbamoyl)cyclohex-1-enyl)phenoxy)methyl)piperidine-1-carboxylate

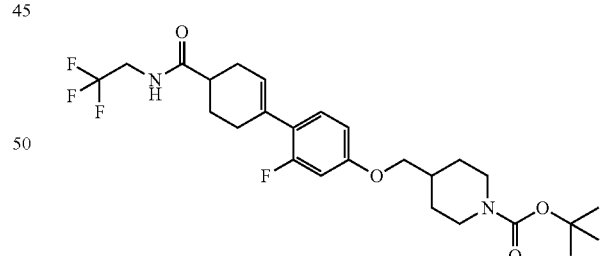

The title compound was prepared in the same manner as in <Example 125>, except that 2,2,2-trifluoroethylamine was used instead of the (S)-1-amino-2-propanol (Amount obtained: 175 mg/Yield: 77%).

$^1$H NMR (400, CDCl$_3$): 7.15 (1H, t), 6.64 (2H, m), 6.04 (1H, m), 5.89 (1H, s), 4.28 (2H, m), 3.99 (1H, m), 3.79 (2H, d), 2.78 (2H, m), 2.54 (5H, m), 1.92 (5H, m), 1.48 (9H, s), 1.28 (2H, m)

Example 143: Preparation of ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone

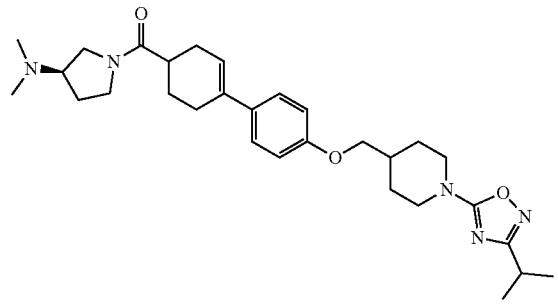 [SMILES: CC(C)c1noc(N2CCC(COc3ccc(C4=CCC(C(=O)N5CC[C@@H](N(C)C)C5)CC4)cc3)CC2)n1]

400 mg of 4-(4-((1-(3-isopropyl-1,2,4-oxadiazol-5-yl)piperidin-4-yl)methoxy)phenyl)cyclohex-3-enecarboxylic acid was dissolved in 30 ml of DMF in a 100 ml flask, and stirred under a nitrogen atmosphere. 0.4 ml of TEA and 215 mg of (R)—N,N-dimethylpyrrolidine-3-amine hydrochloride were sequentially added dropwise thereto, and the resulting mixture was then additionally stirred for 10 minutes. 400 mg of HATU was added dropwise thereto, and the mixture was stirred at room temperature for an hour. After the reaction was terminated, 50 ml of distilled water was slowly added at 0° C., and the resulting solids were filtered, and dried to prepare the title compound as a white solid (Amount obtained: 450 mg/Yield: 69%).

$^1$H NMR (400, CDCl$_3$): 7.32 (2H, d), 6.85 (2H, d), 6.02 (1H, s), 4.24 (2H, d), 3.86 (4H, m), 3.44 (2H, m), 3.12 (2H, m), 2.85 (2H, m), 2.69-1.85 (19H, m), 1.47 (2H, m), 1.32 (6H, d)

Example 144: Preparation of ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone

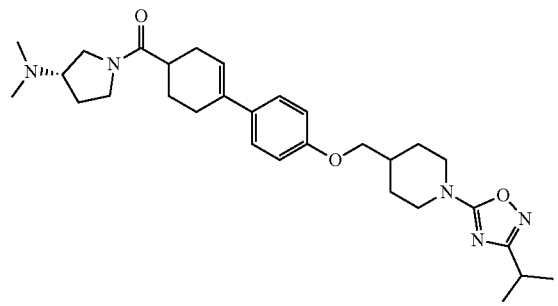 [SMILES: CC(C)c1noc(N2CCC(COc3ccc(C4=CCC(C(=O)N5CC[C@H](N(C)C)C5)CC4)cc3)CC2)n1]

The title compound was prepared in the same manner as in <Example 143>, except that (S)—N,N-dimethylpyrrolidine-3-amine hydrochloride was used instead of the (R)—N,N-dimethylpyrrolidine-3-amine hydrochloride (Amount obtained: 470 mg/Yield: 70%).

$^1$H NMR (400, CDCl$_3$): 7.32 (2H, d), 6.85 (2H, d), 6.02 (1H, s), 4.24 (2H, d), 3.86 (4H, m), 3.44 (2H, m), 3.12 (2H, m), 2.85 (2H, m), 2.69-1.85 (19H, m), 1.47 (2H, m), 1.32 (6H, d)

Example 145: Preparation of ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride

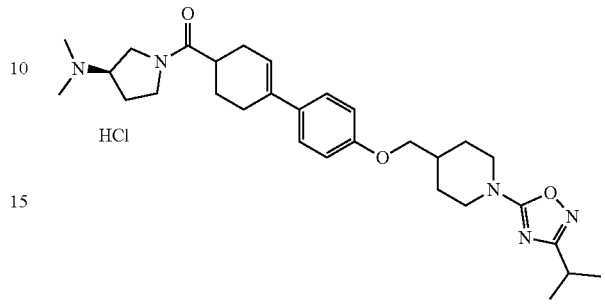

150 mg of ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone was dissolved in 20 ml of dichloromethane in a 100 ml flask, and then stirred under a nitrogen atmosphere. 0.08 ml of 4 N HCl dissolved in dioxane was added dropwise thereto, and the resulting mixture was then stirred at room temperature for 3 hours. After the solvent were removed, 30 ml of acetone was slowly added dropwise. The resulting solids were filtered, washed with 10 ml of ethyl acetate, and then dried to prepare the title compound as a white solid (Amount obtained: 220 mg/Yield: 84%).

$^1$H NMR (400, D$_2$O): 7.07 (2H, d), 6.55 (2H, d), 5.81 (1H, s), 4.12-3.28 (11H, m), 2.93-2.62 (11H, m), 2.44 (2H, m), 2.12 (5H, m), 2.81 (1H, m), 1.52 (4H, m), 1.08 (6H, d), 0.95 (2H, s)

Example 146: Preparation of ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone hydrochloride

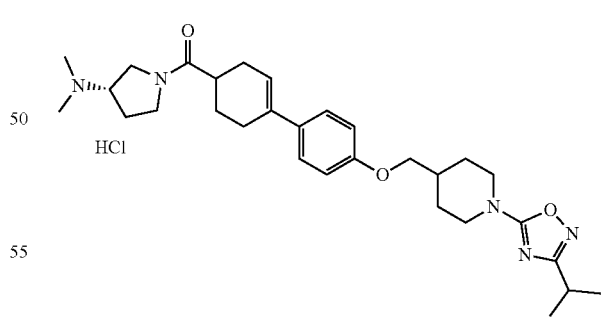

The title compound was prepared in the same manner as in <Example 145>, except that ((S)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 210 mg/Yield: 83%).

$^1$H NMR (400, D$_2$O): 7.07 (2H, d), 6.55 (2H, d), 5.81 (1H, s), 4.12-3.28 (11H, m), 2.93-2.62 (11H, m), 2.44 (2H, m), 2.12 (5H, m), 2.81 (1H, m), 1.52 (4H, m), 1.08 (6H, d), 0.95 (2H, s)

Example 147: Preparation of ((R)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

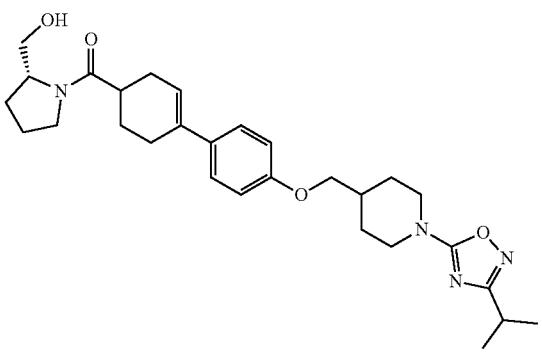 [SMILES: CC(C)c1noc(N2CCC(COc3ccc(C4=CCC(C(=O)N5CCC[C@@H]5CO)CC4)cc3)CC2)n1]

The title compound was prepared in the same manner as in <Example 143>, except that D-prolinol was used instead of the (R)—N,N-dimethylpyrrolidine-3-amine hydrochloride (Amount obtained: 220 mg/Yield: 76%).

$^1$H NMR (400, CDCl$_3$): 7.33 (2H, d), 6.86 (2H, d), 6.06 (1H, s), 5.16 (1H, m), 4.29 (1H, m), 4.22 (2H, d), 3.86 (2H, d), 4.65 (4H, m), 3.13 (2H, m), 2.91 (1H, m), 2.77-2.28 (5H, m), 2.01 (8H, m), 1.61 (1H, m), 1.46 (2H, m), 1.32 (6H, d)

Example 148: Preparation of ((S)-2-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

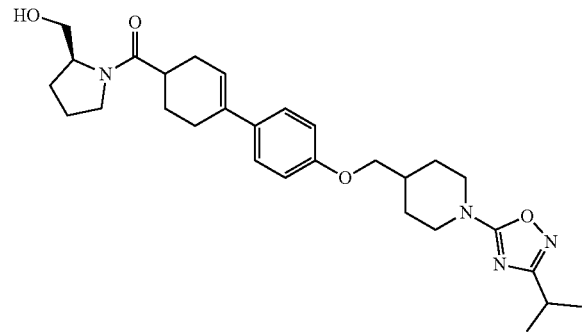 [SMILES: CC(C)c1noc(N2CCC(COc3ccc(C4=CCC(C(=O)N5CCC[C@H]5CO)CC4)cc3)CC2)n1]

The title compound was prepared in the same manner as in <Example 143>, except that L-prolinol was used instead of the (R)—N,N-dimethylpyrrolidine-3-amine hydrochloride (Amount obtained: 180 mg/Yield: 74%).

$^1$H NMR (400, CDCl$_3$): 7.33 (2H, d), 6.86 (2H, d), 6.06 (1H, s), 5.16 (1H, m), 4.29 (1H, m), 4.22 (2H, d), 3.86 (2H, d), 4.65 (4H, m), 3.13 (2H, m), 2.91 (1H, m), 2.77-2.28 (5H, m), 2.01 (8H, m), 1.61 (1H, m), 1.46 (2H, m), 1.32 (6H, d)

Example 149: Preparation of ((R)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

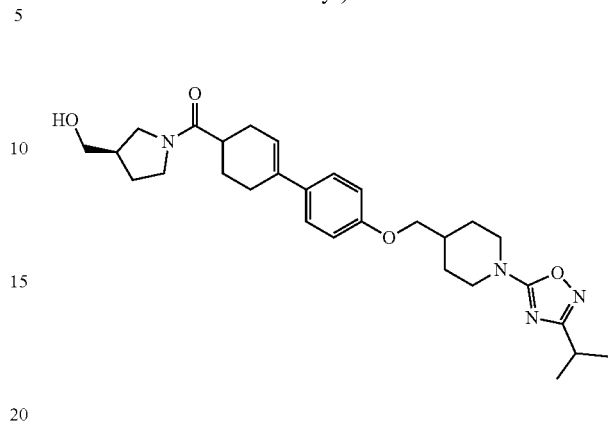

The title compound was prepared in the same manner as in <Example 143>, except that D-β-prolinol was used instead of the (R)—N,N-dimethylpyrrolidine-3-amine hydrochloride (Amount obtained: 175 mg/Yield: 77%).

$^1$H NMR (400, CDCl$_3$): 7.33 (2H, d), 6.86 (2H, d), 6.06 (1H, s), 4.22 (2H, d), 3.86 (2H, d), 3.81-3.24 (6H, m), 3.13 (2H, m), 2.91 (1H, m), 2.77-2.28 (6H, m), 2.01 (6H, m), 1.61 (1H, m), 1.46 (2H, m), 1.32 (6H, d)

Example 150: Preparation of ((S)-3-(hydroxymethyl)pyrrolidin-1-yl)(4-(4-((1-(3-isopropyl-1,2,4-oxadiazol-5-yl)piperidin-4-yl)methoxy)phenyl)cyclohex-3-enyl)methanone

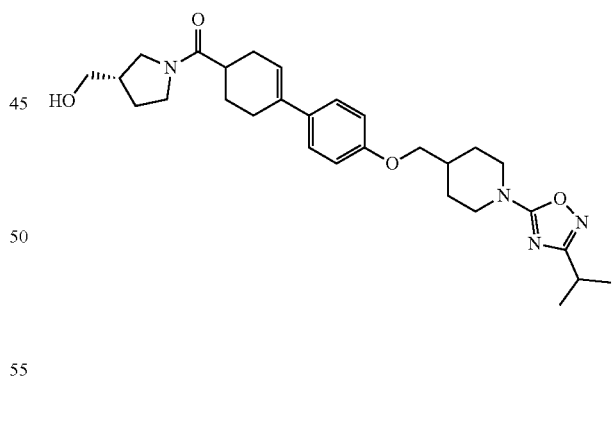

The title compound was prepared in the same manner as in <Example 143>, except that L-β-prolinol was used instead of the (R)—N,N-dimethylpyrrolidine-3-amine hydrochloride (Amount obtained: 210 mg/Yield: 74%).

$^1$H NMR (400, CDCl$_3$): 7.33 (2H, d), 6.86 (2H, d), 6.06 (1H, s), 4.22 (2H, d), 3.86 (2H, d), 3.81-3.24 (6H, m), 3.13 (2H, m), 2.91 (1H, m), 2.77-2.28 (6H, m), 2.01 (6H, m), 1.61 (1H, m), 1.46 (2H, m), 1.32 (6H, d)

Example 151: Preparation of (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone hydrochloride

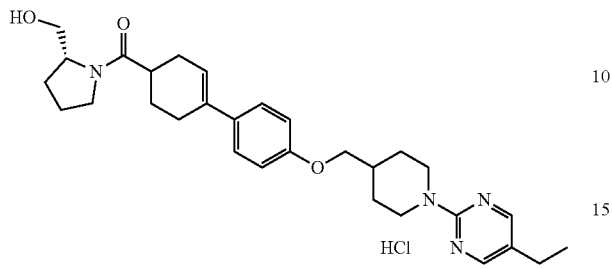

The title compound was prepared in the same manner as in <Example 145>, except that (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 72%).

$^1$H NMR (400, CDCl$_3$): 8.41 (2H, s), 7.33 (2H, d), 6.86 (2H, d), 6.06 (1H, s), 5.02 (2H, d), 4.29 (1H, m), 3.86 (2H, d), 3.79-3.24 (6H, m), 2.75-1.89 (17H, m), 1.65 (1H, m), 1.35 (2H, m), 1.21 (3H, m)

Example 152: Preparation of (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone

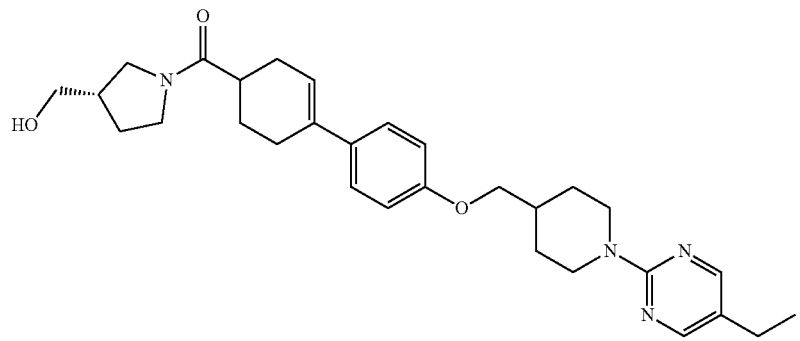 [SMILES: CCc1cnc(N2CCC(COc3ccc(C4=CCC(C(=O)N5CC[C@H](CO)C5)CC4)cc3)CC2)nc1]

300 mg of 4-(4-((1-(5-ethylpyrimidin-2-yl)piperidin-4-yl)methoxy)phenyl)cyclohex-3-enecarboxylic acid was dissolved in 30 ml of DMF in a 100 ml flask, and stirred under a nitrogen atmosphere. 0.2 ml of TEA and 110 mg of L-β-prolinol were sequentially added dropwise thereto, and the resulting mixture was then additionally stirred for 10 minutes. 300 mg of HATU was added dropwise thereto, and the mixture was stirred at room temperature for an hour. After the reaction was terminated, 50 ml of distilled water was slowly added at 0° C., and the resulting solids were filtered, and then dried to prepare the title compound (Amount obtained: 230 mg/Yield: 74%).

$^1$H NMR (400, CDCl$_3$): 8.18 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 153: Preparation of (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone

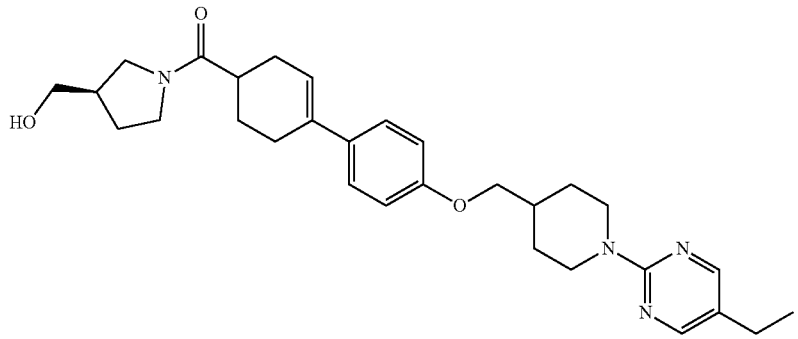 [SMILES: CCc1cnc(N2CCC(COc3ccc(C4=CCC(C(=O)N5CC[C@@H](CO)C5)CC4)cc3)CC2)nc1]

The title compound was prepared in the same manner as in <Example 152>, except that D-β-prolinol was used instead of the L-β-prolinol (Amount obtained: 240 mg/Yield: 82%).

$^1$H NMR (400, CDCl$_3$): 8.18 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 154: Preparation of ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone

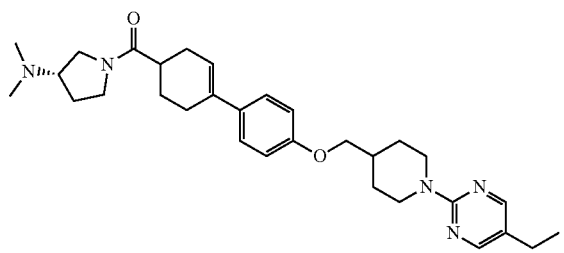 [SMILES: CCc1cnc(N2CCC(COc3ccc(C4=CCC(C(=O)N5CC[C@H](N(C)C)C5)CC4)cc3)CC2)nc1]

The title compound was prepared in the same manner as in <Example 152>, except that (S)—N,N-dimethylpyrrolidine-3-amine hydrochloride was used instead of the L-β-prolinol (Amount obtained: 470 mg/Yield: 80%).

$^1$H NMR (400, CDCl$_3$): 8.18 (2H, s), 7.33 (2H, d), 6.86 (2H, d), 6.06 (1H, s), 4.78 (2H, d), 3.93-3.71 (4H, m), 3.59-3.18 (2H, m), 2.92 (2H, m), 2.86-2.41 (7H, m), 2.30 (6H, s), 2.22-1.71 (8H, m), 1.35 (2H, m), 1.21 (3H, m)

Example 155: Preparation of ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone

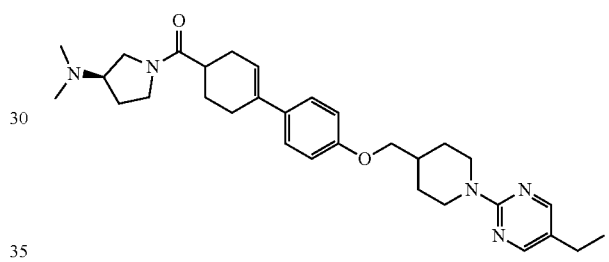

The title compound was prepared in the same manner as in <Example 152>, except that (R)—N,N-dimethylpyrrolidine-3-amine hydrochloride was used instead of the L-β-prolinol (Amount obtained: 440 mg/Yield: 76%).

$^1$H NMR (400, CDCl$_3$): 8.18 (2H, s), 7.33 (2H, d), 6.86 (2H, d), 6.06 (1H, s), 4.78 (2H, d), 3.93-3.71 (4H, m), 3.59-3.18 (2H, m), 2.92 (2H, m), 2.86-2.41 (7H, m), 2.30 (6H, s), 2.22-1.71 (8H, m), 1.35 (2H, m), 1.21 (3H, m)

Example 156: Preparation of ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone hydrochloride

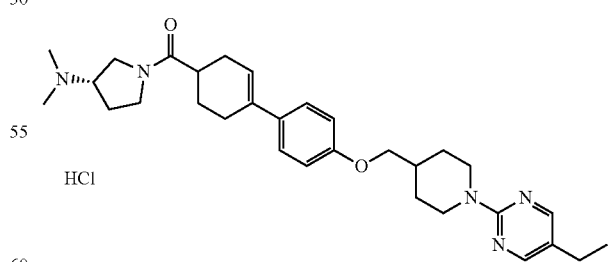

HCl

The title compound was prepared in the same manner as in <Example 145>, except that ((S)-3-(dimethylamino)pyrrolidin-1-yl)(4-(4-((1-(5-ethylpyrimidin-2-yl)piperidin-4-yl)methoxy)phenyl)cyclohex-3-enyl)methanone was used instead of the ((R)-3-(dimethylamino)pyrrolidin-1-yl)(4-(4-((1-(3-isopropyl-1,2,4-oxadiazol-5-yl)piperidin-4-yl)

methoxy)phenyl)cyclohex-3-enyl)methanone (Amount obtained: 180 mg/Yield: 76%).

$^1$H NMR (400, D$_2$O): 8.28 (2H, s), 7.33 (2H, d), 6.86 (2H, d), 6.06 (1H, s), 4.31 (1H, d), 3.95-3.31 (4H, m), 3.14 (2H, m), 2.86 (6H, s), 2.72 (1H, m), 2.53-1.87 (12H, m), 1.63 (1H, m), 1.31 (2H, m), 1.09 (3H, m)

Example 157: Preparation of ((R)-3-(dimethylamino)pyrrolidin-1-yl)(4-(4-((1-(5-ethylpyrimidin-2-yl)piperidin-4-yl)methoxy)phenyl)cyclohex-3-enyl) methanone hydrochloride

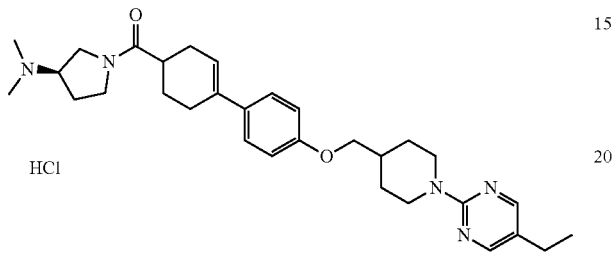

The title compound was prepared in the same manner as in <Example 145>, except that ((R)-3-(dimethylamino)pyrrolidin-1-yl)(4-(4-((1-(5-ethylpyrimidin-2-yl)piperidin-4-yl)methoxy)phenyl)cyclohex-3-enyl)methanone was used instead of the ((R)-3-(dimethylamino)pyrrolidin-1-yl)(4-(4-((1 1-(3-isopropyl-1,2,4-oxadiazol-5-yl)piperidin-4-yl)methoxy)phenyl)cyclohex-3-enyl)methanone (Amount obtained: 170 mg/Yield: 71%).

$^1$H NMR (400, D$_2$O): 8.28 (2H, s), 7.33 (2H, d), 6.86 (2H, d), 6.06 (1H, s), 4.31 (1H, d), 3.95-3.31 (4H, m), 3.14 (2H, m), 2.86 (6H, s), 2.72 (1H, m), 2.53-1.87 (12H, m), 1.63 (1H, m), 1.31 (2H, m), 1.09 (3H, m)

Example 158: Preparation of (4-(4-((1-(5-ethylpyrimidin-2-yl)piperidin-4-yl)methoxy)phenyl)cyclohex-3-enyl)((S)-3-(hydroxymethyl)pyrrolidin-1-yl) methanone hydrochloride

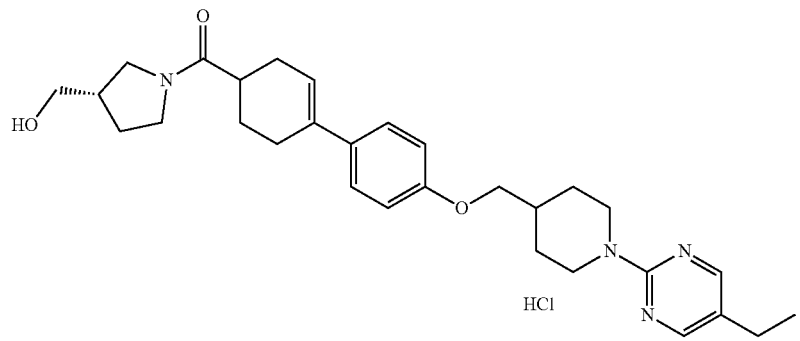 [SMILES: CCc1cnc(N2CCC(COc3ccc(C4=CCC(C(=O)N5CC[C@H](CO)C5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)((S)-3-(hydroxymethyl)pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 95 mg/Yield: 71%).

¹H NMR (400, CDCl₃): 8.43 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 159: Preparation of (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone hydrochloride

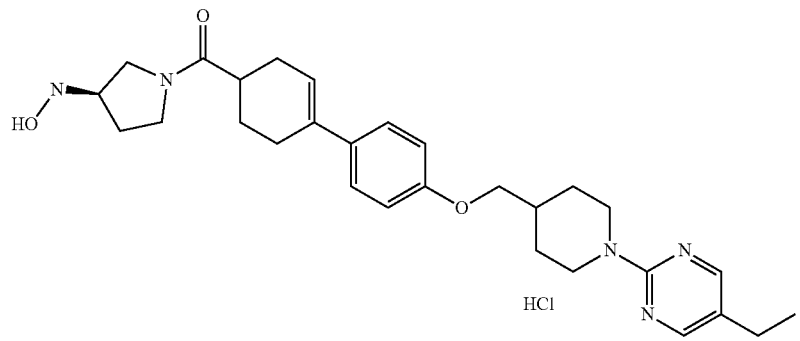 [SMILES: CCc1cnc(N2CCC(COc3ccc(C4=CCC(C(=O)N5CC[C@@H](NO)C5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)((R)-3-(hydroxymethyl)pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 73%).

¹H NMR (400, CDCl₃): 8.43 (2H, s), 7.33 (2H, d), 6.86 (2H, d), 6.06 (1H, s), 4.78 (2H, d), 3.86 (2H, d), 3.79-3.24 (6H, m), 2.92 (2H, m), 2.77-2.28 (8H, m), 2.19-1.65 (10H, m), 1.35 (2H, m), 1.21 (3H, m)

Example 160: Preparation of (4-(4-((1-(5-ethylpyrimidin-2-yl)piperidin-4-yl)methoxy)phenyl)cyclohex-3-enyl)((S)-3-fluoropyrrolidin-1-yl)methanone

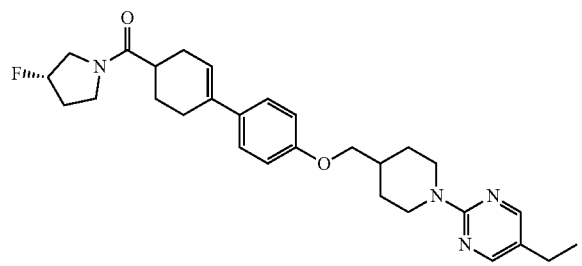 [SMILES: CCc1cnc(N2CCC(COc3ccc(C4=CCC(C(=O)N5CC[C@H](F)C5)CC4)cc3)CC2)nc1]

The title compound was prepared in the same manner as in <Example 152>, except that (S)-3-fluoropyrrolidine was used instead of the L-β-prolinol (Amount obtained: 195 mg/Yield: 76%).

¹H NMR (400, CDCl₃): 8.19 (2H, s), 7.33 (2H, d), 6.86 (2H, d), 6.06 (1H, s), 5.31 (1H, m), 4.78 (2H, d), 4.01-3.51 (6H, m), 2.92 (2H, m), 2.77-1.87 (14H, m), 1.35 (2H, m), 1.21 (3H, m)

Example 161: Preparation of (4-(4-((1-(5-ethylpyrimidin-2-yl)piperidin-4-yl)methoxy)phenyl)cyclohex-3-enyl)((S)-3-fluoropyrrolidin-1-yl)methanone hydrochloride

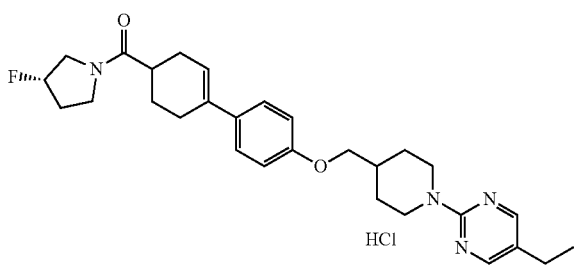 [SMILES: CCc1cnc(N2CCC(COc3ccc(C4=CCC(C(=O)N5CC[C@H](F)C5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)((S)-3-fluoropyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 105 mg/Yield: 73%).

¹H NMR (400, CDCl₃): 8.41 (2H, s), 7.33 (2H, d), 6.86 (2H, d), 6.06 (1H, s), 5.31 (1H, m), 5.01 (2H, d), 4.01-3.51 (6H, m), 2.92 (2H, m), 2.77-1.87 (14H, m), 1.35 (2H, m), 1.21 (3H, m)

Example 162: Preparation of (4-(4-((1-(5-ethylpyrimidin-2-yl)piperidin-4-yl)methoxy)phenyl)cyclohex-3-enyl)(pyrrolidin-1-yl)methanone

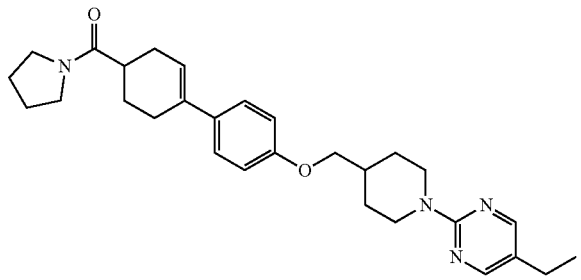 [SMILES: CCc1cnc(N2CCC(COc3ccc(C4=CCC(C(=O)N5CCCC5)CC4)cc3)CC2)nc1]

The title compound was prepared in the same manner as in <Example 152>, except that pyrrolidine was used instead of the L-β-prolinol (Amount obtained: 250 mg/Yield: 84%).

¹H NMR (400, CDCl₃): 8.19 (2H, s), 7.33 (2H, d), 6.86 (2H, d), 6.06 (1H, s), 4.78 (2H, d), 3.85 (2H, d), 3.52 (4H, m), 2.92 (2H, m), 2.71-2.28 (7H, m), 2.17-1.85 (9H, m), 1.35 (2H, m), 1.21 (3H, m)

Example 163: Preparation of (4-(4-((1-(5-ethylpyrimidin-2-yl)piperidin-4-yl)methoxy)phenyl)cyclohex-3-enyl)(piperidin-1-yl)methanone

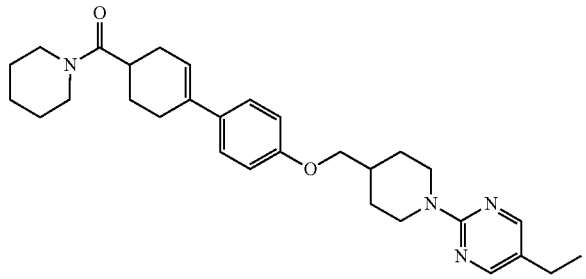 [SMILES: CCc1cnc(N2CCC(COc3ccc(C4=CCC(C(=O)N5CCCCC5)CC4)cc3)CC2)nc1]

The title compound was prepared in the same manner as in <Example 152>, except that piperidine was used instead of the L-β-prolinol (Amount obtained: 250 mg/Yield: 83%).

¹H NMR (400, CDCl₃): 8.19 (2H, s), 7.33 (2H, d), 6.86 (2H, d), 6.06 (1H, s), 4.78 (2H, d), 3.85 (2H, d), 3.67-3.52 (4H, m), 2.92 (2H, m), 2.80 (1H, m), 2.61-1.85 (11H, m), 1.74-1.54 (6H, m), 1.35 (2H, m), 1.21 (3H, m)

Example 164: Preparation of (4-(4-((1-(5-ethylpyrimidin-2-yl)piperidin-4-yl)methoxy)phenyl)cyclohex-3-enyl)(4-hydroxypiperidin-1-yl)methanone

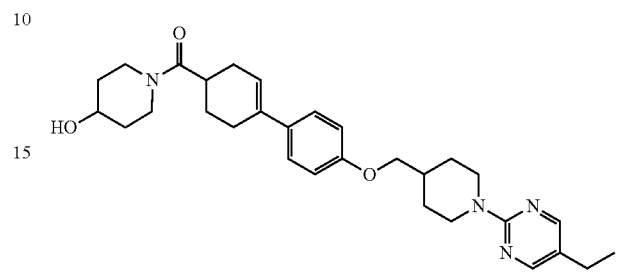

The title compound was prepared in the same manner as in <Example 152>, except that 4-hydroxy piperidine was used instead of the L-β-prolinol (Amount obtained: 215 mg/Yield: 77%).

¹H NMR (400, CDCl₃): 8.19 (2H, s), 7.33 (2H, d), 6.86 (2H, d), 6.06 (1H, s), 4.78 (2H, d), 4.18 (1H, m), 3.89 (2H, m), 3.85 (2H, d), 3.28 (2H, m), 2.92 (2H, m), 2.80 (1H, m), 2.61-2.28 (6H, m), 2.09 (1H, m), 1.98 (6H, m), 1.55 (2H, m), 1.35 (2H, m), 1.21 (3H, m)

Example 165: Preparation of (4-(4-((1-(5-ethylpyrimidin-2-yl)piperidin-4-yl)methoxy)phenyl)cyclohex-3-enyl)(4-(hydroxymethyl)piperidin-1-yl)methanone

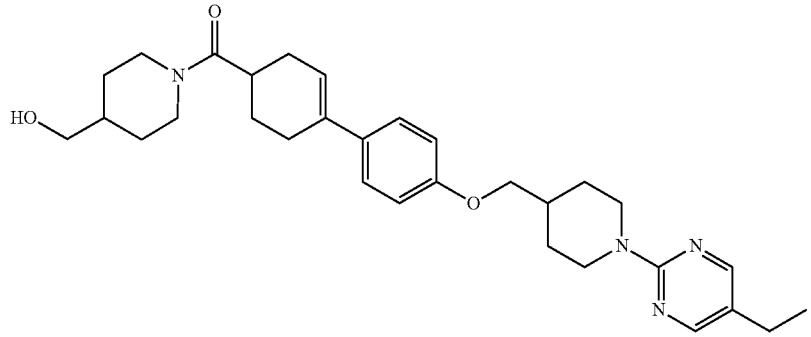 [SMILES: CCc1cnc(N2CCC(COc3ccc(C4=CCC(C(=O)N5CCC(CO)CC5)CC4)cc3)CC2)nc1]

The title compound was prepared in the same manner as in <Example 152>, except that 4-piperidinemethanol was used instead of the L-β-prolinol (Amount obtained: 225 mg/Yield: 75%).

¹H NMR (400, CDCl₃): 8.19 (2H, s), 7.33 (2H, d), 6.86 (2H, d), 6.06 (1H, s), 4.78 (3H, m), 4.08 (1H, d), 3.85 (2H, d), 3.55 (2H, m), 3.09 (1H, m), 2.92 (2H, m), 2.81 (1H, m), 2.65-2.28 (7H, m), 2.11 (1H, m), 2.04-1.75 (7H, m), 1.35 (2H, m), 1.21 (3H, m)

Example 166: Preparation of (4-(4-((1-(5-ethylpyrimidin-2-yl)piperidin-4-yl)methoxy)phenyl)cyclohex-3-enyl)(pyrrolidin-1-yl)methanone hydrochloride

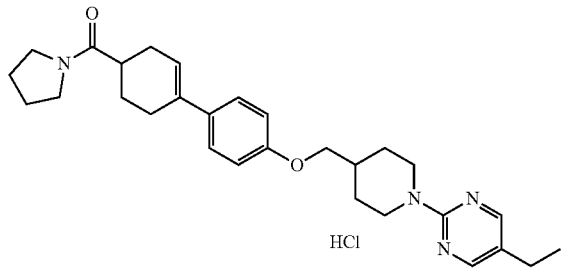 [SMILES: CCc1cnc(N2CCC(COc3ccc(C4=CCC(C(=O)N5CCCC5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)(pyrrolidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 100 mg/Yield: 74%).

¹H NMR (400, CDCl₃): 8.41 (2H, s), 7.33 (2H, d), 6.86 (2H, d), 6.06 (1H, s), 5.03 (2H, d), 3.85 (2H, d), 3.52 (4H, m), 2.92 (2H, m), 2.71-2.28 (7H, m), 2.17-1.85 (9H, m), 1.35 (2H, m), 1.21 (3H, m)

Example 167: Preparation of (4-(4-((1-(5-ethylpyrimidin-2-yl)piperidin-4-yl)methoxy)phenyl)cyclohex-3-enyl)(piperidin-1-yl)methanone hydrochloride

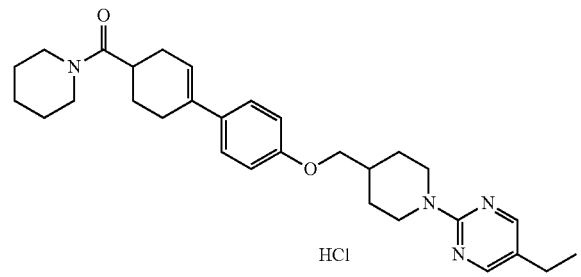 [SMILES: CCc1cnc(N2CCC(COc3ccc(C4=CCC(C(=O)N5CCCCC5)CC4)cc3)CC2)nc1 ; Cl]

The title compound was prepared in the same manner as in <Example 145>, except that (4-(4-((1-(5-ethylpyrimidin-2-yl)piperidin-4-yl)methoxy)phenyl)cyclohex-3-enyl)(piperidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 71%).

¹H NMR (400, CDCl₃): 8.41 (2H, s), 7.33 (2H, d), 6.86 (2H, d), 6.06 (1H, s), 5.03 (2H, d), 3.85 (2H, d), 3.67-3.52 (4H, m), 2.92 (2H, m), 2.80 (1H, m), 2.61-1.85 (11H, m), 1.74-1.54 (6H, m), 1.35 (2H, m), 1.21 (3H, m)

Example 168: Preparation of (4-(4-((1-(5-ethylpyrimidin-2-yl)piperidin-4-yl)methoxy)phenyl)cyclohex-3-enyl)(4-hydroxypiperidin-1-yl)methanone hydrochloride

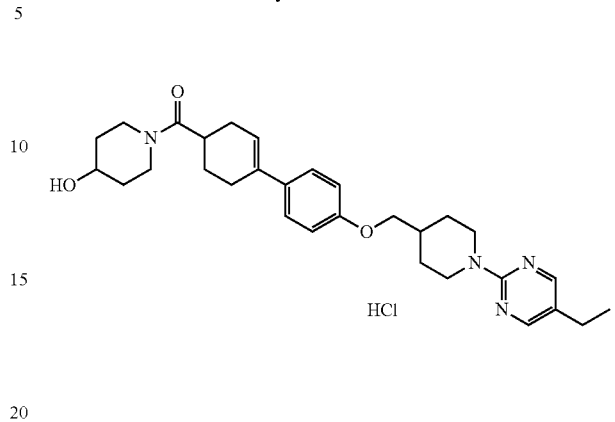

The title compound was prepared in the same manner as in <Example 145>, except that (4-(4-((1-(5-ethylpyrimidin-2-yl)piperidin-4-yl)methoxy)phenyl)cyclohex-3-enyl)(4-hydroxypiperidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 85 mg/Yield: 77%).

¹H NMR (400, CDCl₃): 8.41 (2H, s), 7.33 (2H, d), 6.86 (2H, d), 6.06 (1H, s), 5.03 (2H, d), 4.18 (1H, m), 3.89 (2H, m), 3.85 (2H, d), 3.28 (2H, m), 2.92 (2H, m), 2.80 (1H, m), 2.61-2.28 (6H, m), 2.09 (1H, m), 1.98 (6H, m), 1.55 (2H, m), 1.35 (2H, m), 1.21 (3H, m)

Example 169: Preparation of (4-(4-((1-(5-ethylpyrimidin-2-yl)piperidin-4-yl)methoxy)phenyl)cyclohex-3-enyl)(4-(hydroxymethyl)piperidin-1-yl)methanone hydrochloride

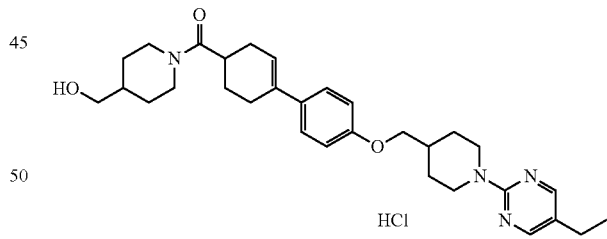

The title compound was prepared in the same manner as in <Example 145>, except that (4-(4-((1-(5-ethylpyrimidin-2-yl)piperidin-4-yl)methoxy)phenyl)cyclohex-3-enyl)(4-(hydroxymethyl)piperidin-1-yl)methanone was used instead of the ((R)-3-(dimethylamino)pyrrolidin-1-yl)(4-(4-((1-(3-isopropyl-1,2,4-oxadiazol-5-yl)piperidin-4-yl)methoxy)phenyl)cyclohex-3-enyl)methanone (Amount obtained: 95 mg/Yield: 76%).

¹H NMR (400, CDCl₃): 8.41 (2H, s), 7.33 (2H, d), 6.86 (2H, d), 6.06 (1H, s), 5.03 (2H, m), 4.72 (1H, d), 4.08 (1H, d), 3.85 (2H, d), 3.55 (2H, m), 3.09 (1H, m), 2.92 (2H, m), 2.81 (1H, m), 2.65-2.28 (7H, m), 2.11 (1H, m), 2.04-1.75 (7H, m), 1.35 (2H, m), 1.21 (3H, m)

Example 170: Preparation of azetidin-1-yl(4-(4-((1-(5-ethylpyrimidin-2-yl)piperidin-4-yl)methoxy)phenyl)cyclohex-3-enyl)methanone

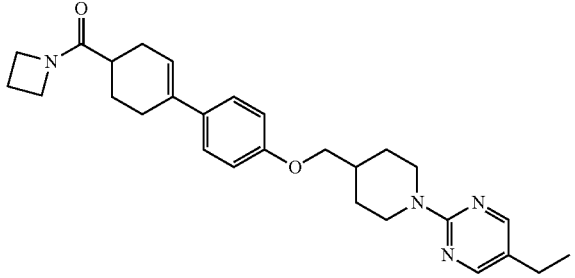 [SMILES: CCc1cnc(N2CCC(COc3ccc(C4=CCC(C(=O)N5CCC5)CC4)cc3)CC2)nc1]

The title compound was prepared in the same manner as in <Example 152>, except that azetidine was used instead of the L-β-prolinol (Amount obtained: 180 mg/Yield: 76%).

$^1$H NMR (400, CDCl$_3$): 8.19 (2H, s), 7.33 (2H, d), 6.86 (2H, d), 6.06 (1H, s), 4.78 (3H, m), 4.15 (4H, m), 3.85 (2H, d), 2.91 (2H, m), 2.61-1.81 (14H, m), 1.35 (2H, m), 1.21 (3H, m)

Example 171: Preparation of (4-(4-((1-(5-ethylpyrimidin-2-yl)piperidin-4-yl) methoxy)phenyl)cyclohex-3-enyl)(3-hydroxyazetidin-1-yl)methanone

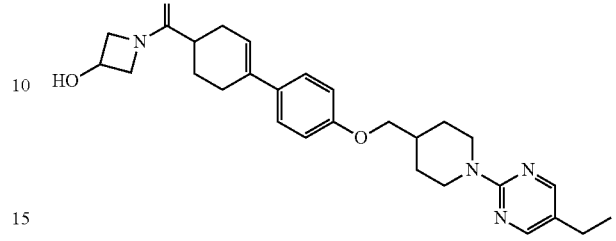

The title compound was prepared in the same manner as in <Example 152>, except that azetidine was used instead of the L-β-prolinol (Amount obtained: 200 mg/Yield: 81%).

$^1$H NMR (400, CDCl$_3$): 8.19 (2H, s), 7.33 (2H, d), 6.86 (2H, d), 6.06 (1H, s), 4.78 (2H, m), 4.35 (4H, m), 3.85 (2H, d), 2.91 (2H, m), 2.71-1.81 (13H, m), 1.35 (2H, m), 1.21 (3H, m)

Example 172: Preparation of (4-(4-((1-(5-ethylpyrimidin-2-yl)piperidin-4-yl) methoxy)phenyl)cyclohex-3-enyl)(4-(2-hydroxyethyl)piperazin-1-yl) methanone

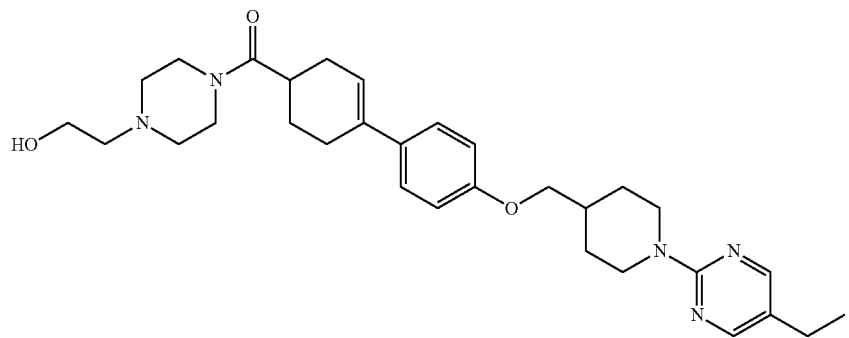 [SMILES: CCc1cnc(N2CCC(COc3ccc(C4=CCC(C(=O)N5CCN(CCO)CC5)CC4)cc3)CC2)nc1]

The title compound was prepared in the same manner as in <Example 152>, except that 4-hydroxyethylpiperazine was used instead of the L-β-prolinol (Amount obtained: 220 mg/Yield: 79%).

$^1$H NMR (400, CDCl$_3$): 8.19 (2H, s), 7.33 (2H, d), 6.86 (2H, d), 6.06 (1H, s), 4.78 (2H, m), 3.85 (2H, d), 3.65 (6H, m), 2.91 (2H, m), 2.86-1.81 (12H, m), 1.35 (2H, m), 1.21 (3H, m)

Example 173: Preparation of (4-(4-((1-(5-ethylpyrimidin-2-yl)piperidin-4-yl)methoxy)phenyl)cyclohex-3-enyl)(4-(2-hydroxyethyl)piperidin-1-yl)methanone

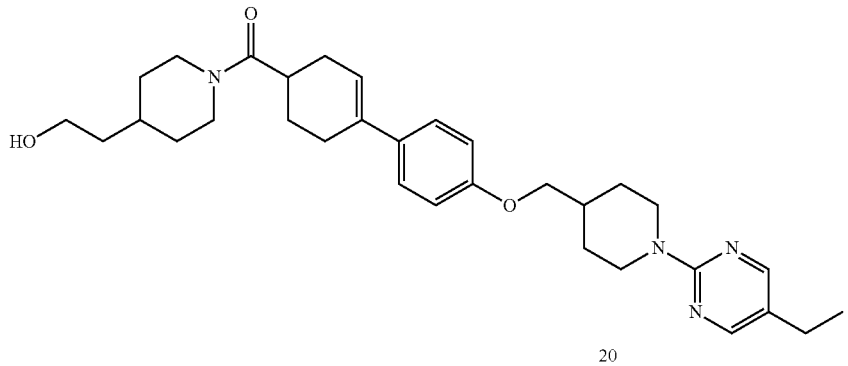

The title compound was prepared in the same manner as in <Example 152>, except that 4-piperidine ethanol was used instead of the L-β-prolinol (Amount obtained: 230 mg/Yield: 77%).

$^1$H NMR (400, CDCl$_3$): 8.19 (2H, s), 7.33 (2H, d), 6.86 (2H, d), 6.06 (1H, s), 4.78 (2H, m), 3.69 (1H, d), 3.99 (1H, d), 3.85 (2H, d), 3.75 (2H, m), 3.09 (1H, m), 2.91 (2H, m), 2.86-1.41 (17H, m), 1.35 (2H, m), 1.21 (3H, m)

Example 174: Preparation of N-ethoxy-4-(4-((1-(5-ethylpyrimidin-2-yl)piperidin-4-yl) methoxy)phenyl)cyclohex-3-enecarboxamide

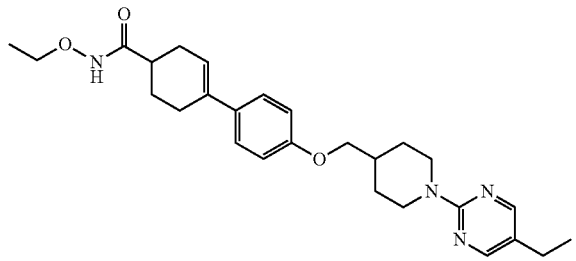 [SMILES: CCONC(=O)C1CC=C(c2ccc(OCC3CCN(c4ncc(CC)cn4)CC3)cc2)CC1]

The title compound was prepared in the same manner as in <Example 152>, except that O-ethylhydroxylamine hydrochloride was used instead of the L-β-prolinol (Amount obtained: 230 mg/Yield: 81%).

$^1$H NMR (400, CDCl$_3$): 8.19 (2H, s), 7.33 (2H, d), 6.86 (2H, d), 6.06 (1H, s), 4.78 (2H, m), 4.01 (2H, m), 3.85 (2H, d), 2.91 (2H, m), 2.71-1.81 (12H, m), 1.35 (5H, m), 1.21 (3H, m)

Example 175: Preparation of N-ethyl-4-(4-((1-(5-ethylpyrimidin-2-yl)piperidin-4-yl) methoxy)phenyl)-N-(2-hydroxyethyl)cyclohex-3-enecarboxamide

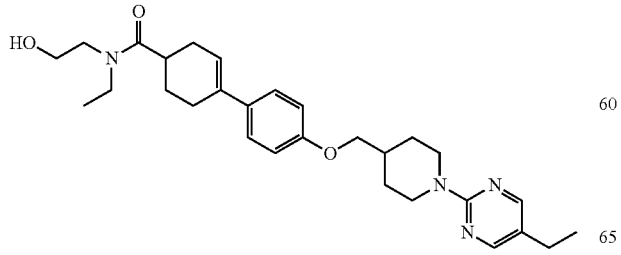

The title compound was prepared in the same manner as in <Example 152>, except that 2-(ethylamino)ethanol was used instead of the L-β-prolinol (Amount obtained: 205 mg/Yield: 82%).

$^1$H NMR (400, CDCl$_3$): 8.19 (2H, s), 7.33 (2H, d), 6.86 (2H, d), 6.06 (1H, s), 4.78 (2H, m), 3.85 (4H, m), 3.71 (1H, s), 3.52 (4H, m), 2.91 (2H, m), 2.81-1.81 (12H, m), 1.35 (2H, m), 1.21 (6H, m)

Example 176: Preparation of 4-(4-((1-(5-ethylpyrimidin-2-yl)piperidin-4-yl)methoxy)phenyl)-N-(2-hydroxyethyl)cyclohex-3-enecarboxamide

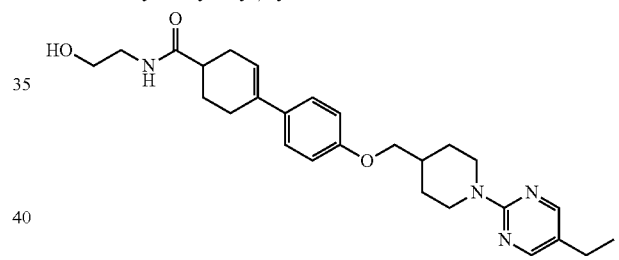

The title compound was prepared in the same manner as in <Example 152>, except that 2-aminoethanol was used instead of the L-β-prolinol (Amount obtained: 260 mg/Yield: 85%).

$^1$H NMR (400, CDCl$_3$): 8.19 (2H, s), 7.33 (2H, d), 6.86 (2H, d), 6.06 (2H, m), 4.78 (2H, m), 3.85 (2H, d), 3.78 (2H, m), 3.51 (2H, m), 2.91 (2H, m), 2.48 (7H, m), 2.21-1.81 (5H, m), 1.35 (2H, m), 1.21 (3H, m)

Example 177: Preparation of 4-(4-((1-(5-ethylpyrimidin-2-yl)piperidin-4-yl) methoxy)phenyl)-N-(3-hydroxy-2,2-dimethylpropyl)cyclohex-3-enecarboxamide

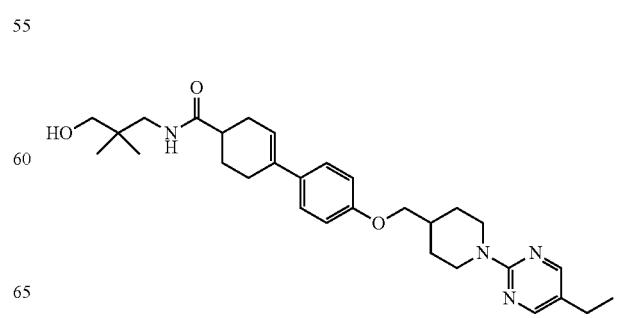

The title compound was prepared in the same manner as in <Example 152>, except that 3-amino-2,2-dimethylpropanol was used instead of the L-β-prolinol (Amount obtained: 265 mg/Yield: 85%).

¹H NMR (400, CDCl₃): 8.19 (2H, s), 7.33 (2H, d), 6.86 (2H, d), 6.06 (1H, s), 5.98 (1H, m), 4.78 (2H, m), 3.85 (2H, d), 3.49 (2H, m), 3.16 (4H, m), 2.91 (2H, m), 2.48 (7H, m), 2.21-1.81 (5H, m), 1.35 (2H, m), 1.21 (3H, m), 0.89 (6H, d)

Example 178: Preparation of 1-(4-(4-((1-(5-ethylpyrimidin-2-yl)piperidin-4-yl)methoxy)phenyl)cyclohex-3-enecarbonyl)piperidine-4-carboxamide

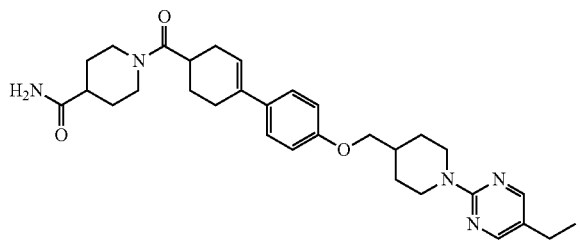 [SMILES: CCc1cnc(N2CCC(COc3ccc(C4=CCC(C(=O)N5CCC(C(N)=O)CC5)CC4)cc3)CC2)nc1]

The title compound was prepared in the same manner as in <Example 152>, except that isonipecotamide was used instead of the L-β-prolinol (Amount obtained: 240 mg/Yield: 79%).

¹H NMR (400, CDCl₃): 8.19 (2H, s), 7.33 (2H, d), 6.86 (2H, d), 6.06 (1H, s), 5.39 (2H, m), 4.78 (2H, m), 4.68 (1H, m), 4.02 (1H, d), 3.85 (2H, d), 3.65 (6H, m), 3.14 (1H, m), 2.91 (2H, m), 2.86-2.18 (9H, m), 2.15-1.59 (13H, m), 1.35 (2H, m), 1.21 (3H, m)

Example 179: Preparation of 4-(4-((1-(5-ethylpyrimidin-2-yl)piperidin-4-yl) methoxy)phenyl)-N-(3-methoxypropyl)cyclohex-3-enecarboxamide

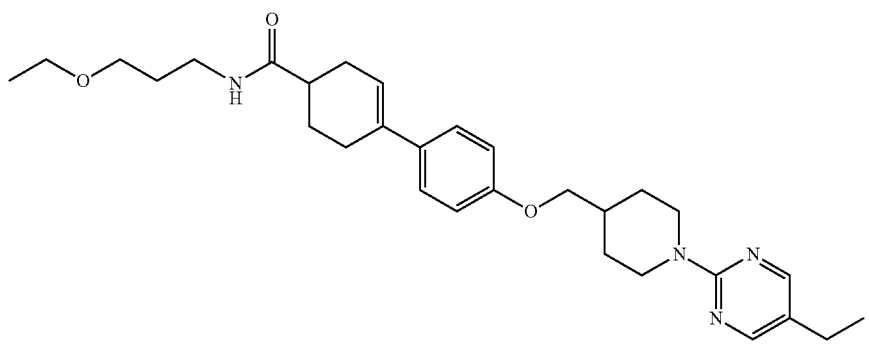 [SMILES: CCOCCCNC(=O)C1CC=C(c2ccc(OCC3CCN(c4ncc(CC)cn4)CC3)cc2)CC1]

The title compound was prepared in the same manner as in <Example 152>, except that 3-ethoxypropylamine was used instead of the L-β-prolinol (Amount obtained: 240 mg/Yield: 78%).

¹H NMR (400, CDCl₃): 8.19 (2H, s), 7.33 (2H, d), 6.86 (2H, d), 6.31 (1H, m), 6.06 (1H, s), 4.78 (2H, m), 3.85 (2H, d), 3.48 (6H, m), 2.91 (2H, m), 2.86-1.79 (14H, m), 1.35 (2H, m), 1.21 (6H, m)

Example 180: Preparation of 4-(4-((1-(5-ethylpyrimidin-2-yl)piperidin-4-yl)methoxy)phenyl)-N-(furan-2-ylmethyl)cyclohex-3-enecarboxamide

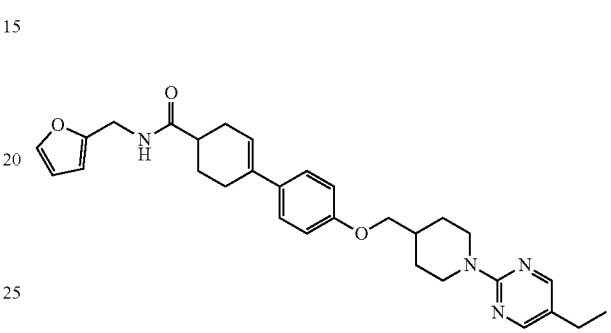

The title compound was prepared in the same manner as in <Example 152>, except that furfurylamine was used instead of the L-β-prolinol (Amount obtained: 180 mg/Yield: 76%).

¹H NMR (400, CDCl₃): 8.19 (2H, s), 7.37 (1H, s), 7.33 (2H, d), 6.86 (2H, d), 6.31 (2H, m), 6.06 (1H, s), 5.89 (1H, m), 4.78 (2H, m), 4.51 (2H, d), 3.85 (2H, d), 2.91 (2H, m), 2.59-1.81 (12H, m), 1.35 (2H, m), 1.21 (3H, m)

Example 181: Preparation of 4-(4-((1-(5-ethylpyrimidin-2-yl)piperidin-4-yl)methoxy)phenyl)-N,N-bis(2-hydroxyethyl)cyclohex-3-enecarboxamide

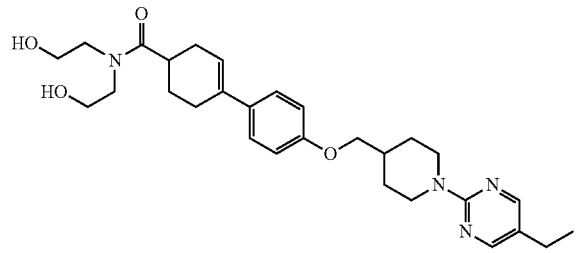 [SMILES: CCc1cnc(N2CCC(COc3ccc(C4=CCC(C(=O)N(CCO)CCO)CC4)cc3)CC2)nc1]

The title compound was prepared in the same manner as in <Example 152>, except that diethanolamine was used instead of the L-β-prolinol (Amount obtained: 185 mg/Yield: 77%).

$^1$H NMR (400, CDCl$_3$): 8.19 (2H, s), 7.33 (2H, d), 6.86 (2H, d), 6.06 (1H, s), 4.78 (2H, m), 3.88 (6H, m), 3.69 (4H, m), 3.15 (2H, d), 2.91 (3H, m), 2.59-1.83 (11H, m), 1.35 (2H, m), 1.21 (3H, m)

Example 182: Preparation of (4-hydroxypiperidin-1-yl)(4-(4-((1-(3-isopropyl-1,2,4-oxadiazol-5-yl)piperidin-4-yl)methoxy)phenyl)cyclohex-3-enyl)methanone

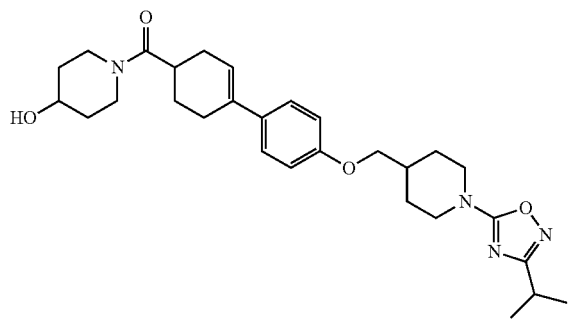 [SMILES: CC(C)c1noc(N2CCC(COc3ccc(C4=CCC(C(=O)N5CCC(O)CC5)CC4)cc3)CC2)n1]

The title compound was prepared in the same manner as in <Example 143>, except that 4-hydroxypiperidine was used instead of the (R)—N,N-dimethylpyrrolidine-3-amine hydrochloride (Amount obtained: 230 mg/Yield: 80%).

*1644 $^1$H NMR (400, CDCl$_3$): 7.33 (2H, d), 6.86 (2H, d), 6.06 (1H, s), 5.16 (1H, m), 4.19 (3H, m), 3.98 (1H, s), 3.85 (3H, m), 3.21 (4H, m), 2.88 (2H, m), 2.62-1.85 (11H, m), 1.59 (6H, m), 1.32 (6H, d)

Example 183: Preparation of (4-(hydroxymethyl)piperidin-1-yl)(4-(4-((1-(3-isopropyl-1,2,4-oxadiazol-5-yl)piperidin-4-yl)methoxy)phenyl)cyclohex-3-enyl)methanone

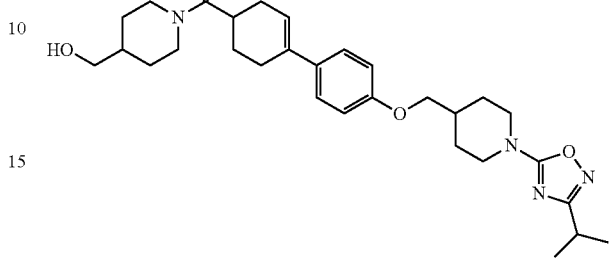

The title compound was prepared in the same manner as in <Example 143>, except that 4-piperidine methanol was used instead of the (R)—N,N-dimethylpyrrolidine-3-amine hydrochloride (Amount obtained: 240 mg/Yield: 82%).

$^1$H NMR (400, CDCl$_3$): 7.33 (2H, d), 6.86 (2H, d), 6.06 (1H, s), 4.72 (1H, s), 4.22 (2H, d), 4.04 (1H, d), 3.85 (2H, d), 3.56 (2H, m), 3.11 (3H, m), 2.88 (2H, m), 2.62-1.75 (13H, m), 1.45 (3H, m), 1.32 (6H, d)

Example 184: Preparation of N-cyclopropyl-4-(4-((1-(3-isopropyl-1,2,4-oxadiazol-5-yl)piperidin-4-yl)methoxy)phenyl)cyclohex-3-enecarboxamide

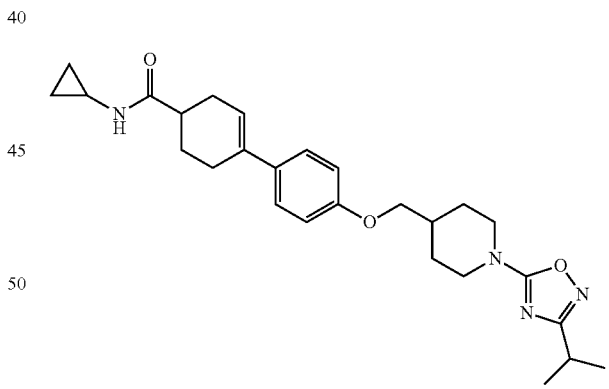

The title compound was prepared in the same manner as in <Example 143>, except that cyclopropylamine was used instead of the (R)—N,N-dimethylpyrrolidine-3-amine hydrochloride (Amount obtained: 235 mg/Yield: 81%).

$^1$H NMR (400, CDCl$_3$): 7.33 (2H, d), 6.86 (2H, d), 6.06 (1H, s), 5.70 (1H, s), 4.21 (2H, d), 3.85 (2H, d), 3.11 (2H, m), 2.91 (1H, m), 2.76 (1H, m), 2.42 (5H, m), 1.98 (5H, m), 1.59 (6H, m), 1.32 (6H, d), 0.81 (2H, m), 0.51 (2H, m)

Example 185: Preparation of N-(3-hydroxypropyl)-4-(4-((1-(3-isopropyl-1,2,4-oxadiazol-5-yl)piperidin-4-yl)methoxy)phenyl)cyclohex-3-enecarboxamide

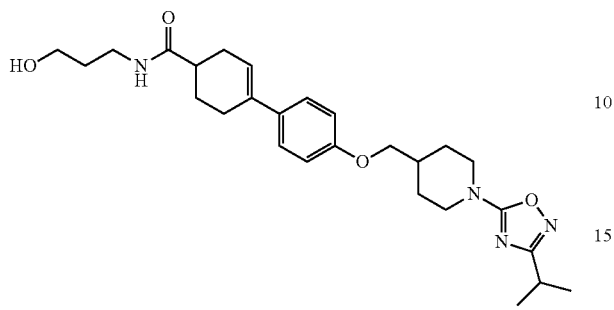

The title compound was prepared in the same manner as in <Example 143>, except that 3-aminopropanol was used instead of the (R)—N,N-dimethylpyrrolidine-3-amine hydrochloride (Amount obtained: 220 mg/Yield: 79%).

$^1$H NMR (400, CDCl$_3$): 7.33 (2H, d), 6.86 (2H, d), 6.06 (1H, s), 5.96 (1H, m), 4.21 (2H, m), 3.85 (2H, m), 3.66 (2H, m), 3.48 (2H, m), 3.20 (1H, m), 3.11 (2H, m) 2.89 (1H, m), 2.48 (5H, m), 2.01 (5H, m), 1.71 (2H, m), 1.59 (6H, m), 1.32 (6H, d)

Example 186: Preparation of (4-(2-hydroxyethyl)piperidin-1-yl)(4-(4-((1-(3-isopropyl-1,2,4-oxadiazol-5-yl)piperidin-4-yl)methoxy)phenyl)cyclohex-3-enyl)methanone

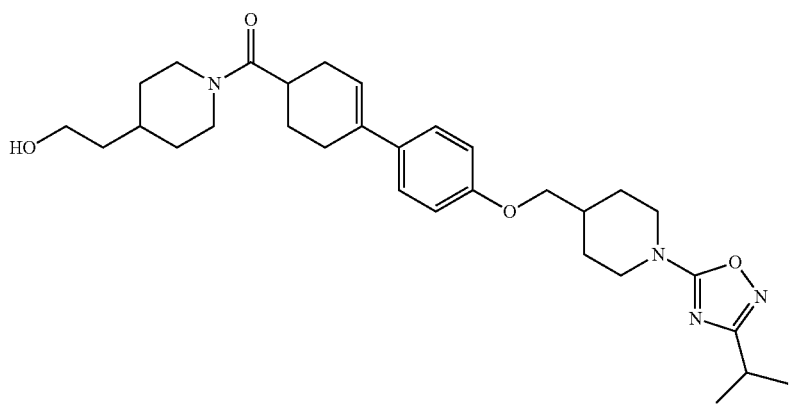

The title compound was prepared in the same manner as in <Example 143>, except that 4-piperidine ethanol was used instead of the (R)—N,N-dimethylpyrrolidine-3-amine hydrochloride (Amount obtained: 205 mg/Yield: 77%).

$^1$H NMR (400, CDCl$_3$): 7.33 (2H, d), 6.86 (2H, d), 6.06 (1H, s), 4.69 (1H, d), 4.21 (2H, m), 3.99 (1H, d), 3.85 (2H, d), 3.74 (2H, m), 3.20 (3H, m), 2.89 (1H, m), 2.81 (1H, m), 2.64-2.24 (5H, m), 2.12-1.69 (8H, m), 1.66 (2H, m), 1.46 (2H, m), 1.32 (6H, d), 1.19 (2H, m)

Example 187: Preparation of (4-(2-hydroxyethyl)piperazin-1-yl)(4-(4-((1-(3-isopropyl-1,2,4-oxadiazol-5-yl)piperidin-4-yl)methoxy)phenyl)cyclohex-3-enyl)methanone

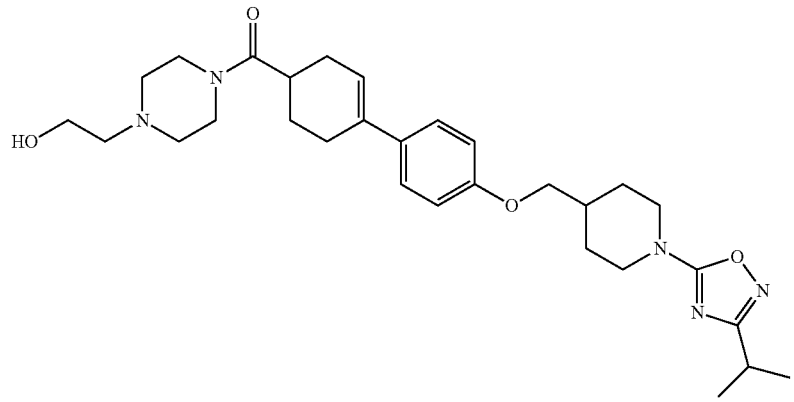 [SMILES: CC(C)c1noc(N2CCC(COc3ccc(C4=CCC(C(=O)N5CCN(CCO)CC5)CC4)cc3)CC2)n1]

The title compound was prepared in the same manner as in <Example 143>, except that 4-hydroxyethyl piperazine was used instead of the (R)—N,N-dimethylpyrrolidine-3-amine hydrochloride (Amount obtained: 180 mg/Yield: 72%).

$^1$H NMR (400, CDCl$_3$): 7.33 (2H, d), 6.86 (2H, d), 6.06 (1H, s), 4.21 (2H, m), 3.85 (2H, d), 3.71 (6H, m), 3.12 (2H, m), 2.89 (1H, m), 2.81-2.24 (12H, m), 2.12-1.85 (5H, m), 1.46 (2H, m), 1.32 (6H, d)

Example 188: Preparation of 4-(4-((1-(3-isopropyl-1,2,4-oxadiazol-5-yl)piperidin-4-yl)methoxy)phenyl)-N-(methoxymethyl)cyclohex-3-enecarboxamide

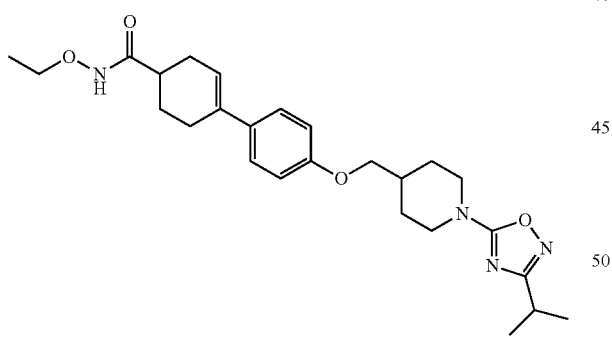

The title compound was prepared in the same manner as in <Example 143>, except that O-ethylhydroxylamine hydrochloride was used instead of the (R)—N,N-dimethylpyrrolidine-3-amine hydrochloride (Amount obtained: 170 mg/Yield: 71%).

$^1$H NMR (400, CDCl$_3$): 8.14 (1H, s), 7.33 (2H, d), 6.86 (2H, d), 6.06 (1H, s), 4.21 (2H, m), 3.99 (2H, m), 3.85 (2H, d), 3.12 (2H, m), 2.89 (1H, m), 2.62-2.28 (5H, m), 2.14-1.87 (5H, m), 1.46 (2H, m), 1.32 (6H, d)

Example 189: Preparation of N-cyclopropyl-4-(4-((1-(5-ethylpyrimidin-2-yl)piperidin-4-yl)methoxy)phenyl)cyclohex-3-enecarboxamide

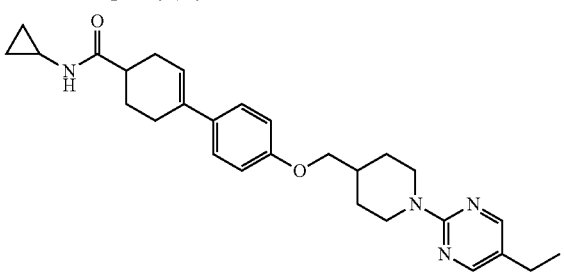

The title compound was prepared in the same manner as in <Example 152>, except that cyclopropylamine was used instead of the L-β-prolinol (Amount obtained: 180 mg/Yield: 76%).

$^1$H NMR (400, CDCl$_3$): 8.19 (2H, s), 7.33 (2H, d), 6.86 (2H, d), 6.06 (1H, s), 5.66 (1H, s), 4.78 (3H, m), 3.85 (2H, d), 2.91 (2H, m), 2.76 (1H, s), 2.61-2.30 (7H, m), 2.09 (2H, m), 1.91 (3H, m), 1.35 (2H, m), 1.21 (3H, m), 0.81 (2H, m), 0.50 (2H, m)

Example 190: Preparation of tert-butyl 4-((4-(4-(2-hydroxyethylcarbamoyl)cyclohex-1-enyl)phenoxy)methyl)piperidine-1-carboxylate

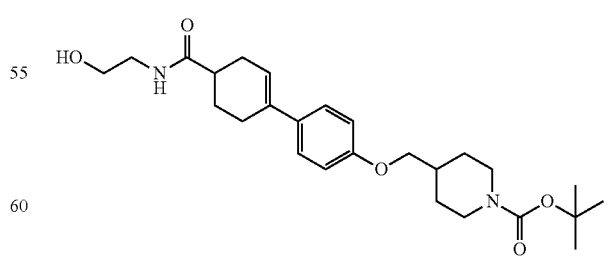

400 mg of 4-(4-((1-(tert-butoxycarbonyl)piperidin-4-yl)methoxy)phenyl)cyclohex-3-enecarboxylic acid was dissolved in 30 ml of DMF in a 100 ml flask, and then stirred under a nitrogen atmosphere. 0.3 ml of TEA was added dropwise thereto, 90 mg of 2-aminoethanol was in turn added dropwise, and the resulting mixture was additionally stirred for 10 minutes. 400 mg of HATU was added dropwise thereto, and the mixture was stirred at room temperature for an hour. After the reaction was terminated, 50 ml of distilled water was slowly added at 0° C., and the resulting solids were filtered, and then dried to prepare the title compound as a white solid (Amount obtained: 190 mg/Yield: 77%).

$^1$H NMR (400, CDCl$_3$): 7.33 (2H, d), 6.86 (2H, d), 6.14 (1H, m), 6.04 (1H, s), 4.18 (2H, s), 3.79 (4H, m), 3.48 (2H, m), 2.75 (3H, m), 2.48 (5H, m), 2.11 (1H, m), 1.89 (4H, m), 1.48 (9H, s), 1.29 (2H, m)

Example 191: Preparation of tert-butyl 4-((4-(4-(3-hydroxy-2,2-dimethylpropylcarbamoyl)cyclohex-1-enyl)phenoxy)methyl)piperidine-1-carboxylate

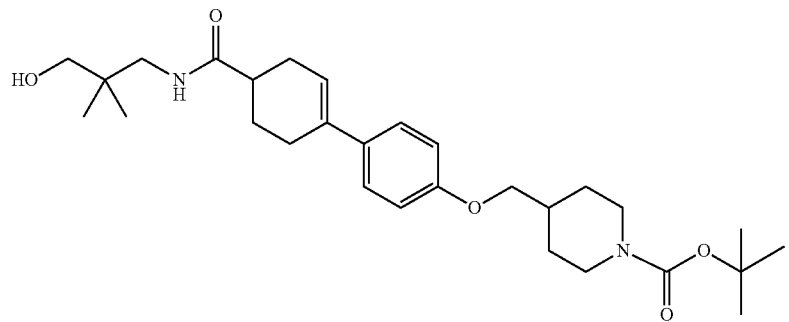 [SMILES: CC(C)(CO)CNC(=O)C1CC=C(c2ccc(OCC3CCN(C(=O)OC(C)(C)C)CC3)cc2)CC1]

The title compound was prepared in the same manner as in <Example 190>, except that 3-amino-2,2-dimethylpropanol was used instead of the 2-aminoethanol (Amount obtained: 230 mg/Yield: 84%).

$^1$H NMR (400, CDCl$_3$): 7.33 (2H, d), 6.86 (2H, d), 6.04 (1H, s), 5.99 (1H, m), 4.18 (2H, s), 4.01 (1H, m), 3.80 (2H, d), 3.16 (4H, m), 2.75 (2H, m), 2.48 (5H, m), 2.11 (1H, m), 1.89 (4H, m), 1.48 (9H, s), 1.29 (2H, m), 0.89 (6H, d)

Example 192: Preparation of tert-butyl 4-((4-(4-(methoxymethylcarbamoyl)cyclohex-1-enyl)phenoxy)methyl)piperidine-1-carboxylate

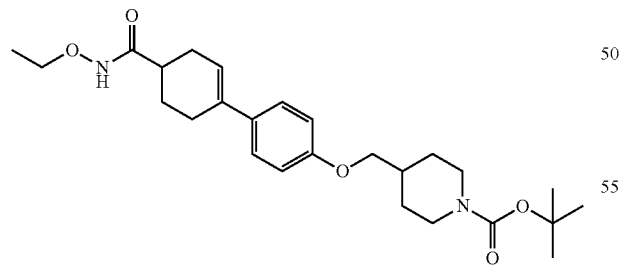

The title compound was prepared in the same manner as in <Example 190>, except that O-ethylhydroxylamine hydrochloride was used instead of the 2-aminoethanol (Amount obtained: 220 mg/Yield: 81%).

$^1$H NMR (400, CDCl$_3$): 8.15 (1H, s), 7.33 (2H, d), 6.86 (2H, d), 6.04 (1H, s), 4.18 (2H, s), 4.00 (2H, m), 3.81 (2H, m), 3.48 (2H, m), 2.75 (2H, m), 2.48 (5H, m), 2.11 (1H, m), 1.89 (4H, m), 1.48 (9H, s), 1.29 (5H, m)

Example 193: Preparation of tert-butyl 4-((4-(4-(4-(pyrrolidin-1-yl)piperidine-1-carbonyl)cyclohex-1-enyl)phenoxy)methyl)piperidine-1-carboxylate

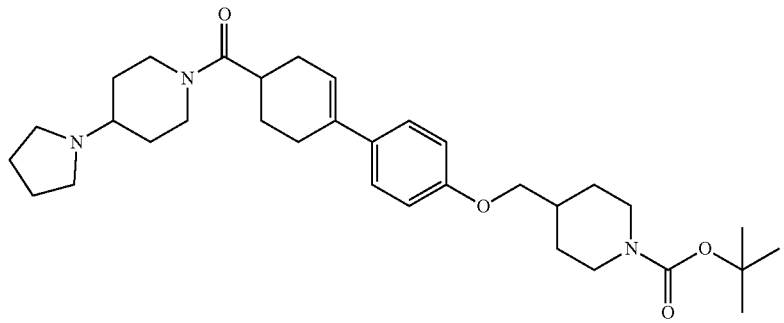 [SMILES: CC(C)(C)OC(=O)N1CCC(COc2ccc(C3=CCC(C(=O)N4CCC(N5CCCC5)CC4)CC3)cc2)CC1]

The title compound was prepared in the same manner as in <Example 190>, except that 4-(pyrrolidin-1-yl)piperidine was used instead of the 2-aminoethanol (Amount obtained: 180 mg/Yield: 76%).

$^1$H NMR (400, CDCl$_3$): 7.31 (3H, d), 6.82 (2H, d), 6.04 (1H, s), 4.59 (1H, s), 4.15 (2H, s), 3.95 (1H, d), 3.81 (1H, s), 3.09 (1H, m), 2.75-2.48 (11H, m), 2.29 (2H, d), 2.05-1.82 (11H, m), 1.47 (11H, s), 1.31 (2H, m)

Example 194: Preparation of tert-butyl 4-((4-(4-(cyclobutylcarbamoyl)cyclohex-1-enyl)phenoxy)methyl)piperidine-1-carboxylate

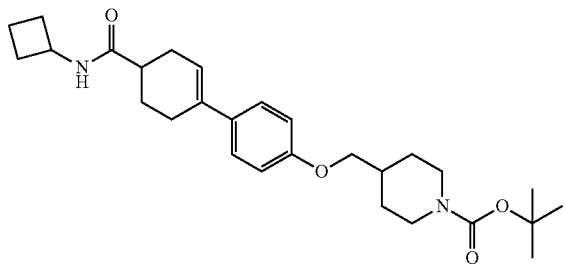 [SMILES: CC(C)(C)OC(=O)N1CCC(COc2ccc(C3=CCC(C(=O)NC4CCC4)CC3)cc2)CC1]

The title compound was prepared in the same manner as in <Example 190>, except that cyclobutylamine hydrochloride was used instead of the 2-aminoethanol (Amount obtained: 170 mg/Yield: 71%).

$^1$H NMR (400, CDCl$_3$): 7.32 (2H, d), 6.85 (2H, d), 6.04 (1H, m), 5.69 (1H, d), 4.46 (1H, m), 4.18 (2H, s), 3.82 (2H, d), 2.75 (2H, t), 2.44-2.34 (7H, m), 2.12-1.71 (9H, m), 1.48 (9H, s), 1.29 (2H, m)

Example 195: Preparation of tert-butyl 4-((4-(4-(cyclopentylcarbamoyl)cyclohex-1-enyl)phenoxy)methyl)piperidine-1-carboxylate

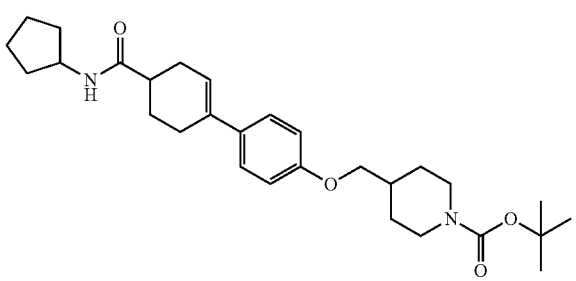 [SMILES: CC(C)(C)OC(=O)N1CCC(COc2ccc(C3=CCC(C(=O)NC4CCCC4)CC3)cc2)CC1]

The title compound was prepared in the same manner as in <Example 190>, except that cyclopentylamine was used instead of the 2-aminoethanol (Amount obtained: 195 mg/Yield: 79%).

$^1$H NMR (400, CDCl$_3$): 7.31 (2H, d), 6.85 (2H, d), 6.04 (1H, m), 5.54 (1H, m), 4.30-4.18 (3H, m), 3.81 (2H, d), 2.81 (2H, m), 2.56-2.32 (5H, m), 2.10-1.58 (12H, m), 1.48 (9H, s), 1.41-1.22 (4H, m)

Example 196: Preparation of tert-butyl 4-((4-(4-(4-morpholinopiperidine-1-carbonyl)cyclohex-1-enyl)phenoxy)methyl)piperidine-1-carboxylate

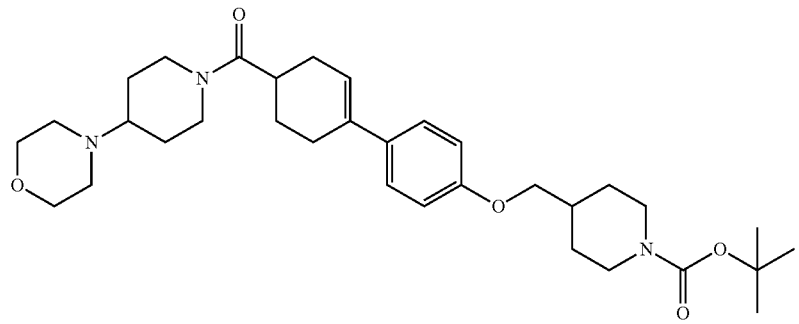 [SMILES: CC(C)(C)OC(=O)N1CCC(COc2ccc(C3=CCC(C(=O)N4CCC(N5CCOCC5)CC4)CC3)cc2)CC1]

The title compound was prepared in the same manner as in <Example 190>, except that 4-morpholinopiperidine was used instead of the 2-aminoethanol (Amount obtained: 805 mg/Yield: 77%).
¹H NMR (400, CDCl₃): 7.33 (2H, m), 6.86 (2H, m), 6.05 (1H, m), 4.72 (1H, m), 4.16-4.02 (3H, m), 4.16-4.02 (3H, m), 3.82-3.74 (6H, m), 3.12 (1H, m), 2.83-2.26 (13H, m), 1.98-1.82 (7H, m), 1.48 (9H, s), 1.33 (2H, m)

Example 197: Preparation of 4-(4-((1-(5-ethylpyrimidin-2-yl)piperidin-4-yl) methoxy)phenyl)-N-methoxy-N-methylcyclohex-3-enecarboxamide

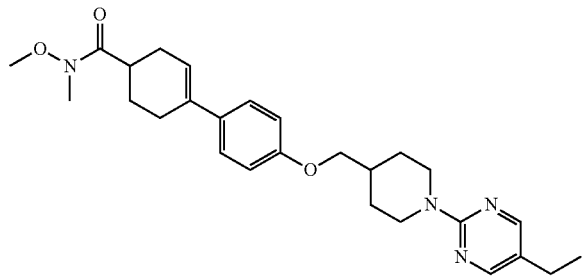 [SMILES: CCc1cnc(N2CCC(COc3ccc(C4=CCC(C(=O)N(C)OC)CC4)cc3)CC2)nc1]

The title compound was prepared in the same manner as in <Example 152>, except that N,O-dimethylhydroxylamine hydrochloride was used instead of the L-β-prolinol (Amount obtained: 220 mg/Yield: 79%).
¹H NMR (400, CDCl₃): 8.19 (2H, s), 7.34 (2H, m), 6.88 (2H, m), 6.07 (1H, m), 4.80 (2H, m), 3.85 (2H, d), 3.74 (3H, s), 3.24 (3H, s), 2.99-2.88 (3H, m), 2.54-2.33 (6H, m), 2.13-1.83 (5H, m), 1.41 (2H, m), 1.22 (3H, m)

Example 198: Preparation of 4-(4-((1-(5-ethylpyrimidin-2-yl)piperidin-4-yl)methoxy)phenyl)-N-methoxycyclohex-3-enecarboxamide

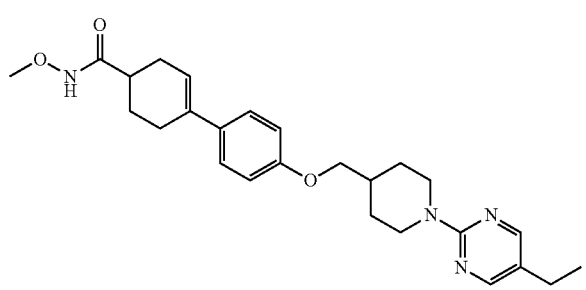 [SMILES: CCc1cnc(N2CCC(COc3ccc(C4=CCC(C(=O)NOC)CC4)cc3)CC2)nc1]

The title compound was prepared in the same manner as in <Example 152>, except that O-methylhydroxylamine hydrochloride was used instead of the L-β-prolinol (Amount obtained: 240 mg/Yield: 83%).
¹H NMR (400, CDCl₃): 8.24 (2H, s), 7.33 (2H, m), 6.87 (2H, m), 6.03 (1H, s), 4.80 (2H, m), 3.84 (5H, m), 2.96 (2H, m), 2.57-1.93 (13H, m), 1.41 (2H, m), 1.20 (3H, m)

Example 199: Preparation of tert-butyl 4-((4-(4-(ethyl(2-hydroxyethyl)carbamoyl)cyclohex-1-enyl)phenoxy)methyl)piperidine-1-carboxylate

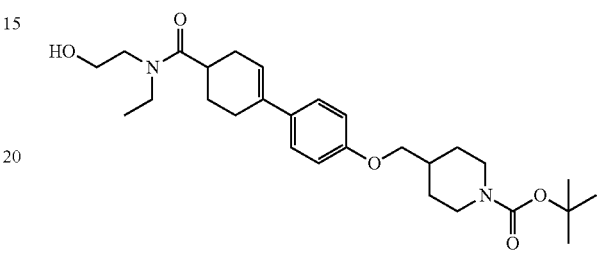

The title compound was prepared in the same manner as in <Example 190>, except that 2-(ethylamino)ethanol was used instead of the 2-aminoethanol (Amount obtained: 170 mg/Yield: 72%).
¹H NMR (400, CDCl₃): 7.32 (2H, m), 6.85 (2H, m), 6.05 (1H, s), 4.16 (2H, s), 3.80 (3H, m), 3.73 (1H, m), 3.57-3.44 (4H, m), 2.87-1.71 (12H, m), 1.47 (9H, s), 1.31-1.13 (5H, m)

Example 200: Preparation of tert-butyl 4-((4-(4-(4-(2-hydroxyethyl)piperidine-1-carbonyl)cyclohex-1-enyl)phenoxy)methyl)piperidine-1-carboxylate

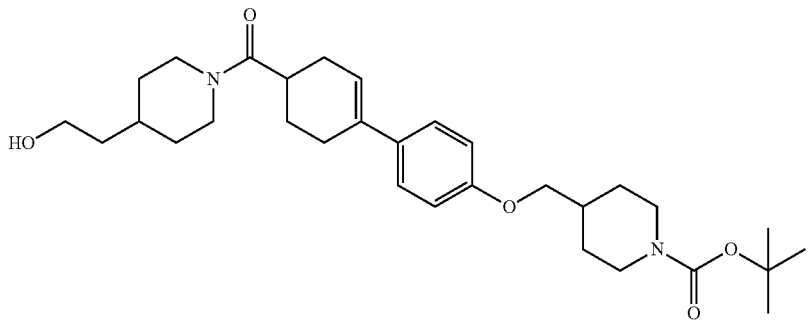 [SMILES: CC(C)(C)OC(=O)N1CCC(COc2ccc(C3=CCC(C(=O)N4CCC(CCO)CC4)CC3)cc2)CC1]

The title compound was prepared in the same manner as in <Example 190>, except that 4-hydroxyethylpiperidine was used instead of the 2-aminoethanol (Amount obtained: 343 mg/Yield: 71%).

$^{1}$H NMR (400, CDCl$_{3}$): 7.32 (2H, m), 6.84 (2H, m), 6.04 (1H, m), 4.68 (1H, m), 4.16 (2H, s), 3.99 (1H, m), 3.81 (4H, m), 3.09 (1H, m), 2.78 (3H, m), 2.60 (4H, m), 2.29 (1H, m), 1.97-1.47 (20H, m), 2.31 (4H, m)

Example 201: Preparation of tert-butyl 4-((4-(4-(4-(2-hydroxyethyl)piperazine-1-carbonyl)cyclohex-1-enyl)phenoxy)methyl)piperidine-1-carboxylate

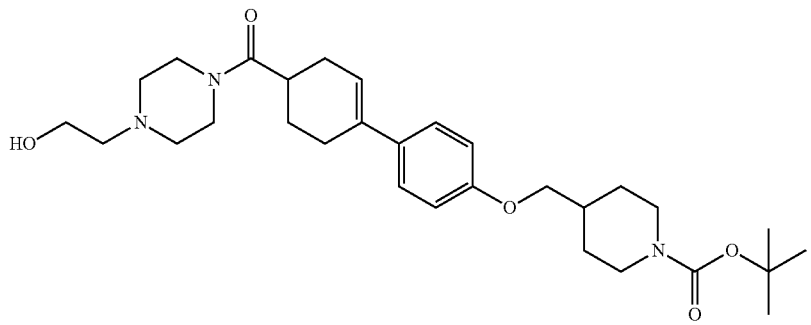 [SMILES: CC(C)(C)OC(=O)N1CCC(COc2ccc(C3=CCC(C(=O)N4CCN(CCO)CC4)CC3)cc2)CC1]

The title compound was prepared in the same manner as in <Example 190>, except that 1-hydroxyethylpiperazine was used instead of the 2-aminoethanol (Amount obtained: 331 mg/Yield: 68%).

$^{1}$H NMR (400, CDCl$_{3}$): 7.32 (2H, m), 6.85 (2H, m), 6.04 (1H, m), 4.16 (2H, s), 3.81-3.59 (8H, m), 2.78-2.49 (14H, m), 1.98-1.84 (5H, m), 1.47 (9H, s), 1.28 (2H, m)

Example 202: Preparation of tert-butyl 4-((4-(4-(pyrrolidine-1-carbonyl)cyclohex-1-enyl)phenoxy)methyl)piperidine-1-carboxylate

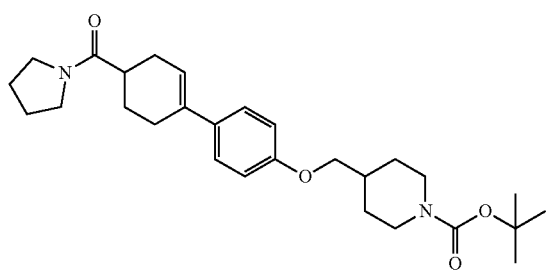

The title compound was prepared in the same manner as in <Example 190>, except that pyrrolidine was used instead of the 2-aminoethanol (Amount obtained: 357 mg/Yield: 74%).

$^{1}$H NMR (400, CDCl$_{3}$): 7.32 (2H, m), 6.85 (2H, m), 6.06 (1H, m), 4.16 (2H, s), 3.81 (2H, m), 3.54 (4H, m), 2.75-2.28 (7H, m), 2.00-1.81 (8H, m), 1.48 (9H, s), 1.31 (2H, m)

Example 203: Preparation of tert-butyl 4-((4-(4-(4-ethylpiperazine-1-carbonyl)cyclohex-1-enyl)phenoxy)methyl)piperidine-1-carboxylate

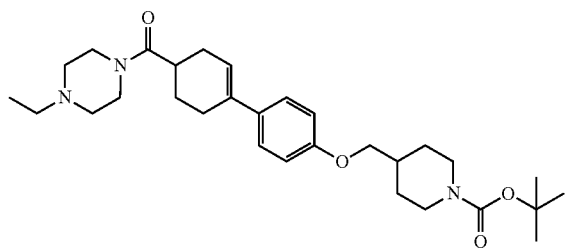 [SMILES: CCN1CCN(C(=O)C2CC=C(c3ccc(OCC4CCN(C(=O)OC(C)(C)C)CC4)cc3)CC2)CC1]

The title compound was prepared in the same manner as in <Example 190>, except that 1-ethylpiperazine was used instead of the 2-aminoethanol (Amount obtained: 330 mg/Yield: 59%).

$^{1}$H NMR (400, CDCl$_{3}$): 7.32 (2H, m), 6.85 (2H, m), 6.04 (1H, m), 4.16 (2H, s), 3.81-3.59 (6H, m), 2.78 (3H, m), 2.52-2.26 (10H, m), 1.98-1.81 (6H, m), 1.47 (9H, s), 1.31 (2H, m), 1.141 (3H, m)

Example 204: Preparation of tert-butyl 4-((4-(4-(piperidine-1-carbonyl)cyclohex-1-enyl)phenoxy)methyl)piperidine-1-carboxylate

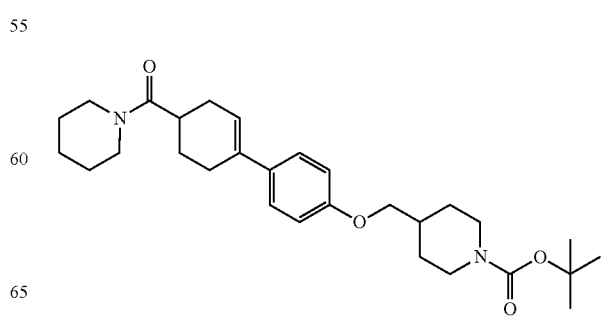

The title compound was prepared in the same manner as in <Example 190>, except that piperidine was used instead of the 2-aminoethanol (Amount obtained: 345 mg/Yield: 67%).

$^1$H NMR (400, CDCl$_3$): 7.32 (2H, m), 6.85 (2H, m), 6.05 (1H, m), 4.15 (2H, s), 3.81 (2H, m), 3.62-3.49 (4H, m), 2.79 (3H, m), 2.52 (3H, m), 2.31 (1H, m), 1.98-1.58 (11H, m), 1.47 (9H, m), 1.28 (2H, m)

Example 205: Preparation of tert-butyl 4-((4-(4-(3-ethoxypropylcarbamoyl)cyclohex-1-enyl)phenoxy)methyl)piperidine-1-carboxylate

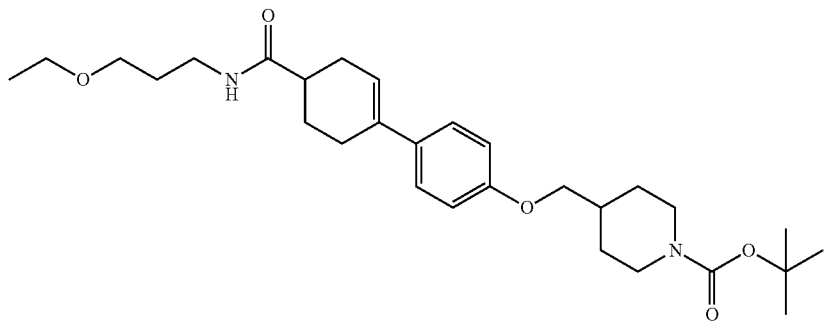 [SMILES: CCOCCCNC(=O)C1CC=C(c2ccc(OCC3CCN(C(=O)OC(C)(C)C)CC3)cc2)CC1]

The title compound was prepared in the same manner as in <Example 190>, except that 3-ethoxypropane-1-amine was used instead of the 2-aminoethanol (Amount obtained: 339 mg/Yield: 64%).

$^1$H NMR (400, CDCl$_3$): 7.33 (2H, m), 6.86 (2H, m), 6.36 (1H, m), 6.04 (1H, m), 4.17 (2H, s), 3.81 (2H, d), 3.57-3.40 (6H, m), 2.78 (2H, m), 2.52-2.36 (5H, m), 2.13 (1H, m), 1.97 (1H, m), 1.85-1.77 (5H, m), 1.47 (9H, s), 1.31-1.21 (5H, m)

Example 206: Preparation of tert-butyl 4-((4-(4-(bis(2-hydroxyethyl)carbamoyl)cyclohex-1-enyl)phenoxy)methyl)piperidine-1-carboxylate

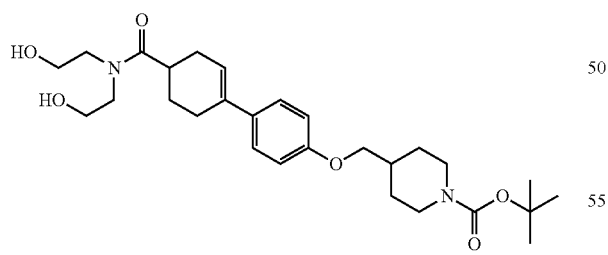

The title compound was prepared in the same manner as in <Example 190>, except that diethanolamine was used instead of the 2-aminoethanol (Amount obtained: 351 mg/Yield: 70%).

$^1$H NMR (400, CDCl$_3$): 7.32 (2H, m), 6.86 (2H, m), 6.05 (1H, m), 4.16 (2H, m), 3.91 (2H, m), 3.84 (4H, m), 3.63 (4H, m), 3.31 (2H, s), 2.90-2.30 (7H, m), 2.04-1.82 (5H, m), 1.48 (9H, s), 1.32 (2H, m)

Example 207: Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

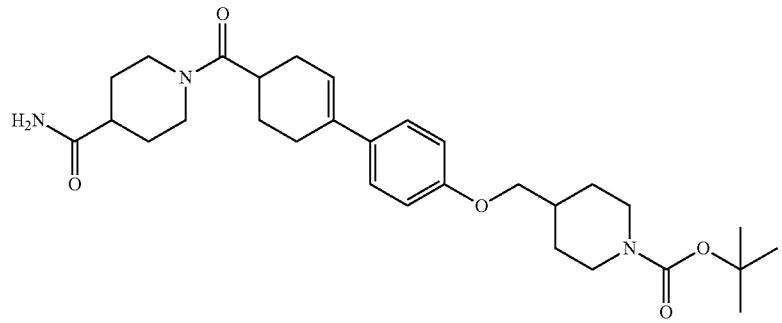

The title compound was prepared in the same manner as in <Example 143>, except that isonipecotamide was used instead of the (R)—N,N-dimethylpyrrolidine-3-amine hydrochloride (Amount obtained: 142 mg/Yield: 53%).

$^1$H NMR (400, CDCl$_3$): 7.32 (2H, m), 6.86 (2H, m), 6.05 (1H, m), 5.68 (2H, m), 4.67 (1H, m), 4.16-3.98 (3H, m), 3.81 (2H, m), 3.17 (1H, m), 2.89-2.40 (8H, m), 1.99-1.63 (10H, m), 1.47 (9H, m), 1.29 (2H, m)

Example 208: Preparation of (4-(4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone

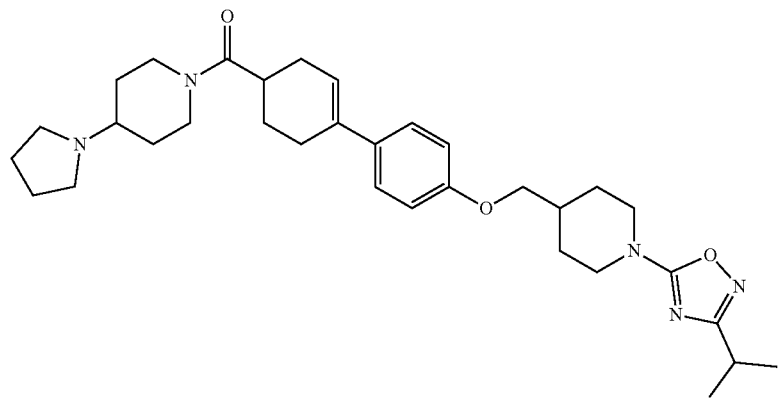 [SMILES: CC(C)c1noc(N2CCC(COc3ccc(C4=CCC(C(=O)N5CCC(N6CCCC6)CC5)CC4)cc3)CC2)n1]

The title compound was prepared in the same manner as in <Example 143>, except that 4-(pyrrolidin-1-yl)piperidine was used instead of the (R)—N,N-dimethylpyrrolidine-3-amine hydrochloride (Amount obtained: 159 mg/Yield: 51%).

$^1$H NMR (400, CDCl$_3$): 7.54 (2H, m), 6.86 (2H, m), 6.05 (1H, m) 4.67 (1H, m), 4.23 (2H, m), 4.05 (2H, m), 3.85 (2H, m), 3.14 (3H, m), 2.94-2.46 (12H, m), 2.30 (1H, m), 2.10-1.94 (12H, m), 1.62-1.51 (4H, m), 1.31 (6H, d)

Example 209: Preparation of (4-(4-((1-(3-isopropyl-1,2,4-oxadiazol-5-yl)piperidin-4-yl)methoxy)phenyl)cyclohex-3-enyl)(4-morpholinopiperidin-1-yl)methanone

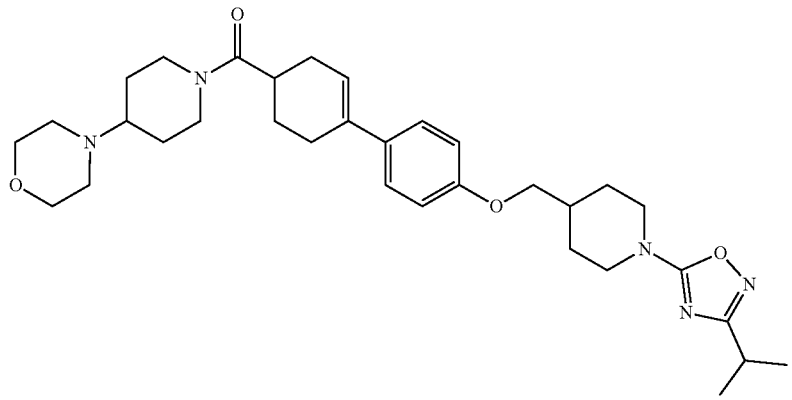 [SMILES: CC(C)c1noc(N2CCC(COc3ccc(C4=CCC(C(=O)N5CCC(N6CCOCC6)CC5)CC4)cc3)CC2)n1]

The title compound was prepared in the same manner as in <Example 143>, except that 4-morpholinopiperidine was used instead of the (R)—N,N-dimethylpyrrolidine-3-amine hydrochloride (Amount obtained: 155 mg/Yield: 58%).

$^1$H NMR (400, CDCl$_3$): 7.33 (2H, m), 6.86 (2H, m), 6.05 (1H, m), 4.75 (1H, m), 4.23 (2H, m), 4.02 (1H, m), 3.85 (2H, d), 3.52 (4H, m), 3.14 (3H, m), 2.97 (1H, s), 2.94-2.80 (3H, m), 2.59-2.47 (9H, m), 2.30 (1H, m), 2.07-1.91 (7H, m), 1.50 (4H, m), 1.29 (6H, d)

Example 210: Preparation of N-cyclopentyl-4-(4-((1-(3-isopropyl-1,2,4-oxadiazol-5-yl)piperidin-4-yl)methoxy)phenyl)cyclohex-3-enecarboxamide

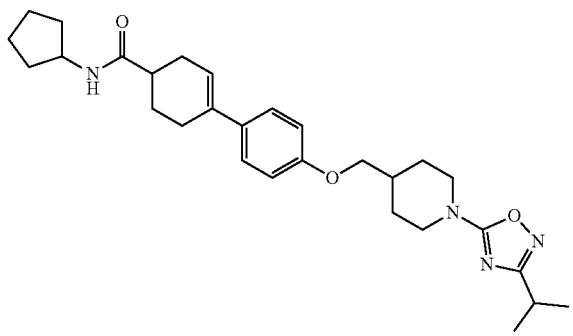 [SMILES: CC(C)c1noc(N2CCC(COc3ccc(C4=CCC(C(=O)NC5CCCC5)CC4)cc3)CC2)n1]

The title compound was prepared in the same manner as in <Example 143>, except that cyclopentylamine was used instead of the (R)—N,N-dimethylpyrrolidine-3-amine hydrochloride (Amount obtained: 171 mg/Yield: 65%).

$^1$H NMR (400, CDCl$_3$): 7.33 (2H, m), 6.86 (2H, m), 6.04 (1H, m), 5.51 (1H, m), 4.26-4.20 (3H, m), 3.85 (2H, d), 3.14 (2H, m), 2.92 (1H, m), 2.46-2.37 (5H, m), 2.06-1.94 (7H, m), 1.68-1.61 (5H, m), 1.47-1.36 (4H, m), 1.32 (6H, d)

Example 211: Preparation of N-cyclobutyl-4-(4-((1-(3-isopropyl-1,2,4-oxadiazol-5-yl)piperidin-4-yl)methoxy)phenyl)cyclohex-3-enecarboxamide

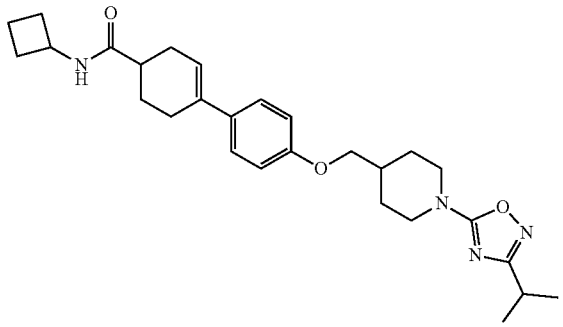 [SMILES: CC(C)c1noc(N2CCC(COc3ccc(C4=CCC(C(=O)NC5CCC5)CC4)cc3)CC2)n1]

The title compound was prepared in the same manner as in <Example 143>, except that cyclobutylamine hydrochloride was used instead of the (R)—N,N-dimethylpyrrolidine-3-amine hydrochloride (Amount obtained: 170 mg/Yield: 63%).

$^1$H NMR (400, CDCl$_3$): 7.33 (2H, m), 6.68 (2H, m), 6.04 (1H, m), 5.71 (1H, m), 4.45 (1H, m), 4.23 (2H, m), 3.85 (2H, m), 3.13 (2H, m), 2.92 (1H, m), 2.42-2.34 (7H, m), 2.07-1.72 (9H, m), 1.47 (2H, m), 1.31 (6H, d)

Example 212: Preparation of (3,4-dihydroisoquinolin-2(1H)-yl)(4-(4-((1-(3-isopropyl-1,2,4-oxadiazol-5-yl)piperidin-4-yl)methoxy)phenyl)cyclohex-3-enyl)methanone

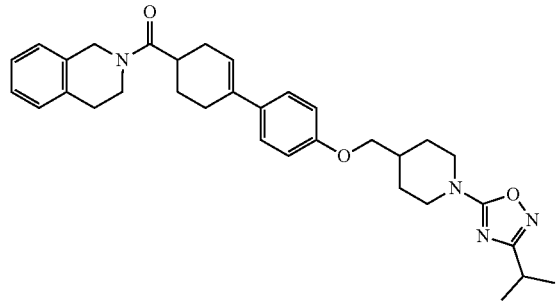 [SMILES: CC(C)c1noc(N2CCC(COc3ccc(C4=CCC(C(=O)N5CCc6ccccc6C5)CC4)cc3)CC2)n1]

The title compound was prepared in the same manner as in <Example 143>, except that 1,2,3,4-tetrahydroisoquinoline was used instead of the (R)—N,N-dimethylpyrrolidine-3-amine hydrochloride (Amount obtained: 183 mg/Yield: 65%).

¹H NMR (400, CDCl₃): 7.32 (2H, m), 7.23-7.12 (4H, m), 6.87 (2H, m), 6.08 (1H, m), 4.80-4.74 (2H, m), 4.23 (2H, m), 3.91-3.78 (4H, m), 3.15 (2H, m), 3.08-2.87 (4H, m), 2.60 (3H, m), 2.36 (1H, m), 2.08-1.91 (5H, m), 1.60 (2H, m), 1.31 (6H, d)

Example 213: Preparation of (4-(4-((1-(3-isopropyl-1,2,4-oxadiazol-5-yl)piperidin-4-yl)methoxy)phenyl)cyclohex-3-enyl)(1-methyl-3,4-dihydroisoquinolin-2(1H)-yl)methanone

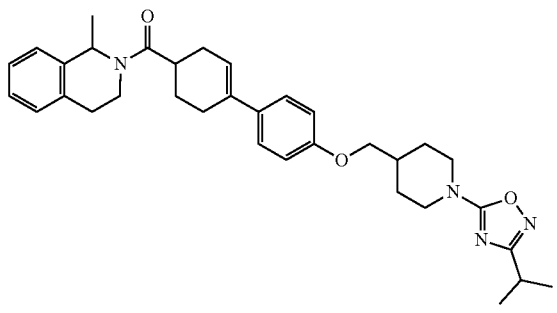 [SMILES: CC(C)c1noc(N2CCC(COc3ccc(C4=CCC(C(=O)N5CCc6ccccc6C5C)CC4)cc3)CC2)n1]

The title compound was prepared in the same manner as in <Example 143>, except that 1-methyl-1,2,3,4-tetrahydroisoquinoline was used instead of the (R)—N,N-dimethylpyrrolidine-3-amine hydrochloride (Amount obtained: 174 mg/Yield: 60%).

¹H NMR (400, CDCl₃): 7.35 (2H, m), 7.24-7.12 (4H, m), 6.89 (2H, m), 6.12 (1H, m), 5.74-5.16 (1H, m), 4.79-3.56 (6H, m), 3.15-1.90 (15H, m), 1.62 (2H, m), 1.51-1.40 (4H, m), 1.31 (6H, d)

Example 214: Preparation of isoindolin-2-yl(4-(4-((1-(3-isopropyl-1,2,4-oxadiazol-5-yl)piperidin-4-yl)methoxy)phenyl)cyclohex-3-enyl)methanone

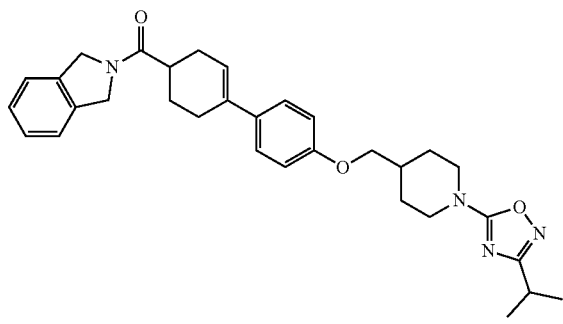 [SMILES: CC(C)c1noc(N2CCC(COc3ccc(C4=CCC(C(=O)N5Cc6ccccc6C5)CC4)cc3)CC2)n1]

The title compound was prepared in the same manner as in <Example 143>, except that isoindoline was used instead of the (R)—N,N-dimethylpyrrolidine-3-amine hydrochloride (Amount obtained: 170 mg/Yield: 69%).

¹H NMR (400, CDCl₃): 7.33-7.28 (7H, m), 6.88 (2H, m), 6.10 (1H, m), 4.95 (4H, d), 4.24 (2H, m), 3.92 (2H, m), 3.15 (2H, m), 2.94 (1H, m), 2.79 (1H, m), 2.64-2.37 (4H, m), 2.12-1.93 (5H, m), 1.51 (2H, m), 1.31 (6H, d)

Example 215: Preparation of 1,4'-bipiperidin-1'-yl (4-(4-((1-(3-isopropyl-1,2,4-oxadiazol-5-yl)piperidin-4-yl)methoxy)phenyl)cyclohex-3-enyl)methanone The title compound was prepared in the same manner as in <Example 143>, except that 1,4'-bipiperidine was used instead of the (R)—N,N-dimethylpyrrolidine-3-amine hydrochloride (Amount obtained: 165 mg/Yield: 71%).

¹H NMR (400, CDCl₃): 7.33 (2H, m), 6.87 (2H, m), 6.05 (1H, m), 4.78 (1H, m), 4.23 (2H, m), 4.07 (1H, m), 3.85 (2H, m), 3.14 (3H, m), 2.94 (1H, m), 2.79 (1H, m), 2.56-2.25 (9H, m), 2.07-1.40 (18H, m), 1.31 (6H, d)

Example 216: Preparation of tert-butyl 4-((4-(4-(1,4'-bipiperidine-1'-carbonyl)cyclohex-1-enyl)phenoxy)methyl)piperidine-1-carboxylate

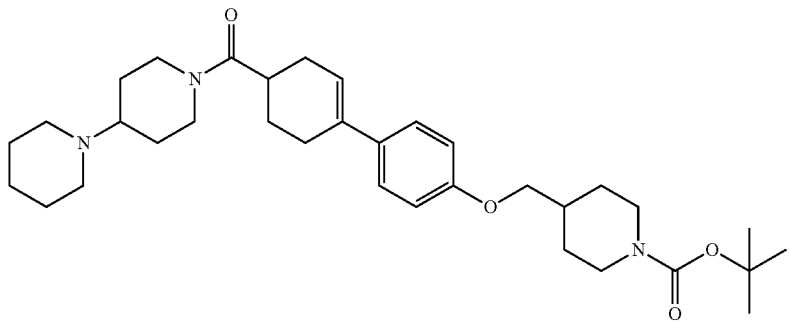 [SMILES: CC(C)(C)OC(=O)N1CCC(COc2ccc(C3=CCC(C(=O)N4CCC(N5CCCCC5)CC4)CC3)cc2)CC1]

The title compound was prepared in the same manner as in <Example 190>, except that 1,4'-bipiperidine was used instead of the 2-aminoethanol (Amount obtained: 169 mg/Yield: 75%).

¹H NMR (400, CDCl₃): 7.33 (2H, m), 6.86 (2H, m), 6.05 (1H, m), 4.76 (1H, m), 4.16-4.05 (3H, m), 3.81 (2H, m), 3.08 (1H, m), 2.83 (3H, m), 2.57-2.51 (9H, m), 2.30 (1H, m), 2.00-1.82 (7H, m), 1.63 (4H, m), 1.45 (13H, m), 1.31 (2H, m)

Example 217: Preparation of (4-(4-((1-(5-ethylpyrimidin-2-yl)piperidin-4-yl)methoxy)phenyl)cyclohex-3-enyl)(3-(hydroxyimino)pyrrolidin-1-yl)methanone

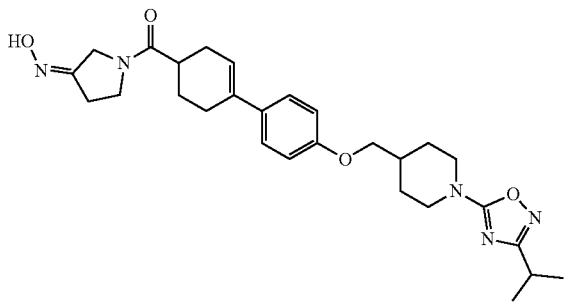 [SMILES: CC(C)c1noc(N2CCC(COc3ccc(C4=CCC(C(=O)N5CC/C(=N/O)C5)CC4)cc3)CC2)n1]

600 mg of 1-(4-(4-((1-(3-isopropyl-1,2,4-oxadiazol-5-yl)piperidin-4-yl)methoxy)phenyl)cyclohex-3-enecarbonyl)piperidine-4-carboxamide was dissolved in a THF/water mixture (30 ml/10 ml) in a 100 ml flask, and stirred under nitrogen. 200 mg of sodium bicarbonate was added dropwise thereto, 170 mg of hydroxylamine hydrochloride was in turn added dropwise, and the resulting mixture was stirred at room temperature for 3 hours. After the reaction was terminated, the reaction mixture was distilled under reduced pressure to remove the solvent. Then, 50 ml of distilled water was slowly added thereto at 0° C., and the resulting solids were filtered to obtain a mixture including E and Z forms at a ratio of 3:1 (Amount obtained: 485 mg/Yield: 68%).

Example 218: Preparation of (4-(4-((1-(5-ethylpyrimidin-2-yl)piperidin-4-yl)methoxy)phenyl)cyclohex-3-enyl)(4-(pyrrolidin-1-yl)piperidin-1-yl)methanone

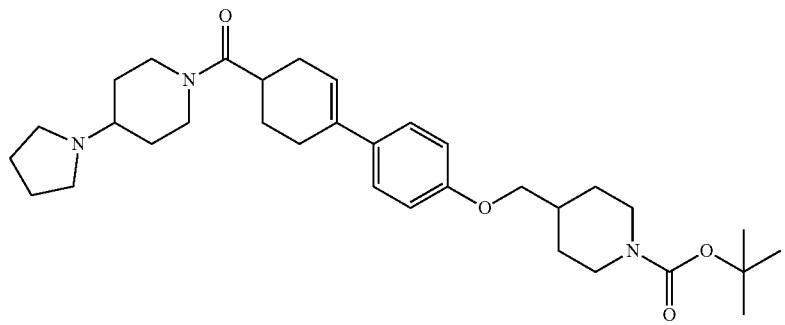 [SMILES: CC(C)(C)OC(=O)N1CCC(COc2ccc(C3=CCC(C(=O)N4CCC(N5CCCC5)CC4)CC3)cc2)CC1]

The title compound was prepared in the same manner as in <Example 152>, except that 4-(pyrrolidin-1-yl)piperidine was used instead of the L-β-prolinol (Amount obtained: 171 mg/Yield: 69%).

$^1$H NMR (400, CDCl$_3$): 8.23 (2H, s), 7.32 (2H, m), 6.87 (2H, m), 6.05 (1H, m), 4.79 (2H, m), 4.59 (1H, m), 4.02 (1H, m), 3.84 (2H, d), 3.16 (1H, m), 2.95 (2H, m), 2.82-2.94 (11H, m), 2.29 (2H, m), 2.12-1.82 (11H, m), 1.51 (2H, m), 1.40 (2H, m), 1.31 (3H, m)

Example 219: Preparation of 1,4'-bipiperidin-1'-yl (4-(4-((1-(5-ethylpyrimidin-2-yl)piperidin-4-yl)methoxy)phenyl)cyclohex-3-enyl)methanone

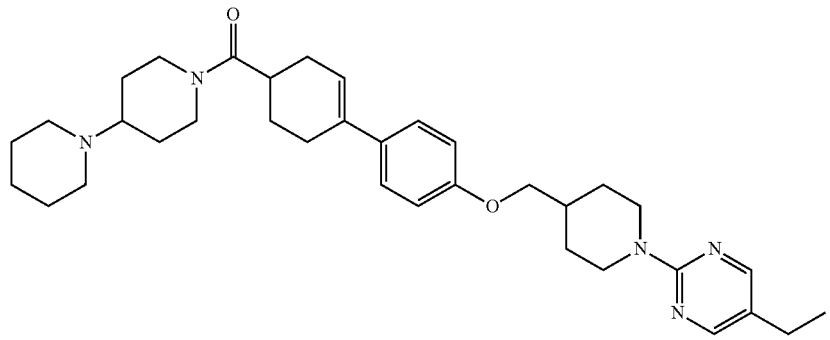 [SMILES: CCc1cnc(N2CCC(COc3ccc(C4=CCC(C(=O)N5CCC(N6CCCCC6)CC5)CC4)cc3)CC2)nc1]

The title compound was prepared in the same manner as in <Example 152>, except that 1,4'-bipiperidine was used instead of the L-β-prolinol (Amount obtained: 180 mg/Yield: 77%).

$^1$H NMR (400, CDCl$_3$): 8.18 (2H, s), 7.33 (2H, m), 6.87 (2H, m), 6.05 (1H, m), 4.79 (3H, m), 4.05 (1H, m), 3.84 (2H, d), 3.08 (1H, m), 2.95 (2H, m), 2.83 (1H, m), 2.58-2.44 (11H, m), 2.30 (1H, m), 2.12-1.87 (7H, m), 1.61 (4H, m), 1.52-1.30 (6H, m), 1.22 (3H, m)

Example 220: Preparation of (4-(4-((1-(5-ethylpyrimidin-2-yl)piperidin-4-yl)methoxy)phenyl)cyclohex-3-enyl)(4-morpholinopiperidin-1-yl)methanone

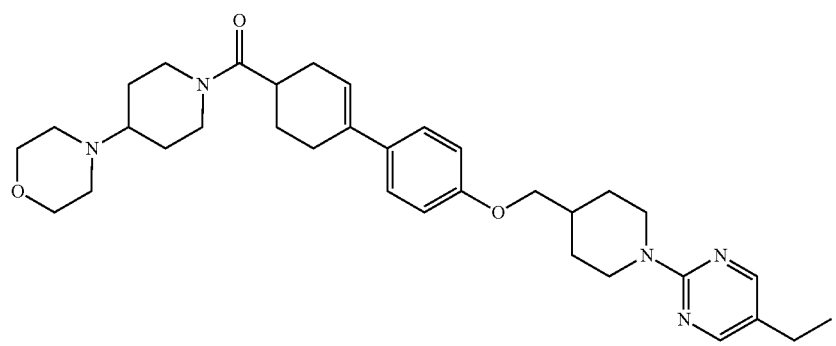 [SMILES: CCc1cnc(N2CCC(COc3ccc(C4=CCC(C(=O)N5CCC(N6CCOCC6)CC5)CC4)cc3)CC2)nc1]

The title compound was prepared in the same manner as in <Example 152>, except that 4-morpholinopiperidine was used instead of the L-β-prolinol (Amount obtained: 162 mg/Yield: 58%).

$^1$H NMR (400, CDCl$_3$): 8.18 (2H, s), 7.33 (2H, m), 6.87 (2H, m), 6.05 (1H, m), 4.80-4.69 (3H, m), 4.05 (1H, m), 3.84 (2H, d), 3.76 (4H, m), 3.12 (1H, m), 2.95 (2H, m), 2.82 (1H, m), 2.65-2.44 (11H, m), 2.30 (1H, m), 2.13 (1H, m), 1.96-1.93 (7H, m), 1.48-1.30 (4H, m), 1.22 (3H, m)

Example 221: Preparation of tert-butyl 4-((4-(4-(furan-2-ylmethylcarbamoyl)cyclohex-1-enyl)phenoxy)methyl)piperidine-1-carboxylate

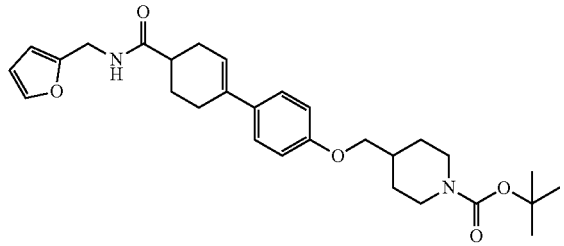 [SMILES: CC(C)(C)OC(=O)N1CCC(COc2ccc(C3=CCC(C(=O)NCc4ccco4)CC3)cc2)CC1]

The title compound was prepared in the same manner as in <Example 190>, except that furfurylamine was used instead of the 2-aminoethanol (Amount obtained: 169 mg/Yield: 70%).

$^1$H NMR (400, CDCl$_3$): 7.36 (1H, m), 7.31 (2H, m), 6.85 (2H, m), 6.34 (1H, m), 6.24 (1H, m), 6.03 (1H, m), 5.97 (1H, m), 4.49 (2H, m), 4.16 (2H, s), 3.81 (2H, m), 2.97 (1H, m), 2.78 (2H, m), 2.55-2.39 (5H, m), 2.12 (1H, m), 1.99-1.81 (4H, m), 1.47 (9H, s), 2.31 (2H, m)

Example 222: Preparation of tert-butyl 4-((4-(4-(methoxycarbamoyl)cyclohex-1-enyl)phenoxy)methyl)piperidine-1-carboxylate

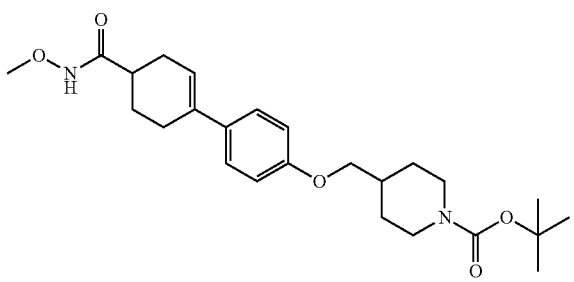 [SMILES: CONC(=O)C1CC=C(c2ccc(OCC3CCN(C(=O)OC(C)(C)C)CC3)cc2)CC1]

The title compound was prepared in the same manner as in <Example 190>, except that O-methylhydroxylamine hydrochloride was used instead of the 2-aminoethanol (Amount obtained: 166 mg/Yield: 72%).

$^1$H NMR (400, CDCl$_3$): 8.24 (1H, m), 7.33 (2H, m), 6.86 (2H, m), 6.03 (1H, m), 4.17 (2H, m), 3.85-3.80 (5H, m), 2.79 (2H, m), 2.57-2.35 (5H, m), 2.09 (1H, m), 2.01-1.82 (4H, m), 1.59 (1H, m), 1.47 (9H, s), 1.32 (2H, m)

Example 223: Preparation of tert-butyl 4-((4-(4-(methoxy(methyl)carbamoyl)cyclohex-1-enyl)phenoxy)methyl)piperidine-1-carboxylate

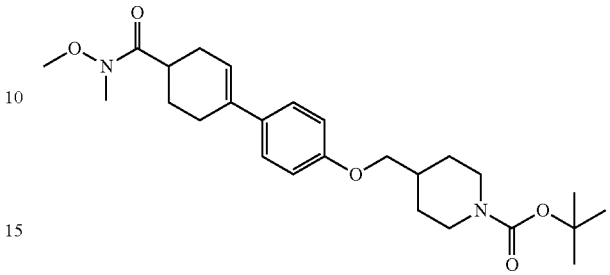

The title compound was prepared in the same manner as in <Example 190>, except that N,O-dimethylhydroxylamine hydrochloride was used instead of the 2-aminoethanol (Amount obtained: 171 mg/Yield: 74%).

$^1$H NMR (400, CDCl$_3$): 7.34 (2H, m), 6.86 (2H, m), 6.07 (1H, m), 4.16 (2H, s), 3.82 (2H, m), 3.74 (3H, s), 3.24 (3H, s), 2.99-2.73 (4H, m), 2.52-2.33 (4H, m), 2.07-1.82 (5H, m), 1.47 (9H, s), 2.33 (2H, m)

Example 224: Preparation of tert-butyl 4-((4-(4-(2,5-dihydro-1H-pyrrole-1-carbonyl)cyclohex-1-enyl)phenoxy)methyl)piperidine-1-carboxylate

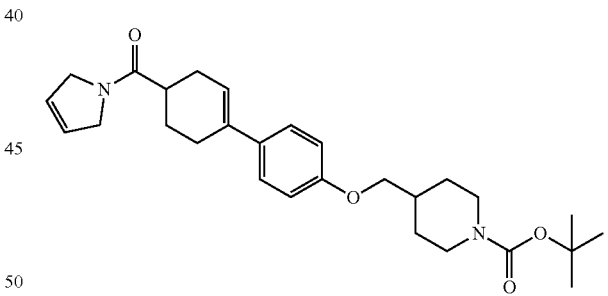

The title compound was prepared in the same manner as in <Example 190>, except that 2,5-dihydro-1H-pyrrole was used instead of the 2-aminoethanol (Amount obtained: 167 mg/Yield: 63%).

$^1$H NMR (400, CDCl$_3$): 7.34 (2H, m), 6.87 (2H, m), 6.08 (1H, m), 5.93 (1H, m), 5.85 (1H, m), 4.37 (2H, m), 4.60 (2H, m), 4.17 (2H, s), 3.82 (2H, d), 3.53 (1H, m), 2.79 (2H, m), 2.66-2.47 (4H, m), 2.36 (1H, m), 2.05-1.82 (6H, m), 1.47 (9H, s), 1.32 (2H, m)

Example 225: Preparation of tert-butyl 4-((4-(4-(4-hydroxypiperidine-1-carbonyl)cyclohex-1-enyl)phenoxy)methyl)piperidine-1-carboxylate

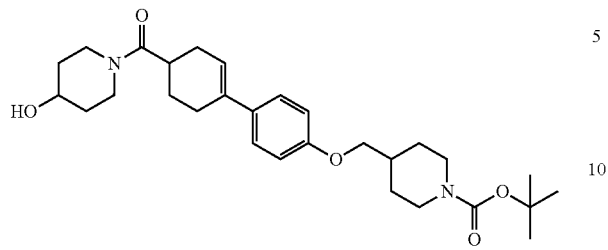

The title compound was prepared in the same manner as in <Example 190>, except that 4-hydroxypiperidine was used instead of the 2-aminoethanol (Amount obtained: 174 mg/Yield: 70%).

$^1$H NMR (400, CDCl$_3$): 7.33 (2H, m), 6.86 (2H, m), 6.05 (1H, m), 4.16 (3H, m), 3.97 (1H, m), 3.87-3.80 (3H, m), 3.32-3.20 (2H, m), 2.97-2.72 (4H, m), 2.54-2.47 (3H, m), 2.31 (1H, m), 2.01-2.56 (8H, m), 1.56-1.51 (2H, m), 1.47 (9H, s), 1.32 (2H, m)

Example 226: Preparation of tert-butyl 4-((4-(4-(4-(hydroxymethyl)piperidine-1-carbonyl)cyclohex-1-enyl)phenoxy)methyl)piperidine-1-carboxylate

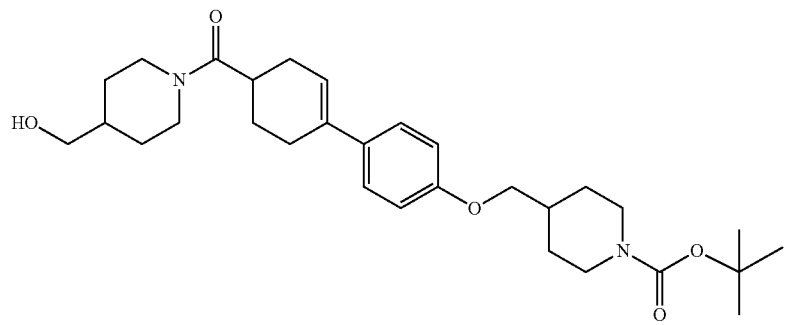 [SMILES: CC(C)(C)OC(=O)N1CCC(COc2ccc(C3=CCC(C(=O)N4CCC(CO)CC4)CC3)cc2)CC1]

The title compound was prepared in the same manner as in <Example 190>, except that piperidinemethanol was used instead of the 2-aminoethanol (Amount obtained: 167 mg/Yield: 65%).

$^1$H NMR (400, CDCl$_3$): 7.33 (2H, m), 6.86 (2H, m), 6.05 (1H, m), 4.73 (1H, m), 4.16 (2H, s), 4.04 (1H, m), 3.81 (2H, d), 3.54 (2H, m), 3.07 (1H, m), 2.80 (3H, m), 2.59-2.46 (4H, m), 2.30 (1H, m), 2.00-1.70 (10H, m), 1.47 (9H, m), 1.31 (4H, m)

Example 227: Preparation of 1-(4-(4-((1-(5-ethylpyrimidin-2-yl)piperidin-4-yl)methoxy)phenyl)cyclohex-3-enecarbonyl)piperidine-4-carbonitrile

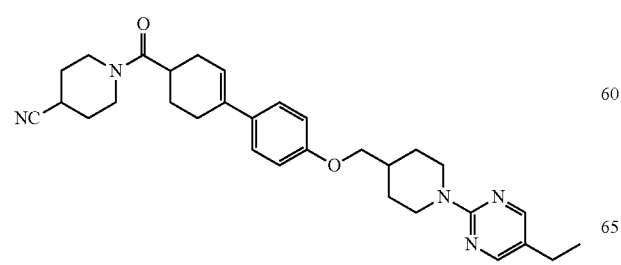

The title compound was prepared in the same manner as in <Example 152>, except that piperidine-4-carbonitrile was used instead of the L-β-prolinol (Amount obtained: 165 mg/Yield: 62%).

¹H NMR (400, CDCl₃): 8.19 (2H, s), 7.32 (2H, m), 6.87 (2H, m), 6.04 (1H, m), 4.80 (2H, m), 3.85-3.55 (6H, m), 2.95 (3H, m), 2.82 (1H, m), 2.58-2.44 (5H, m), 2.28 (1H, m), 2.11-1.89 (9H, m), 1.41 (2H, m), 1.22 (3H, m)

Example 228: Preparation of (4-(4-((1-(5-ethylpyrimidin-2-yl)piperidin-4-yl)methoxy)phenyl)cyclohex-3-enyl)(spiro[indene-1,4'-piperidin]-1'-yl)methanone

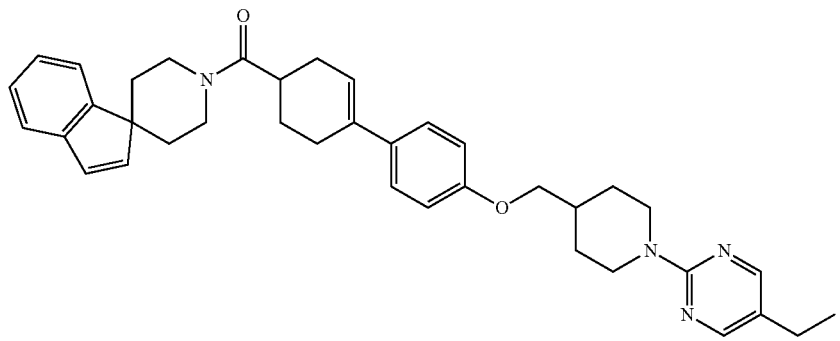 [SMILES: CCc1cnc(N2CCC(COc3ccc(C4=CCC(C(=O)N5CCC6(C=Cc7ccccc76)CC5)CC4)cc3)CC2)nc1]

The title compound was prepared in the same manner as in <Example 152>, except that 4-spiroindene-piperidine hydrochloride was used instead of the L-O-prolinol (Amount obtained: 183 mg/Yield: 74%).

¹H NMR (400, CDCl₃): 8.19 (2H, s), 7.37-7.22 (7H, m), 6.91-6.83 (4H, m), 6.08 (1H, m), 4.80 (3H, m), 4.13 (1H, m), 3.85 (2H, d), 3.50 (1H, m), 3.19-2.87 (4H, m), 2.62-2.37 (6H, m), 2.10-1.93 (7H, m), 1.48-1.31 (4H, m), 1.23 (3H, m)

Example 229: Preparation of (4-(4-((1-(5-ethylpyrimidin-2-yl)piperidin-4-yl)methoxy)phenyl)cyclohex-3-enyl)(1,4-dioxa-8-azaspiro[4.5]decan-8-yl)methanone

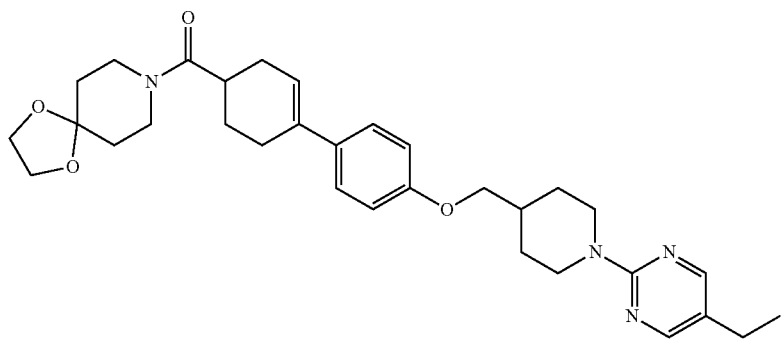 [SMILES: CCc1cnc(N2CCC(COc3ccc(C4=CCC(C(=O)N5CCC6(CC5)OCCO6)CC4)cc3)CC2)nc1]

The title compound was prepared in the same manner as in <Example 152>, except that 1,4-dioxa-8-azaspiro[4.5]decane was used instead of the L-O-prolinol (Amount obtained: 175 mg/Yield: 69%).

¹H NMR (400, CDCl₃): 8.19 (2H, s), 7.32 (2H, m), 6.87 (2H, m), 6.05 (1H, m), 4.80 (2H, m), 4.01 (4H, s), 3.84-3.63 (6H, m), 2.95-2.82 (3H, m), 2.58-2.46 (5H, m), 2.31 (1H, m), 2.11-1.88 (5H, m), 1.75-1.70 (5H, m), 1.40 (2H, m), 1.22 (3H, m)

Example 230: Preparation of N-cyclopentyl-4-(4-((1-(5-ethylpyrimidin-2-yl)piperidin-4-yl)methoxy)phenyl)cyclohex-3-enecarboxamide

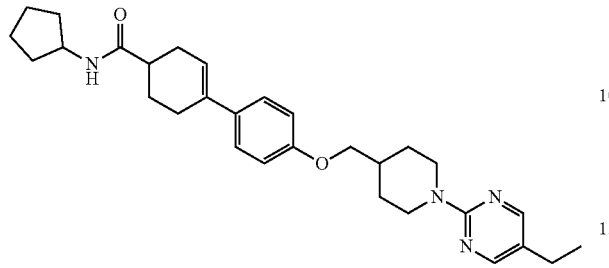

The title compound was prepared in the same manner as in <Example 152>, except that pentylamine was used instead of the L-β-prolinol (Amount obtained: 153 mg/Yield: 58%).

$^1$H NMR (400, CDCl$_3$): 8.23 (2H, s), 7.33 (2H, m), 6.87 (2H, m), 6.03 (1H, m), 5.55 (2H, m), 4.79 (2H, d), 4.26 (1H, m), 3.84 (2H, d), 2.95 (2H, m), 2.50-2.36 (7H, m), 2.09-1.92 (7H, m), 1.68-1.61 (4H, m), 1.40-1.33 (4H, m), 2.12 (3H, m)

Example 231: Preparation of N-cyclobutyl-4-(4-((1-(5-ethylpyrimidin-2-yl)piperidin-4-yl)methoxy)phenyl)cyclohex-3-enecarboxamide

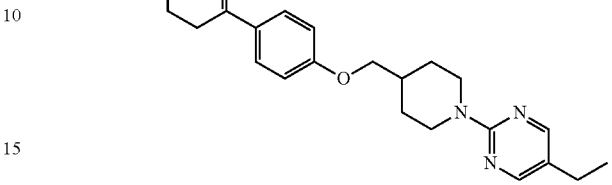

The title compound was prepared in the same manner as in <Example 152>, except that cyclobutylamine hydrochloride was used instead of the L-β-prolinol (Amount obtained: 165 mg/Yield: 68%).

$^1$H NMR (400, CDCl$_3$): 8.18 (2H, m), 7.31 (2H, m), 6.86 (2H, m), 6.04 (1H, m), 5.74 (1H, m), 4.79 (2H, d), 4.47 (1H, m), 3.84 (2H, d), 2.95 (2H, m), 2.51-2.35 (9H, m), 2.09-2.06 (2H, m), 1.96-1.80 (5H, m), 1.75-1.69 (2H, m), 1.39 (2H, m), 1.22 (3H, m)

Example 232: Preparation of (3,4-dihydroisoquinolin-2(1H)-yl)(4-(4-((1-(5-ethylpyrimidin-2-yl)piperidin-4-yl)methoxy)phenyl)cyclohex-3-enyl)methanone

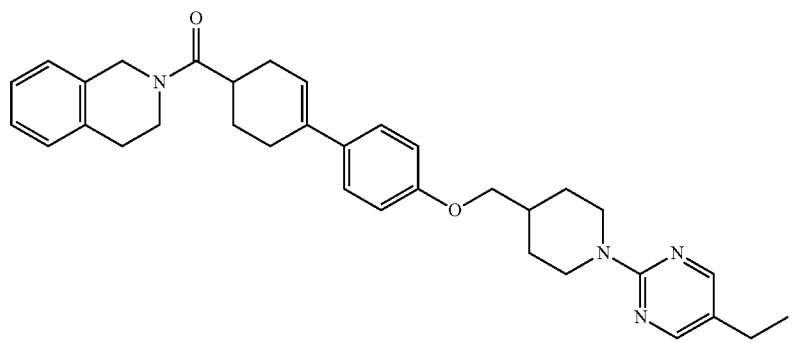 [SMILES: CCc1cnc(N2CCC(COc3ccc(C4=CCC(C(=O)N5CCc6ccccc6C5)CC4)cc3)CC2)nc1]

The title compound was prepared in the same manner as in <Example 152>, except that 1,2,3,4-tetrahydroisoquinoline was used instead of the L-β-prolinol (Amount obtained: 173 mg/Yield: 69%).

$^1$H NMR (400, CDCl$_3$): 8.19 (2H, m), 7.34 (2H, m), 7.24-7.12 (4H, m), 6.87 (2H, m), 6.07 (1H, m), 4.74-4.73 (4H, m), 3.91-3.78 (4H, m), 2.97-2.89 (5H, m), 2.60-2.44 (5H, m), 2.36 (1H, m), 2.13-1.93 (5H, m), 1.41 (2H, m), 1.24 (3H, m)

Example 233: Preparation of tert-butyl 4-((4-(4-(5-hydroxypentylcarbamoyl)cyclohex-1-enyl)phenoxy)methyl)piperidine-1-carboxylate

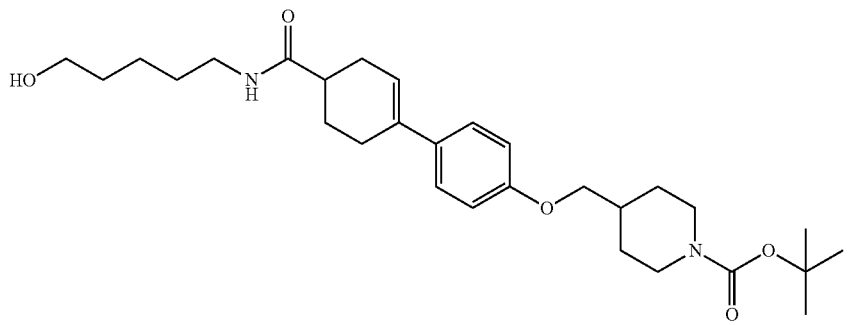 [SMILES: CC(C)(C)OC(=O)N1CCC(COc2ccc(C3=CCC(C(=O)NCCCCCO)CC3)cc2)CC1]

The title compound was prepared in the same manner as in <Example 190>, except that 5-aminopentanol was used instead of the 2-aminoethanol (Amount obtained: 166 mg/Yield: 67%).

$^{1}$H NMR (400, CDCl$_3$): 7.31 (2H, m), 6.84 (2H, m), 6.03 (1H, m), 5.73 (1H, m), 4.15 (2H, s), 3.81 (2H, d), 3.66 (2H, m), 3.32 (2H, m), 2.97 (2H, d), 2.78 (2H, m), 2.50-2.38 (5H, m), 2.09 (1H, m), 1.96-1.73 (5H, m), 1.58-1.52 (5H, m), 1.47 (9H, s), 1.44-1.22 (5H, m)

Example 234: Preparation of 4-(4-((1-(5-ethylpyrimidin-2-yl)piperidin-4-yl)methoxy)phenyl)-N-(5-hydroxypentyl)cyclohex-3-enecarboxamide

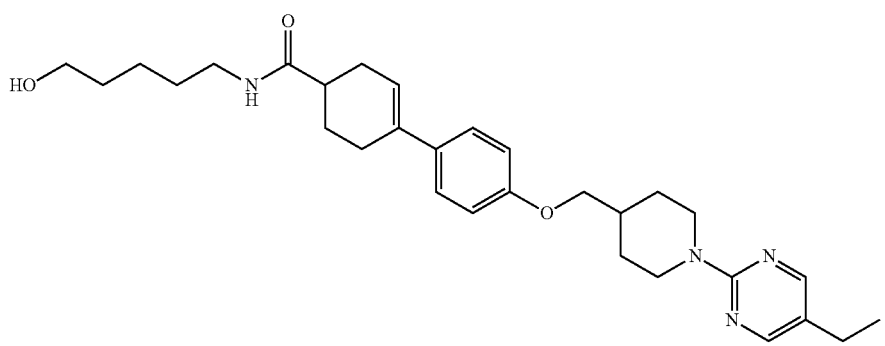 [SMILES: CCc1cnc(N2CCC(COc3ccc(C4=CCC(C(=O)NCCCCCO)CC4)cc3)CC2)nc1]

The title compound was prepared in the same manner as in <Example 152>, except that 5-aminopentanol was used instead of the L-β-prolinol (Amount obtained: 172 mg/Yield: 71%).

$^{1}$H NMR (400, CDCl$_3$): 8.18 (2H, s), 7.32 (2H, m), 6.86 (2H, m), 6.03 (1H, m), 5.66 (1H, m), 4.79 (2H, d), 3.84 (2H, d), 3.67 (2H, m), 3.33 (2H, m), 2.95 (2H, m), 2.50-2.38 (7H, m), 2.09-1.87 (5H, m), 1.69-1.30 (10H, m), 1.22 (3H, m)

Example 235: Preparation of (2,5-dihydro-1H-pyrrol-1-yl)(4-(4-((1-(5-ethylpyrimidin-2-yl)piperidin-4-yl)methoxy)phenyl)cyclohex-3-enyl)methanone

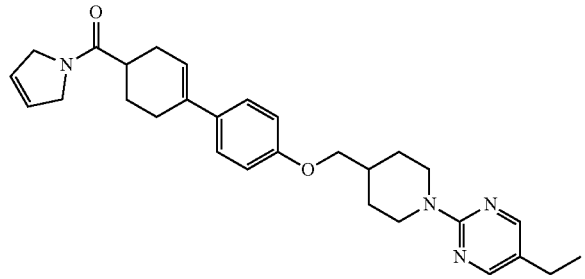 [SMILES: CCc1cnc(N2CCC(COc3ccc(C4=CCC(C(=O)N5CC=CC5)CC4)cc3)CC2)nc1]

The title compound was prepared in the same manner as in <Example 152>, except that 2,5-dihydro-1H-pyrrole was used instead of the L-β-prolinol (Amount obtained: 184 mg/Yield: 85%).
$^1$H NMR (400, CDCl$_3$): 8.18 (2H, s), 7.34 (2H, m), 6.88 (2H, m), 6.08 (1H, m), 5.93-5.84 (2H, m), 4.80 (2H, d), 4.37 (3H, m), 3.85 (2H, d), 3.53 (1H, m), 2.95 (2H, m), 2.65-2.32 (7H, m), 2.10-1.88 (6H, m), 1.37 (2H, m), 1.22 (3H, m)

Example 236: Preparation of tert-butyl 4-((4-(4-((2-hydroxyethyl)(methyl)carbamoyl)cyclohex-1-enyl)phenoxy)methyl)piperidine-1-carboxylate

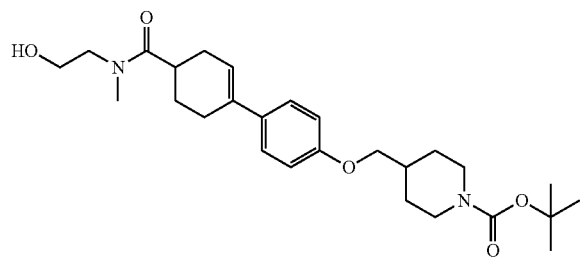 [SMILES: CN(CCO)C(=O)C1CC=C(c2ccc(OCC3CCN(C(=O)OC(C)(C)C)CC3)cc2)CC1]

The title compound was prepared in the same manner as in <Example 190>, except that 2-(methylamino)ethanol was used instead of the 2-aminoethanol (Amount obtained: 162 mg/Yield: 64%).
$^1$H NMR (400, CDCl$_3$): 7.33 (2H, m), 6.86 (2H, m), 6.07 (1H, m), 4.16 (2H, s), 3.84 (4H, m), 3.63-3.57 (2H, m), 3.18 (3H, s), 2.83-2.73 (3H, m), 2.54-2.46 (3H, m), 2.36 (1H, m), 2.03-1.82 (5H, m), 1.48 (9H, s), 1.32 (2H, m)

Example 237: Preparation of tert-butyl 4-((4-(4-(1,3-dihydroxypropan-2-ylcarbamoyl)cyclohex-1-enyl)phenoxy)methyl)piperidine-1-carboxylate

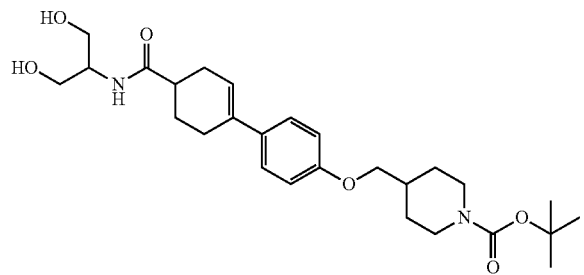 [SMILES: CC(C)(C)OC(=O)N1CCC(COc2ccc(C3=CCC(C(=O)NC(CO)CO)CC3)cc2)CC1]

The title compound was prepared in the same manner as in <Example 190>, except that 2-amino-1,3-propanediol was used instead of the 2-aminoethanol (Amount obtained: 166 mg/Yield: 68%).
$^1$H NMR (400, DMSO-$_{d6}$): 7.50 (1H, d), 7.35 (2H, m), 6.88 (2H, m), 6.04 (1H, m), 4.61 (2H, m), 4.03 (2H, m), 3.97 (2H, m), 3.82 (2H, d), 3.74 (1H, m), 3.41 (4H, m), 2.72 (2H, m), 2.44-2.19 (5H, m), 1.92-1.89 (2H, m), 1.74 (2H, m), 1.66 (1H, m), 1.39 (9H, s), 1.23 (2H, m)

Example 238: Preparation of tert-butyl 4-((4-(4-(3-hydroxypropylcarbamoyl)cyclohex-1-enyl)phenoxy)methyl)piperidine-1-carboxylate

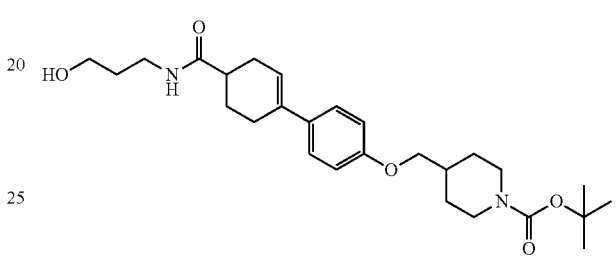

The title compound was prepared in the same manner as in <Example 190>, except that 3-aminopropanol was used instead of the 2-aminoethanol (Amount obtained: 172 mg/Yield: 69%).
$^1$H NMR (400, CDCl$_3$): 7.32 (2H, m), 6.85 (2H, m), 6.03 (2H, m), 4.16 (2H, s), 3.81 (2H, d), 3.67 (2H, m), 3.50 (2H, m), 3.27 (1H, m), 2.78 (2H, m), 2.53-2.41 (5H, m), 2.12 (1H, m), 1.98-1.82 (4H, m), 1.73 (2H, m), 1.48 (9H, s), 1.31 (2H, m)

Example 239: Preparation of tert-butyl 4-((4-(4-(1,2,3,4-tetrahydroisoquinoline-2-carbonyl)cyclohex-1-enyl)phenoxy)methyl)piperidine-1-carboxylate

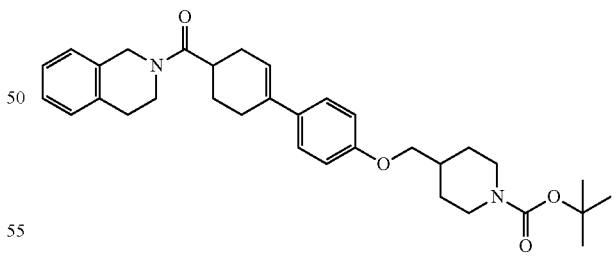

The title compound was prepared in the same manner as in <Example 190>, except that 1,2,3,4-tetrahydroisoquinoline was used instead of the 2-aminoethanol (Amount obtained: 185 mg/Yield: 81%).
$^1$H NMR (400, CDCl$_3$): 7.35 (2H, m), 7.25-7.12 (4H, m), 6.86 (2H, m), 6.07 (1H, m), 4.84 (2H, m), 4.18 (2H, s), 3.91-3.78 (4H, m), 2.97-2.88 (3H, m), 2.79 (2H, m), 2.60-2.50 (3H, m), 2.33 (1H, m), 2.06-1.93 (3H, m), 1.86 (2H, m), 1.59 (1H, s), 1.48 (9H, s), 1.33 (2H, m)

Example 240: Preparation of tert-butyl 4-((4-(4-(isoindoline-2-carbonyl)cyclohex-1-enyl)phenoxy)methyl)piperidine-1-carboxylate

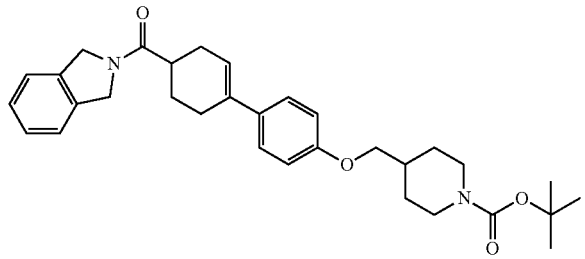 [SMILES: CC(C)(C)OC(=O)N1CCC(COc2ccc(C3=CCC(C(=O)N4Cc5ccccc5C4)CC3)cc2)CC1]

The title compound was prepared in the same manner as in <Example 190>, except that isoindoline was used instead of the 2-aminoethanol (Amount obtained: 181 mg/Yield: 77%).

¹H NMR (400, CDCl₃): 7.36-7.29 (6H, m), 6.88 (2H, m), 6.10 (1H, m), 4.95 (2H, s), 4.86 (2H, s), 4.17 (2H, s), 3.83 (2H, d), 2.82-2.73 (3H, m), 2.63-2.37 (4H, m), 2.12 (1H, m), 2.02 (2H, m), 1.86 (2H, m), 1.64 (1H, s), 1.48 (9H, s), 1.33 (2H, m)

Example 241: Preparation of (4-(4-((1-(5-ethylpyrimidin-2-yl)piperidin-4-yl)methoxy)phenyl)cyclohex-3-enyl)(isoindolin-2-yl)methanone

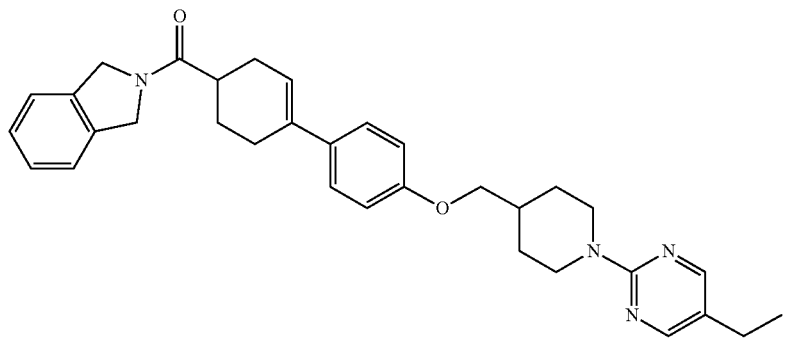 [SMILES: CCc1cnc(N2CCC(COc3ccc(C4=CCC(C(=O)N5Cc6ccccc6C5)CC4)cc3)CC2)nc1]

The title compound was prepared in the same manner as in <Example 152>, except that isoindoline was used instead of the L-β-prolinol (Amount obtained: 180 mg/Yield: 76%).

¹H NMR (400, CDCl₃): 8.19 (2H, s), 7.64-7.23 (6H, m), 6.89 (2H, m), 6.10 (1H, m), 4.95 (2H, s), 4.86 (2H, s), 4.80 (2H, d), 3.86 (2H, d), 2.96 (2H, m), 2.82 (1H, m), 2.63-2.36 (6H, m), 2.12-2.09 (2H, m), 2.02-1.93 (3H, m), 1.42-4.31 (2H, m), 1.22 (3H, m)

Example 242: Preparation of 4-(4-((1-(5-ethylpyrimidin-2-yl)piperidin-4-yl)methoxy)phenyl)-N-(3-hydroxypropyl)-N-methylcyclohex-3-enecarboxamide

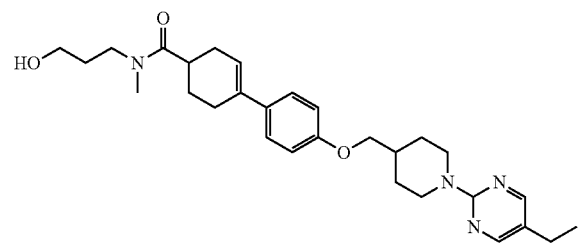 [SMILES: CCC1=CNC(N2CCC(COc3ccc(C4=CCC(C(=O)N(C)CCCO)CC4)cc3)CC2)N=C1]

The title compound was prepared in the same manner as in <Example 152>, except that 3-methylaminopropanol was used instead of the L-β-prolinol (Amount obtained: 175 mg/Yield: 73%).

¹H NMR (400, CDCl₃): 8.18 (2H, s), 7.31 (2H, d), 6.86 (2H, d), 6.05 (1H, d), 4.76 (2H, d), 4.03 (1H, s), 3.84 (2H, d), 3.58 (2H, t), 3.50 (2H, s), 3.09 (3H, s), 2.96-2.80 (4H, m), 2.88-2.82 (5H, m), 2.55-2.44 (1H, m), 2.10-2.00 (2H, m), 1.99-1.89 (3H, m), 1.75 (2H, m), 1.38-1.31 (2H, m), 1.22 (3H, t)

Example 243: Preparation of N-(3-hydroxypropyl)-4-(4-((1-(3-isopropyl-1,2,4-oxadiazol-5-yl)piperidin-4-yl)methoxy)phenyl)-N-methylcyclobex-3-enecarboxamide

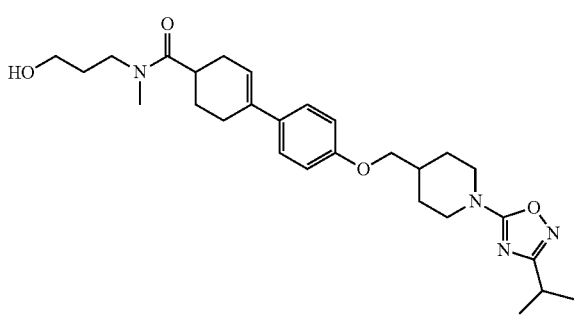

The title compound was prepared in the same manner as in <Example 143>, except that 3-methylaminopropanol was used instead of the (R)—N,N-dimethylpyrrolidine-3-amine hydrochloride (Amount obtained: 174 mg/Yield: 71%).

¹H NMR (400, CDCl₃): 7.31 (2H, d), 6.84 (2H, d), 6.05 (1H, m), 4.21 (2H, d), 4.01 (1H, t), 3.84 (2H, d), 3.52 (2H, t), 3.50 (2H, m), 3.11 (5H, m), 2.90 (2H, m), 2.55-2.48 (3H, m), 2.34 (1H, m), 2.06-1.90 (5H, m), 1.73 (2H, m), 1.47 (2H, m), 1.31 (6H, d)

Example 244: Preparation of N-(furan-2-ylmethyl)-4-(4-((1-(3-isopropyl-1,2,4-oxadiazol-5-yl)piperidin-4-yl)methoxy)phenyl)cyclohex-3-enecarboxamide

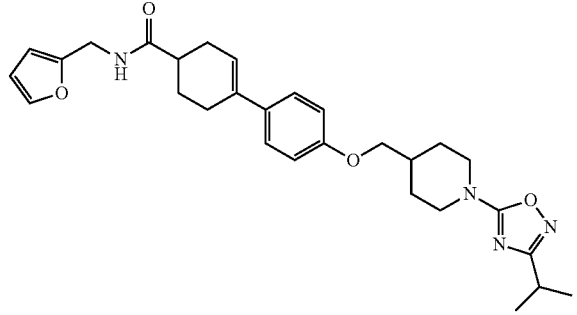 [SMILES: CC(C)c1noc(N2CCC(COc3ccc(C4=CCC(C(=O)NCc5ccco5)CC4)cc3)CC2)n1]

The title compound was prepared in the same manner as in <Example 143>, except that furfurylamine was used instead of the (R)—N,N-dimethylpyrrolidine-3-amine hydrochloride (Amount obtained: 159 mg/Yield: 62%).

$^1$H NMR (400, CDCl$_3$): 7.37 (1H, s), 7.30 (2H, d), 6.83 (2H, d), 6.34 (1H, t), 6.25 (1H, d), 6.03 (1H, s), 5.88 (1H, t), 4.48 (2H, d), 4.21 (2H, d), 3.84 (2H, d), 3.10 (2H, t), 2.90 (1H, m), 2.46 (2H, m), 2.06 (2H, m), 1.89 (3H, m), 1.49 (2H, m), 1.31 (6H, d)

Example 245: Preparation of N-(3-ethoxypropyl)-4-(4-((1-(3-isopropyl-1,2,4-oxadiazol-5-yl)piperidin-4-yl)methoxy)phenyl)cyclohex-3-enecarboxamide

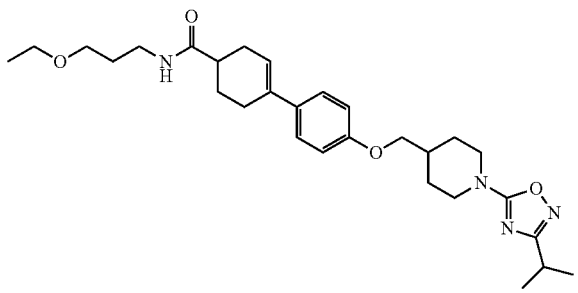 [SMILES: CCOCCCNC(=O)C1CC=C(c2ccc(OCC3CCN(c4nc(C(C)C)no4)CC3)cc2)CC1]

The title compound was prepared in the same manner as in <Example 143>, except that 3-ethoxypropylamine was used instead of the (R)—N,N-dimethylpyrrolidine-3-amine hydrochloride (Amount obtained: 167 mg/Yield: 64%).

$^1$H NMR (400, CDCl$_3$): 7.32 (2H, d), 6.84 (2H, d), 6.33 (1H, t), 6.04 (1H, s), 4.21 (2H, d), 3.84 (2H, d), 3.55 (2H, t), 3.47 (2H, q), 3.40 (2H, q), 3.11 (2H, m), 2.90 (1H, m), 2.52-2.36 (5H, m), 2.13-2.05 (2H, m), 1.97 (2H, d), 1.85-1.77 (3H, m), 1.47 (2H, m), 1.31 (6H, d), 1.23 (3H, t)

Example 246: Preparation of 4-(4-((1-(3-isopropyl-1,2,4-oxadiazol-5-yl)piperidin-4-yl)methoxy)phenyl)-N-methoxycyclohex-3-enecarboxamide

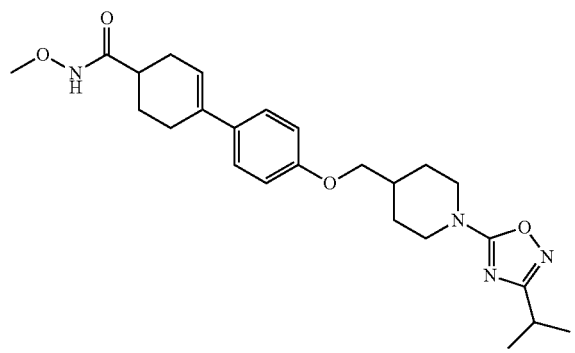 [SMILES: CONC(=O)C1CC=C(c2ccc(OCC3CCN(c4nc(C(C)C)no4)CC3)cc2)CC1]

The title compound was prepared in the same manner as in <Example 143>, except that O-methylhydroxylamine hydrochloride was used instead of the (R)—N,N-dimethyl-pyrrolidine-3-amine hydrochloride (Amount obtained: 170 mg/Yield: 67%).

$^1$H NMR (400, CDCl$_3$): 8.39 (1H, s), 7.30 (2H, d), 6.83 (2H, d), 6.03 (1H, s), 4.22 (2H, d), 3.84 (2H, d), 3.80 (3H, s), 3.10 (2H, t), 2.90 (1H, m), 2.56-2.35 (5H, m), 2.05 (2H, m), 1.93 (2H, d), 1.43 (2H, m), 1.31 (6H, d)

Example 247: Preparation of 4-(4-((1-(3-isopropyl-1,2,4-oxadiazol-5-yl)piperidin-4-yl)methoxy)phenyl)-N-methoxy-N-methylcyclohex-3-enecarboxamide

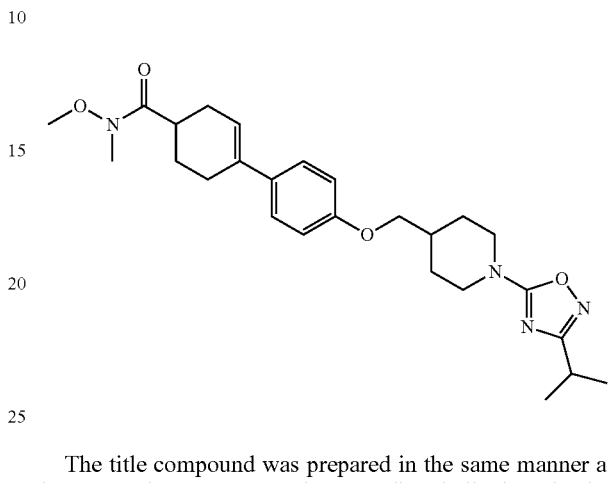

The title compound was prepared in the same manner as in <Example 143>, except that N,O-dimethylhydroxylamine was used instead of the (R)—N,N-dimethylpyrrolidine-3-amine hydrochloride (Amount obtained: 176 mg/Yield: 73%).

$^1$H NMR (400, CDCl$_3$): 7.33 (2H, d), 6.85 (2H, d), 6.07 (1H, d), 4.21 (2H, d), 3.84 (2H, d), 3.74 (3H, s), 3.24 (3H, s), 3.07 (2H, m), 2.89 (1H, m), 2.52-2.33 (4H, m), 2.04 (4H, m), 1.97 (2H, d), 1.83 (1H, m), 1.46 (2H, m), 1.30 (6H, s)

Example 248: Preparation of N,N-bis(2-hydroxyethyl)-4-(4-((1-(3-isopropyl-1,2,4-oxadiazol-5-yl)piperidin-4-yl)methoxy)phenyl)cyclohex-3-enecarboxamide

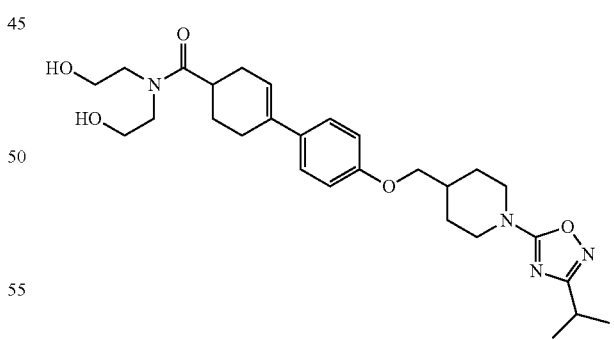

The title compound was prepared in the same manner as in <Example 143>, except that diethanolamine was used instead of the (R)—N,N-dimethylpyrrolidine-3-amine hydrochloride (Amount obtained: 157 mg/Yield: 55%).

$^1$H NMR (400, CDCl$_3$): 7.31 (2H, d), 6.84 (2H, d), 6.05 (1H, d), 4.20 (2H, d), 3.90 (2H, s), 3.84 (4H, m), 3.60 (4H, m), 3.27 (2H, s), 3.10 (4H, m), 2.92 (2H, m), 2.50 (2H, m), 2.30 (2H, m), 2.05-1.87 (5H, m), 1.44 (2H, m), 1.30 (6H, d)

Example 249: Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

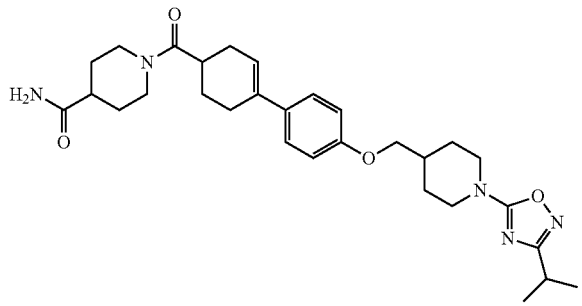 [SMILES: CC(C)c1noc(N2CCC(COc3ccc(C4=CCC(C(=O)N5CCC(C(N)=O)CC5)CC4)cc3)CC2)n1]

The title compound was prepared in the same manner as in <Example 143>, except that isonipecotamide was used instead of the (R)—N,N-dimethylpyrrolidine-3-amine hydrochloride (Amount obtained: 167 mg/Yield: 65%).

$^1$H NMR (400, CDCl$_3$): 7.32 (2H, d), 6.85 (2H, d), 6.05 (1H, d), 5.49 (1H, s), 5.36 (1H, s), 4.67 (1H, m), 4.21 (2H, d), 4.04 (1H, d), 3.85 (2H, d), 3.11 (2H, m), 2.89 (1H, m), 2.77-2.53 (2H, m), 2.50-2.31 (4H, m), 2.27 (1H, m), 2.06-1.94 (7H, m), 1.66 (2H, m), 1.41 (2H, m), 1.23 (6H, d)

Example 250: Preparation of 1-(4-(4-((1-(5-ethylpyrimidin-2-yl)piperidin-4-yl)methoxy)phenyl)cyclohex-3-enecarbonyl)pyrrolidin-3-one

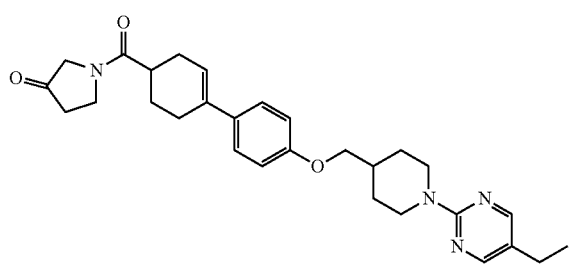 [SMILES: CCc1cnc(N2CCC(COc3ccc(C4=CCC(C(=O)N5CCC(=O)C5)CC4)cc3)CC2)nc1]

The title compound was prepared in the same manner as in <Example 152>, except that pyrrolidin-3-one hydrochloride was used instead of the L-β-prolinol (Amount obtained: 189 mg/Yield: 81%).

$^1$H NMR (400, CDCl$_3$): 8.19 (2H, s), 7.31 (2H, m), 6.86 (2H, d), 6.04 (1H, t), 4.77 (2H, d), 3.99 (4H, m), 3.83 (2H, d), 2.92 (2H, t), 2.75 (2H, t), 2.66 (2H, t), 2.57 (2H, m), 2.48 (2H, q), 2.36 (1H, m), 2.10 (2H, m), 1.95 (2H, d), 1.40 (2H, m), 1.28 (6H, d)

Example 251: Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

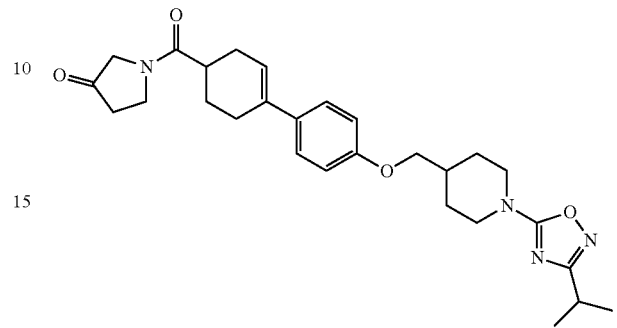

The title compound was prepared in the same manner as in <Example 143>, except that pyrrolidin-3-one hydrochloride was used instead of the (R)—N,N-dimethylpyrrolidine-3-amine hydrochloride (Amount obtained: 177 mg/Yield: 65%).

$^1$H NMR (400, CDCl$_3$): 7.32 (2H, m), 6.85 (2H, d), 6.33 (1H, t), 6.05 (1H, t), 4.21 (2H, d), 4.04-3.95 (4H, m), 3.84 (2H, d), 3.14 (2H, t), 2.89 (1H, q), 2.77 (2H, t), 2.68 (2H, t), 2.55 (3H, t), 2.60-2.33 (3H, m), 2.06 (3H, m), 1.94 (2H, d), 1.44 (2H, m), 1.35 (6H, s)

Example 252: Preparation of 1-(4-(4-((1-(3-isopropyl-1,2,4-oxadiazol-5-yl)piperidin-4-yl)methoxy)phenyl)cyclohex-3-enecarbonyl)piperidine-4-carboxamide

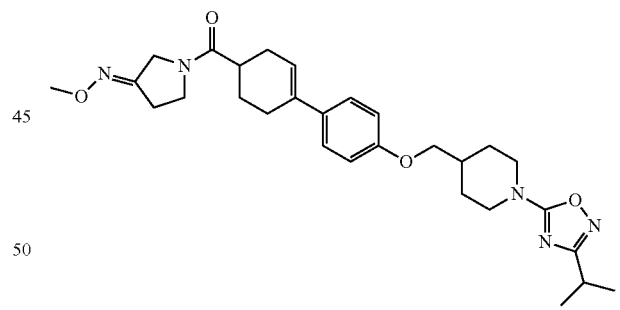

The title compound was prepared in the same manner as in <Example 217>, except that O-methylhydroxylamine hydrochloride was used instead of the hydroxylamine hydrochloride (Amount obtained: 170 mg/Yield: 56%).

$^1$H NMR (400, CDCl$_3$): 7.32 (2H, d), 6.86 (2H, d), 6.05 (1H, s), 4.23 (4H, m), 3.91 (3H, s), 3.82-3.77 (4H, m), 3.11 (2H, t), 2.94 (2H, q), 2.89-2.45 (5H, m), 2.30 (1H, m), 2.05-1.90 (5H, m), 1.46 (2H, m), 1.30 (6H, s)

Example 253: Preparation of (Z)-(3,3-bis(hydroxymethyl)-4-(methoxyimino)pyrrolidin-1-yl)(4-(4-((1-(5-ethylpyrimidin-2-yl)piperidin-4-yl)methoxy)phenyl)cyclohex-3-enyl)methanone

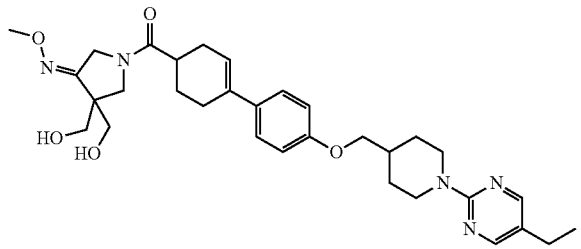 [SMILES: CCc1cnc(N2CCC(COc3ccc(C4=CCC(C(=O)N5C/C(=N\OC)C(CO)(CO)C5)CC4)cc3)CC2)nc1]

The title compound was prepared in the same manner as in <Example 152>, except that (Z)-4,4-bis(hydroxymethyl)pyrrolidin-3-one O-methyl oxime was used instead of the L-β-prolinol (Amount obtained: 190 mg/Yield: 79%).

$^1$H NMR (400, CDCl$_3$): 8.18 (2H, s) 7.30 (2H, d), 6.85 (2H, d), 6.03 (1H, s), 4.77 (2H, d), 4.32 (2H, d), 3.92-3.67 (11H, m), 2.91 (2H, t), 2.80 (1H, s), 2.70-2.46 (7H, m), 2.32 (1H, m), 2.09-1.88 (3H, m), 1.36 (2H, m), 1.19 (2H, t)

Example 254: Preparation of (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate

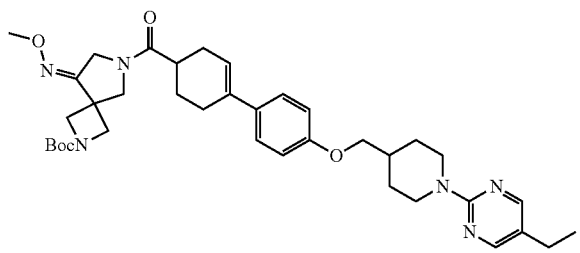 [SMILES: CCc1cnc(N2CCC(COc3ccc(C4=CCC(C(=O)N5C/C(=N\OC)C6(CN(C(=O)OC(C)(C)C)C6)C5)CC4)cc3)CC2)nc1]

The title compound was prepared in the same manner as in <Example 152>, except that (Z)-tert-butyl 8-(methoxyimino)-2,6-diazaspiro[3.4]octane-2-carboxylate was used instead of the L-β-prolinol (Amount obtained: 177 mg/Yield: 68%).

$^1$H NMR (400, CDCl$_3$): 8.18 (2H, s) 7.29 (2H, d), 6.85 (2H, d), 6.03 (1H, s), 4.77 (2H, d), 4.32 (2H, d), 4.20 (2H, m), 3.95-3.89 (7H, m), 3.83 (2H, d), 2.92 (2H, t), 2.59-2.44 (6H, m), 2.32 (1H, d), 2.10 (1H, s), 1.96 (4H, m), 1.47 (9H, s), 1.36-1.28 (4H, m))

Example 255: Preparation of (Z)-(4-(4-((1-(5-ethylpyrimidin-2-yl)piperidin-4-yl)methoxy)phenyl)cyclohex-3-enyl)(8-(methoxyimino)-2,6-diazaspiro[3.4]octan-6-yl)methanone hydrochloride

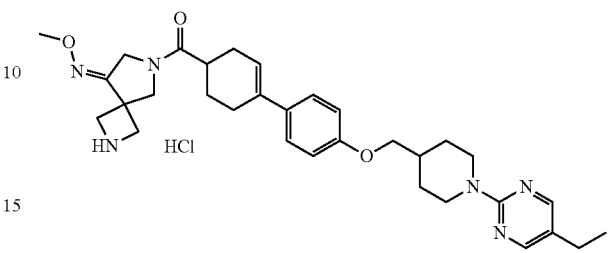

150 mg of the compound (Z)-tert-butyl 6-(4-(4-((1-(5-ethylpyrimidin-2-yl)piperidin-4-yl)methoxy)phenyl)cyclohex-3-enecarbonyl)-8-(methoxyimino)-2,6-diazaspiro[3.4]octane-2-carboxylate prepared in <Example 254> was dissolved in 20 ml of ethyl acetate in a 100 ml flask, and then stirred under a nitrogen atmosphere. 0.08 ml of 4 N HCl dissolved in dioxane was added dropwise thereto, and the resulting mixture was then stirred at room temperature for 3 hours. The resulting solids were filtered, washed with 10 ml of ethyl acetate, and then dried to prepare the title compound as a white solid (Amount obtained: 130 mg/Yield: 73%).

$^1$H NMR (400, MeOD): 8.50 (2H, s), 7.34 (2H, d), 6.87 (2H, d), 6.06 (1H, s), 4.61 (2H, d), 3.99 (3H, s), 3.63 (8H, s), 3.49 (2H, m), 2.67 (2H, q), 2.54 (1H, s), 2.43 (1H, s), 2.16 (3H, m), 1.79 (1H, m), 1.52 (2H, q), 1.30 (4H, m)

Example 256: Preparation of tert-butyl 4-((4-(4-(4-(cyclopropylmethyl)piperazine-1-carbonyl)cyclohex-1-enyl)phenoxy)methyl)piperidine-1-carboxylate

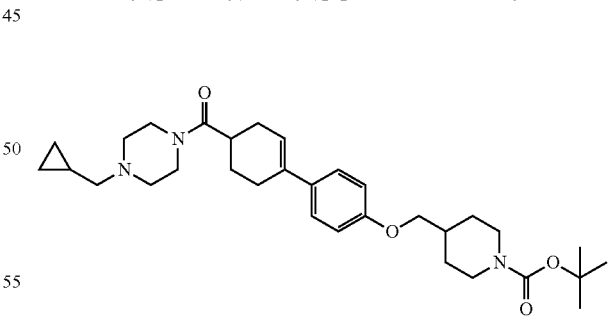

The title compound was prepared in the same manner as in <Example 190>, except that 1-cyclopropylmethyl piperazine was used instead of the 2-aminoethanol (Amount obtained: 169 mg/Yield: 71%).

$^1$H NMR (400, CDCl$_3$): 7.32 (2H, d), 6.84 (2H, d), 6.05 (1H, d), 4.17 (2H, s), 3.82 (2H, d), 3.72 (2H, s), 3.61 (2H, s), 2.77 (3H, m), 2.57-2.46 (7H, m), 2.28 (3H, m), 2.00-1.82 (5H, m), 1.48 (9H, s), 1.28 (2H, m), 0.89 (1H, m), 0.55 (2H, q), 0.12 (2H, q)

Example 257: Preparation of tert-butyl 4-((4-(4-(3,3-difluoropyrrolidine-1-carbonyl)cyclohex-1-enyl)phenoxy)methyl)piperidine-1-carboxylate

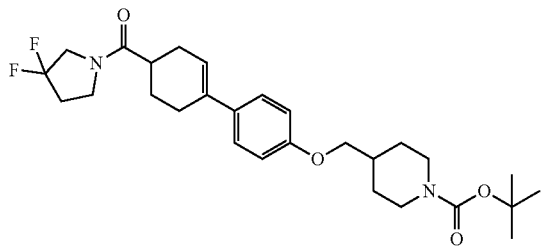 [SMILES: CC(C)(C)OC(=O)N1CCC(COc2ccc(C3=CCC(C(=O)N4CCC(F)(F)C4)CC3)cc2)CC1]

The title compound was prepared in the same manner as in <Example 190>, except that 3,3-difluoropyrrolidine hydrochloride was used instead of the 2-aminoethanol (Amount obtained: 174 mg/Yield: 76%).
$^1$H NMR (400, CDCl$_3$): 7.30 (2H, d), 6.84 (2H, d), 6.05 (1H, d), 4.16 (2H, s), 3.92-3.73 (2H, m), 2.78 (2H, t), 2.56 (1H, m), 2.49-2.29 (6H, m), 2.04-1.97 (3H, m), 1.82 (2H, d), 1.47 (9H, s), 1.25 (2H, m)

Example 258: Preparation of (3,3-difluoropyrrolidin-1-yl)(4-(4-((1-(5-ethylpyrimidin-2-yl)piperidin-4-yl)methoxy)phenyl)cyclohex-3-enyl)methanone

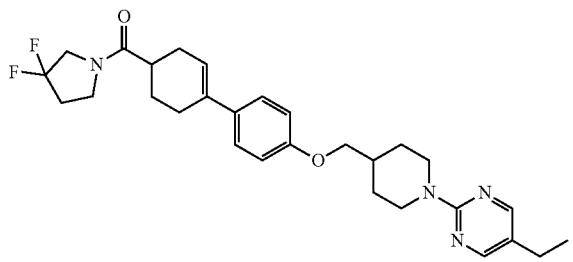 [SMILES: CCc1cnc(N2CCC(COc3ccc(C4=CCC(C(=O)N5CCC(F)(F)C5)CC4)cc3)CC2)nc1]

The title compound was prepared in the same manner as in <Example 152>, except that 3,3-difluoropyrrolidine hydrochloride was used instead of the L-β-prolinol (Amount obtained: 175 mg/Yield: 73%).
$^1$H NMR (400, CDCl$_3$): 8.19 (2H, s), 7.32 (2H, d), 6.85 (2H, d), 6.05 (1H, d), 4.77 (2H, d), 3.92-3.74 (6H, m), 2.92 (2H, m), 2.56-2.32 (9H, m), 2.11-1.88 (5H, m), 1.37 (2H, m), 1.22 (3H, t)

Example 259: Preparation of (3,3-difluoropyrrolidin-1-yl)(4-(4-((1-(3-isopropyl-1,2,4-oxadiazol-5-yl)piperidin-4-yl)methoxy)phenyl)cyclohex-3-enyl)methanone

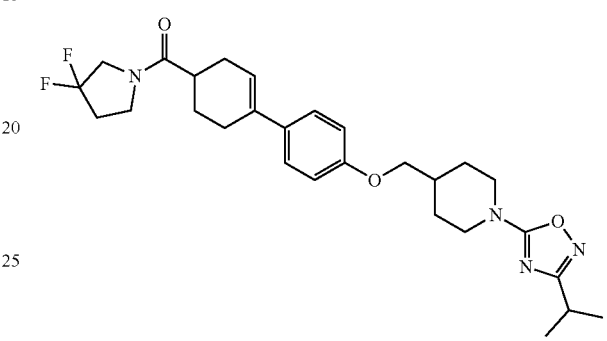

The title compound was prepared in the same manner as in <Example 143>, except that 3,3-difluoropyrrolidine hydrochloride was used instead of the (R)—N,N-dimethylpyrrolidine-3-amine hydrochloride (Amount obtained: 182 mg/Yield: 77%).
$^1$H NMR (400, CDCl$_3$): 7.32 (2H, d), 6.84 (2H, d), 6.05 (1H, d), 4.21 (2H, d), 3.92-3.74 (6H, m), 3.11 (2H, m), 2.94 (1H, m), 2.56-2.33 (7H, m), 2.06-1.94 (5H, m), 1.47 (2H, m), 1.31 (6H, d)

Example 260: Preparation of N-(5-hydroxypentyl)-4-(4-((1-(3-isopropyl-1,2,4-oxadiazol-5-yl)piperidin-4-yl)methoxy)phenyl)cyclohex-3-enecarboxamide

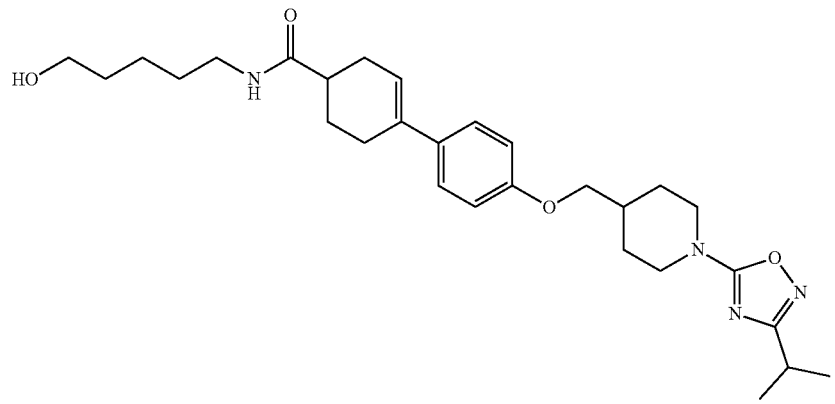 [SMILES: CC(C)c1noc(N2CCC(COc3ccc(C4=CCC(C(=O)NCCCCCO)CC4)cc3)CC2)n1]

The title compound was prepared in the same manner as in <Example 143>, except that 5-aminopentanol was used instead of the (R)—N,N-dimethylpyrrolidine-3-amine hydrochloride (Amount obtained: 185 mg/Yield: 78%).

$^1$H NMR (400, CDCl$_3$): 7.30 (2H, d), 6.84 (2H, d), 6.04 (1H, d), 5.67 (1H, t), 4.19 (2H, d), 3.85 (2H, d), 3.65 (2H, t), 3.31 (2H, q), 3.07 (2H, m), 2.90 (1H, m), 2.51-2.38 (5H, m), 2.03 (2H, m), 1.85 (3H, m), 1.58 (5H, m), 1.43 (5H, m), 1.30 (6H, d)

Example 261: Preparation of tert-butyl 4-((4-(4-(2,2-trifluoroethylcarbamoyl)cyclohex-1-enyl)phenoxy)methyl)piperidine-1-carboxylate

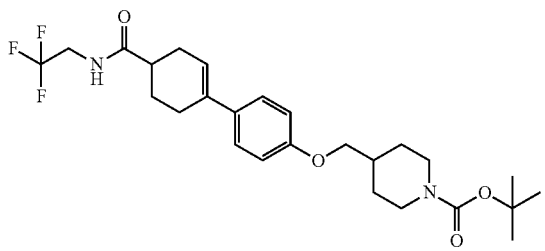 [SMILES: CC(C)(C)OC(=O)N1CCC(COc2ccc(C3=CCC(C(=O)NCC(F)(F)F)CC3)cc2)CC1]

The title compound was prepared in the same manner as in <Example 190>, except that 2,2,2-trifluoroethylamine was used instead of the 2-aminoethanol (Amount obtained: 164 mg/Yield: 70%).

$^1$H NMR (400, CDCl$_3$): 7.31 (2H, d), 6.84 (2H, d), 6.03 (1H, d), 5.90 (1H, t), 4.17 (2H, s), 3.97 (2H, m), 3.81 (2H, d), 2.76 (2H, t), 2.57-2.42 (5H, m), 2.13-2.09 (1H, m), 1.99-1.85 (2H, m), 1.84 (2H, d), 1.47 (9H, s), 1.24 (2H, m)

Example 262: Preparation of tert-butyl 4-((4-(4-(4-cyanocyclolohexanecarbonyl)cyclohex-1-enyl)phenoxy)methyl)piperidine-1-carboxylate

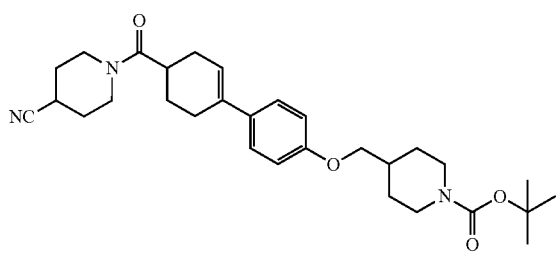 [SMILES: CC(C)(C)OC(=O)N1CCC(COc2ccc(C3=CCC(C(=O)N4CCC(C#N)CC4)CC3)cc2)CC1]

The title compound was prepared in the same manner as in <Example 190>, except that 2,2,2-trifluoroethylamine was used instead of the 2-aminoethanol (Amount obtained: 165 mg/Yield: 67%).

$^1$H NMR (400, CDCl$_3$): 7.30 (2H, d), 6.84 (2H, d), 6.04 (1H, s), 4.17 (2H, s), 3.87-3.76 (4H, m), 3.63-3.50 (2H, m), 2.93 (1H, m), 2.82-2.73 (3H, m), 2.73-2.47 (3H, m), 2.28 (1H, m), 1.97-1.82 (9H, m), 1.47 (9H, s), 1.23 (2H, m)

Example 263: Preparation of tert-butyl 4-((4-(4-(1,4-dioxa-8-azaspiro[4.5]decane-8-carbonyl)cyclohex-1-enyl)phenoxy)methyl)piperidine-1-carboxylate

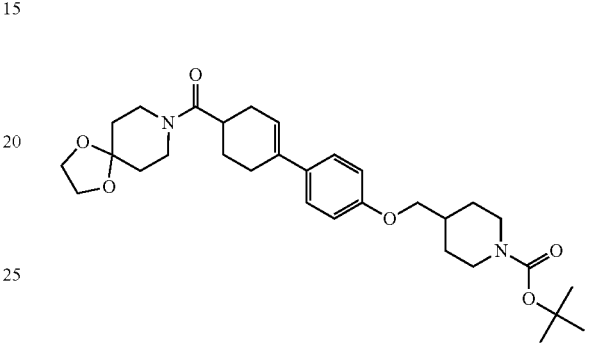

The title compound was prepared in the same manner as in <Example 190>, except that 1,4-dioxa-8-azaspiro[4.5]decane was used instead of the 2-aminoethanol (Amount obtained: 177 mg/Yield: 74%).

$^1$H NMR (400, CDCl$_3$): 7.32 (2H, d), 6.84 (2H, d), 6.05 (1H, d), 4.17 (2H, s), 4.01 (4H, s), 3.82-3.70 (4H, m), 3.63 (2H, t), 2.83-2.76 (3H, m), 2.53-2.47 (2H, m), 2.31 (1H, m), 2.02-1.90 (3H, m), 1.81 (2H, d), 1.73 (4H, m), 1.48 (9H, s), 1.25 (2H, m)

Example 264: Preparation of tert-butyl 4-((4-(4-(spiro[indene-1,4'-piperidin]-1'-ylcarbonyl)cyclohex-1-enyl)phenoxy)methyl)piperidine-1-carboxylate

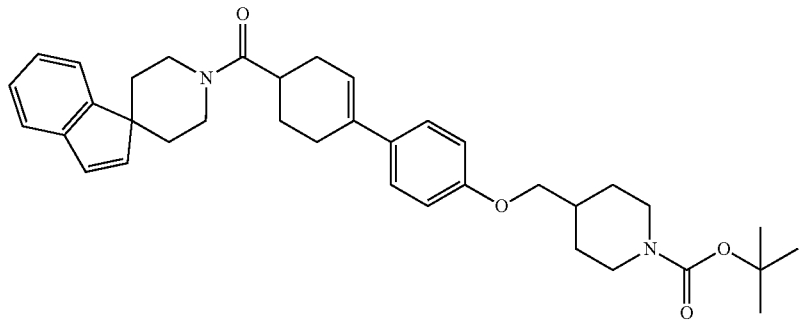 [SMILES: CC(C)(C)OC(=O)N1CCC(COc2ccc(C3=CCC(C(=O)N4CCC5(C=Cc6ccccc65)CC4)CC3)cc2)CC1]

The title compound was prepared in the same manner as in <Example 190>, except that 2,3-dihydrospiro[indene-1,4'-piperidine] was used instead of the 2-aminoethanol (Amount obtained: 183 mg/Yield: 75%).

¹H NMR (400, CDCl₃): 7.37-7.31 (4H, m), 7.29-7.22 (2H, m), 6.91 (1H, dd), 6.87-6.83 (3H, m), 6.08 (1H, t), 4.76 (2H, d), 4.10 (3H, m), 3.81 (2H, d), 3.47 (2H, t), 3.05 (1H, t), 2.89 (1H, m), 2.79 (2H, m), 2.73-2.52 (3H, m), 2.37 (1H, m), 2.11-1.93 (5H, m), 1.83 (2H, d), 1.47-1.32 (11H, m), 1.23 (2H, m)

Example 265: Preparation of tert-butyl 4-((4-(4-(3-oxopyrrolidine-1-carbonyl)cyclohex-1-enyl)phenoxy)methyl)piperidine-1-carboxylate

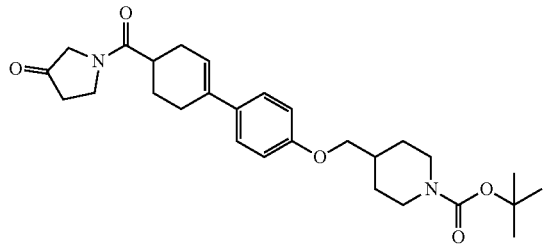

The title compound was prepared in the same manner as in <Example 190>, except that pyrrolidin-3-one hydrochloride was used instead of the 2-aminoethanol (Amount obtained: 159 mg/Yield: 64%).

¹H NMR (400, CDCl₃): 7.32 (2H, d), 6.84 (2H, d), 6.06 (1H, d), 4.17 (2H, s), 3.99 (4H, m), 3.81 (2H, d), 2.75 (5H, m), 2.60-2.42 (5H, m), 2.33-2.30 (1H, m), 2.06-1.94 (33H, m), 1.89 (2H, d), 1.48 (9H, s), 1.27 (2H, m)

Example 266: Preparation of 1-(4-(4-((1-(3-isopropyl-1,2,4-oxadiazol-5-yl)piperidin-4-yl)methoxy)phenyl)cyclohex-3-enecarbonyl)piperidine-4-carbonitrile

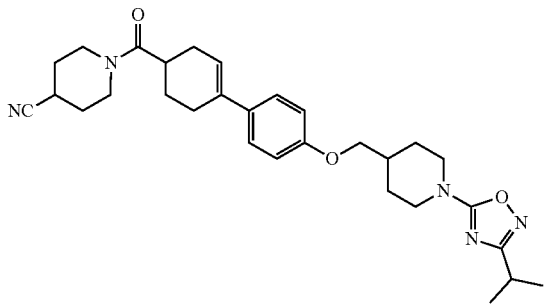 [SMILES: CC(C)c1noc(N2CCC(COc3ccc(C4=CCC(C(=O)N5CCC(C#N)CC5)CC4)cc3)CC2)n1]

The title compound was prepared in the same manner as in <Example 143>, except that piperidine-4-carbonitrile was used instead of the (R)—N,N-dimethylpyrrolidine-3-amine hydrochloride (Amount obtained: 174 mg/Yield: 70%).

¹H NMR (400, CDCl₃): 7.31 (2H, d), 6.86 (2H, d), 6.05 (1H, d), 4.20 (2H, d), 3.84-3.50 (6H, m), 2.11 (2H, m), 2.93 (2H, m), 2.78 (1H, m), 2.52 (3H, m), 2.28 (1H, m), 2.05-1.89 (9H, m), 1.43 (2H, m), 1.29 (9H, s)

Example 267: Preparation of (4-(4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone

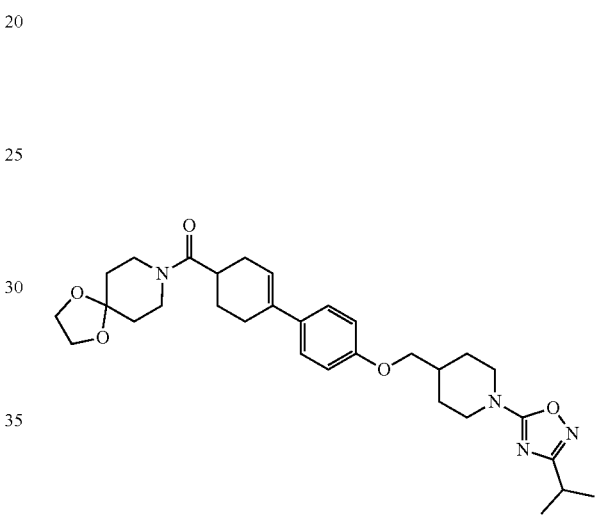

The title compound was prepared in the same manner as in <Example 143>, except that 1,4-dioxa-8-azaspiro[4.5]decane was used instead of the (R)—N,N-dimethylpyrrolidine-3-amine hydrochloride (Amount obtained: 180 mg/Yield: 76%).

¹H NMR (400, CDCl₃): 7.32 (2H, d), 6.84 (2H, d), 6.05 (1H, d), 4.20 (2H, d), 4.01 (4H, s), 3.85 (2H, d), 3.75 (2H, m), 3.63 (2H, t), 3.11 (2H, m), 2.94-2.83 (2H, m), 2.51 (3H, m), 2.31 (1H, m), 2.06-1.90 (5H, m), 1.73 (4H, m), 1.44 (2H, m), 1.31 (6H, d)

Example 268: Preparation of (2,3-dihydrospiro[indene-1,4'-piperidin]-1'-yl)(4-(4-((1-(3-isopropyl-1,2,4-oxadiazol-5-yl)piperidin-4-yl)methoxy)phenyl)cyclohex-3-enyl)methanone

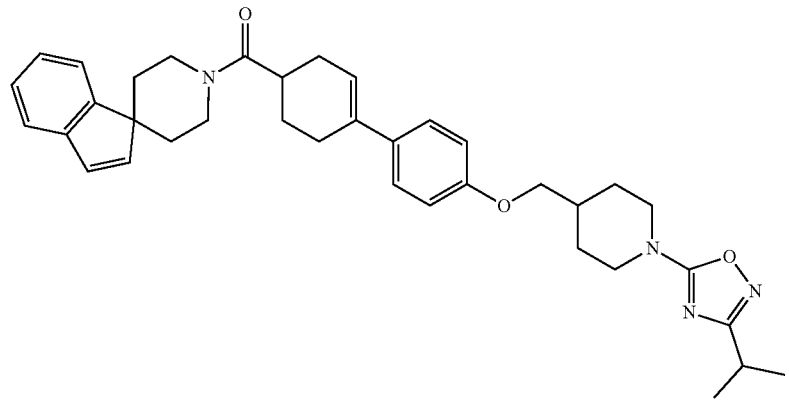 [SMILES: CC(C)c1noc(N2CCC(COc3ccc(C4=CCC(C(=O)N5CCC6(C=Cc7ccccc76)CC5)CC4)cc3)CC2)n1]

The title compound was prepared in the same manner as in <Example 143>, except that 3-dihydrospiro[indene-1,4'-piperidine] was used instead of the (R)—N,N-dimethylpyrrolidine-3-amine hydrochloride (Amount obtained: 194 mg/Yield: 82%).

$^1$H NMR (400, CDCl$_3$): 7.35-7.22 (8H, m), 6.91-6.84 (4H, m), 6.09 (1H, t), 4.75 (1H, d), 4.20 (2H, d), 4.10 (1H, d), 3.84 (2H, d), 3.49 (1H, m), 3.08 (3H, m), 2.89 (2H, m), 2.62-2.34 (4H, m), 2.19-1.94 (7H, m), 1.46 (4H, m), 1.31 (6H, d)

Example 269: Preparation of (3-(ethoxyimino)pyrrolidin-1-yl)(4-(4-((1-(5-ethylpyrimidin-2-yl)piperidin-4-yl)methoxy)phenyl)cyclohex-3-enyl)methanone

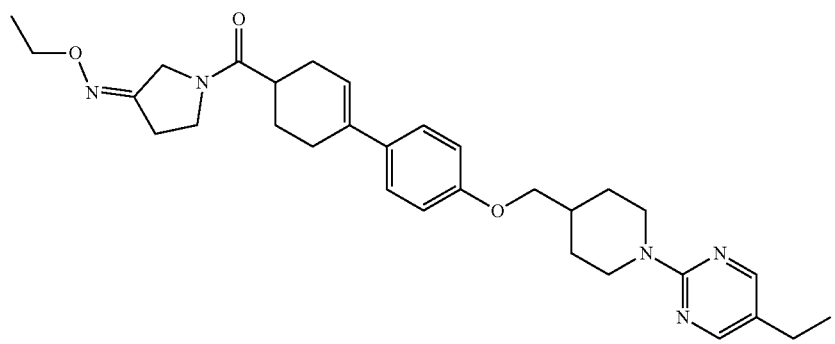 [SMILES: CCO/N=C1/CCN(C(=O)C2CC=C(c3ccc(OCC4CCN(c5ncc(CC)cn5)CC4)cc3)CC2)C1]

The title compound was prepared in the same manner as in <Example 217>, except that O-ethylhydroxylamine hydrochloride was used instead of the hydroxylamine hydrochloride (Amount obtained: 177 mg/Yield: 71%).

$^1$H NMR (400, CDCl$_3$): 8.19 (2H, s), 7.32 (2H, d), 6.86 (2H, d), 6.05 (1H, d), 4.77 (2H, d), 4.24 (2H, d), 4.12 (2H, m), 3.85-3.77 (4H, m), 2.95 (3H, m), 2.78-2.45 (7H, m), 2.34 (1H, m), 2.10-1.90 (5H, m), 1.36 (2H, m), 1.29 (3H, t), 1.20 (3H, t)

Example 270: Preparation of tert-butyl 4-((4-(4-(4-(methoxyimino)piperidine-1-carbonyl)cyclohex-1-enyl)phenoxy)methyl)piperidine-1-carboxylate

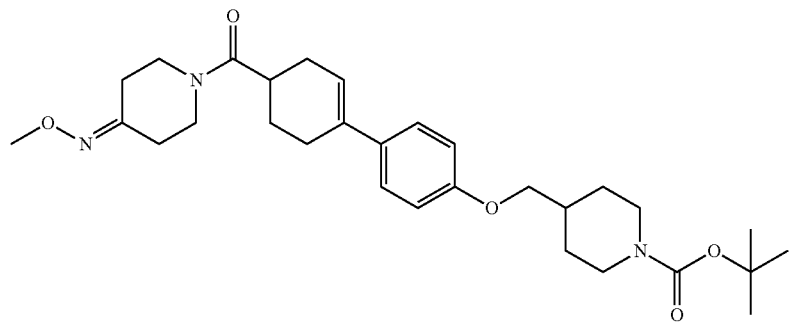 [SMILES: CON=C1CCN(C(=O)C2CC=C(c3ccc(OCC4CCN(C(=O)OC(C)(C)C)CC4)cc3)CC2)CC1]

The title compound was prepared in the same manner as in <Example 217>, except that O-methylhydroxylamine hydrochloride was used instead of the hydroxylamine hydrochloride (Amount obtained: 173 mg/Yield: 75%).

$^1$H NMR (400, CDCl$_3$): 7.30 (2H, d), 6.84 (2H, d), 6.05 (1H, d), 4.17 (2H, s), 3.86 (3H, s), 3.80-3.70 (6H, m), 2.82-2.48 (10H, m), 2.30 (1H, m), 2.02-1.91 (3H, m), 1.82 (2H, d), 1.48 (9H, s), 1.25 (2H, m)

Example 271: Preparation of tert-butyl 4-((4-(4-(4-(hydroxyimino)piperidine-1-carbonyl)cyclohex-1-enyl)phenoxy)methyl)piperidine-1-carboxylate

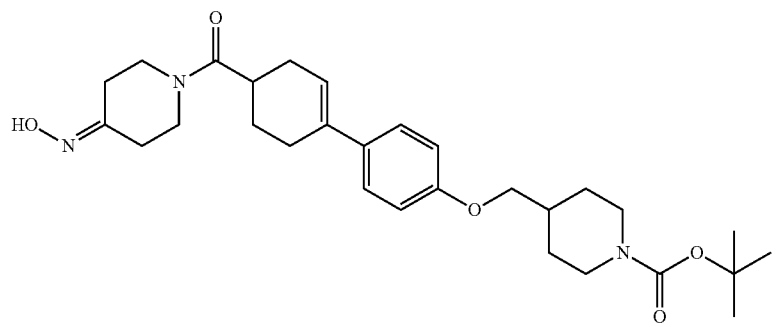 [SMILES: CC(C)(C)OC(=O)N1CCC(COc2ccc(C3=CCC(C(=O)N4CCC(=NO)CC4)CC3)cc2)CC1]

The title compound was prepared in the same manner as in <Example 217>, except that tert-butyl 4-((4-(4-(4-oxopiperidine-1-carbonyl)cyclohex-1-enyl)phenoxy)methyl)piperidine-1-carboxylate was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 161 mg/Yield: 66%).

$^1$H NMR (400, CDCl$_3$): 7.32 (2H, d), 6.84 (2H, d), 6.05 (1H, d), 4.16 (2H, s), 3.93-3.76 (6H, m), 2.83-2.73 (5H, m), 2.66-2.41 (5H, m), 2.30 (1H, m), 2.04-1.91 (3H, m), 1.82 (2H, d), 1.48 (9H, s), 1.22 (2H, m)

Example 272: Preparation of tert-butyl 4-((4-(4-(4-oxopiperidine-1-carbonyl)cyclohex-1-enyl)phenoxy)methyl)piperidine-1-carboxylate

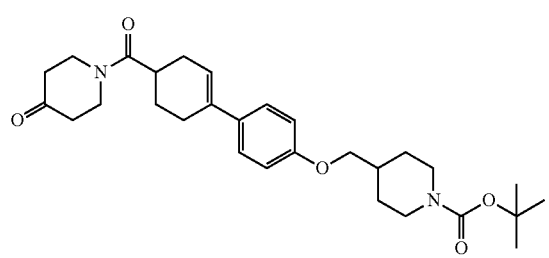 [SMILES: CC(C)(C)OC(=O)N1CCC(COc2ccc(C3=CCC(C(=O)N4CCC(=O)CC4)CC3)cc2)CC1]

The title compound was prepared in the same manner as in <Example 190>, except that piperidin-4-one hydrochloride was used instead of the 2-aminoethanol (Amount obtained: 172 mg/Yield: 75%).

$^1$H NMR (400, CDCl$_3$): 7.32 (2H, d), 6.84 (2H, d), 6.06 (1H, d), 4.16 (2H, s), 3.99-3.87 (6H, m), 2.89 (1H, m), 2.85 (2H, m), 2.61-2.56 (7H, m), 2.35 (1H, m), 2.07-1.98 (3H, m), 1.84 (2H, d), 1.48 (9H, s), 1.24 (2H, m)

Example 273: Preparation of tert-butyl 4-((4-(4-(3-(methoxyimino)pyrrolidine-1-carbonyl)cyclohex-1-enyl)phenoxy)methyl)piperidine-1-carboxylate

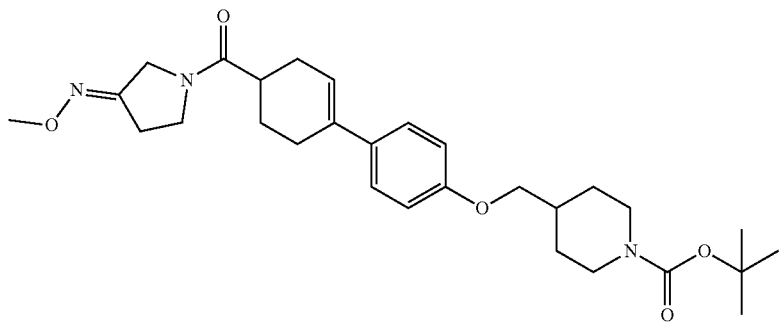 [SMILES: CO/N=C1\CCN(C(=O)C2CC=C(c3ccc(OCC4CCN(C(=O)OC(C)(C)C)CC4)cc3)CC2)C1]

The title compound was prepared in the same manner as in <Example 217>, except that O-methylhydroxylamine hydrochloride was used instead of the hydroxylamine hydrochloride (Amount obtained: 169 mg/Yield: 69%).

$^1$H NMR (400, CDCl$_3$): 7.32 (2H, d), 6.84 (2H, d), 6.06 (1H, d), 4.26 (2H, d), 4.16 (2H, s), 3.90 (3H, s), 3.77 (4H, m), 2.86-2.49 (8H, m), 2.32 (1H, m), 2.04-1.85 (5H, m), 1.48 (9H, s), 1.23 (2H, m)

Example 274: Preparation of 1-(4-(4-((1-(5-ethylpyrimidin-2-yl)piperidin-4-yl)methoxy)phenyl)cyclohex-3-enecarbonyl)piperidin-4-one

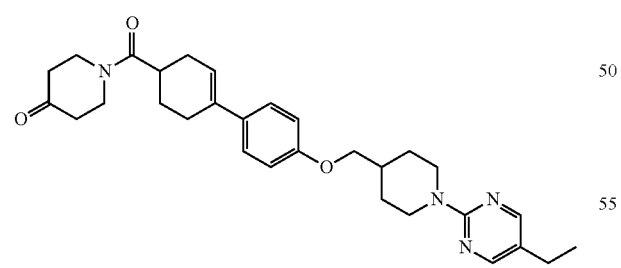

The title compound was prepared in the same manner as in <Example 152>, except that piperidin-4-one hydrochloride was used instead of the L-β-prolinol (Amount obtained: 180 mg/Yield: 77%).

$^1$H NMR (400, CDCl$_3$): 8.19 (2H, s), 7.31 (2H, d), 6.86 (2H, d), 6.06 (1H, d), 4.76 (2H, d), 3.96-3.83 (6H, m), 2.96-2.89 (3H, m), 2.61-2.45 (9H, m), 2.36 (1H, m), 2.11-2.03 (2H, m), 1.95 (2H, d), 1.34 (2H, m), 1.21 (3H, t)

Example 275: Preparation of 1-(4-(4-((1-(3-isopropyl-1,2,4-oxadiazol-5-yl)piperidin-4-yl)methoxy)phenyl)cyclohex-3-enecarbonyl)piperidin-4-one

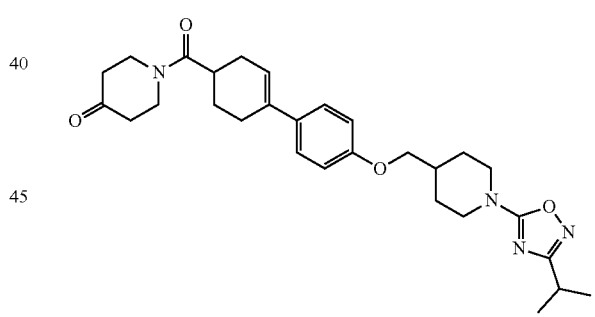

The title compound was prepared in the same manner as in <Example 143>, except that piperidin-4-one hydrochloride was used instead of the (R)—N,N-dimethylpyrrolidine-3-amine hydrochloride (Amount obtained: 184 mg/Yield: 77%).

$^1$H NMR (400, CDCl$_3$): 7.32 (2H, d), 6.85 (2H, d), 6.06 (1H, d), 4.21 (2H, d), 3.98-3.84 (6H, m), 3.14 (2H, m), 2.90 (2H, m), 2.61-2.53 (7H, m), 2.35 (1H, m), 2.07-1.92 (5H, m), 1.51 (2H, m), 1.41 (6H, d)

Example 276: Preparation of (4-(hydroxyimino)piperidin-1-yl)(4-(4-((1-(3-isopropyl-1,2,4-oxadiazol-5-yl)piperidin-4-yl)methoxy)phenyl)cyclohex-3-enyl)methanone

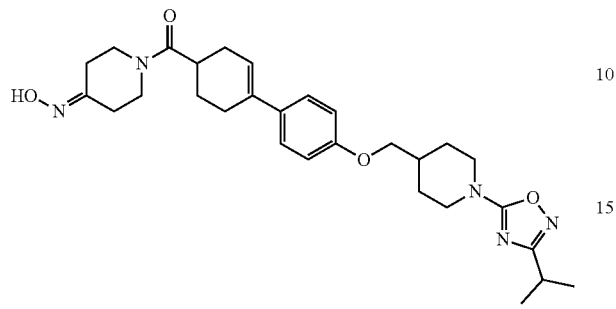

The title compound was prepared in the same manner as in <Example 217>, except that 1-(4-(4-((1-(3-isopropyl-1,2,4-oxadiazol-5-yl)piperidin-4-yl)methoxy)phenyl)cyclohex-3-enecarbonyl)piperidin-4-one was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 183 mg/Yield: 76%).

$^1$H NMR (400, CDCl$_3$): 7.51 (1H, m), 7.31 (2H, d), 6.86 (2H, d), 6.06 (1H, d), 4.51 (2H, s), 3.84 (2H, d), 3.79-3.66 (4H, m), 3.11 (2H, m), 2.92 (2H, m), 2.87 (2H, m), 2.58-2.42 (5H, m), 2.33 (1H, m), 2.05 (2H, m), 1.94 (3H, m), 1.45 (2H, m), 1.43 (9H, s)

Example 277: Preparation of (4-(4-((1-(5-ethylpyrimidin-2-yl)piperidin-4-yl)methoxy)phenyl)cyclohex-3-enyl)(4-(hydroxyimino)piperidin-1-yl)methanone

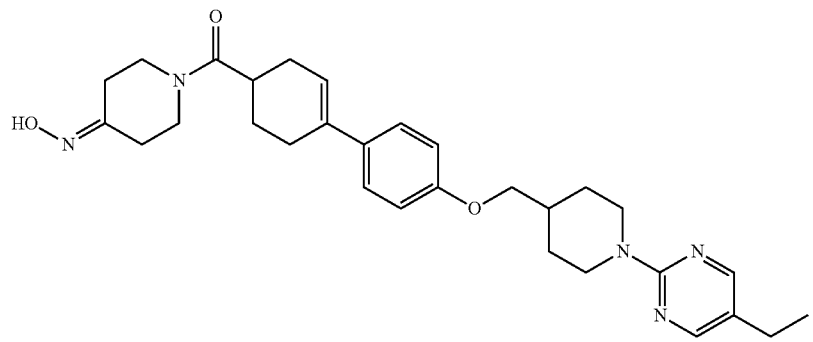 [SMILES: CCc1cnc(N2CCC(COc3ccc(C4=CCC(C(=O)N5CCC(=NO)CC5)CC4)cc3)CC2)nc1]

The title compound was prepared in the same manner as in <Example 217>, except that 1-(4-(4-((1-(5-ethylpyrimidin-2-yl)piperidin-4-yl)methoxy)phenyl)cyclohex-3-enecarbonyl)piperidin-4-one was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 166 mg/Yield: 65%).

$^1$H NMR (400, CDCl$_3$): 8.19 (2H, s), 8.14 (1H, d), 7.31 (2H, d), 6.85 (2H, d), 6.05 (1H, d), 4.76 (2H, d), 3.84-3.70 (6H, m), 2.95 (2H, m), 2.84 (1H, m), 2.70 (2H, m), 2.67-2.42 (7H, m), 2.33 (1H, m), 2.10-1.91 (5H, m), 1.34 (2H, m), 1.20 (3H, t)

Example 278: Preparation of (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone

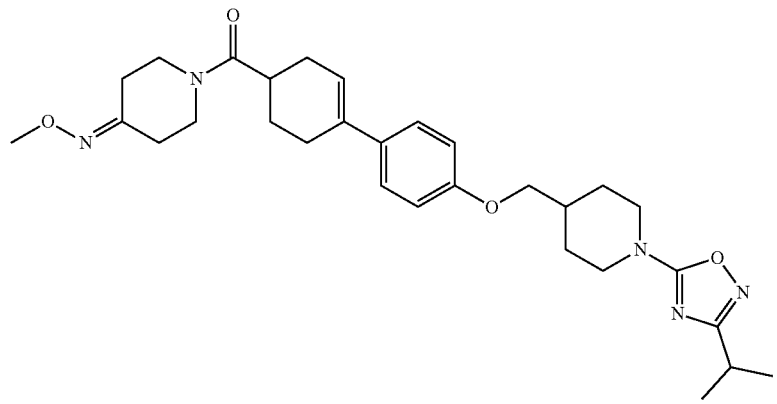 [SMILES: CON=C1CCN(C(=O)C2CC=C(c3ccc(OCC4CCN(c5nc(C(C)C)no5)CC4)cc3)CC2)CC1]

The title compound was prepared in the same manner as in <Example 217>, except that O-methylhydroxylamine hydrochloride was used instead of the hydroxylamine hydrochloride (Amount obtained: 179 mg/Yield: 73%).

$^1$H NMR (400, CDCl$_3$): 7.32 (2H, d), 6.85 (2H, d), 6.05 (1H, d), 4.21 (2H, d), 3.86 (3H, s), 3.83-3.70 (5H, m), 3.63 (1H, m), 3.11 (2H, m), 2.92 (2H, m), 2.62-2.45 (7H, m), 2.40 (1H, m), 2.05-1.93 (5H, m), 1.44 (2H, m), 1.29 (6H, d)

Example 279: Preparation of (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone

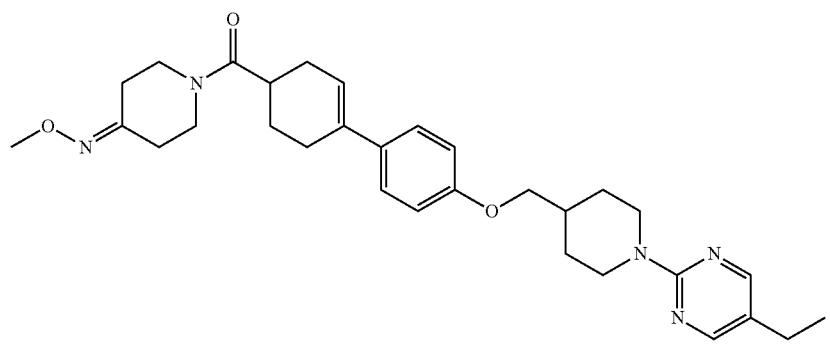 [SMILES: CCc1cnc(N2CCC(COc3ccc(C4=CCC(C(=O)N5CCC(=NOC)CC5)CC4)cc3)CC2)nc1]

The title compound was prepared in the same manner as in <Example 217>, except that O-methylhydroxylamine hydrochloride was used instead of the hydroxylamine hydrochloride (Amount obtained: 173 mg/Yield: 69%).

$^1$H NMR (400, CDCl$_3$): 8.19 (2H, s), 7.31 (2H, d), 6.85 (2H, d), 6.05 (1H, d), 4.77 (2H, d), 3.87 (3H, s), 3.85-3.70 (5H, m), 3.63 (1H, m), 2.95 (2H, m), 2.88 (1H, m), 2.65-2.39 (9H, m), 2.40 (1H, m), 2.00-1.93 (5H, m), 1.33 (2H, m), 1.18 (3H, t)

Example 280: Preparation of tert-butyl 4-((4-(4-(3-oxoazetidine-1-carbonyl)cyclohex-1-enyl)phenoxy)methyl)piperidine-1-carboxylate

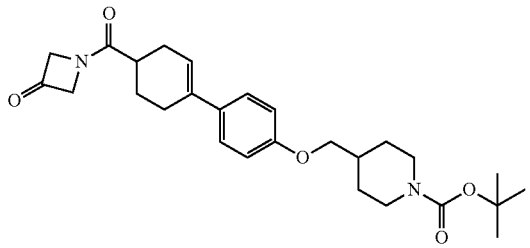 [SMILES: CC(C)(C)OC(=O)N1CCC(COc2ccc(C3=CCC(C(=O)N4CC(=O)C4)CC3)cc2)CC1]

The title compound was prepared in the same manner as in <Example 190>, except that azetidin-3-one hydrochloride was used instead of the 2-aminoethanol (Amount obtained: 172 mg/Yield: 75%).

$^1$H NMR (400, CDCl$_3$): 7.32 (2H, d), 6.84 (2H, d), 6.05 (1H, d), 4.85 (4H, d), 4.16 (2H, s), 3.81 (2H, d), 2.78 (2H, t), 2.63-2.37 (5H, m), 2.10-1.82 (5H, m), 1.48 (9H, s), 1.24 (2H, m)

Example 281: Preparation of tert-butyl 4-((4-(4-(3-(hydroxyimino)azetidine-1-carbonyl)cyclohex-1-enyl)phenoxy)methyl)piperidine-1-carboxylate

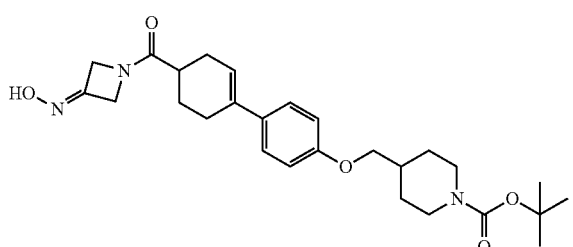

The title compound was prepared in the same manner as in <Example 217>, except that tert-butyl 4-((4-(4-(3-oxoazetidine-1-carbonyl)cyclohex-1-enyl)phenoxy)methyl)piperidine-1-carboxylate was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 167 mg/Yield: 66%).

$^1$H NMR (400, CDCl$_3$): 7.80 (1H, s), 7.31 (2H, d), 6.84 (2H, d), 6.04 (1H, d), 4.89 (2H, d), 4.74 (2H, d), 4.15 (2H, s), 3.87 (2H, d), 2.76 (2H, t), 2.58-2.29 (5H, m), 2.06-1.82 (6H, m), 1.48 (9H, s), 1.27 (2H, m)

Example 282: Preparation of tert-butyl 4-((4-(4-(3-(methoxyimino)azetidine-1-carbonyl)cyclohex-1-enyl)phenoxy)methyl)piperidine-1-carboxylate

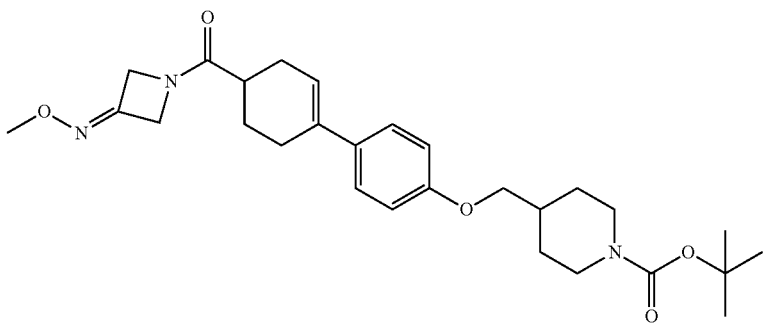 [SMILES: CON=C1CN(C(=O)C2CC=C(c3ccc(OCC4CCN(C(=O)OC(C)(C)C)CC4)cc3)CC2)C1]

The title compound was prepared in the same manner as in <Example 217>, except that O-methylhydroxylamine hydrochloride was used instead of the hydroxylamine hydrochloride (Amount obtained: 175 mg/Yield: 73%).

$^1$H NMR (400, CDCl$_3$): 7.32 (2H, d), 6.84 (2H, d), 6.04 (1H, d), 4.85 (2H, m), 4.69 (2H, d), 4.17 (2H, s), 3.91 (3H, s), 3.82 (2H, d), 2.76 (3H, m), 2.53-2.47 (5H, m), 2.29 (2H, m), 2.09-1.82 (9H, m), 1.48 (9H, s), 1.27 (2H, m)

Example 283: Preparation of 1-(4-(4-((1-(5-ethylpyrimidin-2-yl)piperidin-4-yl) methoxy)phenyl)cyclohex-3-enecarbonyl)azetidin-3-one

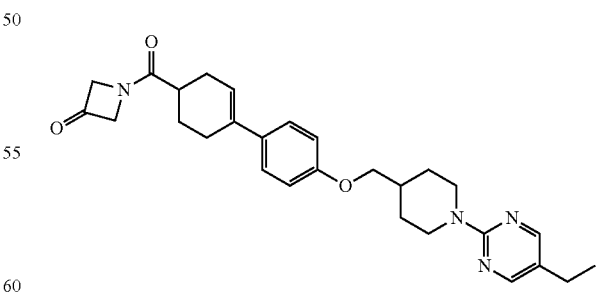

The title compound was prepared in the same manner as in <Example 152>, except that azetidin-3-one hydrochloride was used instead of the L-β-prolinol (Amount obtained: 175 mg/Yield: 77%).

$^1$H NMR (400, CDCl$_3$): 8.19 (2H, s), 7.32 (2H, d), 6.85 (2H, d), 6.05 (1H, d), 5.02-4.76 (2H, m), 3.85 (2H, d), 2.95

(2H, m), 2.63-2.59 (3H, m), 2.58-2.48 (3H, m), 2.36 (1H, m), 2.11-2.06 (2H, m), 1.98-1.91 (3H, m), 1.34 (2H, m), 1.20 (3H, t)

Example 284: Preparation of 1-(4-(4-((1-(3-isopropyl-1,2,4-oxadiazol-5-yl)piperidin-4-yl)methoxy)phenyl)cyclohex-3-enecarbonyl)azetidin-3-one

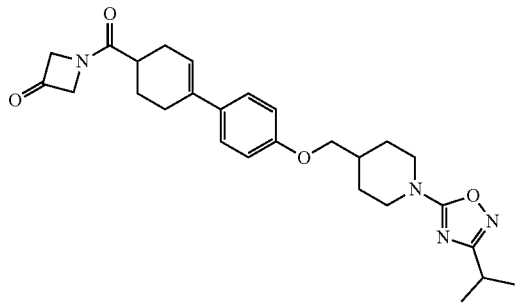 [SMILES: CC(C)c1noc(N2CCC(COc3ccc(C4=CCC(C(=O)N5CC(=O)C5)CC4)cc3)CC2)n1]

The title compound was prepared in the same manner as in <Example 143>, except that azetidin-3-one hydrochloride was used instead of the (R)—N,N-dimethylpyrrolidine-3-amine hydrochloride (Amount obtained: 180 mg/Yield: 75%).

$^1$H NMR (400, CDCl$_3$): 7.32 (2H, d), 6.85 (2H, d), 6.06 (1H, d), 4.88 (2H, s), 4.83 (2H, s), 4.21 (2H, d), 3.84 (2H, d), 3.12 (2H, m), 2.92 (1H, m), 2.63-2.53 (4H, m), 2.38 (1H, m), 2.07 (2H, m), 1.97-2.91 (3H, m), 1.44 (2H, m), 1.41 (9H, d)

Example 285: Preparation of (3-(hydroxyimino)azetidin-1-yl)(4-(4-((1-(3-isopropyl-1,2,4-oxadiazol-5-yl)piperidin-4-yl)methoxy)phenyl)cyclohex-3-enyl)methanone

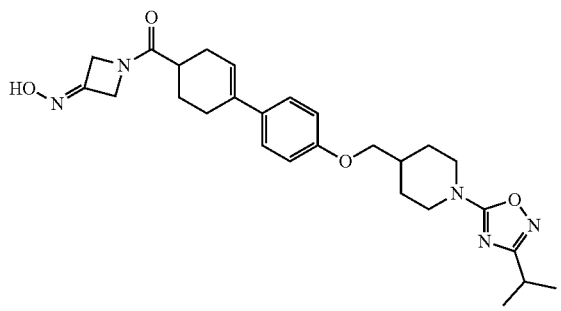 [SMILES: CC(C)c1noc(N2CCC(COc3ccc(C4=CCC(C(=O)N5CC(=NO)C5)CC4)cc3)CC2)n1]

The title compound was prepared in the same manner as in <Example 217>, except that 1-(4-(4-((1-(3-isopropyl-1,2,4-oxadiazol-5-yl)piperidin-4-yl)methoxy)phenyl)cyclohex-3-enecarbonyl)azetidin-3-one was used instead of the 1-(4-(4-((1-(3-isopropyl-1,2,4-oxadiazol-5-yl)piperidin-4-yl)methoxy)phenyl)cyclohex-3-enecarbonyl)piperidine-4-carboxamide (Amount obtained: 184 mg/Yield: 78%).

$^1$H NMR (400, CDCl$_3$): 8.11 (1H, s), 7.32 (2H, d), 6.84 (2H, d), 6.04 (1H, d), 4.87 (2H, d), 4.75 (2H, d), 4.21 (2H, d), 3.84 (2H, d), 3.11 (2H, m), 2.93 (1H, m), 2.58-2.42 (4H, m), 2.30 (1H, m), 2.09-2.02 (2H, m), 1.97-1.89 (3H, m), 1.43 (2H, m), 1.30 (6H, d)

Example 286: Preparation of (4-(4-((1-(3-isopropyl-1,2,4-oxadiazol-5-yl)piperidin-4-yl)methoxy)phenyl)cyclohex-3-enyl)(3-(methoxyimino)azetidin-1-yl)methanone

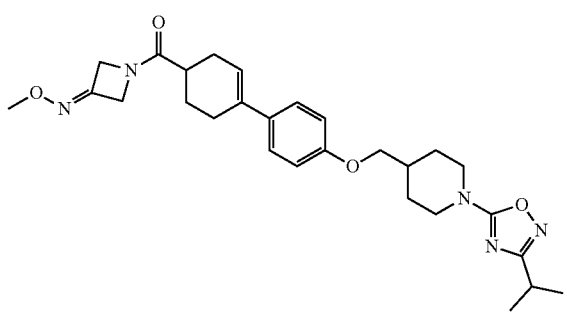 [SMILES: CON=C1CN(C(=O)C2CC=C(c3ccc(OCC4CCN(c5nc(C(C)C)no5)CC4)cc3)CC2)C1]

The title compound was prepared in the same manner as in <Example 217>, except that O-methylhydroxylamine hydrochloride was used instead of the hydroxylamine hydrochloride (Amount obtained: 179 mg/Yield: 71%).

$^1$H NMR (400, CDCl$_3$): 7.32 (2H, d), 6.84 (2H, d), 4.85 (2H, m), 4.69 (2H, m), 4.21 (2H, d), 3.96 (3H, s), 3.84 (2H, d), 3.11 (2H, m), 2.89 (1H, m), 2.59-5.47 (4H, m), 2.29 (1H, m), 2.07-1.89 (5H, m), 1.46 (2H, m), 1.36 (6H, d)

Example 287: Preparation of (4-(4-((1-(5-ethylpyrimidin-2-yl)piperidin-4-yl)methoxy)phenyl)cyclohex-3-enyl)(3-(methoxyimino)azetidin-1-yl)methanone

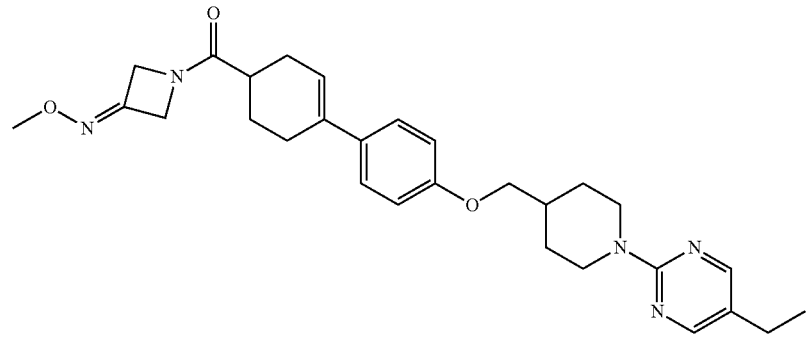 [SMILES: CCc1cnc(N2CCC(COc3ccc(C4=CCC(C(=O)N5CC(=NOC)C5)CC4)cc3)CC2)nc1]

The title compound was prepared in the same manner as in <Example 217>, except that O-methylhydroxylamine hydrochloride was used instead of the hydroxylamine hydrochloride (Amount obtained: 177 mg/Yield: 73%).

¹H NMR (400, CDCl₃): 8.20 (2H, s), 7.29 (2H, d), 6.85 (2H, d), 6.04 (1H, d), 4.85 (2H, s), 4.79 (2H, d), 4.72 (2H, d), 3.96 (3H, s), 3.84 (2H, d), 2.92 (2H, m), 2.55-2.41 (6H, m), 2.28 (1H, m), 2.14-1.92 (5H, m), 1.39 (2H, m), 1.20 (3H, t)

Example 288: Preparation of tert-butyl 4-((4-(4-(3-hydroxyazetidine-1-carbonyl)cyclohex-1-enyl)phenoxy)methyl)piperidine-1-carboxylate

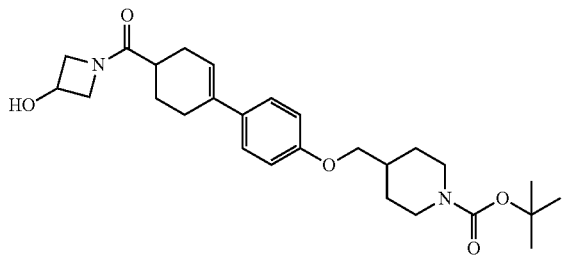 [SMILES: CC(C)(C)OC(=O)N1CCC(COc2ccc(C3=CCC(C(=O)N4CC(O)C4)CC3)cc2)CC1]

470 mg of tert-butyl 4-((4-(4-(3-oxoazetidine-1-carbonyl)cyclohex-1-enyl)phenoxy)methyl)piperidine-1-carboxylate was dissolved in 100 ml of THF in a 1,000 ml flask while stirring under nitrogen. After the resulting mixture was cooled to a temperature of 5° C., 80 mg of sodium borohydride was slowly added dropwise, and the mixture was then stirred for 5 minutes. After the reaction was terminated, 300 ml of distilled water was slowly added thereto, and the mixture was extracted with 500 ml of ethyl acetate, washed with 100 ml of brine, dried with anhydrous magnesium sulfate, concentrated, and then isolated by silica column chromatography to prepare the title compound (Amount obtained: 432 mg/Yield: 71%).

¹H NMR (400, CDCl₃): 7.30 (2H, d), 6.84 (2H, d), 6.03 (1H, d), 4.71 (1H, m), 4.42 (1H, t), 4.28-4.07 (4H, m), 3.92 (1H, dd), 3.81 (2H, d), 2.76 (2H, t), 2.63 (1H, d), 2.52-2.43 (4H, m), 2.27 (1H, m), 2.01-1.82 (5H, m), 1.48 (9H, s), 1.26 (2H, m)

Example 289: Preparation of (3-hydroxyazetidin-1-yl)(4-(4-((1-(3-isopropyl-1,2,4-oxadiazol-5-yl)piperidin-4-yl)methoxy)phenyl)cyclohex-3-enyl)methanone

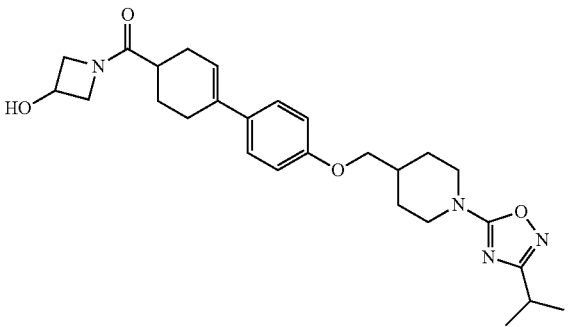 [SMILES: CC(C)c1noc(N2CCC(COc3ccc(C4=CCC(C(=O)N5CC(O)C5)CC4)cc3)CC2)n1]

The title compound was prepared in the same manner as in <Example 288>, except that 1-(4-(4-((1-(3-isopropyl-1,2,4-oxadiazol-5-yl)piperidin-4-yl)methoxy)phenyl)cyclohex-3-enecarbonyl)azetidin-3-one was used instead of the tert-butyl 4-((4-(4-(3-oxoazetidine-1-carbonyl)cyclohex-1-enyl)phenoxy)methyl)piperidine-1-carboxylate (Amount obtained: 402 mg/Yield: 66%).

¹H NMR (400, CDCl₃): 7.30 (2H, d), 6.84 (2H, d), 6.04 (1H, d), 4.70 (1H, m), 4.43 (1H, t), 4.30 (1H, dd), 4.23 (2H, d), 4.09 (1H, m), 3.92 (1H, dd), 3.84 (2H, m), 3.14 (2H, m), 2.97 (2H, d), 2.88 (1H, m), 2.55 (1H, m), 2.53-2.43 (3H, m), 2.27 (1H, m), 2.07-2.02 (1H, m), 1.94 (3H, m), 1.84 (1H, m), 1.44 (2H, m), 1.31 (6H, d)

Example 290: Preparation of ((+)-4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone

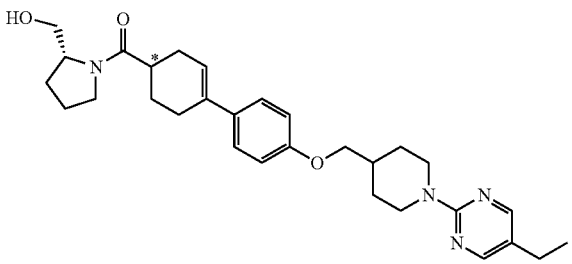 [SMILES: CCc1cnc(N2CCC(COc3ccc(C4=CCC(C(=O)N5CCC[C@@H]5CO)CC4)cc3)CC2)nc1]

The (4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone disclosed in <Example 118> was a mixture of diastereomers. Each of the respective diastereomer was synthesized according to the above Scheme 2.

350 mg ((+)-4-bromocyclohex-3-enyl)((R)-2-(hydroxymethyl)pyrrolidin-1-yl)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 580 mg of 5-ethyl-2-(4-((4-(4,4,5,5-tetramethyl-1,3,2-dioxaborolan-2-yl)phenoxy)methyl)piperidin-1-yl)pyrimidine were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was then extracted with 100 ml of ethyl acetate, washed with 50 ml of brine, dried with anhydrous magnesium sulfate, concentrated, and then isolated by silica column chromatography to obtain the title compound (Amount obtained: 420 mg/Yield: 69%).

¹H NMR (400, CDCl₃): 8.19 (2H, s), 7.31 (2H, d), 6.87 (1H, d), 6.07 (1H, m), 5.21 (2H, d), 4.76 (2H, d), 4.28 (2H, m), 3.83 (2H, d), 3.60 (4H, m), 2.92 (2H, m), 2.72 (7H, m), 2.02 (8H, m), 1.62 (2H, m), 1.34 (2H, m), 1.20 (3H, t)

Example 291: Preparation of ((−)-4-(4-((1-(5-ethyl-pyrimidin-2-yl)piperidin-4-yl)methoxy)phenyl)cyclohex-3-enyl)((R)-2-(hydroxymethyl)pyrrolidin-1-yl)methanone

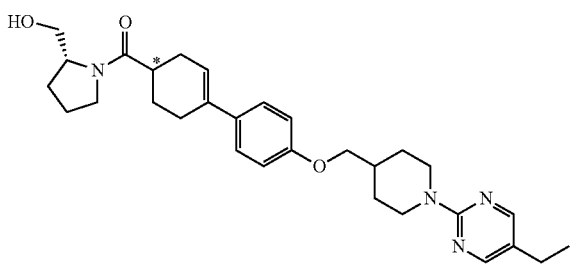 [SMILES: CCc1cnc(N2CCC(COc3ccc(C4=CCC(C(=O)N5CCC[C@@H]5CO)CC4)cc3)CC2)nc1]

350 mg of ((−)-4-bromocyclohex-3-enyl)((R)-2-(hydroxymethyl)pyrrolidin-1-yl)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 580 mg of 5-ethyl-2-(4-((4-(4,4,5,5-tetramethyl-1,3,2-dioxaborolan-2-yl)phenoxy)methyl)piperidin-1-yl)pyrimidine were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was extracted with 100 ml of ethyl acetate, washed with 50 ml of brine, dried with anhydrous magnesium sulfate, concentrated, and then isolated by silica column chromatography to obtain the title compound (Amount obtained: 450 mg/Yield: 71%).

$^1$H NMR (400, CDCl$_3$): 8.18 (2H, s), 7.31 (1H, d), 6.83 (2H, d), 6.04 (1H, m), 5.11 (1H, d), 4.74 (2H, d), 4.26 (1H, m), 3.83 (2H, d), 3.60 (4H, m), 2.93 (2H, m), 2.67 (1H, m), 2.48 (5H, m), 2.30 (1H, m), 2.00 (8H, m), 1.57 (4H, m), 1.35 (2H, m), 1.20 (3H, t)

Example 292: Preparation of (4-(4-((1-(5-ethylpyrimidin-2-yl)piperidin-4-yl)methoxy)-3-fluorophenyl)cyclohex-3-enyl)(piperidin-1-yl)methanone

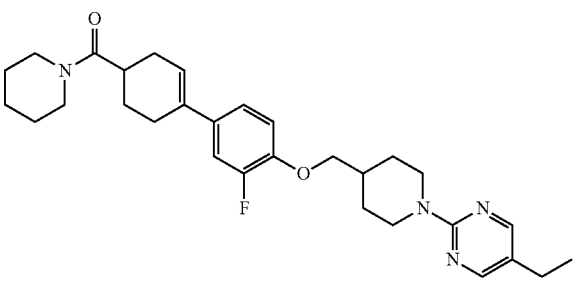 [SMILES: CCc1cnc(N2CCC(COc3ccc(C4=CCC(C(=O)N5CCCCC5)CC4)cc3F)CC2)nc1]

500 mg of 4-(4-((1-(5-ethylpyrimidin-2-yl)piperidin-4-yl)methoxy)-3-fluorophenyl)cyclohex-3-enecarboxylic acid was put into a 100 ml flask under a nitrogen atmosphere, 20 ml of dichloromethane was added thereto, and the resulting mixture was dissolved while stirring. 0.38 ml of triethylamine, 360 mg of piperidine, and 610 mg of HATU were added dropwise thereto. The mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 450 mg/Yield: 74%).

$^1$H NMR (400, CDCl$_3$): 8.18 (2H, s), 7.15 (1H, dd), 7.07 (1H, d), 6.90 (1H, t), 6.07 (1H, m), 4.76 (2H, d), 3.90 (2H, d), 3.54 (4H, m), 2.95 (3H, m), 2.51 (5H, m), 2.30 (1H, m), 2.15 (1H, m), 1.91 (4H, m), 1.57 (8H, m), 1.36 (2H, m), 1.19 (3H, t)

Example 293: Preparation of (4-(4-((1-(5-ethylpyrimidin-2-yl)piperidin-4-yl)methoxy)-3-fluorophenyl)cyclohex-3-enyl)(pyrrolidin-1-yl)methanone

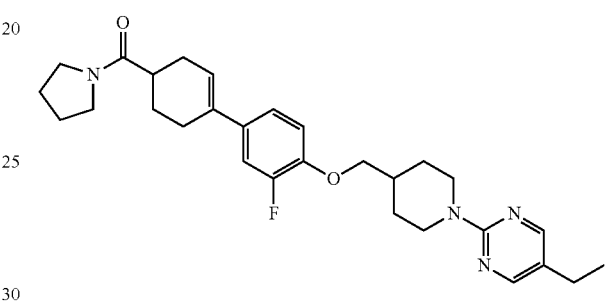

The title compound was prepared in the same manner as in <Example 292>, except that pyrrolidine was used instead of the piperidine (Amount obtained: 480 mg/Yield: 80%).

$^1$H NMR (400, CDCl$_3$): 8.19 (2H, s), 7.12 (2H, dd), 6.90 (1H, t), 6.08 (1H, d), 4.76 (2H, d), 3.89 (2H, d), 3.54 (4H, m), 2.95 (2H, m), 2.47 (6H, m), 2.32 (1H, m), 2.15 (1H, m), 1.91 (8H, m), 1.34 (2H, m), 1.22 (3H, t)

Example 294: Preparation of (4-(4-((1-(5-ethylpyrimidin-2-yl)piperidin-4-yl)methoxy)-3-fluorophenyl)cyclohex-3-enyl)(4-hydroxypiperidin-1-yl)methanone

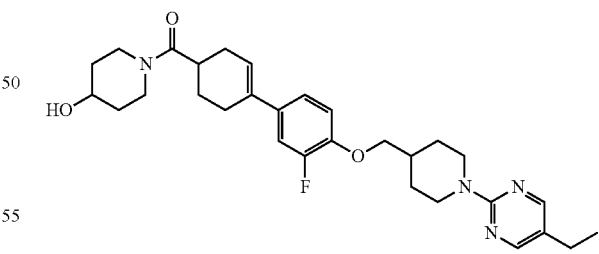

The title compound was prepared in the same manner as in <Example 291>, except that 4-piperidinemethanol was used instead of the piperidine (Amount obtained: 480 mg/Yield: 76%).

$^1$H NMR (400, CDCl$_3$): 8.19 (2H, s), 7.15 (1H, dd), 7.09 (1H, d), 6.90 (1H, t), 6.07 (1H, m), 4.71/6 (3H, m), 4.01 (1H, d), 3.89 (2H, d), 3.50 (2H, m), 2.08 (1H, t), 2.94 (2H, m), 2.80 (1H, m), 2.52 (6H, m), 2.31 (1H, m), 2.15 (1H, m), 1.81 (8H, m), 1.20 (9H, m)

Example 295: Preparation of 1-(4-(4-((1-(5-ethylpy-rimidin-2-yl)piperidin-4-yl)methoxy)-3-fluorophe-nyl)cyclohex-3-enecarbonyl)azetidin-3-one

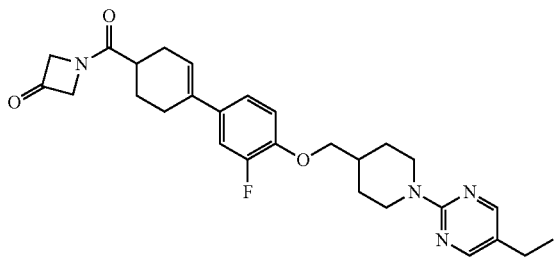 [SMILES: CCc1cnc(N2CCC(COc3ccc(C4=CCC(C(=O)N5CC(=O)C5)CC4)cc3F)CC2)nc1]

The title compound was prepared in the same manner as in <Example 292>, except that azetidin-3-one hydrochloride was used instead of the piperidine (Amount obtained: 325 mg/Yield: 56%).

$^1$H NMR (400, CDCl$_3$): 8.19 (2H, s), 7.23 (1H, dd), 7.09 (1H, d), 6.90 (1H, t), 6.07 (1H, m), 4.80 (6H, m), 3.89 (2H, d), 2.95 (2H, m), 2.50 (7H, m), 2.14 (2H, m), 1.95 (3H, m), 1.33 (2H, m), 1.15 (3H, t)

Example 296: Preparation of (4-(4-((1-(5-ethylpy-rimidin-2-yl)piperidin-4-yl)methoxy)-3-fluorophe-nyl)cyclohex-3-enyl)(4-(2-hydroxyethyl)piperidin-1-yl)methanone

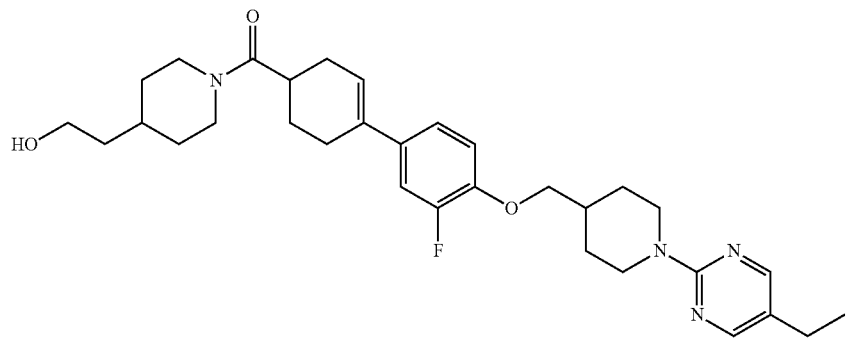 [SMILES: CCc1cnc(N2CCC(COc3ccc(C4=CCC(C(=O)N5CCC(CCO)CC5)CC4)cc3F)CC2)nc1]

The title compound was prepared in the same manner as in <Example 291>, except that 4-piperidineethanol was used instead of the piperidine (Amount obtained: 520 mg/Yield: 77%).

$^1$H NMR (400, CDCl$_3$): 8.19 (2H, s), 7.15 (1H, dd), 7.06 (1H, d), 6.90 (1H, t), 6.07 (1H, m), 4.76 (2H, d), 4.67 (1H, d), 3.99 (1H, d), 3.80 (2H, d), 3.74 (2H, t), 3.07 (1H, t), 2.93 (2H, m), 2.80 (1H, m), 2.51 (7H, m), 2.30 (1H, m), 2.14 (1H, m), 1.70 (14H, m), 1.34 (2H, m), 1.15 (3H, t)

Example 297: Preparation of 1,4'-bipiperidin-1'-yl (4-(4-((1-(5-ethylpyrimidin-2-yl)piperidin-4-yl)methoxy)-3-fluorophenyl)cyclohex-3-enyl)metha-none

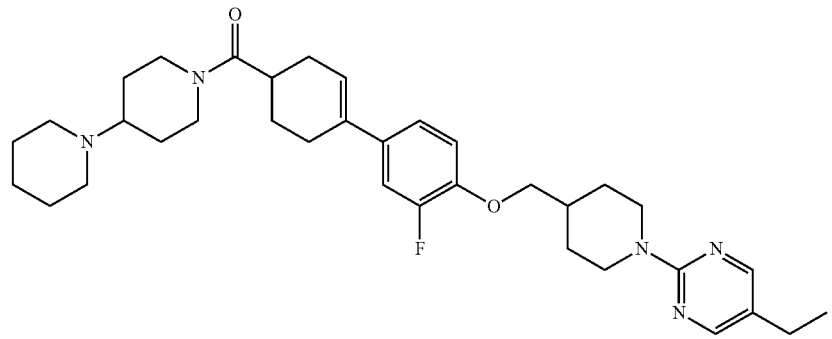 [SMILES: CCc1cnc(N2CCC(COc3ccc(C4=CCC(C(=O)N5CCC(N6CCCCC6)CC5)CC4)cc3F)CC2)nc1]

The title compound was prepared in the same manner as in <Example 292>, except that 4-piperidinopiperidine was used instead of the piperidine (Amount obtained: 480 mg/Yield: 68%).

¹H NMR (400, CDCl₃): 8.18 (2H, s), 7.14 (1H, dd), 7.08 (1H, d), 6.90 (1H, t), 6.06 (1H, m), 4.76 (3H, d), 4.05 (1H, d), 3.89 (2H, d), 3.12 (1H, t), 2.92 (2H, m), 2.65 (12H, t), 2.31 (1H, m), 2.16 (2H, m), 1.67 (11H, m), 1.34 (2H, m), 1.18 (3H, t)

Example 298: Preparation of (4-(4-((1-(5-ethylpy-rimidin-2-yl)piperidin-4-yl)methoxy)-3-fluorophe-nyl)cyclohex-3-enyl)(4-(pyrrolidin-1-yl)piperidin-1-yl)methanone

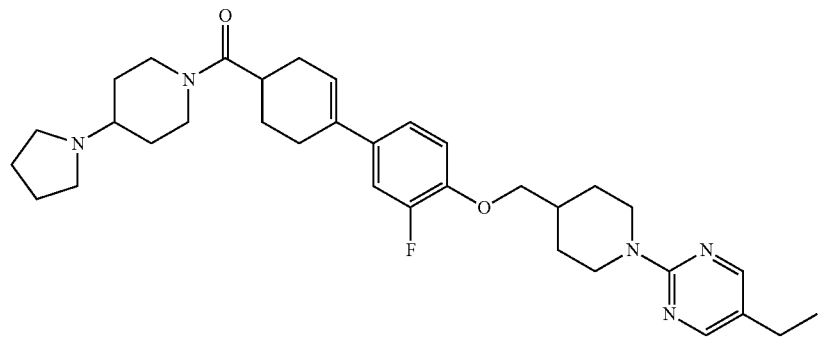 [SMILES: CCc1cnc(N2CCC(COc3ccc(C4=CCC(C(=O)N5CCC(N6CCCC6)CC5)CC4)cc3F)CC2)nc1]

The title compound was prepared in the same manner as in <Example 291>, except that 4-(1-pyrrolidinyl)piperidine was used instead of the piperidine (Amount obtained: 450 mg/Yield: 65%).

¹H NMR (400, CDCl₃): 8.18 (2H, s), 7.14 (1H, dd), 7.08 (1H, d), 6.90 (1H, t), 6.07 (1H, m), 4.76 (2H, d), 4.62 (1H, d), 3.95 (1H, d), 3.89 (2H, d), 3.13 (1H, t), 2.92 (2H, m), 2.55 (12H, m), 2.34 (2H, m), 2.15 (1H, m), 1.84 (11H, m), 1.52 (2H, m), 1.33 (2H, m), 1.18 (3H, t)

Example 299: Preparation of (4-(4-((1-(5-ethylpy-rimidin-2-yl)piperidin-4-yl)methoxy)-3-fluorophe-nyl)cyclohex-3-enyl)(morpholino)methanone

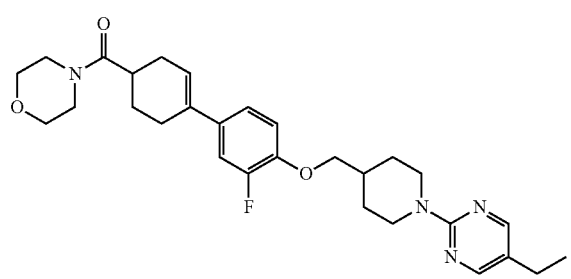

The title compound was prepared in the same manner as in <Example 292>, except that morpholine was used instead of the piperidine (Amount obtained: 520 mg/Yield: 84%).

¹H NMR (400, CDCl₃): 8.19 (2H, s), 7.14 (1H, dd), 7.06 (1H, d), 6.90 (1H, t), 6.07 (1H, m), 4.77 (2H, d), 3.89 (2H, d), 3.61 (8H, m), 2.96 (2H, m), 2.77 (1H, m), 2.50 (5H, m), 2.31 (1H, m), 2.15 (1H, m), 1.91 (4H, m), 1.33 (2H, m), 1.18 (3H, t)

Example 300: Preparation of (4-(4-((1-(5-ethylpy-rimidin-2-yl)piperidin-4-yl)methoxy)-3-fluorophe-nyl)cyclohex-3-enyl)(thiomorpholino)methanone

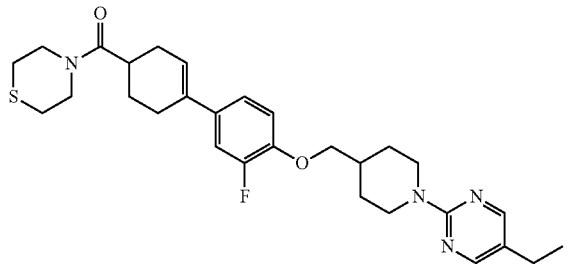 [SMILES: CCc1cnc(N2CCC(COc3ccc(C4=CCC(C(=O)N5CCSCC5)CC4)cc3F)CC2)nc1]

The title compound was prepared in the same manner as in <Example 291>, except that thiomorpholine was used instead of the piperidine (Amount obtained: 520 mg/Yield: 82%).

¹H NMR (400, CDCl₃): 8.19 (2H, s), 7.15 (1H, dd), 7.06 (1H, d), 6.90 (1H, t), 6.07 (1H, m), 4.77 (2H, d), 3.83 (6H, m), 2.93 (2H, m), 2.64 (5H, m), 2.48 (5H, m), 2.31 (1H, m), 2.14 (1H, m), 1.90 (4H, m), 1.34 (2H, m), 1.20 (3H, t)

Example 301: Preparation of azetidin-1-yl(4-(4-((1-(5-ethylpyrimidin-2-yl)piperidin-4-yl)methoxy)-3-fluorophenyl)cyclohex-3-enyl)methanone

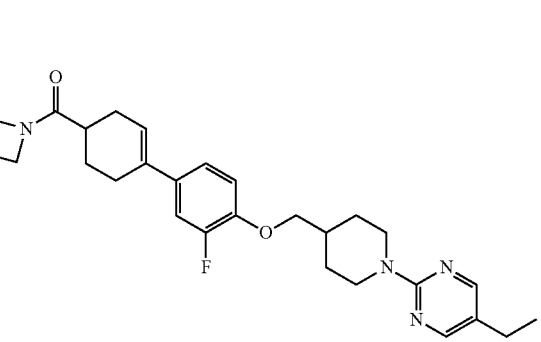

The title compound was prepared in the same manner as in <Example 292>, except that azetidine hydrochloride was used instead of the piperidine (Amount obtained: 380 mg/Yield: 67%).

¹H NMR (400, CDCl₃): 8.18 (2H, s), 7.14 (1H, dd), 7.06 (1H, d), 6.89 (1H, t), 6.07 (1H, m), 4.76 (2H, d), 4.24 (2H, t), 4.06 (2H, t), 3.90 (2H, d), 2.95 (2H, m), 2.41 (10H, m), 2.14 (1H, m), 1.91 (3H, m), 1.83 (1H, m), 1.34 (2H, m0, 1.18 (3H, t)

Example 302: Preparation of N-cyclopropyl-4-(4-((1-(5-ethylpyrimidin-2-yl)piperidin-4-yl)methoxy)-3-fluorophenyl)cyclohex-3-enecarboxamide

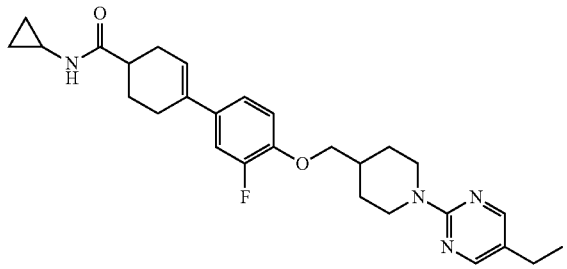 [SMILES: CCc1cnc(N2CCC(COc3ccc(C4=CCC(C(=O)NC5CC5)CC4)cc3F)CC2)nc1]

The title compound was prepared in the same manner as in <Example 291>, except that cyclopropylamine was used instead of the piperidine (Amount obtained: 350 mg/Yield: 61%).

$^1$H NMR (400, CDCl$_3$): 8.19 (2H, s), 7.15 (1H, dd), 7.06 (1H, d), 6.90 (1H, t), 6.07 (1H, m), 4.76 (2H, d), 4.67 (1H, d), 3.99 (1H, d), 3.80 (2H, d), 3.74 (2H, t), 3.07 (1H, t), 2.93 (2H, m), 2.80 (1H, m), 2.51 (7H, m), 2.30 (1H, m), 2.14 (1H, m), 1.70 (14H, m), 1.34 (2H, m), 1.15 (3H, t)

Example 303: Preparation of N-cyclobutyl-4-(4-((1-(5-ethylpyrimidin-2-yl)piperidin-4-yl)methoxy)-3-fluorophenyl)cyclohex-3-enecarboxamide

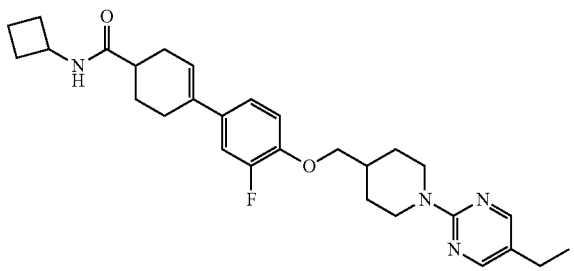

The title compound was prepared in the same manner as in <Example 292>, except that aminocyclobutane was used instead of the piperidine (Amount obtained: 410 mg/Yield: 69%).

$^1$H NMR (400, CDCl$_3$): 8.18 (2H, s), 7.13 (1H, dd), 7.05 (1H, d), 6.89 (1H, t), 6.06 (1H, m), 5.48 (1H, d), 4.79 (2H, d), 4.22 (1H, m), 3.89 (2H, m), 2.95 (2H, m), 2.46 (7H, m), 2.01 (7H, m), 1.63 (6H, m), 1.37 (4H, m), 1.22 (3H, t)

Example 304: Preparation of N-cyclopentyl-4-(4-((1-(5-ethylpyrimidin-2-yl)piperidin-4-yl)methoxy)-3-fluorophenyl)cyclohex-3-enecarboxamide

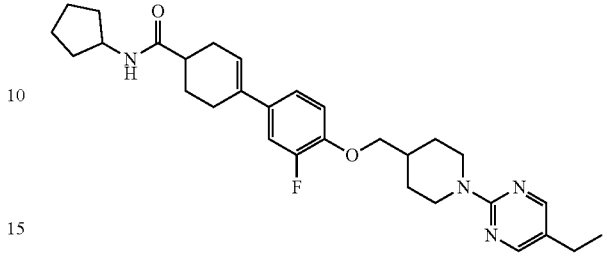

The title compound was prepared in the same manner as in <Example 292>, except that cyclopentylamine was used instead of the piperidine (Amount obtained: 450 mg/Yield: 74%).

$^1$H NMR (400, CDCl$_3$): 8.18 (2H, s), 7.14 (1H, dd), 7.08 (1H, d), 6.89 (1H, t), 6.06 (1H, m), 5.68 (1H, d), 4.76 (2H, d), 4.43 (1H, m), 3.95 (2H, d), 2.92 (2H, m), 2.41 (9H, m), 2.11 (2H, m), 1.98 (2H, m), 1.86 (3H, m), 1.73 (2H, m), 1.34 (2H, m), 1.20 (3H, t)

Example 305: Preparation of N-cyclohexyl-4-(4-((1-(5-ethylpyrimidin-2-yl)piperidin-4-yl)methoxy)-3-fluorophenyl)cyclohex-3-enecarboxamide

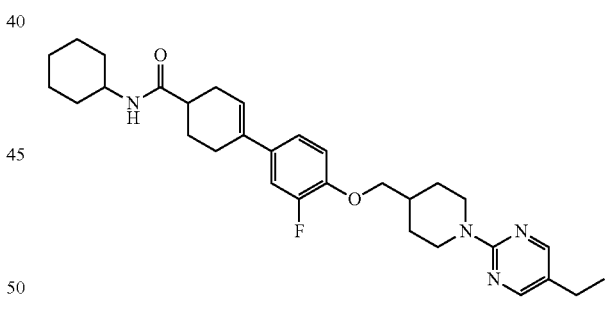

The title compound was prepared in the same manner as in <Example 292>, except that cyclohexylamine was used instead of the piperidine (Amount obtained: 440 mg/Yield: 70%).

$^1$H NMR (400, CDCl$_3$): 8.18 (2H, s), 7.13 (1H, dd), 7.06 (1H, d), 6.87 (1H, t), 6.07 (1H, m), 5.40 (1H, d), 4.76 (2H, d), 3.90 (2H, d), 3.82 (1H, m), 2.92 (2H, m), 2.48 (7H, m), 2.14 (2H, m), 1.93 (5H, m), 1.72 (2H, m), 1.68 (3H, s), 1.40 (4H, m), 1.16 (6H, m)

Example 306: Preparation of (4-(4-((1-(5-ethylpyrimidin-2-yl)piperidin-4-yl)methoxy)-3-fluorophenyl)cyclohex-3-enyl)(1,4-dioxa-8-azaspiro[4.5]decan-8-yl)methanone

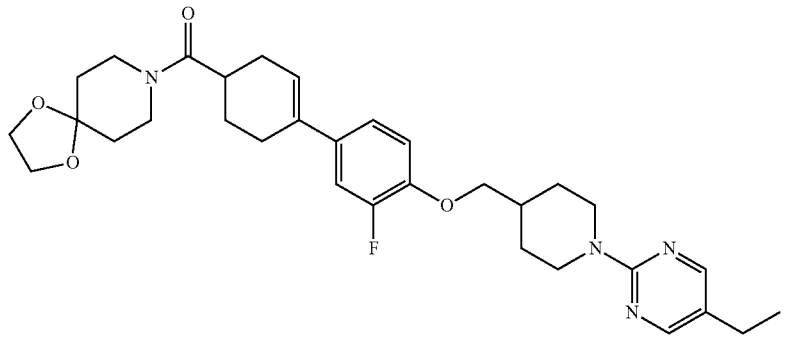 [SMILES: CCc1cnc(N2CCC(COc3ccc(C4=CCC(C(=O)N5CCC6(CC5)OCCO6)CC4)cc3F)CC2)nc1]

The title compound was prepared in the same manner as in <Example 292>, except that 4-piperidone ethylene ketal was used instead of the piperidine (Amount obtained: 490 mg/Yield: 72%).

*2140 $^1$H NMR (400, CDCl$_3$): 8.18 (2H, s), 7.14 (1H, dd), 7.08 (1H, d), 6.90 (1H, t), 6.07 (1H, m), 4.76 (2H, d), 4.03 (4H, s), 3.89 (2H, d), 3.73 (2H, m), 3.61 (2H, m), 2.95 (2H, m), 2.82 (1H, m), 2.49 (6H, m), 2.32 (1H, m), 2.16 (1H, m), 1.92 (5H, m), 1.73 (4H, m), 1.33 (2H, m), 1.20 (3H, t)

Example 307: Preparation of 4-(4-((1-(5-ethylpyrimidin-2-yl)piperidin-4-yl) methoxy)-3-fluorophenyl)-N-(2,2,2-trifluoroethyl)cyclohex-3-enecarboxamide

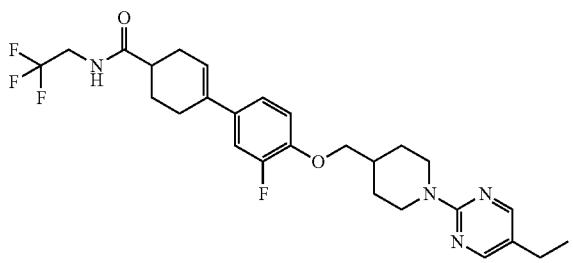 [SMILES: CCc1cnc(N2CCC(COc3ccc(C4=CCC(C(=O)NCC(F)(F)F)CC4)cc3F)CC2)nc1]

The title compound was prepared in the same manner as in <Example 292>, except that 2,2,2-trifluoroethylamine was used instead of the piperidine (Amount obtained: 430 mg/Yield: 69%).

$^1$H NMR (400, CDCl$_3$): 8.19 (2H, s), 7.14 (1H, dd), 7.07 (1H, d), 6.90 (1H, t), 6.06 (1H, m), 5.81 (1H, t), 4.77 (2H, d), 4.00 (2H, m), 3.81 (2H, d), 2.93 (2H, m), 2.44 (7H, m), 2.14 (2H, m), 1.95 (3H, m), 1.34 (2H, m), 1.20 (3H, t)

Example 308: Preparation of 1-(4-(4-((1-(5-ethylpyrimidin-2-yl)piperidin-4-yl)methoxy)-3-fluorophenyl)cyclohex-3-enecarbonyl)piperidin-4-one

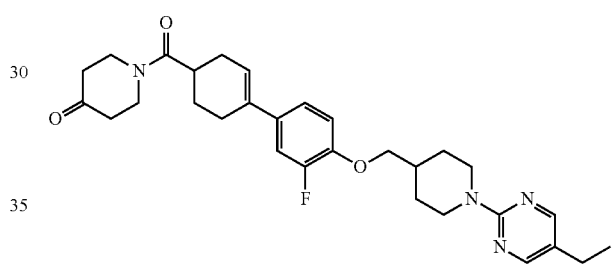

The title compound was prepared in the same manner as in <Example 292>, except that 4-piperidone was used instead of the piperidine (Amount obtained: 450 mg/Yield: 72%).

$^1$H NMR (400, CDCl$_3$): 8.18 (2H, s), 7.14 (1H, dd), 7.07 (1H, d), 6.88 (1H, t), 6.08 (1H, m), 4.76 (2H, d), 3.92 (1H, d), 2.90 (3H, m), 2.50 (9H, m), 2.34 (1H, m), 2.16 (1H, m), 2.06 (1H, m), 1.94 (3H, m), 1.33 (2H, m), 1.18 (3H, t)

Example 309: Preparation of (4-(4-((1-(5-ethylpyrimidin-2-yl)piperidin-4-yl)methoxy)-3-fluorophenyl)cyclohex-3-enyl)(3-hydroxyazetidin-1-yl)methanone

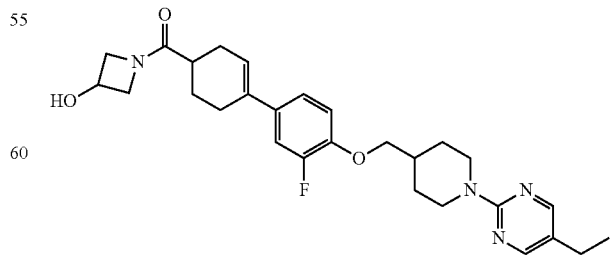

The title compound was prepared in the same manner as in <Example 292>, except that 3-hydroxyazetidine hydrochloride was used instead of the piperidine (Amount obtained: 400 mg/Yield: 67%).

$^1$H NMR (400, CDCl$_3$): 8.19 (2H, s), 7.14 (1H, dd), 7.06 (1H, d), 6.90 (1H, t), 6.07 (1H, m), 4.76 (3H, m), 4.44 (1H, m), 4.30 (1H, m), 4.07 (1H, m), 3.90 (3H, m), 2.95 (2H, m), 2.48 (6H, m), 2.31 (2H, m), 2.16 (2H, m), 1.97 (3H, m), 1.86 (1H, m), 1.35 (2H, m), 1.18 (3H, t)

Example 310: Preparation of tert-butyl 4-((6-(4-(4-hydroxypiperidine-1-carbonyl)cyclohex-1-enyl)pyridin-3-yloxy)methyl)piperidine-1-carboxylate

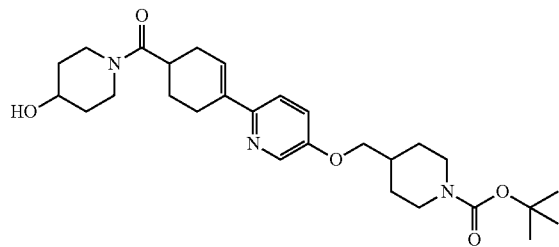

500 mg of 4-(5-((1-(tert-butoxycarbonyl)piperidin-4-yl)methoxy)pyridin-2-yl)cyclohex-3-enecarboxylic acid was put into a 100 ml flask under a nitrogen atmosphere, 20 ml of dichloromethane was added thereto, and the resulting mixture was dissolved while stirring. 0.35 ml of triethylamine, 360 mg of 4-hydroxypiperidine, and 585 mg of HATU were added dropwise thereto. The mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 450 mg/Yield: 75%).

$^1$H NMR (400, CDCl$_3$): 8.23 (2H, d), 7.31 (1H, t), 7.14 (1H, dd), 6.56 (1H, m), 4.18 (3H, m), 3.97 (1H, m), 3.84 (3H, m), 3.28 (2H, m), 2.77 (4H, m), 2.53 (2H, m), 2.35 (1H, m), 1.78 (9H, m), 1.54 (11H, m), 1.21 (2H, m)

Example 311: Preparation of tert-butyl 4-((6-(4-(piperidine-1-carbonyl)cyclohex-1-enyl)pyridin-3-yloxy)methyl)piperidine-1-carboxylate

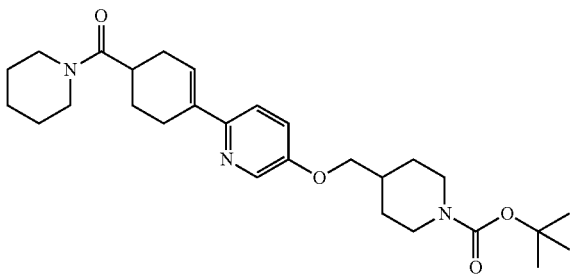 [SMILES: CC(C)(C)OC(=O)N1CCC(COc2ccc(C3=CCC(C(=O)N4CCCCC4)CC3)nc2)CC1]

The title compound was prepared in the same manner as in <Example 310>, except that piperidine was used instead of the 4-hydroxypiperidine (Amount obtained: 480 mg/Yield: 82%).

$^1$H NMR (400, CDCl$_3$): 8.24 (2H, d), 7.32 (1H, d), 7.14 (1H, dd), 6.57 (1H, m), 4.18 (2H, m), 3.85 (2H, d), 3.61 (4H, m), 2.81 (4H, m), 2.53 (3H, m), 1.81 (5H, m), 1.64 (9H, m), 1.43 (9H, m), 1.25 (2H, m)

Example 312: Preparation of tert-butyl 4-((6-(4-(pyrrolidine-1-carbonyl)cyclohex-1-enyl)pyridin-3-yloxy)methyl)piperidine-1-carboxylate

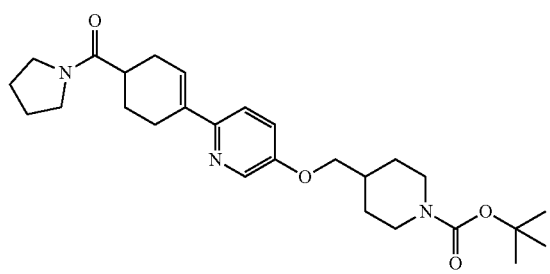 [SMILES: CC(C)(C)OC(=O)N1CCC(COc2ccc(C3=CCC(C(=O)N4CCCC4)CC3)nc2)CC1]

The title compound was prepared in the same manner as in <Example 310>, except that pyrrolidine was used instead of the 4-hydroxypiperidine (Amount obtained: 490 mg/Yield: 86%).

$^1$H NMR (400, CDCl$_3$): 8.19 (2H, s), 7.15 (1H, dd), 7.06 (1H, d), 6.90 (1H, t), 6.07 (1H, m), 4.76 (2H, d), 4.67 (1H, d), 3.99 (1H, d), 3.80 (2H, d), 3.74 (2H, t), 3.07 (1H, t), 2.93 (2H, m), 2.80 (1H, m), 2.51 (7H, m), 2.30 (1H, m), 2.14 (1H, m), 1.70 (14H, m), 1.34 (2H, m), 1.15 (3H, t)

Example 313: Preparation of 4-(4-((1-(5-ethylpyrimidin-2-yl)piperidin-4-yl)methoxy)-3-fluorophenyl)-N-(2-hydroxyethyl)cyclohex-3-enecarboxamide

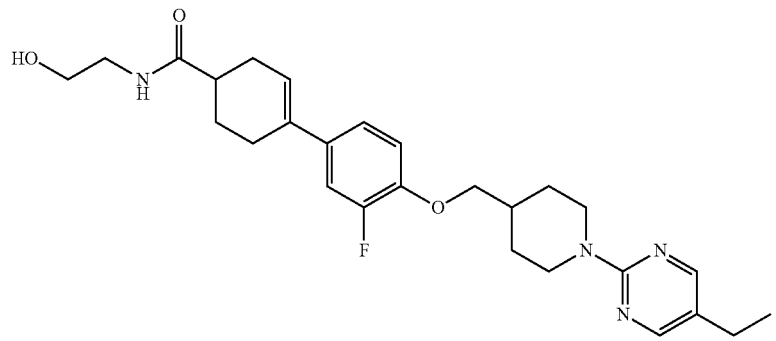 [SMILES: CCc1cnc(N2CCC(COc3ccc(C4=CCC(C(=O)NCCO)CC4)cc3F)CC2)nc1]

The title compound was prepared in the same manner as in <Example 292>, except that 2-aminoethanol was used instead of the piperidine (Amount obtained: 420 mg/Yield: 72%).

$^1$H NMR (400, CDCl$_3$): 8.18 (2H, s), 7.13 (1H, dd), 7.05 (1H, d), 6.89 (1H, t), 6.06 (2H, s), 4.76 (2H, d), 3.88 (2H, d), 3.75 (2H, m), 3.48 (2H, m), 2.94 (2H, m), 2.61 (1H, m), 2.47 (7H, m), 2.11 (2H, m), 1.90 (3H, m), 1.36 (2H, m), 1.21 (3H, t)

Example 314: Preparation of N-(2,2-difluoroethyl)-4-(4-((1-(5-ethylpyrimidin-2-yl)piperidin-4-yl)methoxy)-3-fluorophenyl)cyclohex-3-enecarboxamide

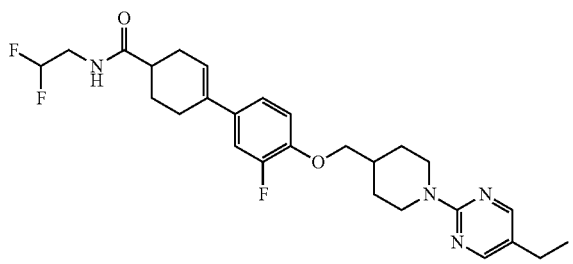 [SMILES: CCc1cnc(N2CCC(COc3ccc(C4=CCC(C(=O)NCC(F)F)CC4)cc3F)CC2)nc1]

The title compound was prepared in the same manner as in <Example 292>, except that 2,2-difluoroethylamine was used instead of the piperidine (Amount obtained: 330 mg/Yield: 55%).

$^1$H NMR (400, CDCl$_3$): 8.19 (2H, s), 7.14 (1H, dd), 7.06 (1H, d), 6.90 (1H, t), 6.03 (1H, m), 5.82 (2H, m), 4.77 (2H, d), 3.90 (2H, d), 3.69 (2H, m), 2.92 (2H, m), 2.44 (7H, m), 2.13 (2H, m), 191 (3H, m), 1.37 (2H, m), 1.21 (3H, t)

Example 315: Preparation of (4-(6-((1-(3-isopropyl-1,2,4-oxadiazol-5-yl)piperidin-4-yl)methoxy)pyridin-3-yl)cyclohex-3-enyl)(pyrrolidin-1-yl)methanone

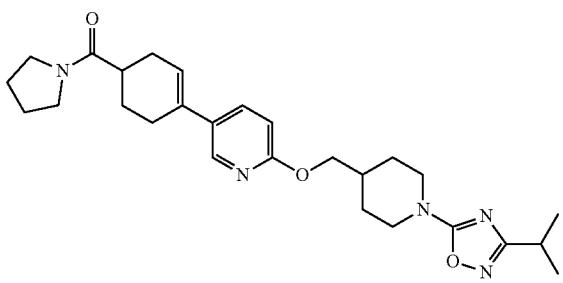 [SMILES: CC(C)c1noc(N2CCC(COc3ccc(C4=CCC(C(=O)N5CCCC5)CC4)cn3)CC2)n1]

500 mg of 4-(6-((1-(3-isopropyl-1,2,4-oxadiazol-5-yl)piperidin-4-yl)methoxy)pyridin-3-yl)cyclohex-3-enecarboxylic acid was put into a 100 ml flask under a nitrogen atmosphere, 20 ml of dichloromethane was added thereto, and the resulting mixture was then dissolved while stirring. 0.31 ml of triethylamine, 300 mg of pyrrolidine, and 540 mg of HATU were added dropwise thereto. The resulting mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 470 mg/Yield: 81%).

$^1$H NMR (400, CDCl$_3$): 8.14 (1H, d), 7.61 (1H, dd), 6.68 (1H, d), 6.07 (1H, m), 4.20 (4H, m), 3.51 (4H, m), 3.12 (3H, m), 2.98 (1H, s), 2.88 (1H, m), 2.66 (1H, m), 2.55 (2H, m), 2.47 (1H, m), 2.34 (1H, m), 2.04 (6H, m), 1.88 (5H, m), 1.43 (5H, m), 1.30 (6H, d)

Example 316: Preparation of (4-(6-((1-(3-isopropyl-1,2,4-oxadiazol-5-yl)piperidin-4-yl)methoxy)pyridin-3-yl)cyclohex-3-enyl)(piperidin-1-yl)methanone

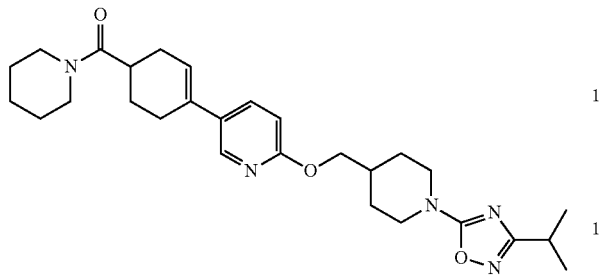

The title compound was prepared in the same manner as in <Example 315>, except that piperidine was used instead of the pyrrolidine (Amount obtained: 440 mg/Yield: 74%).

$^1$H NMR (400, CDCl$_3$): 8.14 (1H, d), 7.61 (1H, dd), 6.68 (1H, d), 6.06 (1H, m), 4.21 (4H, m), 3.60 (2H, m), 3.51 (2H, m), 3.13 (2H, m), 2.92 (1H, m), 2.86 (1H, m), 2.50 (3H, m), 2.05 (5H, m), 1.66 (3H, m), 1.46 (2H, m), 1.30 (6H, t)

Example 317: Preparation of (4-(6-((1-(3-isopropyl-1,2,4-oxadiazol-5-yl)piperidin-4-yl)methoxy)pyridin-3-yl)cyclohex-3-enyl)(morpholino)methanone

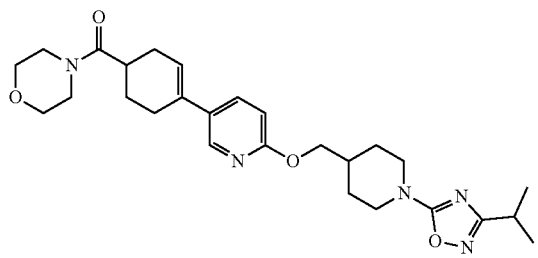 [SMILES: CC(C)c1noc(N2CCC(COc3ccc(C4=CCC(C(=O)N5CCOCC5)CC4)cn3)CC2)n1]

The title compound was prepared in the same manner as in <Example 315>, except that morpholine was used instead of the pyrrolidine (Amount obtained: 440 mg/Yield: 74%).

$^1$H NMR (400, CDCl$_3$): 8.13 (1H, d), 7.61 (1H, dd), 7.69 (1H, d), 6.05 (1H, m), 4.18 (4H, m), 3.70 (6H, m), 3.57 (2H, m), 3.13 (2H, m), 2.92 (1H, m), 2.86 (1H, m), 2.52 (3H, m), 2.30 (1H, m), 2.02 (5H, m), 1.44 (2H, m), 1.29 (6H, d)

Example 318: Preparation of (4-(6-((1-(3-isopropyl-1,2,4-oxadiazol-5-yl)piperidin-4-yl)methoxy)pyridin-3-yl)cyclohex-3-enyl)(thiomorpholino)methanone

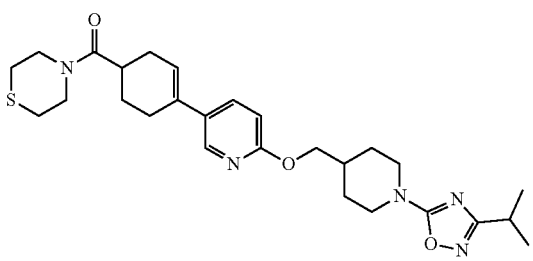 [SMILES: CC(C)c1noc(N2CCC(COc3ccc(C4=CCC(C(=O)N5CCSCC5)CC4)cn3)CC2)n1]

The title compound was prepared in the same manner as in <Example 315>, except that thiomorpholine was used instead of the pyrrolidine (Amount obtained: 410 mg/Yield: 67%).

$^1$H NMR (400, CDCl$_3$): 8.13 (1H, d), 7.61 (1H, dd), 6.69 (1H, d), 6.05 (1H, d), 4.20 (4H, m), 3.97 (1H, m), 3.85 (3H, m), 3.11 (2H, m), 2.92 (1H, m), 2.81 (1H, m), 2.68 (4H, m), 2.51 (3H, m), 2.31 (1H, m), 2.00 (5H, m), 1.44 (2H, m), 1.29 (6H, d)

Example 319: Preparation of 1-(4-(6-((1-(3-isopropyl-1,2,4-oxadiazol-5-yl)piperidin-4-yl)methoxy)pyridin-3-yl)cyclohex-3-enecarbonyl)piperidine-4-carbonitrile

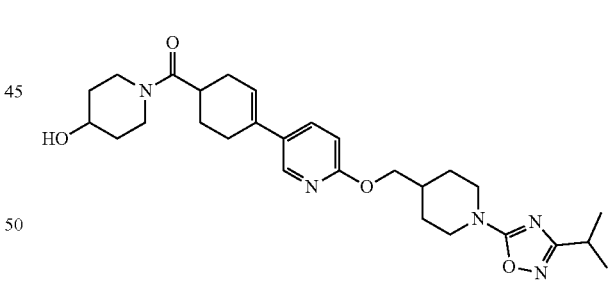

The title compound was prepare in the same manner as in <Example 315>, except that 4-hydroxypiperidine was used instead of the pyrrolidine (Amount obtained: 450 mg/Yield: 73%).

$^1$H NMR (400, CDCl$_3$): 8.13 (1H, d), 7.61 (1H, dd), 6.69 (1H, d), 6.06 (1H, s), 4.21 (5H, m), 3.98 (1H, m), 3.84 (1H, m), 3.31 (2H, m), 3.13 (2H, m), 2.92 (1H, m), 2.85 (1H, m), 2.51 (2H, m), 2.33 (1H, m), 2.10 (7H, m), 1.65 (6H, m), 1.54 (2H, m), 1.44 (2H, m), 1.29 (6H, d)

Example 320: Preparation of (4-(2-hydroxyethyl)piperidin-1-yl)(4-(6-((1-(3-isopropyl-1,2,4-oxadiazol-5-yl)piperidin-4-yl)methoxy)pyridin-3-yl)cyclohex-3-enyl)methanone

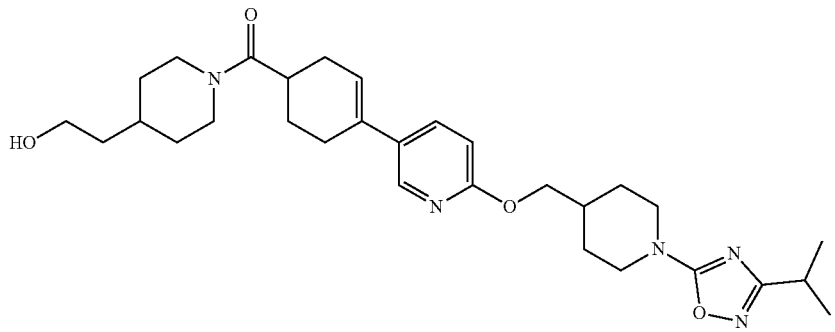 [SMILES: CC(C)c1noc(N2CCC(COc3ccc(C4=CCC(C(=O)N5CCC(CCO)CC5)CC4)cn3)CC2)n1]

The title compound was prepared in the same manner as in <Example 315>, except that 4-piperidineethanol was used instead of the pyrrolidine (Amount obtained: 500 mg/Yield: 77%).

$^1$H NMR (400, CDCl$_3$): 8.13 (1H, d), 7.61 (1H, dd), 6.68 (1H, d), 6.05 (1H, d), 4.66 (1H, d), 4.19 (4H, m), 3.96 (1H, d), 3.72 (2H, s), 3.10 (3H, m), 2.91 (1H, m), 2.81 (2H, m), 2.31 (4H, m), 2.27 (1H, m), 1.93 (5H, m), 1.82 (4H, m), 1.68 (2H, s), 1.55 (2H, m), 1.42 (3H, m), 1.29 (6H, d), 1.16 (2H, m)

Example 321: Preparation of 1-(4-(4-((1-(5-ethylpyrimidin-2-yl)piperidin-4-yl)methoxy)-3-fluorophenyl)cyclohex-3-enecarbonyl)piperidine-4-carbonitrile

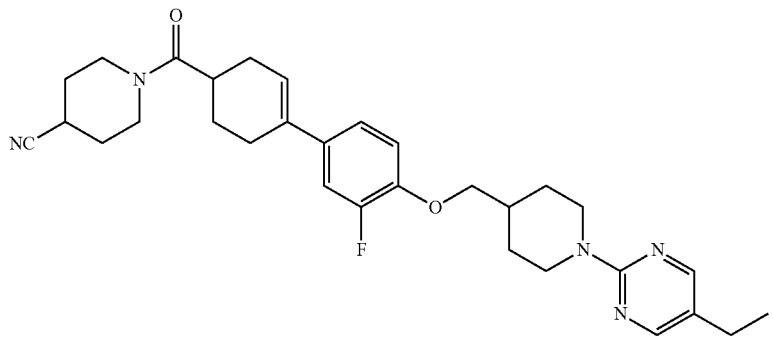 [SMILES: CCc1cnc(N2CCC(COc3ccc(C4=CCC(C(=O)N5CCC(C#N)CC5)CC4)cc3F)CC2)nc1]

The title compound was prepared in the same manner as in <Example 292>, except that piperidine-4-carbonitrile was used instead of the piperidine (Amount obtained: 490 mg/Yield: 76%).

$^1$H NMR (400, CDCl$_3$): 8.18 (1H, d), 7.10 (2H, m), 6.90 (1H, t), 6.07 (1H, s), 4.76 (2H, d), 3.70 (6H, m), 2.92 (3H, m), 2.77 (1H, m), 2.49 (5H, m), 2.31 (1H, m), 2.15 (1H, m), 1.92 (8H, m), 1.34 (2H, m), 1.20 (3H, t)

Example 322: Preparation of 4-(4-((1-(5-ethylpyrimidin-2-yl)piperidin-4-yl)methoxy)-3-fluorophenyl)-N-(2-fluoroethyl)cyclohex-3-enecarboxamide

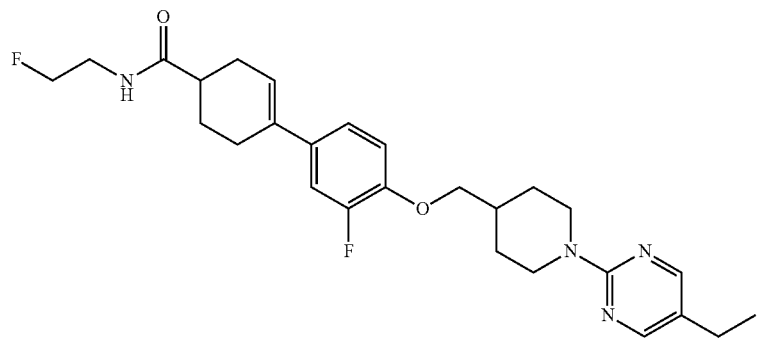 [SMILES: CCc1cnc(N2CCC(COc3ccc(C4=CCC(C(=O)NCCF)CC4)cc3F)CC2)nc1]

The title compound was prepared in the same manner as in <Example 292>, except that 2-fluoroethylamine hydrochloride was used instead of the piperidine (Amount obtained: 380 mg/Yield: 65%).

$^1$H NMR (400, CDCl$_3$): 8.18 (2H, s), 7.14 (1H, dd), 7.08 (1H, m), 6.90 (1H, t), 6.07 (1H, m), 5.95 (1H, m), 4.76 (2H, d), 4.59 (1H, t), 4.47 (1H, t), 3.89 (2H, d), 3.64 (1H, t), 3.58 (1H, t), 2.47 (7H, m), 2.15 (2H, m), 1.89 (3H, m), 1.33 (2H, m), 1.20 (3H, t)

Example 323: Preparation of 4-(4-((1-(5-ethylpyrimidin-2-yl)piperidin-4-yl)methoxy)-3-fluorophenyl)-N,N-bis(2-hydroxyethyl)cyclohex-3-enecarboxamide

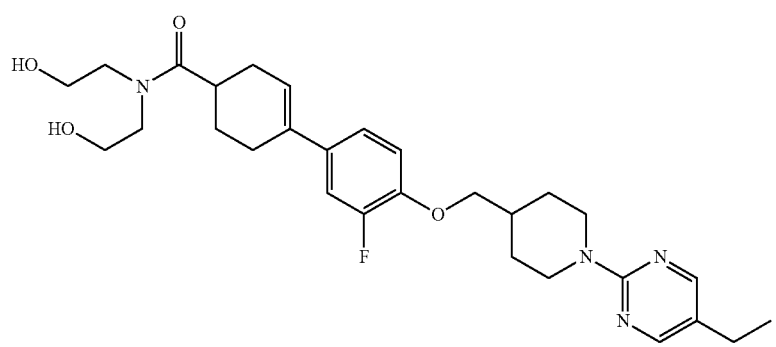 [SMILES: CCc1cnc(N2CCC(COc3ccc(C4=CCC(C(=O)N(CCO)CCO)CC4)cc3F)CC2)nc1]

The title compound was prepared in the same manner as in <Example 292>, except that diethanolamine was used instead of the piperidine (Amount obtained: 350 mg/Yield: 56%).

$^1$H NMR (400, CDCl$_3$): 8.18 (2H, s), 7.14 (1H, dd), 7.06 (1H, m), 6.90 (1H, t), 6.07 (1H, m), 4.76 (2H, d), 3.85 (6H, m), 3.62 (4H, m), 3.13 (2H, m), 2.92 (4H, m), 2.50 (6H, m), 2.15 (1H, m), 1.97 (4H, m), 1.36 (2H, m), 1.20 (3H, t)

Example 324: Preparation of 1-(4-(4-((1-(5-ethylpyrimidin-2-yl)piperidin-4-yl)methoxy)-3-fluorophenyl)cyclohex-3-enecarbonyl)piperidine-4-carboxamide

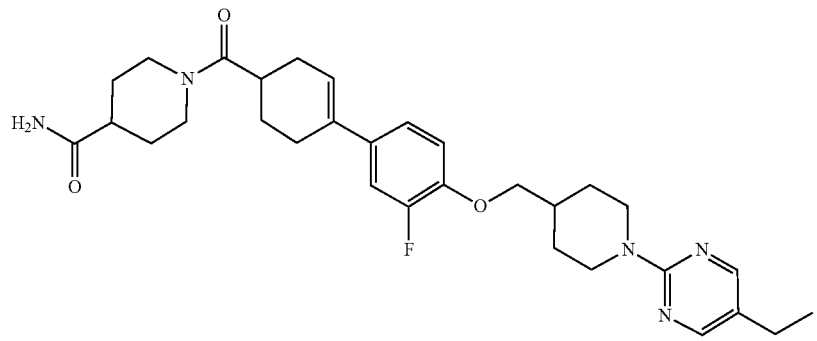 [SMILES: CCc1cnc(N2CCC(COc3ccc(C4=CCC(C(=O)N5CCC(C(N)=O)CC5)CC4)cc3F)CC2)nc1]

The title compound was prepared in the same manner as in <Example 292>, except that isonipecotamide was used instead of the piperidine (Amount obtained: 380 mg/Yield: 58%).

$^1$H NMR (400, CDCl$_3$): 8.18 (2H, s), 7.14 (1H, dd), 7.06 (1H, m), 6.90 (1H, t), 6.07 (1H, m), 5.95 (1H, m), 4.76 (2H, d), 4.59 (1H, t), 4.47 (1H, t), 3.89 (2H, d), 3.64 (1H, t), 3.58 (1H, t), 2.47 (7H, m), 2.15 (2H, m), 1.89 (3H, m), 1.33 (2H, m), 1.20 (3H, t)

Example 325: Preparation of tert-butyl 4-((6-(4-(4-(hydroxymethyl)piperidine-1-carbonyl)cyclohex-1-enyl)pyridin-3-yloxy)methyl)piperidine-1-carboxylate

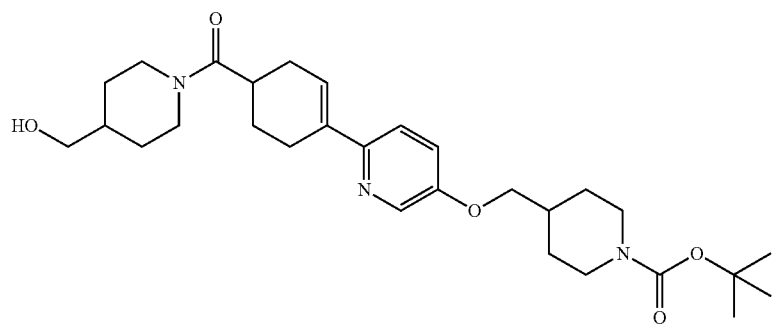 [SMILES: CC(C)(C)OC(=O)N1CCC(COc2ccc(C3=CCC(C(=O)N4CCC(CO)CC4)CC3)nc2)CC1]

The title compound was prepared in the same manner as in <Example 310>, except that 4-piperidinemethanol was used instead of the 4-hydroxypiperidine (Amount obtained: 400 mg/Yield: 65%).

$^1$H NMR (400, CDCl$_3$): 8.23 (1H, d), 7.31 (1H, d), 7.14 (1H, dd), 6.56 (1H, d), 6.90 (1H, t), 4.75 (1H, d), 4.20 (2H, s), 4.03 (1H, d), 3.85 (2H, d), 3.56 (2H, m), 3.11 (1H, t), 2.79 (4H, m), 2.59 (3H, m), 2.36 (1H, m), 1.95 (8H, m), 1.47 (11H, m), 1.20 (4H, m)

Example 326: Preparation of tert-butyl 4-((6-(4-(4-(2-hydroxyethyl)piperidine-1-carbonyl)cyclohex-1-enyl)pyridin-3-yloxy)methyl)piperidine-1-carboxylate

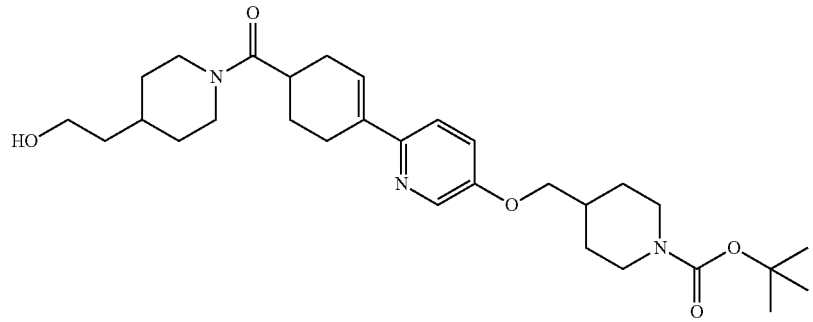 [SMILES: CC(C)(C)OC(=O)N1CCC(COc2ccc(C3=CCC(C(=O)N4CCC(CCO)CC4)CC3)nc2)CC1]

The title compound was prepared in the same manner as in <Example 310>, except that 4-piperidineethanol was used instead of the 4-hydroxypiperidine (Amount obtained: 450 mg/Yield: 71%).
$^1$H NMR (400, CDCl$_3$): 8.23 (1H, d), 7.31 (1H, d), 7.14 (1H, dd), 6.57 (1H, s), 4.67 (1H, d), 4.17 (2H, m), 3.95 (1H, d), 3.86 (2H, d), 3.74 (2H, t), 3.10 (1H, t), 2.82 (4H, m), 2.50 (5H, m), 1.80 (9H, m), 1.55 (18H, m), 1.21 (6H, m)

Example 327: Preparation of tert-butyl 4-((6-(4-(morpholine-4-carbonyl)cyclohex-1-enyl)pyridin-3-yloxy)methyl)piperidine-1-carboxylate

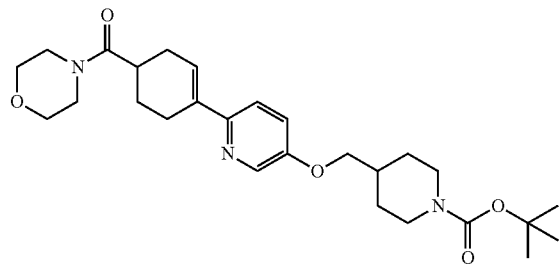 [SMILES: CC(C)(C)OC(=O)N1CCC(COc2ccc(C3=CCC(C(=O)N4CCOCC4)CC3)nc2)CC1]

The title compound was prepared in the same manner as in <Example 310>, except that morpholine was used instead of the 4-hydroxypiperidine (Amount obtained: 460 mg/Yield: 79%).
$^1$H NMR (400, CDCl$_3$): 8.25 (1H, d), 7.33 (1H, d), 7.15 (1H, dd), 6.56 (1H, m), 4.16 (2H, s), 3.85 (2H, d), 3.67 (8H, m), 2.80 (4H, m), 2.51 (3H, m), 2.00 (6H, m), 1.46 (9H, s), 1.28 (2H, m)

Example 328: Preparation of tert-butyl 4-((6-(4-(thiomorpholine-4-carbonyl)cyclohex-1-enyl)pyridin-3-yloxy)methyl)piperidine-1-carboxylate

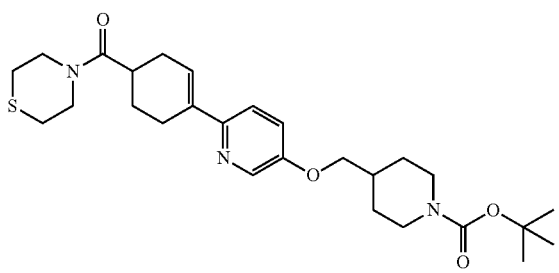 [SMILES: CC(C)(C)OC(=O)N1CCC(COc2ccc(C3=CCC(C(=O)N4CCSCC4)CC3)nc2)CC1]

The title compound was prepared in the same manner as in <Example 310>, except that thiomorpholine was used instead of the 4-hydroxypiperidine (Amount obtained: 420 mg/Yield: 70%).
$^1$H NMR (400, CDCl$_3$): 8.24 (2H, d), 7.31 (1H, d), 7.14 (1H, dd), 6.56 (1H, m), 4.17 (2H, s), 3.86 (12H, m), 2.67 (20H, m), 2.32 (2H, m), 1.93 (10H, m), 1.64 (5H, m), 1.47 (18H, s), 1.27 (4H, m)

Example 329: Preparation of (4-(hydroxymethyl)piperidin-1-yl)(4-(5-(((1-(3-isopropyl-1,2,4-oxadiazol-5-yl)piperidin-4-yl)methoxy)pyridin-2-yl)cyclohex-3-enyl)methanone

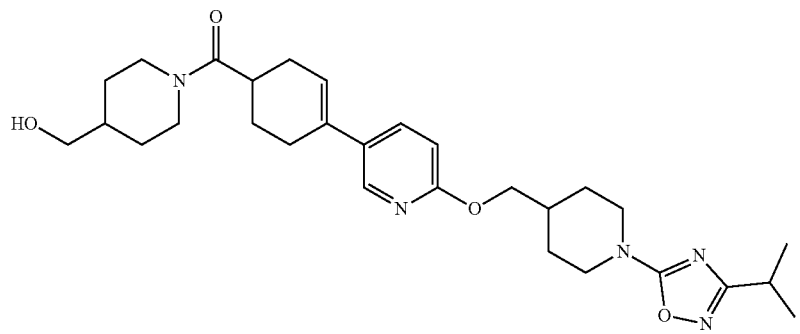 [SMILES: CC(C)c1noc(N2CCC(COc3ccc(C4=CCC(C(=O)N5CCC(CO)CC5)CC4)cn3)CC2)n1]

The title compound was prepared in the same manner as in <Example 310>, except that 4-piperidinemethanol was used instead of the pyrrolidine (Amount obtained: 380 mg/Yield: 61%).

$^1$H NMR (400, CDCl$_3$): 8.13 (1H, d), 7.61 (1H, dd), 6.69 (1H, d), 6.05 (1H, d), 4.71 (1H, d), 4.19 (4H, m), 4.00 (1H, d), 3.55 (2H, m), 3.10 (3H, m), 2.93 (1H, m), 2.86 (2H, m), 2.54 (4H, m), 2.32 (1H, m), 2.04 (6H, m), 1.96 (2H, m), 1.86 (3H, m), 1.41 (2H, m), 1.31 (6H, d), 1.20 (2H, m)

Example 330: Preparation of azetidin-1-yl(4-(3-fluoro-4-((1-(3-isopropyl-1,2,4-oxadiazol-5-yl)piperidin-4-yl)methoxy)phenyl)cyclohex-3-enyl)methanone

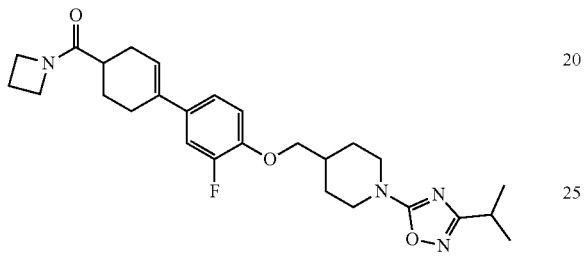

500 mg of 4-(3-fluoro-4-((1-(3-isopropyl-1,2,4-oxadiazol-5-yl)piperidin-4-yl)methoxy)phenyl)cyclohex-3-enecarboxylic acid was put into a 100 ml flask under a nitrogen atmosphere, 20 ml of dichloromethane was added thereto, and the resulting mixture was dissolved while stirring. 0.32 ml of triethylamine, 180 mg of azetidine hydrochloride, and 530 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 400 mg/Yield: 69%).

$^1$H NMR (400, CDCl$_3$): 7.14 (1H, dd), 7.08 (1H, d), 6.89 (1H, t), 6.07 (1H, m), 4.22 (4H, m), 4.06 (2H, t), 3.89 (2H, d), 3.14 (2H, m), 2.92 (1H, m), 2.49 (7H, m), 2.19 (1H, m), 1.96 (3H, m), 1.83 (1H, m), 1.46 (2H, m), 1.29 (6H, d)

Example 331: Preparation of (4-(3-fluoro-4-((1-(3-isopropyl-1,2,4-oxadiazol-5-yl)piperidin-4-yl)methoxy)phenyl)cyclohex-3-enyl)(pyrrolidin-1-yl)methanone

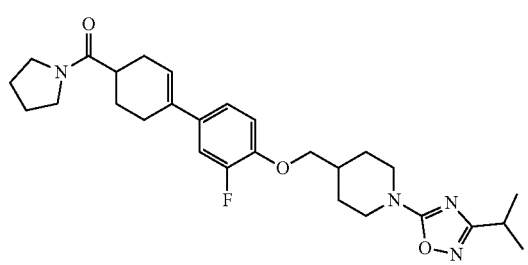 [SMILES: CC(C)c1noc(N2CCC(COc3ccc(C4=CCC(C(=O)N5CCCC5)CC4)cc3F)CC2)n1]

The title compound was prepared in the same manner as in <Example 330>, except that pyrrolidine was used instead of the azetidine hydrochloride (Amount obtained: 385 mg/Yield: 65%).

$^1$H NMR (400, CDCl$_3$): 7.12 (1H, dd), 7.07 (1H, d), 6.89 (1H, t), 6.09 (1H, m), 4.20 (2H, d), 3.91 (2H, d), 3.53 (4H, m), 3.12 (2H, m), 2.92 (1H, m), 2.51 (5H, m), 2.01 (9H, m), 1.43 (2H, m), 1.29 (6H, d)

Example 332: Preparation of (4-(3-fluoro-4-((1-(3-isopropyl-1,2,4-oxadiazol-5-yl)piperidin-4-yl)methoxy)phenyl)cyclohex-3-enyl)(piperidin-1-yl)methanone

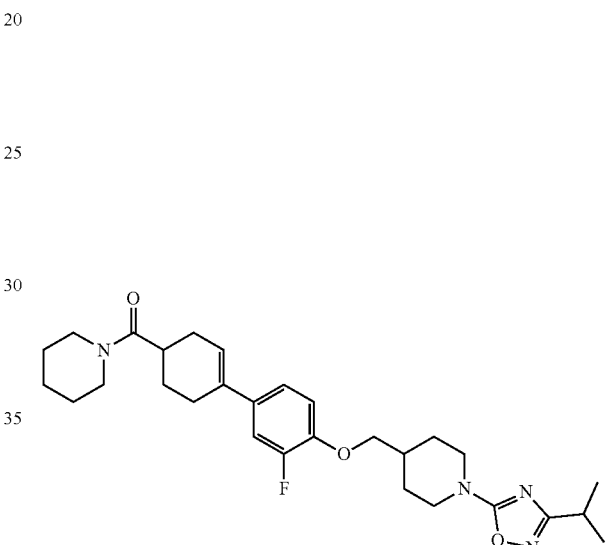

The title compound was prepared in the same manner as in <Example 330>, except that piperidine was used instead of the azetidine hydrochloride (Amount obtained: 430 mg/Yield: 70%).

$^1$H NMR (400, CDCl$_3$): 7.12 (1H, dd), 7.07 (1H, d), 6.89 (1H, t), 6.09 (1H, m), 4.20 (2H, d), 3.90 (2H, d), 3.52 (4H, m), 3.14 (2H, m), 2.91 (2H, m), 2.49 (3H, m), 2.30 (1H, m), 2.10 (1H, m), 1.96 (1H, m), 1.93 (4H, m), 1.59 (10H, m), 1.44 (2H, m), 1.29 (6H, d)

Example 333: Preparation of (4-(3-fluoro-4-((1-(3-isopropyl-1,2,4-oxadiazol-5-yl)piperidin-4-yl)methoxy)phenyl)cyclohex-3-enyl)(4-(hydroxymethyl)piperidin-1-yl)methanone

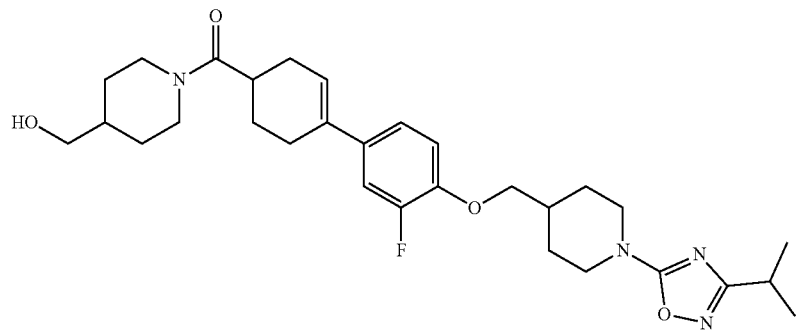 [SMILES: CC(C)c1noc(N2CCC(COc3ccc(C4=CCC(C(=O)N5CCC(CO)CC5)CC4)cc3F)CC2)n1]

The title compound was prepared in the same manner as in <Example 330>, except that 4-piperidinemethanol was used instead of the azetidine hydrochloride (Amount obtained: 460 mg/Yield: 71%).

$^1$H NMR (400, CDCl$_3$): 7.14 (1H, dd), 7.09 (1H, d), 6.89 (1H, t), 6.08 (1H, m), 4.74 (1H, d), 4.20 (2H, d), 4.03 (1H, d), 3.89 (2H, d), 3.55 (2H, m), 3.14 (3H, m), 2.91 (2H, m), 2.48 (5H, m), 2.19 (1H, m), 1.99 (3H, m), 1.88 (2H, m), 1.80 (2H, m), 1.57 (1H, t), 1.47 (2H, m), 1.29 (6H, d), 1.19 (2H, m)

Example 334: Preparation of (4-(3-fluoro-4-((1-(3-isopropyl-1,2,4-oxadiazol-5-yl)piperidin-4-yl)methoxy)phenyl)cyclohex-3-enyl)(3-hydroxyazetidin-1-yl)methanone

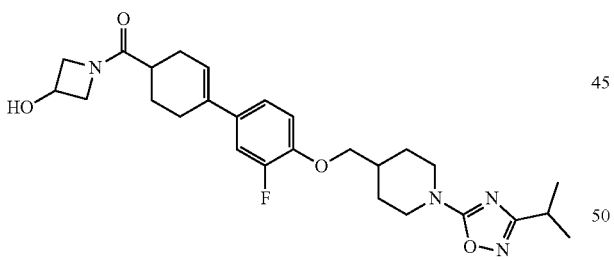

The title compound was prepared in the same manner as in <Example 330>, except that 3-hydroxyazetidine hydrochloride was used instead of the azetidine hydrochloride (Amount obtained: 300 mg/Yield: 51%).

$^1$H NMR (400, CDCl$_3$): 7.14 (1H, dd), 7.06 (1H, d), 6.89 (1H, t), 6.08 (1H, m), 4.22 (4H, m), 4.06 (2H, t), 3.89 (2H, d), 3.14 (2H, m), 2.92 (1H, m), 2.49 (7H, m), 2.19 (1H, m), 1.96 (3H, m), 1.83 (1H, m), 1.46 (2H, m), 1.29 (6H, d)

Example 335: Preparation of (4-(3-fluoro-4-((1-(3-isopropyl-1,2,4-oxadiazol-5-yl)piperidin-4-yl)methoxy)phenyl)cyclohex-3-enyl)(4-(2-hydroxyethyl)piperidin-1-yl)methanone

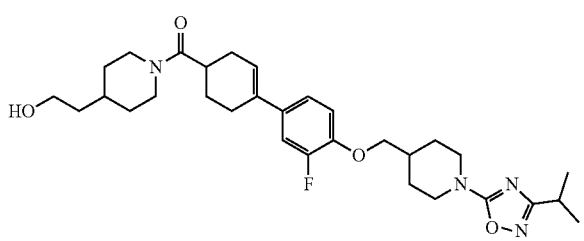 [SMILES: CC(C)c1noc(N2CCC(COc3ccc(C4=CCC(C(=O)N5CCC(CCO)CC5)CC4)cc3F)CC2)n1]

The title compound was prepared in the same manner as in <Example 330>, except that 4-piperidineethanol was used instead of the azetidine hydrochloride (Amount obtained: 380 mg/Yield: 57%).

$^1$H NMR (400, CDCl$_3$): 7.14 (1H, dd), 7.09 (1H, d), 6.89 (1H, t), 6.08 (1H, m), 4.66 (1H, d), 4.20 (2H, d), 3.91 (3H, m), 3.75 (2H, m), 3.11 (3H, m), 2.92 (2H, m), 2.80 (1H, m), 2.55 (4H, m), 2.31 (1H, m), 2.10 (1H, m), 1.76 (7H, m), 1.54 (2H, m), 1.47 (2H, m), 1.24 (6H, d), 1.15 (2H, m)

Example 336: Preparation of (4-(3-fluoro-4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone

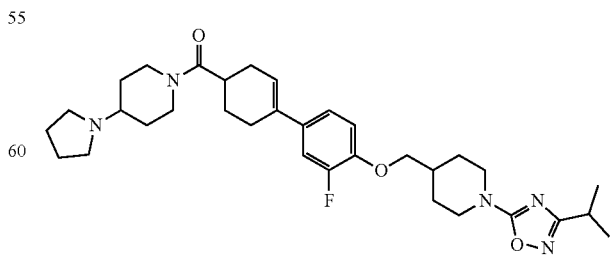

The title compound was prepared in the same manner as in <Example 330>, except that 4-(1-pyrrolidinyl)piperidine was used instead of the azetidine hydrochloride (Amount obtained: 450 mg/Yield: 65%).

¹H NMR (400, CDCl₃): 7.14 (1H, dd), 7.07 (1H, d), 6.89 (1H, t), 6.07 (1H, m), 4.63 (1H, m), 4.20 (2H, d), 3.90 (3H, m), 3.15 (3H, m), 2.92 (1H, m), 2.50 (11H, m), 2.11 (2H, m), 2.05 (5H, m), 1.92 (5H, m), 1.47 (3H, m), 1.31 (6H, d)

Example 337: Preparation of (3-(hydroxyimino) azetidin-1-yl)(4-(6-((1-(3-isopropyl-1,2,4-oxadiazol-5-yl)piperidin-4-yl)methoxy)pyridin-3-yl)cyclohex-3-enyl)methanone

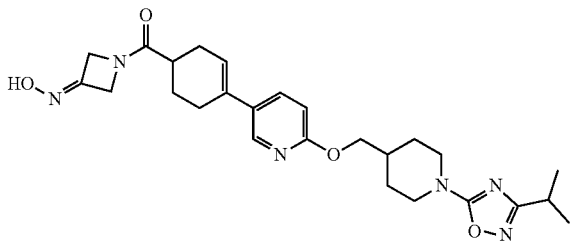 [SMILES: CC(C)c1noc(N2CCC(COc3ccc(C4=CCC(C(=O)N5CC(=NO)C5)CC4)cn3)CC2)n1]

300 mg of (3-(hydroxyimino)azetidin-1-yl)(4-(6-((1-(3-isopropyl-1,2,4-oxadiazol-5-yl)piperidin-4-yl)methoxy) pyridin-3-yl)cyclohex-3-enyl)methanone was put into a 100 ml flask under a nitrogen atmosphere, 20 ml of ethanol was added thereto, and the resulting mixture was then dissolved while stirring. 25 mg of sodium hydroxide and 73 mg of hydroxylamine hydrochloride were added dropwise thereto, and the mixture was stirred at 20° C. for 2 hours. After the reaction was terminated, 30 ml of ethyl acetate and 30 ml of distilled water were added thereto, and the reaction mixture was extracted, dried with anhydrous magnesium sulfate, concentrated, and then isolated by silica column chromatography to obtain the title compound (Amount obtained: 160 mg/Yield: 48%).

¹H NMR (400, CDCl₃): 8.13 (1H, d), 7.73 (1H, m), 7.63 (1H, dd), 6.69 (1H, d), 6.05 (1H, d), 4.88 (2H, d), 4.73 (2H, m), 4.20 (4H, m), 3.11 (2H, m), 2.92 (1H, m), 2.45 (5H, m), 2.10 (2H, m), 1.93 (3H, m), 1.66 (5H, m), 1.49 (2H, m), 1.29 (8H, m)

Example 338: Preparation of 1-(4-(6-((1-(3-isopropyl-1,2,4-oxadiazol-5-yl)piperidin-4-yl)methoxy) pyridin-3-yl)cyclohex-3-enecarbonyl)piperidine-4-carbonitrile

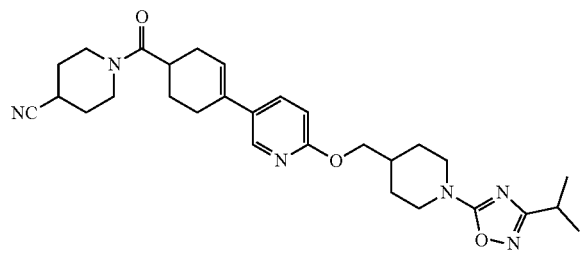 [SMILES: CC(C)c1noc(N2CCC(COc3ccc(C4=CCC(C(=O)N5CCC(C#N)CC5)CC4)cn3)CC2)n1]

The title compound was prepared in the same manner as in <Example 315>, except that piperidine-4-carbonitrile was used instead of the pyrrolidine (Amount obtained: 410 mg/Yield: 66%).

¹H NMR (400, CDCl₃): 8.12 (1H, d), 7.60 (1H, dd), 6.68 (1H, d), 6.05 (1H, s), 4.20 (4H, m), 3.74 (2H, m), 3.54 (2H, m), 3.10 (2H, m), 2.91 (2H, m), 2.81 (1H, m), 2.48 (5H, m), 2.30 (1H, m), 1.91 (10H, m), 1.45 (2H, m), 1.26 (6H, d)

Example 339: Preparation of azetidin-1-yl(4-(6-((1-(3-isopropyl-1,2,4-oxadiazol-5-yl)piperidin-4-yl) methoxy)pyridin-3-yl)cyclohex-3-enyl)methanone

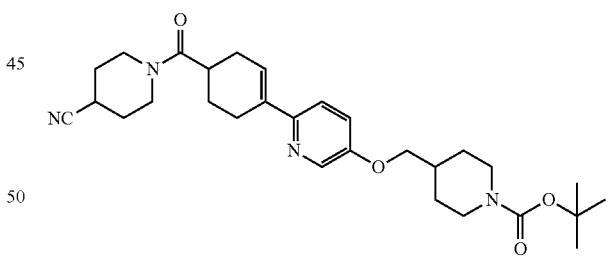

The title compound was prepared in the same manner as in <Example 315>, except that azetidine hydrochloride was used instead of the pyrrolidine (Amount obtained: 340 mg/Yield: 62%).

¹H NMR (400, CDCl₃): 8.12 (1H, d), 7.60 (1H, dd), 6.68 (1H, d), 6.05 (1H, d), 4.08 (2H, m), 3.12 (2H, m), 3.91 (1H, m), 2.47 (4H, m), 2.31 (3H, m), 1.98 (6H, m), 1.45 (3H, m), 1.29 (6H, d)

Example 340: Preparation of tert-butyl 4-((6-(4-(4-cyanopiperidine-1-carbonyl)cyclohex-1-enyl)pyridin-3-yloxy)methyl)piperidine-1-carboxylate The title compound was prepared in the same manner as in <Example 310>, except that piperidine-4-carbonitrile was used instead of the 4-hydroxypiperidine (Amount obtained: 400 mg/Yield: 66%).

¹H NMR (400, CDCl₃): 8.24 (1H, d), 7.33 (1H, m), 7.15 (1H, dd), 6.55 (1H, s), 4.18 (2H, m), 3.67 (6H, m), 2.93 (1H, m), 2.79 (4H, m), 2.53 (2H, m), 2.35 (1H, m), 1.91 (11H, m), 1.48 (9H, s), 1.21 (2H, m)

Example 341: Preparation of tert-butyl 4-((6-(4-((2-hydroxyethyl)(methyl)carbamoyl)cyclohex-1-enyl)pyridin-3-yloxy)methyl)piperidine-1-carboxylate

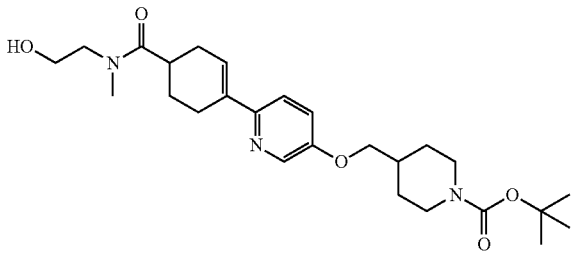 [SMILES: CN(CCO)C(=O)C1CC=C(c2ccc(OCC3CCN(C(=O)OC(C)(C)C)CC3)cn2)CC1]

The title compound was prepared in the same manner as in <Example 310>, except that 2-(methylamino)ethanol was used instead of the 4-hydroxypiperidine (Amount obtained: 450 mg/Yield: 79%).

¹H NMR (400, CDCl₃): 8.24 (1H, d), 7.34 (1H, d), 7.15 (1H, dd), 6.56 (1H, m), 4.18 (2H, m), 3.85 (4H, m), 3.63 (2H, m), 3.17 (2H, s), 2.79 (5H, m), 2.50 (3H, m), 1.90 (10H, m), 1.48 (9H, s), 1.31 (2H, m)

Example 342: Preparation of tert-butyl 4-((6-(4-(4-oxopiperidine-1-carbonyl)cyclohex-1-enyl)pyridin-3-yloxy)methyl)piperidine-1-carboxylate

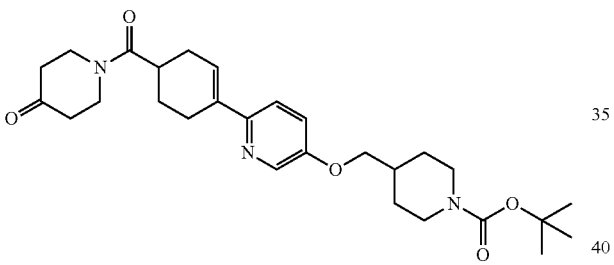

The title compound was prepared in the same manner as in <Example 310>, except that 1-methyl-4-piperidone was used instead of the 4-hydroxypiperidine (Amount obtained: 480 mg/Yield: 80%).

¹H NMR (400, CDCl₃): 8.24 (1H, d), 7.32 (1H, d), 7.15 (1H, dd), 6.57 (1H, m), 4.17 (2H, m), 3.91 (6H, m), 2.94 (1H, m), 2.53 (10H, m), 2.09 (3H, m), 1.85 (2H, d), 1.48 (9H, s), 1.34 (2H, m)

Example 343: Preparation of tert-butyl 4-((6-(4-(4-cyanopiperazine-1-carbonyl)cyclohex-1-enyl)pyridin-3-yloxy)methyl)piperidine-1-carboxylate

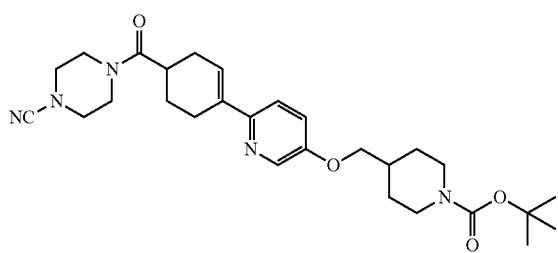 [SMILES: CC(C)(C)OC(=O)N1CCC(COc2ccc(C3=CCC(C(=O)N4CCN(C#N)CC4)CC3)nc2)CC1]

300 mg of tert-butyl 4-((6-(4-(piperazine-1-carbonyl)cyclohex-1-enyl)pyridin-3-yloxy)methyl)piperidine-1-carboxylate hydrochloride was put into a 100 ml flask under a nitrogen atmosphere, 20 ml of dichloromethane was added thereto, and the resulting mixture was then dissolved while stirring. 0.13 ml of triethylamine and 15 mg of cyanogen bromide were added dropwise thereto, and the mixture was stirred at 20° C. for 2 hours. After the reaction was terminated, 30 ml of ethyl acetate and 30 ml of distilled water were added thereto, and the reaction mixture was extracted, dried with anhydrous magnesium sulfate, concentrated, and then isolated by silica column chromatography to obtain the title compound (Amount obtained: 400 mg/Yield: 65%).

¹H NMR (400, CDCl₃): 8.23 (1H, d), 7.31 (1H, d), 7.14 (1H, dd), 6.55 (1H, m), 4.19 (3H, m), 3.86 (2H, d), 3.56 (6H, m), 3.31 (2H, m), 2.79 (4H, m), 2.50 (2H, m), 2.36 (1H, m), 1.95 (5H, m), 1.64 (5H, s), 1.47 (9H, s), 1.28 (2H, m)

Example 344: Preparation of tert-butyl 4-((6-(4-(4-(hydroxyimino)piperidine-1-carbonyl)cyclohex-1-enyl)pyridin-3-yloxy)methyl)piperidine-1-carboxylate

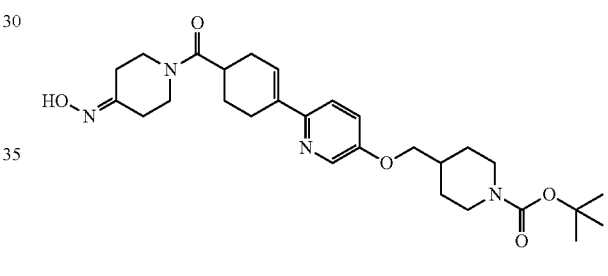

300 mg of tert-butyl 4-((6-(4-(4-oxopiperidine-1-carbonyl)cyclohex-1-enyl)pyridin-3-yloxy)methyl)piperidine-1-carboxylate was put into a 100 ml flask under a nitrogen atmosphere, 20 ml of ethanol was added thereto, and the resulting mixture was then dissolved while stirring. 23 mg of sodium hydroxide and 69 mg of hydroxylamine hydrochloride were added dropwise thereto, and the mixture was stirred at 20° C. for 2 hours. After the reaction was terminated, 30 ml of ethyl acetate and 30 ml of distilled water were added thereto, and the reaction mixture was extracted, dried with anhydrous magnesium sulfate, concentrated, and then isolated by silica column chromatography to obtain the title compound (Amount obtained: 180 mg/Yield: 70%).

¹H NMR (400, CDCl₃): 8.24 (1H, d), 7.43 (1H, d), 7.32 (1H, d), 7.14 (1H, dd), 6.56 (1H, m), 4.18 (2H, m), 3.76 (6H, m), 2.56 (11H, m), 1.95 (5H, m), 1.48 (9H, s), 1.25 (2H, m)

Example 345: Preparation of 1-(4-(3-fluoro-4-((1-(3-isopropyl-1,2,4-oxadiazol-5-yl)piperidin-4-yl)methoxy)phenyl)cyclohex-3-enecarbonyl)piperidin-4-one

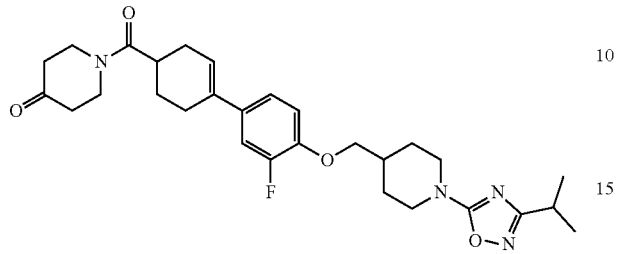

The title compound was prepared in the same manner as in <Example 330>, except that 4-piperidone was used instead of the azetidine hydrochloride (Amount obtained: 510 mg/Yield: 81%).

$^1$H NMR (400, CDCl$_3$): 7.12 (1H, dd), 7.08 (1H, d), 6.90 (1H, t), 6.09 (1H, m), 4.20 (2H, d), 3.92 (6H, m), 3.14 (2H, m), 2.92 (2H, m), 2.53 (7H, m), 2.33 (1H, m), 2.04 (5H, m), 1.45 (2H, m), 1.29 (6H, d)

Example 346: Preparation of (4-ethylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone

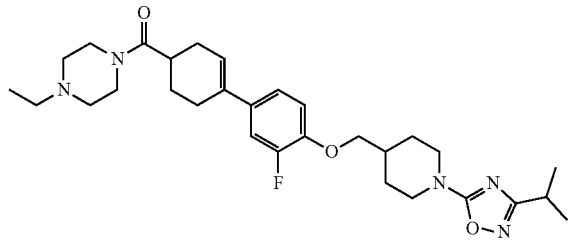 [SMILES: CCN1CCN(C(=O)C2CC=C(c3ccc(OCC4CCN(c5nc(C(C)C)no5)CC4)c(F)c3)CC2)CC1]

The title compound was prepared in the same manner as in <Example 330>, except that 1-ethylpiperazine was used instead of the azetidine hydrochloride (Amount obtained: 510 mg/Yield: 79%).

$^1$H NMR (400, CDCl$_3$): 8.18 (2H, s), 7.11 (1H, dd), 7.06 (1H, d), 6.90 (1H, t), 6.07 (1H, m), 4.76 (2H, d), 3.89 (2H, d), 3.77 (4H, m), 2.92 (2H, m), 2.88 (1H, m), 2.48 (11H, m), 2.31 (1H, m), 2.15 (1H, m), 1.83 (4H, m), 1.33 (2H, m), 1.18 (3H, t), 1.10 (3H, t)

Example 347: Preparation of (4-(3-fluoro-4-((1-(3-isopropyl-1,2,4-oxadiazol-5-yl)piperidin-4-yl)methoxy)phenyl)cyclohex-3-enyl)(4-(3-hydroxypropyl)piperazin-1-yl)methanone

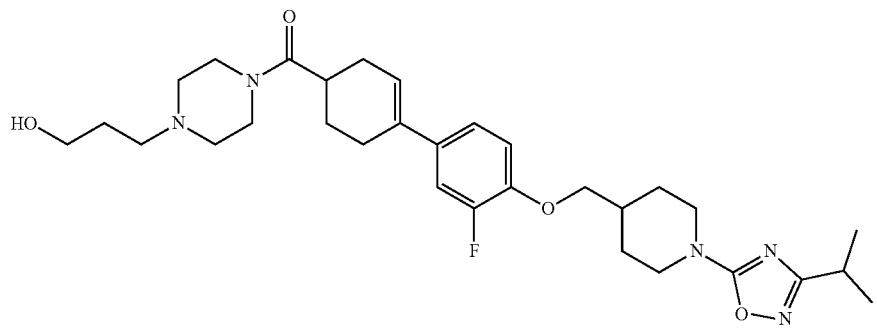 [SMILES: CC(C)c1noc(N2CCC(COc3ccc(C4=CCC(C(=O)N5CCN(CCCO)CC5)CC4)cc3F)CC2)n1]

The title compound was prepared in the same manner as in <Example 330>, except that 1-(2-hydroxyethyl)piperazine was used instead of the azetidine hydrochloride (Amount obtained: 380 mg/Yield: 56%).

$^1$H NMR (400, CDCl$_3$): 8.18 (2H, s), 7.11 (1H, dd), 7.06 (1H, d), 6.90 (1H, t), 6.06 (1H, m), 4.76 (3H, m), 3.90 (2H, d), 3.84 (2H, t), 3.68 (4H, m), 2.96 (2H, m), 2.89 (1H, m), 2.64 (2H, t), 2.50 (9H, m), 2.30 (1H, m), 2.18 (1H, m), 1.91 (4H, m), 1.77 (2H, m), 1.34 (2H, m), 1.20 (3H, t)

Example 348: Preparation of (4-cyclopropylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone

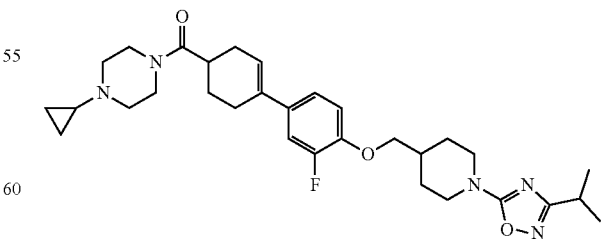

The title compound was prepared in the same manner as in <Example 330>, except that 1-cyclopropylpiperazine was used instead of the azetidine hydrochloride (Amount obtained: 410 mg/Yield: 62%).

¹H NMR (400, CDCl₃): 8.18 (2H, s), 7.11 (1H, dd), 7.07 (1H, d), 6.90 (1H, t), 6.07 (1H, m), 4.76 (2H, d), 3.90 (2H, d), 3.62 (4H, m), 2.92 (2H, m), 2.80 (1H, m), 2.48 (9H, m), 2.32 (1H, m), 2.18 (1H, m), 1.92 (4H, m), 1.63 (1H, m), 1.34 (2H, m), 1.18 (3H, t), 0.46 (4H, m)

Example 349: Preparation of (4-(6-((1-(5-ethylpyrimidin-2-yl)piperidin-4-yl)methoxy)pyridin-3-yl)cyclohex-3-enyl)(pyrrolidin-1-yl)methanone

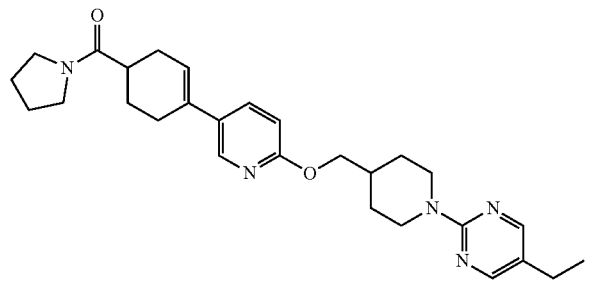 [SMILES: CCc1cnc(N2CCC(COc3ccc(C4=CCC(C(=O)N5CCCC5)CC4)cn3)CC2)nc1]

500 mg of 4-(6-((1-(5-ethylpyrimidin-2-yl)piperidin-4-yl)methoxy)pyridin-3-yl)cyclohex-3-enecarboxylic acid was put into a 100 ml flask under a nitrogen atmosphere, 20 ml of dichloromethane was added thereto, and the resulting mixture was then dissolved while stirring. 0.33 ml of triethylamine, 0.14 ml of pyrrolidine, and 510 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 410 mg/Yield: 72%).

¹H NMR (400, CDCl₃): 8.18 (2H, s), 8.15 (1H, d), 7.61 (1H, dd), 6.69 (1H, d), 6.05 (1H, m), 4.78 (2H, d), 4.17 (2H, d), 3.50 (4H, m), 2.92 (2H, m), 2.88 (1H, m), 2.49 (5H, m), 2.30 (1H, m), 2.11 (1H, m), 1.92 (4H, m), 1.56 (10H, m), 1.35 (2H, m), 1.20 (3H, t)

Example 350: Preparation of (4-(6-((1-(5-ethylpyrimidin-2-yl)piperidin-4-yl)methoxy)pyridin-3-yl)cyclohex-3-enyl)(piperidin-1-yl)methanone

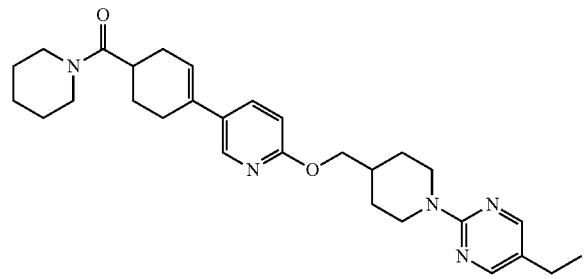 [SMILES: CCc1cnc(N2CCC(COc3ccc(C4=CCC(C(=O)N5CCCCC5)CC4)cn3)CC2)nc1]

The title compound was prepared in the same manner as in <Example 349>, except that piperidine was used instead of the pyrrolidine (Amount obtained: 450 mg/Yield: 75%).

¹H NMR (400, CDCl₃): 8.18 (2H, s), 8.15 (1H, d), 7.61 (1H, dd), 6.69 (1H, d), 6.06 (1H, m), 4.78 (2H, d), 4.17 (2H, d), 3.50 (4H, m), 2.92 (2H, m), 2.51 (7H, m), 2.05 (9H, m), 1.37 (2H, m), 1.20 (3H, t)

Example 351: Preparation of (4-(6-((1-(5-ethylpyrimidin-2-yl)piperidin-4-yl)methoxy)pyridin-3-yl)cyclohex-3-enyl)(morpholino)methanone

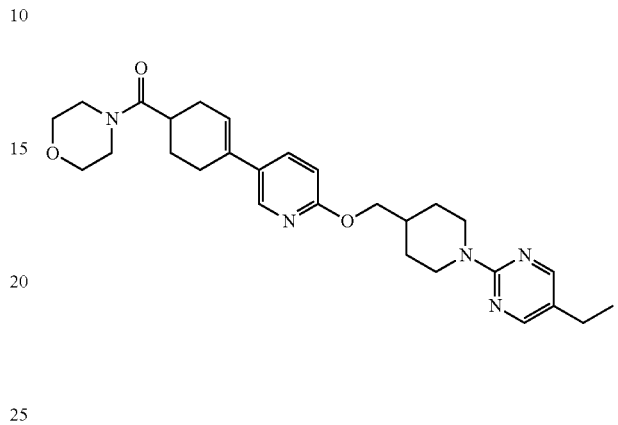

The title compound was prepared in the same manner as in <Example 349>, except that morpholine was used instead of the pyrrolidine (Amount obtained: 470 mg/Yield: 77%).

¹H NMR (400, CDCl₃): 8.18 (2H, s), 8.14 (1H, d), 7.60 (1H, dd), 6.69 (1H, d), 6.05 (1H, m), 4.75 (2H, d), 4.17 (2H, d), 3.62 (8H, m), 2.92 (2H, m), 2.78 (1H, m), 2.50 (5H, m), 2.30 (1H, m), 2.00 (5H, m), 1.32 (2H, m), 1.20 (3H, t)

Example 352: Preparation of (4-(6-((1-(5-ethylpyrimidin-2-yl)piperidin-4-yl)methoxy)pyridin-3-yl)cyclohex-3-enyl)(thiomorpholino)methanone

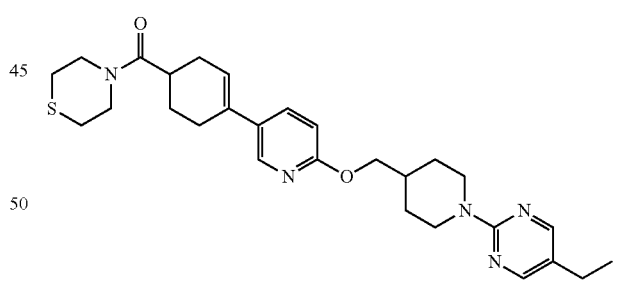

The title compound was prepared in the same manner as in <Example 349>, except that thiomorpholine was used instead of the pyrrolidine (Amount obtained: 430 mg/Yield: 73%).

¹H NMR (400, CDCl₃): 8.18 (2H, s), 8.14 (1H, d), 7.60 (1H, dd), 6.69 (1H, d), 6.04 (1H, m), 4.75 (2H, d), 4.17 (2H, d), 3.89 (4H, m), 2.92 (2H, m), 2.78 (1H, m), 2.67 (4H, m), 2.48 (5H, m), 2.30 (1H, m), 2.00 (5H, m), 1.35 (2H, m), 1.20 (3H, t)

Example 353: Preparation of (4-(6-((1-(5-ethylpyrimidin-2-yl)piperidin-4-yl)methoxy)pyridin-3-yl)cyclohex-3-enyl)(4-hydroxypiperidin-1-yl)methanone

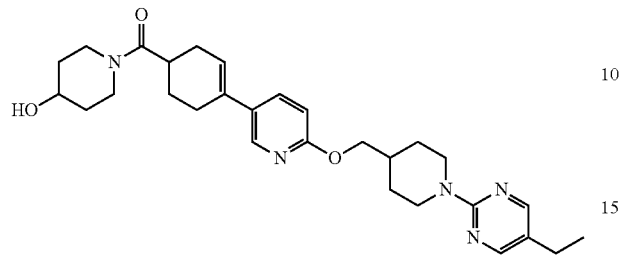

The title compound was prepared in the same manner as in <Example 349>, except that 4-hydroxypiperidine was used instead of the pyrrolidine (Amount obtained: 450 mg/Yield: 75%).

$^1$H NMR (400, CDCl$_3$): 8.18 (2H, s), 8.15 (1H, d), 7.61 (1H, dd), 6.69 (1H, d), 6.06 (1H, m), 4.75 (2H, d), 4.17 (3H, m), 3.98 (1H, s), 3.85 (1H, m), 3.29 (2H, m), 2.92 (2H, m), 2.81 (1H, m), 2.50 (5H, m), 2.30 (1H, m), 1.92 (7H, m), 1.55 (2H, m), 1.31 (2H, m), 1.20 (3H, t)

Example 354: Preparation of (4-(6-((1-(5-ethylpyrimidin-2-yl)piperidin-4-yl)methoxy)pyridin-3-yl)cyclohex-3-enyl)(4-(hydroxymethyl)piperidin-1-yl)methanone

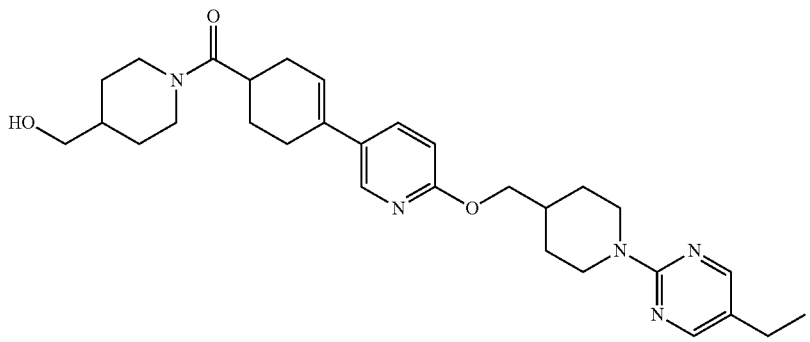 [SMILES: CCc1cnc(N2CCC(COc3ccc(C4=CCC(C(=O)N5CCC(CO)CC5)CC4)cn3)CC2)nc1]

The title compound was prepared in the same manner as in <Example 349>, except that 4-piperidinemethanol was used instead of the pyrrolidine (Amount obtained: 390 mg/Yield: 69%).

$^1$H NMR (400, CDCl$_3$): 8.18 (2H, s), 8.14 (1H, d), 7.60 (1H, dd), 6.69 (1H, d), 6.05 (1H, m), 4.74 (3H, m), 4.18 (2H, d), 4.04 (1H, d), 3.53 (2H, m), 3.08 (1H, t), 2.92 (2H, m), 2.80 (1H, m), 2.51 (6H, m), 2.30 (1H, m), 1.90 (9H, m), 1.33 (2H, m), 1.19 (5H, m)

Example 355: Preparation of (4-cyclopropylpiperazin-1-yl)(4-(6-((1-(3-isopropyl-1,2,4-oxadiazol-5-yl)piperidin-4-yl)methoxy)pyridin-3-yl)cyclohex-3-enyl)methanone

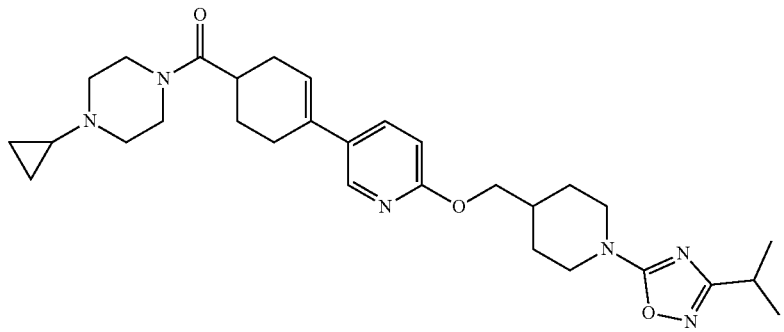 [SMILES: CC(C)c1noc(N2CCC(COc3ccc(C4=CCC(C(=O)N5CCN(C6CC6)CC5)CC4)cn3)CC2)n1]

The title compound was prepared in the same manner as in <Example 349>, except that 1-cyclopropylpiperazine was used instead of the pyrrolidine (Amount obtained: 420 mg/Yield: 71%).

¹H NMR (400, CDCl₃): 8.13 (1H, d), 7.62 (1H, dd), 6.70 (1H, d), 6.05 (1H, d), 4.19 (4H, m), 3.64 (2H, m), 3.52 (2H, t), 3.12 (2H, m), 2.88 (2H, m), 2.50 (7H, m), 2.31 (1H, m), 2.05 (2H, m), 1.90 (3H, m), 1.65 (1H, m), 1.43 (2H, m), 1.29 (6H, d)

Example 356: Preparation of 4-(4-((1-(5-bromopyridin-2-yl)piperidin-4-yl)methoxy)phenyl)-N-(2-hydroxyethyl)cyclohex-3-enecarboxamide

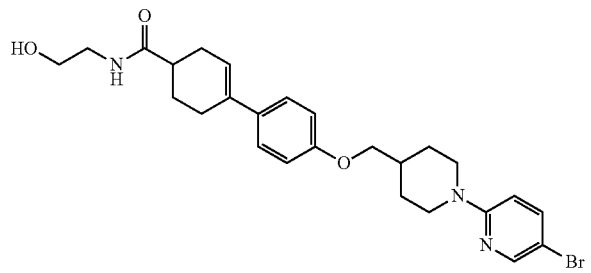 [SMILES: O=C(NCCO)C1CC=C(c2ccc(OCC3CCN(c4ccc(Br)cn4)CC3)cc2)CC1]

500 mg of N-(2-hydroxyethyl)-4-(4-(piperidin-4-ylmethoxy)phenyl)cyclohex-3-enecarboxamide hydrochloride was dissolved in 20 ml of DMF in a 100 ml flask, and then stirred under nitrogen. 0.31 ml of N,N-diisopropylethylamine was added dropwise thereto, and 170 mg of 2,5-dibromopyridine was then added dropwise. The resulting mixture was gradually heated to a temperature of 60° C., and then stirred for 4 hours. After the reaction was terminated, the reaction mixture was slowly cooled to room temperature. Then, 30 ml of distilled water was slowly added thereto, and the reaction mixture was extracted with 60 ml of ethyl acetate, washed with 20 ml of brine, dried with anhydrous magnesium sulfate, concentrated, and then isolated by silica column chromatography to obtain the title compound (Amount obtained: 320 mg/Yield: 60%).

¹H NMR (400, CDCl₃): 8.19 (1H, d), 7.52 (1H, dd), 7.31 (1H, d), 6.86 (2H, d), 6.58 (1H, d), 6.04 (2H, s), 4.29 (2H, d), 3.83 (2H, d), 3.77 (2H, t), 3.48 (2H, m), 2.89 (2H, m), 2.50 (5H, m), 2.10 (4H, m), 1.93 (4H, m), 1.45 (2H, m), 1.29 (2H, t)

Example 357: Preparation of 4-(4-((1-(5-bromopyrimidin-2-yl)piperidin-4-yl)methoxy)phenyl)-N-(2-hydroxyethyl)cyclohex-3-enecarboxamide

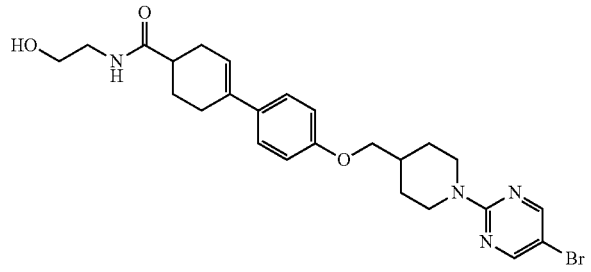 [SMILES: O=C(NCCO)C1CC=C(c2ccc(OCC3CCN(c4ncc(Br)cn4)CC3)cc2)CC1]

The title compound was prepared in the same manner as in <Example 356>, except that 2,5-dibromopyrimidine was used instead of the 2,5-dibromopyridine (Amount obtained: 350 mg/Yield: 63%).

¹H NMR (400, CDCl₃): 8.42 (2H, s), 7.83 (1H, t), 7.30 (2H, d), 6.85 (2H, d), 6.04 (1H, s), 4.66 (3H, m), 3.82 (2H, d), 3.39 (2H, m), 3.11 (2H, m), 2.92 (2H, t), 2.34 (3H, m), 2.24 (2H, m), 2.04 (1H, m), 1.93 (2H, m), 1.60 (2H, m), 1.22 (2H, m)

Example 358: Preparation of N-(2-hydroxyethyl)-4-(4-((1-(pyridin-2-yl)piperidin-4-yl)methoxy)phenyl)cyclohex-3-enecarboxamide

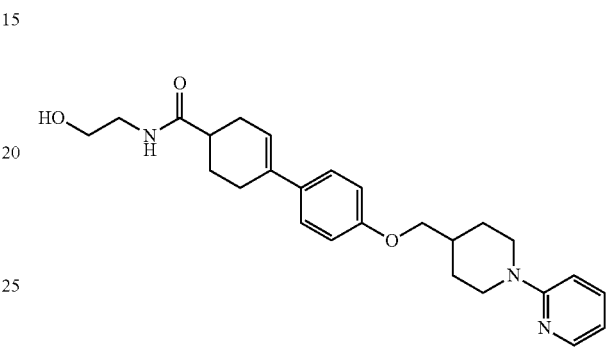

The title compound was prepared in the same manner as in <Example 356>, except that 2-bromopyridine was used instead of the 2,5-dibromopyridine (Amount obtained: 330 mg/Yield: 61%).

¹H NMR (400, CDCl₃): 8.08 (1H, d), 7.82 (1H, t), 7.49 (1H, m), 7.30 (2H, d), 6.86 (2H, d), 6.80 (1H, d), 6.57 (1H, t), 6.04 (1H, s), 4.66 (1H, t), 4.31 (2H, d), 3.83 (2H, d), 3.40 (2H, m), 3.15 (2H, m), 2.77 (2H, m), 2.40 (5H, m), 1.80 (4H, m), 1.62 (1H, m), 1.24 (2H, m)

Example 359: Preparation of 4-(4-((1-(5-ethylpyrimidin-2-yl)piperidin-4-yl)methoxy)-3-fluorophenyl)-N-(2-hydroxyethyl)-N-methylcyclohex-3-enecarboxamide

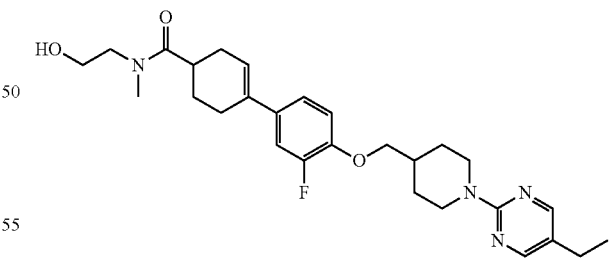

The title compound was prepared in the same manner as in <Example 292>, except that 2-(methylamino)ethanol was used instead of the piperidine (Amount obtained: 450 mg/Yield: 75%).

¹H NMR (400, CDCl₃): 8.18 (2H, s), 7.15 (1H, dd), 7.10 (1H, d), 6.90 (1H, t), 6.09 (1H, d), 4.76 (2H, d), 3.91 (2H, d), 3.84 (2H, q), 3.62 (2H, m), 3.13 (3H, m), 2.92 (4H, m), 2.45 (6H, m), 2.17 (1H, m), 1.95 (4H, m), 1.34 (2H, m), 1.20 (3H, t)

Example 360: Preparation of N-ethyl-4-(4-((1-(5-ethylpyrimidin-2-yl)piperidin-4-yl)methoxy)-3-fluorophenyl)-N-(2-hydroxyethyl)cyclohex-3-enecarboxamide

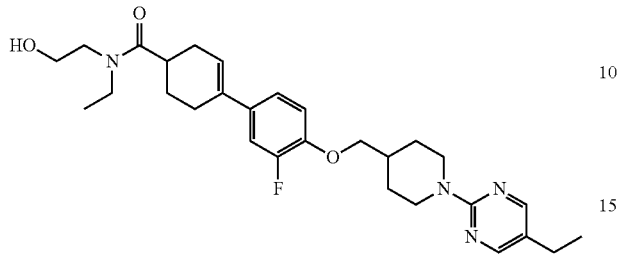

The title compound was prepared in the same manner as in <Example 292>, except that 2-(ethylamino)ethanol was used instead of the piperidine (Amount obtained: 440 mg/Yield: 73%).
¹H NMR (400, CDCl₃): 8.18 (2H, s), 7.13 (1H, dd), 7.07 (1H, d), 6.89 (1H, t), 6.08 (1H, d), 4.76 (2H, d), 3.89 (2H, d), 3.80 (2H, t), 3.60 (5H, m), 2.92 (2H, m), 2.78 (1H, m), 2.45 (5H, m), 2.30 (1H, m), 2.15 (1H, m), 1.94 (4H, m), 1.34 (2H, m), 1.22 (6H, m)

Example 361: Preparation of 1-(4-(3-fluoro-4-((1-(3-isopropyl-1,2,4-oxadiazol-5-yl)piperidin-4-yl)methoxy)phenyl)cyclohex-3-enecarbonyl)piperidine-4-carboxamide

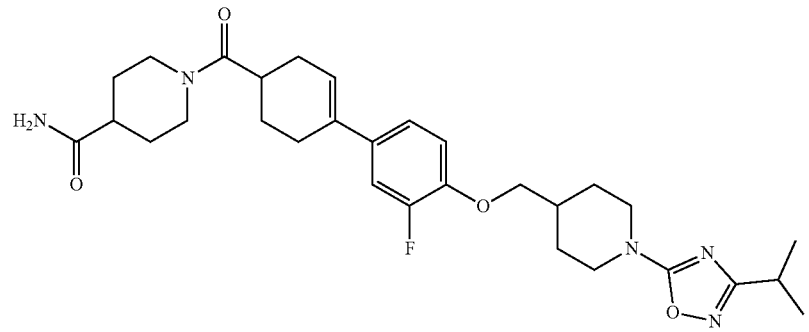 [SMILES: CC(C)c1noc(N2CCC(COc3ccc(C4=CCC(C(=O)N5CCC(C(N)=O)CC5)CC4)cc3F)CC2)n1]

The title compound was prepared in the same manner as in <Example 330>, except that isonipecotamide was used instead of the azetidine hydrochloride (Amount obtained: 400 mg/Yield: 69%).
¹H NMR (400, CDCl₃): 7.14 (1H, dd), 7.09 (1H, d), 6.89 (1H, t), 6.07 (1H, d), 5.47 (2H, d), 4.68 (1H, m), 4.20 (2H, d), 4.02 (1H, d), 3.91 (2H, d), 3.08 (3H, m), 2.88 (1H, m), 2.75 (2H, m), 2.47 (4H, m), 2.30 (1H, m), 2.09 (1H, m), 1.98 (6H, m), 1.71 (3H, m), 1.46 (2H, m), 1.29 (6H, d)

Example 362: Preparation of 1,4'-bipiperidin-1'-yl (4-(3-fluoro-4-((1-(3-isopropyl-1,2,4-oxadiazol-5-yl)piperidin-4-yl)methoxy)phenyl)cyclohex-3-enyl)methanone

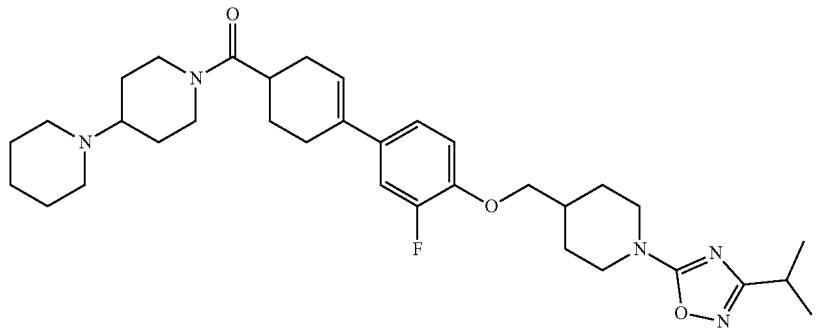 [SMILES: CC(C)c1noc(N2CCC(COc3ccc(C4=CCC(C(=O)N5CCC(N6CCCCC6)CC5)CC4)cc3F)CC2)n1]

The title compound was prepared in the same manner as in <Example 330>, except that 4-piperidinopiperidine was used instead of the azetidine hydrochloride (Amount obtained: 390 mg/Yield: 68%).

¹H NMR (400, CDCl₃): 7.14 (1H, dd), 7.09 (1H, d), 6.89 (1H, t), 6.06 (1H, d), 4.80 (1H, m), 4.23 (2H, d), 4.06 (1H, m), 3.89 (2H, d), 3.47 (2H, q), 3.11 (2H, m), 2.88 (1H, m), 2.50 (15H, m), 2.07 (3H, m), 1.96 (5H, m), 1.70 (11H, m), 1.31 (6H, d), 1.20 (3H, t)

Example 363: Preparation of N-cyclopropyl-4-(3-fluoro-4-((1-(3-isopropyl-1,2,4-oxadiazol-5-yl)piperidin-4-yl)methoxy)phenyl)cyclohex-3-enecarboxamide

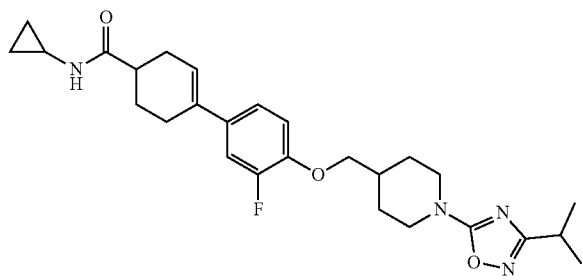 [SMILES: CC(C)c1noc(N2CCC(COc3ccc(C4=CCC(C(=O)NC5CC5)CC4)cc3F)CC2)n1]

The title compound was prepared in the same manner as in <Example 330>, except that cyclopropylamine was used instead of the azetidine hydrochloride (Amount obtained: 400 mg/Yield: 72%).

¹H NMR (400, CDCl₃): 7.13 (1H, dd), 7.07 (1H, d), 6.89 (1H, t), 6.05 (1H, m), 5.67 (1H, m), 4.20 (2H, d), 3.89 (2H, d), 3.15 (2H, m), 2.92 (1H, m), 2.74 (1H, m), 2.40 (5H, m), 2.08 (2H, m), 1.96 (2H, d), 1.85 (1H, m), 1.44 (2H, m), 1.30 (6H, d), 0.79 (2H, m), 0.50 (2H, m)

Example 364: Preparation of N-cyclobutyl-4-(3-fluoro-4-((1-(3-isopropyl-1,2,4-oxadiazol-5-yl)piperidin-4-yl)methoxy)phenyl)cyclohex-3-enecarboxamide

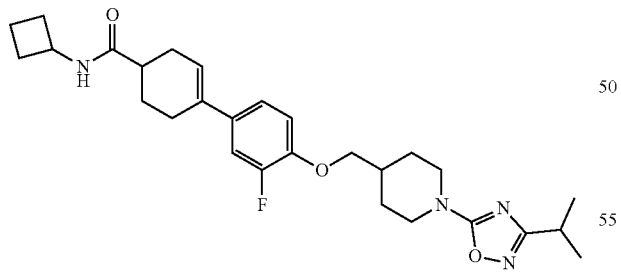

The title compound was prepared in the same manner as in <Example 330>, except that aminocyclobutane was used instead of the azetidine hydrochloride (Amount obtained: 430 mg/Yield: 74%).

¹H NMR (400, CDCl₃): 7.11 (1H, dd), 7.07 (1H, d), 6.89 (1H, t), 6.07 (1H, m), 5.64 (1H, d), 4.45 (1H, m), 4.23 (2H, d), 3.90 (2H, d), 3.12 (2H, m), 2.92 (1H, m), 2.40 (7H, m), 2.10 (2H, m), 1.94 (2H, d), 1.86 (3H, m), 1.76 (2H, m), 1.44 (2H, m), 1.29 (6H, d)

Example 365: Preparation of N-cyclopentyl-4-(3-fluoro-4-((1-(3-isopropyl-1,2,4-oxadiazol-5-yl)piperidin-4-yl)methoxy)phenyl)cyclohex-3-enecarboxamide

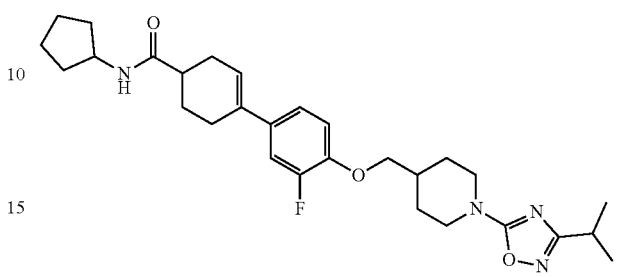

The title compound was prepared in the same manner as in <Example 330>, except that cyclopentylamine was used instead of the azetidine hydrochloride (Amount obtained: 430 mg/Yield: 74%).

¹H NMR (400, CDCl₃): 7.14 (1H, dd), 7.08 (1H, d), 6.89 (1H, t), 6.06 (1H, m), 5.47 (1H, d), 4.23 (3H, m), 3.91 (2H, d), 3.14 (2H, m), 2.90 (1H, m), 2.40 (5H, m), 2.05 (6H, m), 1.88 (1H, m), 1.65 (5H, m), 1.38 (4H, m), 1.27 (6H, d)

Example 366: Preparation of N-cyclohexyl-4-(3-fluoro-4-((1-(3-isopropyl-1,2,4-oxadiazol-5-yl)piperidin-4-yl)methoxy)phenyl)cyclohex-3-enecarboxamide

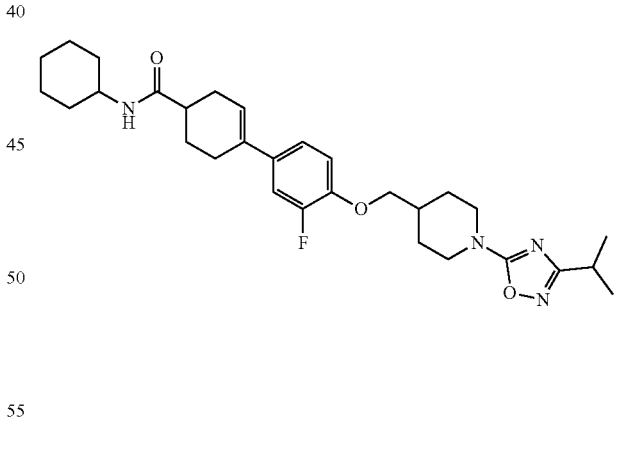

The title compound was prepared in the same manner as in <Example 330>, except that cyclohexylamine was used instead of the azetidine hydrochloride (Amount obtained: 450 mg/Yield: 75%).

¹H NMR (400, CDCl₃): 7.14 (1H, dd), 7.08 (1H, d), 6.89 (1H, t), 6.06 (1H, m), 5.38 (1H, d), 4.20 (2H, d), 3.90 (2H, d), 3.82 (1H, m), 3.12 (2H, m), 2.89 (1H, m), 2.40 (5H, m), 2.08 (2H, m), 1.90 (5H, m), 1.71 (2H, m), 1.62 (3H, m), 1.40 (4H, m), 1.29 (6H, d), 1.16 (3H, m)

Example 367: Preparation of (4-ethylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone

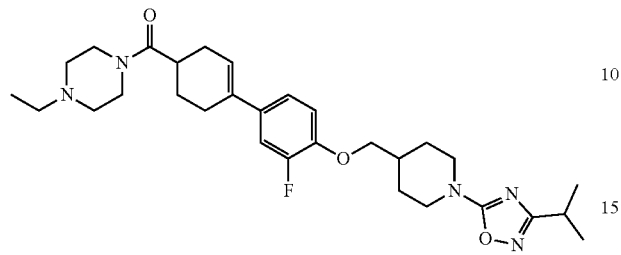

The title compound was prepared in the same manner as in <Example 330>, except that 1-ethylpiperazine was used instead of the azetidine hydrochloride (Amount obtained: 400 mg/Yield: 70%).

$^1$H NMR (400, CDCl$_3$): 7.12 (1H, dd), 7.07 (1H, d), 6.89 (1H, t), 6.08 (1H, m), 5.47 (1H, d), 4.23 (2H, d), 3.91 (2H, d), 3.60 (4H, m), 3.12 (2H, m), 2.92 (1H, m), 2.80 (1H, m), 2.47 (9H, m), 2.30 (1H, m), 2.10 (1H, m), 1.44 (2H, m), 1.29 (6H, d), 1.11 (3H, t)

Example 368: Preparation of (4-(3-fluoro-4-((1-(3-isopropyl-1,2,4-oxadiazol-5-yl)piperidin-4-yl)methoxy)phenyl)cyclohex-3-enyl)(4-(3-hydroxypropyl)piperazin-1-yl)methanone

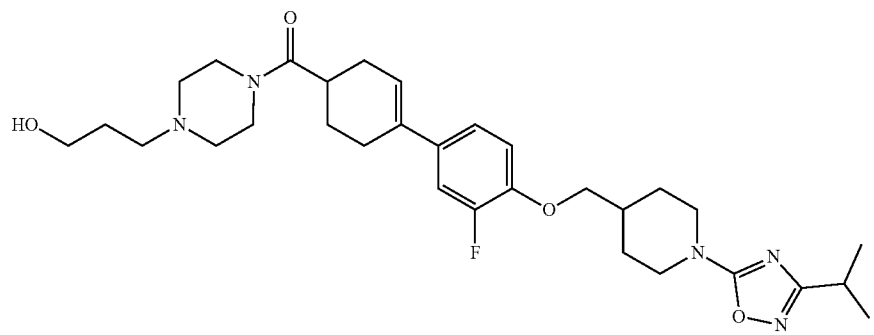 [SMILES: CC(C)c1noc(N2CCC(COc3ccc(C4=CCC(C(=O)N5CCN(CCCO)CC5)CC4)cc3F)CC2)n1]

The title compound was prepared in the same manner as in <Example 330>, except that 1-(3-hydroxypropyl)piperazine was used instead of the azetidine hydrochloride (Amount obtained: 350 mg/Yield: 63%).

$^1$H NMR (400, CDCl$_3$): 7.14 (1H, dd), 7.06 (1H, d), 6.89 (1H, t), 6.07 (1H, m), 4.20 (2H, d), 3.90 (2H, d), 3.82 (2H, t), 3.62 (4H, m), 3.12 (2H, m), 2.90 (1H, m), 2.77 (1H, m), 2.67 (2H, t), 2.52 (7H, m), 2.30 (1H, m), 2.10 (1H, m), 1.94 (4H, m), 1.77 (2H, m), 1.46 (2H, m), 1.28 (6H, d)

Example 369: Preparation of (4-cyclopropylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone

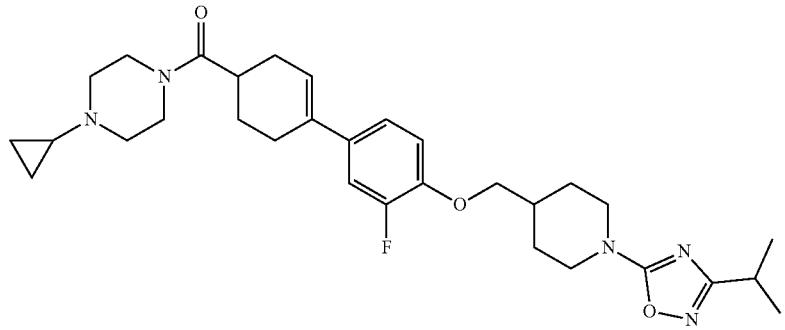 [SMILES: CC(C)c1noc(N2CCC(COc3ccc(C4=CCC(C(=O)N5CCN(C6CC6)CC5)CC4)cc3F)CC2)n1]

The title compound was prepared in the same manner as in <Example 330>, except that 1-cyclopropylpiperazine was used instead of the azetidine hydrochloride (Amount obtained: 410 mg/Yield: 71%).

$^1$H NMR (400, CDCl$_3$): 7.12 (1H, dd), 7.07 (1H, d), 6.89 (1H, t), 6.08 (1H, m), 4.23 (2H, d), 3.90 (2H, d), 3.58 (4H, m), 3.12 (2H, m), 2.92 (1H, m), 2.50 (9H, m), 2.11 (1H, m), 1.98 (4H, m), 1.64 (1H, m), 1.43 (2H, m), 1.29 (6H, d), 0.45 (4H, m)

Example 370: Preparation of (4-(3-fluoro-4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone

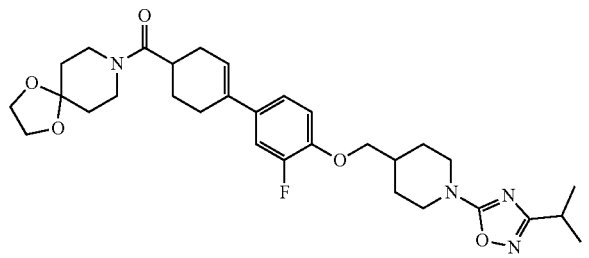 [SMILES: CC(C)c1noc(N2CCC(COc3ccc(C4=CCC(C(=O)N5CCC6(CC5)OCCO6)CC4)cc3F)CC2)n1]

The title compound was prepared in the same manner as in <Example 330>, except that 4-piperidone ethylene ketal was used instead of the azetidine hydrochloride (Amount obtained: 460 mg/Yield: 75%).

$^1$H NMR (400, CDCl$_3$): 7.12 (1H, dd), 7.07 (1H, d), 6.89 (1H, t), 6.08 (1H, m), 4.23 (2H, d), 4.01 (4H, s), 3.91 (2H, d), 3.77 (2H, m), 3.63 (2H, m), 3.12 (2H, m), 1.90 (2H, m), 2.49 (3H, m), 2.30 (1H, m), 2.10 (1H, m), 1.90 (4H, m), 1.73 (4H, m), 1.44 (2H, m), 1.29 (6H, d)

Example 371: Preparation of 4-(3-fluoro-4-((1-(3-isopropyl-1,2,4-oxadiazol-5-yl)piperidin-4-yl)methoxy)phenyl)-N-(3-hydroxy-2,2-dimethylpropyl)cyclohex-3-enecarboxamide

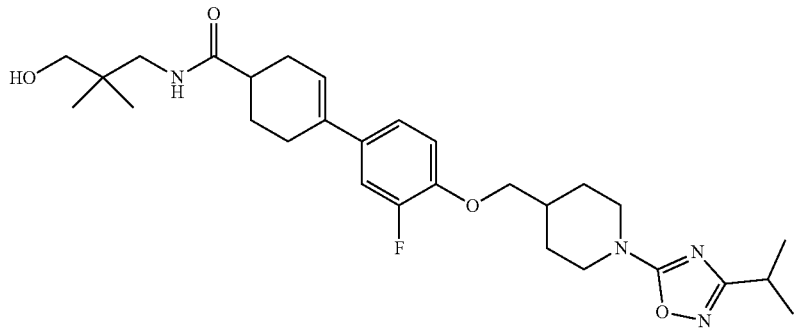 [SMILES: CC(C)c1noc(N2CCC(COc3ccc(C4=CCC(C(=O)NCC(C)(C)CO)CC4)cc3F)CC2)n1]

The title compound was prepared in the same manner as in <Example 330>, except that 3-amino-2,2-dimethyl-1-propanol was used instead of the azetidine hydrochloride (Amount obtained: 380 mg/Yield: 68%).

$^1$H NMR (400, CDCl$_3$): 7.14 (1H, dd), 7.06 (1H, d), 6.89 (1H, t), 6.07 (2H, m), 4.20 (2H, d), 3.92 (3H, m), 3.14 (6H, m), 2.90 (1H, m), 2.49 (5H, m), 2.11 (2H, m), 1.91 (3H, m), 1.41 (2H, m), 1.29 (6H, d), 0.90 (6H, d)

Example 372: Preparation of 4-(3-fluoro-4-((1-(3-isopropyl-1,2,4-oxadiazol-5-yl)piperidin-4-yl)methoxy)phenyl)-N,N-bis(2-hydroxyethyl)cyclohex-3-enecarboxamide

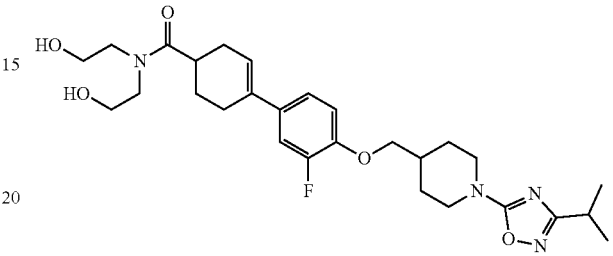

The title compound was prepared in the same manner as in <Example 330>, except that diethanolamine was used instead of the azetidine hydrochloride (Amount obtained: 410 mg/Yield: 71%).

$^1$H NMR (400, CDCl$_3$): 7.14 (1H, dd), 7.09 (1H, d), 6.89 (1H, t), 6.08 (1H, m), 4.23 (2H, d), 3.90 (6H, m), 3.61 (4H, m), 3.12 (4H, m), 2.90 (2H, m), 2.45 (4H, m), 2.00 (5H, m), 1.43 (2H, m), 1.30 (9H, m)

Example 373: Preparation of azetidin-1-yl(4-(4-((1-(3-isopropyl-1,2,4-oxadiazol-5-yl)piperidin-4-yl)methoxy)-3-(trifluoromethyl)phenyl)cyclohex-3-enyl)methanone

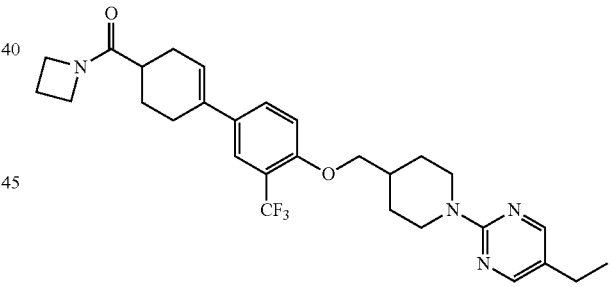

500 mg of 4-(4-((1-(5-ethylpyrimidin-2-yl)piperidin-4-yl)methoxy)-3-(trifluoromethyl)phenyl)cyclohex-3-enecarboxylic acid was put into a 100 ml flask under a nitrogen atmosphere, 20 ml of dichloromethane was added thereto, and the resulting mixture was then dissolved while stirring. 0.32 ml of triethylamine, 0.16 ml of azetidine hydrochloride, and 490 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 400 mg/Yield: 71%).

$^1$H NMR (400, CDCl$_3$): 8.19 (2H, s), 7.57 (1H, d), 7.46 (1H, dd), 6.91 (1H, d), 6.08 (1H, d), 4.77 (2H, d), 4.24 (2H, t), 4.09 (2H, d), 3.90 (2H, d), 2.90 (2H, m), 2.47 (6H, m), 2.32 (3H, m), 2.15 (1H, m), 1.90 (4H, m), 1.36 (2H, m), 1.20 (3H, t)

Example 374: Preparation of (4-(4-((1-(3-isopropyl-1,2,4-oxadiazol-5-yl)piperidin-4-yl)methoxy)-3-(trifluoromethyl)phenyl)cyclohex-3-enyl)(pyrrolidin-1-yl)methanone

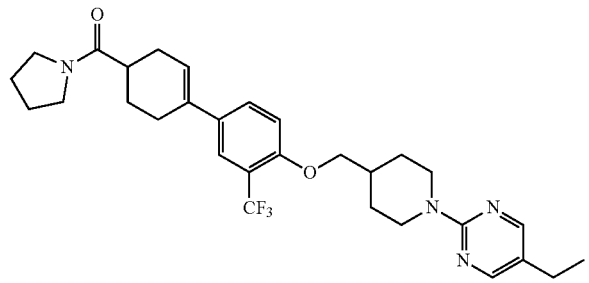

The title compound was prepared in the same manner as in <Example 373>, except that pyrrolidine was used instead of the azetidine hydrochloride (Amount obtained: 450 mg/Yield: 75%).

$^1$H NMR (400, CDCl$_3$): 8.19 (2H, s), 7.58 (1H, d), 7.47 (1H, dd), 6.91 (1H, d), 6.10 (1H, d), 4.77 (2H, d), 3.90 (2H, d), 3.51 (5H, m), 2.93 (2H, m), 2.50 (9H, m), 2.00 (12H, m), 1.38 (2H, m), 1.20 (3H, m)

Example 375: Preparation of (4-(4-((1-(5-ethylpyrimidin-2-yl)piperidin-4-yl)methoxy)-3-(trifluoromethyl)phenyl)cyclohex-3-enyl)(piperidin-1-yl)methanone

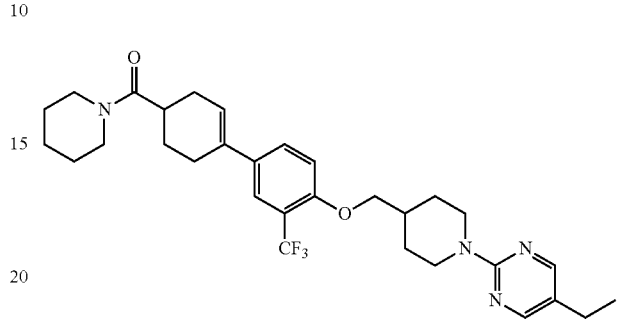

The title compound was prepared in the same manner as in <Example 373>, except that piperidine was used instead of the azetidine hydrochloride (Amount obtained: 480 mg/Yield: 77%).

$^1$H NMR (400, CDCl$_3$): 8.19 (2H, s), 7.58 (1H, d), 7.47 (1H, dd), 6.91 (1H, d), 6.09 (1H, d), 4.77 (2H, d), 3.90 (2H, d), 3.58 (4H, m), 2.92 (2H, m), 2.80 (1H, m), 2.50 (5H, m), 2.30 (1H, m), 2.15 (1H, m), 1.90 (4H, m), 1.67 (2H, m), 1.56 (5H, m), 1.35 (2H, m), 1.20 (3H, t)

Example 376: Preparation of 4-(4-((1-(5-ethylpyrimidin-2-yl)piperidin-4-yl)methoxy)-3-fluorophenyl)-N-(3-hydroxypropyl)-N-methylcyclohex-3-enecarboxamide

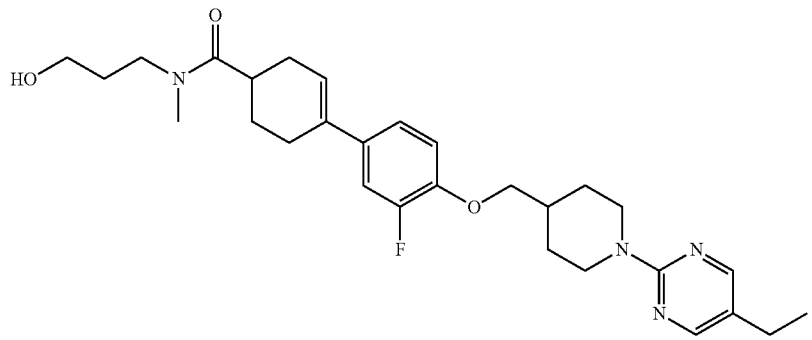 [SMILES: CCc1cnc(N2CCC(COc3ccc(C4=CCC(C(=O)N(C)CCCO)CC4)cc3F)CC2)nc1]

The title compound was prepared in the same manner as in <Example 292>, except that 3-(methylamino)-1-propanol was used instead of the piperidine (Amount obtained: 440 mg/Yield: 74%).

¹H NMR (400, CDCl₃): 8.17 (2H, s), 7.10 (1H, dd), 7.05 (1H, d), 6.89 (1H, t), 6.07 (1H, m), 4.75 (2H, d), 3.87 (2H, d), 3.57 (2H, d), 3.48 (2H, d), 3.08 (3H, s), 2.90 (3H, m), 2.50 (5H, m), 2.30 (1H, m), 2.00 (6H, m), 1.72 (2H, m), 1.35 (2H, m), 1.18 (3H, t)

Example 377: Preparation of (4-(4-((1-(5-ethylpyrimidin-2-yl)piperidin-4-yl)methoxy)-3-fluorophenyl)cyclohex-3-enyl)(4-(hydroxyimino)piperidin-1-yl)methanone

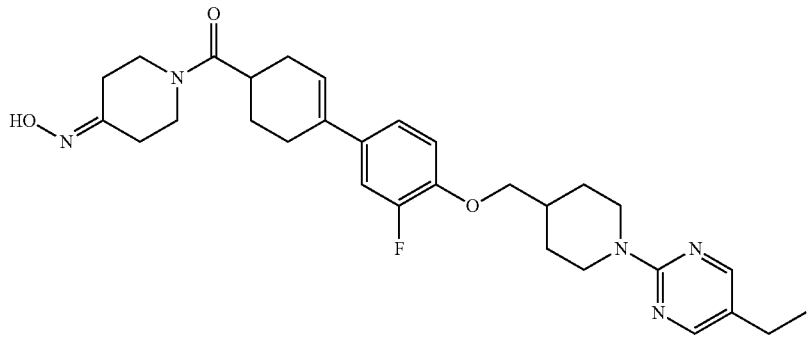 [SMILES: CCc1cnc(N2CCC(COc3ccc(C4=CCC(C(=O)N5CCC(=NO)CC5)CC4)cc3F)CC2)nc1]

300 mg of 1-(4-(4-((1-(5-ethylpyrimidin-2-yl)piperidin-4-yl)methoxy)-3-fluorophenyl)cyclohex-3-enecarbonyl)piperidin-4-one was put into a 100 ml flask under a nitrogen atmosphere, 20 ml of ethanol was added thereto, and the resulting mixture was then dissolved while stirring. 23 mg of sodium hydroxide and 70 mg of hydroxylamine hydrochloride were added dropwise thereto, and the mixture was stirred at 60° C. for 2 hours. After the reaction was terminated, 30 ml of ethyl acetate and 30 ml of distilled water were added thereto, and the reaction mixture was extracted, dried with anhydrous magnesium sulfate, concentrated, and then isolated by silica column chromatography to obtain the title compound (Amount obtained: 200 mg/Yield: 65%).

¹H NMR (400, CDCl₃): 8.19 (2H, s), 7.55 (1H, d), 7.14 (1H, dd), 7.07 (1H, d), 6.90 (1H, t), 6.08 (1H, d), 4.79 (2H, d), 3.91 (2H, d), 3.70 (4H, m), 2.70 (5H, m), 2.52 (7H, m), 2.30 (1H, m), 2.14 (1H, m), 1.95 (4H, m), 1.37 (2H, m), 1.20 (3H, t)

Example 378: Preparation of 4-(4-((1-(5-ethylpyrimidin-2-yl)piperidin-4-yl)methoxy)-3-fluorophenyl)-N-(3-hydroxy-2,2-dimethylpropyl)cyclohex-3-enecarboxamide

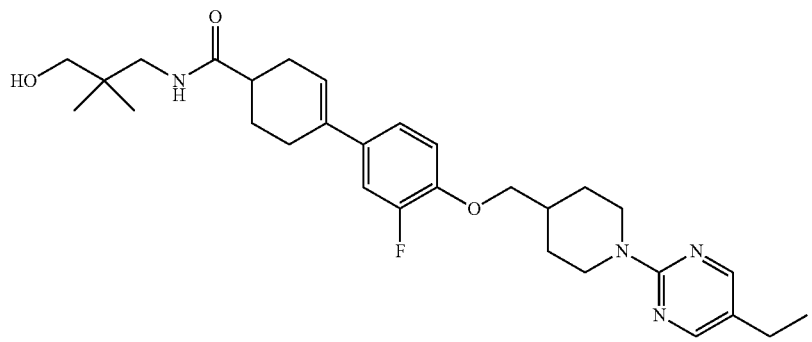 [SMILES: CCc1cnc(N2CCC(COc3ccc(C4=CCC(C(=O)NCC(C)(C)CO)CC4)cc3F)CC2)nc1]

The title compound was prepared in the same manner as in <Example 292>, except that 3-amino-2,2-dimethyl-1-propanol was used instead of the piperidine (Amount obtained: 350 mg/Yield: 66%).

¹H NMR (400, CDCl₃): 8.17 (2H, s), 7.09 (1H, dd), 7.04 (1H, d), 6.88 (1H, t), 6.04 (1H, s), 5.95 (1H, t), 4.75 (2H, d), 3.90 (3H, m), 3.12 (4H, m), 2.91 (2H, m), 2.46 (7H, m), 2.11 (2H, m), 1.91 (3H, m), 1.32 (2H, m), 1.20 (3H, t), 0.88 (2H, d)

Example 379: Preparation of (4-(4-((1-(5-ethylpyrimidin-2-yl)piperidin-4-yl)methoxy)-3-fluorophenyl)cyclohex-3-enyl)(4-methylpiperazin-1-yl)methanone

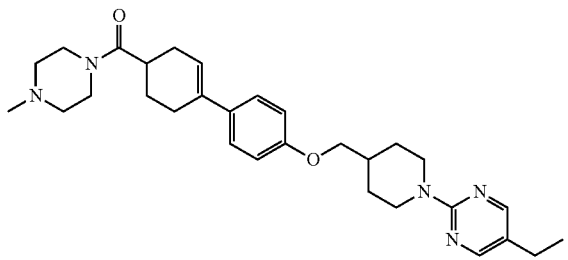 [SMILES: CCc1cnc(N2CCC(COc3ccc(C4=CCC(C(=O)N5CCN(C)CC5)CC4)cc3)CC2)nc1]

500 mg of 4-(4-((1-(5-ethylpyrimidin-2-yl)piperidin-4-yl)methoxy)phenyl)cyclohex-3-enecarboxylic acid was put into a 100 ml flask under a nitrogen atmosphere, 20 ml of dichloromethane was thereto, and the resulting mixture was then dissolved while stirring. 0.34 ml of triethylamine, 0.16 ml of 1-methylpiperazine, and 530 mg of HATU were added dropwise thereto, and the mixture was stirred at 20° C. for an hour. After the reaction was terminated, 20 ml of dichloromethane was additionally added thereto, and an organic layer as washed with 20 ml of distilled water, dried with anhydrous magnesium sulfate, concentrated, and then isolated by silica column chromatography to obtain the title compound (Amount obtained: 510 mg/Yield: 80%).

¹H NMR (400, CDCl₃): 8.22 (2H, s), 7.31 (2H, d), 6.87 (2H, d), 6.06 (1H, t), 4.64 (2H, d), 3.82 (2H, d), 2.86 (3H, m), 2.73 (3H, s), 2.44 (4H, m), 2.23 (2H, m), 2.03 (1H, m), 1.88 (2H, d), 1.61 (1H, m), 1.21 (2H, m), 1.10 (3H, t)

Example 380: Preparation of (4-(4-((1-(5-ethylpyrimidin-2-yl)piperidin-4-yl)methoxy)phenyl)cyclohex-3-enyl)(4-(3-hydroxypropyl)piperazin-1-yl)methanone

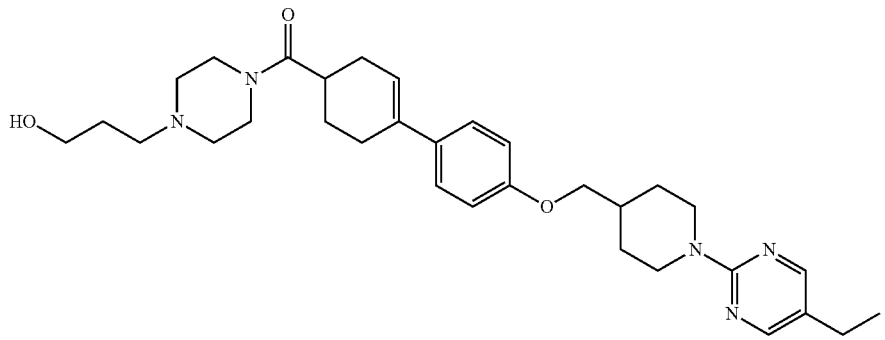 [SMILES: CCc1cnc(N2CCC(COc3ccc(C4=CCC(C(=O)N5CCN(CCCO)CC5)CC4)cc3)CC2)nc1]

The title compound was prepared in the same manner as in <Example 379>, except that 1-(3-hydroxypropyl)piperazine was used instead of the 1-methylpiperazine (Amount obtained: 410 mg/Yield: 70%).

¹H NMR (400, CDCl₃): 8.15 (2H, s), 7.23 (2H, d), 6.77 (2H, d), 5.97 (1H, s), 4.70 (2H, d), 3.76 (7H, m), 3.12 (5H, m), 2.88 (8H, m), 2.40 (7H, m), 1.93 (7H, m), 1.74 (1H, m), 1.31 (2H, m), 1.16 (3H, t)

Example 381: Preparation of (4-(3-fluoro-4-((1-(3-isopropyl-1,2,4-oxadiazol-5-yl)piperidin-4-yl)methoxy)phenyl)cyclohex-3-enyl)(piperazin-1-yl)methanone

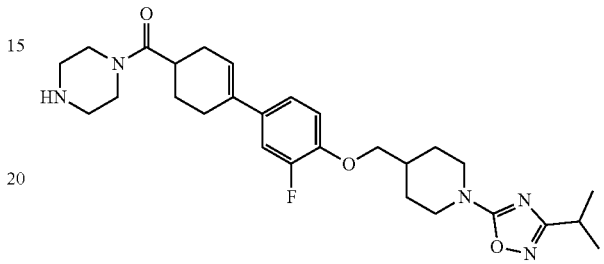

The title compound was prepared in the same manner as in <Example 330>, except that anhydrous piperazine was used instead of the azetidine hydrochloride (Amount obtained: 300 mg/Yield: 62%).

¹H NMR (400, CDCl₃): 7.10 (1H, dd), 7.05 (1H, d), 6.87 (1H, t), 6.06 (1H, d), 4.18 (2H, d), 3.88 (2H, d), 3.64 (2H, m), 3.48 (2H, m), 3.12 (2H, m), 2.88 (5H, m), 2.77 (1H, m), 2.50 (3H, m), 2.30 (1H, m), 2.10 (1H, m), 1.95 (4H, m), 1.42 (2H, m), 1.27 (6H, d)

Example 382: Preparation of (4-(3-fluoro-4-((1-(3-isopropyl-1,2,4-oxadiazol-5-yl)piperidin-4-yl)methoxy)phenyl)cyclohex-3-enyl)(4-methylpiperazin-1-yl)methanone

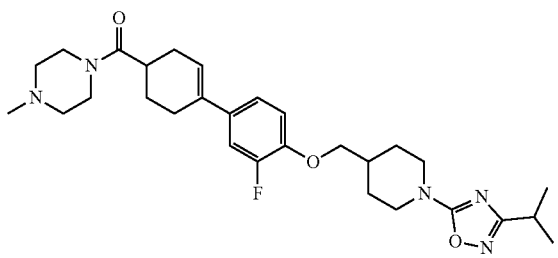

*2442

The title compound was prepared in the same manner as in <Example 330>, except that 1-methylpiperazine was used instead of the azetidine hydrochloride (Amount obtained: 430 mg/Yield: 73%).

¹H NMR (400, CDCl₃): 7.12 (1H, dd), 7.07 (1H, d), 6.87 (1H, t), 6.06 (1H, d), 4.18 (2H, d), 3.88 (2H, d), 3.67 (2H, m), 3.55 (2H, t), 3.12 (2H, m), 2.89 (1H, m), 2.77 (1H, m), 2.45 (10H, m), 2.05 (6H, m), 1.41 (2H, m), 1.27 (6H, d)

Example 383: Preparation of tert-butyl 4-(4-(4-((1-(5-ethylpyrimidin-2-yl)piperidin-4-yl)methoxy)-3-fluorophenyl)cyclohex-3-enecarbonyl)piperazine-1-carboxylate

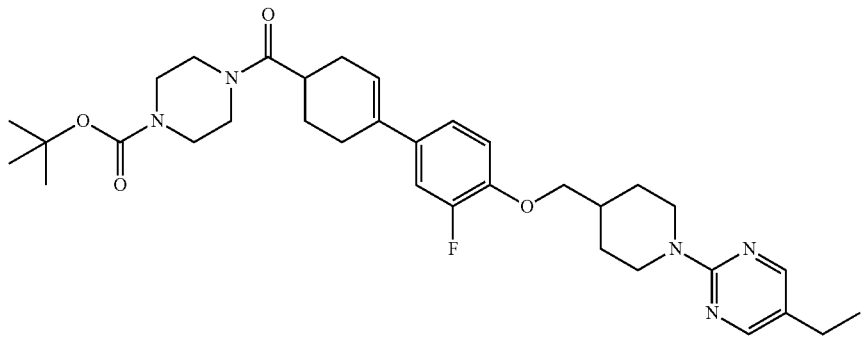 [SMILES: CCc1cnc(N2CCC(COc3ccc(C4=CCC(C(=O)N5CCN(C(=O)OC(C)(C)C)CC5)CC4)cc3F)CC2)nc1]

The title compound was prepared in the same manner as in <Example 292>, except that 1-(tert-butoxycarbonyl)piperazine was used instead of the piperidine (Amount obtained: 470 mg/Yield: 75%).

¹H NMR (400, CDCl₃): 8.17 (2H, s), 7.12 (1H, dd), 7.04 (1H, d), 6.88 (1H, t), 6.05 (1H, d), 4.75 (2H, d), 3.87 (2H, d), 3.63 (2H, m), 3.46 (6H, m), 2.94 (2H, m), 2.87 (1H, m), 2.45 (5H, m), 2.25 (1H, m), 2.14 (1H, m), 1.93 (4H, m), 1.46 (9H, s), 1.31 (2H, m), 1.18 (3H, t)

Example 384: Preparation of (4-(4-((1-(5-ethylpyrimidin-2-yl)piperidin-4-yl) methoxy)-3-fluorophenyl)cyclohex-3-enyl)(4-methylpiperazin-1-yl)methanone

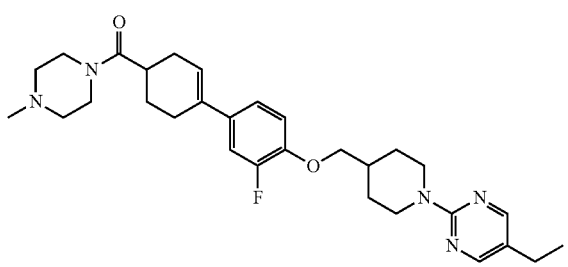 [SMILES: CCc1cnc(N2CCC(COc3ccc(C4=CCC(C(=O)N5CCN(C)CC5)CC4)cc3F)CC2)nc1]

The title compound was prepared in the same manner as in <Example 292>, except that 1-methylpiperazine was used instead of the piperidine (Amount obtained: 500 mg/Yield: 80%).

¹H NMR (400, CDCl₃): 8.17 (2H, s), 7.13 (1H, dd), 7.07 (1H, d), 6.88 (1H, t), 6.05 (1H, d), 4.75 (2H, d), 3.87 (2H, d), 3.68 (2H, m), 3.55 (2H, t), 2.91 (2H, m), 2.76 (1H, m), 2.50 (9H, m), 2.32 (3H, s), 2.28 (1H, m), 1.90 (4H, m), 1.32 (2H, m), 1.18 (3H, t)

Example 385: Preparation of 2-((1-(5-ethylpyrimidin-2-yl)piperidin-4-yl)methoxy)-5-(4-(piperidine-1-carbonyl)cyclohex-1-enyl)benzonitrile

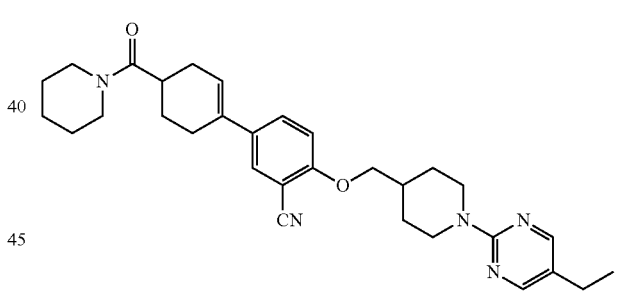

500 mg of 4-(3-cyano-4-((1-(5-ethylpyrimidin-2-yl)piperidin-4-yl)methoxy)phenyl)cyclohex-3-enecarboxylic acid was put into a 100 ml flask under a nitrogen atmosphere, 20 ml of dichloromethane was added thereto, and the resulting mixture was then dissolved while stirring. 0.32 ml of triethylamine, 0.14 ml of piperidine, and 510 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 480 mg/Yield: 78%).

¹H NMR (400, CDCl₃): 8.17 (2H, s), 7.53 (2H, m), 6.87 (1H, d), 6.07 (1H, m), 4.76 (2H, d), 3.90 (2H, d), 3.59 (2H, m), 3.48 (2H, m), 2.92 (2H, m), 2.88 (1H, m), 2.50 (5H, m), 2.26 (1H, m), 2.18 (1H, m), 1.97 (3H, m), 1.86 (1H, m), 1.60 (6H, m), 1.33 (2H, m), 1.18 (3H, t)

Example 386: Preparation of 2-((1-(5-ethylpyrimidin-2-yl)piperidin-4-yl)methoxy)-5-(4-(pyrrolidine-1-carbonyl)cyclohex-1-enyl)benzonitrile

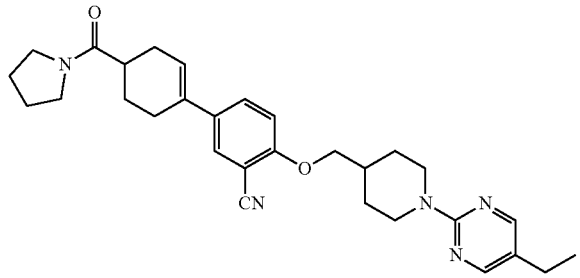 [SMILES: CCc1cnc(N2CCC(COc3ccc(C4=CCC(C(=O)N5CCCC5)CC4)cc3C#N)CC2)nc1]

The title compound was prepared in the same manner as in <Example 385>, except that pyrrolidine was used instead of the piperidine (Amount obtained: 470 mg/Yield: 77%).

$^1$H NMR (400, CDCl$_3$): 8.17 (2H, s), 7.53 (2H, m), 6.88 (1H, d), 6.09 (1H, m), 4.76 (2H, d), 3.90 (2H, d), 3.49 (4H, m), 2.93 (2H, m), 2.50 (7H, m), 2.17 (1H, m), 1.96 (5H, m), 1.84 (3H, m), 1.34 (2H, m), 1.18 (3H, t)

Example 387: Preparation of 5-(4-(azetidine-1-carbonyl)cyclohex-1-enyl)-2-((1-(5-ethylpyrimidin-2-yl)piperidin-4-yl)methoxy)benzonitrile

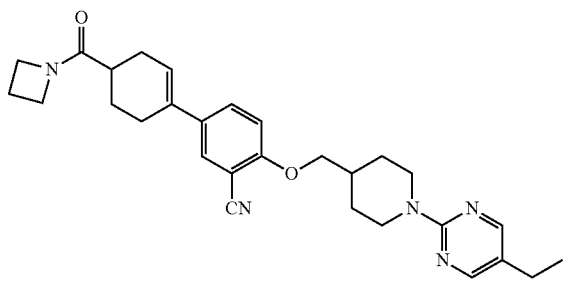 [SMILES: CCc1cnc(N2CCC(COc3ccc(C4=CCC(C(=O)N5CCC5)CC4)cc3C#N)CC2)nc1]

The title compound was prepared in the same manner as in <Example 385>, except that azetidine hydrochloride was used instead of the piperidine (Amount obtained: 400 mg/Yield: 67%).

$^1$H NMR (400, CDCl$_3$): 8.17 (2H, s), 7.52 (2H, m), 6.87 (1H, d), 6.06 (1H, m), 4.76 (2H, d), 4.22 (2H, t), 4.07 (2H, d), 3.90 (2H, d), 3.11 (1H, q), 2.92 (2H, m), 2.50 (6H, m), 2.25 (4H, m), 1.96 (3H, m), 1.83 (1H, m), 1.32 (4H, m), 1.18 (3H, t)

Example 388: Preparation of 2-((1-(5-ethylpyrimidin-2-yl)piperidin-4-yl)methoxy)-5-(4-(morpholine-4-carbonyl)cyclohex-1-enyl)benzonitrile

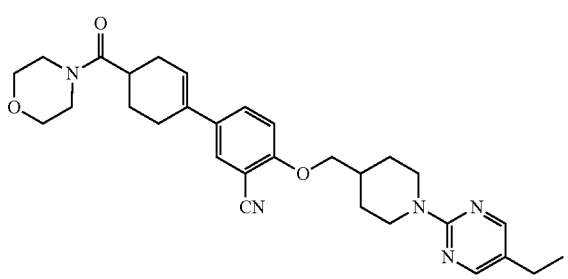 [SMILES: CCc1cnc(N2CCC(COc3ccc(C4=CCC(C(=O)N5CCOCC5)CC4)cc3C#N)CC2)nc1]

The title compound was prepared in the same manner as in <Example 385>, except that morpholine was used instead of the piperidine (Amount obtained: 410 mg/Yield: 68%).

$^1$H NMR (400, CDCl$_3$): 8.17 (2H, s), 7.52 (2H, m), 6.88 (1H, d), 6.07 (1H, m), 4.76 (2H, d), 3.90 (2H, d), 3.67 (6H, m), 3.58 (2H, s), 2.92 (2H, m), 2.86 (1H, m), 2.50 (5H, m), 2.20 (2H, m), 1.95 (4H, m), 1.74 (1H, s), 1.33 (2H, m), 1.18 (3H, t)

Example 389: Preparation of 2-((1-(5-ethylpyrimidin-2-yl)piperidin-4-yl)methoxy)-5-(4-(thiomorpholine-4-carbonyl)cyclohex-1-enyl)benzonitrile

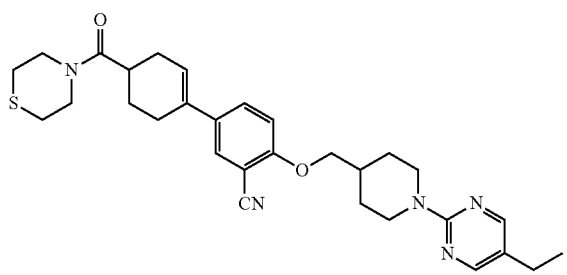 [SMILES: CCc1cnc(N2CCC(COc3ccc(C4=CCC(C(=O)N5CCSCC5)CC4)cc3C#N)CC2)nc1]

The title compound was prepared in the same manner as in <Example 385>, except that thiomorpholine was used instead of the piperidine (Amount obtained: 450 mg/Yield: 75%).

$^1$H NMR (400, CDCl$_3$): 8.17 (2H, s), 7.52 (2H, m), 6.88 (1H, d), 6.07 (1H, m), 4.76 (2H, d), 3.90 (6H, m), 2.92 (2H, m), 2.78 (1H, m), 2.64 (4H, m), 2.45 (5H, m), 2.20 (2H, m), 1.95 (4H, m), 1.35 (2H, m), 1.18 (3H, t)

Example 390: Preparation of 2-((1-(5-ethylpyrimidin-2-yl)piperidin-4-yl)methoxy)-5-(4-(4-hydroxypiperidine-1-carbonyl)cyclohex-1-enyl)benzonitrile

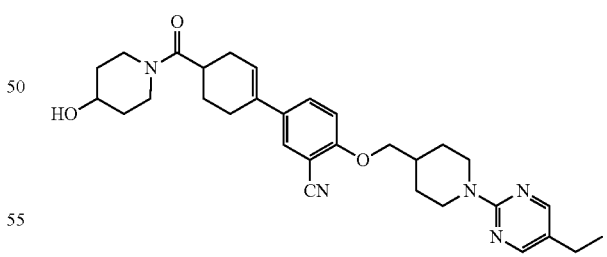

The title compound was prepared in the same manner as in <Example 385>, except that 4-hydroxypiperidine was used instead of the piperidine (Amount obtained: 420 mg/Yield: 71%).

$^1$H NMR (400, CDCl$_3$): 8.17 (2H, s), 7.51 (2H, m), 6.88 (1H, d), 6.07 (1H, s), 4.76 (2H, d), 4.13 (1H, m), 3.90 (4H, m), 3.32 (2H, m), 2.92 (2H, m), 2.82 (1H, m), 2.48 (5H, m), 2.28 (1H, m), 2.16 (1H, m), 1.95 (8H, m), 1.54 (2H, m), 1.36 (3H, m), 1.18 (3H, t)

Example 391: Preparation of 2-((1-(5-ethylpyrimidin-2-yl)piperidin-4-yl)methoxy)-5-(4-(4-(hydroxymethyl)piperidine-1-carbonyl)cyclohex-1-enyl)benzonitrile

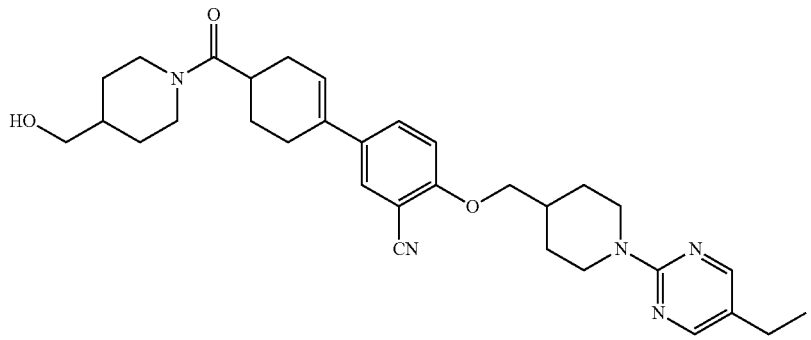 [SMILES: CCc1cnc(N2CCC(COc3ccc(C4=CCC(C(=O)N5CCC(CO)CC5)CC4)cc3C#N)CC2)nc1]

The title compound was prepared in the same manner as in <Example 385>, except that 4-piperidinemethanol was used instead of the piperidine (Amount obtained: 410 mg/Yield: 68%).

$^1$H NMR (400, CDCl$_3$): 8.17 (2H, s), 7.53 (2H, m), 6.87 (1H, d), 6.07 (1H, m), 4.72 (3H, m), 3.98 (3H, m), 3.55 (2H, m), 3.10 (1H, m), 2.92 (2H, m), 2.78 (1H, m), 2.50 (6H, m), 2.30 (1H, m), 2.18 (1H, m), 1.80 (7H, m), 1.32 (2H, m), 1.18 (5H, m)

Example 392: Preparation of tert-butyl 4-((2-fluoro-4-(4-(pyrrolidine-1-carbonyl)cyclohex-1-enyl)phenoxy)methyl)piperidine-1-carboxylate

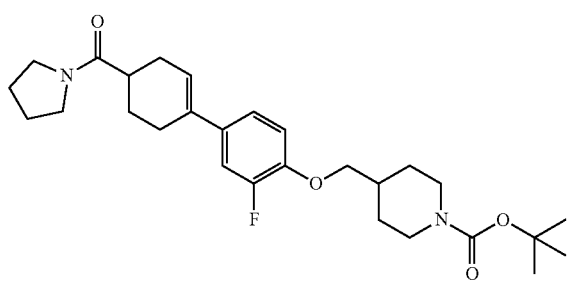 [SMILES: CC(C)(C)OC(=O)N1CCC(COc2ccc(C3=CCC(C(=O)N4CCCC4)CC3)cc2F)CC1]

500 mg of 4-(4-((1-(tert-butoxycarbonyl)piperidin-4-yl)methoxy)-3-fluorophenyl)cyclohex-3-enecarboxylic acid was put into a 100 ml flask under a nitrogen atmosphere, 20 ml of dichloromethane was added thereto, and the resulting mixture was then dissolved while stirring. 0.31 ml of triethylamine, 0.12 ml of pyrrolidine, and 500 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 430 mg/Yield: 71%).

$^1$H NMR (400, CDCl$_3$): 7.12 (1H, dd), 7.07 (1H, d), 6.87 (1H, t), 6.08 (1H, d), 4.14 (2H, s), 3.85 (2H, d), 3.51 (4H, m), 3.46 (6H, m), 2.50 (7H, m), 2.02 (4H, m), 1.88 (5H, m), 1.47 (9H, s), 1.27 (2H, m)

Example 393: Preparation of (4-(3-amino-4-((1-(5-ethylpyrimidin-2-yl)piperidin-4-yl)methoxy)phenyl)cyclohex-3-enyl)(pyrrolidin-1-yl)methanone

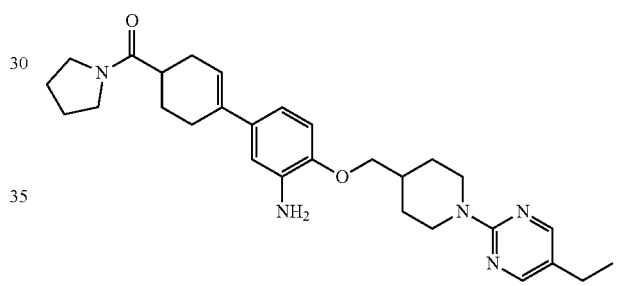

500 mg of 4-(3-amino-4-((1-(5-ethylpyrimidin-2-yl)piperidin-4-yl)methoxy)phenyl)cyclohex-3-enecarboxylic acid was put into a 100 ml flask under a nitrogen atmosphere, 20 ml of dichloromethane was added thereto, and the resulting mixture was then dissolved while stirring. 0.31 ml of triethylamine, 0.13 ml of pyrrolidine, and 500 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 380 mg/Yield: 63%).

$^1$H NMR (400, CDCl$_3$): 8.17 (2H, s), 6.74 (1H, d), 6.69 (2H, m), 6.00 (1H, m), 4.78 (2H, d), 3.85 (2H, d), 3.76 (2H, s), 3.48 (4H, m), 2.92 (2H, m), 2.62 (1H, m), 2.45 (5H, m), 2.25 (1H, m), 2.12 (1H, m), 1.90 (9H, m), 1.36 (2H, m), 1.18 (3H, t)

Example 394: Preparation of 2-((1-(5-ethylpyrimi-din-2-yl)piperidin-4-yl)methoxy)-5-(4-(4-(2-hydroxyethyl)piperidine-1-carbonyl)cyclohex-1-enyl)benzonitrile

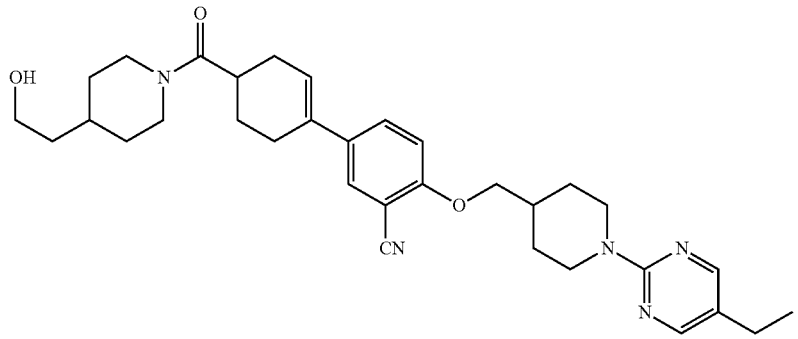 [SMILES: CCc1cnc(N2CCC(COc3ccc(C4=CCC(C(=O)N5CCC(CCO)CC5)CC4)cc3C#N)CC2)nc1]

The title compound was prepared in the same manner as in <Example 385>, except that 4-piperidineethanol was used instead of the piperidine (Amount obtained: 430 mg/Yield: 71%).

$^1$H NMR (400, CDCl$_3$): 8.17 (2H, s), 7.53 (2H, m), 6.87 (1H, d), 6.07 (1H, m), 4.76 (2H, d), 4.64 (1H, d), 3.92 (3H, m), 3.72 (2H, s), 3.06 (1H, t), 2.92 (2H, m), 2.78 (1H, m), 2.50 (6H, m), 2.20 (2H, m), 1.98 (3H, m), 1.80 (4H, m), 1.56 (2H, m), 1.30 (4H, m), 1.18 (5H, t)

Example 395: Preparation of (4-cyclopropylpiper-azin-1-yl)(4-(4-((1-(5-ethylpyrimidin-2-yl)piperidin-4-yl)methoxy)phenyl)cyclohex-3-enyl)methanone

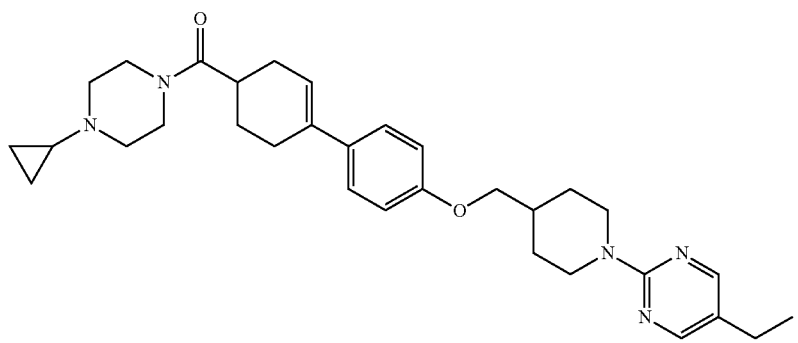 [SMILES: CCc1cnc(N2CCC(COc3ccc(C4=CCC(C(=O)N5CCN(C6CC6)CC5)CC4)cc3)CC2)nc1]

The title compound was prepared in the same manner as in <Example 379>, except that 1-cyclopropylpiperazine was used instead of the 1-methylpiperazine (Amount obtained: 410 mg/Yield: 67%).

$^1$H NMR (400, CDCl$_3$): 8.17 (2H, s), 7.31 (2H, d), 6.83 (2H, d), 6.03 (1H, d), 4.74 (2H, d), 3.81 (2H, d), 3.62 (2H, m), 3.50 (2H, t), 2.93 (2H, m), 2.87 (1H, m), 2.50 (9H, m), 2.30 (1H, m), 2.08 (1H, m), 1.93 (4H, m), 1.63 (2H, m), 1.36 (2H, m), 1.18 (3H, t), 0.43 (4H, m)

Example 396: Preparation of (4-(4-((1-(5-ethylpyrimidin-2-yl)piperidin-4-yl) methoxy)-3-(trifluoromethyl)phenyl)cyclohex-3-enyl)(4-hydroxypiperidin-1-yl)methanone

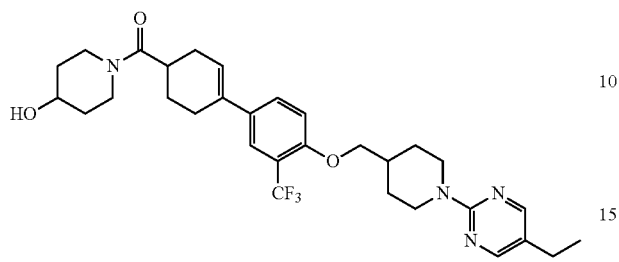

The title compound was prepared in the same manner as in <Example 373>, except that 4-hydroxypiperidine was used instead of the azetidine hydrochloride (Amount obtained: 430 mg/Yield: 73%).

$^1$H NMR (400, CDCl$_3$): 8.17 (2H, s), 7.56 (1H, d), 7.45 (2H, dd), 6.90 (1H, d), 6.06 (1H, m), 4.78 (2H, d), 4.14 (1H, m), 3.96 (1H, s), 3.81 (3H, m), 3.31 (2H, m), 2.95 (2H, m), 2.80 (1H, m), 2.50 (5H, m), 2.30 (1H, m), 2.14 (1H, m), 1.92 (6H, m), 1.60 (6H, m), 1.22 (5H, m), 1.19 (3H, t), 0.86 (2H, t)

Example 397: Preparation of (4-cyclopropylpiperazin-1-yl)(4-(4-((1-(3-isopropyl-1,2,4-oxadiazol-5-yl)piperidin-4-yl)methoxy)phenyl)cyclohex-3-enyl) methanone

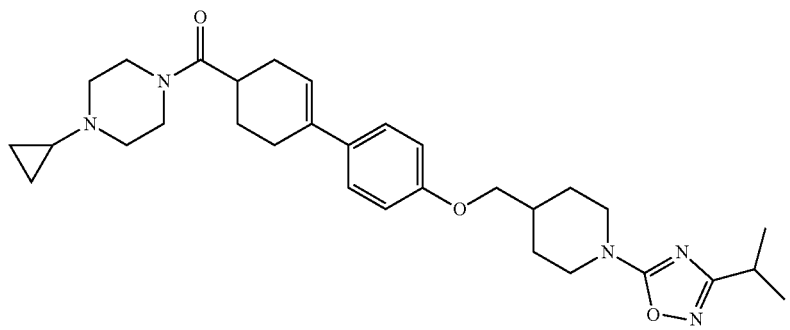 [SMILES: CC(C)c1noc(N2CCC(COc3ccc(C4=CCC(C(=O)N5CCN(C6CC6)CC5)CC4)cc3)CC2)n1]

500 mg of 4-(4-((1-(3-isopropyl-1,2,4-oxadiazol-5-yl)piperidin-4-yl)methoxy)phenyl)cyclohex-3-enecarboxylic acid was put into a 100 ml flask under a nitrogen atmosphere, 20 ml of dichloromethane was added thereto, and the resulting mixture was then dissolved while stirring. 0.32 ml of triethylamine, 160 mg of 1-cyclopropylpiperazine, and 510 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 430 mg/Yield: 69%).

$^1$H NMR (400, CDCl$_3$): 7.31 (2H, d), 6.82 (2H, d), 6.03 (1H, m), 4.18 (2H, d), 3.82 (2H, d), 3.64 (2H, m), 3.53 (2H, m), 3.12 (2H, m), 2.89 (1H, m), 2.77 (1H, m), 2.66 (4H, m), 2.50 (3H, m), 2.30 (1H, m), 2.00 (5H, m), 1.67 (1H, m), 1.45 (2H, m), 1.28 (6H, d), 0.49 (4H, m)

Example 398: Preparation of 1-(4-(4-((1-(5-ethylpyrimidin-2-yl)piperidin-4-yl)methoxy)-3-(trifluoromethyl)phenyl)cyclohex-3-enecarbonyl)piperidine-4-carbonitrile

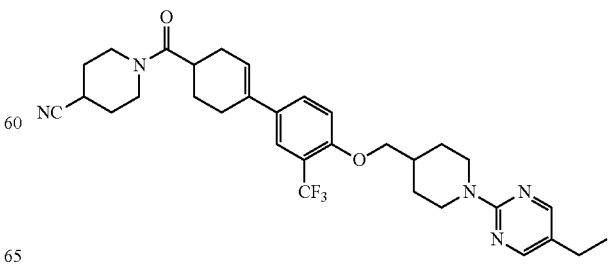

Example 399: Preparation of 1-(4-(4-((1-(5-ethylpyrimidin-2-yl)piperidin-4-yl)methoxy)-3-(trifluoromethyl)phenyl)cyclohex-3-enecarbonyl)piperidine-4-carboxamide The title compound was prepared in the same manner as in <Example 373>, except that piperidine-4-carbonitrile was used instead of the azetidine hydrochloride (Amount obtained: 390 mg/Yield: 66%).

$^1$H NMR (400, CDCl$_3$): 8.17 (2H, s), 7.56 (1H, s), 7.45 (1H, d), 6.90 (1H, d), 6.06 (1H, s), 4.75 (2H, d), 3.70 (8H, m), 2.93 (2H, m), 2.77 (1H, m), 2.48 (5H, m), 2.30 (1H, m), 2.12 (1H, m), 1.90 (8H, m), 1.31 (2H, m), 1.18 (6H, m)

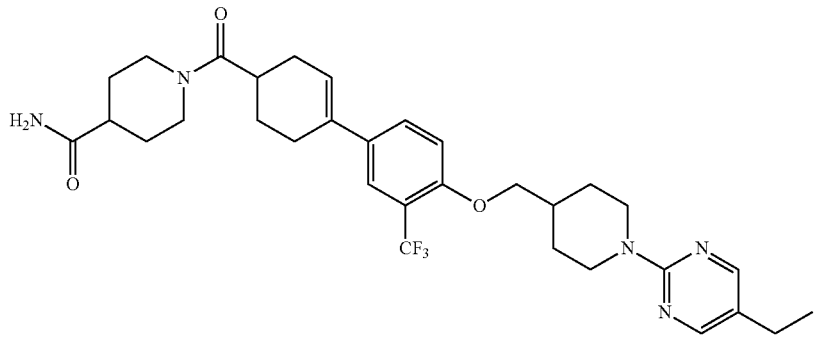 [SMILES: CCc1cnc(N2CCC(COc3ccc(C4=CCC(C(=O)N5CCC(C(N)=O)CC5)CC4)cc3C(F)(F)F)CC2)nc1]

The title compound was prepared in the same manner as in <Example 373>, except that isonipecotamide was used instead of the azetidine hydrochloride (Amount obtained: 410 mg/Yield: 68%).

$^1$H NMR (400, CDCl$_3$): 8.17 (2H, s), 7.56 (1H, s), 7.45 (1H, d), 6.90 (1H, d), 6.06 (1H, m), 5.47 (2H, d), 4.78 (2H, d), 4.64 (1H, m), 4.04 (2H, d), 3.88 (2H, d), 3.13 (1H, t), 2.91 (2H, m), 2.77 (2H, m), 2.50 (6H, m), 2.30 (1H, m), 2.13 (1H, m), 1.95 (6H, m), 1.72 (2H, m), 1.34 (2H, m), 1.18 (3H, t)

Example 400: Preparation of (4-(4-((1-(5-ethylpyrimidin-2-yl)piperidin-4-yl)methoxy)-3-(trifluoromethyl)phenyl)cyclohex-3-enyl)(morpholino)methanone

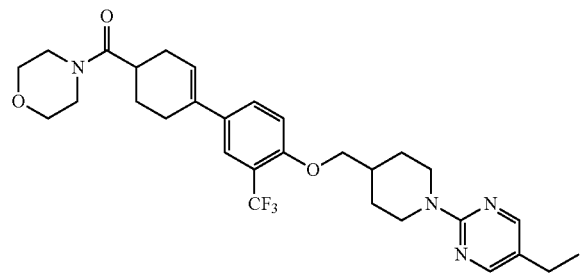 [SMILES: CCc1cnc(N2CCC(COc3ccc(C4=CCC(C(=O)N5CCOCC5)CC4)cc3C(F)(F)F)CC2)nc1]

The title compound was prepared in the same manner as in <Example 373>, except that morpholine was used instead of the azetidine hydrochloride (Amount obtained: 440 mg/Yield: 74%).

$^1$H NMR (400, CDCl$_3$): 8.17 (2H, s), 7.56 (1H, d), 7.45 (1H, dd), 6.90 (1H, d), 6.06 (1H, m), 4.75 (2H, d), 3.98 (2H, d), 3.69 (4H, m), 2.93 (2H, m), 2.76 (1H, m), 2.49 (5H, m), 2.30 (1H, m), 2.14 (1H, m), 1.91 (4H, m), 1.34 (2H, m), 1.18 (3H, t)

Example 401: Preparation of isopropyl 4-((2-fluoro-4-(4-(pyrrolidine-1-carbonyl)cyclohex-1-enyl)phenoxy)methyl)piperidine-1-carboxylate

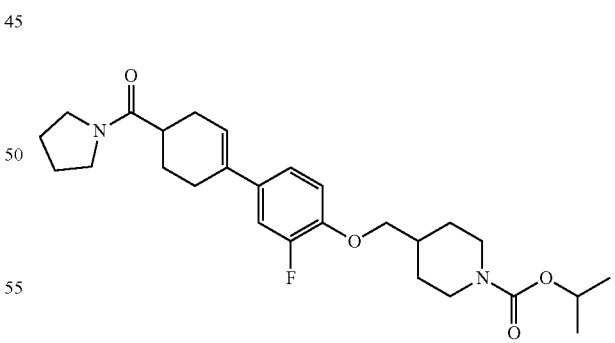

500 mg of (4-(3-fluoro-4-(piperidin-4-ylmethoxy)phenyl)cyclohex-3-enyl)(pyrrolidin-1-yl)methanone hydrochloride was put into a 100 ml flask under a nitrogen atmosphere, a H$_2$O/acetonitrile mixture (10 ml/10 ml) was added thereto, and the resulting mixture was then dissolved while stirring. 0.40 ml of triethylamine and 0.15 ml of isopropyl chloroformate were added dropwise thereto, and the mixture was stirred at 60° C. for 3 hours. After the reaction was terminated, the reaction mixture was extracted twice with 30 ml of ethyl acetate, and the resulting organic layer was washed with 30 ml of distilled water, dried with anhydrous magnesium sulfate, concentrated, and then isolated by silica column chromatography to obtain the title compound (Amount obtained: 350 mg/Yield: 59%).

$^1$H NMR (400, CDCl$_3$): 7.12 (1H, dd), 7.07 (1H, d), 6.87 (1H, t), 6.08 (1H, m), 4.91 (1H, m), 4.20 (2H, s), 3.85 (2H, d), 3.49 (4H, m), 2.78 (2H, t), 2.55 (4H, m), 2.30 (1H, m), 1.95 (9H, m), 1.25 (8H, m)

Example 402: Preparation of trichloromethyl 4-((2-fluoro-4-(4-(pyrrolidine-1-carbonyl)cyclohex-1-enyl)phenoxy)methyl)piperidine-1-carboxylate

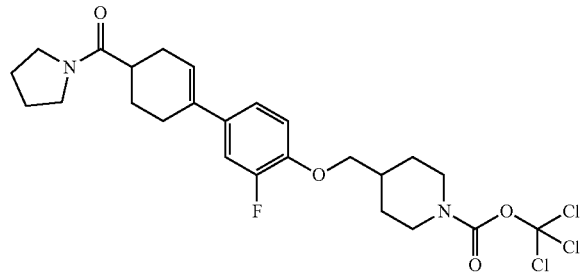 [SMILES: O=C(OC(Cl)(Cl)Cl)N1CCC(COc2ccc(C3=CCC(C(=O)N4CCCC4)CC3)cc2F)CC1]

The title compound was prepared in the same manner as in <Example 401>, except that triphosgene was used instead of the azetidine hydrochloride (Amount obtained: 400 mg/Yield: 67%).

$^1$H NMR (400, CDCl$_3$): 7.26 (1H, d), 7.10 (1H, d), 6.87 (1H, t), 6.08 (1H, s), 4.74 (2H, d), 3.89 (2H, m), 3.53 (4H, m), 3.12 (1H, t), 2.94 (1H, t), 2.40 (5H, m), 2.11 (1H, m), 1.91 (8H, m), 1.39 (2H, m)

Example 403: Preparation of phenyl 4-((2-fluoro-4-(4-(pyrrolidine-1-carbonyl)cyclohex-1-enyl)phenoxy)methyl)piperidine-1-carboxylate

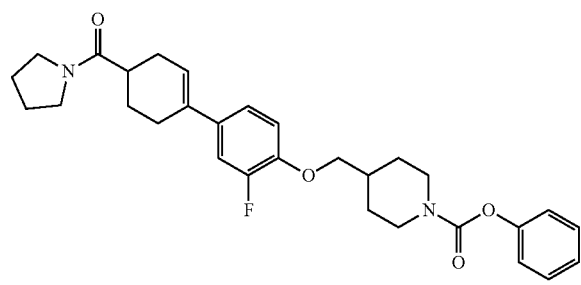 [SMILES: O=C(Oc1ccccc1)N1CCC(COc2ccc(C3=CCC(C(=O)N4CCCC4)CC3)cc2F)CC1]

The title compound was prepared in the same manner as in <Example 401>, except that phenyl chloroformate was used instead of the azetidine hydrochloride (Amount obtained: 430 mg/Yield: 72%).

$^1$H NMR (400, CDCl$_3$): 7.37 (2H, t), 7.16 (1H, m), 7.08 (4H, m), 6.89 (1H, t), 6.08 (1H, m), 4.35 (2H, m), 3.91 (2H, s), 3.52 (4H, m), 3.00 (2H, m), 2.64 (1H, m), 2.50 (3H, m), 2.30 (1H, m), 2.10 (1H, m), 1.90 (8H, m), 1.40 (2H, m)

Example 404: Preparation of 4-nitrophenyl 4-((2-fluoro-4-(4-(pyrrolidine-1-carbonyl)cyclohex-1-enyl)phenoxy)methyl)piperidine-1-carboxylate

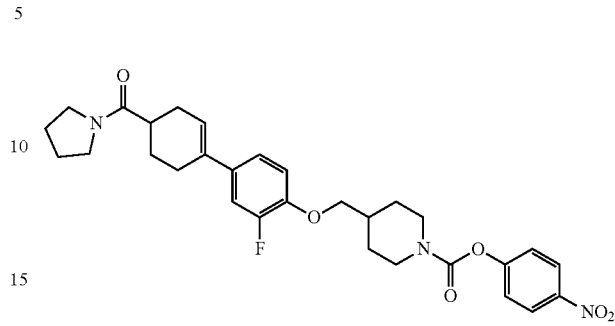

The title compound was prepared in the same manner as in <Example 401>, except that 4-nitrophenyl chloroformate was used instead of the azetidine hydrochloride (Amount obtained: 400 mg/Yield: 68%).

$^1$H NMR (400, CDCl$_3$): 8.24 (2H, m), 7.31 (2H, m), 7.11 (2H, m), 6.88 (1H, t), 6.09 (1H, m), 4.33 (2H, t), 3.51 (4H, m), 3.00 (2H, m), 2.64 (1H, m), 2.51 (3H, m), 2.30 (1H, m), 2.11 (1H, m), 1.91 (8H, m), 1.42 (2H, m)

Example 405: Preparation of 1,1,1,3,3,3-hexafluoropropan-2-yl 4-((2-fluoro-4-(4-(pyrrolidine-1-carbonyl)cyclohex-1-enyl)phenoxy)methyl)piperidine-1-carboxylate

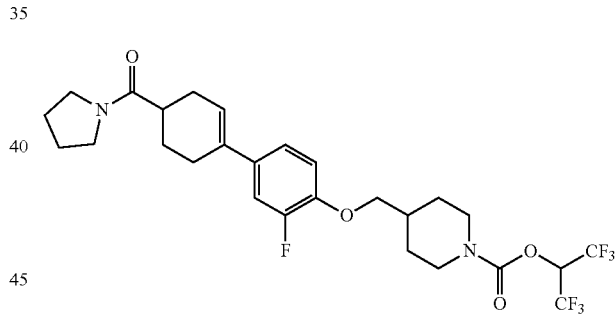

500 mg of trichloromethyl 4-((2-fluoro-4-(4-(pyrrolidine-1-carbonyl)cyclohex-1-enyl)phenoxy)methyl)piperidine-1-carboxylate was put into a 100 ml flask under a nitrogen atmosphere, 20 ml of tetrahydrofuran was added thereto, and the resulting mixture was then dissolved while stirring. 0.40 ml of triethylamine and 0.17 ml of 1,1,1,3,3,3-hexafluoro-2-propanol were added dropwise thereto, and the mixture was stirred at 20° C. for 2 hours. After the reaction was terminated, the reaction mixture was extracted twice with 20 ml of ethyl acetate, and the resulting organic layer was washed with 20 ml of distilled water, dried with anhydrous magnesium sulfate, concentrated, and then isolated by silica column chromatography to obtain the title compound (Amount obtained: 370 mg/Yield: 63%).

$^1$H NMR (400, CDCl$_3$): 7.12 (1H, dd), 7.07 (1H, d), 6.87 (1H, t), 6.08 (1H, m), 5.76 (1H, m), 4.22 (2H, t), 3.88 (2H, d), 3.52 (4H, m), 2.95 (2H, m), 2.50 (5H, m), 2.00 (9H, m), 1.33 (2H, m)

Example 406: Preparation of 1,1,1-trifluoropropan-2-yl 4-((2-fluoro-4-(4-(pyrrolidine-1-carbonyl)cyclohex-1-enyl)phenoxy)methyl)piperidine-1-carboxylate

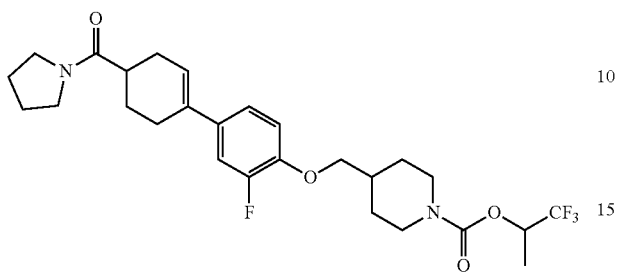

The title compound was prepared in the same manner as in <Example 405>, except that 1,1,1-trifluoro-2-propanol was used instead of the 1,1,1,3,3,3-hexafluoro-2-propanol (Amount obtained: 450 mg/Yield: 75%).

$^1$H NMR (400, CDCl$_3$): 7.10 (1H, dd), 7.01 (1H, d), 6.87 (1H, t), 6.08 (1H, m), 5.25 (1H, m), 4.14 (2H, m), 3.86 (2H, m), 3.51 (4H, m), 2.84 (2H, m), 2.50 (5H, m), 2.03 (4H, m), 1.90 (5H, m), 1.39 (2H, d), 1.26 (3H, m)

Example 407: Preparation of 1,3-difluoropropan-2-yl 4-((2-fluoro-4-(4-(pyrrolidine-1-carbonyl)cyclohex-1-enyl)phenoxy)methyl)piperidine-1-carboxylate

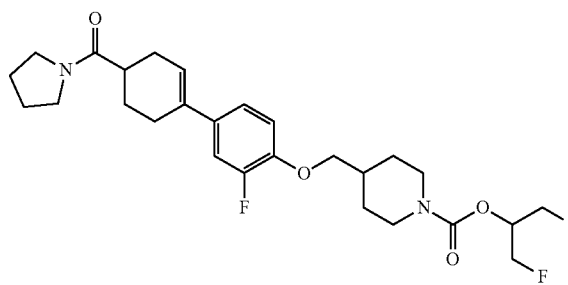

The title compound was prepared in the same manner as in <Example 405>, except that 1,3-difluoro-2-propanol was used instead of the 1,1,1,3,3,3-hexafluoro-2-propanol (Amount obtained: 470 mg/Yield: 79%).

$^1$H NMR (400, CDCl$_3$): 7.10 (1H, dd), 7.05 (1H, d), 6.86 (1H, t), 6.08 (1H, m), 5.15 (1H, m), 4.67 (2H, m), 4.52 (2H, d), 4.12 (2H, m), 3.86 (2H, m), 3.49 (4H, m), 2.85 (2H, m), 2.52 (5H, m), 1.98 (9H, m), 1.29 (2H, m)

Example 408: Preparation of 1-methylcyclopropyl 4-((2-fluoro-4-(4-(pyrrolidine-1-carbonyl)cyclohex-1-enyl)phenoxy)methyl)piperidine-1-carboxylate

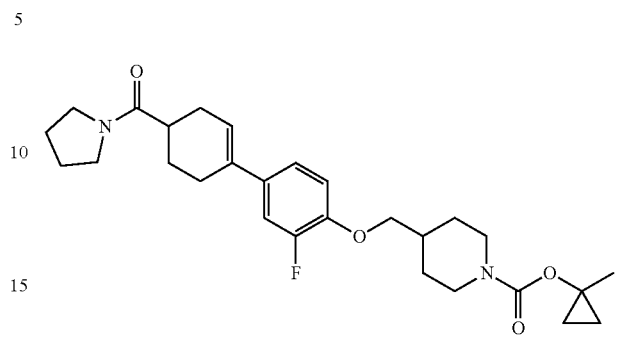

The title compound was prepared in the same manner as in <Example 405>, except that 1-methylcyclopropanol was used instead of the 1,1,1,3,3,3-hexafluoro-2-propanol (Amount obtained: 430 mg/Yield: 71%).

$^1$H NMR (400, CDCl$_3$): 7.10 (1H, dd), 7.05 (1H, d), 6.86 (1H, t), 6.08 (1H, m), 4.14 (2H, m), 3.86 (2H, d), 3.52 (4H, m), 2.75 (2H, t), 2.50 (5H, m), 1.98 (9H, m), 1.55 (2H, s), 1.24 (2H, m), 0.85 (2H, m), 0.62 (2H, m)

Example 409: Preparation of (4-(3-fluoro-4-((1-(1-(trifluoromethyl)cyclopentanecarbonyl)piperidin-4-yl)methoxy)phenyl)cyclohex-3-enyl)(pyrrolidin-1-yl)methanone

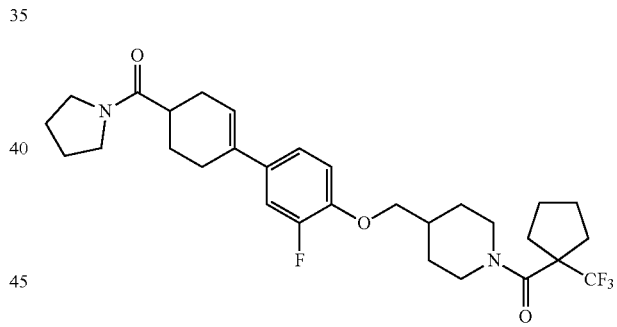

500 mg of (4-(3-fluoro-4-(piperidin-4-ylmethoxy)phenyl)cyclohex-3-enyl)(pyrrolidin-1-yl)methanone hydrochloride was put into a 100 ml flask under a nitrogen atmosphere, 20 ml of dichloromethane was added thereto, and the resulting mixture was then dissolved while stirring. 0.30 ml of triethylamine, 0.19 ml of 1-(trifluoromethyl)cyclopentane-1-carboxylic acid, and 430 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 350 mg/Yield: 60%).

$^1$H NMR (400, CDCl$_3$): 7.10 (1H, dd), 7.05 (1H, d), 6.87 (1H, t), 6.08 (1H, m), 4.42 (2H, s), 3.86 (2H, d), 3.51 (4H, m), 2.85 (2H, m), 2.52 (7H, m), 2.16 (3H, m), 1.92 (9H, m), 1.68 (5H, m), 1.27 (2H, m)

Example 410: Preparation of (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone

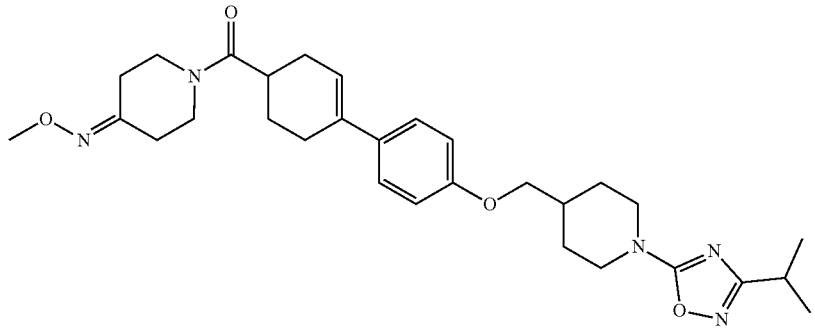 [SMILES: CON=C1CCN(C(=O)C2CC=C(c3ccc(OCC4CCN(c5nc(C(C)C)no5)CC4)cc3)CC2)CC1]

150 mg of (4-(3-fluoro-4-((1-(3-isopropyl-1,2,4-oxadiazol-5-yl)piperidin-4-yl)methoxy)phenyl)cyclohex-3-enyl)(4-(hydroxyimino)piperidin-1-yl)methanone was put into a 50 ml flask under a nitrogen atmosphere, 15 ml of tetrahydrofuran was added thereto, and the resulting mixture was then dissolved while stirring. 30 mg of sodium hydroxide and 10 mg of methyl iodide were added dropwise thereto, and the mixture was stirred at 40° C. for 3 hours. After the reaction was terminated, 30 ml of ethyl acetate and 20 ml of distilled water were added thereto, and the reaction mixture was extracted, dried with anhydrous magnesium sulfate, concentrated, and then isolated by silica column chromatography to obtain the title compound (Amount obtained: 100 mg/Yield: 72%).

$^1$H NMR (400, CDCl$_3$): 7.13 (1H, dd), 7.07 (1H, d), 6.86 (1H, t), 6.06 (1H, m), 4.18 (2H, d), 3.88 (4H, m), 3.71 (4H, m), 3.12 (2H, m), 2.89 (2H, m), 2.50 (7H, m), 2.30 (1H, m), 2.10 (1H, m), 1.93 (4H, m), 1.45 (2H, m), 1.29 (6H, d)

Example 411: Preparation of (4-(3-fluoro-4-((1-(3-isopropyl-1,2,4-oxadiazol-5-yl)piperidin-4-yl)methoxy)phenyl)cyclohex-3-enyl)(4-(hydroxyimino)piperidin-1-yl)methanone 300 mg of 1-(4-(3-fluoro-4-((1-(3-isopropyl-1,2,4-oxadiazol-5-yl)piperidin-4-yl)methoxy)phenyl)cyclohex-3-enecarbonyl)piperidin-4-one was put into a 100 ml flask under a nitrogen atmosphere, 20 ml of ethanol were added thereto, and the resulting mixture was then dissolved while stirring. 90 mg of potassium carbonate and 80 mg of hydroxylamine hydrochloride were added dropwise thereto, and the mixture was stirred at 60° C. for 2 hours. After the reaction was terminated, 30 ml of ethyl acetate and 30 ml of distilled water were added thereto, and the reaction mixture was extracted, dried with anhydrous magnesium sulfate, concentrated, and then isolated by silica column chromatography to obtain the title compound (Amount obtained: 180 mg/Yield: 60%).

$^1$H NMR (400, CDCl$_3$): 7.13 (1H, dd), 7.08 (1H, d), 6.88 (1H, t), 6.06 (1H, m), 4.22 (2H, d), 3.88 (2H, d), 3.76 (4H, m), 3.13 (2H, m), 2.90 (2H, m), 2.68 (2H, m), 2.50 (5H, m), 2.31 (1H, m), 1.98 (6H, m), 1.42 (2H, m), 1.28 (6H, d)

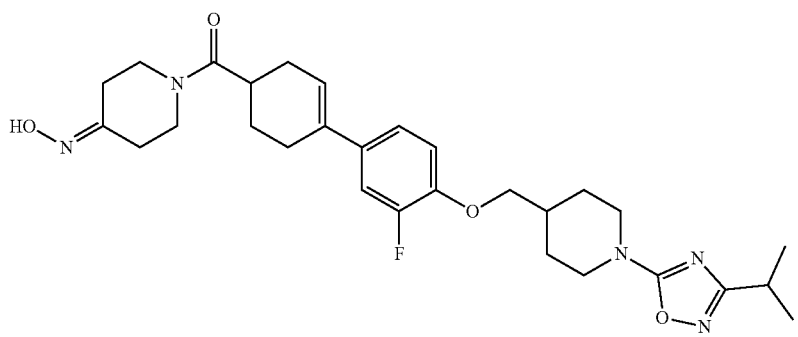 [SMILES: CC(C)c1noc(N2CCC(COc3ccc(C4=CCC(C(=O)N5CCC(=NO)CC5)CC4)cc3F)CC2)n1]

Example 412: Preparation of 4-(4-(4-((1-(5-ethylpyrimidin-2-yl)piperidin-4-yl)methoxy)phenyl)cyclohex-3-enecarbonyl)-N-propylpiperazine-1-carboxamide

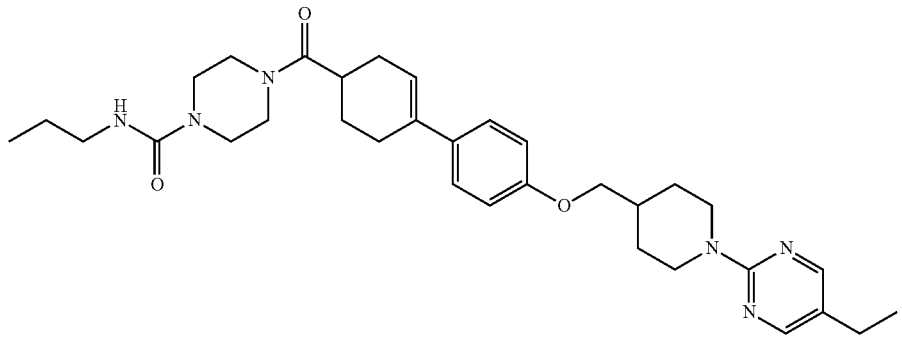 [SMILES: CCCNC(=O)N1CCN(C(=O)C2CC=C(c3ccc(OCC4CCN(c5ncc(CC)cn5)CC4)cc3)CC2)CC1]

300 mg of (4-(4-((1-(5-ethylpyrimidin-2-yl)piperidin-4-yl)methoxy)phenyl)cyclohex-3-enyl)(piperazin-1-yl)methanone hydrochloride was put into a 100 ml flask under a nitrogen atmosphere, 20 ml of dichloromethane was added thereto, and the resulting mixture was then dissolved while stirring. 0.3 ml of propylamine and 120 mg of triphosgene were added dropwise thereto at 0° C., and the mixture was stirred at 0° C. for 2 hours. After the reaction was terminated, 30 ml of ethyl acetate and 30 ml of distilled water were added thereto, and the reaction mixture was extracted, dried with anhydrous magnesium sulfate, concentrated, and then isolated by silica column chromatography to obtain the title compound (Amount obtained: 140 mg/Yield: 45%).

$^1$H NMR (400, CDCl$_3$): 8.17 (2H, s), 7.30 (2H, d), 6.83 (2H, d), 6.02 (1H, m), 4.74 (2H, d), 4.24 (1H, d), 3.99 (1H, m), 3.83 (2H, d), 3.67 (2H, m), 3.56 (2H, m), 3.49 (2H, m), 3.31 (2H, m), 3.10 (2H, q), 2.90 (2H, m), 2.78 (1H, m), 2.50 (5H, m), 2.28 (1H, m), 2.08 (1H, m), 1.90 (4H, m), 1.32 (2H, m), 1.15 (12H, d)

Example 413: Preparation of 4-(4-(4-((1-(5-ethylpyrimidin-2-yl)piperidin-4-yl)methoxy)phenyl)cyclohex-3-enecarbonyl)-N-isopropylpiperazine-1-carboxamide

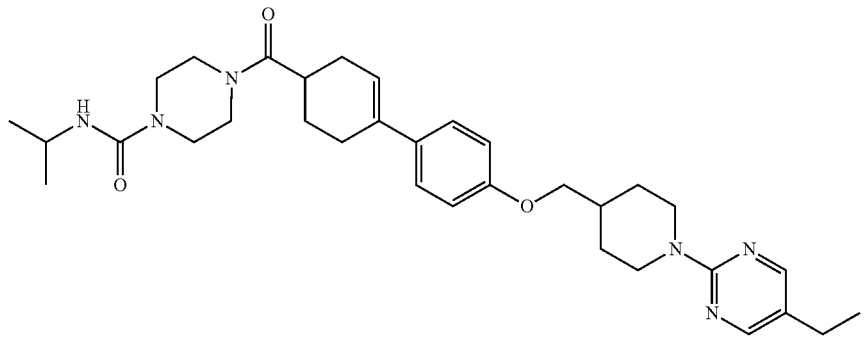 [SMILES: CCc1cnc(N2CCC(COc3ccc(C4=CCC(C(=O)N5CCN(C(=O)NC(C)C)CC5)CC4)cc3)CC2)nc1]

The title compound was prepared in the same manner as in <Example 412>, except that isopropylamine was used instead of the propylamine (Amount obtained: 120 mg/Yield: 38%).

$^1$H NMR (400, CDCl$_3$): 8.17 (2H, s), 7.30 (2H, d), 6.83 (2H, d), 6.02 (1H, m), 4.74 (2H, d), 4.50 (1H, t), 3.83 (2H, d), 3.69 (2H, m), 3.56 (2H, m), 3.48 (2H, m), 3.33 (2H, m), 3.21 (2H, q), 2.91 (2H, m), 2.78 (1H, m), 2.46 (5H, m), 2.30 (1H, m), 2.08 (1H, m), 1.93 (4H, m), 1.53 (2H, m), 1.35 (4H, m), 1.18 (3H, t), 0.90 (5H, m)

Example 414: Preparation of 1-(4-(4-(4-((1-(5-ethylpyrimidin-2-yl)piperidin-4-yl) methoxy)phenyl)cyclohex-3-enecarbonyl)piperazin-1-yl)-3-methylbut-2-en-1-one

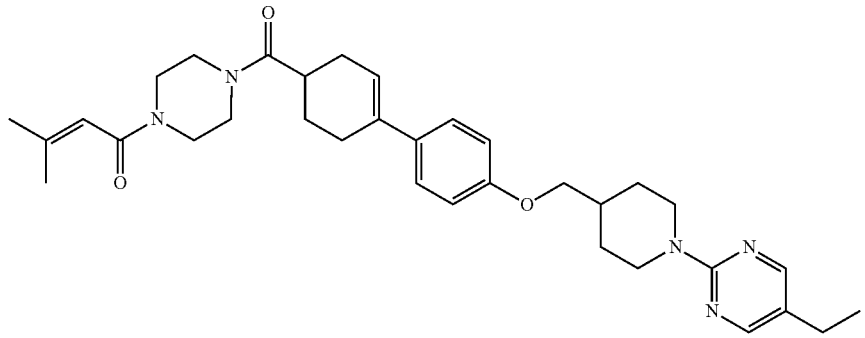 [SMILES: CCc1cnc(N2CCC(COc3ccc(C4=CCC(C(=O)N5CCN(C(=O)C=C(C)C)CC5)CC4)cc3)CC2)nc1]

300 mg of (4-(4-((1-(5-ethylpyrimidin-2-yl)piperidin-4-yl)methoxy)phenyl)cyclohex-3-enyl)(piperazin-1-yl)methanone hydrochloride was put into a 100 ml flask under a nitrogen atmosphere, 30 ml of dichloromethane was added thereto, and the resulting mixture was then dissolved while stirring. 0.40 ml of triethylamine, 120 mg of 3-methylcrotonic acid, and 250 mg of HATU were added dropwise thereto, and the mixture was stirred at 20° C. for an hour. After the reaction was terminated, 30 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 210 mg/Yield: 72%).

$^1$H NMR (400, CDCl$_3$): 8.17 (2H, s), 7.29 (2H, d), 6.83 (2H, d), 6.03 (1H, m), 5.79 (1H, s), 4.78 (2H, d), 3.81 (2H, d), 3.60 (8H, m), 2.91 (2H, m), 2.79 (1H, m), 2.50 (5H, m), 2.29 (1H, m), 2.07 (1H, m), 1.94 (10H, m), 1.38 (2H, m), 1.18 (3H, t)

Example 415: Preparation of (4-(4-((1-(5-ethylpyrimidin-2-yl)piperidin-4-yl)methoxy)-3-methylphenyl)cyclohex-3-enyl)(piperidin-1-yl)methanone

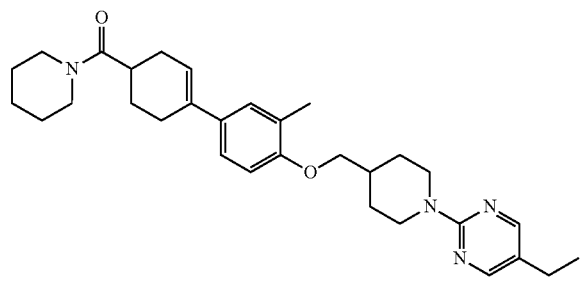 [SMILES: CCc1cnc(N2CCC(COc3ccc(C4=CCC(C(=O)N5CCCCC5)CC4)cc3C)CC2)nc1]

500 mg of 4-(4-((1-(5-ethylpyrimidin-2-yl)piperidin-4-yl)methoxy)-3-methylphenyl)cyclohex-3-enecarboxylic acid was put into a 100 ml flask under a nitrogen atmosphere, 30 ml of dichloromethane were added thereto, and the resulting mixture was then dissolved while stirring. 0.33 ml of triethylamine, 0.12 ml of piperidine, and 520 mg of HATU were added dropwise thereto, and the mixture was stirred at 20° C. for an hour. After the reaction was terminated, 30 ml of dichloromethane was additionally added thereto, and the resulting organic layer was washed with 30 ml of distilled water, dried with anhydrous magnesium sulfate, concentrated, and then isolated by silica column chromatography to obtain the title compound (Amount obtained: 490 mg/Yield: 82%).

$^1$H NMR (400, CDCl$_3$): 8.17 (2H, s), 7.15 (2H, m), 6.72 (1H, d), 6.01 (1H, m), 4.78 (2H, d), 3.83 (2H, d), 3.59 (4H, m), 3.20 (1H, m), 2.98 (2H, d), 2.91 (2H, m), 2.78 (1H, m), 2.50 (5H, m), 2.28 (4H, m), 2.11 (1H, m), 1.90 (4H, m), 1.60 (7H, m), 1.38 (2H, m), 1.18 (3H, t)

Example 416: Preparation of (4-(4-((1-(5-ethylpyrimidin-2-yl)piperidin-4-yl) methoxy)-3-methylphenyl)cyclohex-3-enyl)(pyrrolidin-1-yl)methanone

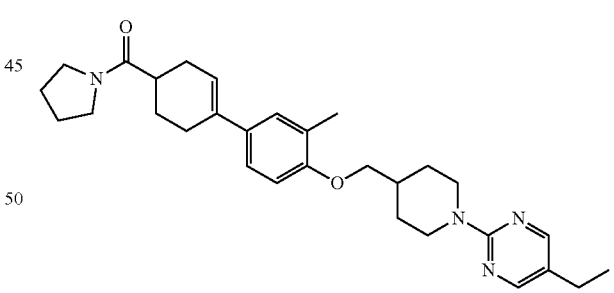

The title compound was prepared in the same manner as in <Example 412>, except that pyrrolidine was used instead of the piperidine (Amount obtained: 440 mg/Yield: 74%).

$^1$H NMR (400, CDCl$_3$): 8.17 (2H, s), 7.18 (2H, m), 6.72 (1H, d), 6.03 (1H, m), 4.75 (2H, d), 3.83 (2H, d), 3.51 (4H, m), 3.10 (1H, q), 2.94 (3H, m), 2.64 (1H, m), 2.50 (5H, m), 2.30 (1H, m), 2.22 (3H, s), 2.11 (1H, m), 1.90 (9H, m), 1.40 (3H, m), 1.18 (3H, t)

Example 417: Preparation of (4-(4-((1-(5-ethylpyrimidin-2-yl)piperidin-4-yl) methoxy)-3-methylphenyl)cyclohex-3-enyl)(morpholino)methanone

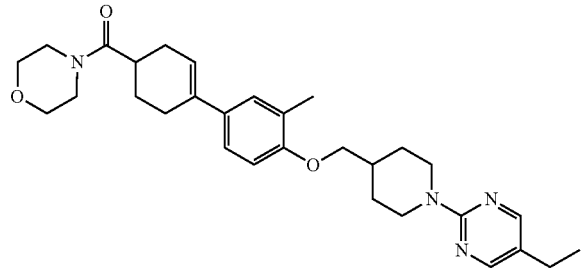 [SMILES: CCc1cnc(N2CCC(COc3ccc(C4=CCC(C(=O)N5CCOCC5)CC4)cc3C)CC2)nc1]

The title compound was prepared in the same manner as in <Example 415>, except that morpholine was used instead of the piperidine (Amount obtained: 460 mg/Yield: 77%).

$^1$H NMR (400, CDCl$_3$): 8.17 (2H, s), 7.15 (2H, m), 6.73 (1H, d), 6.01 (1H, m), 4.75 (2H, d), 3.83 (2H, d), 3.68 (6H, m), 3.56 (2H, s), 3.07 (1H, q), 2.91 (2H, m), 2.75 (1H, m), 2.50 (5H, m), 2.23 (4H, m), 2.11 (1H, m), 1.96 (4H, m), 1.76 (1H, s), 1.36 (3H, m), 1.18 (3H, t)

Example 418: Preparation of (4-(4-((1-(5-ethylpyrimidin-2-yl)piperidin-4-yl)methoxy)-3-methylphenyl)cyclohex-3-enyl)(thiomorpholino)methanone

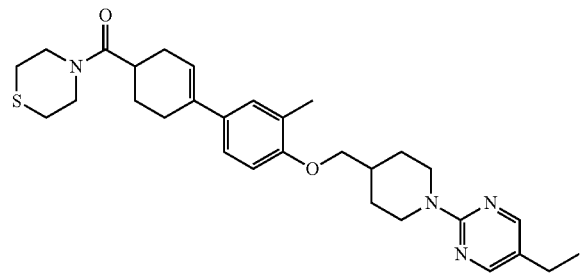 [SMILES: CCc1cnc(N2CCC(COc3ccc(C4=CCC(C(=O)N5CCSCC5)CC4)cc3C)CC2)nc1]

The title compound was prepared in the same manner as in <Example 415>, except that thiomorpholine was used instead of the piperidine (Amount obtained: 440 mg/Yield: 74%).

$^1$H NMR (400, CDCl$_3$): 8.17 (2H, s), 7.30 (2H, m), 6.73 (1H, d), 6.00 (1H, m), 4.75 (2H, d), 3.95 (1H, m), 3.83 (5H, m), 2.95 (2H, m), 2.73 (1H, m), 2.65 (4H, m), 2.48 (5H, m), 2.21 (4H, m), 2.10 (1H, m), 1.88 (4H, m), 1.36 (2H, m), 1.18 (3H, t)

Example 419: Preparation of (4-(3-fluoro-4-((1-(2-fluoro-2-methylpropyl)piperidin-4-yl)methoxy)phenyl)cyclohex-3-enyl)(pyrrolidin-1-yl)methanone

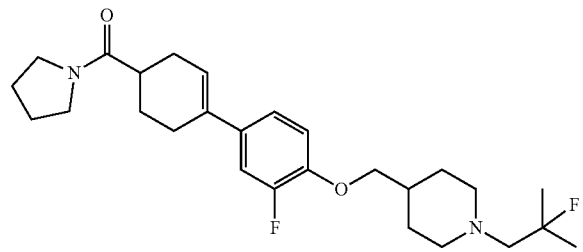 [SMILES: CC(C)(F)CN1CCC(COc2ccc(C3=CCC(C(=O)N4CCCC4)CC3)cc2F)CC1]

300 mg of (4-(3-fluoro-4-(piperidin-4-ylmethoxy)phenyl)cyclohex-3-enyl)(pyrrolidin-1-yl)methanone hydrochloride was put into a 50 ml flask under a nitrogen atmosphere, 15 ml of THF was added thereto, and the resulting mixture was then dissolved while stirring. 0.25 ml of triethylamine and 0.12 ml of 1-bromo-2-fluoro-2-methylpropane were added dropwise thereto, and the mixture was stirred at 40° C. for 3 hours. After the reaction was terminated, the reaction mixture was extracted twice with 30 ml of ethyl acetate, and the resulting organic layer was washed with 30 ml of distilled water, dried with anhydrous magnesium sulfate, concentrated, and then isolated by silica column chromatography to obtain the title compound (Amount obtained: 210 mg/Yield: 84%).

$^1$H NMR (400, CDCl$_3$): 7.12 (1H, d), 7.07 (1H, d), 6.88 (2H, d), 6.07 (1H, m), 3.84 (2H, d), 3.52 (4H, m), 2.99 (2H, d), 2.61 (3H, m), 2.42 (3H, m), 2.30 (1H, m), 2.16 (2H, m), 2.00 (3H, m), 1.84 (6H, m), 1.67 (1H, s), 1.35 (8H, m)

Example 420: Preparation of (4-(3-fluoro-4-((1-(1-methyl-1H-tetrazol-5-yl)piperidin-4-yl)methoxy)phenyl)cyclohex-3-enyl)(pyrrolidin-1-yl)methanone

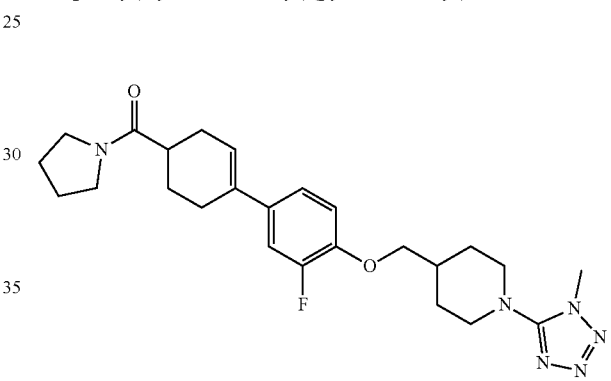

500 mg of 4-((2-fluoro-4-(4-(pyrrolidine-1-carbonyl)cyclohex-1-enyl)phenoxy)methyl)piperidine-1-carbonitrile was put into a 100 ml flask under a nitrogen atmosphere, 30 ml of dimethylformamide was added thereto, and the resulting mixture was then dissolved while stirring. 180 mg of ammonium chloride and 230 mg of sodium azide were added dropwise thereto, and the mixture was stirred at 80° C. for 5 hours. After the reaction was terminated, the reaction mixture was extracted with 30 ml of distilled water and 50 ml of ethyl acetate, and the resulting organic layer was washed with 30 ml of distilled water, dried with anhydrous magnesium sulfate, and then concentrated. 0.1 ml of methyl iodide, 0.18 ml of triethylamine, and 20 ml of acetonitrile were added thereto, and the organic layer was stirred at 70° C. for 3 hours. After the reaction was terminated, the reaction mixture was extracted with 30 ml of distilled water and 50 ml of ethyl acetate, and the resulting organic layer was washed with 30 ml of distilled water, dried with anhydrous magnesium sulfate, concentrated, and then isolated by silica column chromatography to obtain the title compound (Amount obtained: 180 mg/Yield: 30%).

$^1$H NMR (400, CDCl$_3$): 7.07 (2H, m), 6.88 (1H, m), 6.08 (1H, m), 4.13 (4H, m), 3.91 (2H, m), 3.51 (4H, m), 2.98 (2H, m), 2.50 (5H, m), 2.02 (9H, m), 1.46 (2H, m)

Example 421: Preparation of (4-(3-fluoro-4-((1-(1-(trifluoromethyl)cyclopropanecarbonyl)piperidin-4-yl)methoxy)phenyl)cyclohex-3-enyl)(pyrrolidin-1-yl)methanone

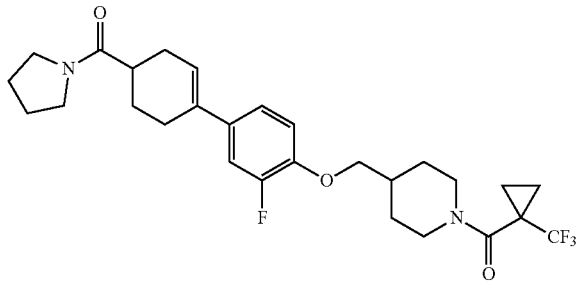 [SMILES: O=C(C1CC=C(c2ccc(OCC3CCN(C(=O)C4(C(F)(F)F)CC4)CC3)c(F)c2)CC1)N1CCCC1]

500 mg of (4-(3-fluoro-4-(piperidin-4-ylmethoxy)phenyl)cyclohex-3-enyl)(pyrrolidin-1-yl)methanone hydrochloride was put into a 100 ml flask under a nitrogen atmosphere, 20 ml of dichloromethane was added thereto, and the resulting mixture was then dissolved while stirring. 0.30 ml of triethylamine, 0.17 ml of 1-(trifluoromethyl)cyclopropane-1-carboxylic acid, and 430 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 370 mg/Yield: 64%).

$^1$H NMR (400, CDCl$_3$): 7.10 (2H, m), 6.87 (1H, t), 6.08 (1H, m), 3.86 (2H, d), 3.51 (4H, m), 3.80 (3H, s), 2.44 (5H, m), 2.11 (1H, m), 1.91 (8H, m), 1.62 (2H, s), 1.31 (4H, m), 1.14 (2H, m)

Example 422: Preparation of (4-(4-((1-(5-ethylpyrimidin-2-yl)piperidin-4-yl)methoxy)-2-fluorophenyl)cyclohex-3-enyl)(morpholino)methanone

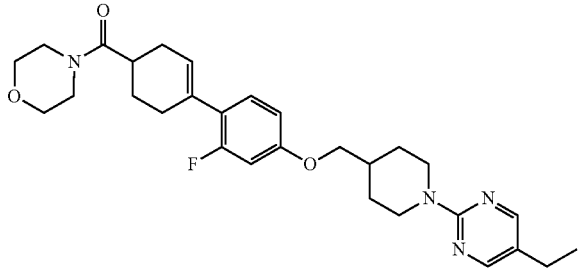 [SMILES: CCc1cnc(N2CCC(COc3ccc(C4=CCC(C(=O)N5CCOCC5)CC4)c(F)c3)CC2)nc1]

500 mg of 4-(4-((1-(5-ethylpyrimidin-2-yl)piperidin-4-yl)methoxy)-2-fluorophenyl)cyclohex-3-enecarboxylic acid was put into a 100 ml flask under a nitrogen atmosphere, 30 ml of dichloromethane was added thereto, and the resulting mixture was then dissolved while stirring. 0.33 ml of triethylamine, 0.16 ml of morpholine, and 520 mg of HATU were added dropwise thereto, and the mixture was stirred at 20° C. for an hour. After the reaction was terminated, 30 ml of dichloromethane was additionally added thereto, and the resulting organic layer was washed with 30 ml of distilled water, dried with anhydrous magnesium sulfate, concentrated, and then isolated by silica column chromatography to obtain the title compound (Amount obtained: 460 mg/Yield: 77%).

$^1$H NMR (400, CDCl$_3$): 8.17 (2H, s), 7.12 (1H, t), 6.64 (1H, d), 6.56 (1H, d), 5.88 (1H, m), 4.75 (2H, d), 3.79 (2H, d), 3.69 (8H, m), 2.93 (2H, m), 2.86 (1H, m), 2.52 (5H, m), 2.27 (1H, m), 2.07 (1H, m), 1.89 (4H, m), 1.35 (2H, m), 1.20 (3H, t)

Example 423: Preparation of (4-(4-((1-(5-ethylpyrimidin-2-yl)piperidin-4-yl)methoxy)-2-fluorophenyl)cyclohex-3-enyl)(thiomorpholino)methanone

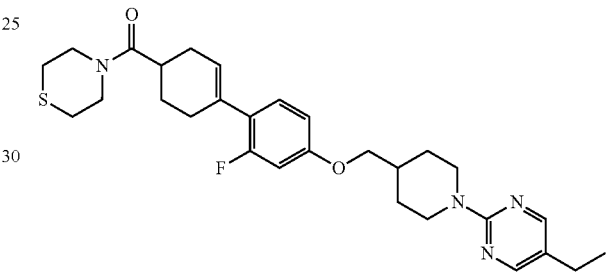

The title compound was prepared in the same manner as in <Example 422>, except that thiomorpholine was used instead of the morpholine (Amount obtained: 430 mg/Yield: 73%).

$^1$H NMR (400, CDCl$_3$): 8.17 (2H, s), 7.12 (1H, t), 6.64 (1H, d), 6.56 (1H, d), 5.88 (1H, m), 4.75 (2H, d), 3.84 (6H, d), 2.93 (2H, m), 2.86 (1H, m), 2.65 (4H, m), 2.48 (5H, m), 2.25 (1H, m), 2.07 (1H, m), 1.86 (4H, m), 1.31 (2H, m), 1.18 (3H, t)

Example 424: Preparation of 1-(4-(4-((1-(5-ethylpyrimidin-2-yl)piperidin-4-yl)methoxy)-2-fluorophenyl)cyclohex-3-enecarbonyl)piperidine-4-carbonitrile

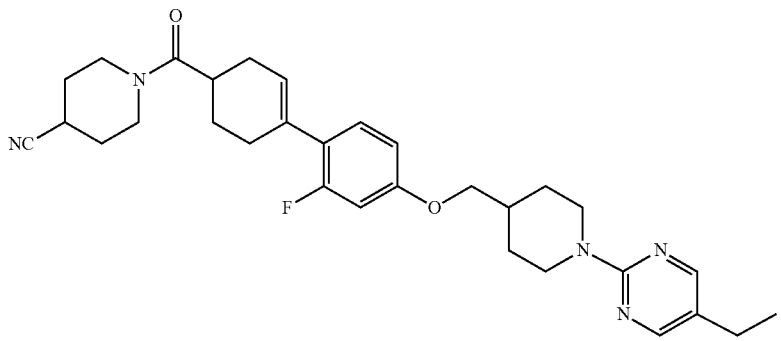 [SMILES: CCc1cnc(N2CCC(COc3ccc(C4=CCC(C(=O)N5CCC(C#N)CC5)CC4)c(F)c3)CC2)nc1]

The title compound was prepared in the same manner as in <Example 422>, except that piperidine-4-carbonitrile was used instead of the morpholine (Amount obtained: 440 mg/Yield: 75%).

¹H NMR (400, CDCl₃): 8.17 (2H, s), 7.12 (1H, t), 6.64 (1H, d), 6.56 (1H, d), 5.87 (1H, m), 4.75 (2H, d), 3.79 (4H, m), 3.55 (2H, m), 2.90 (4H, m), 2.82 (1H, m), 2.26 (1H, m), 2.07 (1H, m), 1.89 (8H, m), 1.32 (2H, m), 1.18 (3H, t)

Example 425: Preparation of azetidin-1-yl(4-(4-((1-(5-ethylpyrimidin-2-yl)piperidin-4-yl)methoxy)-2-fluorophenyl)cyclohex-3-enyl)methanone

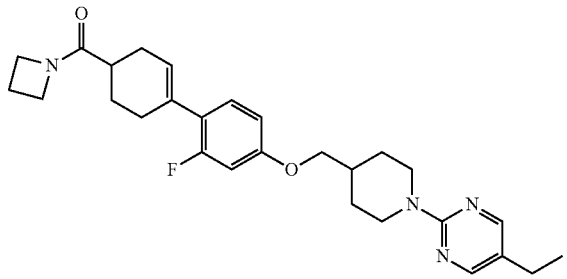 [SMILES: CCc1cnc(N2CCC(COc3ccc(C4=CCC(C(=O)N5CCC5)CC4)c(F)c3)CC2)nc1]

The title compound was prepared in the same manner as in <Example 422>, except that azetidine hydrochloride was used instead of the morpholine (Amount obtained: 390 mg/Yield: 66%).

¹H NMR (400, CDCl₃): 8.17 (2H, s), 7.12 (1H, t), 6.64 (1H, d), 6.56 (1H, d), 5.87 (1H, m), 4.75 (2H, d), 4.22 (2H, t), 4.06 (2H, t), 3.79 (2H, d), 2.92 (2H, m), 2.46 (6H, m), 2.30 (3H, m), 2.08 (1H, m), 1.91 (3H, m), 1.82 (1H, m), 1.32 (2H, m), 1.20 (3H, t)

Example 426: Preparation of (4-(4-((1-(5-ethylpyrimidin-2-yl)piperidin-4-yl) methoxy)-2-fluorophenyl)cyclohex-3-enyl)(piperidin-1-yl)methanone

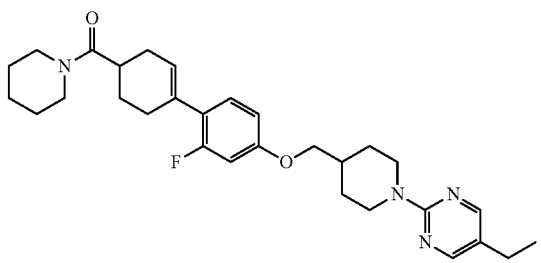 [SMILES: CCc1cnc(N2CCC(COc3ccc(C4=CCC(C(=O)N5CCCCC5)CC4)c(F)c3)CC2)nc1]

The title compound was prepared in the same manner as in <Example 422>, except that piperidine was used instead of the morpholine (Amount obtained: 420 mg/Yield: 72%).

¹H NMR (400, CDCl₃): 8.17 (2H, s), 7.13 (1H, t), 6.63 (1H, d), 6.56 (1H, d), 5.88 (1H, m), 4.75 (2H, d), 3.79 (2H, d), 3.58 (4H, m), 2.86 (2H, m), 2.48 (5H, m), 2.23 (1H, m), 2.07 (1H, m), 1.87 (4H, m), 1.60 (8H, m), 1.32 (2H, m), 1.18 (3H, t)

Example 427: Preparation of (4-(4-((1-(5-ethylpyrimidin-2-yl)piperidin-4-yl)methoxy)-2-fluorophenyl)cyclohex-3-enyl)((R)-2-(hydroxymethyl)pyrrolidin-1-yl)methanone

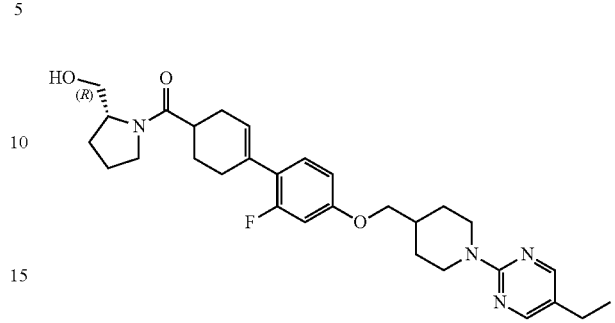

The title compound was prepared in the same manner as in <Example 422>, except that D-prolinol was used instead of the morpholine (Amount obtained: 450 mg/Yield: 75%).

¹H NMR (400, CDCl₃): 8.17 (2H, s), 7.12 (1H, dd), 7.06 (1H, d), 6.89 (1H, t), 6.07 (1H, m), 5.08 (1H, dd), 4.76 (2H, d), 4.29 (1H, m), 3.87 (2H, d), 3.61 (4H, m), 2.92 (2H, m), 2.68 (1H, m), 2.48 (5H, m), 1.62 (4H, m), 1.32 (2H, m), 1.22 (4H, m)

Example 428: Preparation of (4-(4-((1-(5-ethylpyrimidin-2-yl)piperidin-4-yl)methoxy)-3-fluorophenyl)cyclohex-3-enyl)(4-methylpiperazin-1-yl)methanone

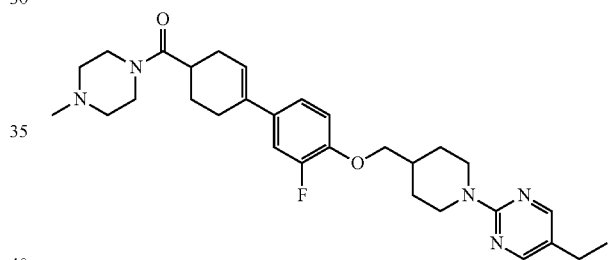

The title compound was prepared in the same manner as in <Example 292>, except that 1-methylpiperazine was used instead of the piperidine (Amount obtained: 430 mg/Yield: 72%).

¹H NMR (400, MeOD): 8.20 (2H, s), 7.17 (2H, m), 7.04 (1H, t), 6.10 (1H, s), 4.74 (2H, d), 4.62 (3H, s), 3.91 (2H, d), 3.69 (4H, m), 2.96 (3H, m), 2.57 (8H, m), 2.44 (5H, m), 2.17 (3H, m), 1.85 (3H, m), 1.79 (1H, m), 1.32 (2H, m), 1.21 (3H, t)

Example 429: Preparation of (−)-(4-(4-((1-(5-ethylpyrimidin-2-yl)piperidin-4-yl)methoxy)-3-fluorophenyl)cyclohex-3-enyl)(pyrrolidin-1-yl)methanone

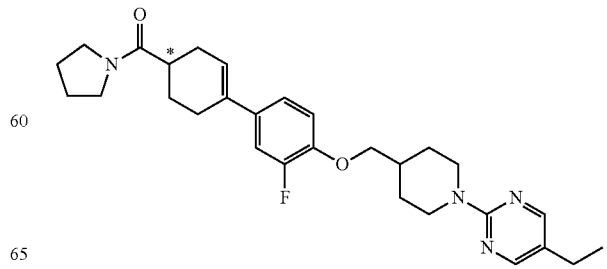

340 mg of (−)-(4-bromocyclohex-3-enyl)(pyrrolidin-1-yl)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 580 mg of 5-ethyl-2-(4-((2-fluoro-4-(4,4,5,5-tetramethyl-1,3,2-dioxaborolan-2-yl)phenoxy)methyl)piperidin-1-yl)pyrimidine were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was extracted with 100 ml of ethyl acetate, washed with 50 ml of brine, dried with anhydrous magnesium sulfate, concentrated, and then isolated by silica column chromatography to obtain the title compound (Amount obtained: 430 mg/Yield: 68%).

$^1$H NMR (400, CDCl$_3$): 8.17 (2H, s), 7.13 (1H, dd), 7.07 (1H, d), 7.06 (1H, d), 6.88 (1H, t), 6.07 (1H, m), 4.75 (2H, d), 3.87 (2H, d), 3.51 (4H, m), 2.93 (2H, m), 2.63 (1H, m), 2.50 (5H, m), 2.30 (1H, m), 2.13 (1H, m), 1.91 (8H, m), 1.34 (2H, m), 1.18 (3H, t)

Example 430: Preparation of (−)-(4-(4-((1-(5-ethyl-pyrimidin-2-yl)piperidin-4-yl)methoxy)-3-fluorophenyl)cyclohex-3-enyl)(4-(2-hydroxyethyl)piperidin-1-yl)methanone

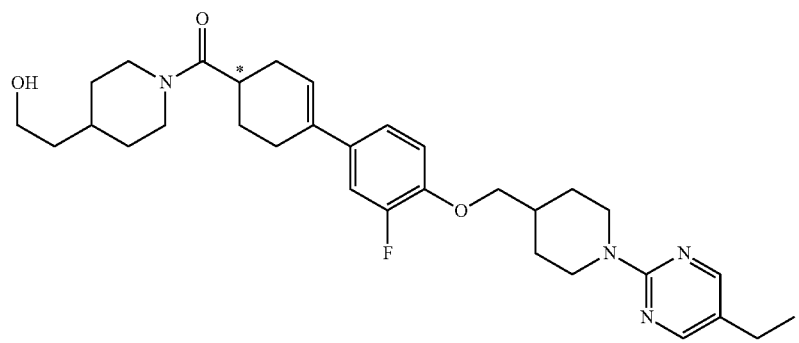 [SMILES: CCc1cnc(N2CCC(COc3ccc(C4=CCC(C(=O)N5CCC(CCO)CC5)CC4)cc3F)CC2)nc1]

380 mg of (−)-(4-bromocyclohex-3-enyl)(4-(2-hydroxyethyl)piperidin-1-yl)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 580 mg of 5-ethyl-2-(4-((2-fluoro-4-(4,4,5,5-tetramethyl-1,3,2-dioxaborolan-2-yl)phenoxy)methyl)piperidin-1-yl)pyrimidine were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was extracted with 100 ml of ethyl acetate, washed with 50 ml of brine, dried with anhydrous magnesium sulfate, concentrated, and then isolated by silica column chromatography to obtain the title compound (Amount obtained: 420 mg/Yield: 63%).

$^1$H NMR (400, CDCl$_3$): 8.16 (2H, s), 7.12 (1H, dd), 7.07 (1H, d), 6.88 (1H, t), 6.05 (1H, m), 4.74 (2H, d), 4.64 (1H, d), 3.89 (3H, m), 3.70 (2H, t), 3.05 (1H, t), 2.93 (2H, m), 2.77 (1H, m), 2.49 (6H, m), 2.24 (1H, m0, 2.12 (1H, m), 1.83 (8H, m), 1.53 (3H, m), 1.35 (2H, m), 1.18 (5H, m)

Example 431: Preparation of (4-(4-((1-(5-ethylpyrimidin-2-yl)piperidin-4-yl)methoxy)-2-fluorophenyl)cyclohex-3-enyl)(4-hydroxypiperidin-1-yl)methanone

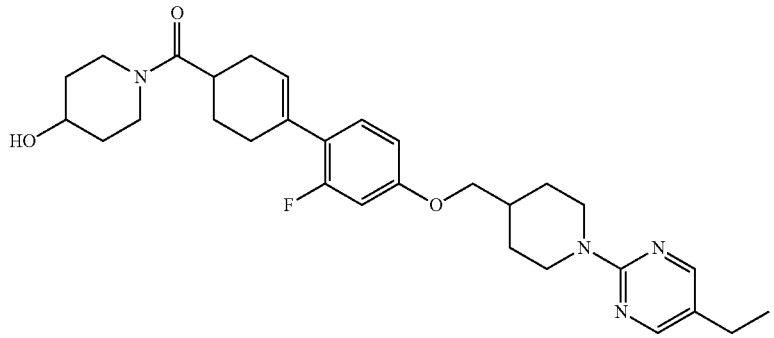 [SMILES: CCc1cnc(N2CCC(COc3ccc(C4=CCC(C(=O)N5CCC(O)CC5)CC4)c(F)c3)CC2)nc1]

The title compound was prepared in the same manner as in <Example 422>, except that 4-hydroxypiperidine was used instead of the morpholine (Amount obtained: 450 mg/Yield: 75%).

$^1$H NMR (400, CDCl$_3$): 8.17 (2H, s), 7.12 (1H, t), 6.63 (1H, dd), 6.56 (1H, dd), 5.88 (1H, m), 4.75 (2H, d), 4.15 (1H, m), 3.85 (1H, m), 3.82 (3H, m), 3.27 (2H, m), 2.90 (3H, m), 2.43 (5H, m), 2.27 (1H, m), 2.07 (1H, m), 1.92 (6H, m), 1.68 (1H, d), 1.52 (2H, m), 1.31 (2H, m), 1.18 (3H, t)

Example 432: Preparation of (4-(4-((1-(5-ethylpyrimidin-2-yl)piperidin-4-yl) methoxy)-2-fluorophenyl)cyclohex-3-enyl)(4-(hydroxymethyl)piperidin-1-yl)methanone

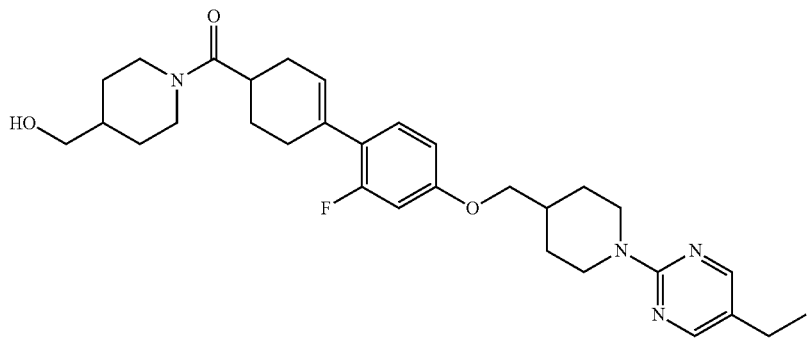 [SMILES: CCc1cnc(N2CCC(COc3ccc(C4=CCC(C(=O)N5CCC(CO)CC5)CC4)c(F)c3)CC2)nc1]

The title compound was prepared in the same manner as in <Example 422>, except that 4-piperidinemethanol was used instead of the morpholine (Amount obtained: 410 mg/Yield: 68%).

$^1$H NMR (400, CDCl$_3$): 8.17 (2H, s), 7.12 (1H, t), 6.63 (1H, dd), 6.56 (1H, dd), 5.88 (1H, m), 4.75 (3H, m), 4.04 (1H, m), 3.80 (2H, d), 3.52 (2H, m), 3.06 (1H, t), 2.87 (3H, m), 2.50 (6H, m), 2.27 (1H, m), 2.07 (1H, m), 1.89 (5H, m), 1.77 (2H, m), 1.48 (1H, t), 1.32 (2H, m), 1.18 (5H, m)

Example 433: Preparation of (4-(4-((1-(5-ethylpyrimidin-2-yl)piperidin-4-yl)methoxy)-2-fluorophenyl)cyclohex-3-enyl)(4-hydroxypiperidin-1-yl)methanone

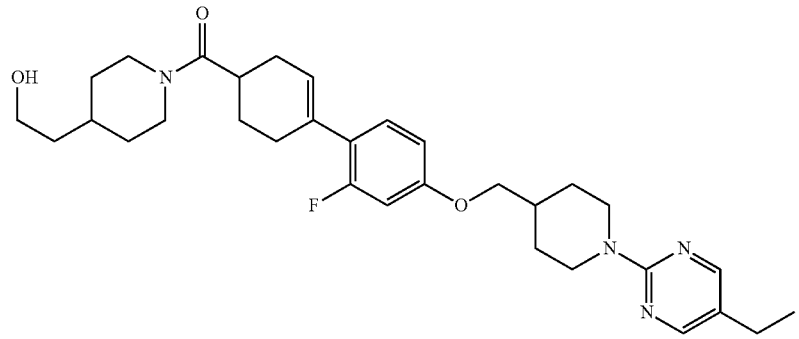 [SMILES: CCc1cnc(N2CCC(COc3ccc(C4=CCC(C(=O)N5CCC(CCO)CC5)CC4)c(F)c3)CC2)nc1]

The title compound was prepared in the same manner as in <Example 422>, except that 4-piperidineethanol was used instead of the morpholine (Amount obtained: 430 mg/Yield: 72%).

$^1$H NMR (400, CDCl$_3$): 8.17 (2H, s), 7.12 (1H, t), 6.63 (1H, dd), 6.56 (1H, dd), 5.88 (1H, m), 4.75 (2H, d), 4.64 (1H, d), 3.96 (1H, d), 3.80 (2H, d), 3.73 (2H, q), 3.05 (1H, t), 2.90 (3H, m), 2.48 (6H, m), 2.27 (1H, m), 2.07 (1H, m), 1.80 (7H, m), 1.53 (6H, m), 1.29 (3H, m), 1.18 (5H, m)

Example 434: Preparation of (4-(4-((1-(5-ethylpyrimidin-2-yl)piperidin-4-yl)methoxy)-3-fluorophenyl)cyclohex-3-enyl)(piperazin-1-yl)methanone

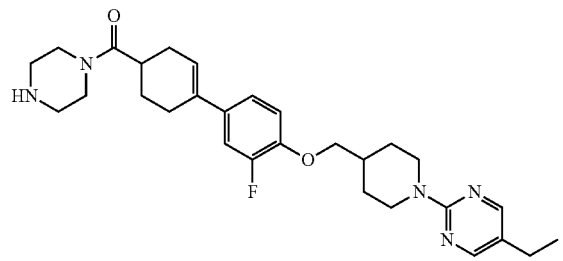 [SMILES: CCc1cnc(N2CCC(COc3ccc(C4=CCC(C(=O)N5CCNCC5)CC4)cc3F)CC2)nc1]

The title compound was prepared in the same manner as in <Example 292>, except that anhydrous piperazine was used instead of the piperidine (Amount obtained: 400 mg/Yield: 66%).

$^1$H NMR (400, CDCl$_3$): 8.17 (2H, s), 7.09 (2H, m), 6.88 (1H, m), 6.05 (1H, d), 4.74 (2H, d), 3.87 (2H, d), 3.65 (4H, m), 2.91 (6H, m), 2.75 (1H, m), 2.48 (4H, m), 2.27 (1H, m), 2.12 (2H, m), 1.80 (12H, m), 1.35 (2H, m), 1.18 (3H, t)

Example 435: Preparation of (4-(3-fluoro-4-((1-(3-(trifluoromethyl)-1,2,4-oxadiazol-5-yl)piperidin-4-yl)methoxy)phenyl)cyclohex-3-enyl)(pyrrolidin-1-yl)methanone

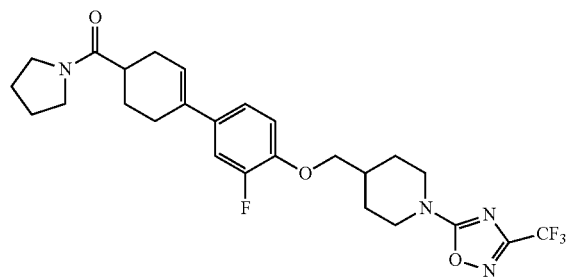 [SMILES: O=C(C1CC=C(c2ccc(OCC3CCN(c4nc(C(F)(F)F)no4)CC3)c(F)c2)CC1)N1CCCC1]

3 g of 4-((2-fluoro-4-(4-(pyrrolidine-1-carbonyl)cyclohex-1-enyl)phenoxy)methyl)piperidine-1-carbonitrile was add to 50 ml of ethyl acetate in a 250 ml flask, and the resulting mixture was dissolved while stirring under nitrogen. 900 mg of (E)-2,2,2-trifluoro-N'-hydroxyacetimidamide was added thereto, 8 ml of a 1 M zinc chloride solution was added dropwise, and the mixture was then stirred for 3 hours or more. After the reaction was terminated, the resulting solids were filtered, and washed with 100 ml of diethyl ether. The resulting solids were added to 100 ml of ethanol, and dissolved while stirring, and 10 ml of a 4 N HCl aqueous solution was added dropwise thereto, and then heated at reflux for 4 hours or more. When the reaction was completed, the resulting mixture was distilled under reduced pressure to remove ethanol, and the pH of the mixture was then made basic with sodium bicarbonate. Then, the mixture was extracted three times with 100 ml of ethyl acetate. The extracted solution was dried with anhydrous magnesium sulfate, concentrated, and then isolated by silica column chromatography to obtain the title compound.

$^1$H NMR (400, CDCl$_3$): 7.26 (1H, dd), 7.08 (1H, d), 6.87 (1H, t), 6.08 (1H, m), 4.08 (2H, d), 3.88 (2H, d), 3.51 (4H, m), 3.03 (2H, m), 2.64 (1H, m), 2.50 (3H, m), 2.31 (1H, m), 2.08 (1H, m), 1.96 (5H, m), 1.85 (3H, m), 1.42 (2H, m)

Example 436: Preparation of 2,2-difluoro-1-(4-((2-fluoro-4-(4-(pyrrolidine-1-carbonyl)cyclohex-1-enyl)phenoxy)methyl)piperidin-1-yl)butan-1-one

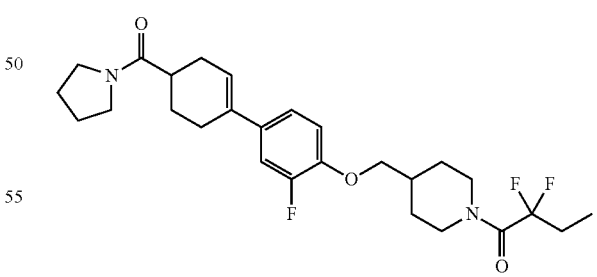

The title compound was prepared in the same manner as in <Example 409>, except that 2,2-difluorobutyric acid was used instead of the 1-(trifluoromethyl)cyclopentane-1-carboxylic acid (Amount obtained: 410 mg/Yield: 69%).

$^1$H NMR (400, CDCl$_3$): 7.26 (1H, dd), 7.08 (1H, d), 6.85 (1H, t), 6.08 (1H, m), 4.58 (1H, d), 4.34 (1H, d), 3.87 (2H, m), 3.51 (4H, m), 3.10 (1H, m), 2.73 (1H, m), 2.61 (4H, m), 2.25 (4H, m), 1.90 (8H, m), 1.32 (2H, m), 1.07 (3H, t)

Example 437: Preparation of 4-(4-((1-(5-ethylpyrimidin-2-yl)piperidin-4-yl)methoxy)-2-fluorophenyl)-N,N-bis(2-hydroxyethyl)cyclohex-3-enecarboxamide

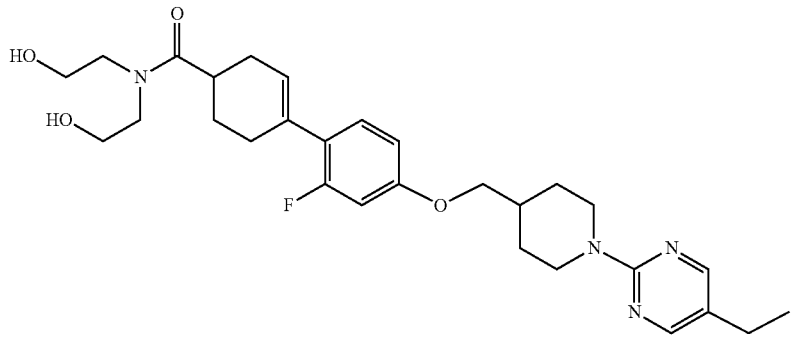 [SMILES: CCc1cnc(N2CCC(COc3ccc(C4=CCC(C(=O)N(CCO)CCO)CC4)c(F)c3)CC2)nc1]

The title compound was prepared in the same manner as in <Example 422>, except that diethanolamine was used instead of the morpholine (Amount obtained: 390 mg/Yield: 66%).

$^1$H NMR (400, CDCl$_3$): 8.17 (2H, s), 7.12(1H, t), 6.63 (1H, dd), 6.56 (2H, m), 5.88 (1H, m), 4.74 (2H, d), 3.80 (6H, m), 3.60 (4H, m), 3.31 (1H, s), 3.21 (1H, s), 2.93 (2H, m), 2.48 (5H, m), 2.30 (1H, m), 2.06 (1H, m), 1.96 (4H, m), 1.32 (2H, m), 1.18 (3H, t)

Example 438: Preparation of N-ethyl-4-(4-((1-(5-ethylpyrimidin-2-yl)piperidin-4-yl) methoxy)-2-fluorophenyl)-N-(2-hydroxyethyl)cyclohex-3-enecarboxamide

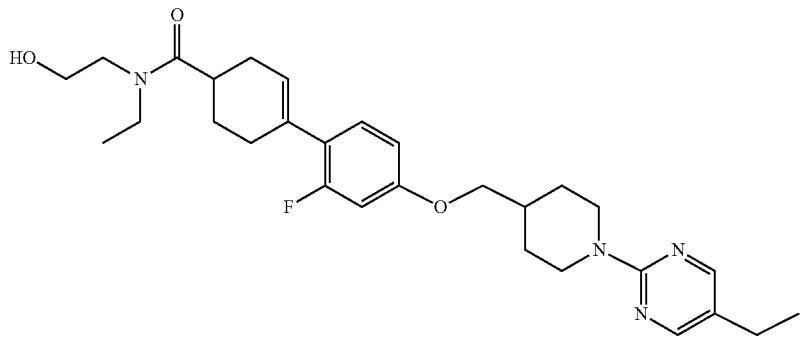 [SMILES: CCc1cnc(N2CCC(COc3ccc(C4=CCC(C(=O)N(CC)CCO)CC4)c(F)c3)CC2)nc1]

The title compound was prepared in the same manner as in <Example 422>, except that 2-(ethylamino)ethanol was used instead of the morpholine (Amount obtained: 400 mg/Yield: 68%).

$^1$H NMR (400, CDCl$_3$): 8.17 (2H, s), 7.12 (1H, t), 6.64 (1H, dd), 6.56 (2H, m), 5.89 (1H, m), 4.75 (2H, d), 3.80 (4H, m), 3.70 (1H, t), 3.50 (4H, m), 2.93 (2H, m), 2.80 (1H, m), 2.48 (5H, m), 2.27 (1H, m), 2.06 (1H, m), 1.90 (4H, m), 1.31 (2H, m), 1.16 (6H, m)

Example 439: Preparation of 2,2-difluoro-1-(4-((2-fluoro-4-(4-(morpholine-4-carbonyl)cyclohex-1-enyl)phenoxy)methyl)piperidin-1-yl)butan-1-one

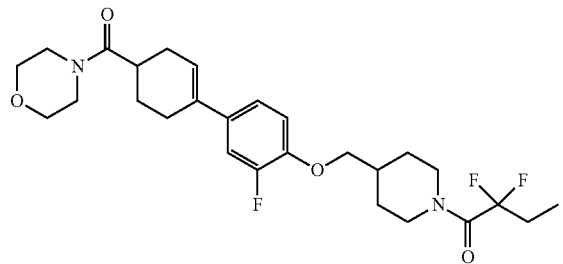 [SMILES: CCC(F)(F)C(=O)N1CCC(COc2ccc(C3=CCC(C(=O)N4CCOCC4)CC3)cc2F)CC1]

500 mg of (4-(3-fluoro-4-(piperidin-4-ylmethoxy)phenyl)cyclohex-3-enyl)(morpholino)methanone hydrochloride was put into a 100 ml flask under a nitrogen atmosphere, 20 ml of dichloromethane was added thereto, and the resulting mixture was then dissolved while stirring. 0.29 ml of triethylamine, 0.17 ml of 2,2-difluorobutyric acid, and 420 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 420 mg/Yield: 71%).

$^1$H NMR (400, CDCl$_3$): 7.12 (1H, dd), 7.05 (1H, d), 6.86 (1H, t), 6.05 (1H, d), 4.58 (1H, m), 4.38 (1H, m), 3.88 (2H, m), 3.69 (6H, m), 3.55 (2H, m), 3.13 (1H, m), 2.75 (2H, m), 2.50 (3H, m), 2.18 (4H, m), 1.93 (4H, m), 1.32 (2H, m), 1.07 (3H, t)

Example 440: Preparation of 1,1,1-trifluoropropan-2-yl 4-((2-fluoro-4-(4-(morpholine-4-carbonyl)cyclohex-1-enyl)phenoxy)methyl)piperidine-1-carboxylate

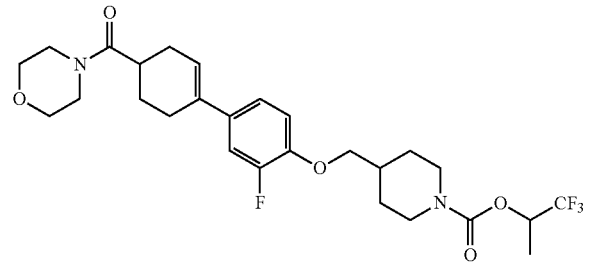 [SMILES: CC(OC(=O)N1CCC(COc2ccc(C3=CCC(C(=O)N4CCOCC4)CC3)cc2F)CC1)C(F)(F)F]

500 mg of trichloromethyl 4-((2-fluoro-4-(4-(morpholine-4-carbonyl)cyclohex-1-enyl)phenoxy)methyl)piperidine-1-carboxylate was put into a 100 ml flask under a nitrogen atmosphere, 20 ml of tetrahydrofuran was added thereto, and the resulting mixture was then dissolved while stirring. 0.39 ml of triethylamine and 0.15 ml of 1,1,1-trifluoro-2-propanol were added dropwise thereto, and the mixture was stirred at 20° C. for 2 hours. After the reaction was terminated, the reaction mixture was extracted twice with 20 ml of ethyl acetate, and the resulting organic layer was washed with 20 ml of distilled water, dried with anhydrous magnesium sulfate, concentrated, and then isolated by silica column chromatography to obtain the title compound (Amount obtained: 400 mg/Yield: 67%).

$^1$H NMR (400, CDCl$_3$): 7.12 (1H, dd), 7.05 (1H, d), 6.87 (1H, t), 6.06 (1H, d), 5.25 (1H, m), 4.17 (2H, m), 3.87 (2H, m), 3.69 (6H, m), 3.55 (2H, m), 2.82 (3H, m), 2.51 (3H, m), 2.25 (1H, m), 1.97 (5H, m), 1.62 (2H, s), 1.39 (3H, d), 1.27 (2H, m)

Example 441: Preparation of (−)-4-(4-((1-(5-ethylpyrimidin-2-yl)piperidin-4-yl)methoxy)-3-fluorophenyl)-N-(2-hydroxyethyl)cyclohex-3-enecarboxamide

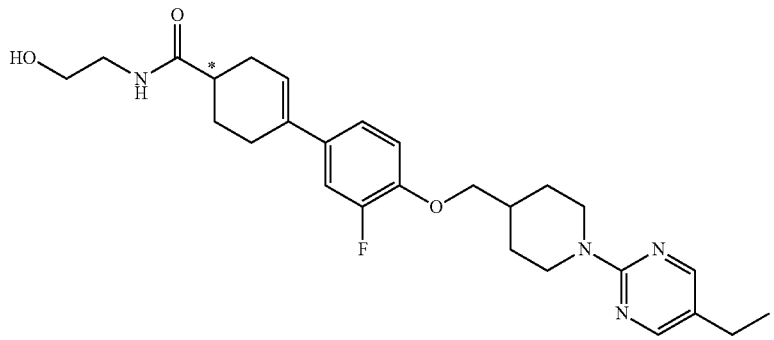 [SMILES: CCc1cnc(N2CCC(COc3ccc(C4=CCC(C(=O)NCCO)CC4)cc3F)CC2)nc1]

The title compound was prepared in the same manner as in <Example 292>, except that 2-aminoethanol was used instead of the piperidine (Amount obtained: 390 mg/Yield: 67%).

$^1$H NMR (400, CDCl$_3$): 8.16 (2H, s), 7.11 (1H, dd), 7.03 (1H, d), 6.87 (1H, t), 6.12 (1H, t), 6.04 (1H, s), 4.74 (2H, d), 3.87 (2H, d), 3.74 (2H, t), 3.45 (2H, m), 2.91 (2H, m), 2.80 (1H, s), 2.42 (7H, m), 2.12 (2H, m), 1.80 (5H, m), 1.35 (2H, m), 1.18 (3H, t)

Example 442: Preparation of (+)-tert-butyl 4-((2-fluoro-4-(4-(morpholine-4-carbonyl)cyclohex-1-enyl)phenoxy)methyl)piperidine-1-carboxylate

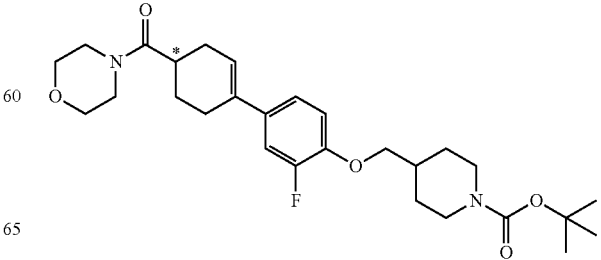

330 mg of (+)-(4-bromocyclohex-3-enyl)(morpholino)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 530 mg of tert-butyl 4-((2-fluoro-4-(4,4,5,5-tetramethyl-1,3,2-dioxaborolan-2-yl)phenoxy)methyl)piperidine-1-carboxylate were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was extracted with 100 ml of ethyl acetate, washed with 50 ml of brine, dried with anhydrous magnesium sulfate, concentrated, and then isolated by silica column chromatography to obtain the title compound (Amount obtained: 430 mg/Yield: 71%).

$^1$H NMR (400, CDCl$_3$): 7.12 (1H, dd), 7.04 (1H, d), 6.87 (1H, t), 6.05 (1H, m), 4.15 (2H, s), 3.85 (2H, d), 3.69 (6H, m), 3.55 (2H, m), 2.74 (3H, m), 2.50 (3H, m), 2.28 (1H, m), 1.88 (5H, m), 1.48 (9H, s), 1.24 (2H, m)

Example 443: Preparation of (−)-tert-butyl 4-((2-fluoro-4-(4-(morpholine-4-carbonyl)cyclohex-1-enyl)phenoxy)methyl)piperidine-1-carboxylate

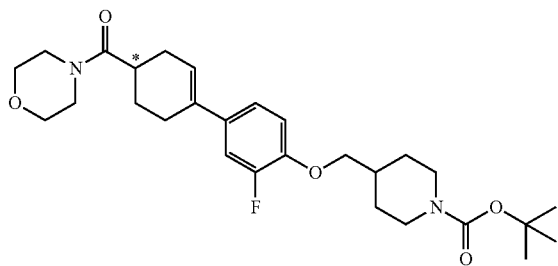 [SMILES: CC(C)(C)OC(=O)N1CCC(COc2ccc(C3=CCC(C(=O)N4CCOCC4)CC3)cc2F)CC1]

330 mg of (−)-(4-bromocyclohex-3-enyl)(morpholino)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 530 mg of tert-butyl 4-((2-fluoro-4-(4,4,5,5-tetramethyl-1,3,2-dioxaborolan-2-yl)phenoxy)methyl)piperidine-1-carboxylate were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was extracted with 100 ml of ethyl acetate, washed with 50 ml of brine, dried with anhydrous magnesium sulfate, concentrated, and then isolated by silica column chromatography to obtain the title compound (Amount obtained: 460 mg/Yield: 75%).

$^1$H NMR (400, CDCl$_3$): 7.12 (1H, dd), 7.04 (1H, d), 6.87 (1H, t), 6.05 (1H, m), 4.15 (2H, s), 3.85 (2H, d), 3.69 (6H, m), 3.55 (2H, m), 2.74 (3H, m), 2.40 (4H, m), 1.90 (5H, m), 1.46 (9H, s), 1.25 (2H, m)

Example 444: Preparation of isopropyl 4-((2-fluoro-4-(4-(morpholine-4-carbonyl)cyclohex-1-enyl)phenoxy)methyl)piperidine-1-carboxylate

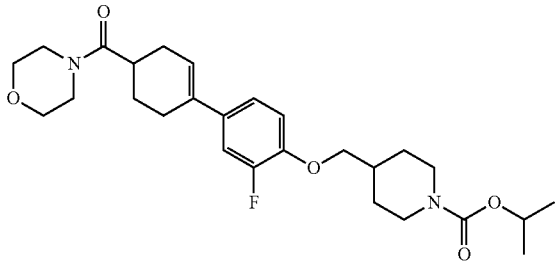 [SMILES: CC(C)OC(=O)N1CCC(COc2ccc(C3=CCC(C(=O)N4CCOCC4)CC3)cc2F)CC1]

The title compound was prepared in the same manner as in <Example 440>, except that isopropanol was used instead of the 1,1,1-trifluoro-2-propanol (Amount obtained: 430 mg/Yield: 74%).

$^1$H NMR (400, CDCl$_3$): 7.12 (1H, dd), 7.04 (1H, d), 6.87 (1H, t), 6.05 (1H, m), 4.91 (1H, m), 4.13 (2H, s), 3.85 (2H, d), 3.69 (6H, m), 3.55 (2H, m), 2.74 (3H, m), 2.52 (3H, m), 2.31 (1H, m), 1.98 (5H, m), 1.23 (8H, m)

Example 445: Preparation of phenyl 4-((2-fluoro-4-(4-(morpholine-4-carbonyl)cyclohex-1-enyl)phenoxy)methyl)piperidine-1-carboxylate

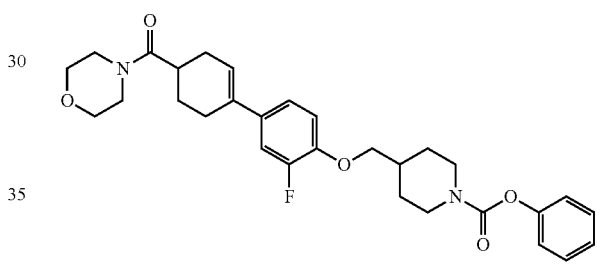

The title compound was prepared in t e same manner as in <Example 440>, except that phenol was used instead of the 1,1,1-trifluoro-2-propanol (Amount obtained: 470 mg/Yield: 79%).

$^1$H NMR (400, CDCl$_3$): 7.37 (2H, m), 7.17 (1H, t), 7.06 (4H, m), 6.87 (1H, t), 6.06 (1H, m), 4.35 (2H, s), 3.91 (2H, s), 3.69 (6H, m), 3.55 (2H, m), 2.95 (2H m), 2.74 (1H, m), 2.50 (3H, m), 2.28 (1H, m), 2.10 (1H, m), 1.95 (4H, m), 1.40 (2H, m)

Example 446: Preparation of 1,1,1,3,3,3-hexafluoropropan-2-yl 4-((2-fluoro-4-(4-(morpholine-4-carbonyl)cyclohex-1-enyl)phenoxy)methyl)piperidine-1-carboxylate

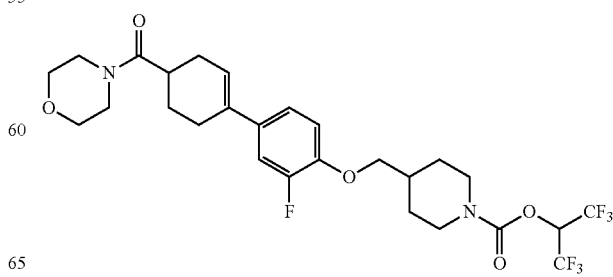

The title compound was prepared in the same manner as in <Example 440>, except that 1,1,1,3,3,3-hexafluoro-2-propanol was used instead of the 1,1,1-trifluoro-2-propanol (Amount obtained: 450 mg/Yield: 77%).

$^1$H NMR (400, CDCl$_3$): 7.13 (1H, d), 7.05 (1H, d), 6.87 (1H, t), 6.06 (1H, d), 5.76 (1H, m), 4.18 (2H, t), 3.88 (2H, d), 3.69 (6H, m), 3.55 (2H, m), 2.96 (2H, m), 2.76 (1H, m), 2.50 (3H, m), 2.30 (1H, m), 2.08 (1H, m), 1.90 (4H, m), 1.33 (2H, m)

Example 447: Preparation of 1,3-difluoropropan-2-yl 4-((2-fluoro-4-(4-(morpholine-4-carbonyl)cyclohex-1-enyl)phenoxy)methyl)piperidine-1-carboxylate

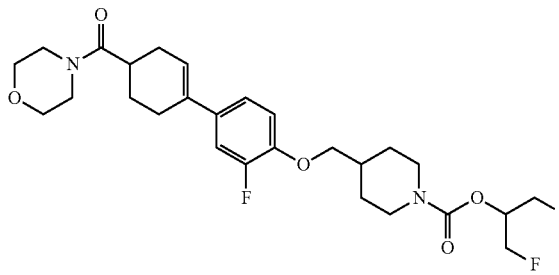

The title compound was prepared in the same manner as in <Example 440>, except that 1,3-difluoro-2-propanol was used instead of the 1,1,1-trifluoro-2-propanol (Amount obtained: 410 mg/Yield: 69%).

$^1$H NMR (400, CDCl$_3$): 7.12 (1H, dd), 7.05 (1H, d), 6.87 (1H, t), 6.05 (1H, m), 5.12 (1H, m), 4.67 (2H, d), 4.55 (2H, d), 4.22 (2H, m), 3.86 (2H, d), 3.69 (6H, m), 3.55 (2H, m), 2.79 (3H, m), 2.52 (3H, m), 2.29 (1H, m), 1.90 (5H, m), 1.27 (2H, m)

Example 448: Preparation of (4-(2-fluoro-4-((1-(3-isopropyl-1,2,4-oxadiazol-5-yl)piperidin-4-yl)methoxy)phenyl)cyclohex-3-enyl)(morpholino)methanone

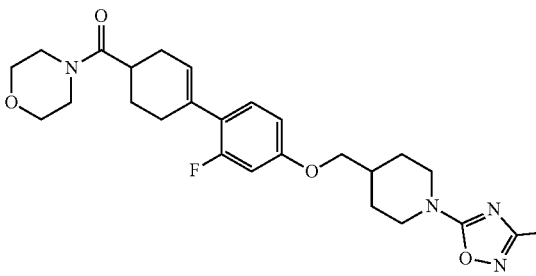

500 mg of 4-(2-fluoro-4-((1-(3-isopropyl-1,2,4-oxadiazol-5-yl)piperidin-4-yl)methoxy)phenyl)cyclohex-3-enecarboxylic acid was put into a 100 ml flask under a nitrogen atmosphere, 20 ml of dichloromethane was thereto, and the resulting mixture was then dissolved while stirring. 0.34 ml of triethylamine, 0.16 ml of morpholine, and 520 mg of HATU were added dropwise thereto, and the mixture was stirred at 20° C. for an hour. After the reaction was terminated, 20 ml of dichloromethane was additionally added thereto, and the resulting organic layer was washed with 20 ml of distilled water, dried with anhydrous magnesium sulfate, concentrated, and then isolated by silica column chromatography to obtain the title compound (Amount obtained: 490 mg/Yield: 82%).

$^1$H NMR (400, CDCl$_3$): 7.13 (1H, t), 6.63 (1H, dd), 6.55 (1H, dd), 5.88 (1H, d), 4.18 (2H, d), 3.81 (2H, d), 3.69 (6H, m), 3.55 (2H, m), 3.12 (2H, m), 2.90 (1H, m), 2.80 (1H, m), 2.50 (3H, m), 2.27 (1H, m), 2.04 (1H, m), 1.86 (4H, m), 1.44 (2H, m), 1.28 (6H, d)

Example 449: Preparation of (4-(2-fluoro-4-((1-(3-isopropyl-1,2,4-oxadiazol-5-yl)piperidin-4-yl)methoxy)phenyl)cyclohex-3-enyl)(thiomorpholino)methanone

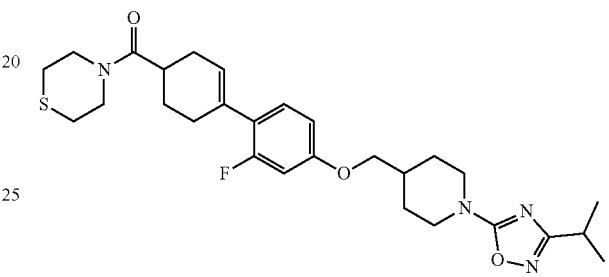

The title compound was prepared in the same manner as in <Example 448>, except that thiomorpholine was used instead of the morpholine (Amount obtained: 430 mg/Yield: 72%).

$^1$H NMR (400, CDCl$_3$): 7.13 (1H, t), 6.63 (1H, dd), 6.55 (1H, dd), 5.88 (1H, d), 4.22 (2H, d), 3.84 (6H, m), 3.12 (2H, m), 2.90 (1H, m), 2.79 (1H, m), 2.67 (4H, m), 2.47 (3H, m), 2.27 (1H, m), 2.04 (1H, m), 1.86 (4H, m), 1.42 (2H, m), 1.28 (6H, d)

Example 450: Preparation of (4-(3-fluoro-4-((1-(1-(trifluoromethyl)cyclopentanecarbonyl)piperidin-4-yl)methoxy)phenyl)cyclohex-3-enyl)(morpholino)methanone

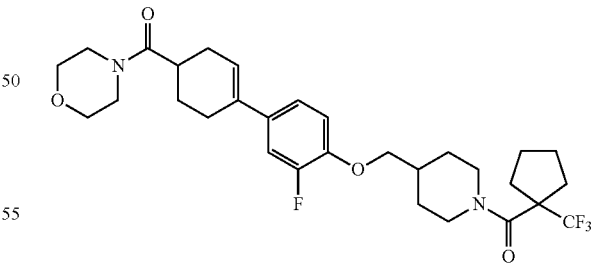

The title compound was prepared in the same manner as in <Example 439>, except that 1-(trifluoromethyl)cyclopentane-1-carboxylic acid was used instead of the 2,2-difluorobutyric acid (Amount obtained: 450 mg/Yield: 75%).

$^1$H NMR (400, CDCl$_3$): 7.09 (1H, dd), 7.04 (1H, d), 6.86 (1H, t), 6.05 (1H, d), 4.42 (2H, s), 3.86 (2H, d), 3.69 (6H, m), 3.55 (2H, m), 2.75 (3H, m), 2.53 (2H, m), 2.45 (3H, m), 2.25 (1H, m), 2.15 (3H, m), 1.97 (4H, m), 1.67 (6H, m), 1.30 (2H, m)

Example 451: Preparation of 1-(4-((2-fluoro-4-(4-(morpholine-4-carbonyl)cyclohex-1-enyl)phenoxy)methyl)piperidin-1-yl)-3-methylbut-2-en-1-one

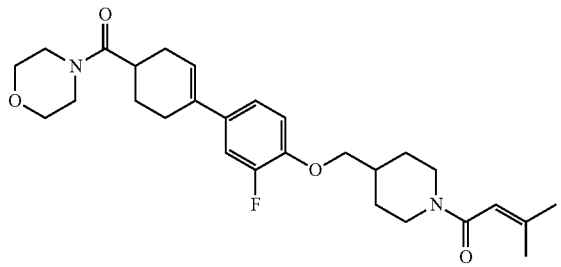 [SMILES: CC(C)=CC(=O)N1CCC(COc2ccc(C3=CCC(C(=O)N4CCOCC4)CC3)cc2F)CC1]

The title compound was prepared in the same manner as in <Example 439>, except that 3-methylcrotonic acid was used instead of the 2,2-difluorobutyric acid (Amount obtained: 470 mg/Yield: 79%).

$^1$H NMR (400, CDCl$_3$): 7.12 (1H, dd), 7.04 (1H, d), 6.87 (1H, t), 6.05 (1H, d), 5.77 (1H, s), 4.67 (1H, d), 4.02 (1H, d), 3.85 (2H, m), 3.70 (6H, m), 3.52 (2H, m), 3.03 (1H, t), 2.72 (2H, m), 2.51 (2H, m), 2.43 (1H, m), 2.31 (1H, m), 2.08 (1H, m), 1.92 (7H, m), 1.82 (3H, s), 1.26 (5H, m)

Example 452: Preparation of (4-(4-((1-(5-ethylpyrimidin-2-yl)piperidin-4-yl)methoxy)-2-fluorophenyl)cyclohex-3-enyl)(4-(trifluoromethyl)piperidin-1-yl)methanone

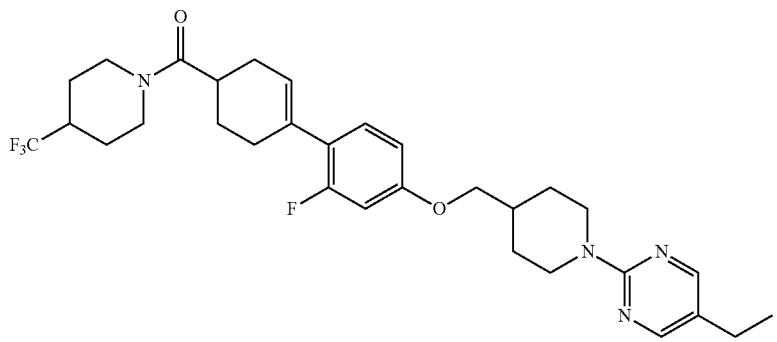 [SMILES: CCc1cnc(N2CCC(COc3ccc(C4=CCC(C(=O)N5CCC(C(F)(F)F)CC5)CC4)c(F)c3)CC2)nc1]

The title compound was prepared in the same manner as in <Example 422>, except that 4-(trifluoromethyl)piperidine was used instead of the morpholine (Amount obtained: 450 mg/Yield: 76%).

$^1$H NMR (400, CDCl$_3$): 8.17 (2H, s), 7.12 (1H, t), 6.64 (1H, dd), 6.56 (1H, dd), 5.88 (1H, d), 4.78 (3H, m), 4.11 (1H, d), 3.80 (2H, d), 3.07 (1H, m), 2.90 (3H, m), 2.47 (6H, m), 2.26 (2H, m), 2.10 (1H, m), 1.90 (6H, m), 1.52 (2H, m), 1.31 (2H, m), 1.16 (3H, t)

Example 453: Preparation of (4,4-difluoropiperidin-1-yl)(4-(4-((1-(5-ethylpyrimidin-2-yl)piperidin-4-yl)methoxy)-2-fluorophenyl)cyclohex-3-enyl)methanone

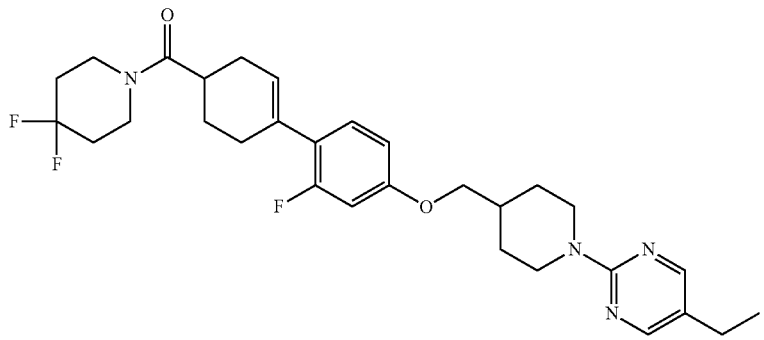 [SMILES: CCc1cnc(N2CCC(COc3ccc(C4=CCC(C(=O)N5CCC(F)(F)CC5)CC4)c(F)c3)CC2)nc1]

The title compound was prepared in the same manner as in <Example 422>, except that 4,4-difluoropiperidine was used instead of the morpholine (Amount obtained: 430 mg/Yield: 72%).

¹H NMR (400, CDCl₃): 8.17 (2H, s), 7.12 (1H, t), 6.64 (1H, dd), 6.56 (1H, dd), 5.88 (1H, d), 4.75 (2H, d), 3.73 (6H, d), 2.90 (3H, m), 2.48 (5H, m), 2.23 (1H, m), 2.00 (9H, m), 1.31 (2H, m), 1.16 (3H, t)

Example 454: Preparation of (3,3-difluoropyrrolidin-1-yl)(4-(4-((1-(5-ethylpyrimidin-2-yl)piperidin-4-yl)methoxy)-2-fluorophenyl)cyclohex-3-enyl)methanone

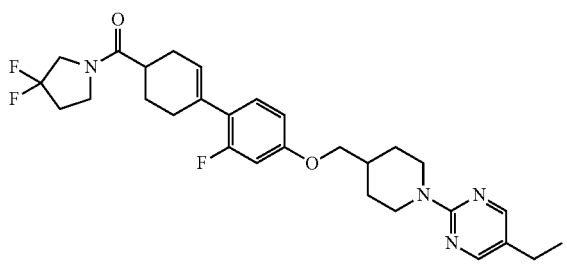 [SMILES: CCc1cnc(N2CCC(COc3ccc(C4=CCC(C(=O)N5CCC(F)(F)C5)CC4)c(F)c3)CC2)nc1]

The title compound was prepared in the same manner as in <Example 422>, except that 3,3-difluoropyrrolidine hydrochloride was used instead of the morpholine (Amount obtained: 410 mg/Yield: 69%).

¹H NMR (400, CDCl₃): 8.17 (2H, s), 7.12 (1H, t), 6.62 (1H, dd), 6.56 (1H, dd), 5.88 (1H, d), 4.75 (2H, d), 3.85 (6H, d), 2.93 (2H, m), 2.50 (9H, m), 2.08 (1H, m), 1.92 (4H, m), 1.31 (2H, m), 1.18 (3H, m)

Example 455: Preparation of (4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone

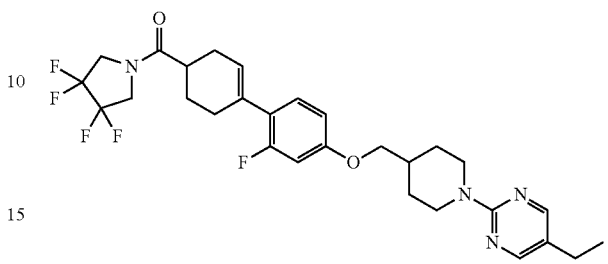

The title compound was prepared in the same manner as in <Example 422>, except that 3,3,4,4-tetrafluoropyrrolidine hydrochloride was used instead of the morpholine (Amount obtained: 400 mg/Yield: 67%).

¹H NMR (400, CDCl₃): 8.17 (2H, s), 7.11 (1H, t), 6.64 (1H, dd), 6.56 (1H, dd), 5.87 (1H, d), 4.75 (2H, d), 4.02 (4H, m), 3.80 (2H, d), 2.93 (2H, m), 2.50 (6H, m), 2.29 (1H, m), 2.08 (1H, m), 1.86 (4H, m), 1.31 (2H, m), 1.16 (3H, t)

Example 456: Preparation of (4-(4-((1-(5-ethylpyrimidin-2-yl)piperidin-4-yl)methoxy)-3-fluorophenyl)cyclohex-3-enyl)(4-(trifluoromethyl)piperidin-1-yl)methanone

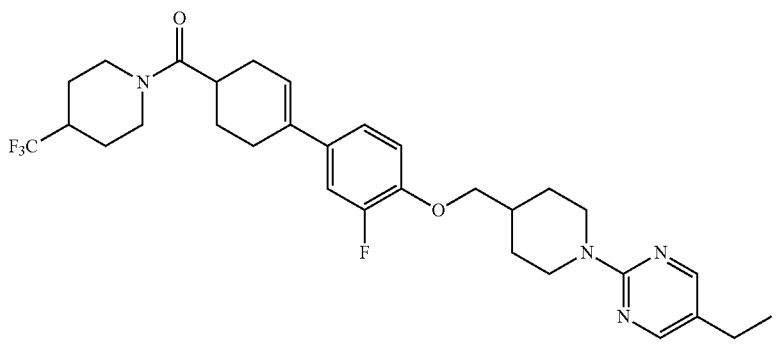

The title compound was prepared in the same manner as in <Example 292>, except that 4-(trifluoromethyl)piperidine was used instead of the piperidine (Amount obtained: 450 mg/Yield: 76%).

¹H NMR (400, CDCl₃): 8.17 (2H, s), 7.13 (1H, dd), 7.05 (1H, d), 6.88 (1H, t), 6.06 (1H, s), 4.78 (3H, m), 4.06 (1H, d), 3.87 (2H, d), 3.07 (1H, t), 2.90 (2H, m), 2.79 (1H, m), 2.50 (6H, m), 2.29 (2H, m), 2.16 (1H, m), 1.93 (6H, m), 1.52 (2H, m), 1.31 (2H, m), 1.18 (3H, t)

Example 457: Preparation of (4,4-difluoropiperidin-1-yl)(4-(4-((1-(5-ethylpyrimidin-2-yl)piperidin-4-yl)methoxy)-3-fluorophenyl)cyclohex-3-enyl)methanone

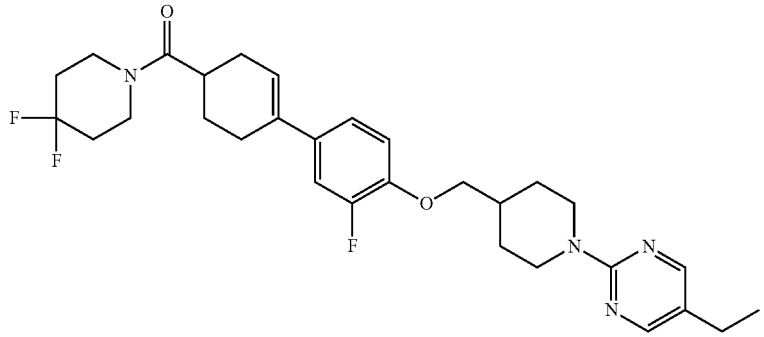

The title compound was prepared in the same manner as in <Example 292>, except that 4,4-difluoropiperidine was used instead of the piperidine (Amount obtained: 470 mg/Yield: 79%).

$^1$H NMR (400, CDCl$_3$): 8.17 (2H, s), 7.13 (1H, dd), 7.04 (1H, d), 6.88 (1H, t), 6.05 (1H, d), 4.75 (2H, d), 3.87 (2H, d), 3.76 (4H, m), 2.93 (2H, m), 2.80 (1H, m), 2.48 (5H, m), 2.30 (1H, m), 2.13 (1H, m), 1.97 (8H, m), 1.32 (2H, m), 1.18 (3H, t)

Example 458: Preparation of ((−)-4-(4-((1-(5-ethylpyrimidin-2-yl)piperidin-4-yl)methoxy)phenyl)cyclohex-3-enyl)((S)-3-fluoropyrrolidin-1-yl)methanone

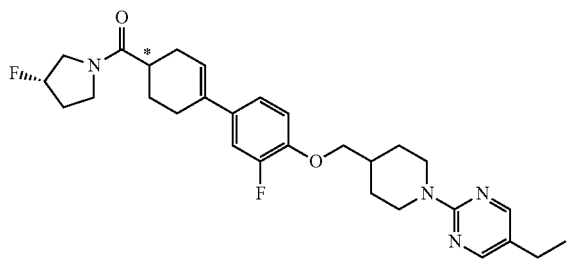 [SMILES: CCc1cnc(N2CCC(COc3ccc(C4=CCC(C(=O)N5CC[C@H](F)C5)CC4)cc3F)CC2)nc1]

330 mg of ((−)-4-bromocyclohex-3-enyl)((S)-3-fluoropyrrolidin-1-yl)methanone was dissolved in a THF/water/ethanol mixture (40 ml/20 ml/10 ml) in a 100 ml flask under a nitrogen atmosphere, and stirred. 50 mg of 1,1-bis(diphenylphosphino)ferrocene-palladium(II)dichloride, 700 mg of potassium phosphate tribasic, and 580 mg of 5-ethyl-2-(4-((4-(4,4,5,5-tetramethyl-1,3,2-dioxaborolan-2-yl)phenoxy)methyl)piperidin-1-yl)pyrimidine were sequentially added dropwise thereto. The resulting mixture was gradually heated and stirred at a temperature of 68° C. for 2 hours. After the reaction was terminated, the reaction mixture was slowly cooled to room temperature. Then, 50 ml of distilled water was slowly added thereto, and the reaction mixture was extracted with 100 ml of ethyl acetate, washed with 50 ml of brine, dried with anhydrous magnesium sulfate, concentrated, and then isolated by silica column chromatography to obtain the title compound (Amount obtained: 460 mg/Yield: 76%).

$^1$H NMR (400, CDCl$_3$): 8.17 (2H, s), 7.29 (2H, d), 6.83 (2H, d), 6.04 (1H, m), 5.26 (1H m), 4.74 (2H, d), 3.79 (6H, m), 2.93 (2H, m), 2.40 (11H, m), 1.91 (3H, m), 1.35 (2H, m), 1.18 (3H, t)

Example 459: Preparation of (3,3-difluoropyrrolidin-1-yl)(4-(4-((1-(5-ethylpyrimidin-2-yl)piperidin-4-yl)methoxy)-3-fluorophenyl)cyclohex-3-enyl)methanone

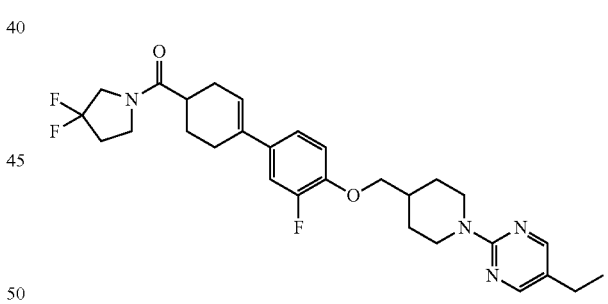

The title compound was prepared in the same manner as in <Example 292>, except that 3,3-difluoropyrrolidine hydrochloride was used instead of the piperidine (Amount obtained: 430 mg/Yield: 73%).

$^1$H NMR (400, CDCl$_3$): 8.17 (2H, s), 7.12 (1H, dd), 7.04 (1H, d), 6.88 (1H, t), 6.06 (1H, s), 4.75 (2H, d), 3.80 (6H, m), 2.90 (2H, m), 2.40 (9H, m), 2.12 (1H, m), 1.97 (4H, m), 1.32 (2H, m), 1.18 (3H, t)

Example 460: Preparation of (4-(4-((1-(5-ethylpyrimidin-2-yl)piperidin-4-yl)methoxy)-3-fluorophenyl)cyclohex-3-enyl)(3,3,4,4-tetrafluoropyrrolidin-1-yl)methanone

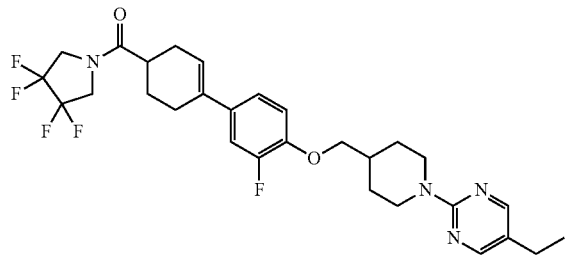 [SMILES: CCc1cnc(N2CCC(COc3ccc(C4=CCC(C(=O)N5CC(F)(F)C(F)(F)C5)CC4)cc3F)CC2)nc1]

The title compound was prepared in the same manner as in <Example 292>, except that 3,3,4,4-tetrafluoropyrrolidine hydrochloride was used instead of the piperidine (Amount obtained: 450 mg/Yield: 77%).

$^1$H NMR (400, CDCl$_3$): 8.17 (2H, s), 7.12 (1H, dd), 7.04 (1H, d), 6.89 (1H, t), 6.04 (1H, d), 4.75 (2H, d), 4.04 (4H, m), 3.87 (2H, d), 2.93 (2H, m), 2.40 (7H, m), 2.14 (1H, m), 1.93 (4H, m), 1.32 (2H, m), 1.18 (3H, t)

Example 461: Preparation of (−)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone

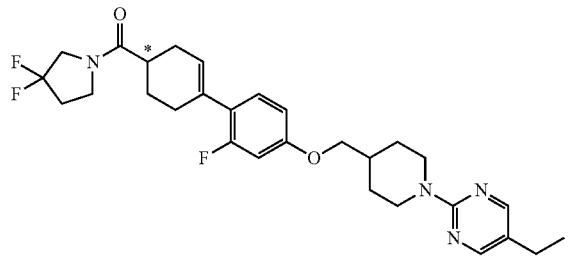 [SMILES: CCc1cnc(N2CCC(COc3ccc(C4=CCC(C(=O)N5CCC(F)(F)C5)CC4)c(F)c3)CC2)nc1]

The title compound was prepared in the same manner as in <Example 443>, except that (−)-(4-bromocyclohex-3-enyl)(3,3-difluoropyrrolidin-1-yl)methanone was used instead of the (+)-(4-bromocyclohex-3-enyl)(morpholino)methanone, and 5-ethyl-2-(4-((3-fluoro-4-(4,4,5,5-tetramethyl-1,3,2-dioxaborolan-2-yl)phenoxy)methyl)piperidin-1-yl)pyrimidine was used instead of the tert-butyl 4-((2-fluoro-4-(4,4,5,5-tetramethyl-1,3,2-dioxaborolan-2-yl)phenoxy)methyl)piperidine-1-carboxylate (Amount obtained: 390 mg/Yield: 67%).

$^1$H NMR (400, CDCl$_3$): 8.17 (2H, s), 7.12 (1H, t), 6.62 (1H, dd), 6.56 (1H, dd), 5.88 (1H, d), 4.75 (2H, d), 3.85 (6H, d), 2.93 (2H, m), 2.50 (9H, m), 2.08 (1H, m), 1.92 (4H, m), 1.31 (2H, m), 1.18 (3H, m)

Example 462: Preparation of (+)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone

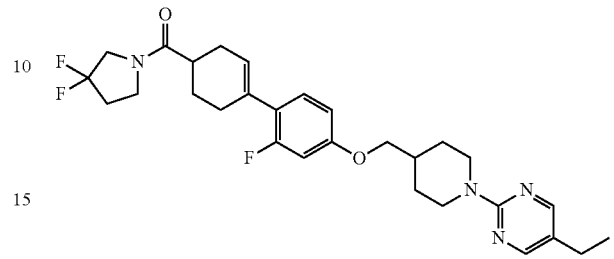

The title compound was prepared in the same manner as in <Example 443>, except that (+)-(4-bromocyclohex-3-enyl)(3,3-difluoropyrrolidin-1-yl)methanone was used instead of the (+)-(4-bromocyclohex-3-enyl)(morpholino)methanone, and 5-ethyl-2-(4-((3-fluoro-4-(4,4,5,5-tetramethyl-1,3,2-dioxaborolan-2-yl)phenoxy)methyl)piperidin-1-yl)pyrimidine was used instead of the tert-butyl 4-((2-fluoro-4-(4,4,5,5-tetramethyl-1,3,2-dioxaborolan-2-yl)phenoxy)methyl)piperidine-1-carboxylate (Amount obtained: 410 mg/Yield: 70%).

$^1$H NMR (400, CDCl$_3$): 8.17 (2H, s), 7.12 (1H, t), 6.62 (1H, dd), 6.56 (1H, dd), 5.88 (1H, d), 4.75 (2H, d), 3.85 (6H, d), 2.93 (2H, m), 2.50 (9H, m), 2.08 (1H, m), 1.92 (4H, m), 1.31 (2H, m), 1.18 (3H, m)

Example 463: Preparation of (−)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone

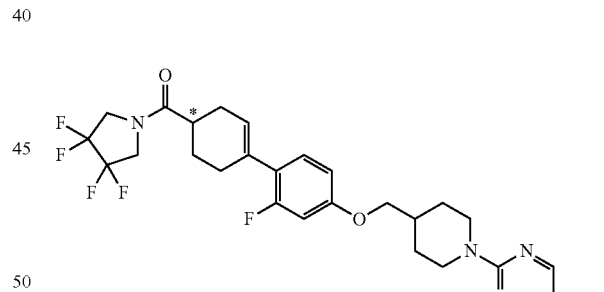

The title compound was prepared in the same manner as in <Example 443>, except that (−)-(4-bromocyclohex-3-enyl)(3,3,4,4-tetrafluoropyrrolidin-1-yl)methanone was used instead of the (+)-(4-bromocyclohex-3-enyl)(morpholino)methanone, and 5-ethyl-2-(4-((3-fluoro-4-(4,4,5,5-tetramethyl-1,3,2-dioxaborolan-2-yl)phenoxy)methyl)piperidin-1-yl)pyrimidine was used instead of the tert-butyl 4-((2-fluoro-4-(4,4,5,5-tetramethyl-1,3,2-dioxaborolan-2-yl)phenoxy)methyl)piperidine-1-carboxylate (Amount obtained: 380 mg/Yield: 65%).

$^1$H NMR (400, CDCl$_3$): 8.17 (2H, s), 7.11 (1H, t), 6.64 (1H, dd), 6.56 (1H, dd), 5.87 (1H, d), 4.75 (2H, d), 4.02 (4H, m), 3.80 (2H, d), 2.93 (2H, m), 2.50 (6H, m), 2.29 (1H, m), 2.08 (1H, m), 1.86 (4H, m), 1.31 (2H, m), 1.16 (3H, t)

Example 464: Preparation of (+)-(4-(4-((1-(5-ethyl-pyrimidin-2-yl)piperidin-4-yl)methoxy)-2-fluorophenyl)cyclohex-3-enyl)(3,3,4,4-tetrafluoropyrrolidin-1-yl)methanone

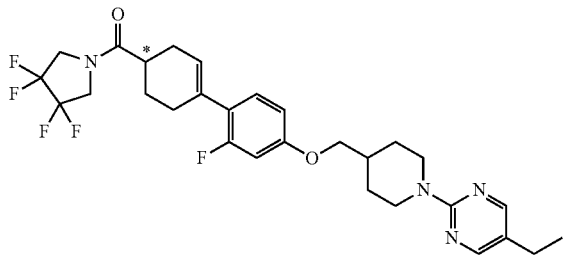

The title compound was prepared in the same manner as in <Example 443>, except that (+)-(4-bromocyclohex-3-enyl)(3,3,4,4-tetrafluoropyrrolidin-1-yl)methanone was used instead of the (+)-(4-bromocyclohex-3-enyl)(morpholino)methanone, and 5-ethyl-2-(4-(((3-fluoro-4-(4,4,5,5-tetramethyl-1,3,2-dioxaborolan-2-yl)phenoxy)methyl)piperidin-1-yl)pyrimidine was used instead of the tert-butyl 4-((2-fluoro-4-(4,4,5,5-tetramethyl-1,3,2-dioxaborolan-2-yl)phenoxy)methyl)piperidine-1-carboxylate (Amount obtained: 410 mg/Yield: 70%).

$^1$H NMR (400, CDCl$_3$): 8.17 (2H, s), 7.11 (1H, t), 6.64 (1H, dd), 6.56 (1H, dd), 5.87 (1H, d), 4.75 (2H, d), 4.02 (4H, m), 3.80 (2H, d), 2.93 (2H, m), 2.50 (6H, m), 2.29 (1H, m), 2.08 (1H, m), 1.86 (4H, m), 1.31 (2H, m), 1.16 (3H, t)

Example 465: Preparation of ((−)-4-(4-((1-(5-ethyl-pyrimidin-2-yl)piperidin-4-yl)methoxy)phenyl)cyclohex-3-enyl)((S)-2-(hydroxymethyl)pyrrolidin-1-yl)methanone (HD-3640)

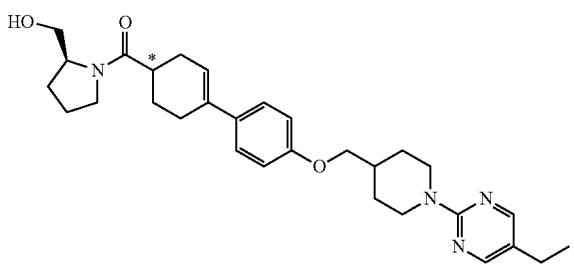 [SMILES: CCc1cnc(N2CCC(COc3ccc(C4=CCC(C(=O)N5CCC[C@H]5CO)CC4)cc3)CC2)nc1]

The title compound was prepared in the same manner as in <Example 443>, except that ((−)-4-bromocyclohex-3-enyl)((S)-2-(hydroxymethyl)pyrrolidin-1-yl)methanone was used instead of the ((−)-4-bromocyclohex-3-enyl)((R)-2-(hydroxymethyl)pyrrolidin-1-yl)methanone (Amount obtained: 400 mg/Yield: 67%).

$^1$H NMR (400, CDCl$_3$): 8.18 (2H, s), 7.31 (1H, d), 6.83 (2H, d), 6.04 (1H, m), 5.11 (1H, d), 4.74 (2H, d), 4.26 (1H, m), 3.83 (2H, d), 3.60 (4H, m), 2.93 (2H, m), 2.67 (1H, m), 2.48 (5H, m), 2.30 (1H, m), 2.00 (8H, m), 1.57 (4H, m), 1.35 (2H, m), 1.20 (3H, t)

Example 466: Preparation of ((+)-4-(4-((1-(5-ethyl-pyrimidin-2-yl)piperidin-4-yl)methoxy)phenyl)cyclohex-3-enyl)((S)-2-(hydroxymethyl)pyrrolidin-1-yl)methanone (HD-3641)

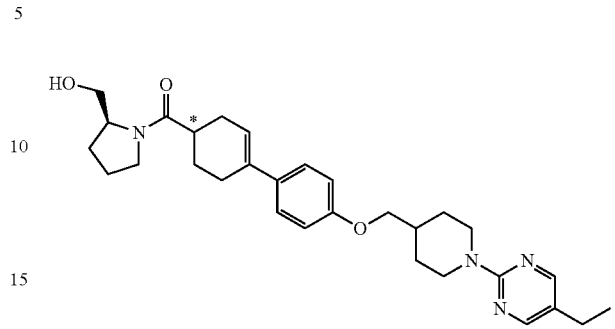

The title compound was prepared in the same manner as in <Example 443>, except that ((+)-4-bromocyclohex-3-enyl)((S)-2-(hydroxymethyl)pyrrolidin-1-yl)methanone was used instead of the ((+)-4-bromocyclohex-3-enyl)((R)-2-(hydroxymethyl)pyrrolidin-1-yl)methanone (Amount obtained: 430 mg/Yield: 71%).

$^1$H NMR (400, CDCl$_3$): 8.18 (2H, s), 7.31 (1H, d), 6.83 (2H, d), 6.04 (1H, m), 5.11 (1H, d), 4.74 (2H, d), 4.26 (1H, m), 3.83 (2H, d), 3.60 (4H, m), 2.93 (2H, m), 2.67 (1H, m), 2.48 (5H, m), 2.30 (1H, m), 2.00 (8H, m), 1.57 (4H, m), 1.35 (2H, m), 1.20 (3H, t)

Comparative Example 1: Preparation of N-(2-fluoro-4-methylsulfonylphenyl)-5-nitro-6-[4-(3-propan-2-yl-1,2,4-oxadiazol-5-yl)piperidin-1-yl]pyrimidine-4-amine

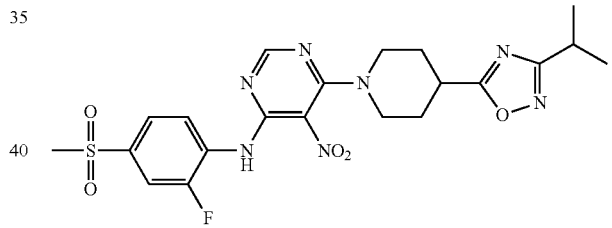

N-(2-fluoro-4-methylsulfonyl)-5-nitro-6-[4-(3-propan-2-yl-1,2,4-oxadiazol-5-yl)piperidin-1-yl]pyrimidine-4-amine was prepared using a method known in International Publication No. WO 2004/065380.

Comparative Example 2: Preparation of 2-(4-methanesulfonylphenyl)-5-({1-[3-(propan-2-yl)-1,2,4-oxadiazol-5-yl]piperidin-4-yl}methoxy)pyridine

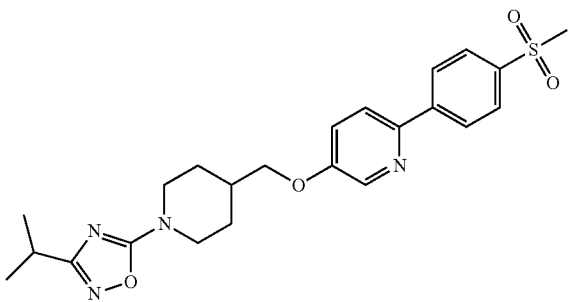 [SMILES: CC(C)c1noc(N2CCC(COc3ccc(-c4ccc(S(C)(=O)=O)cc4)nc3)CC2)n1]

2-(4-Methanesulfonylphenyl)-5-({1-[3-(propan-2-yl)-1,2,4-oxadiazol-5-yl]piperidin-4-yl}methoxy)pyridine was prepared using a method known in International Publication No. WO 2008/070692.

Comparative Example 3: Preparation of Metformin

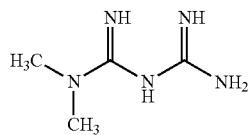

Metformin was prepared using a method known in International Publication No. WO 2010/146604 A2.

Comparative Example 4: Preparation of Sibutramine

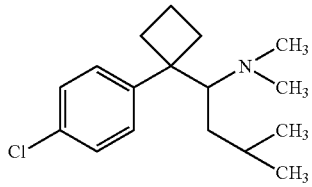 [SMILES: CC(C)CC(N(C)C)C1(c2ccc(Cl)cc2)CCC1]

Sibutramine was prepared using a method known in International Publication No. WO 2002/083631 A1.

Comparative Example 5: Preparation of Forskolin

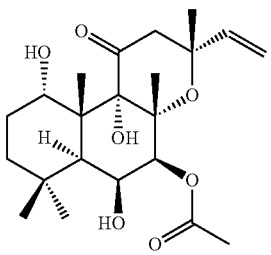

Forskolin was prepared using a method known in International Publication No. WO 1991/017154 A1.

The chemical structures of the compounds prepared in Examples 1 to 466 are summarized and listed in the following Table 1. In Table 1, the group '-Boc' is

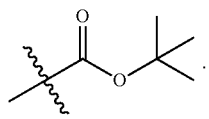 [SMILES: *C(=O)OC(C)(C)C]

TABLE 1

| Examples | Chemical structures |
|---|---|
| 1 | 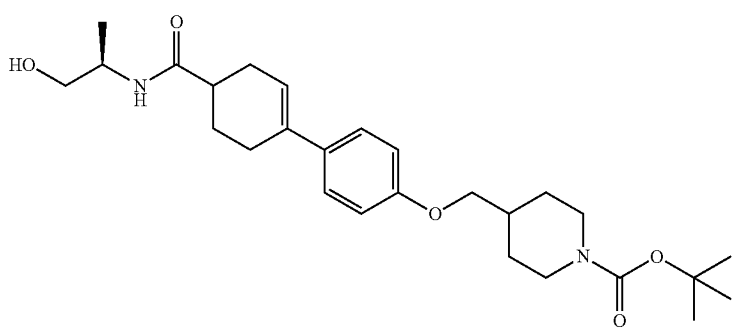 [SMILES: C[C@H](CO)NC(=O)C1CC=C(c2ccc(OCC3CCN(C(=O)OC(C)(C)C)CC3)cc2)CC1] |
| 2 | 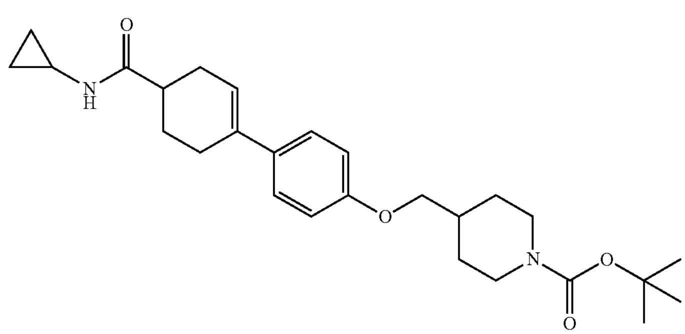 [SMILES: CC(C)(C)OC(=O)N1CCC(COc2ccc(C3=CCC(C(=O)NC4CC4)CC3)cc2)CC1] |

TABLE 1-continued
| Examples | Chemical structures |
|---|---|
| 3 | 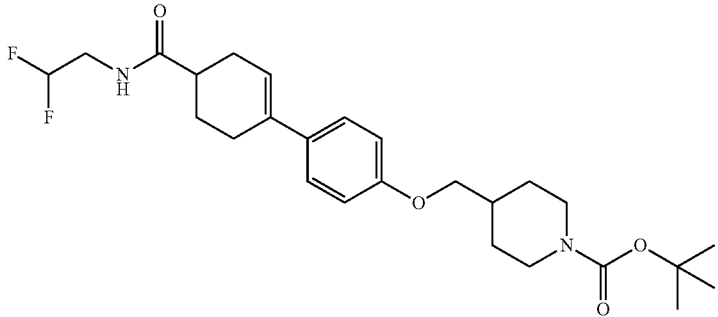 [SMILES: CC(C)(C)OC(=O)N1CCC(COc2ccc(C3=CCC(C(=O)NCC(F)F)CC3)cc2)CC1] |
| 4 | 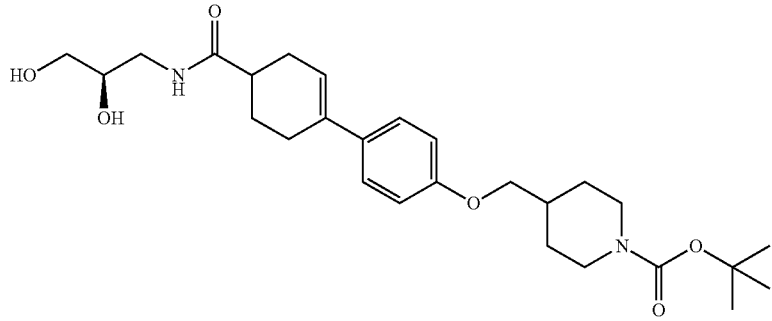 [SMILES: CC(C)(C)OC(=O)N1CCC(COc2ccc(C3=CCC(C(=O)NC[C@@H](O)CO)CC3)cc2)CC1] |
| 5 | 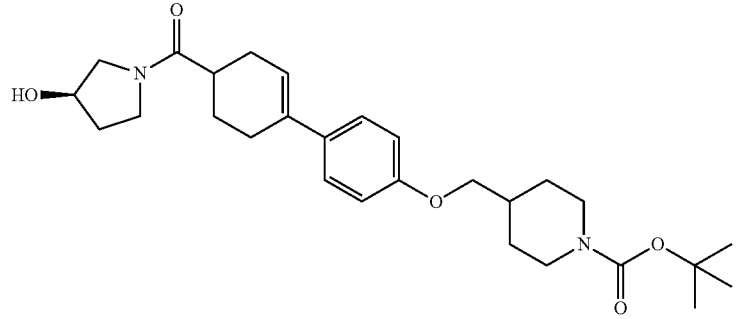 [SMILES: CC(C)(C)OC(=O)N1CCC(COc2ccc(C3=CCC(C(=O)N4CC[C@@H](O)C4)CC3)cc2)CC1] |
| 6 | 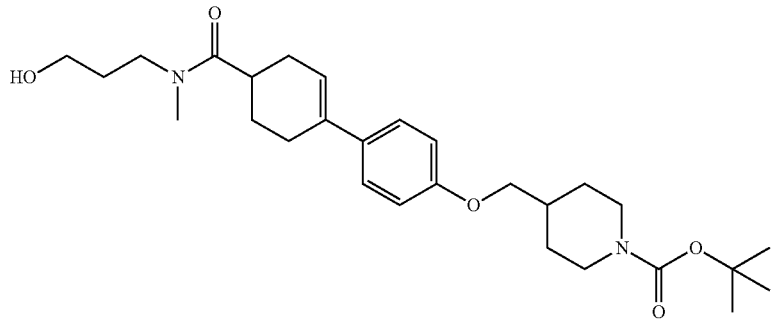 [SMILES: CN(CCCO)C(=O)C1CC=C(c2ccc(OCC3CCN(C(=O)OC(C)(C)C)CC3)cc2)CC1] |

TABLE 1-continued
| Examples | Chemical structures |
|---|---|
| 7 | 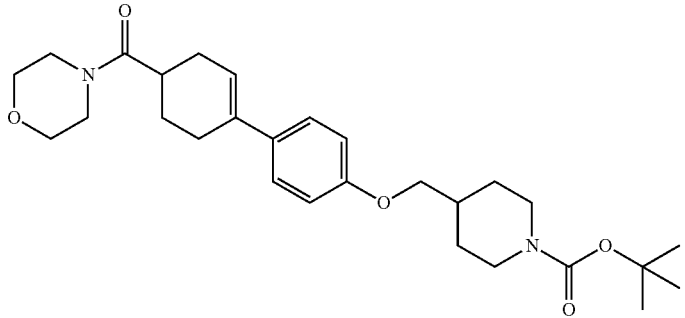 [SMILES: CC(C)(C)OC(=O)N1CCC(COc2ccc(C3=CCC(C(=O)N4CCOCC4)CC3)cc2)CC1] |
| 8 | 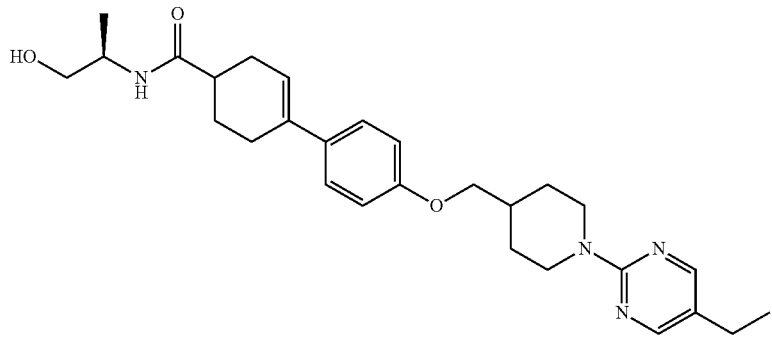 [SMILES: CCc1cnc(N2CCC(COc3ccc(C4=CCC(C(=O)N[C@H](C)CO)CC4)cc3)CC2)nc1] |
| 9 | 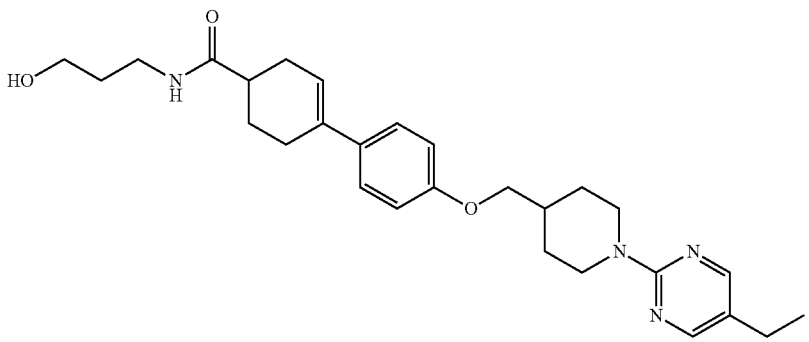 [SMILES: CCc1cnc(N2CCC(COc3ccc(C4=CCC(C(=O)NCCCO)CC4)cc3)CC2)nc1] |
| 10 | 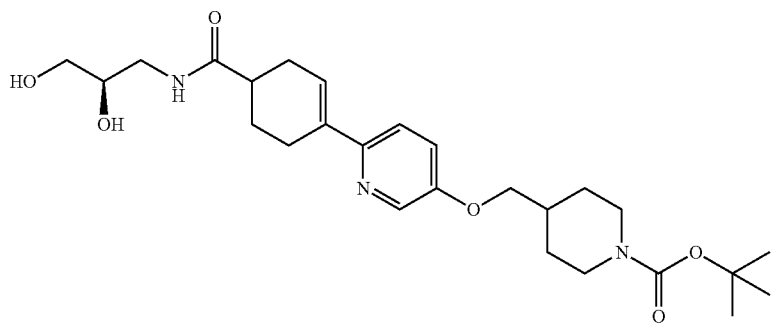 [SMILES: CC(C)(C)OC(=O)N1CCC(COc2ccc(C3=CCC(C(=O)NC[C@@H](O)CO)CC3)nc2)CC1] |

TABLE 1-continued
| Examples | Chemical structures |
|---|---|
| 11 | 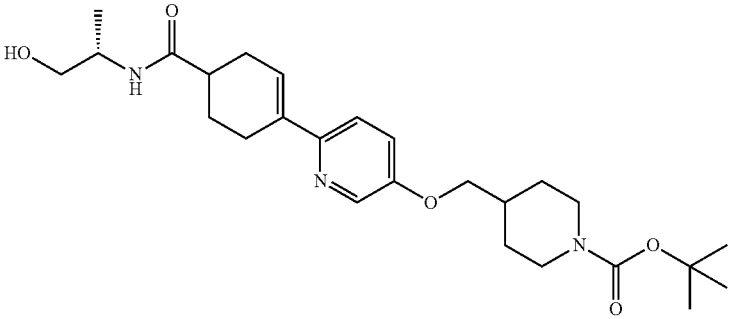 [SMILES: C[C@@H](CO)NC(=O)C1CC=C(c2ccc(OCC3CCN(C(=O)OC(C)(C)C)CC3)cn2)CC1] |
| 12 | 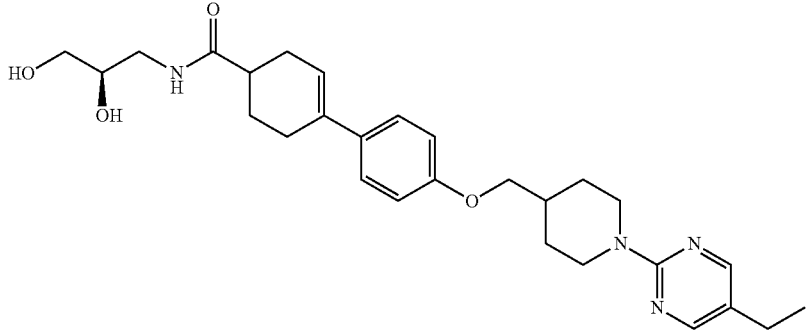 [SMILES: CCc1cnc(N2CCC(COc3ccc(C4=CCC(C(=O)NC[C@@H](O)CO)CC4)cc3)CC2)nc1] |
| 13 | 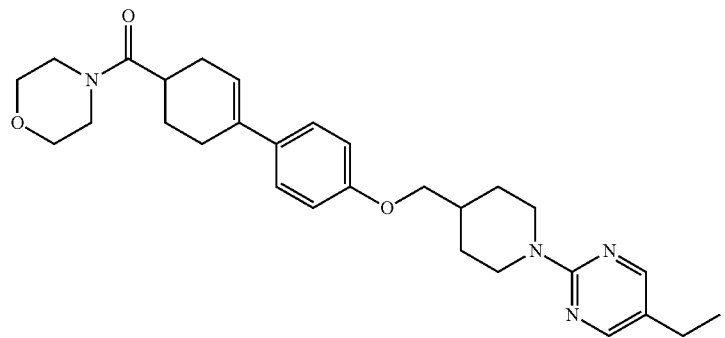 [SMILES: CCc1cnc(N2CCC(COc3ccc(C4=CCC(C(=O)N5CCOCC5)CC4)cc3)CC2)nc1] |
| 14 | 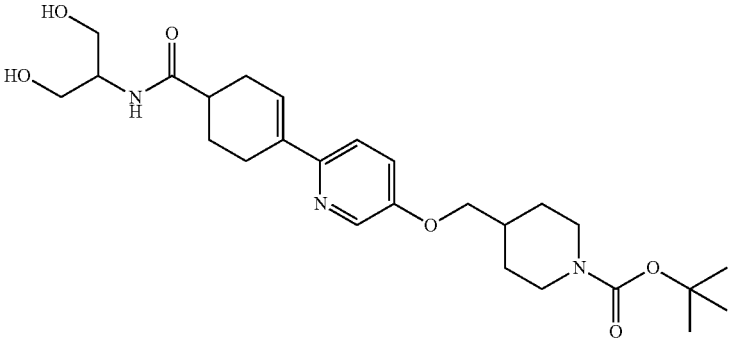 [SMILES: CC(C)(C)OC(=O)N1CCC(COc2ccc(C3=CCC(C(=O)NC(CO)CO)CC3)nc2)CC1] |

TABLE 1-continued
| Examples | Chemical structures |
|---|---|
| 15 | 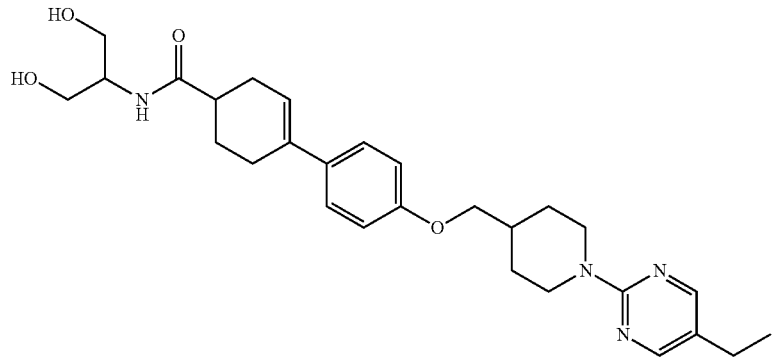 [SMILES: CCc1cnc(N2CCC(COc3ccc(C4=CCC(C(=O)NC(CO)CO)CC4)cc3)CC2)nc1] |
| 16 | 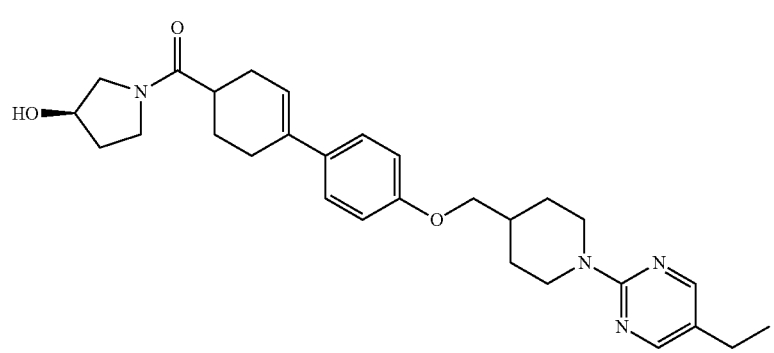 [SMILES: CCc1cnc(N2CCC(COc3ccc(C4=CCC(C(=O)N5CC[C@@H](O)C5)CC4)cc3)CC2)nc1] |
| 17 | 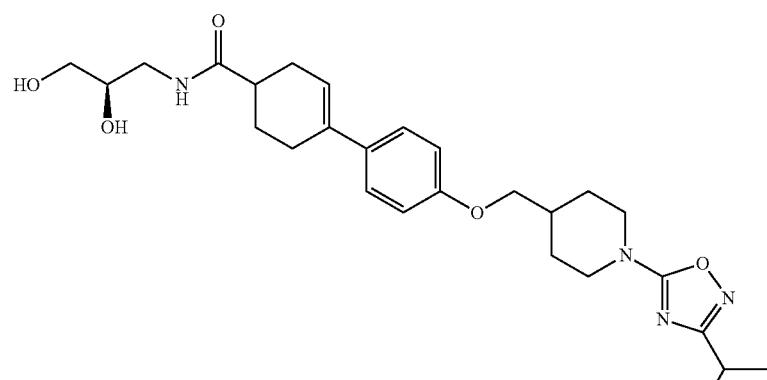 |
| 18 | 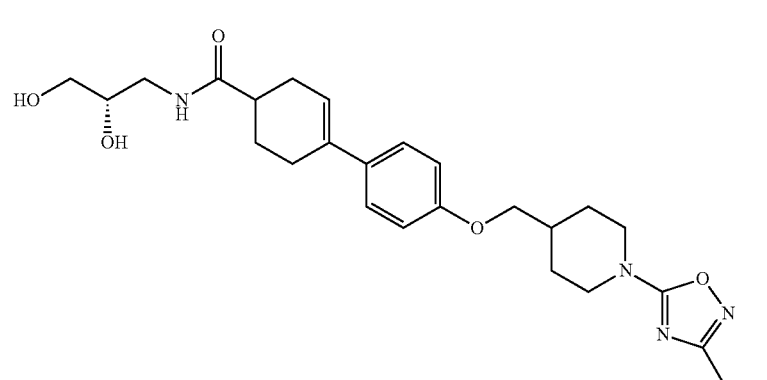 |

TABLE 1-continued
| Examples | Chemical structures |
|---|---|
| 19 | 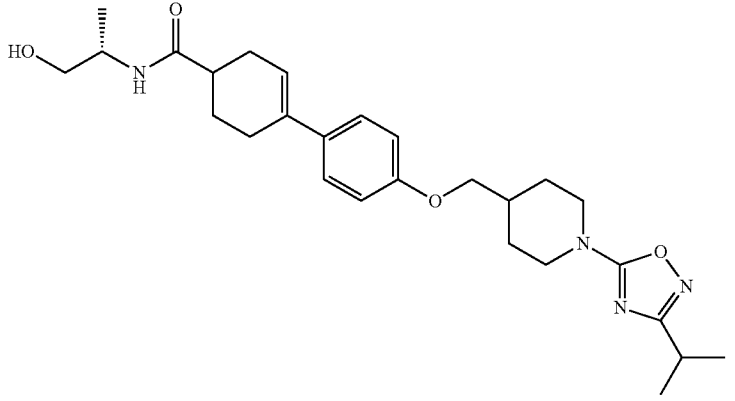 [SMILES: CC(C)c1noc(N2CCC(COc3ccc(C4=CCC(C(=O)N[C@@H](C)CO)CC4)cc3)CC2)n1] |
| 20 | 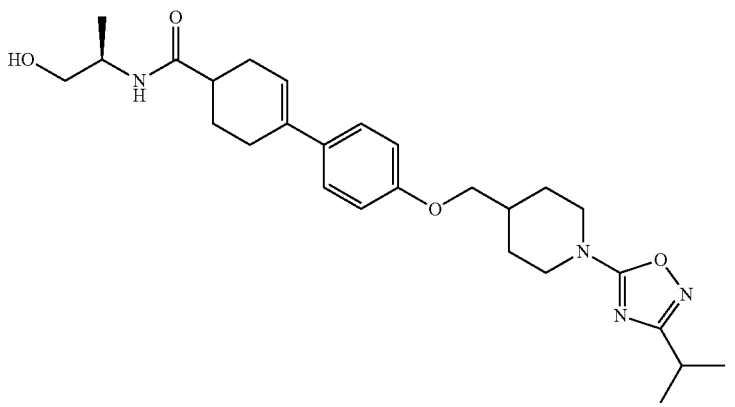 [SMILES: CC(C)c1noc(N2CCC(COc3ccc(C4=CCC(C(=O)N[C@H](C)CO)CC4)cc3)CC2)n1] |
| 21 | 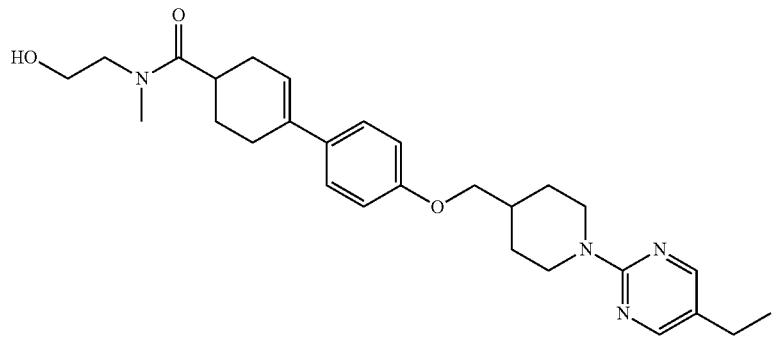 [SMILES: CCc1cnc(N2CCC(COc3ccc(C4=CCC(C(=O)N(C)CCO)CC4)cc3)CC2)nc1] |
| 22 | 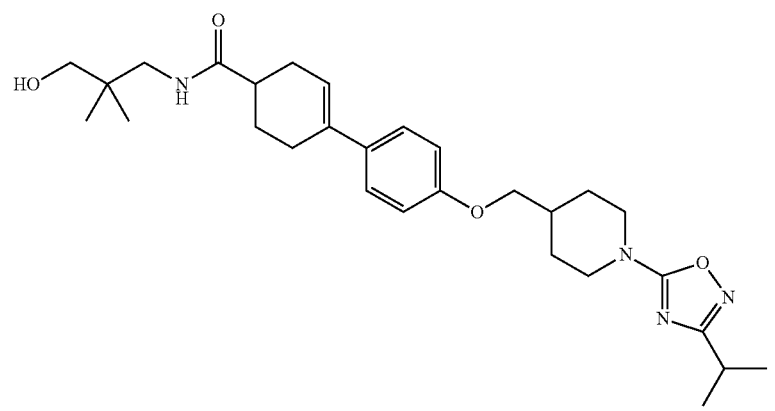 [SMILES: CC(C)c1noc(N2CCC(COc3ccc(C4=CCC(C(=O)NCC(C)(C)CO)CC4)cc3)CC2)n1] |

TABLE 1-continued
| Examples | Chemical structures |
|---|---|
| 23 | 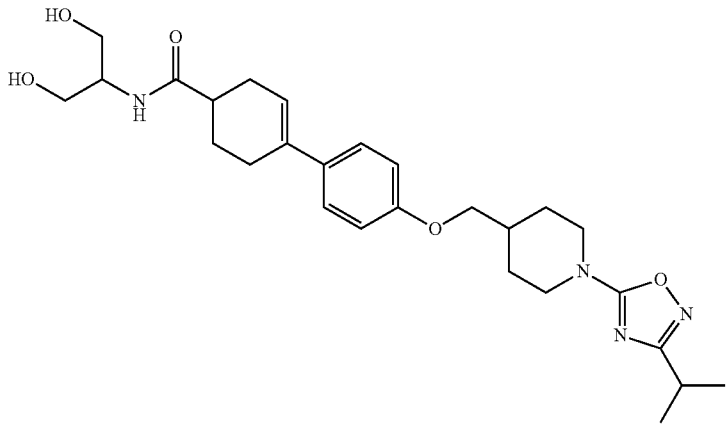 [SMILES: CC(C)c1noc(N2CCC(COc3ccc(C4=CCC(C(=O)NC(CO)CO)CC4)cc3)CC2)n1] |
| 24 | 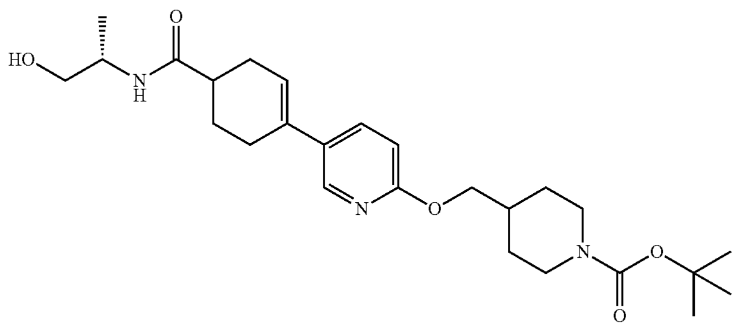 [SMILES: C[C@@H](CO)NC(=O)C1CC=C(c2ccc(OCC3CCN(C(=O)OC(C)(C)C)CC3)nc2)CC1] |
| 25 | 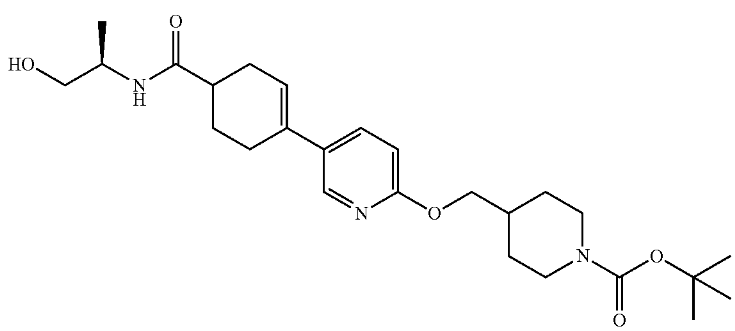 [SMILES: C[C@H](CO)NC(=O)C1CC=C(c2ccc(OCC3CCN(C(=O)OC(C)(C)C)CC3)nc2)CC1] |
| 26 | 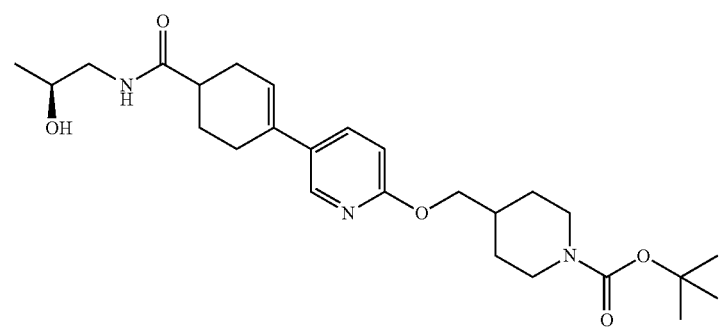 [SMILES: C[C@H](O)CNC(=O)C1CC=C(c2ccc(OCC3CCN(C(=O)OC(C)(C)C)CC3)nc2)CC1] |

TABLE 1-continued

| Examples | Chemical structures |
|---|---|
| 27 | 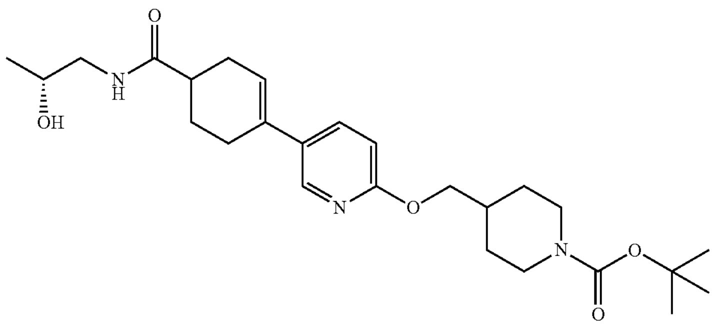 [SMILES: C[C@@H](O)CNC(=O)C1CC=C(c2ccc(OCC3CCN(C(=O)OC(C)(C)C)CC3)nc2)CC1] |
| 28 | 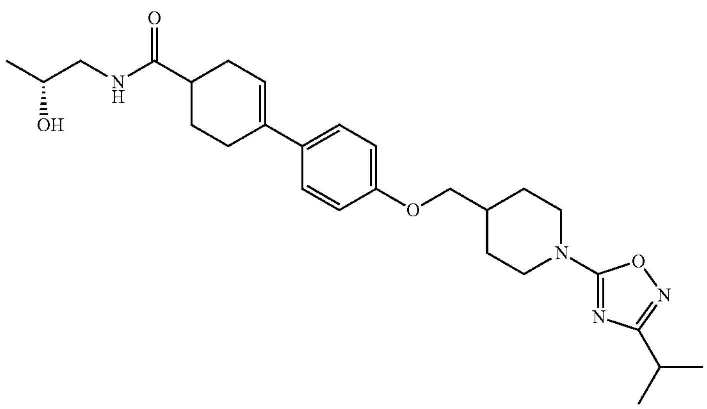 [SMILES: CC(C)c1noc(N2CCC(COc3ccc(C4=CCC(C(=O)NC[C@@H](C)O)CC4)cc3)CC2)n1] |
| 29 | 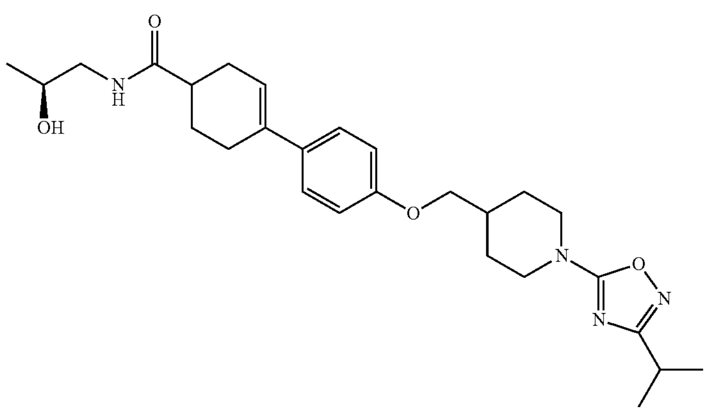 |
| 30 | 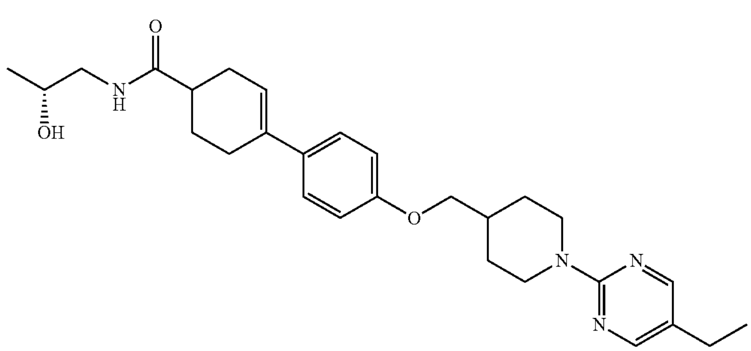 [SMILES: CCc1cnc(N2CCC(COc3ccc(C4=CCC(C(=O)NC[C@@H](C)O)CC4)cc3)CC2)nc1] |

TABLE 1-continued

| Examples | Chemical structures |
|---|---|
| 31 | 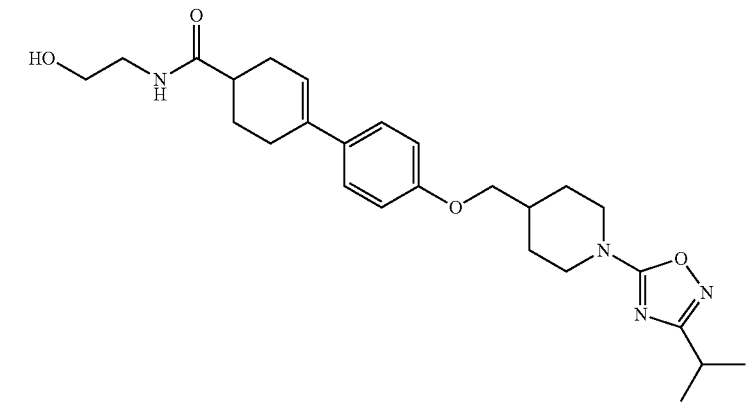 [SMILES: CC(C)c1noc(N2CCC(COc3ccc(C4=CCC(C(=O)NCCO)CC4)cc3)CC2)n1] |
| 32 | 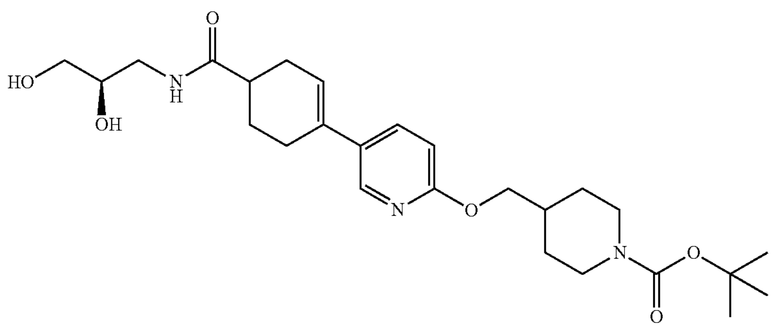 [SMILES: CC(C)(C)OC(=O)N1CCC(COc2ccc(C3=CCC(C(=O)NC[C@@H](O)CO)CC3)cn2)CC1] |
| 33 | 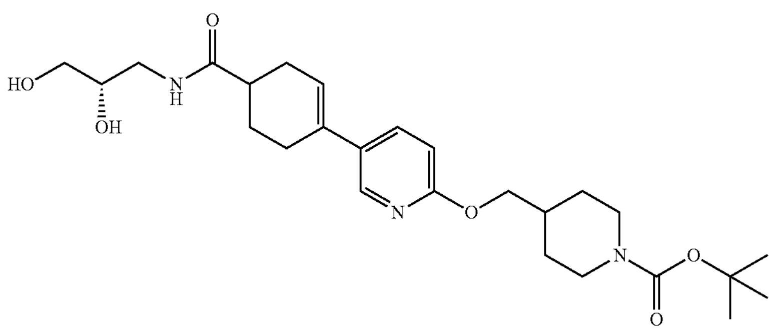 [SMILES: CC(C)(C)OC(=O)N1CCC(COc2ccc(C3=CCC(C(=O)NC[C@H](O)CO)CC3)cn2)CC1] |
| 34 | 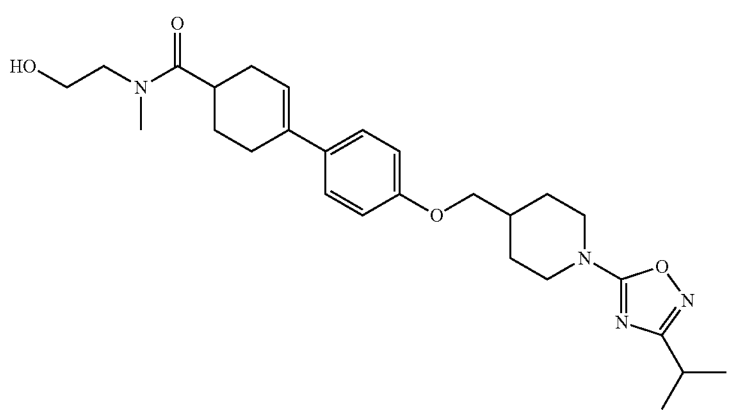 [SMILES: CC(C)c1noc(N2CCC(COc3ccc(C4=CCC(C(=O)N(C)CCO)CC4)cc3)CC2)n1] |

TABLE 1-continued

| Examples | Chemical structures |
|---|---|
| 35 | 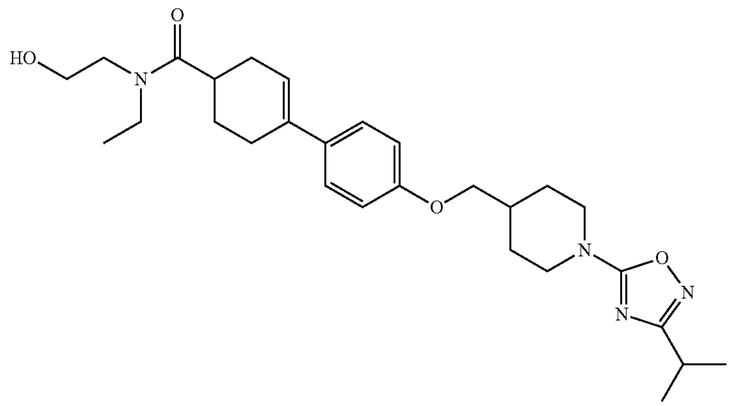 [SMILES: CCN(CCO)C(=O)C1CC=C(c2ccc(OCC3CCN(c4nc(C(C)C)no4)CC3)cc2)CC1] |
| 36 | 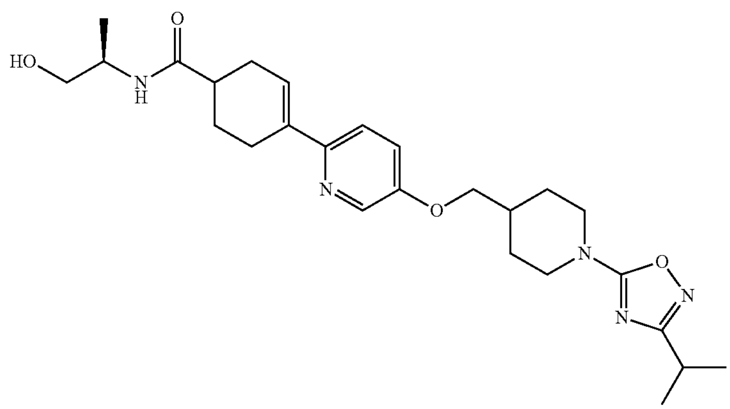 [SMILES: CC(C)c1noc(N2CCC(COc3ccc(C4=CCC(C(=O)N[C@H](C)CO)CC4)nc3)CC2)n1] |
| 37 | 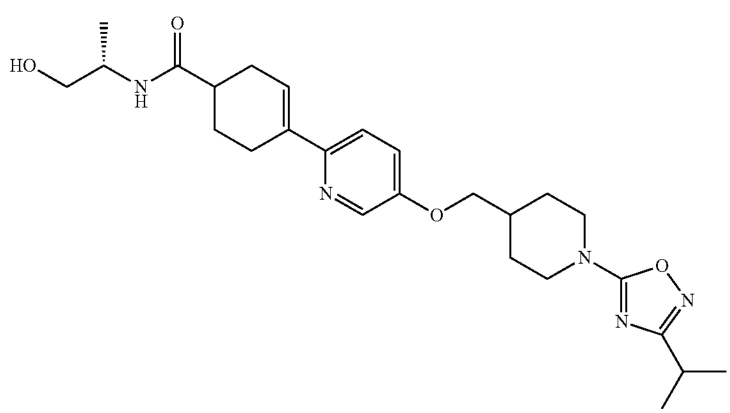 [SMILES: CC(C)c1noc(N2CCC(COc3ccc(C4=CCC(C(=O)N[C@@H](C)CO)CC4)nc3)CC2)n1] |
| 38 | 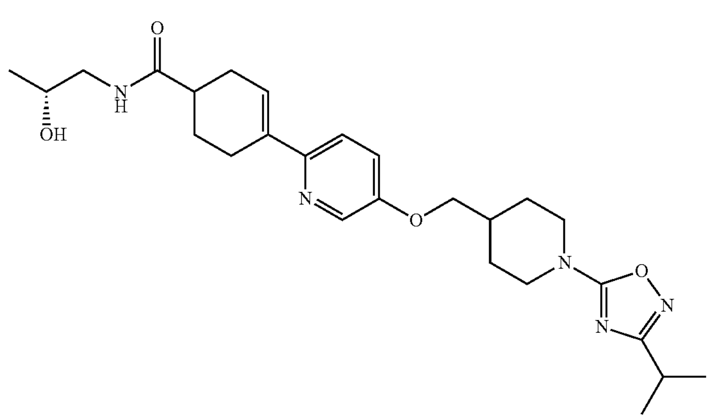 |

TABLE 1-continued
| Examples | Chemical structures |
| --- | --- |
| 39 | 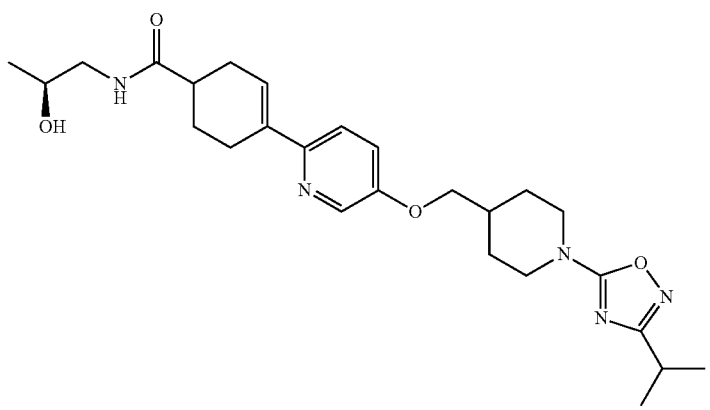 [SMILES: CC(C)c1noc(N2CCC(COc3ccc(C4=CCC(C(=O)NC[C@H](C)O)CC4)nc3)CC2)n1] |
| 40 | 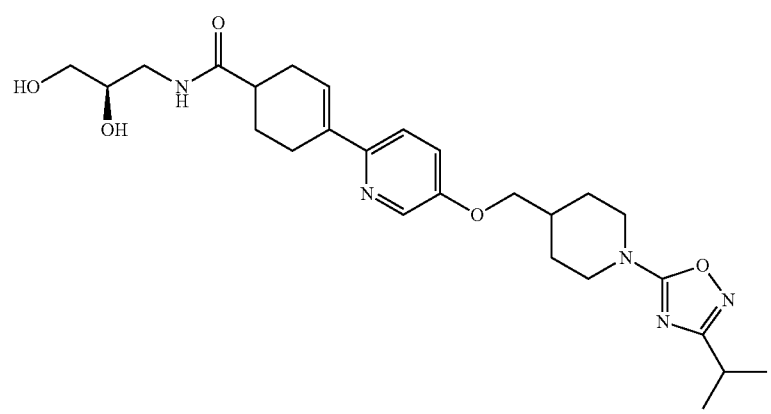 [SMILES: CC(C)c1noc(N2CCC(COc3ccc(C4=CCC(C(=O)NC[C@@H](O)CO)CC4)nc3)CC2)n1] |
| 41 | 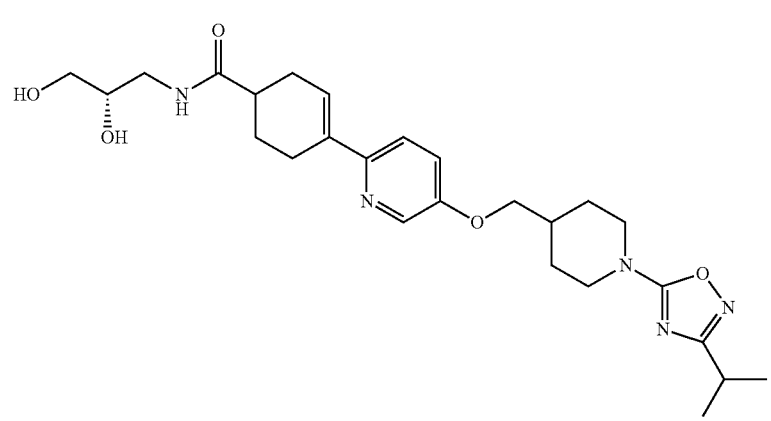 |
| 42 | 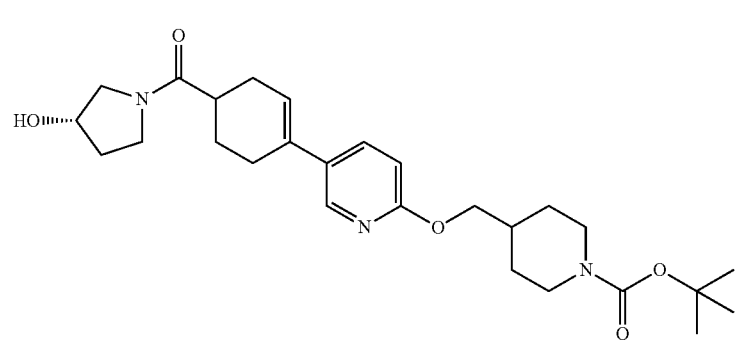 [SMILES: CC(C)(C)OC(=O)N1CCC(COc2ccc(C3=CCC(C(=O)N4CC[C@H](O)C4)CC3)cn2)CC1] |

TABLE 1-continued

| Examples | Chemical structures |
|---|---|
| 43 | 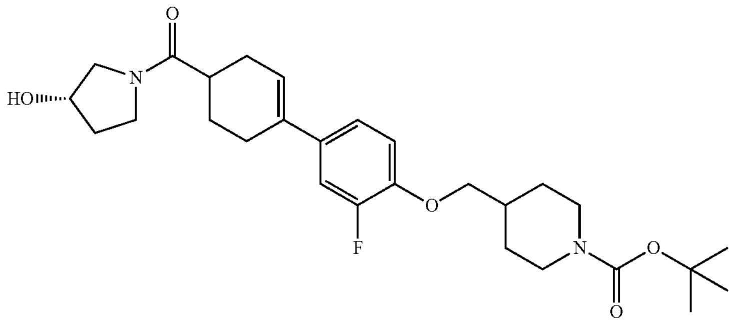 [SMILES: CC(C)(C)OC(=O)N1CCC(COc2ccc(C3=CCC(C(=O)N4CC[C@H](O)C4)CC3)cc2F)CC1] |
| 44 | 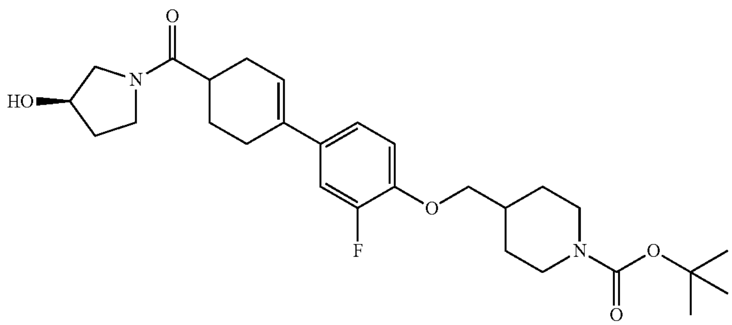 [SMILES: CC(C)(C)OC(=O)N1CCC(COc2ccc(C3=CCC(C(=O)N4CC[C@@H](O)C4)CC3)cc2F)CC1] |
| 45 | 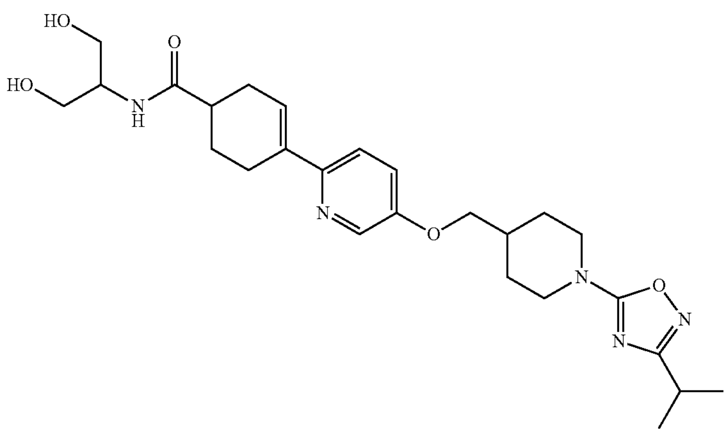 [SMILES: CC(C)c1noc(N2CCC(COc3ccc(C4=CCC(C(=O)NC(CO)CO)CC4)nc3)CC2)n1] |
| 46 | 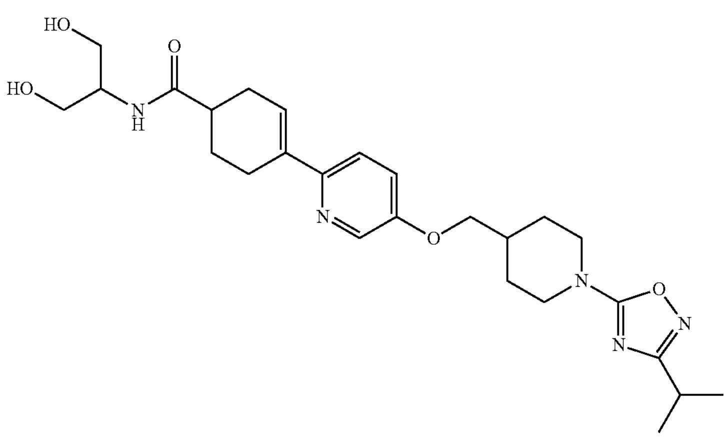 [SMILES: CC(C)c1noc(N2CCC(COc3ccc(C4=CCC(C(=O)NC(CO)CO)CC4)nc3)CC2)n1] |

TABLE 1-continued

| Examples | Chemical structures |
|---|---|
| 47 | 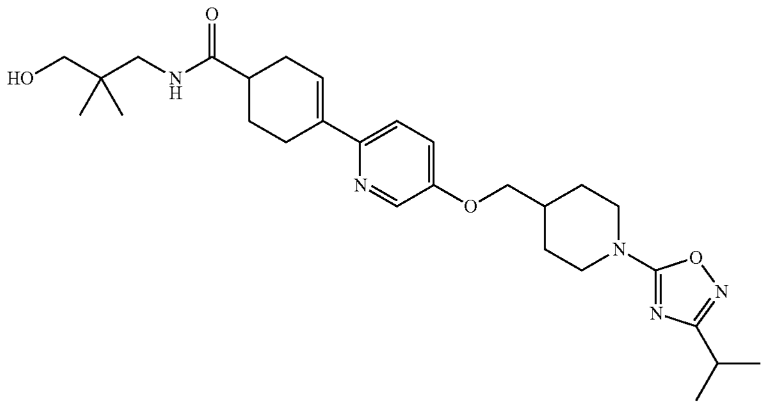 [SMILES: CC(C)c1noc(N2CCC(COc3ccc(C4=CCC(C(=O)NCC(C)(C)CO)CC4)nc3)CC2)n1] |
| 48 | 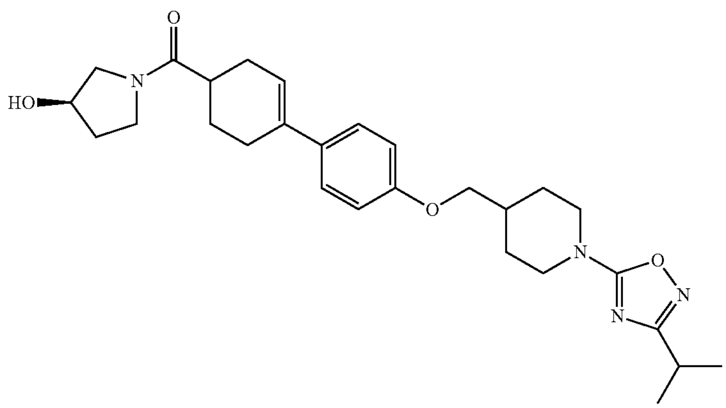 [SMILES: CC(C)c1noc(N2CCC(COc3ccc(C4=CCC(C(=O)N5CC[C@@H](O)C5)CC4)cc3)CC2)n1] |
| 49 | 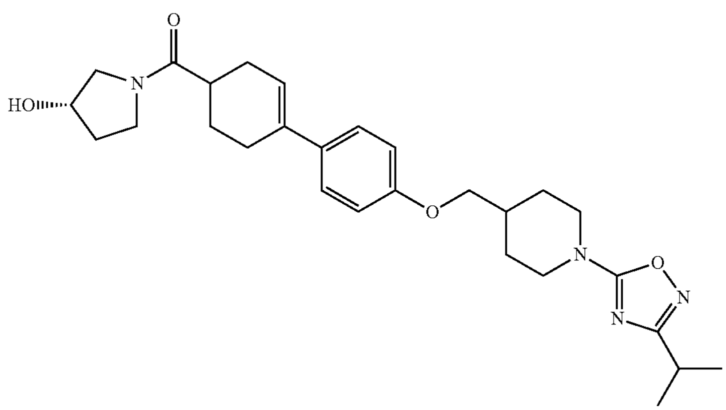 [SMILES: CC(C)c1noc(N2CCC(COc3ccc(C4=CCC(C(=O)N5CC[C@H](O)C5)CC4)cc3)CC2)n1] |
| 50 | 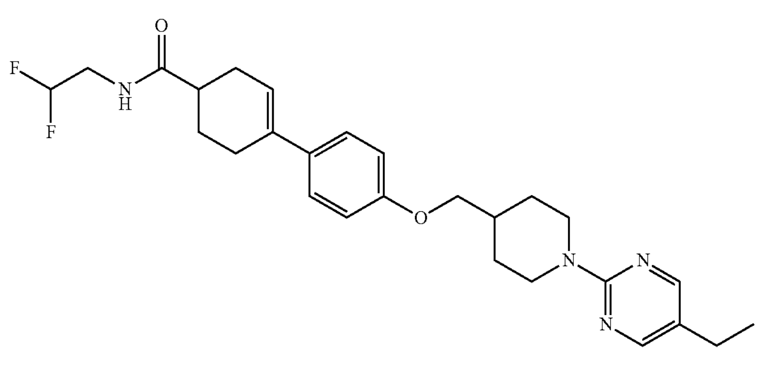 [SMILES: CCc1cnc(N2CCC(COc3ccc(C4=CCC(C(=O)NCC(F)F)CC4)cc3)CC2)nc1] |

TABLE 1-continued
| Examples | Chemical structures |
|---|---|
| 51 | 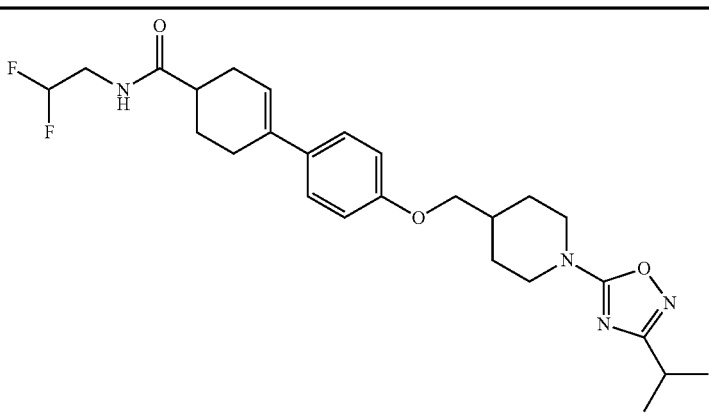 |
| 52 | 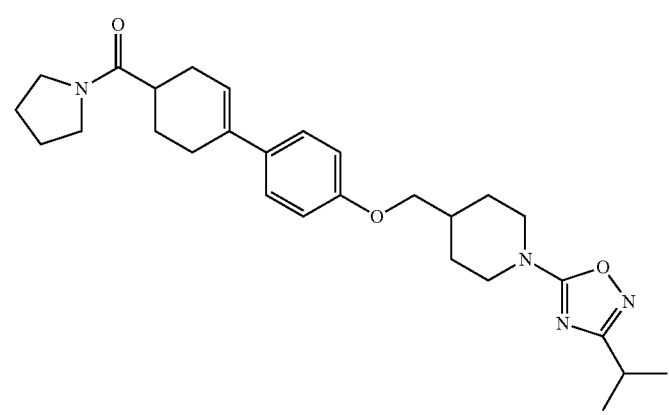 [SMILES: CC(C)c1noc(N2CCC(COc3ccc(C4=CCC(C(=O)N5CCCC5)CC4)cc3)CC2)n1] |
| 53 | 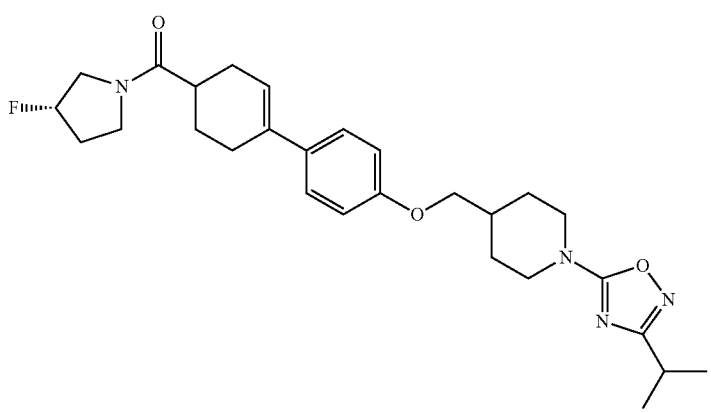 [SMILES: CC(C)c1noc(N2CCC(COc3ccc(C4=CCC(C(=O)N5CC[C@H](F)C5)CC4)cc3)CC2)n1] |
| 54 | 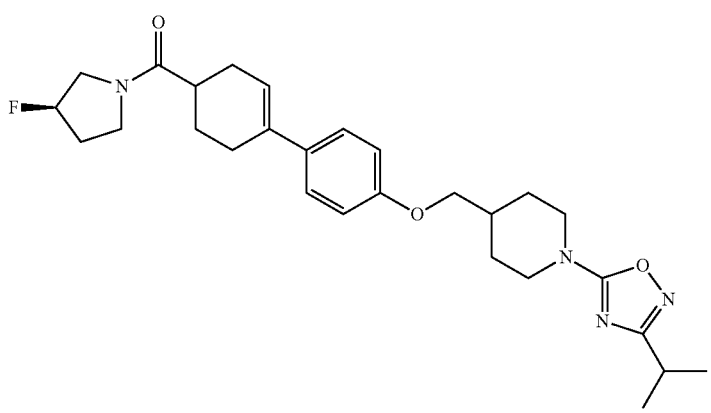 [SMILES: CC(C)c1noc(N2CCC(COc3ccc(C4=CCC(C(=O)N5CC[C@@H](F)C5)CC4)cc3)CC2)n1] |

TABLE 1-continued
| Examples | Chemical structures |
|---|---|
| 55 | 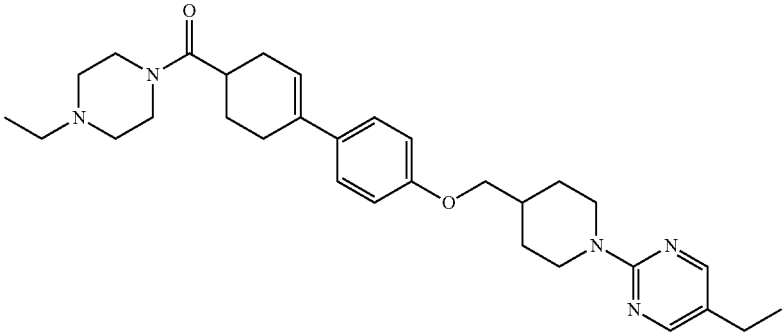 [SMILES: CCc1cnc(N2CCC(COc3ccc(C4=CCC(C(=O)N5CCN(CC)CC5)CC4)cc3)CC2)nc1] |
| 56 | 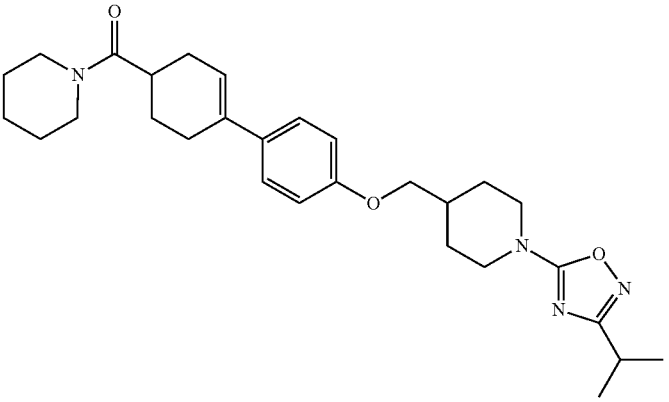 [SMILES: CC(C)c1noc(N2CCC(COc3ccc(C4=CCC(C(=O)N5CCCCC5)CC4)cc3)CC2)n1] |
| 57 | 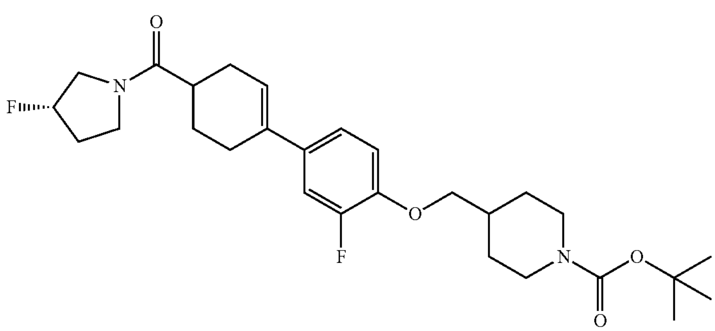 [SMILES: CC(C)(C)OC(=O)N1CCC(COc2ccc(C3=CCC(C(=O)N4CC[C@H](F)C4)CC3)cc2F)CC1] |
| 58 | 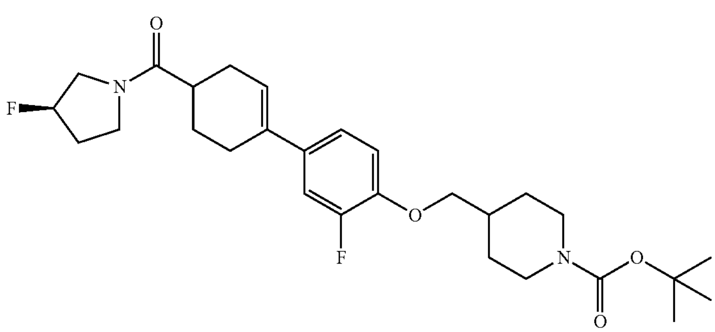 [SMILES: CC(C)(C)OC(=O)N1CCC(COc2ccc(C3=CCC(C(=O)N4CC[C@@H](F)C4)CC3)cc2F)CC1] |

TABLE 1-continued
| Examples | Chemical structures |
|---|---|
| 59 | 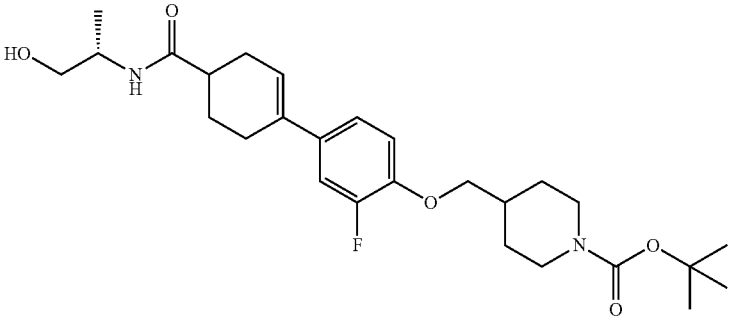 [SMILES: C[C@@H](CO)NC(=O)C1CC=C(c2ccc(OCC3CCN(C(=O)OC(C)(C)C)CC3)c(F)c2)CC1] |
| 60 | 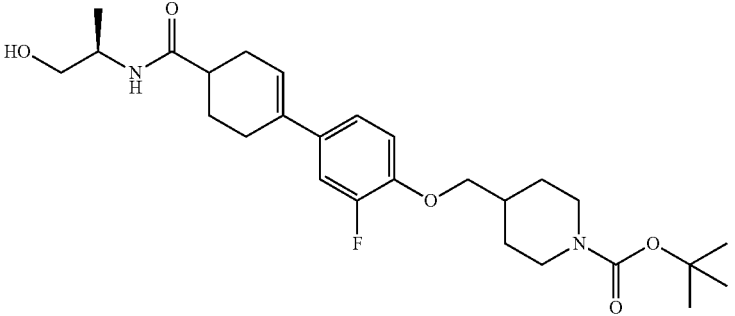 [SMILES: C[C@H](CO)NC(=O)C1CC=C(c2ccc(OCC3CCN(C(=O)OC(C)(C)C)CC3)c(F)c2)CC1] |
| 61 | 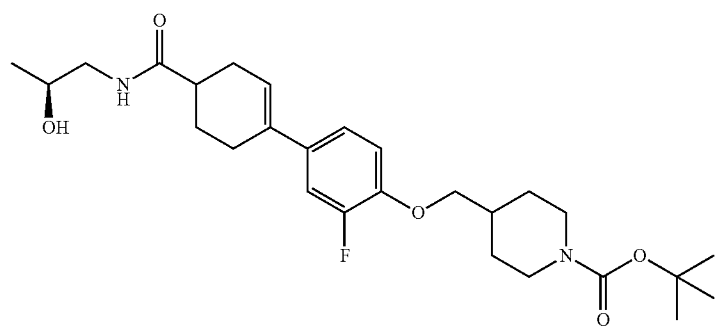 [SMILES: C[C@H](O)CNC(=O)C1CC=C(c2ccc(OCC3CCN(C(=O)OC(C)(C)C)CC3)c(F)c2)CC1] |
| 62 | 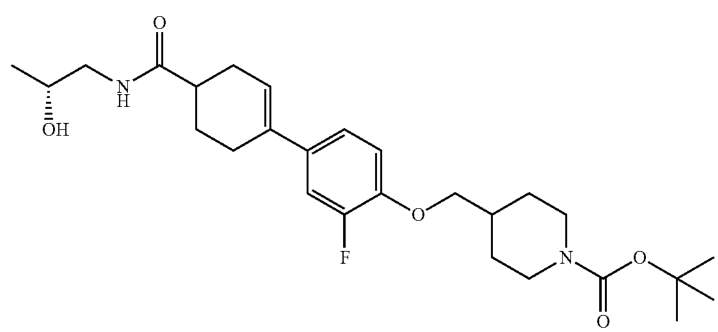 [SMILES: C[C@@H](O)CNC(=O)C1CC=C(c2ccc(OCC3CCN(C(=O)OC(C)(C)C)CC3)c(F)c2)CC1] |

TABLE 1-continued
| Examples | Chemical structures |
|---|---|
| 63 | 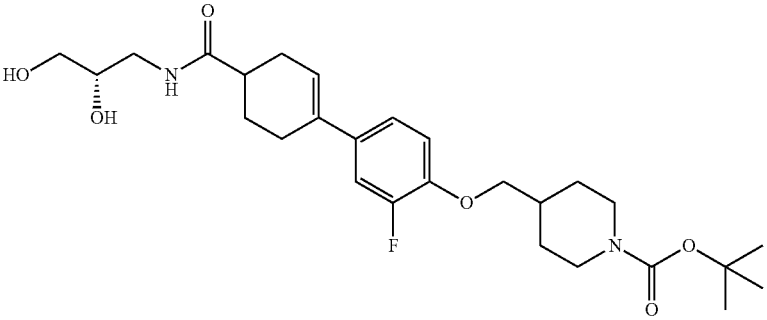 [SMILES: CC(C)(C)OC(=O)N1CCC(COc2ccc(C3=CCC(C(=O)NC[C@H](O)CO)CC3)cc2F)CC1] |
| 64 | 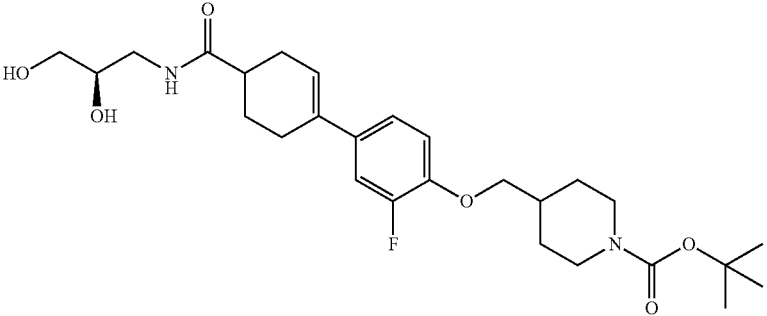 [SMILES: CC(C)(C)OC(=O)N1CCC(COc2ccc(C3=CCC(C(=O)NC[C@@H](O)CO)CC3)cc2F)CC1] |
| 65 | 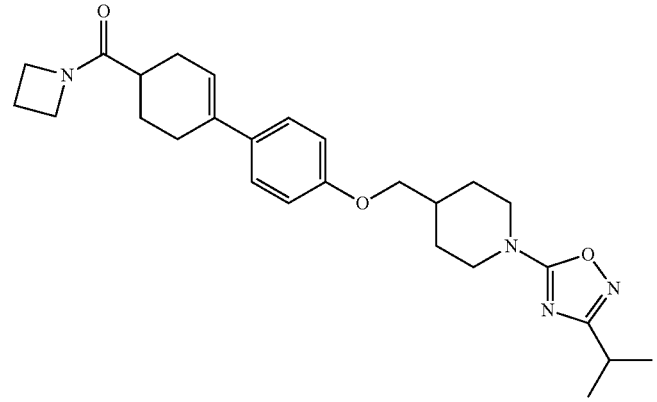 [SMILES: CC(C)c1noc(N2CCC(COc3ccc(C4=CCC(C(=O)N5CCC5)CC4)cc3)CC2)n1] |
| 66 | 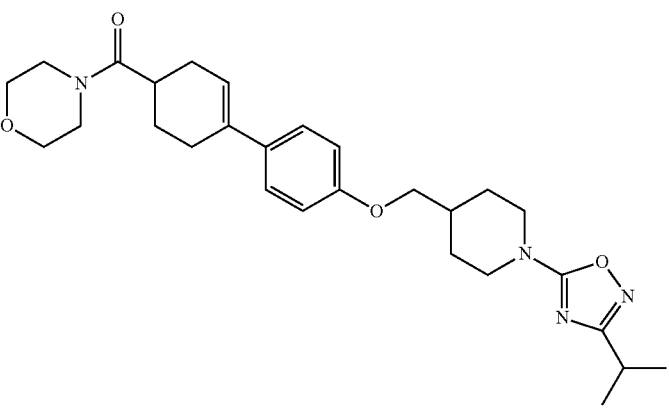 [SMILES: CC(C)c1noc(N2CCC(COc3ccc(C4=CCC(C(=O)N5CCOCC5)CC4)cc3)CC2)n1] |

TABLE 1-continued

| Examples | Chemical structures |
|---|---|
| 67 | 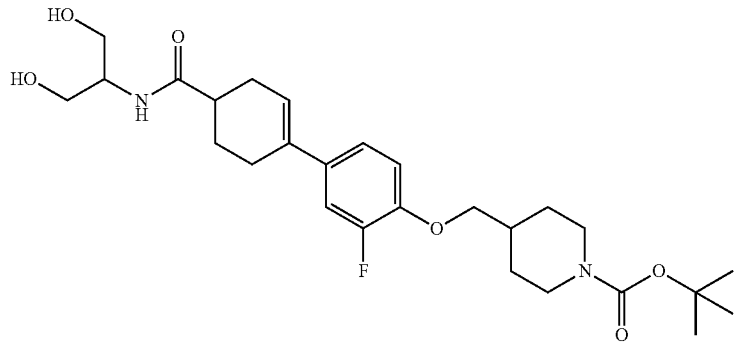 [SMILES: CC(C)(C)OC(=O)N1CCC(COc2ccc(C3=CCC(C(=O)NC(CO)CO)CC3)cc2F)CC1] |
| 68 | 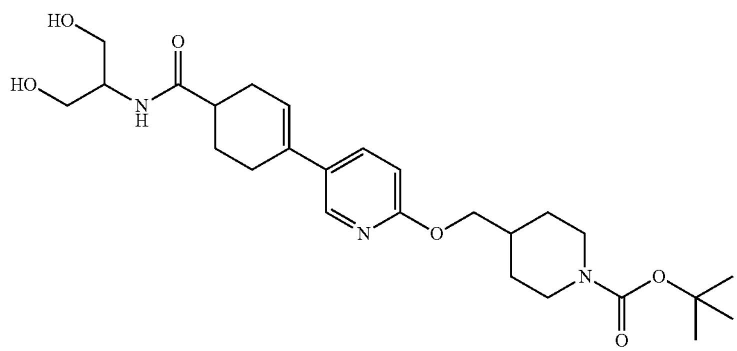 [SMILES: CC(C)(C)OC(=O)N1CCC(COc2ccc(C3=CCC(C(=O)NC(CO)CO)CC3)cn2)CC1] |
| 69 | 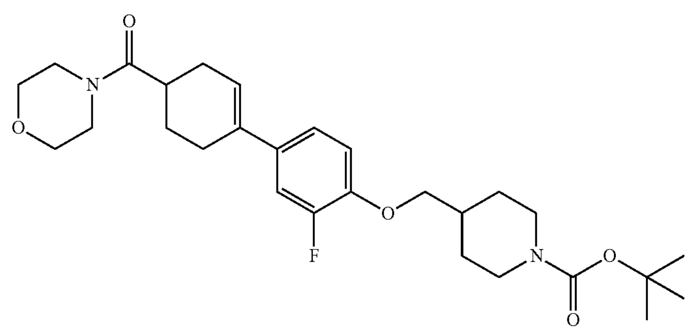 [SMILES: CC(C)(C)OC(=O)N1CCC(COc2ccc(C3=CCC(C(=O)N4CCOCC4)CC3)cc2F)CC1] |
| 70 | 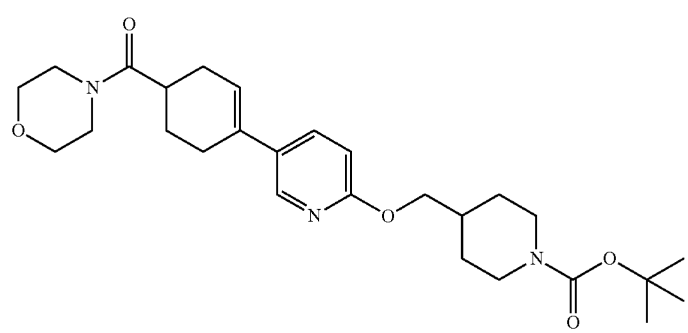 [SMILES: CC(C)(C)OC(=O)N1CCC(COc2ccc(C3=CCC(C(=O)N4CCOCC4)CC3)cn2)CC1] |

TABLE 1-continued

| Examples | Chemical structures |
|---|---|
| 71 | 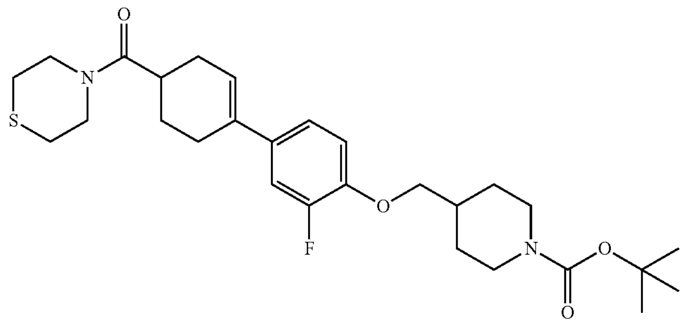 [SMILES: CC(C)(C)OC(=O)N1CCC(COc2ccc(C3=CCC(C(=O)N4CCSCC4)CC3)cc2F)CC1] |
| 72 | 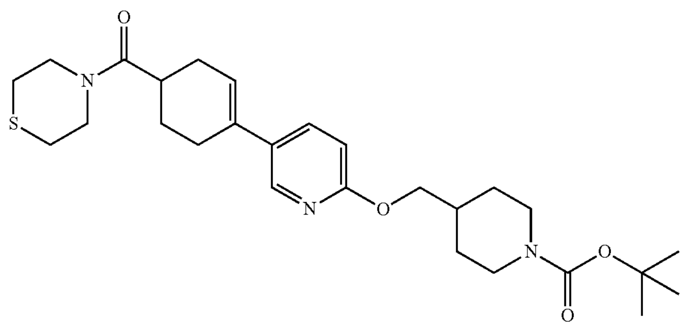 [SMILES: CC(C)(C)OC(=O)N1CCC(COc2ccc(C3=CCC(C(=O)N4CCSCC4)CC3)cn2)CC1] |
| 73 | 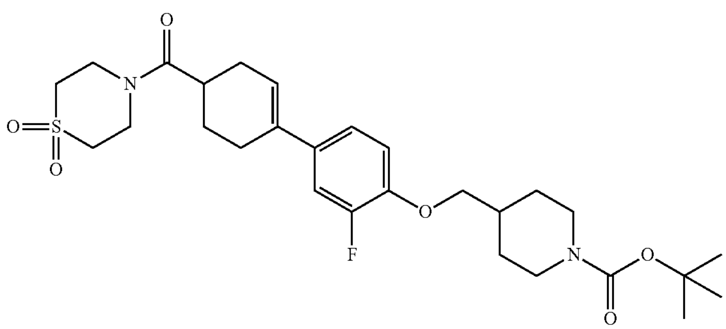 [SMILES: CC(C)(C)OC(=O)N1CCC(COc2ccc(C3=CCC(C(=O)N4CCS(=O)(=O)CC4)CC3)cc2F)CC1] |
| 74 | 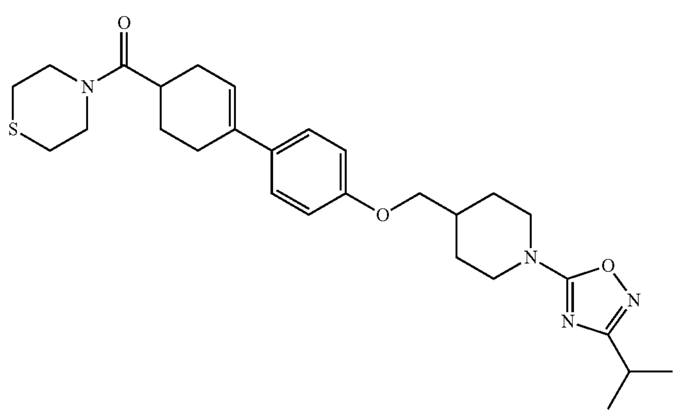 [SMILES: CC(C)c1noc(N2CCC(COc3ccc(C4=CCC(C(=O)N5CCSCC5)CC4)cc3)CC2)n1] |

TABLE 1-continued

| Examples | Chemical structures |
|---|---|
| 75 | 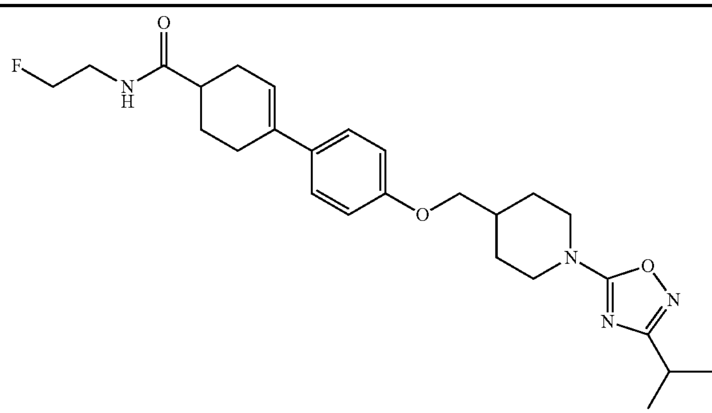 |
| 76 | 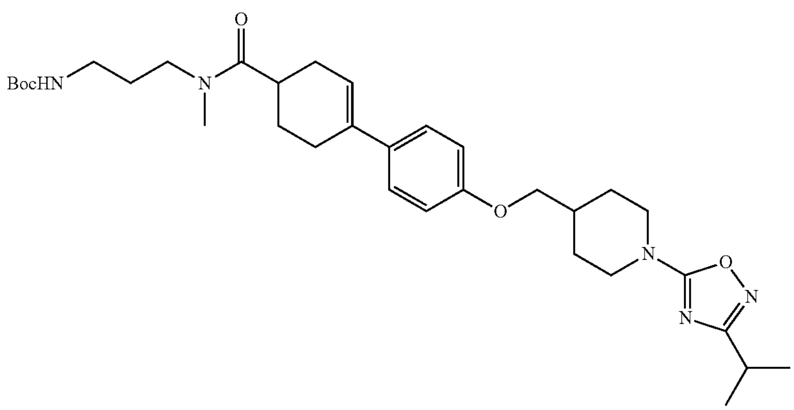 [SMILES: CC(C)c1noc(N2CCC(COc3ccc(C4=CCC(C(=O)N(C)CCCNC(=O)OC(C)(C)C)CC4)cc3)CC2)n1] |
| 77 | 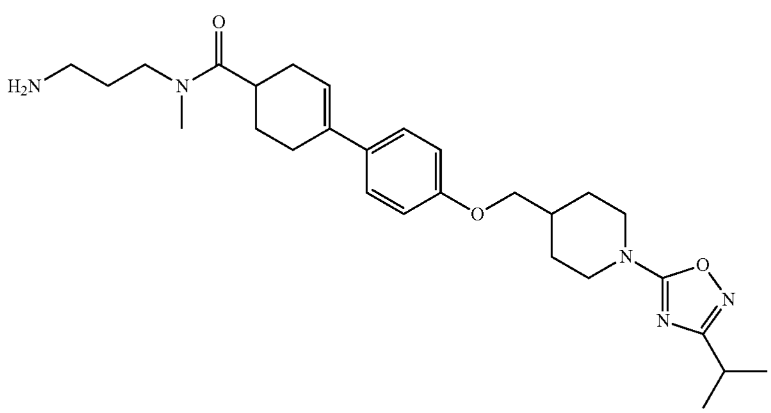 [SMILES: CC(C)c1noc(N2CCC(COc3ccc(C4=CCC(C(=O)N(C)CCCN)CC4)cc3)CC2)n1] |
| 78 | 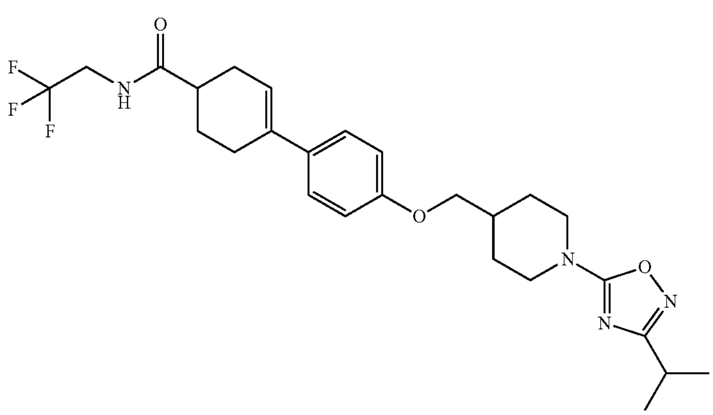 [SMILES: CC(C)c1noc(N2CCC(COc3ccc(C4=CCC(C(=O)NCC(F)(F)F)CC4)cc3)CC2)n1] |

TABLE 1-continued
| Examples | Chemical structures |
|---|---|
| 79 | 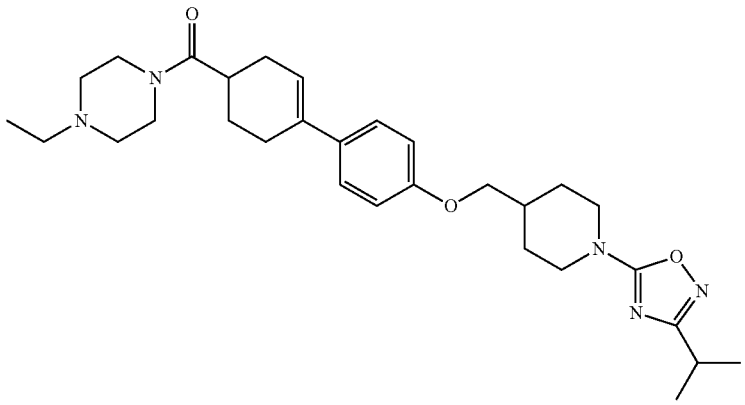 [SMILES: CCN1CCN(C(=O)C2CC=C(c3ccc(OCC4CCN(c5nc(C(C)C)no5)CC4)cc3)CC2)CC1] |
| 80 | 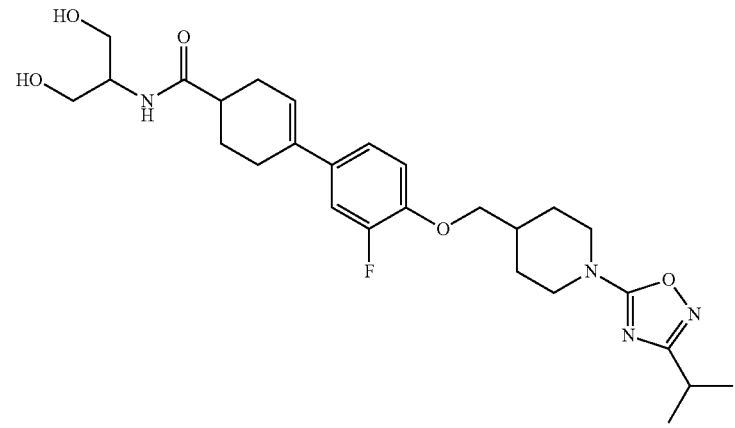 |
| 81 | 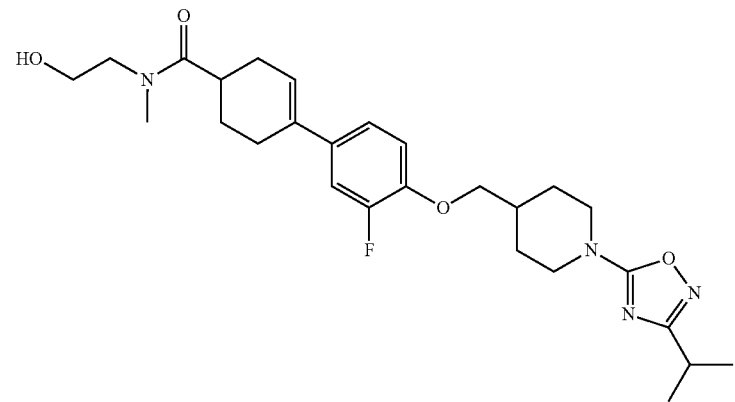 [SMILES: CC(C)c1noc(N2CCC(COc3ccc(C4=CCC(C(=O)N(C)CCO)CC4)cc3F)CC2)n1] |
| 82 | 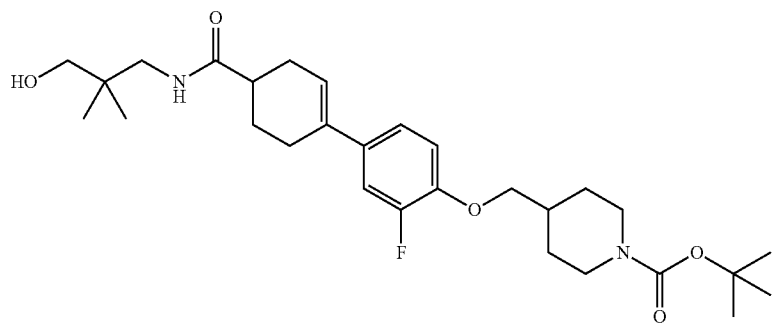 [SMILES: CC(C)(CO)CNC(=O)C1CC=C(c2ccc(OCC3CCN(C(=O)OC(C)(C)C)CC3)c(F)c2)CC1] |

TABLE 1-continued
| Examples | Chemical structures |
|---|---|
| 83 | 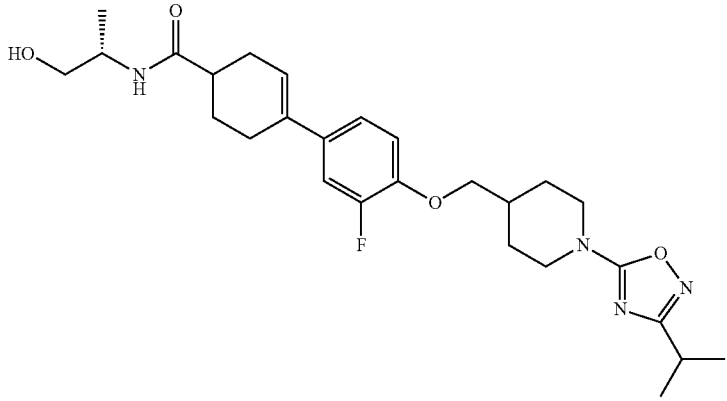 [SMILES: CC(C)c1noc(N2CCC(COc3ccc(C4=CCC(C(=O)N[C@@H](C)CO)CC4)cc3F)CC2)n1] |
| 84 | 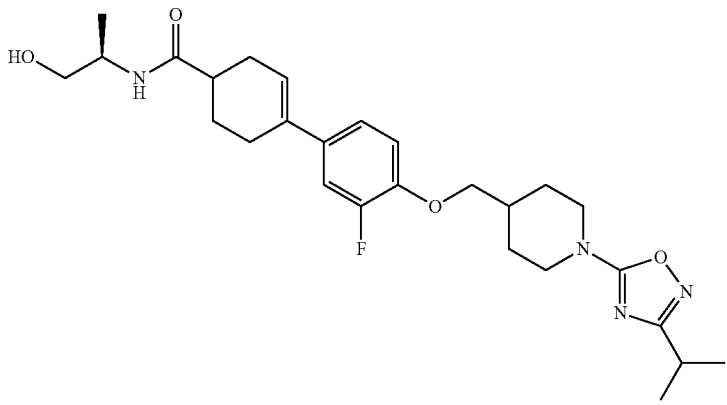 [SMILES: CC(C)c1noc(N2CCC(COc3ccc(C4=CCC(C(=O)N[C@H](C)CO)CC4)cc3F)CC2)n1] |
| 85 | 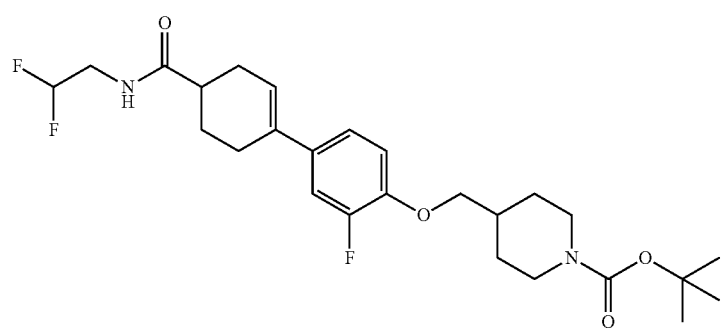 [SMILES: CC(C)(C)OC(=O)N1CCC(COc2ccc(C3=CCC(C(=O)NCC(F)F)CC3)cc2F)CC1] |
| 86 | 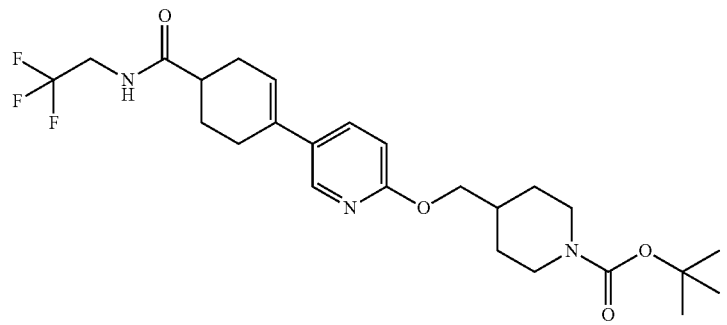 [SMILES: CC(C)(C)OC(=O)N1CCC(COc2ccc(C3=CCC(C(=O)NCC(F)(F)F)CC3)cn2)CC1] |

TABLE 1-continued
| Examples | Chemical structures |
|---|---|
| 87 | 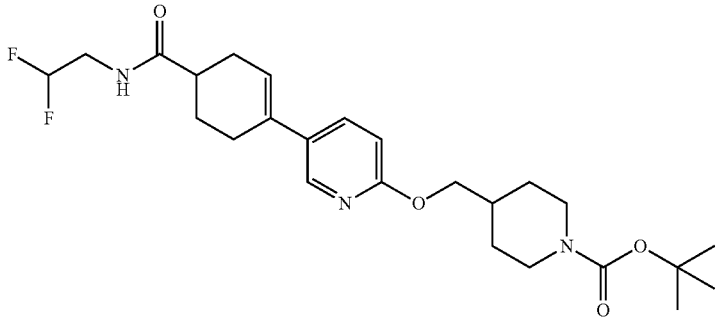 [SMILES: CC(C)(C)OC(=O)N1CCC(COc2ccc(C3=CCC(C(=O)NCC(F)F)CC3)cn2)CC1] |
| 88 | 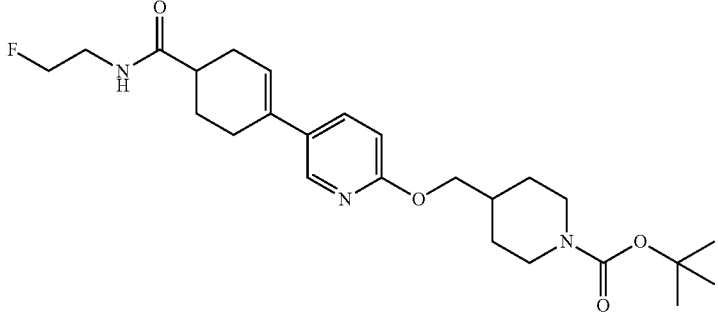 [SMILES: CC(C)(C)OC(=O)N1CCC(COc2ccc(C3=CCC(C(=O)NCCF)CC3)cn2)CC1] |
| 89 | 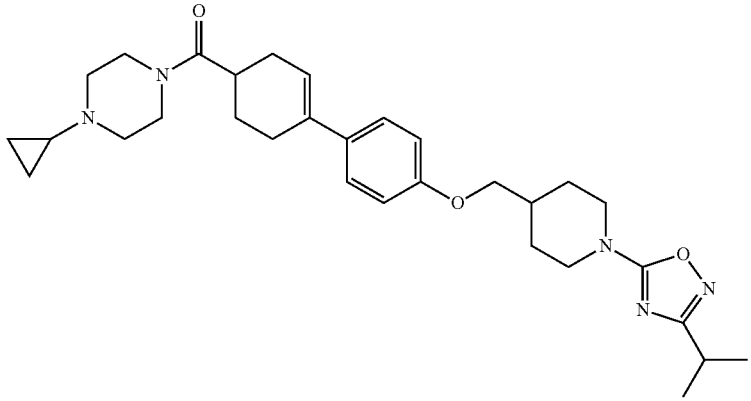 [SMILES: CC(C)c1noc(N2CCC(COc3ccc(C4=CCC(C(=O)N5CCN(C6CC6)CC5)CC4)cc3)CC2)n1] |
| 90 | 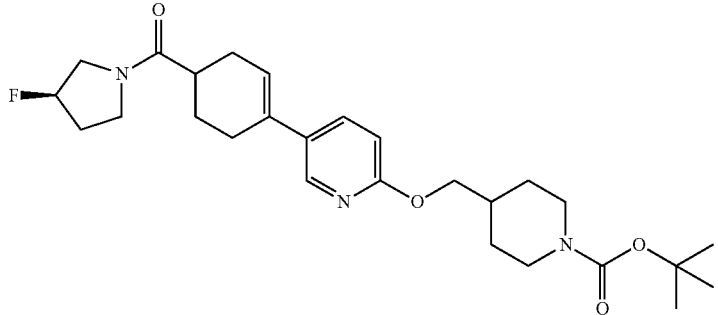 [SMILES: CC(C)(C)OC(=O)N1CCC(COc2ccc(C3=CCC(C(=O)N4CC[C@@H](F)C4)CC3)cn2)CC1] |

TABLE 1-continued
| Examples | Chemical structures |
|---|---|
| 91 | 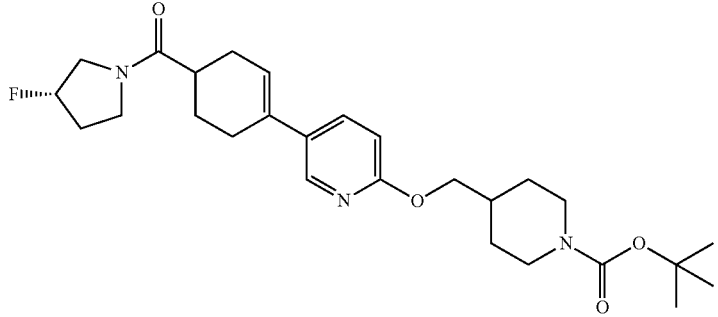 [SMILES: CC(C)(C)OC(=O)N1CCC(COc2ccc(C3=CCC(C(=O)N4CC[C@H](F)C4)CC3)cn2)CC1] |
| 92 | 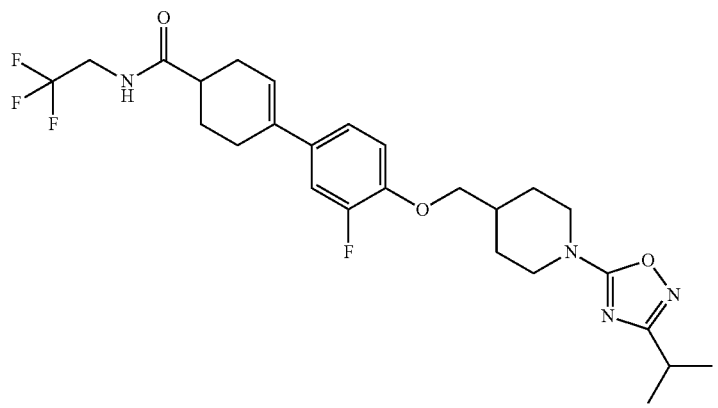 [SMILES: CC(C)c1noc(N2CCC(COc3ccc(C4=CCC(C(=O)NCC(F)(F)F)CC4)cc3F)CC2)n1] |
| 93 | 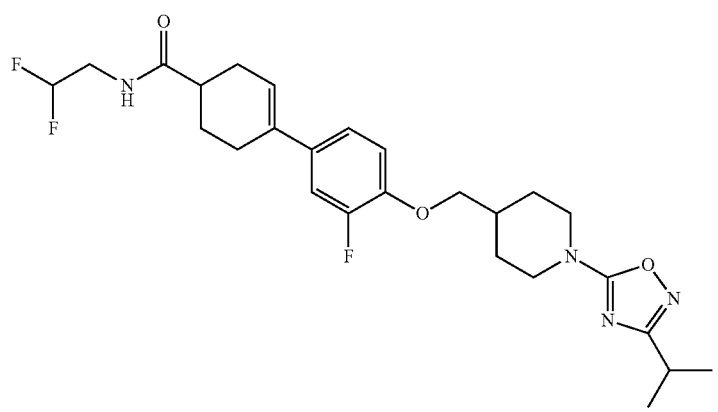 [SMILES: CC(C)c1noc(N2CCC(COc3ccc(C4=CCC(C(=O)NCC(F)F)CC4)cc3F)CC2)n1] |
| 94 | 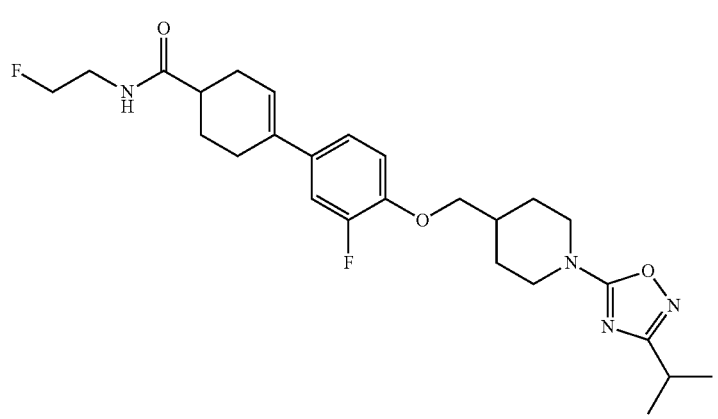 [SMILES: CC(C)c1noc(N2CCC(COc3ccc(C4=CCC(C(=O)NCCF)CC4)cc3F)CC2)n1] |

TABLE 1-continued

| Examples | Chemical structures |
|---|---|
| 95 | 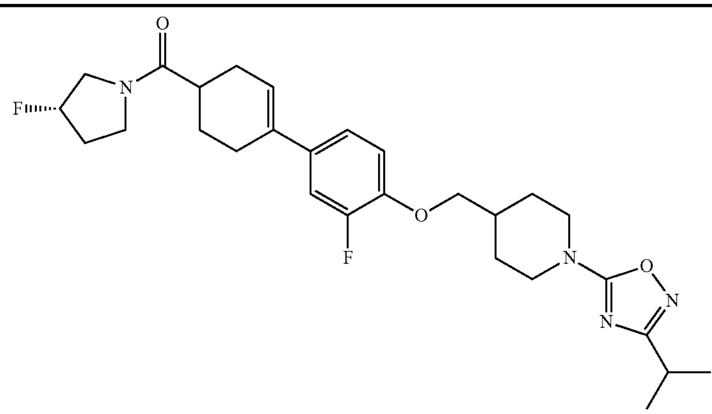 |
| 96 | 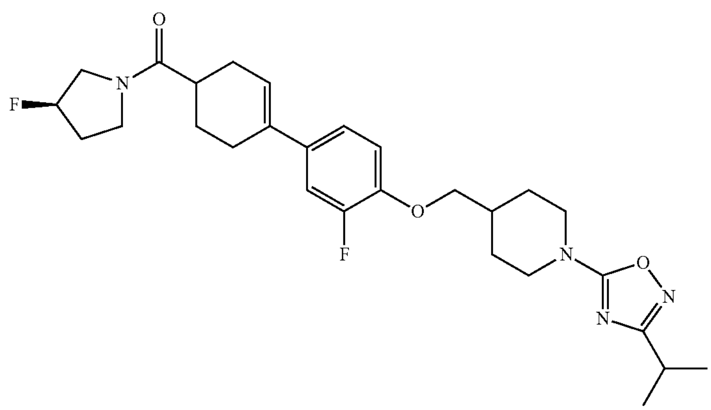 [SMILES: CC(C)c1noc(N2CCC(COc3ccc(C4=CCC(C(=O)N5CC[C@@H](F)C5)CC4)cc3F)CC2)n1] |
| 97 | 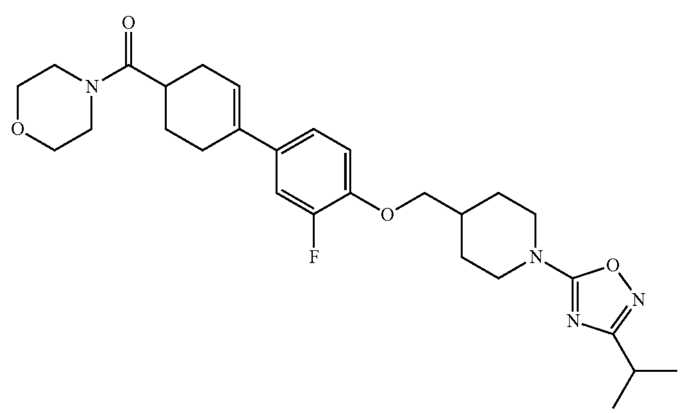 [SMILES: CC(C)c1noc(N2CCC(COc3ccc(C4=CCC(C(=O)N5CCOCC5)CC4)cc3F)CC2)n1] |
| 98 | 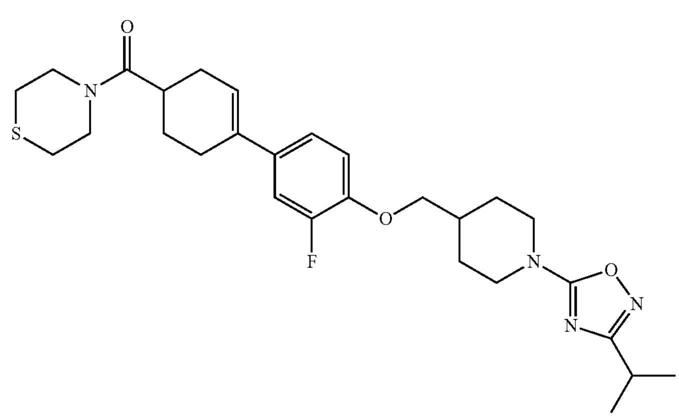 [SMILES: CC(C)c1noc(N2CCC(COc3ccc(C4=CCC(C(=O)N5CCSCC5)CC4)cc3F)CC2)n1] |

TABLE 1-continued
| Examples | Chemical structures |
|---|---|
| 99 | 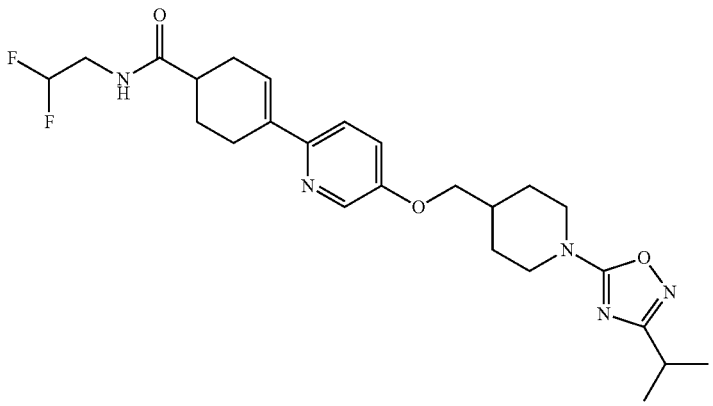 [SMILES: CC(C)c1noc(N2CCC(COc3ccc(C4=CCC(C(=O)NCC(F)F)CC4)nc3)CC2)n1] |
| 100 | 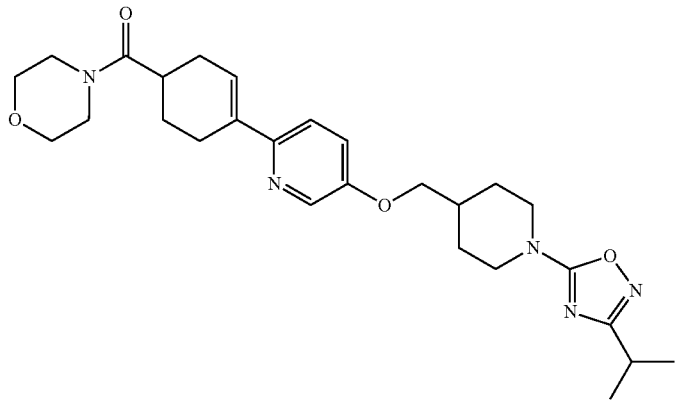 [SMILES: CC(C)c1noc(N2CCC(COc3ccc(C4=CCC(C(=O)N5CCOCC5)CC4)nc3)CC2)n1] |
| 101 | 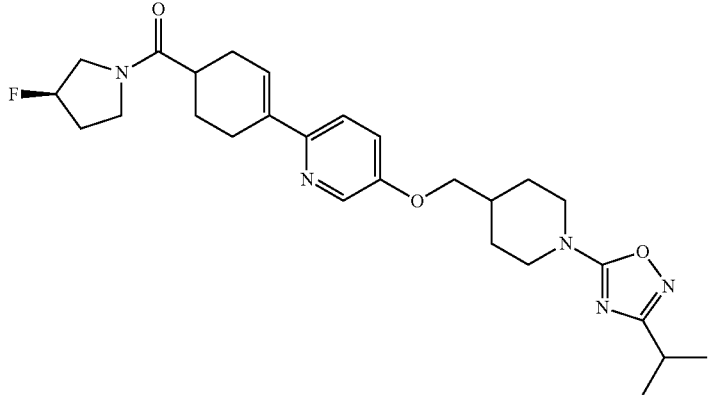 [SMILES: CC(C)c1noc(N2CCC(COc3ccc(C4=CCC(C(=O)N5CC[C@@H](F)C5)CC4)nc3)CC2)n1] |

TABLE 1-continued
| Examples | Chemical structures |
|---|---|
| 102 | 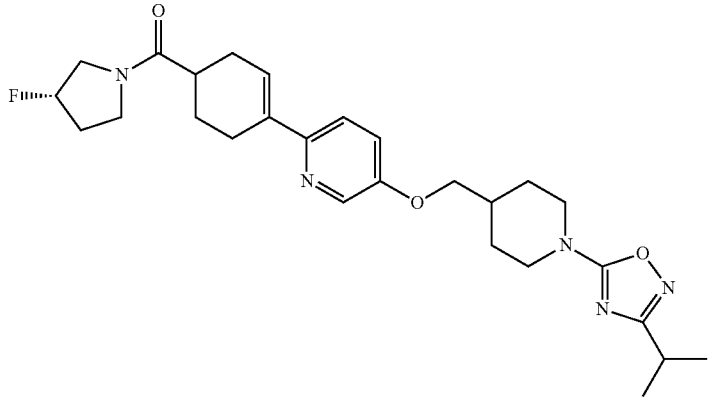 |
| 103 | 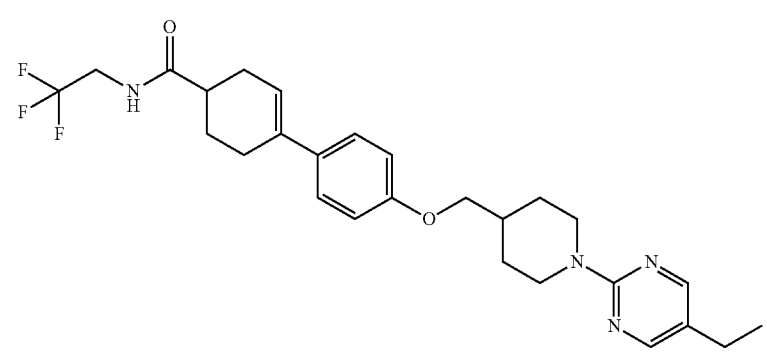 [SMILES: CCc1cnc(N2CCC(COc3ccc(C4=CCC(C(=O)NCC(F)(F)F)CC4)cc3)CC2)nc1] |
| 104 | 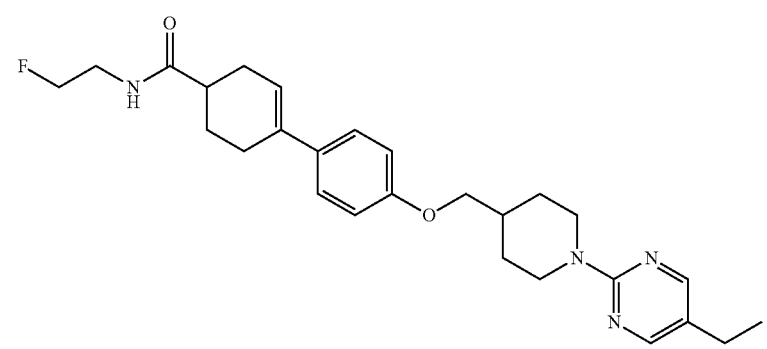 [SMILES: CCc1cnc(N2CCC(COc3ccc(C4=CCC(C(=O)NCCF)CC4)cc3)CC2)nc1] |
| 105 | 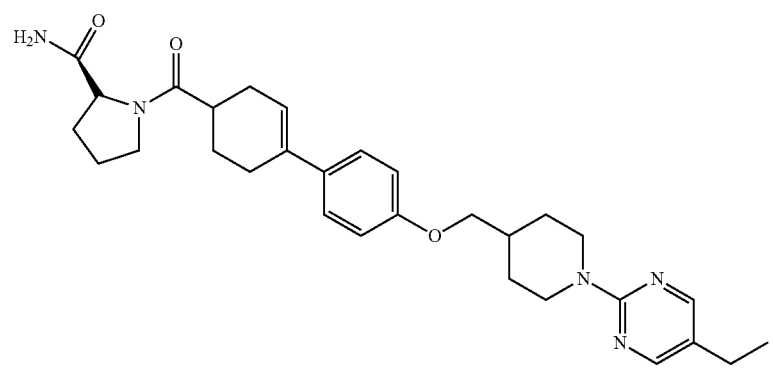 |

TABLE 1-continued

| Examples | Chemical structures |
|---|---|
| 106 | 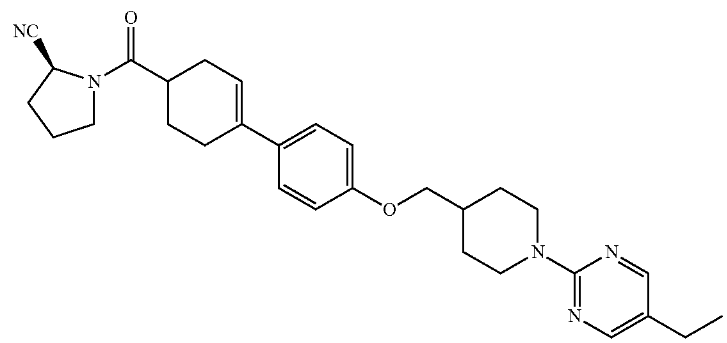 [SMILES: CCc1cnc(N2CCC(COc3ccc(C4=CCC(C(=O)N5CCC[C@H]5C#N)CC4)cc3)CC2)nc1] |
| 107 | 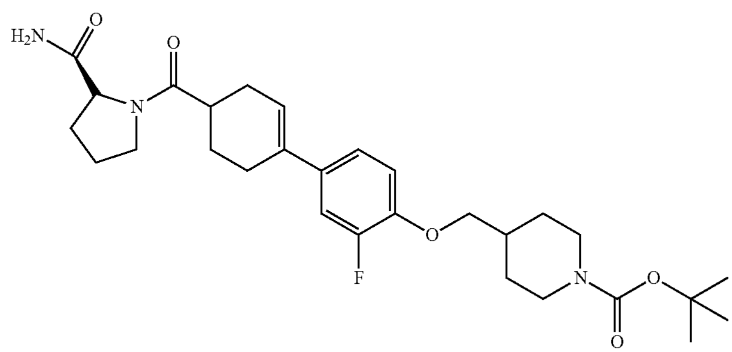 |
| 108 | 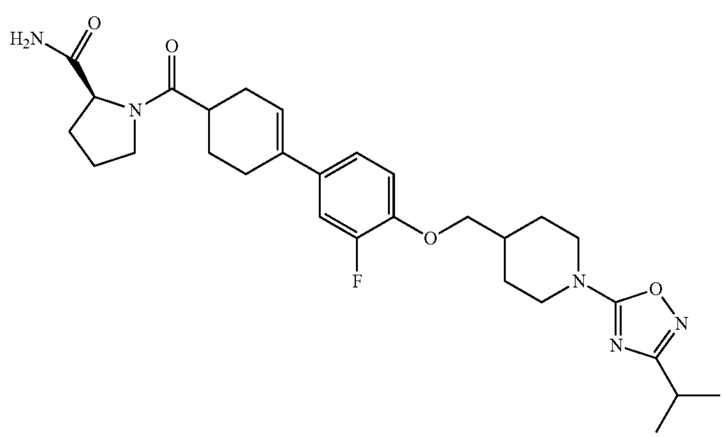 [SMILES: CC(C)c1noc(N2CCC(COc3ccc(C4=CCC(C(=O)N5CCC[C@H]5C(N)=O)CC4)cc3F)CC2)n1] |
| 109 | 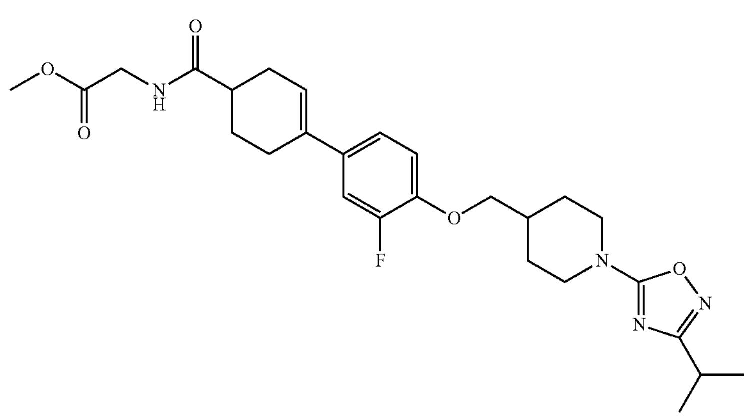 [SMILES: COC(=O)CNC(=O)C1CC=C(c2ccc(OCC3CCN(c4nc(C(C)C)no4)CC3)c(F)c2)CC1] |

TABLE 1-continued
| Examples | Chemical structures |
|---|---|
| 110 | 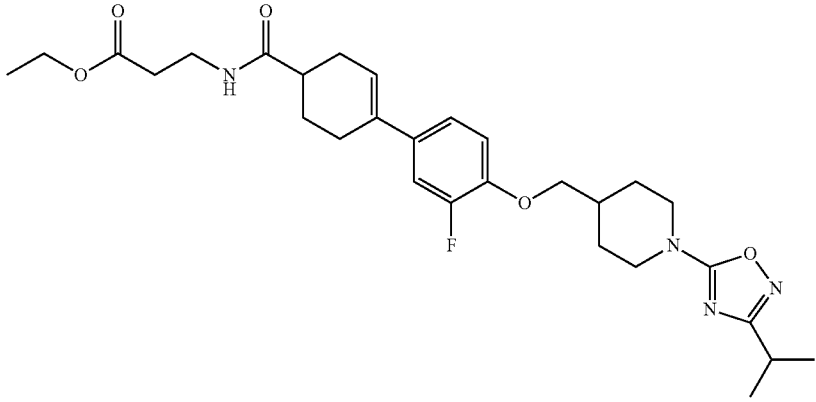 [SMILES: CCOC(=O)CCNC(=O)C1CC=C(c2ccc(OCC3CCN(c4nc(C(C)C)no4)CC3)c(F)c2)CC1] |
| 111 | 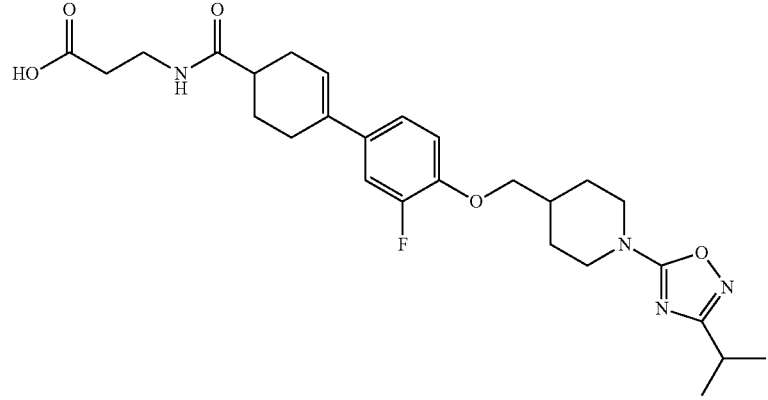 [SMILES: CC(C)c1noc(N2CCC(COc3ccc(C4=CCC(C(=O)NCCC(=O)O)CC4)cc3F)CC2)n1] |
| 112 | 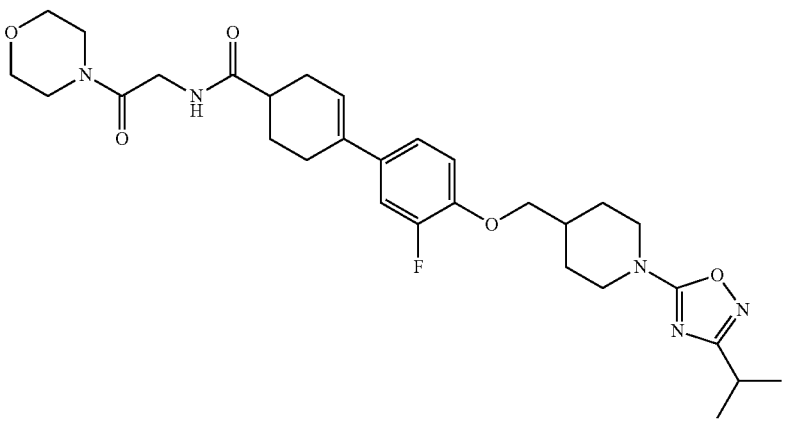 [SMILES: CC(C)c1noc(N2CCC(COc3ccc(C4=CCC(C(=O)NCC(=O)N5CCOCC5)CC4)cc3F)CC2)n1] |

TABLE 1-continued

| Examples | Chemical structures |
| --- | --- |
| 113 | 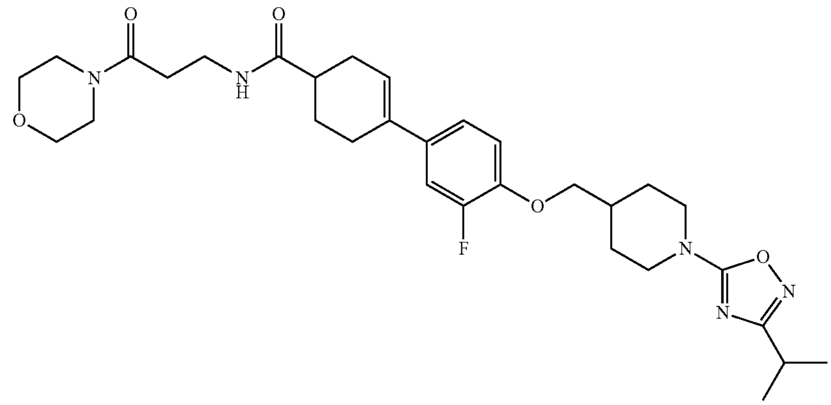 [SMILES: CC(C)c1noc(N2CCC(COc3ccc(C4=CCC(C(=O)NCCC(=O)N5CCOCC5)CC4)cc3F)CC2)n1] |
| 114 | 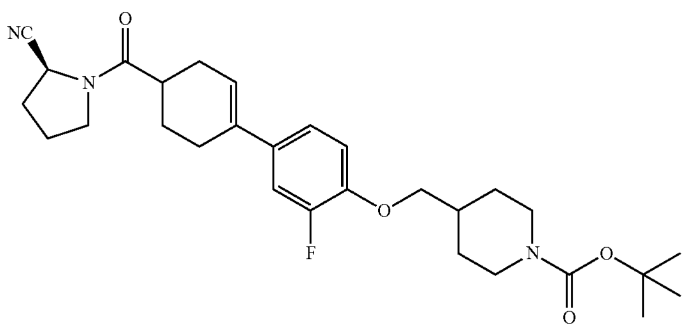 [SMILES: CC(C)(C)OC(=O)N1CCC(COc2ccc(C3=CCC(C(=O)N4CCC[C@H]4C#N)CC3)cc2F)CC1] |
| 115 | 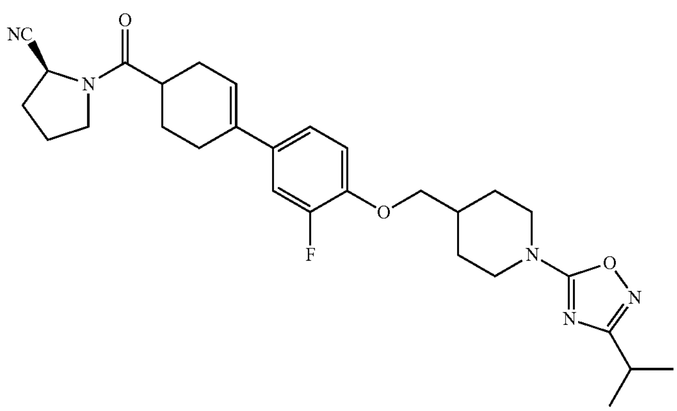 [SMILES: CC(C)c1noc(N2CCC(COc3ccc(C4=CCC(C(=O)N5CCC[C@H]5C#N)CC4)cc3F)CC2)n1] |
| 116 | 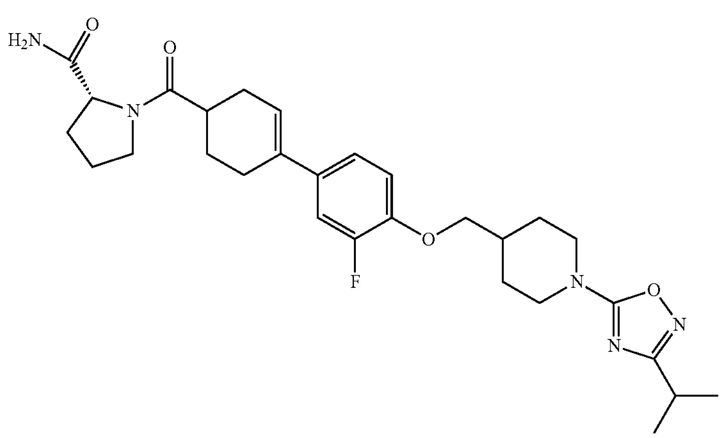 [SMILES: CC(C)c1noc(N2CCC(COc3ccc(C4=CCC(C(=O)N5CCC[C@@H]5C(N)=O)CC4)cc3F)CC2)n1] |

TABLE 1-continued

| Examples | Chemical structures |
|---|---|
| 117 | 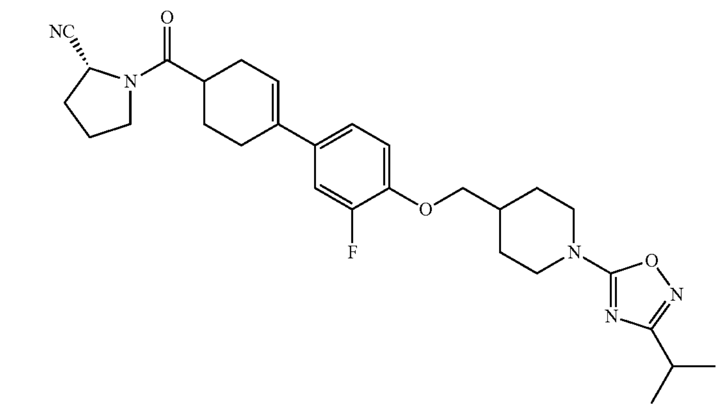 [SMILES: CC(C)c1noc(N2CCC(COc3ccc(C4=CCC(C(=O)N5CCC[C@@H]5C#N)CC4)cc3F)CC2)n1] |
| 118 | 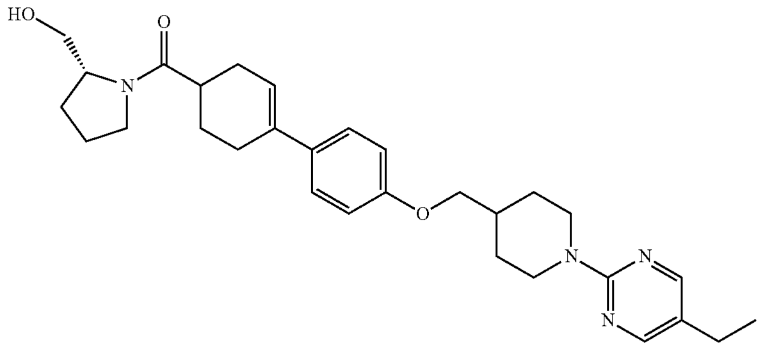 [SMILES: CCc1cnc(N2CCC(COc3ccc(C4=CCC(C(=O)N5CCC[C@@H]5CO)CC4)cc3)CC2)nc1] |
| 119 | 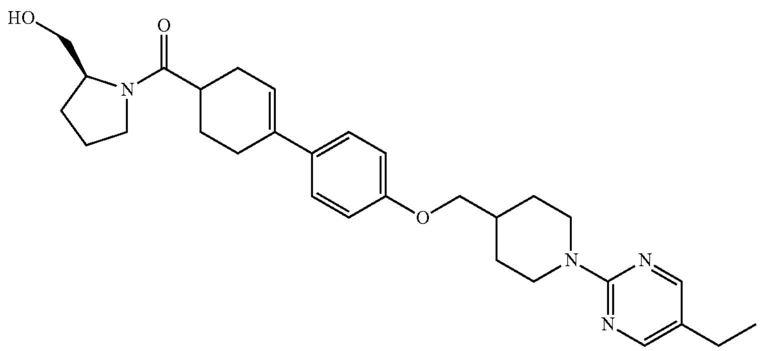 [SMILES: CCc1cnc(N2CCC(COc3ccc(C4=CCC(C(=O)N5CCC[C@H]5CO)CC4)cc3)CC2)nc1] |
| 120 | 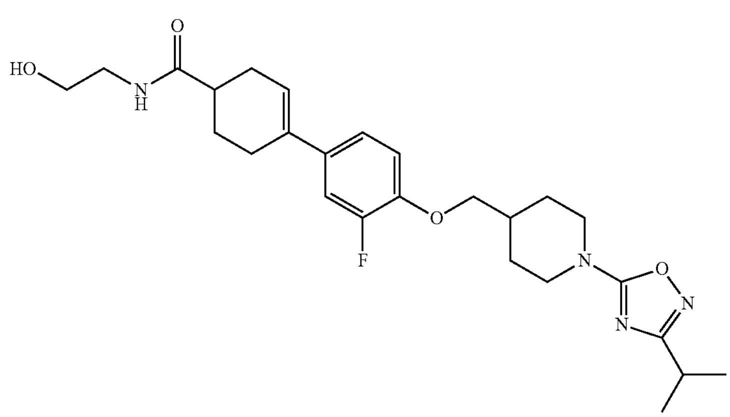 [SMILES: CC(C)c1noc(N2CCC(COc3ccc(C4=CCC(C(=O)NCCO)CC4)cc3F)CC2)n1] |

TABLE 1-continued
| Examples | Chemical structures |
|---|---|
| 121 | 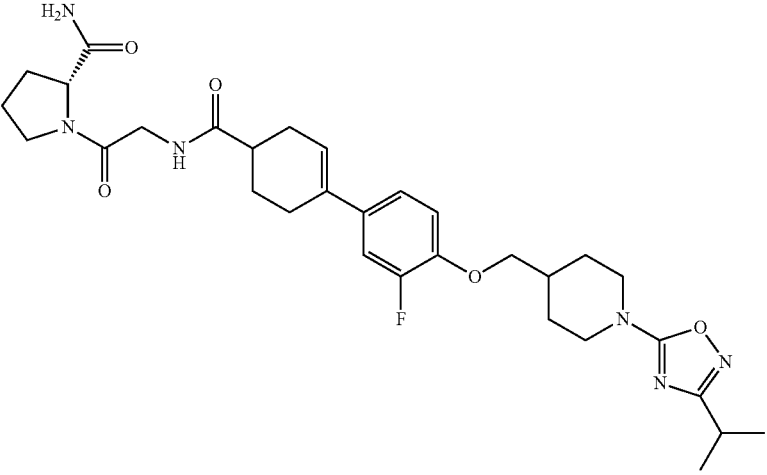 [SMILES: CC(C)c1noc(N2CCC(COc3ccc(C4=CCC(C(=O)NCC(=O)N5CCC[C@@H]5C(N)=O)CC4)cc3F)CC2)n1] |
| 122 | 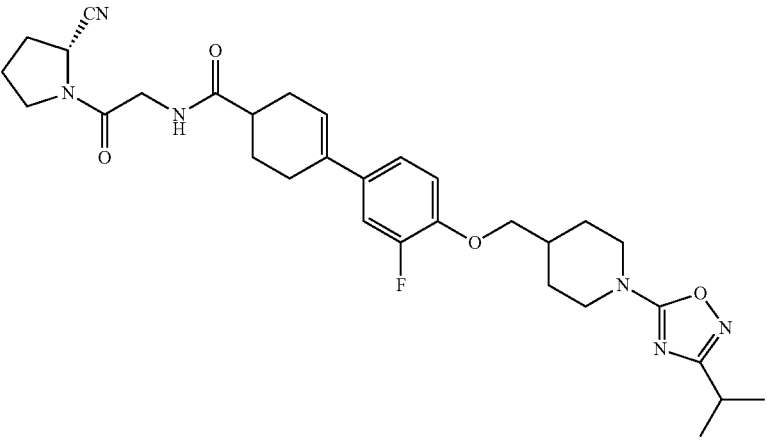 [SMILES: CC(C)c1noc(N2CCC(COc3ccc(C4=CCC(C(=O)NCC(=O)N5CCC[C@@H]5C#N)CC4)cc3F)CC2)n1] |
| 123 | 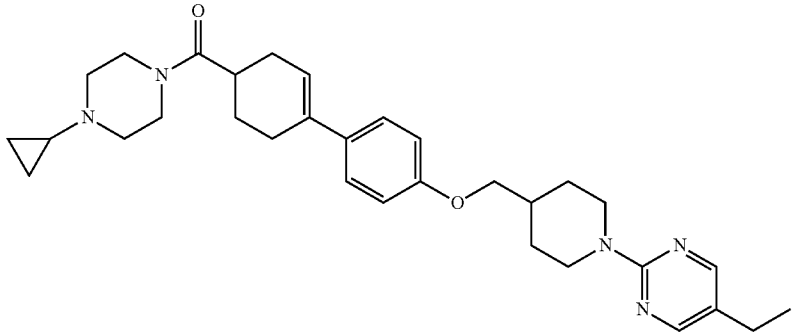 [SMILES: CCc1cnc(N2CCC(COc3ccc(C4=CCC(C(=O)N5CCN(C6CC6)CC5)CC4)cc3)CC2)nc1] |
| 124 | 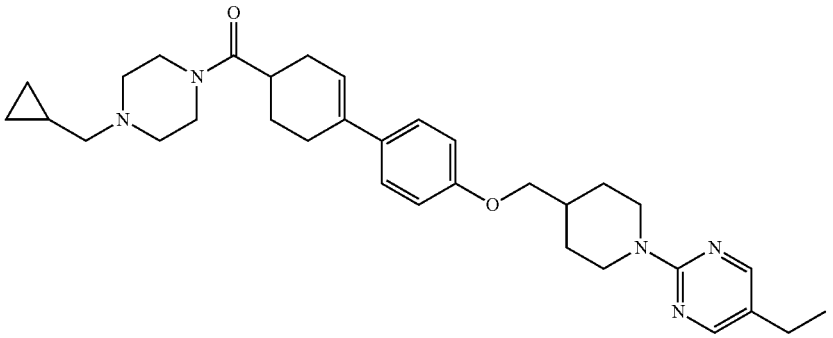 [SMILES: CCc1cnc(N2CCC(COc3ccc(C4=CCC(C(=O)N5CCN(CC6CC6)CC5)CC4)cc3)CC2)nc1] |

TABLE 1-continued
| Examples | Chemical structures |
|---|---|
| 125 | 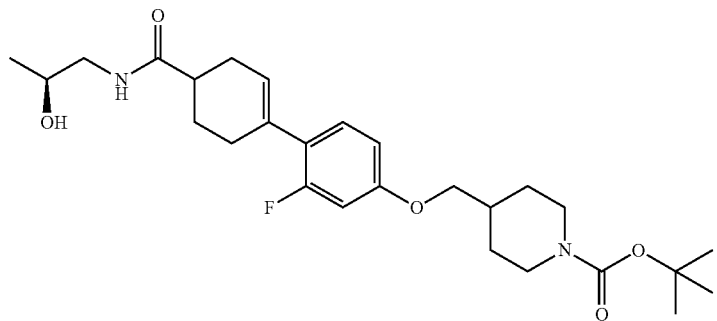 [SMILES: C[C@H](O)CNC(=O)C1CC=C(c2ccc(OCC3CCN(C(=O)OC(C)(C)C)CC3)cc2F)CC1] |
| 126 | 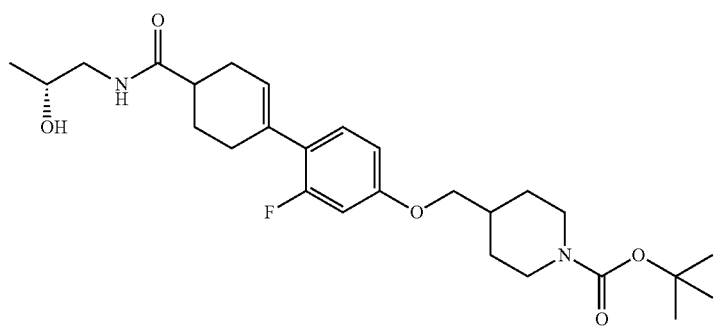 [SMILES: C[C@@H](O)CNC(=O)C1CC=C(c2ccc(OCC3CCN(C(=O)OC(C)(C)C)CC3)cc2F)CC1] |
| 127 | 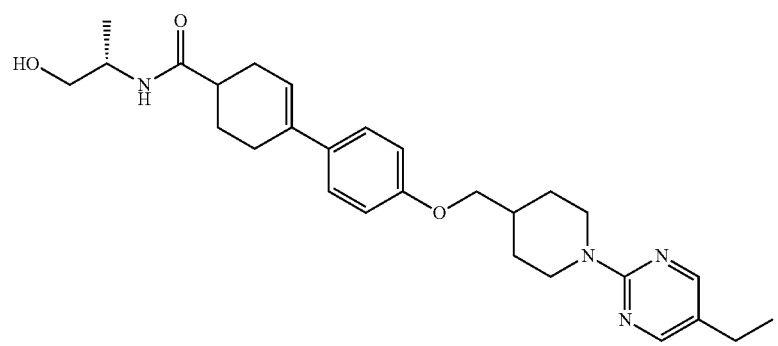 [SMILES: CCc1cnc(N2CCC(COc3ccc(C4=CCC(C(=O)N[C@@H](C)CO)CC4)cc3)CC2)nc1] |
| 128 | 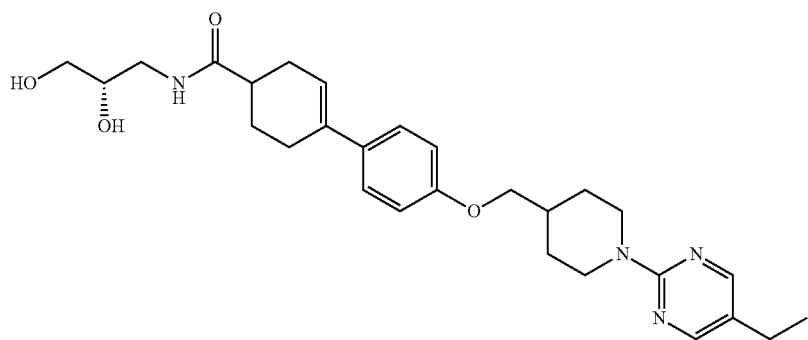 [SMILES: CCc1cnc(N2CCC(COc3ccc(C4=CCC(C(=O)NC[C@H](O)CO)CC4)cc3)CC2)nc1] |

TABLE 1-continued
| Examples | Chemical structures |
|---|---|
| 129 | 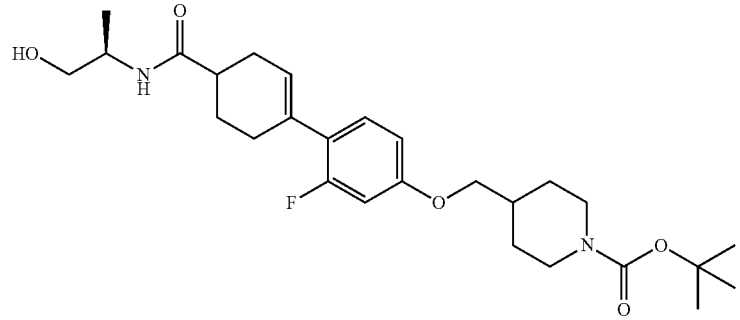 [SMILES: C[C@H](CO)NC(=O)C1CC=C(c2ccc(OCC3CCN(C(=O)OC(C)(C)C)CC3)cc2F)CC1] |
| 130 | 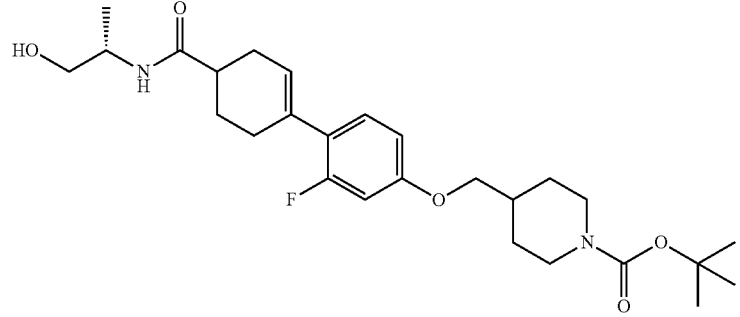 [SMILES: C[C@@H](CO)NC(=O)C1CC=C(c2ccc(OCC3CCN(C(=O)OC(C)(C)C)CC3)cc2F)CC1] |
| 131 | 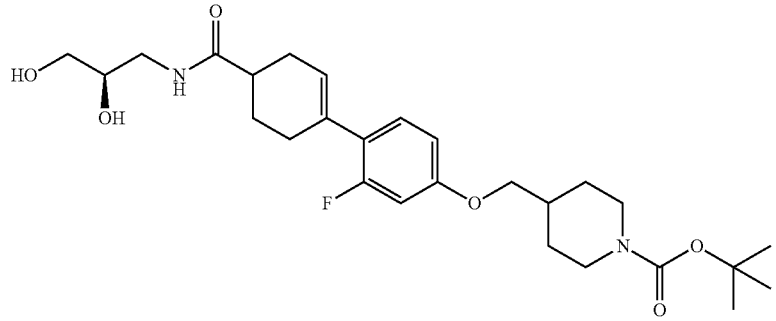 [SMILES: CC(C)(C)OC(=O)N1CCC(COc2ccc(C3=CCC(C(=O)NC[C@@H](O)CO)CC3)c(F)c2)CC1] |
| 132 | 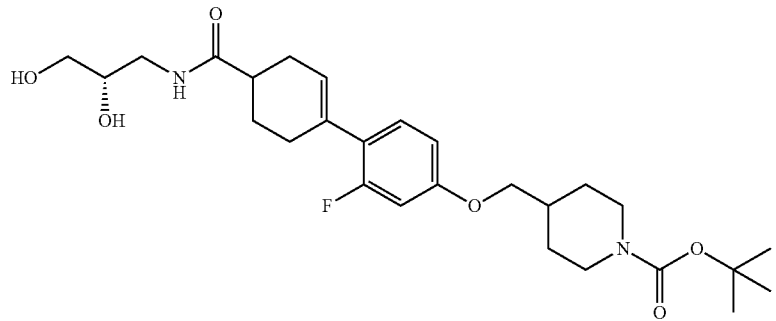 [SMILES: CC(C)(C)OC(=O)N1CCC(COc2ccc(C3=CCC(C(=O)NC[C@H](O)CO)CC3)c(F)c2)CC1] |

US 10,723,699 B2
413                                                                                          414
TABLE 1-continued
| Examples | Chemical structures |
|---|---|
| 133 | 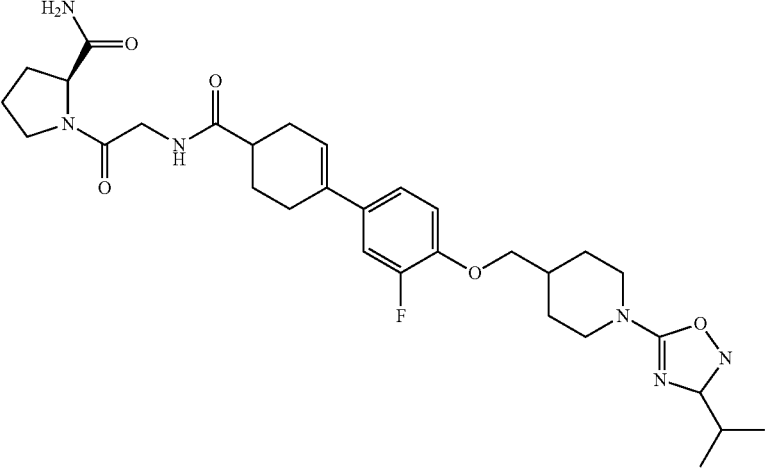 [SMILES: CC(C)C1N=C(N2CCC(COc3ccc(C4=CCC(C(=O)NCC(=O)N5CCC[C@H]5C(N)=O)CC4)cc3F)CC2)ON1] |
| 134 | 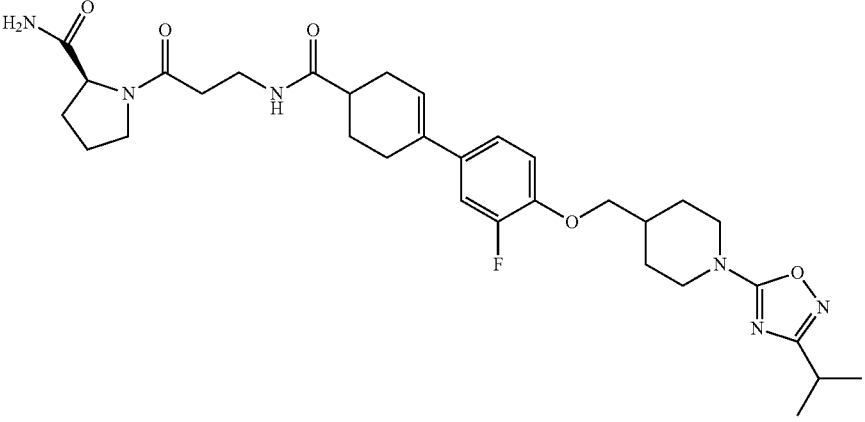 [SMILES: CC(C)c1noc(N2CCC(COc3ccc(C4=CCC(C(=O)NCCC(=O)N5CCC[C@H]5C(N)=O)CC4)cc3F)CC2)n1] |
| 135 | 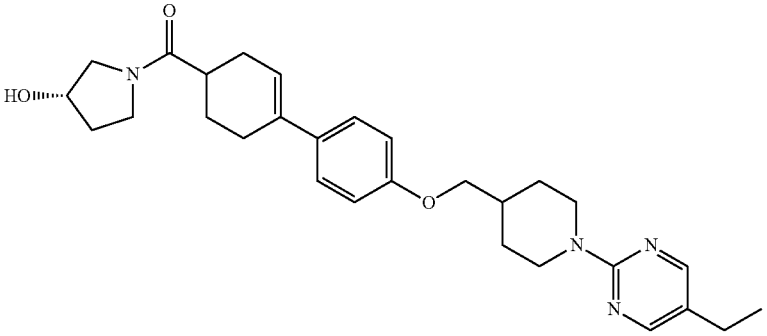 [SMILES: CCc1cnc(N2CCC(COc3ccc(C4=CCC(C(=O)N5CC[C@H](O)C5)CC4)cc3)CC2)nc1] |
| 136 | 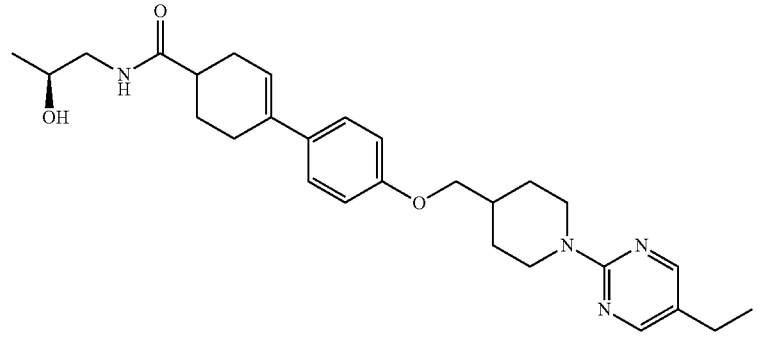 [SMILES: CCc1cnc(N2CCC(COc3ccc(C4=CCC(C(=O)NC[C@H](C)O)CC4)cc3)CC2)nc1] |

TABLE 1-continued

| Examples | Chemical structures |
|---|---|
| 137 | 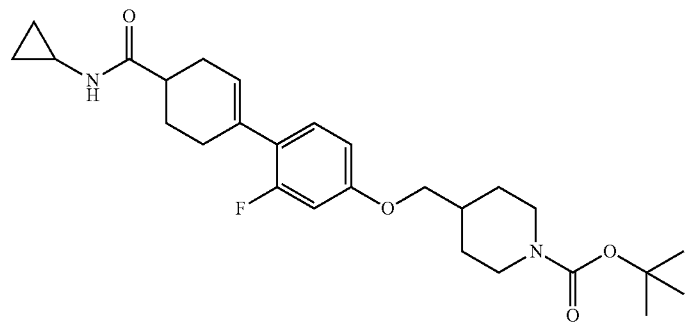 [SMILES: CC(C)(C)OC(=O)N1CCC(COc2ccc(C3=CCC(C(=O)NC4CC4)CC3)c(F)c2)CC1] |
| 138 | 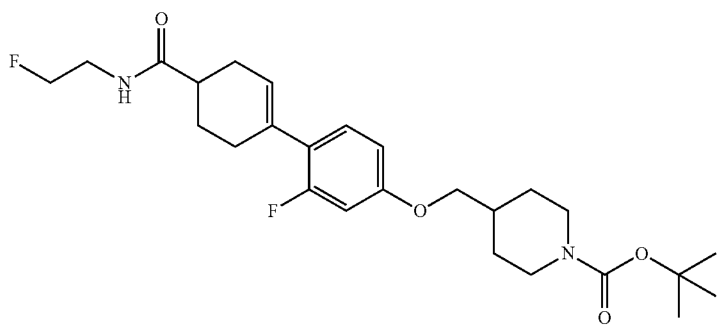 [SMILES: CC(C)(C)OC(=O)N1CCC(COc2ccc(C3=CCC(C(=O)NCCF)CC3)c(F)c2)CC1] |
| 139 | 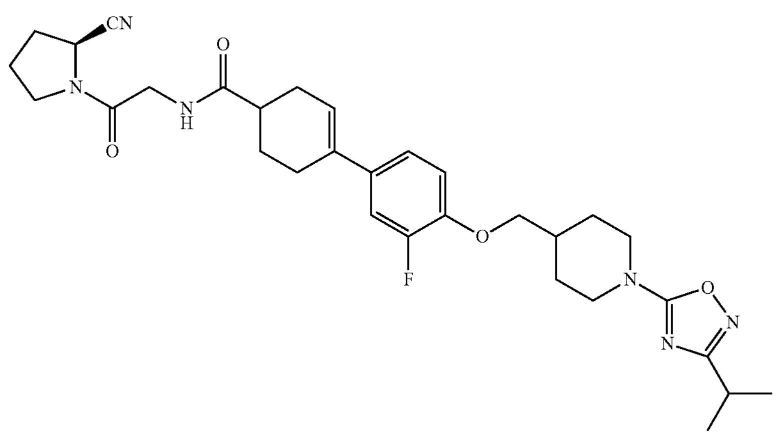 [SMILES: CC(C)c1noc(N2CCC(COc3ccc(C4=CCC(C(=O)NCC(=O)N5CCC[C@H]5C#N)CC4)cc3F)CC2)n1] |
| 140 | 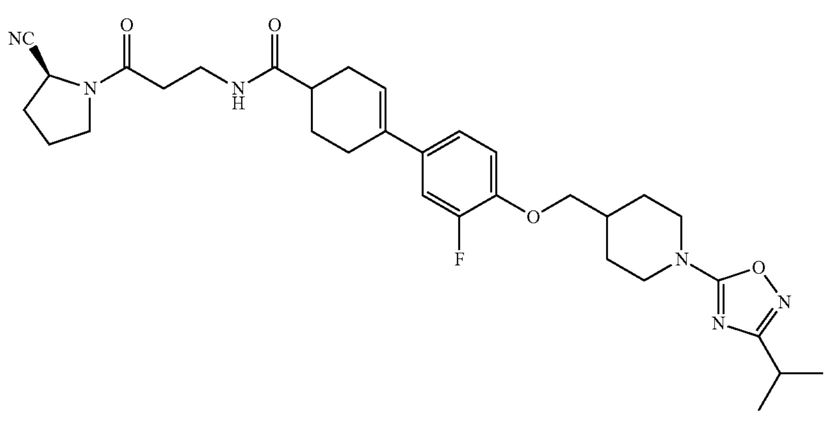 [SMILES: CC(C)c1noc(N2CCC(COc3ccc(C4=CCC(C(=O)NCCC(=O)N5CCC[C@H]5C#N)CC4)cc3F)CC2)n1] |

TABLE 1-continued
| Examples | Chemical structures |
|---|---|
| 141 | 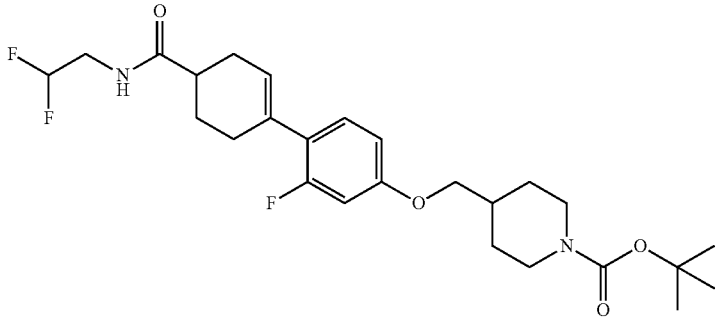 [SMILES: CC(C)(C)OC(=O)N1CCC(COc2ccc(C3=CCC(C(=O)NCC(F)F)CC3)c(F)c2)CC1] |
| 142 | 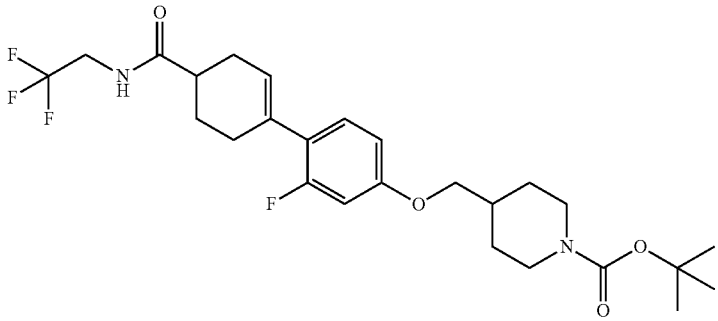 [SMILES: CC(C)(C)OC(=O)N1CCC(COc2ccc(C3=CCC(C(=O)NCC(F)(F)F)CC3)c(F)c2)CC1] |
| 143 | 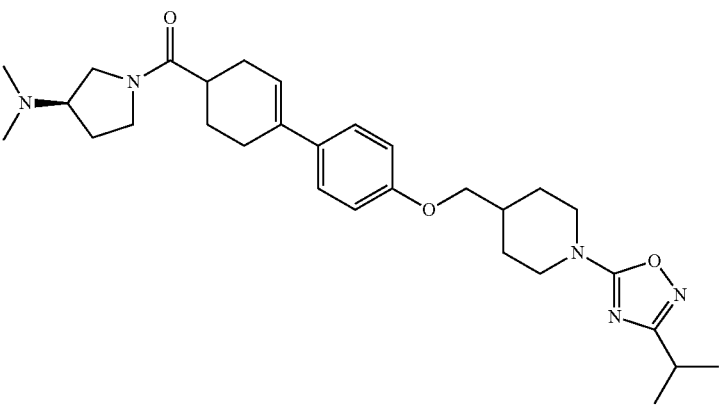 [SMILES: CC(C)c1noc(N2CCC(COc3ccc(C4=CCC(C(=O)N5CC[C@@H](N(C)C)C5)CC4)cc3)CC2)n1] |
| 144 | 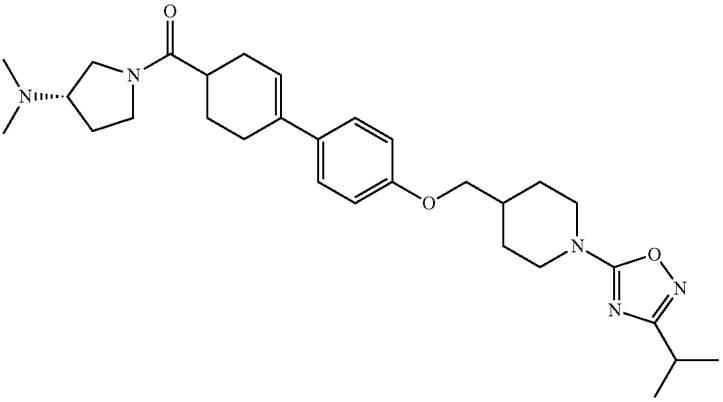 [SMILES: CC(C)c1noc(N2CCC(COc3ccc(C4=CCC(C(=O)N5CC[C@H](N(C)C)C5)CC4)cc3)CC2)n1] |

TABLE 1-continued
| Examples | Chemical structures |
|---|---|
| 145 | 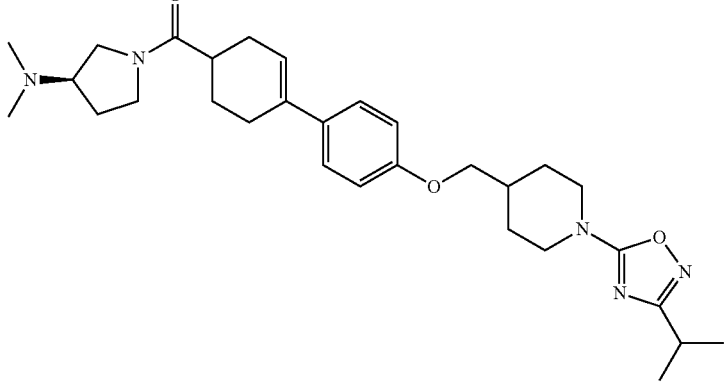 |
| 146 | 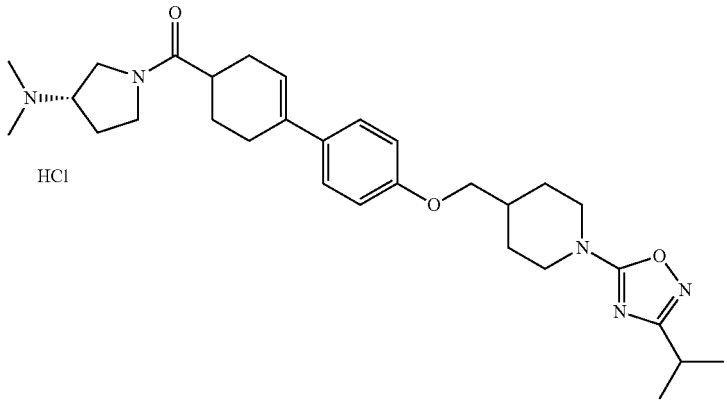 [SMILES: CC(C)c1noc(N2CCC(COc3ccc(C4=CCC(C(=O)N5CC[C@H](N(C)C)C5)CC4)cc3)CC2)n1 ; Cl]<br>HCl |
| 147 | 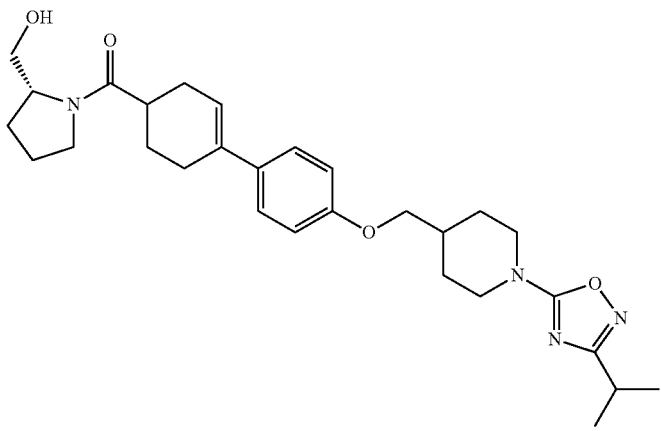 [SMILES: CC(C)c1noc(N2CCC(COc3ccc(C4=CCC(C(=O)N5CCC[C@@H]5CO)CC4)cc3)CC2)n1] |

TABLE 1-continued

| Examples | Chemical structures |
|---|---|
| 148 | 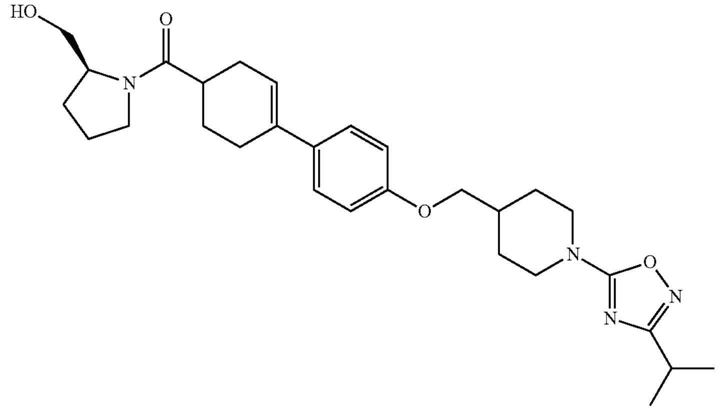 [SMILES: CC(C)c1noc(N2CCC(COc3ccc(C4=CCC(C(=O)N5CCC[C@H]5CO)CC4)cc3)CC2)n1] |
| 149 | 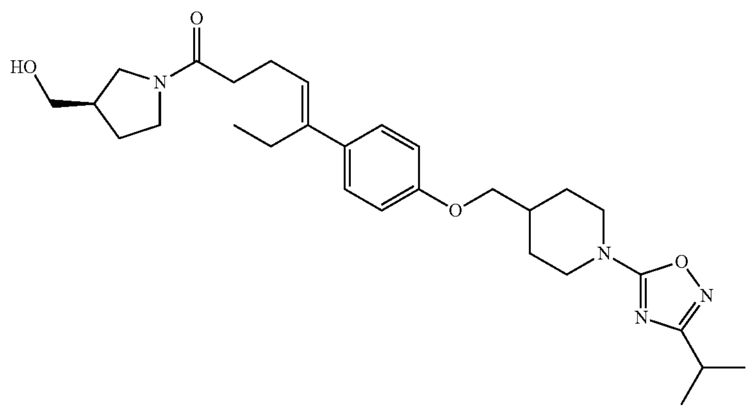 [SMILES: CC/C(=C\CCC(=O)N1CC[C@@H](CO)C1)c1ccc(OCC2CCN(c3nc(C(C)C)no3)CC2)cc1] |
| 150 | 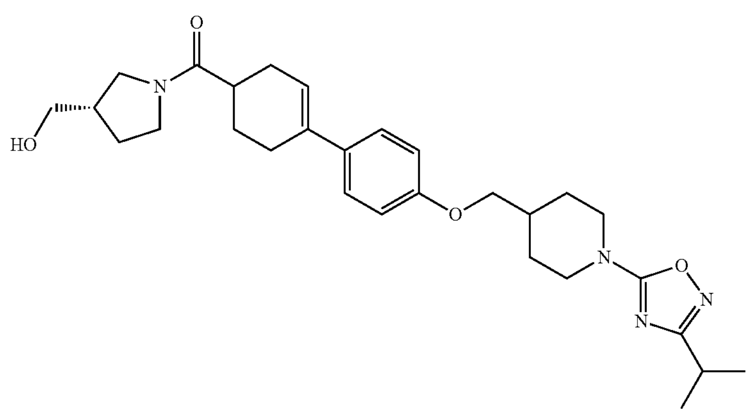 [SMILES: CC(C)c1noc(N2CCC(COc3ccc(C4=CCC(C(=O)N5CC[C@H](CO)C5)CC4)cc3)CC2)n1] |
| 151 | 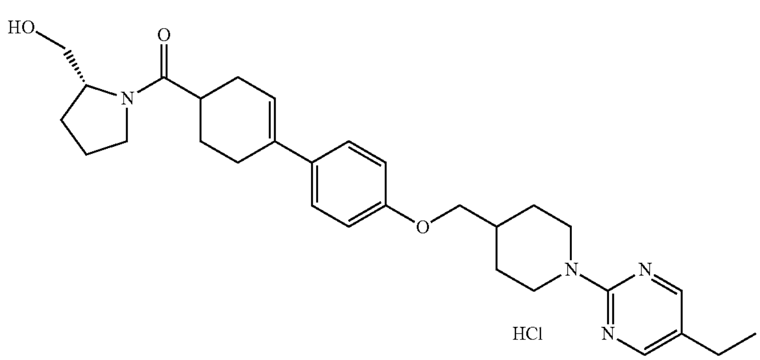 [SMILES: CCc1cnc(N2CCC(COc3ccc(C4=CCC(C(=O)N5CCC[C@@H]5CO)CC4)cc3)CC2)nc1 ; Cl] |

TABLE 1-continued
| Examples | Chemical structures |
|---|---|
| 152 | 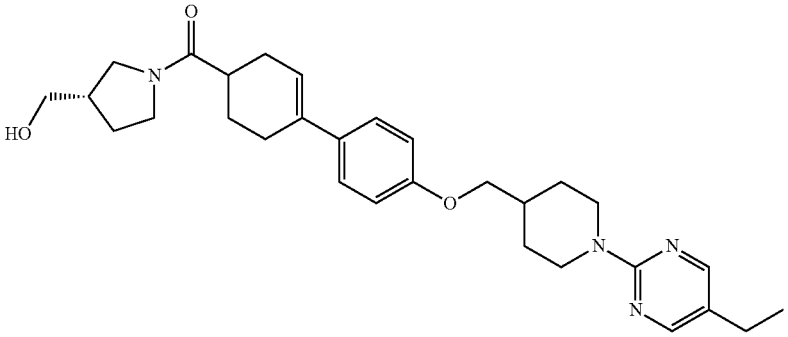 [SMILES: CCc1cnc(N2CCC(COc3ccc(C4=CCC(C(=O)N5CC[C@H](CO)C5)CC4)cc3)CC2)nc1] |
| 153 | 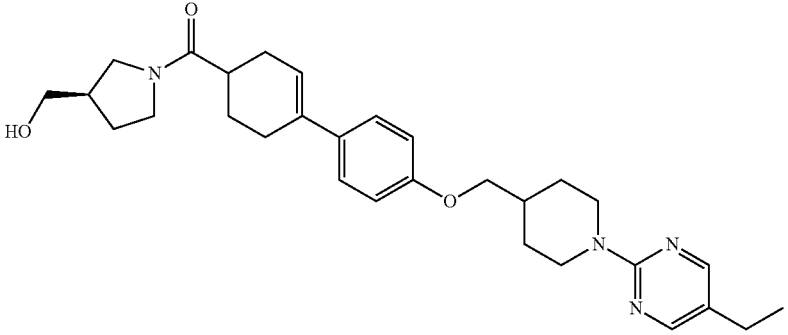 [SMILES: CCc1cnc(N2CCC(COc3ccc(C4=CCC(C(=O)N5CC[C@@H](CO)C5)CC4)cc3)CC2)nc1] |
| 154 | 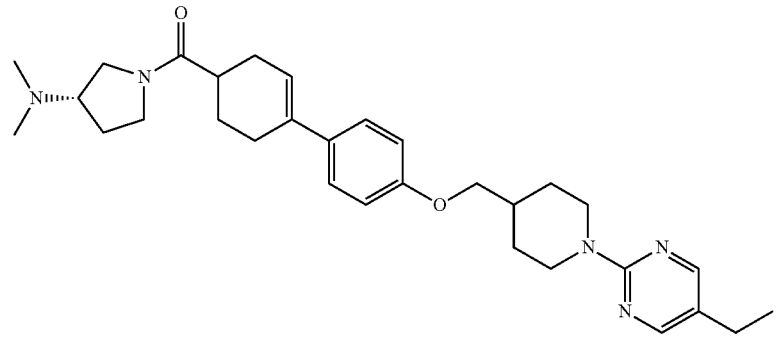 [SMILES: CCc1cnc(N2CCC(COc3ccc(C4=CCC(C(=O)N5CC[C@H](N(C)C)C5)CC4)cc3)CC2)nc1] |
| 155 | 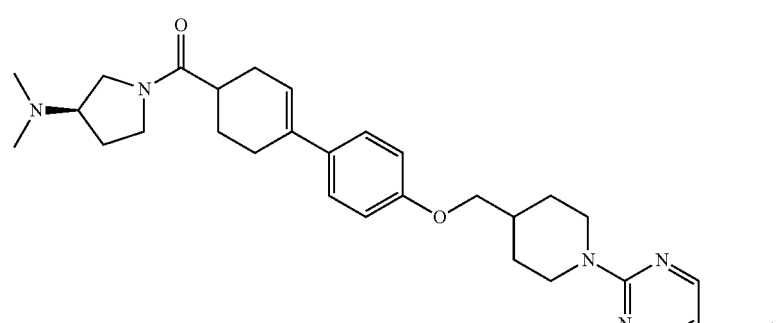 |

TABLE 1-continued
| Examples | Chemical structures |
|---|---|
| 156 | 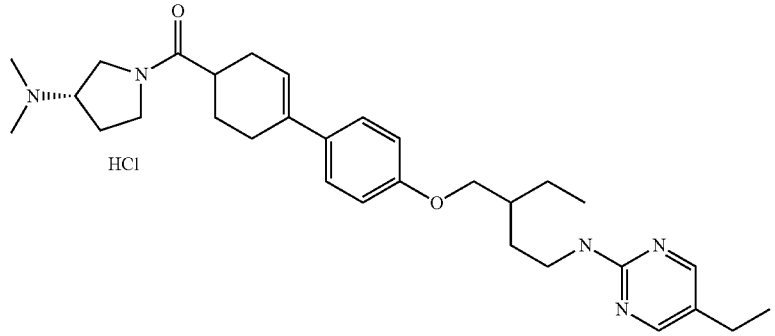 [SMILES: CCc1cnc(NCCC(CC)COc2ccc(C3=CCC(C(=O)N4CC[C@H](N(C)C)C4)CC3)cc2)nc1 ; Cl] |
| 157 | 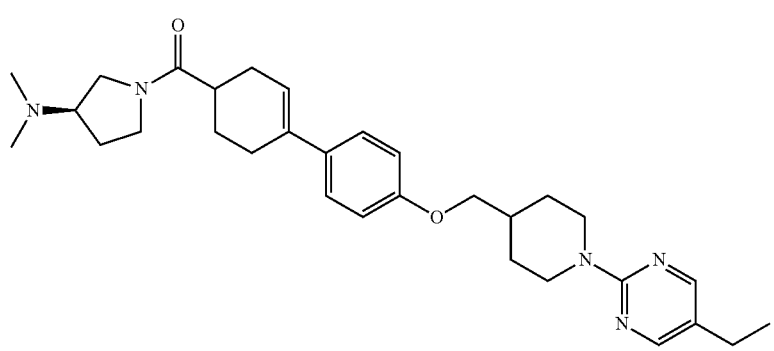 [SMILES: CCc1cnc(N2CCC(COc3ccc(C4=CCC(C(=O)N5CC[C@@H](N(C)C)C5)CC4)cc3)CC2)nc1] |
| 158 | 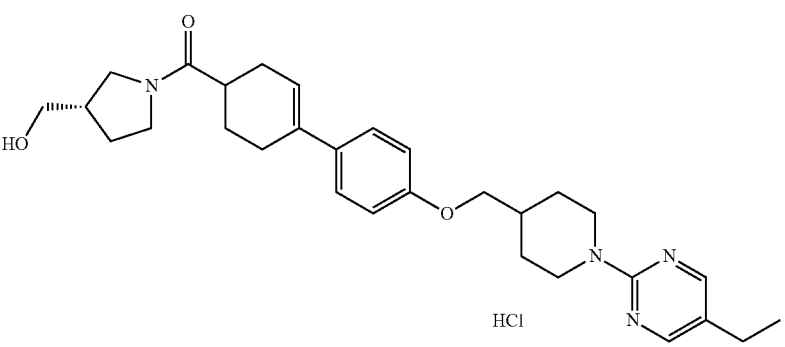 [SMILES: CCc1cnc(N2CCC(COc3ccc(C4=CCC(C(=O)N5CC[C@H](CO)C5)CC4)cc3)CC2)nc1 ; Cl] |
| 159 | 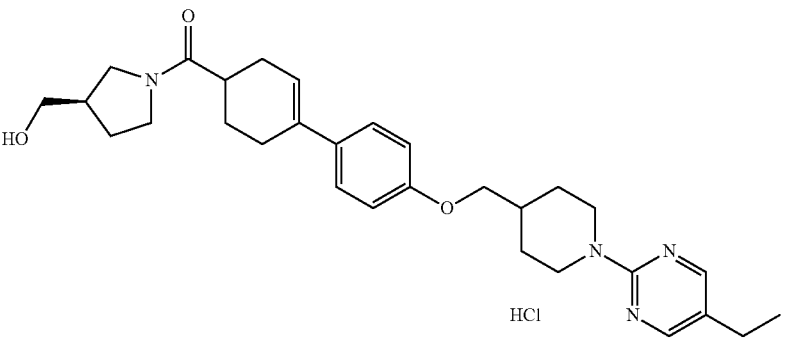 [SMILES: CCc1cnc(N2CCC(COc3ccc(C4=CCC(C(=O)N5CC[C@@H](CO)C5)CC4)cc3)CC2)nc1 ; Cl] |

TABLE 1-continued
| Examples | Chemical structures |
|---|---|
| 160 | 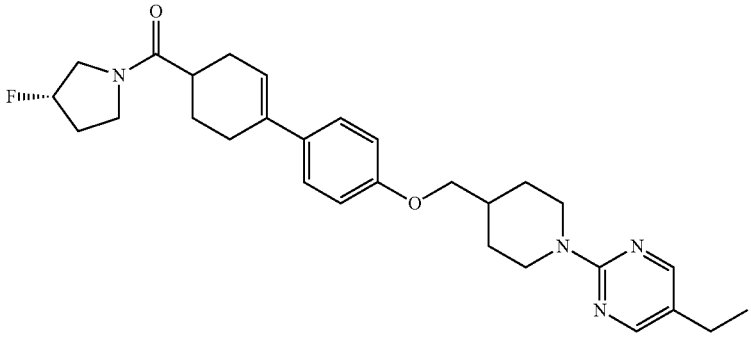 [SMILES: CCc1cnc(N2CCC(COc3ccc(C4=CCC(C(=O)N5CC[C@H](F)C5)CC4)cc3)CC2)nc1] |
| 161 | 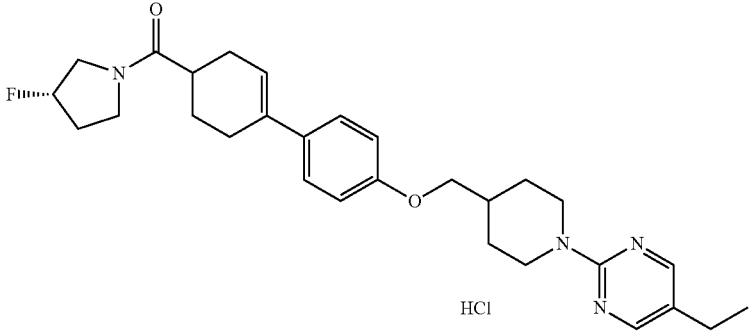 [SMILES: CCc1cnc(N2CCC(COc3ccc(C4=CCC(C(=O)N5CC[C@H](F)C5)CC4)cc3)CC2)nc1 ; Cl]
HCl |
| 162 | 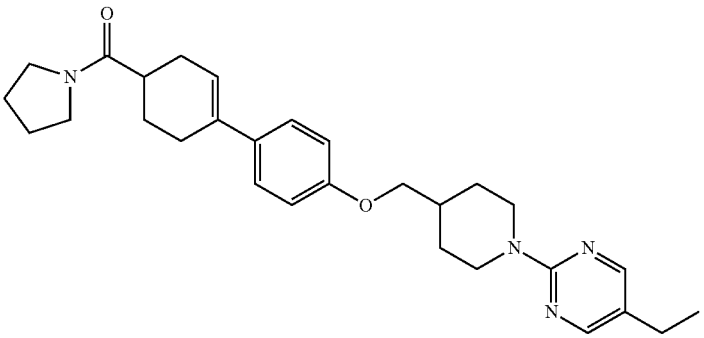 [SMILES: CCc1cnc(N2CCC(COc3ccc(C4=CCC(C(=O)N5CCCC5)CC4)cc3)CC2)nc1] |
| 163 | 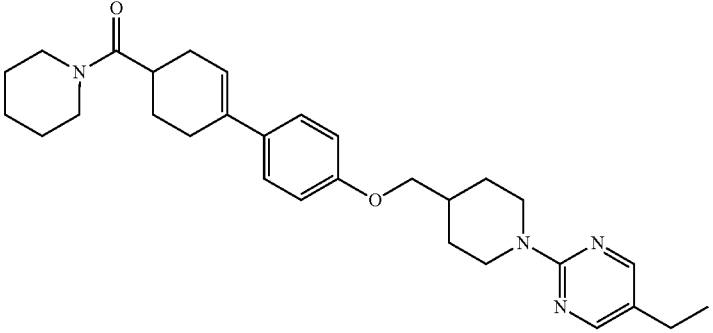 [SMILES: CCc1cnc(N2CCC(COc3ccc(C4=CCC(C(=O)N5CCCCC5)CC4)cc3)CC2)nc1] |

TABLE 1-continued
| Examples | Chemical structures |
|---|---|
| 164 | 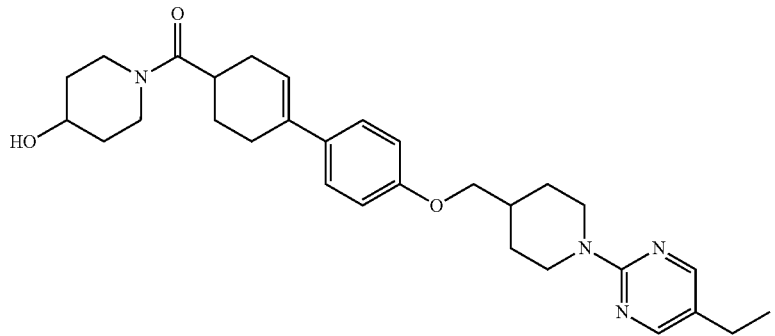 [SMILES: CCc1cnc(N2CCC(COc3ccc(C4=CCC(C(=O)N5CCC(O)CC5)CC4)cc3)CC2)nc1] |
| 165 | 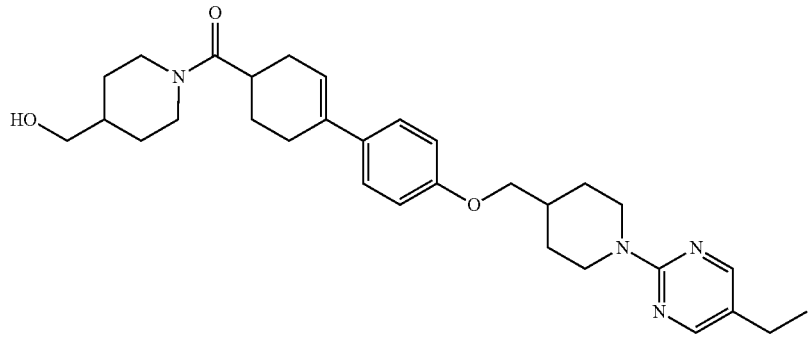 [SMILES: CCc1cnc(N2CCC(COc3ccc(C4=CCC(C(=O)N5CCC(CO)CC5)CC4)cc3)CC2)nc1] |
| 166 | 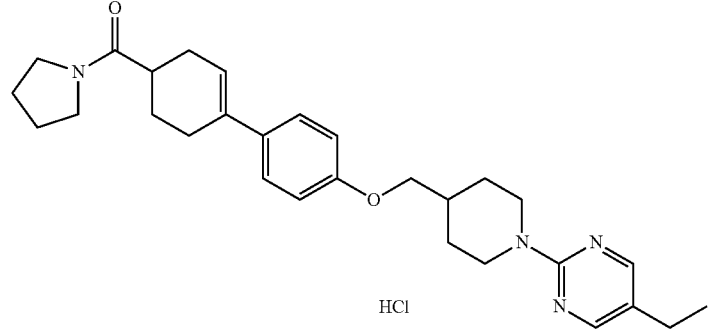 [SMILES: CCc1cnc(N2CCC(COc3ccc(C4=CCC(C(=O)N5CCCC5)CC4)cc3)CC2)nc1 ; Cl] |
| 167 | 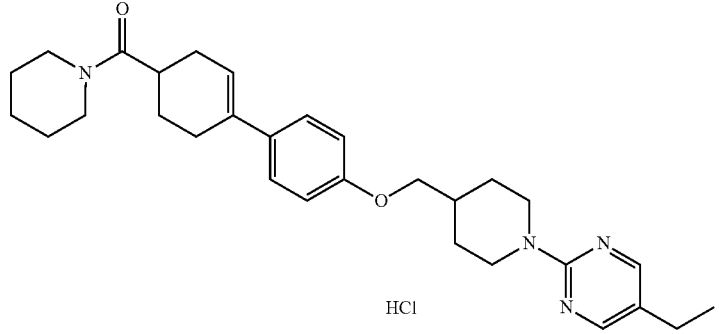 [SMILES: CCc1cnc(N2CCC(COc3ccc(C4=CCC(C(=O)N5CCCCC5)CC4)cc3)CC2)nc1 ; Cl] |

TABLE 1-continued
| Examples | Chemical structures |
|---|---|
| 168 | 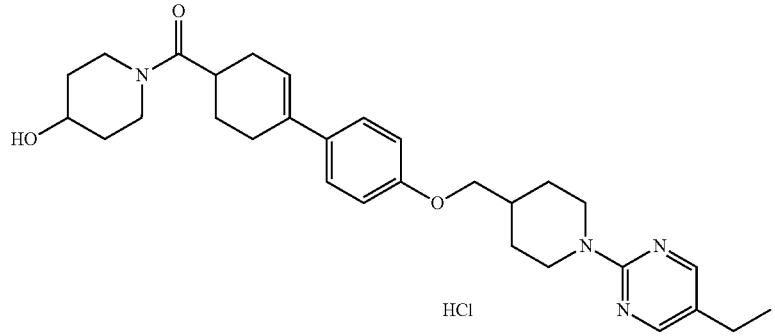 [SMILES: CCc1cnc(N2CCC(COc3ccc(C4=CCC(C(=O)N5CCC(O)CC5)CC4)cc3)CC2)nc1 ; Cl] HCl |
| 169 | 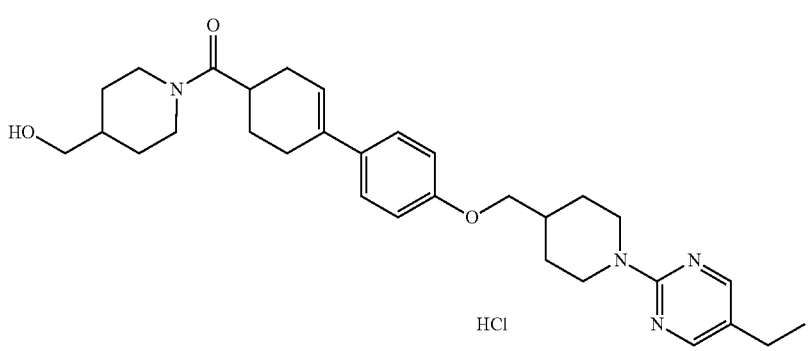 [SMILES: CCc1cnc(N2CCC(COc3ccc(C4=CCC(C(=O)N5CCC(CO)CC5)CC4)cc3)CC2)nc1 ; Cl] HCl |
| 170 | 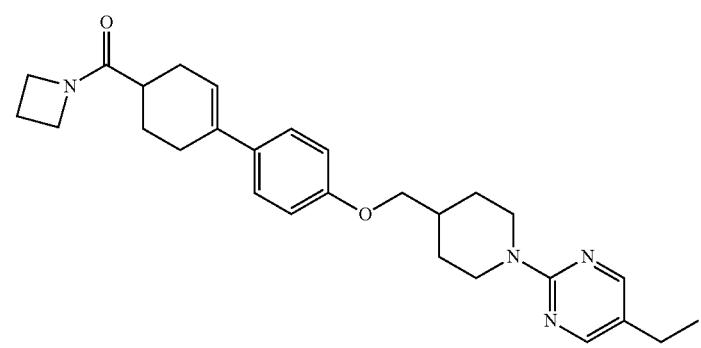 [SMILES: CCc1cnc(N2CCC(COc3ccc(C4=CCC(C(=O)N5CCC5)CC4)cc3)CC2)nc1] |
| 171 | 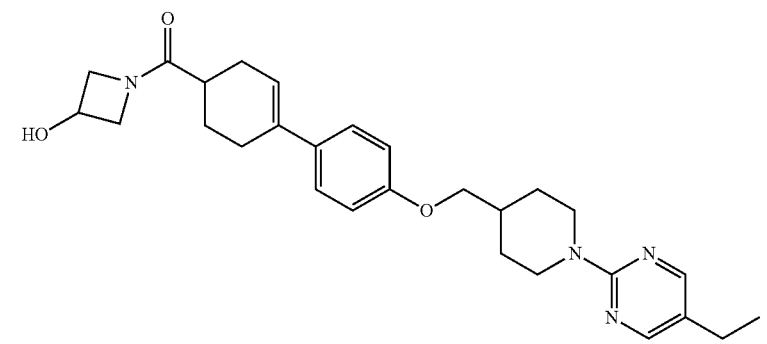 [SMILES: CCc1cnc(N2CCC(COc3ccc(C4=CCC(C(=O)N5CC(O)C5)CC4)cc3)CC2)nc1] |

TABLE 1-continued
| Examples | Chemical structures |
|---|---|
| 172 | 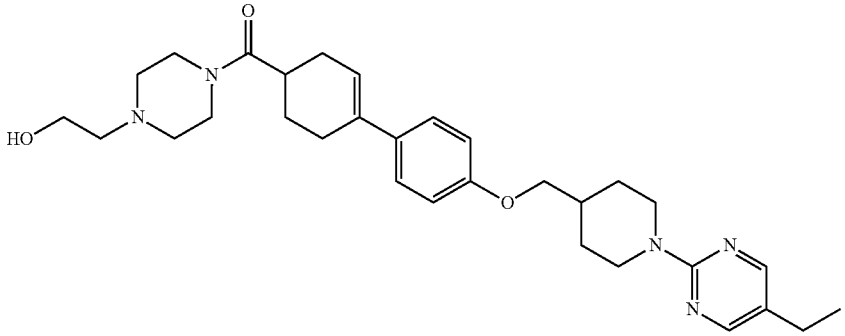 |
| 173 | 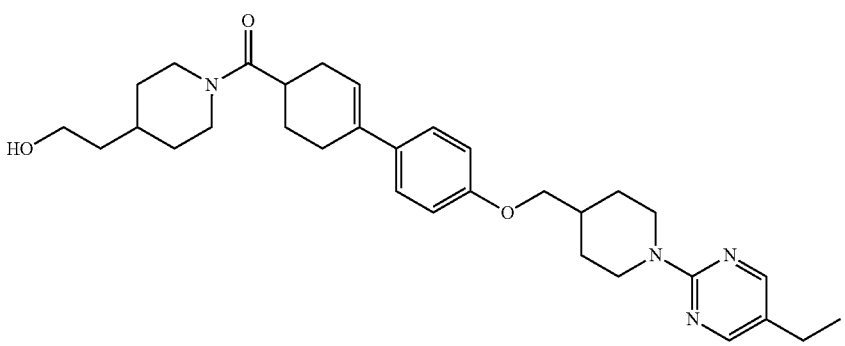 |
| 174 | 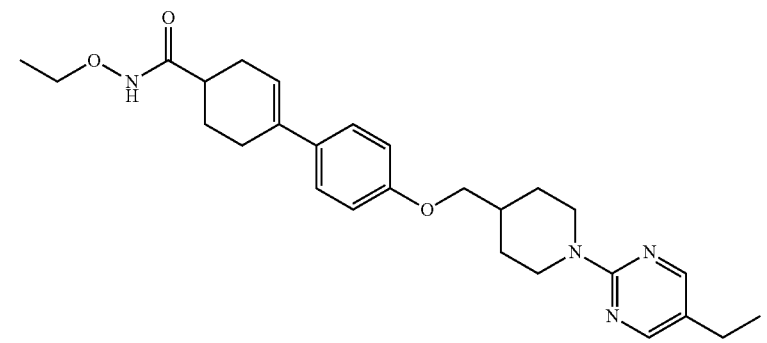 [SMILES: CCONC(=O)C1CC=C(c2ccc(OCC3CCN(c4ncc(CC)cn4)CC3)cc2)CC1] |
| 175 | 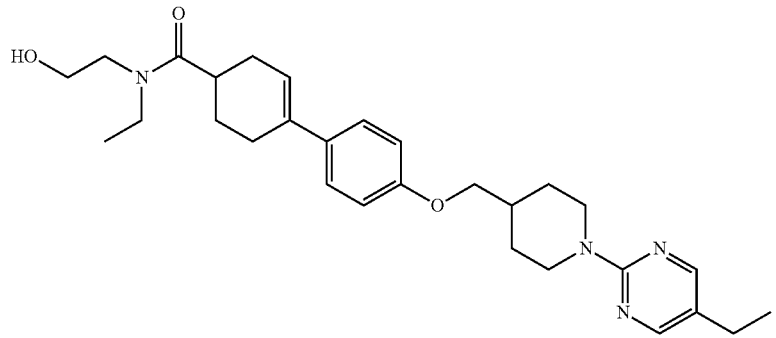 [SMILES: CCc1cnc(N2CCC(COc3ccc(C4=CCC(C(=O)N(CC)CCO)CC4)cc3)CC2)nc1] |

TABLE 1-continued
| Examples | Chemical structures |
|---|---|
| 176 | 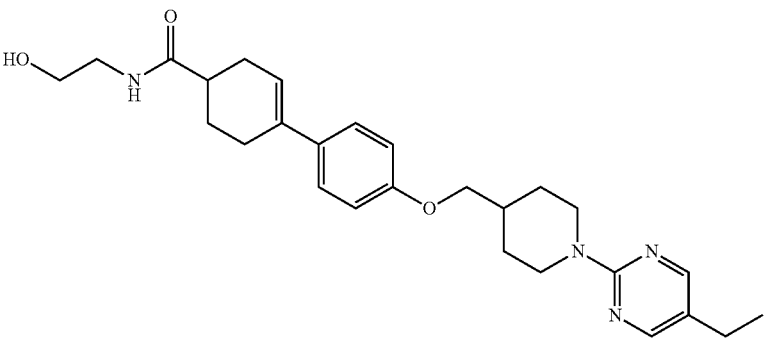 [SMILES: CCc1cnc(N2CCC(COc3ccc(C4=CCC(C(=O)NCCO)CC4)cc3)CC2)nc1] |
| 177 | 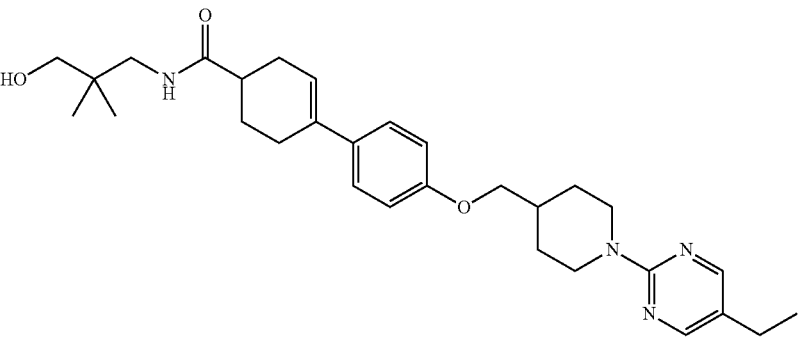 [SMILES: CCc1cnc(N2CCC(COc3ccc(C4=CCC(C(=O)NCC(C)(C)CO)CC4)cc3)CC2)nc1] |
| 178 | 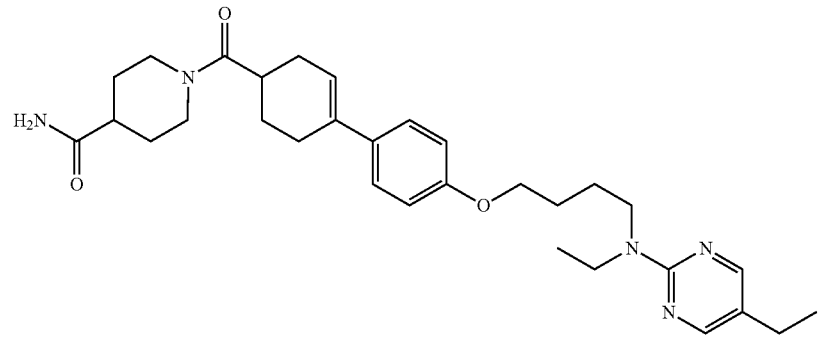 [SMILES: CCc1cnc(N(CC)CCCCOc2ccc(C3=CCC(C(=O)N4CCC(C(N)=O)CC4)CC3)cc2)nc1] |
| 179 | 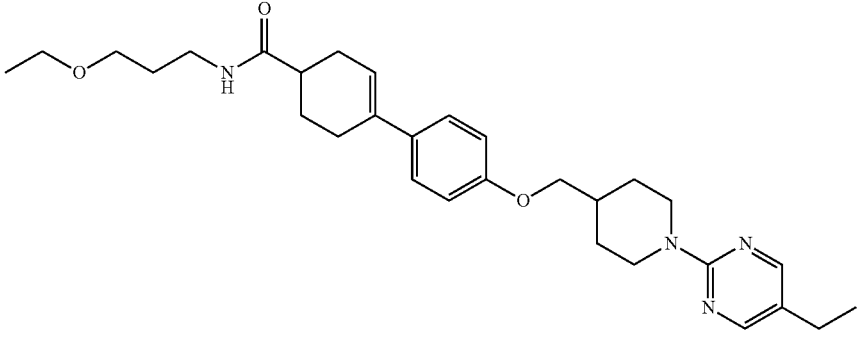 [SMILES: CCOCCCNC(=O)C1CC=C(c2ccc(OCC3CCN(c4ncc(CC)cn4)CC3)cc2)CC1] |

TABLE 1-continued
| Examples | Chemical structures |
|---|---|
| 180 | 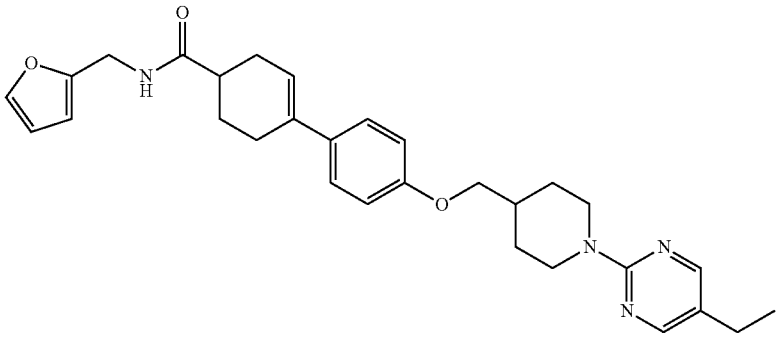 [SMILES: CCc1cnc(N2CCC(COc3ccc(C4=CCC(C(=O)NCc5ccco5)CC4)cc3)CC2)nc1] |
| 181 | 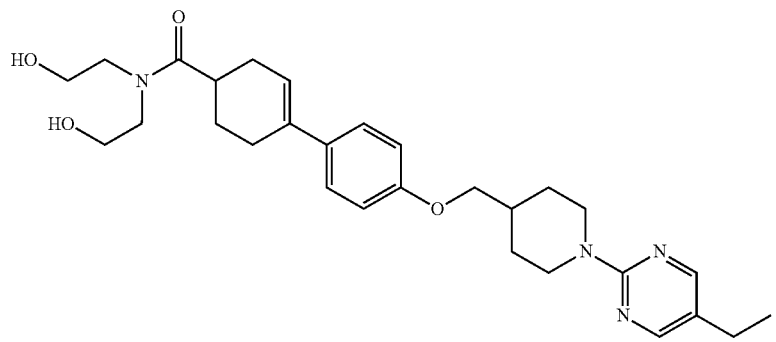 [SMILES: CCc1cnc(N2CCC(COc3ccc(C4=CCC(C(=O)N(CCO)CCO)CC4)cc3)CC2)nc1] |
| 182 | 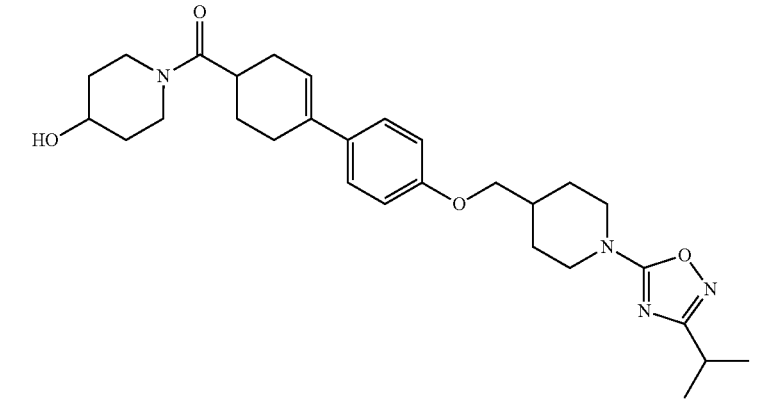 [SMILES: CC(C)c1noc(N2CCC(COc3ccc(C4=CCC(C(=O)N5CCC(O)CC5)CC4)cc3)CC2)n1] |
| 183 | 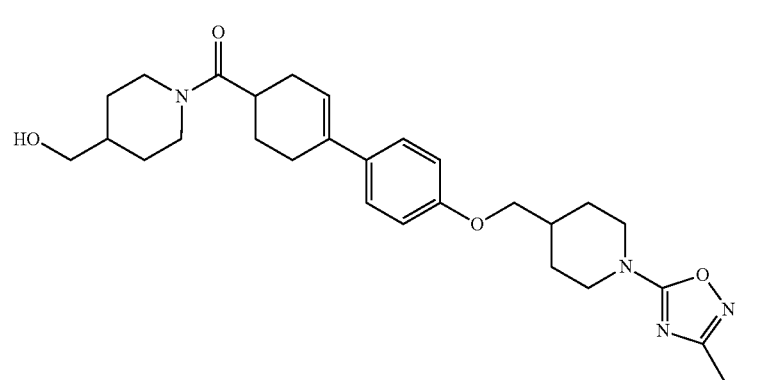 |

TABLE 1-continued
| Examples | Chemical structures |
|---|---|
| 184 | 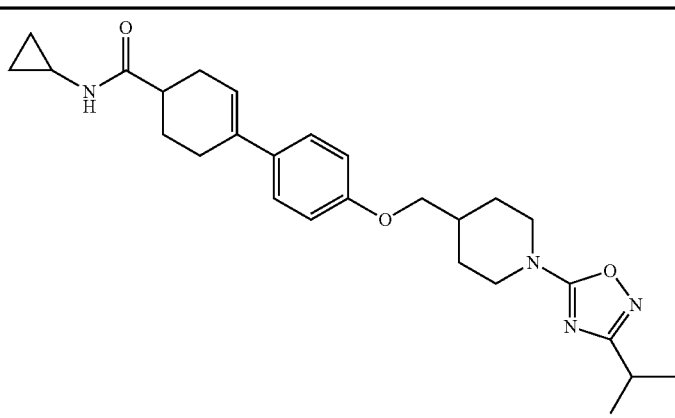 |
| 185 | 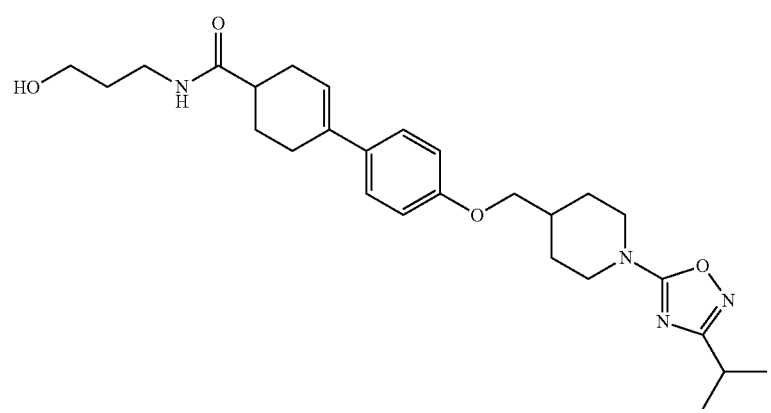 [SMILES: CC(C)c1noc(N2CCC(COc3ccc(C4=CCC(C(=O)NCCCO)CC4)cc3)CC2)n1] |
| 186 | 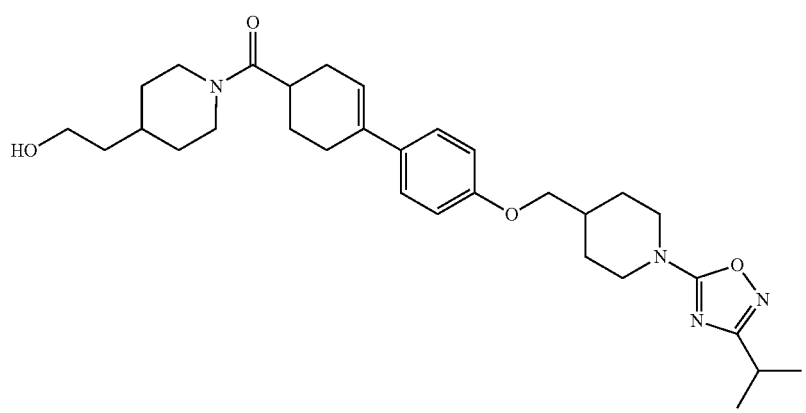 [SMILES: CC(C)c1noc(N2CCC(COc3ccc(C4=CCC(C(=O)N5CCC(CCO)CC5)CC4)cc3)CC2)n1] |
| 187 | 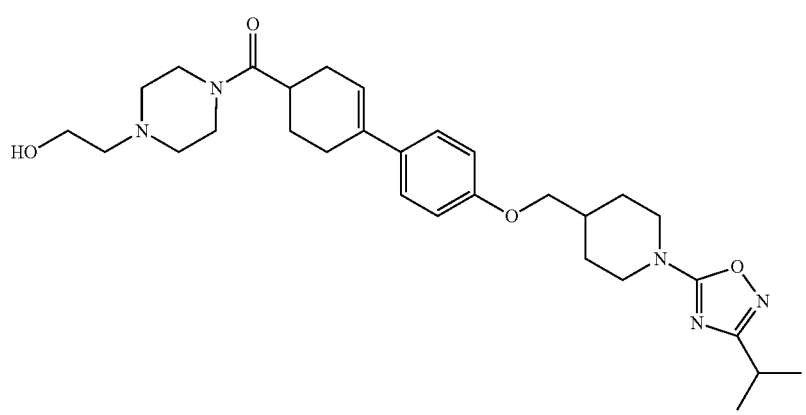 [SMILES: CC(C)c1noc(N2CCC(COc3ccc(C4=CCC(C(=O)N5CCN(CCO)CC5)CC4)cc3)CC2)n1] |

TABLE 1-continued
| Examples | Chemical structures |
| --- | --- |
| 188 | 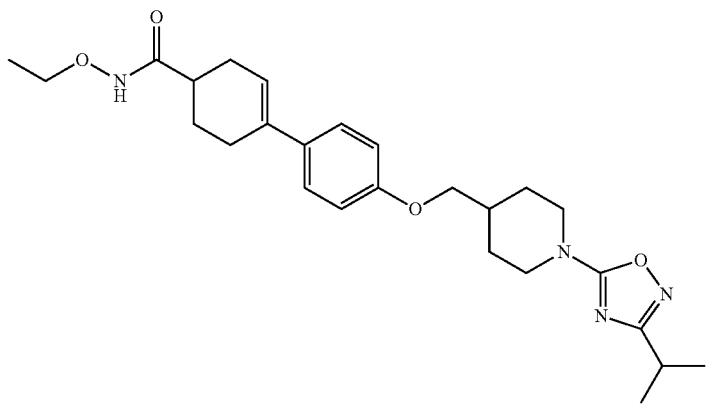 [SMILES: CCONC(=O)C1CC=C(c2ccc(OCC3CCN(c4nc(C(C)C)no4)CC3)cc2)CC1] |
| 189 | 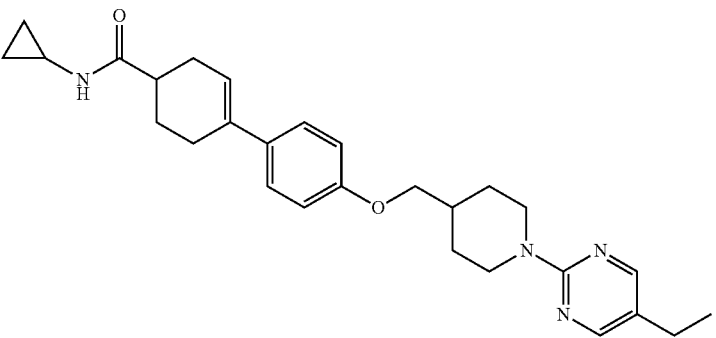 [SMILES: CCc1cnc(N2CCC(COc3ccc(C4=CCC(C(=O)NC5CC5)CC4)cc3)CC2)nc1] |
| 190 | 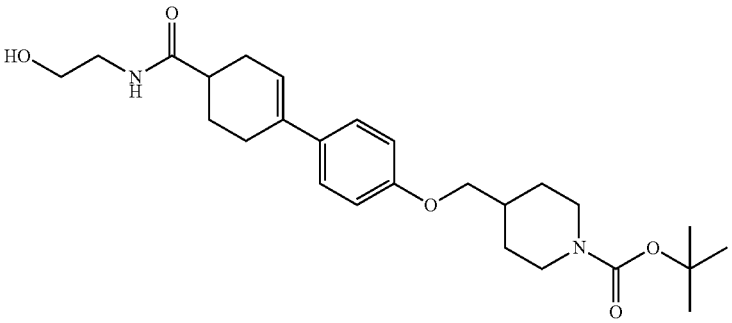 |
| 191 | 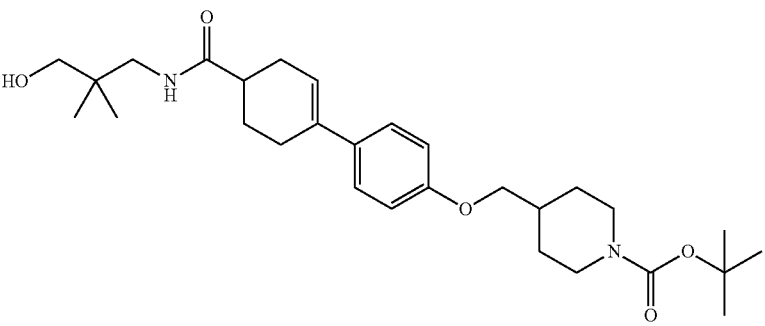 [SMILES: CC(C)(CO)CNC(=O)C1CC=C(c2ccc(OCC3CCN(C(=O)OC(C)(C)C)CC3)cc2)CC1] |

TABLE 1-continued
| Examples | Chemical structures |
|---|---|
| 192 | 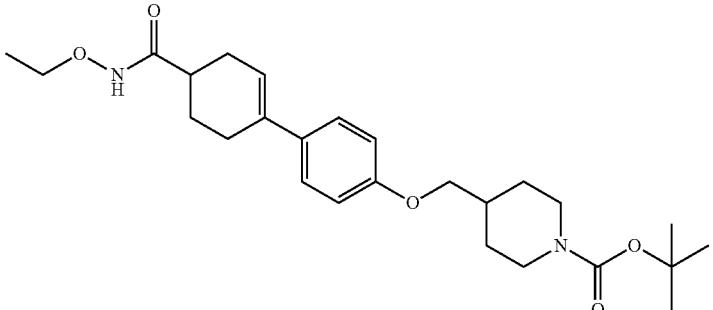 |
| 193 | 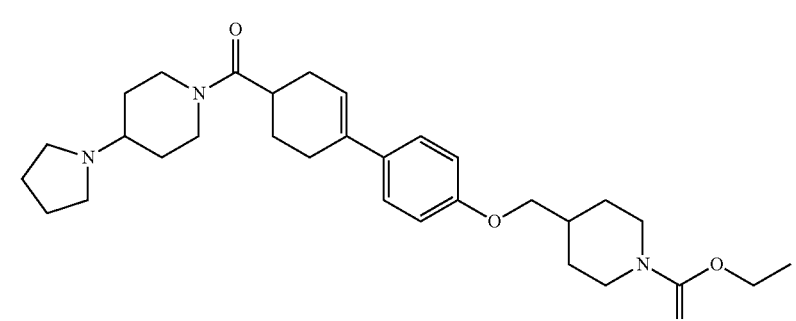 |
| 194 | 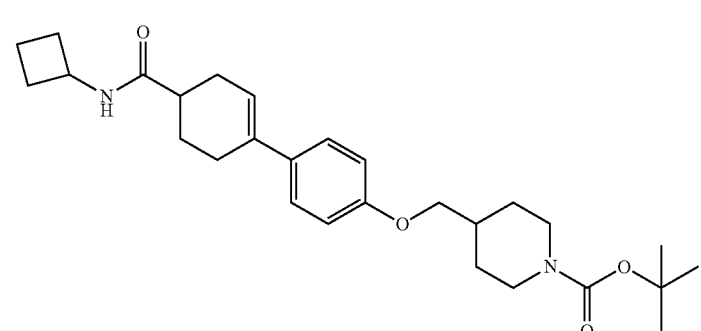 |
| 195 | 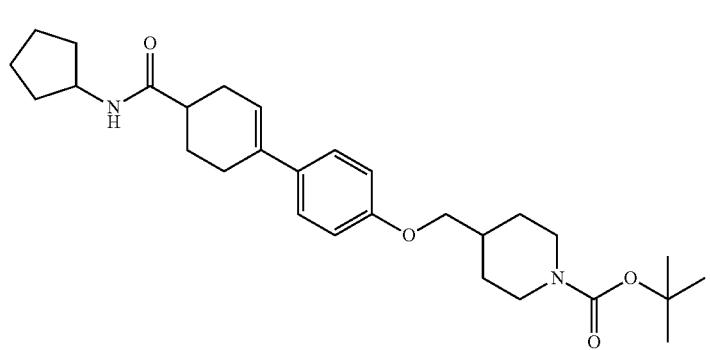 [SMILES: CC(C)(C)OC(=O)N1CCC(COc2ccc(C3=CCC(C(=O)NC4CCCC4)CC3)cc2)CC1] |

TABLE 1-continued
| Examples | Chemical structures |
|---|---|
| 196 | 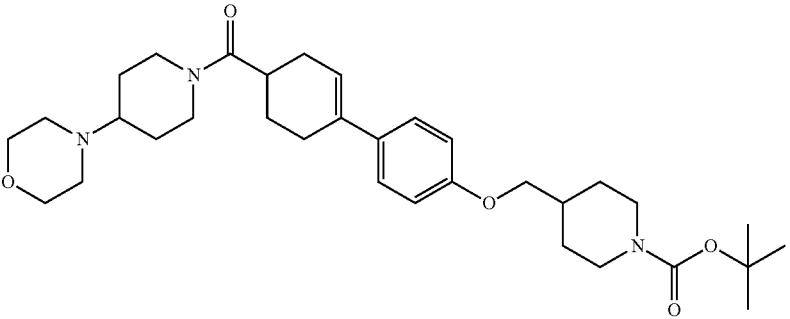 [SMILES: CC(C)(C)OC(=O)N1CCC(COc2ccc(C3=CCC(C(=O)N4CCC(N5CCOCC5)CC4)CC3)cc2)CC1] |
| 197 | 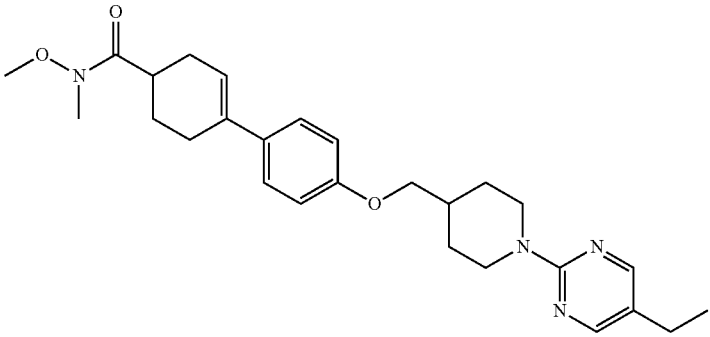 [SMILES: CCc1cnc(N2CCC(COc3ccc(C4=CCC(C(=O)N(C)OC)CC4)cc3)CC2)nc1] |
| 198 | 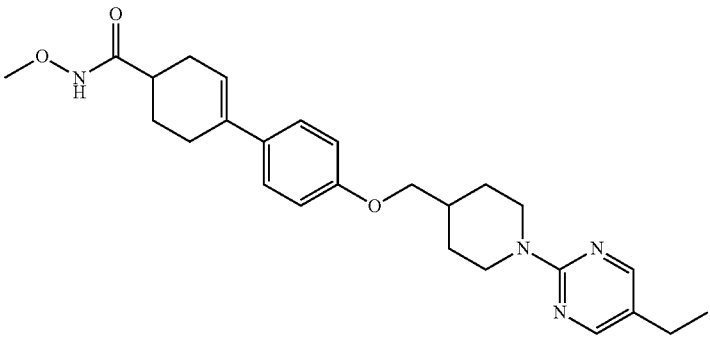 [SMILES: CCc1cnc(N2CCC(COc3ccc(C4=CCC(C(=O)NOC)CC4)cc3)CC2)nc1] |
| 199 | 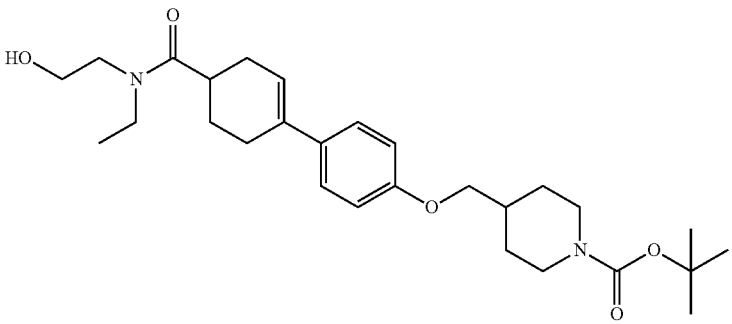 [SMILES: CCN(CCO)C(=O)C1CC=C(c2ccc(OCC3CCN(C(=O)OC(C)(C)C)CC3)cc2)CC1] |

TABLE 1-continued
| Examples | Chemical structures |
|---|---|
| 200 | 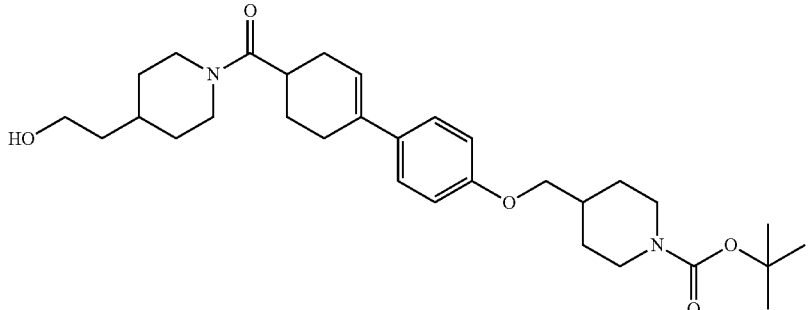 |
| 201 | 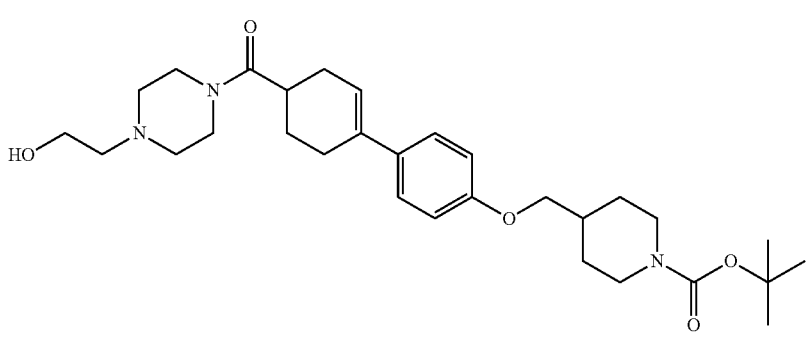 [SMILES: CC(C)(C)OC(=O)N1CCC(COc2ccc(C3=CCC(C(=O)N4CCN(CCO)CC4)CC3)cc2)CC1] |
| 202 | 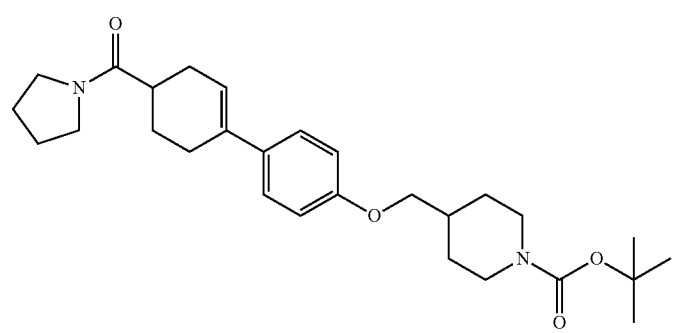 [SMILES: CC(C)(C)OC(=O)N1CCC(COc2ccc(C3=CCC(C(=O)N4CCCC4)CC3)cc2)CC1] |
| 203 | 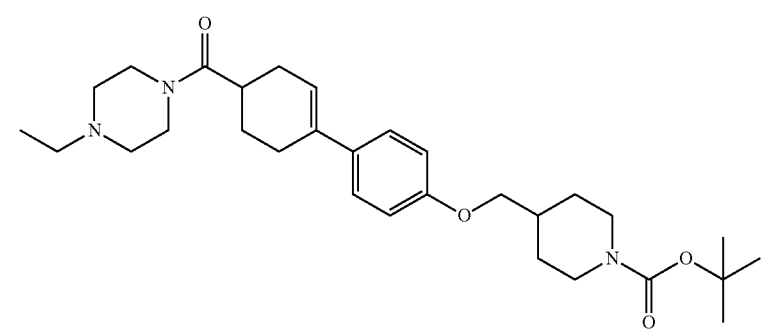 [SMILES: CCN1CCN(C(=O)C2CC=C(c3ccc(OCC4CCN(C(=O)OC(C)(C)C)CC4)cc3)CC2)CC1] |

TABLE 1-continued
| Examples | Chemical structures |
|---|---|
| 204 | 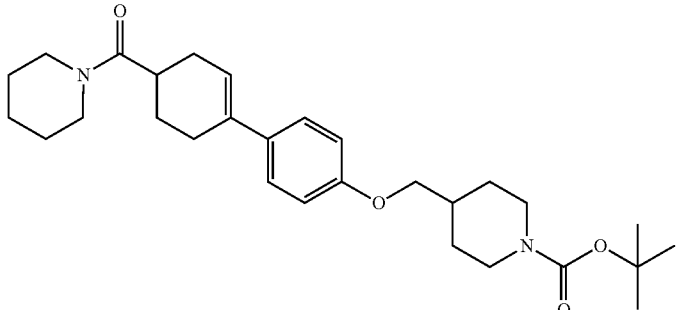 |
| 205 | 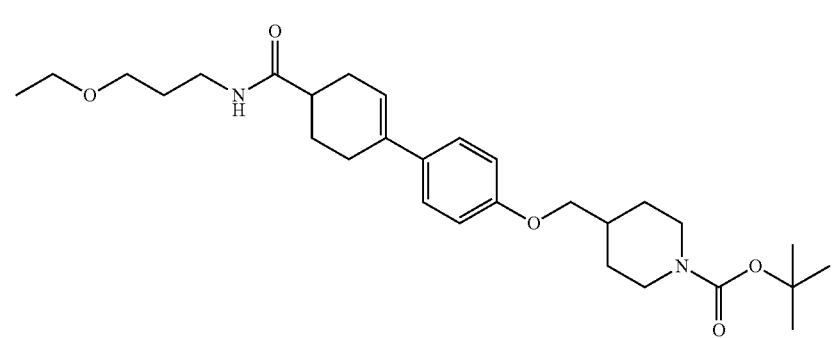 [SMILES: CCOCCCNC(=O)C1CC=C(c2ccc(OCC3CCN(C(=O)OC(C)(C)C)CC3)cc2)CC1] |
| 206 | 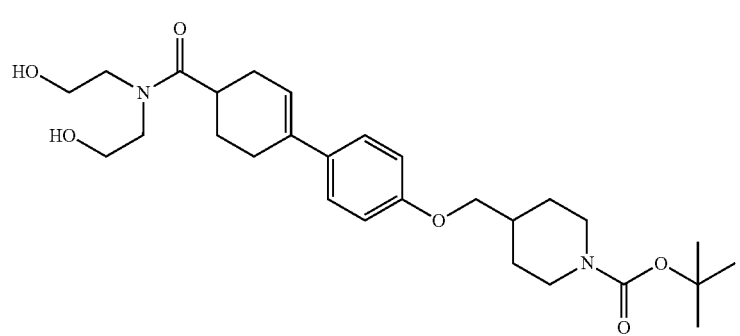 [SMILES: CC(C)(C)OC(=O)N1CCC(COc2ccc(C3=CCC(C(=O)N(CCO)CCO)CC3)cc2)CC1] |
| 207 | 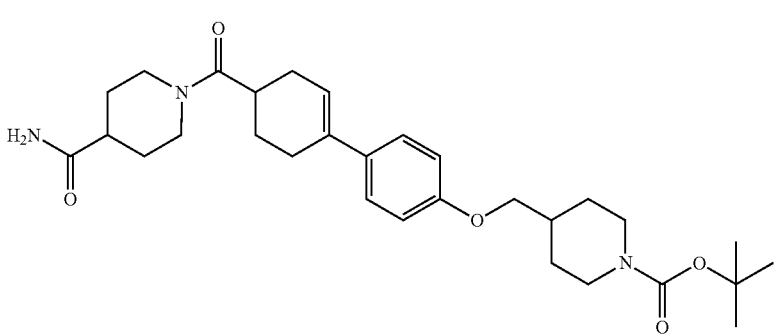 [SMILES: CC(C)(C)OC(=O)N1CCC(COc2ccc(C3=CCC(C(=O)N4CCC(C(N)=O)CC4)CC3)cc2)CC1] |

TABLE 1-continued
| Examples | Chemical structures |
|---|---|
| 208 | 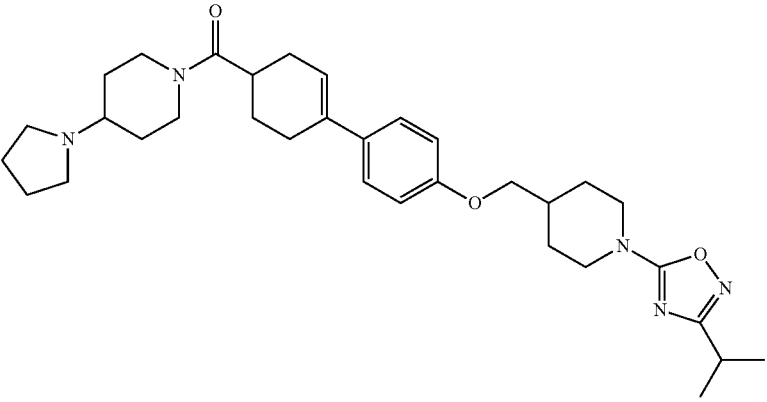 [SMILES: CC(C)c1noc(N2CCC(COc3ccc(C4=CCC(C(=O)N5CCC(N6CCCC6)CC5)CC4)cc3)CC2)n1] |
| 209 | 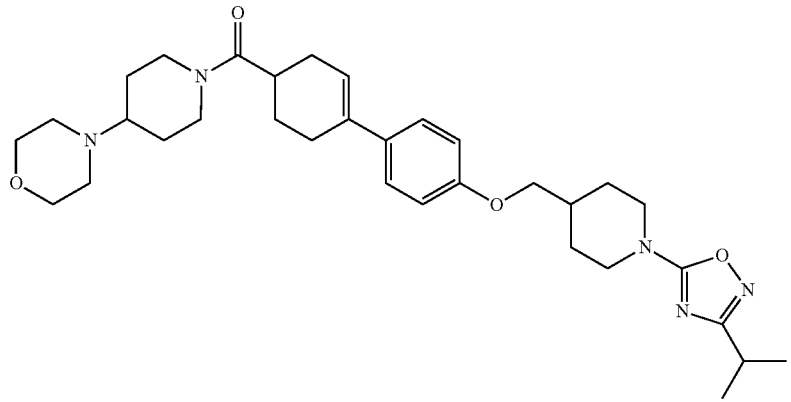 [SMILES: CC(C)c1noc(N2CCC(COc3ccc(C4=CCC(C(=O)N5CCC(N6CCOCC6)CC5)CC4)cc3)CC2)n1] |
| 210 | 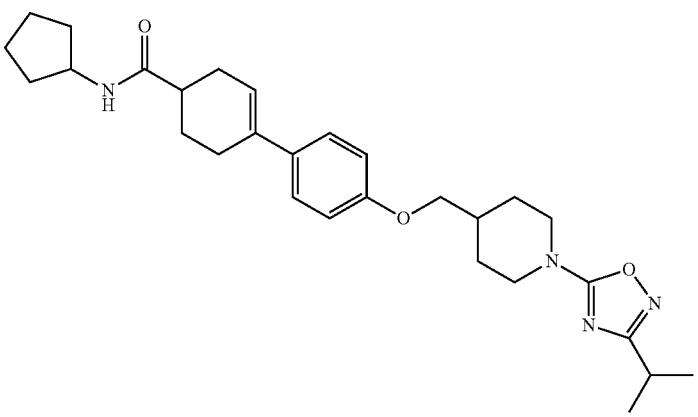 [SMILES: CC(C)c1noc(N2CCC(COc3ccc(C4=CCC(C(=O)NC5CCCC5)CC4)cc3)CC2)n1] |

TABLE 1-continued

| Examples | Chemical structures |
|---|---|
| 211 | 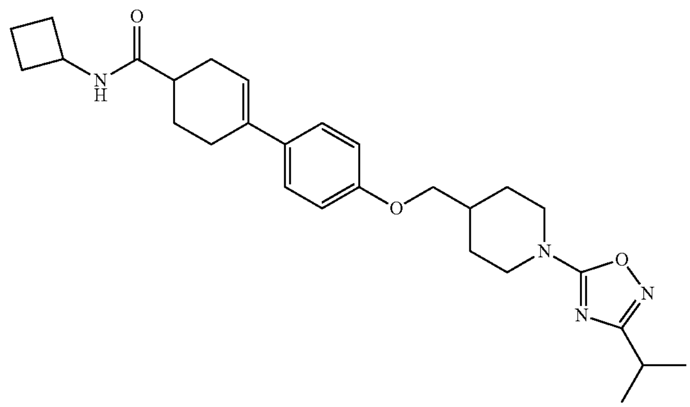 [SMILES: CC(C)c1noc(N2CCC(COc3ccc(C4=CCC(C(=O)NC5CCC5)CC4)cc3)CC2)n1] |
| 212 | 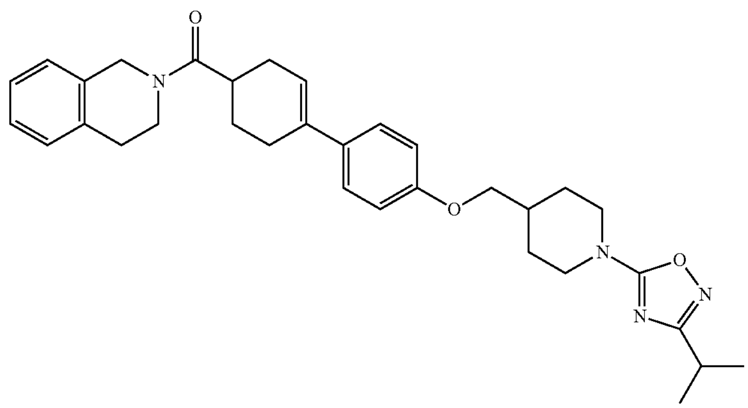 [SMILES: CC(C)c1noc(N2CCC(COc3ccc(C4=CCC(C(=O)N5CCc6ccccc6C5)CC4)cc3)CC2)n1] |
| 213 | 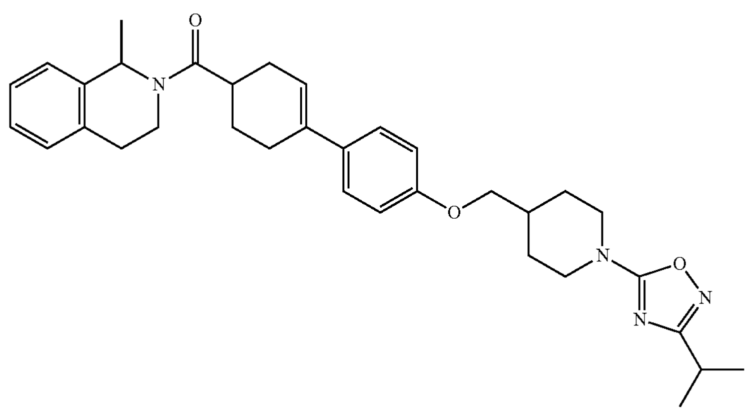 [SMILES: CC(C)c1noc(N2CCC(COc3ccc(C4=CCC(C(=O)N5CCc6ccccc6C5C)CC4)cc3)CC2)n1] |
| 214 | 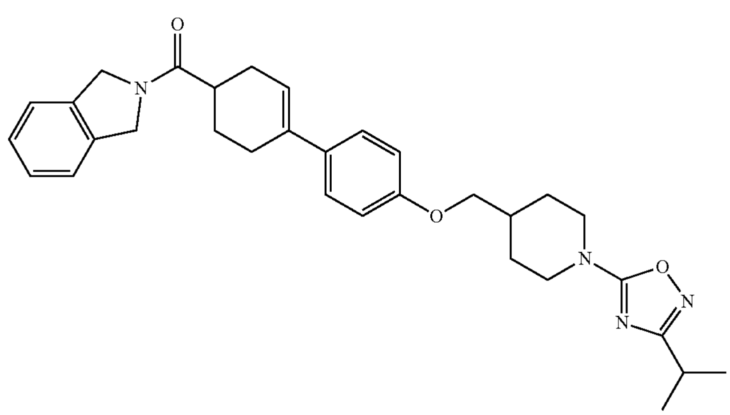 [SMILES: CC(C)c1noc(N2CCC(COc3ccc(C4=CCC(C(=O)N5Cc6ccccc6C5)CC4)cc3)CC2)n1] |

TABLE 1-continued

| Examples | Chemical structures |
|---|---|
| 215 | 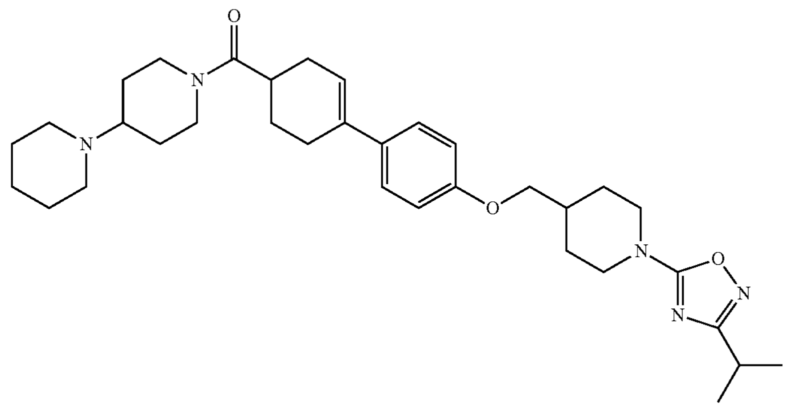 [SMILES: CC(C)c1noc(N2CCC(COc3ccc(C4=CCC(C(=O)N5CCC(N6CCCCC6)CC5)CC4)cc3)CC2)n1] |
| 216 | 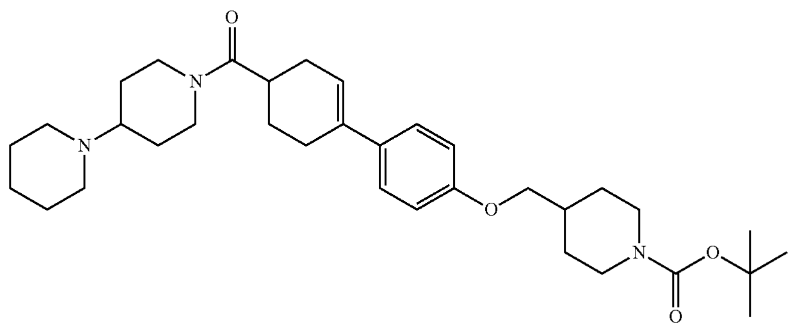 [SMILES: CC(C)(C)OC(=O)N1CCC(COc2ccc(C3=CCC(C(=O)N4CCC(N5CCCCC5)CC4)CC3)cc2)CC1] |
| 217 | 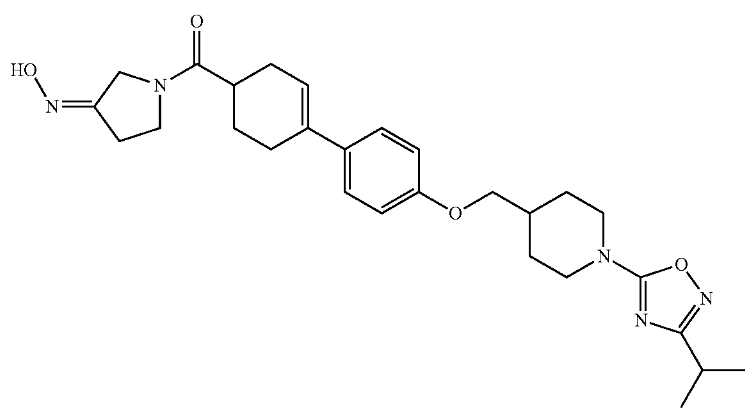 [SMILES: CC(C)c1noc(N2CCC(COc3ccc(C4=CCC(C(=O)N5CC/C(=N/O)C5)CC4)cc3)CC2)n1] |
| 218 | 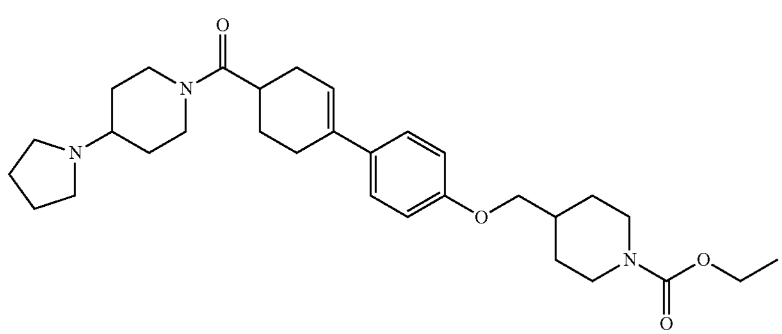 [SMILES: CCOC(=O)N1CCC(COc2ccc(C3=CCC(C(=O)N4CCC(N5CCCC5)CC4)CC3)cc2)CC1] |

TABLE 1-continued
| Examples | Chemical structures |
|---|---|
| 219 | 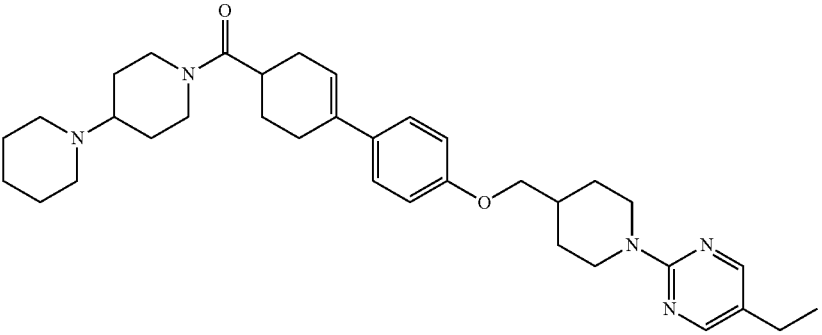 [SMILES: CCc1cnc(N2CCC(COc3ccc(C4=CCC(C(=O)N5CCC(N6CCCCC6)CC5)CC4)cc3)CC2)nc1] |
| 220 | 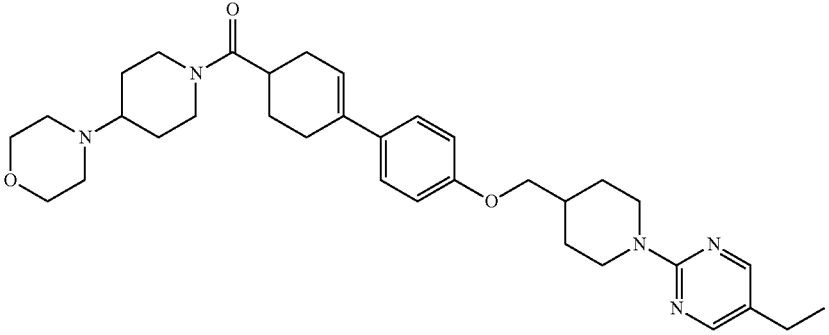 [SMILES: CCc1cnc(N2CCC(COc3ccc(C4=CCC(C(=O)N5CCC(N6CCOCC6)CC5)CC4)cc3)CC2)nc1] |
| 221 | 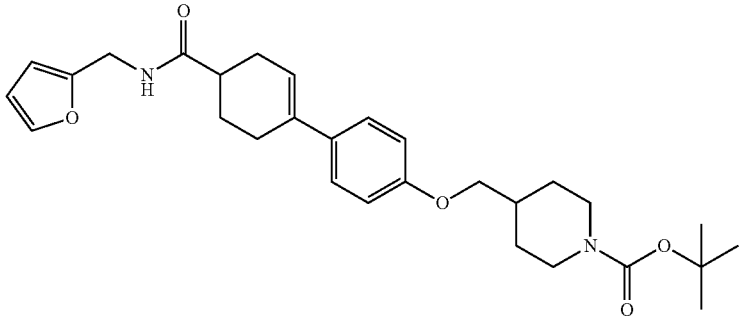 [SMILES: CC(C)(C)OC(=O)N1CCC(COc2ccc(C3=CCC(C(=O)NCc4ccco4)CC3)cc2)CC1] |
| 222 | 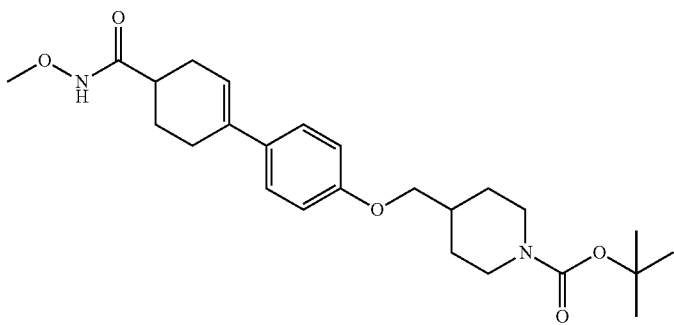 [SMILES: CONC(=O)C1CC=C(c2ccc(OCC3CCN(C(=O)OC(C)(C)C)CC3)cc2)CC1] |

TABLE 1-continued
| Examples | Chemical structures |
|---|---|
| 223 | 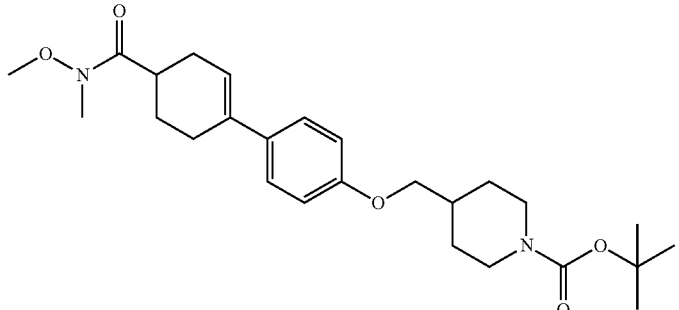 |
| 224 | 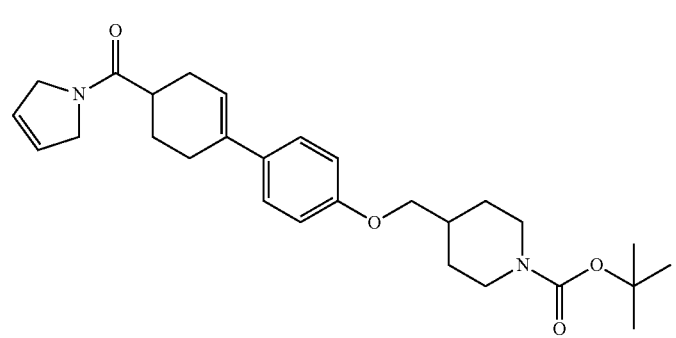 [SMILES: CC(C)(C)OC(=O)N1CCC(COc2ccc(C3=CCC(C(=O)N4CC=CC4)CC3)cc2)CC1] |
| 225 | 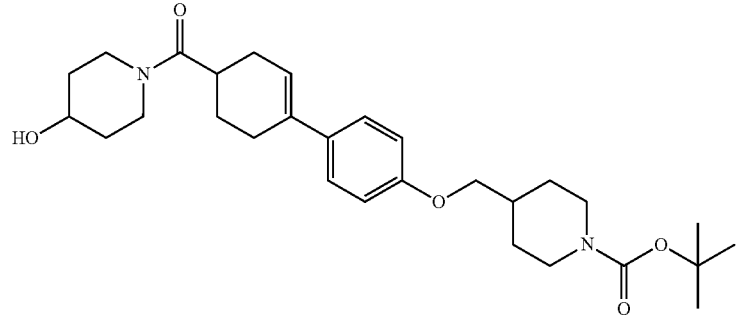 [SMILES: CC(C)(C)OC(=O)N1CCC(COc2ccc(C3=CCC(C(=O)N4CCC(O)CC4)CC3)cc2)CC1] |
| 226 | 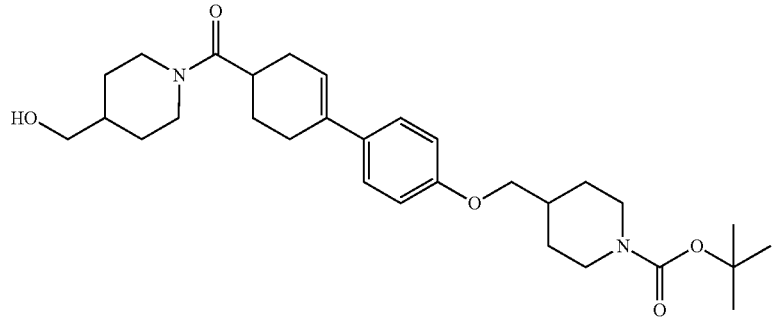 [SMILES: CC(C)(C)OC(=O)N1CCC(COc2ccc(C3=CCC(C(=O)N4CCC(CO)CC4)CC3)cc2)CC1] |

TABLE 1-continued
| Examples | Chemical structures |
|---|---|
| 227 | 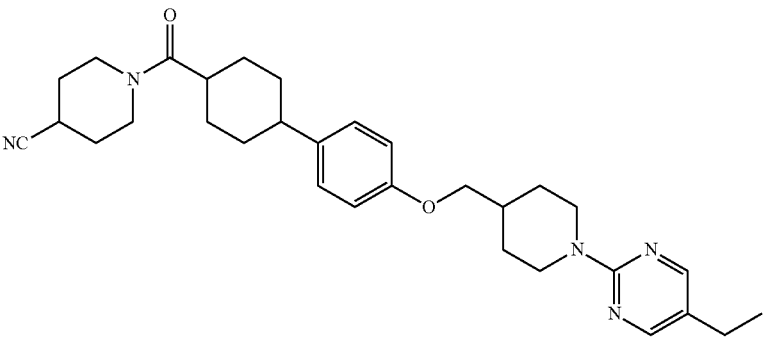 [SMILES: CCc1cnc(N2CCC(COc3ccc(C4CCC(C(=O)N5CCC(C#N)CC5)CC4)cc3)CC2)nc1] |
| 228 | 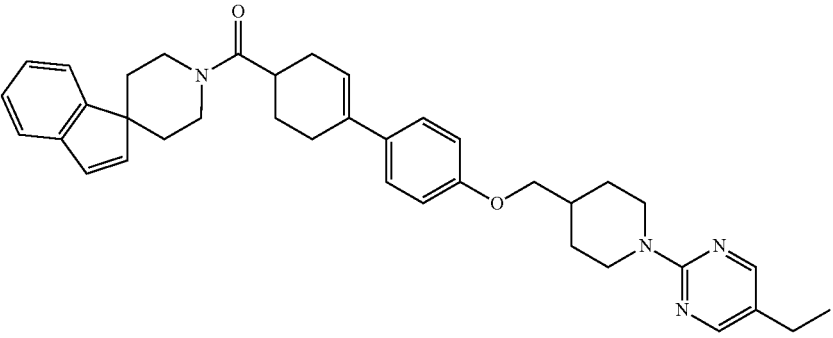 [SMILES: CCc1cnc(N2CCC(COc3ccc(C4=CCC(C(=O)N5CCC6(C=Cc7ccccc76)CC5)CC4)cc3)CC2)nc1] |
| 229 | 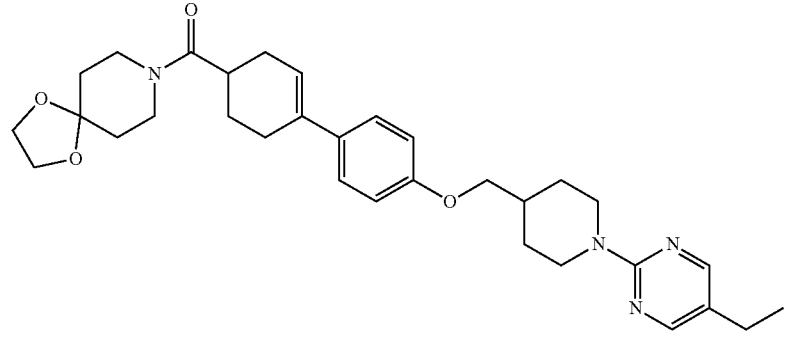 [SMILES: CCc1cnc(N2CCC(COc3ccc(C4=CCC(C(=O)N5CCC6(CC5)OCCO6)CC4)cc3)CC2)nc1] |
| 230 | 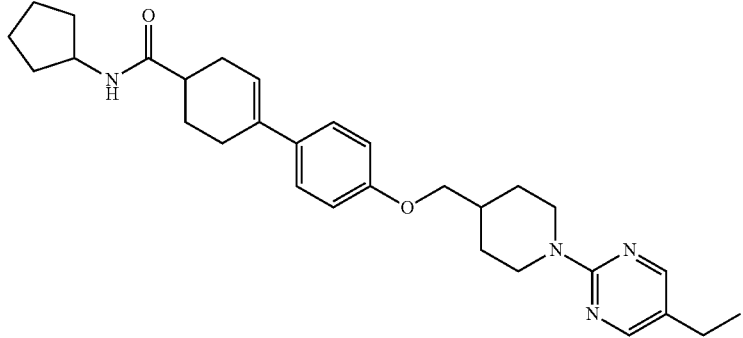 [SMILES: CCc1cnc(N2CCC(COc3ccc(C4=CCC(C(=O)NC5CCCC5)CC4)cc3)CC2)nc1] |

TABLE 1-continued
| Examples | Chemical structures |
|---|---|
| 231 | 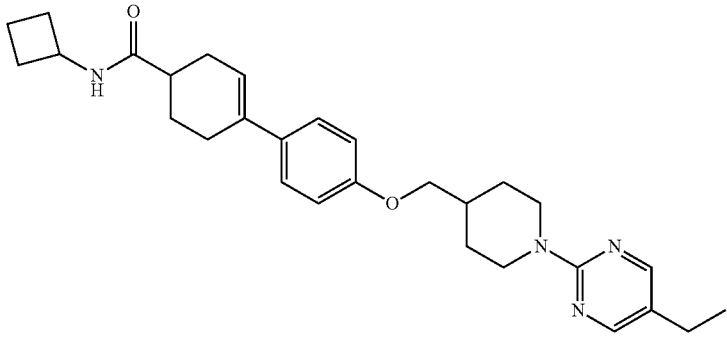 [SMILES: CCc1cnc(N2CCC(COc3ccc(C4=CCC(C(=O)NC5CCC5)CC4)cc3)CC2)nc1] |
| 232 | 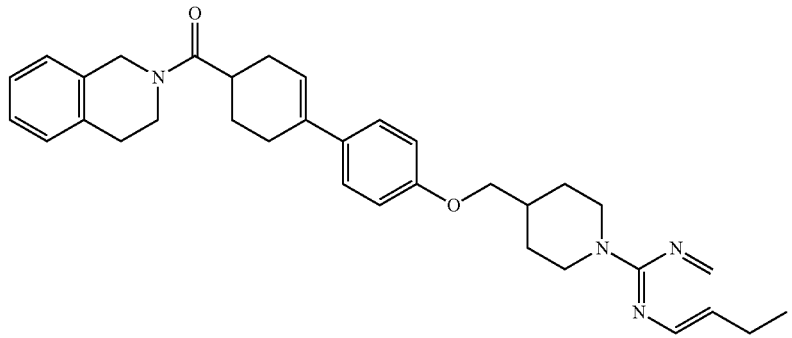 [SMILES: C=N/C(=N\C=C\CC)N1CCC(COc2ccc(C3=CCC(C(=O)N4CCc5ccccc5C4)CC3)cc2)CC1] |
| 233 | 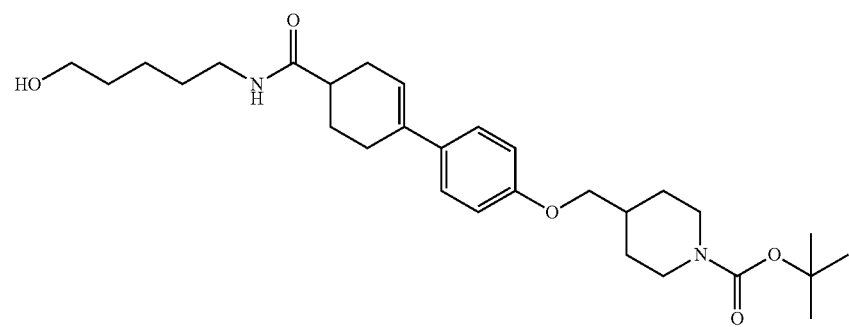 [SMILES: CC(C)(C)OC(=O)N1CCC(COc2ccc(C3=CCC(C(=O)NCCCCCO)CC3)cc2)CC1] |
| 234 | 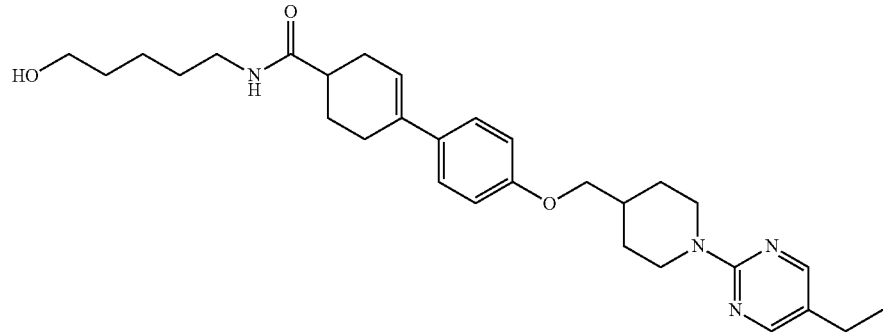 [SMILES: CCc1cnc(N2CCC(COc3ccc(C4=CCC(C(=O)NCCCCCO)CC4)cc3)CC2)nc1] |

TABLE 1-continued
| Examples | Chemical structures |
|---|---|
| 235 | 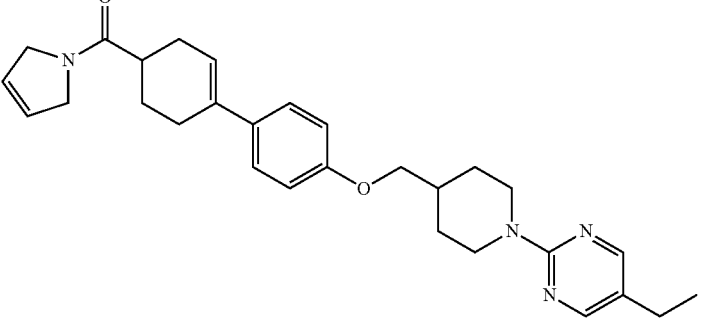 |
| 236 | 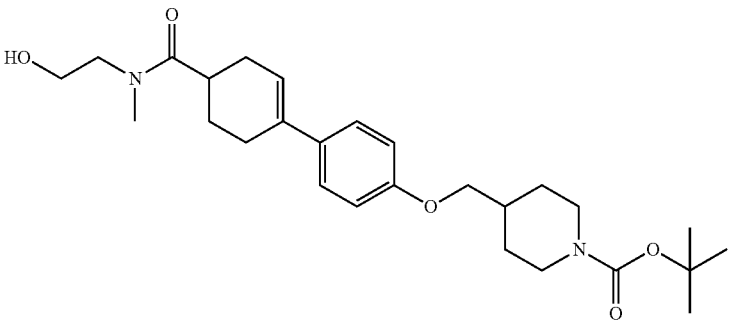 [SMILES: CN(CCO)C(=O)C1CC=C(c2ccc(OCC3CCN(C(=O)OC(C)(C)C)CC3)cc2)CC1] |
| 237 | 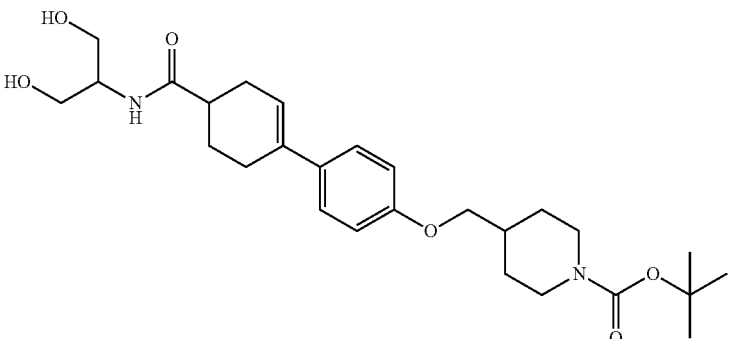 |
| 238 | 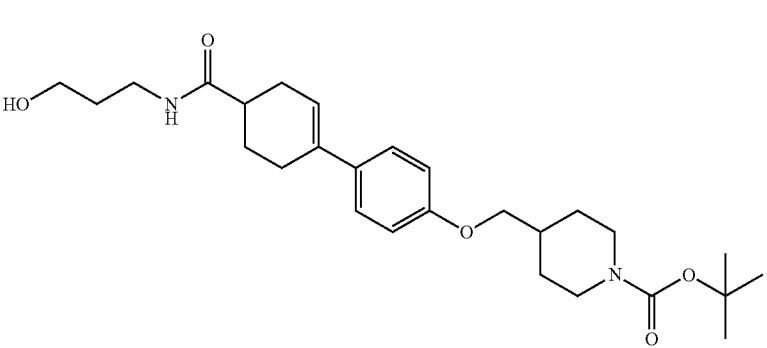 [SMILES: CC(C)(C)OC(=O)N1CCC(COc2ccc(C3=CCC(C(=O)NCCCO)CC3)cc2)CC1] |

TABLE 1-continued
| Examples | Chemical structures |
|---|---|
| 239 | 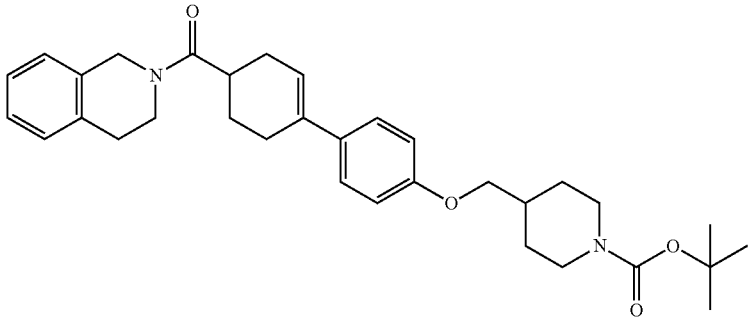 [SMILES: CC(C)(C)OC(=O)N1CCC(COc2ccc(C3=CCC(C(=O)N4CCc5ccccc5C4)CC3)cc2)CC1] |
| 240 | 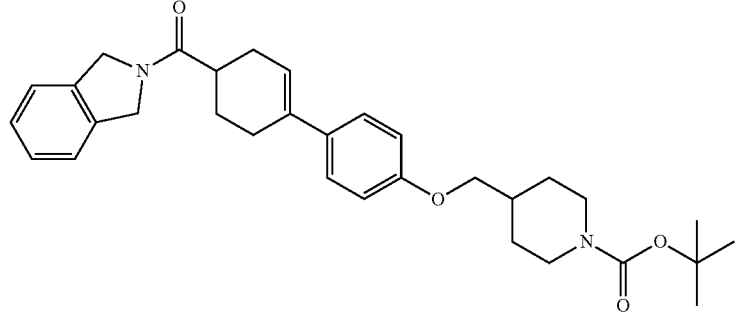 [SMILES: CC(C)(C)OC(=O)N1CCC(COc2ccc(C3=CCC(C(=O)N4Cc5ccccc5C4)CC3)cc2)CC1] |
| 241 | 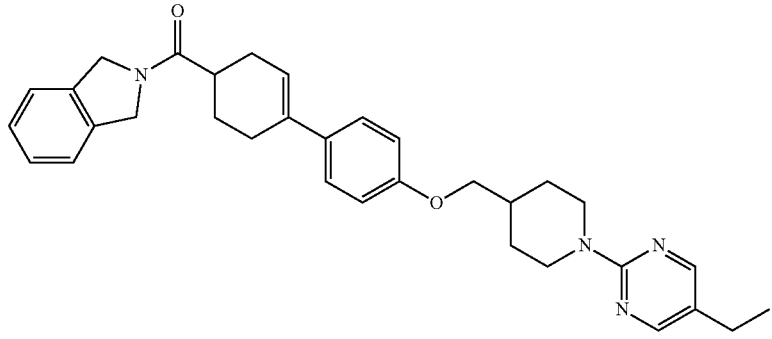 [SMILES: CCc1cnc(N2CCC(COc3ccc(C4=CCC(C(=O)N5Cc6ccccc6C5)CC4)cc3)CC2)nc1] |
| 242 | 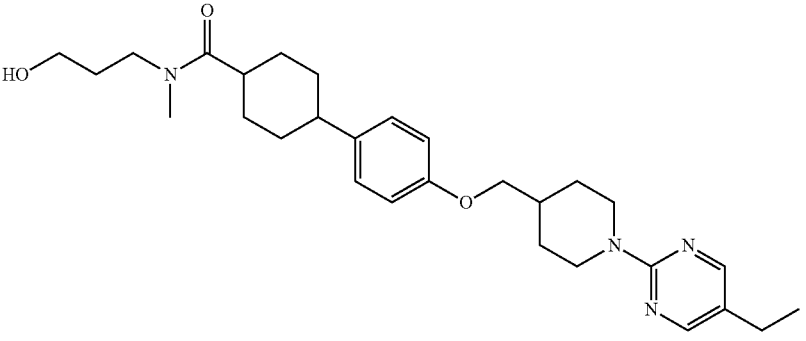 [SMILES: CCc1cnc(N2CCC(COc3ccc(C4CCC(C(=O)N(C)CCCO)CC4)cc3)CC2)nc1] |

TABLE 1-continued
| Examples | Chemical structures |
|---|---|
| 243 | 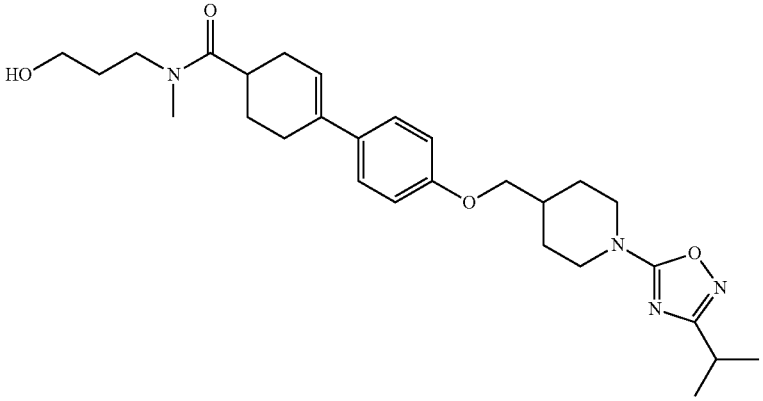 [SMILES: CC(C)c1noc(N2CCC(COc3ccc(C4=CCC(C(=O)N(C)CCCO)CC4)cc3)CC2)n1] |
| 244 | 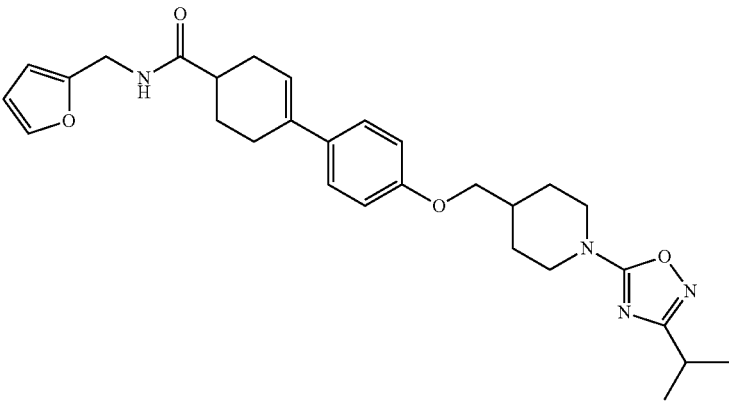 [SMILES: CC(C)c1noc(N2CCC(COc3ccc(C4=CCC(C(=O)NCc5ccco5)CC4)cc3)CC2)n1] |
| 245 | 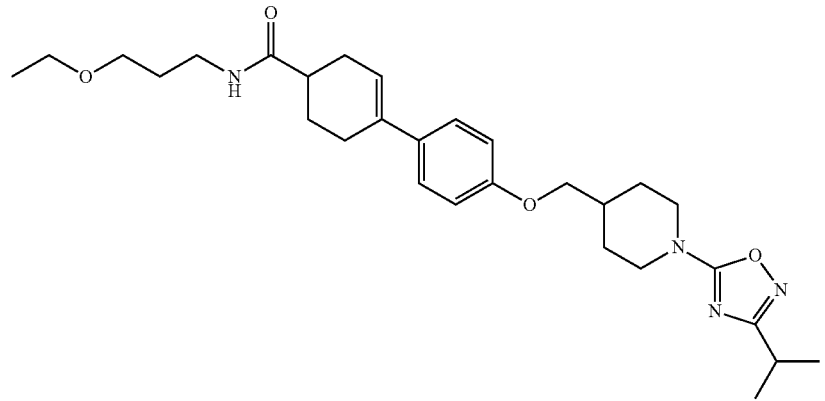 [SMILES: CCOCCCNC(=O)C1CC=C(c2ccc(OCC3CCN(c4nc(C(C)C)no4)CC3)cc2)CC1] |
| 246 | 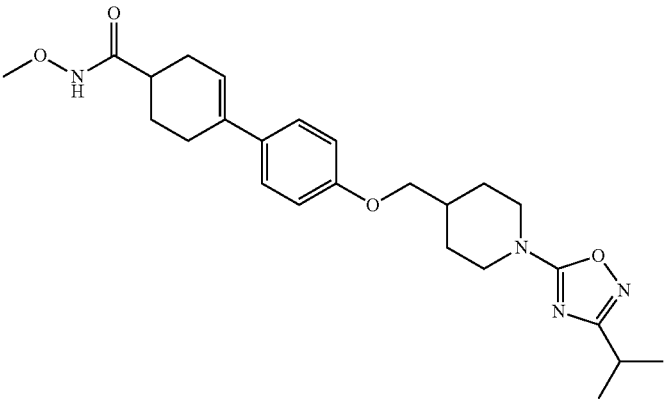 [SMILES: CONC(=O)C1CC=C(c2ccc(OCC3CCN(c4nc(C(C)C)no4)CC3)cc2)CC1] |

TABLE 1-continued
| Examples | Chemical structures |
|---|---|
| 247 | 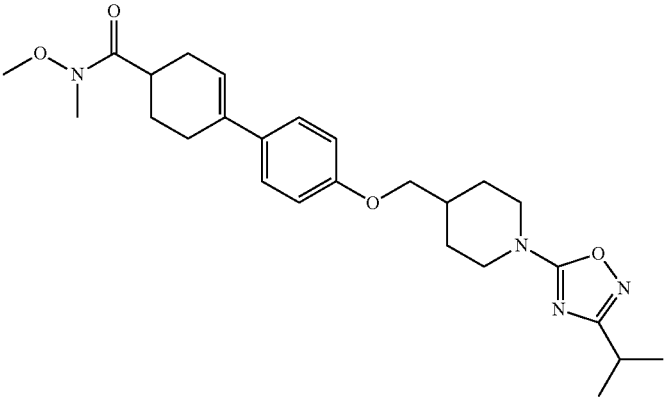 [SMILES: CON(C)C(=O)C1CC=C(c2ccc(OCC3CCN(c4nc(C(C)C)no4)CC3)cc2)CC1] |
| 248 | 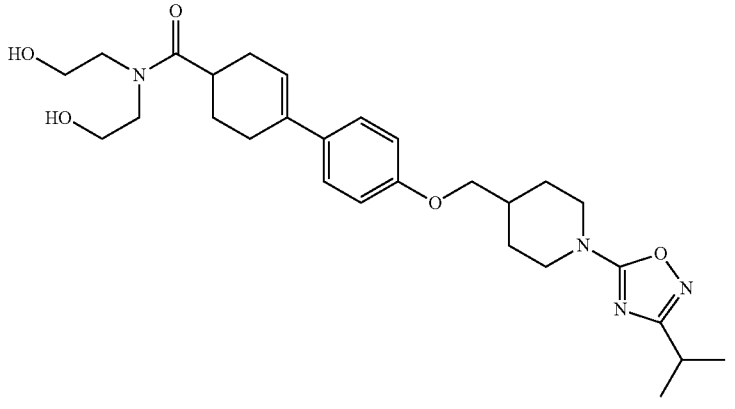 [SMILES: CC(C)c1noc(N2CCC(COc3ccc(C4=CCC(C(=O)N(CCO)CCO)CC4)cc3)CC2)n1] |
| 249 | 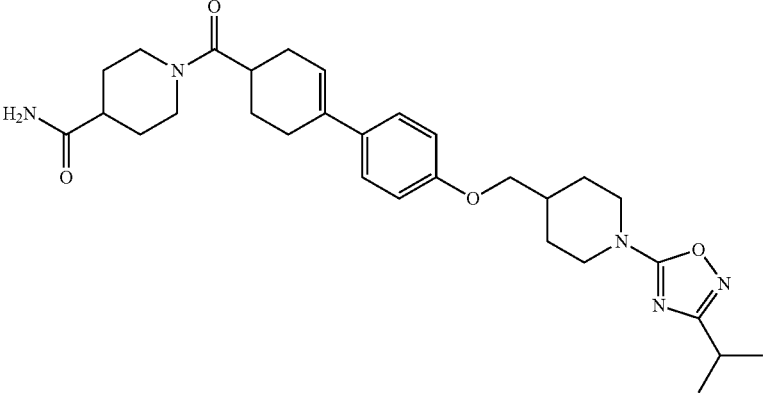 [SMILES: CC(C)c1noc(N2CCC(COc3ccc(C4=CCC(C(=O)N5CCC(C(N)=O)CC5)CC4)cc3)CC2)n1] |
| 250 | 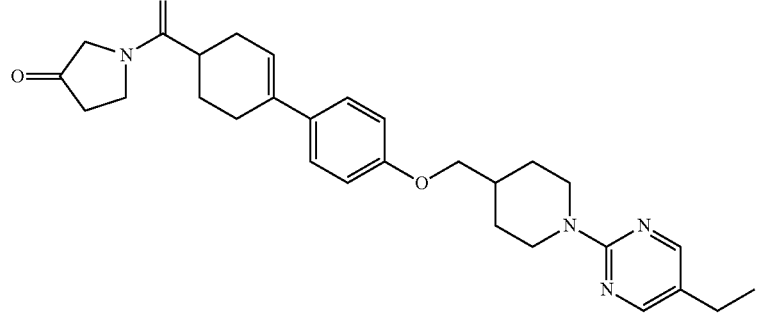 |

TABLE 1-continued

| Examples | Chemical structures |
|---|---|
| 251 | 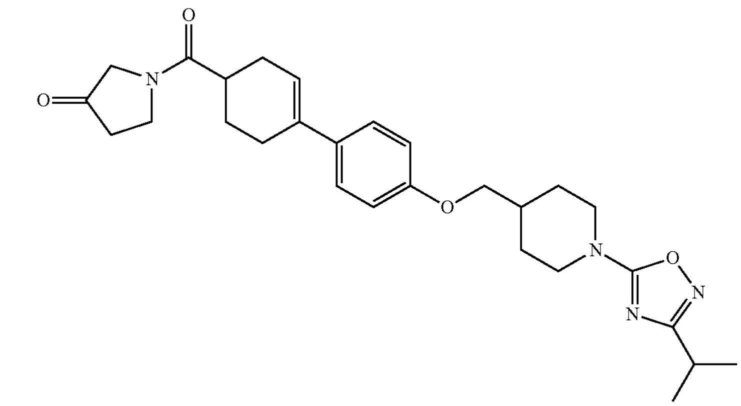 [SMILES: CC(C)c1noc(N2CCC(COc3ccc(C4=CCC(C(=O)N5CCC(=O)C5)CC4)cc3)CC2)n1] |
| 252 | 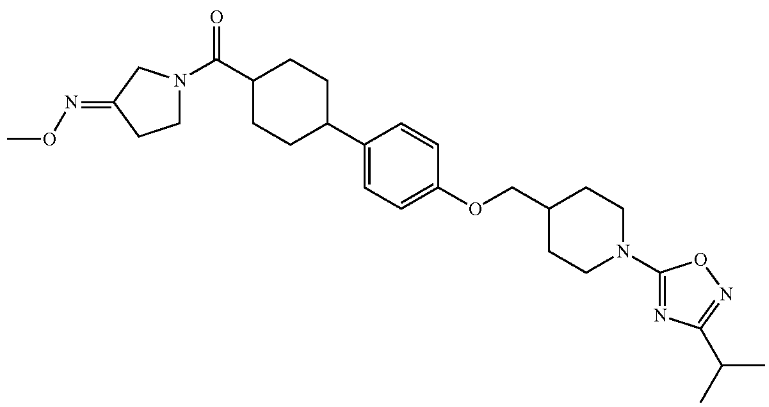 [SMILES: CO/N=C1\CCN(C(=O)C2CCC(c3ccc(OCC4CCN(c5nc(C(C)C)no5)CC4)cc3)CC2)C1] |
| 253 | 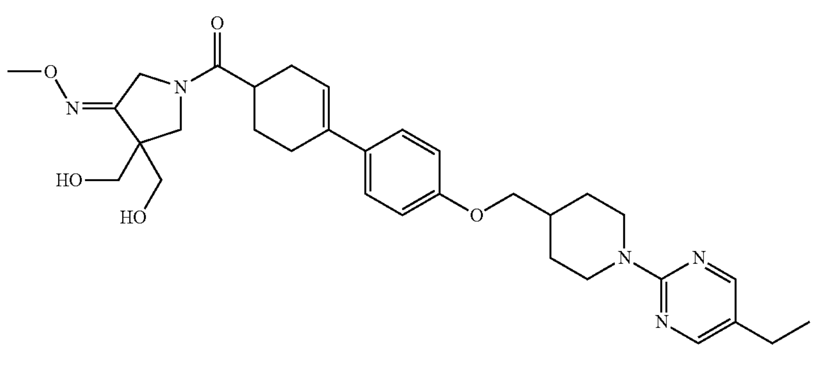 [SMILES: CCc1cnc(N2CCC(COc3ccc(C4=CCC(C(=O)N5C/C(=N\OC)C(CO)(CO)C5)CC4)cc3)CC2)nc1] |
| 254 | 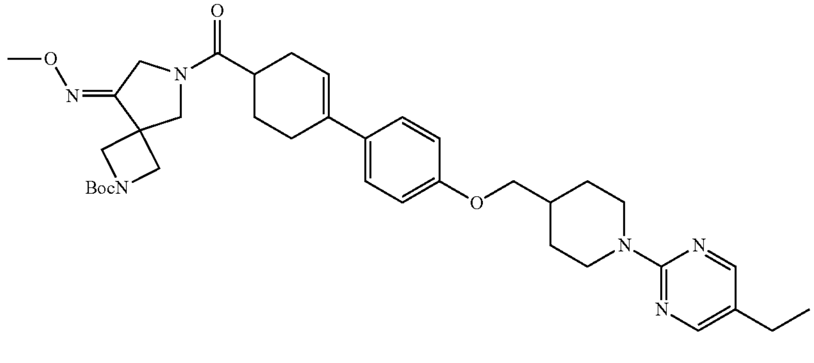 [SMILES: CCc1cnc(N2CCC(COc3ccc(C4=CCC(C(=O)N5C/C(=N\OC)C6(CN(C(=O)OC(C)(C)C)C6)C5)CC4)cc3)CC2)nc1] |

TABLE 1-continued
| Examples | Chemical structures |
|---|---|
| 255 | 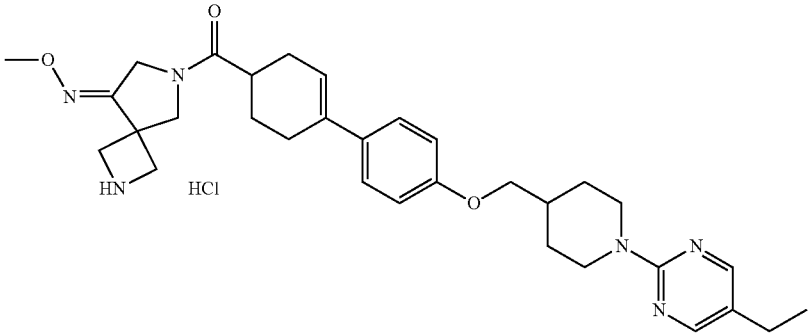 [SMILES: CCc1cnc(N2CCC(COc3ccc(C4=CCC(C(=O)N5C/C(=N\OC)C6(CNC6)C5)CC4)cc3)CC2)nc1 ; Cl] |
| 256 | 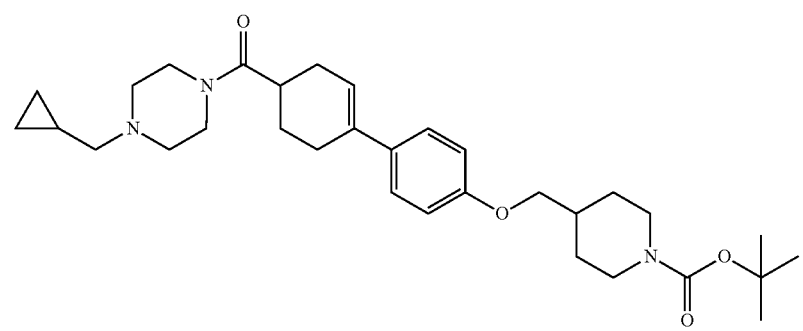 [SMILES: CC(C)(C)OC(=O)N1CCC(COc2ccc(C3=CCC(C(=O)N4CCN(CC5CC5)CC4)CC3)cc2)CC1] |
| 257 | 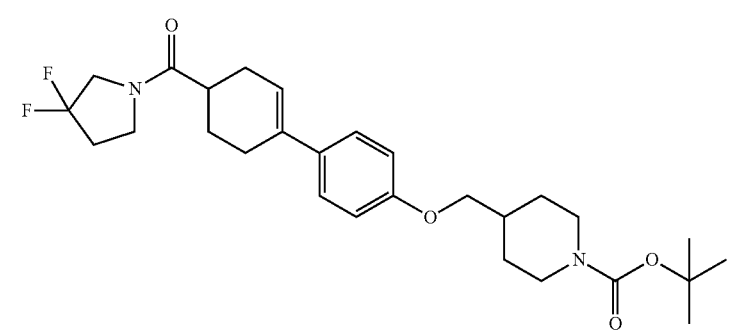 [SMILES: CC(C)(C)OC(=O)N1CCC(COc2ccc(C3=CCC(C(=O)N4CCC(F)(F)C4)CC3)cc2)CC1] |
| 258 | 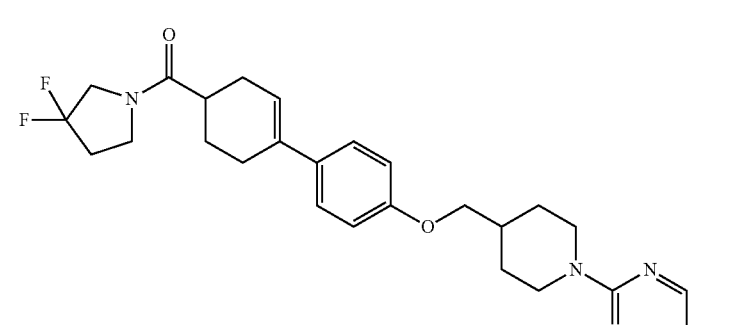 |

TABLE 1-continued

| Examples | Chemical structures |
|---|---|
| 259 | 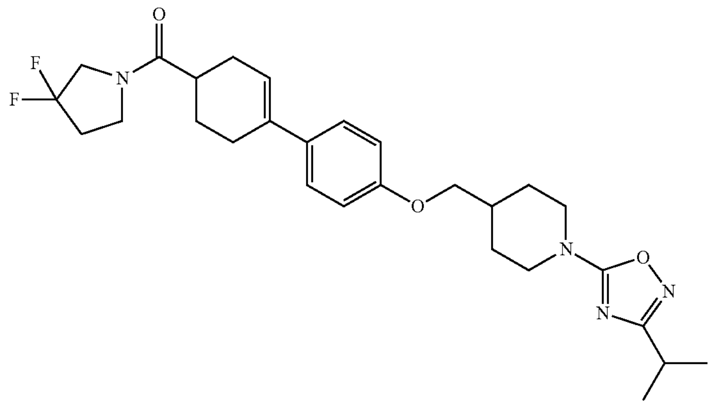 [SMILES: CC(C)c1noc(N2CCC(COc3ccc(C4=CCC(C(=O)N5CCC(F)(F)C5)CC4)cc3)CC2)n1] |
| 260 | 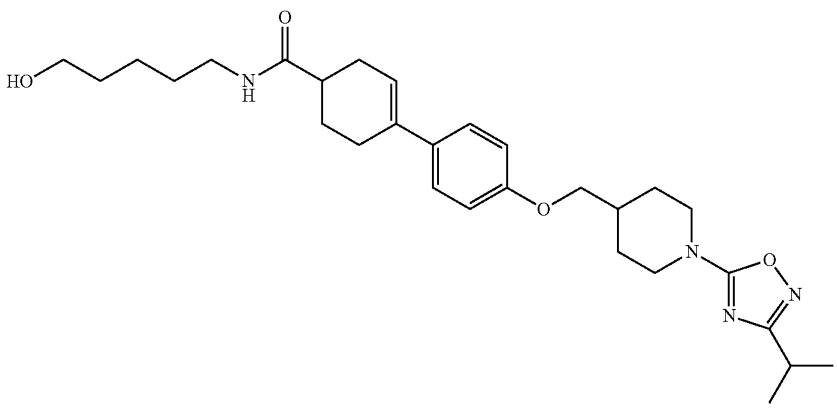 [SMILES: CC(C)c1noc(N2CCC(COc3ccc(C4=CCC(C(=O)NCCCCCO)CC4)cc3)CC2)n1] |
| 261 | 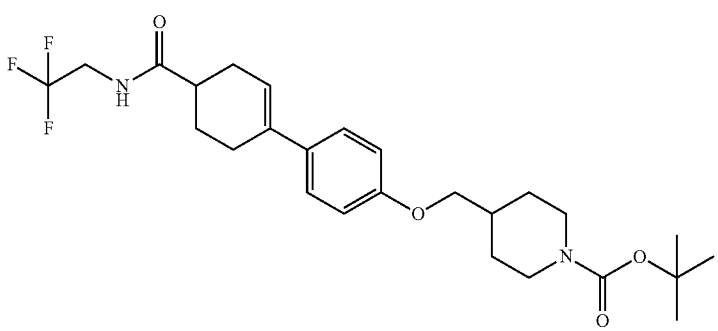 [SMILES: CC(C)(C)OC(=O)N1CCC(COc2ccc(C3=CCC(C(=O)NCC(F)(F)F)CC3)cc2)CC1] |
| 262 | 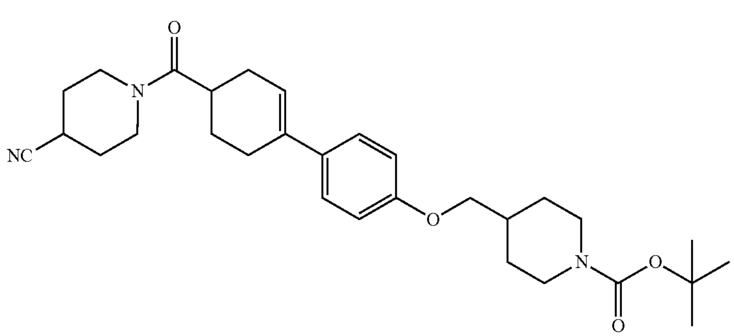 [SMILES: CC(C)(C)OC(=O)N1CCC(COc2ccc(C3=CCC(C(=O)N4CCC(C#N)CC4)CC3)cc2)CC1] |

TABLE 1-continued
| Examples | Chemical structures |
|---|---|
| 263 | 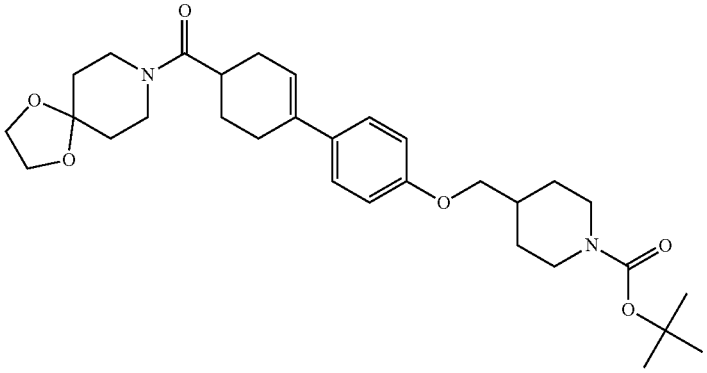 [SMILES: CC(C)(C)OC(=O)N1CCC(COc2ccc(C3=CCC(C(=O)N4CCC5(CC4)OCCO5)CC3)cc2)CC1] |
| 264 | 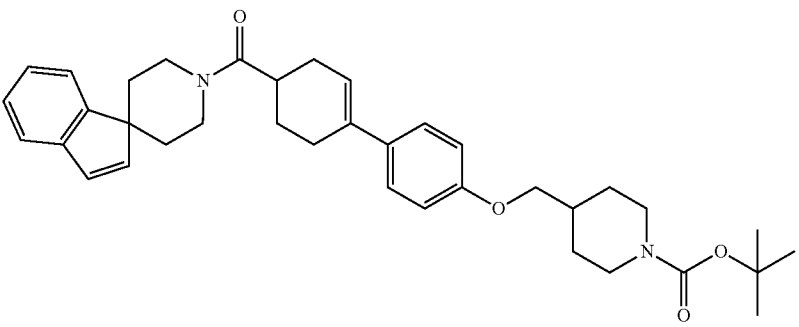 [SMILES: CC(C)(C)OC(=O)N1CCC(COc2ccc(C3=CCC(C(=O)N4CCC5(C=Cc6ccccc65)CC4)CC3)cc2)CC1] |
| 265 | 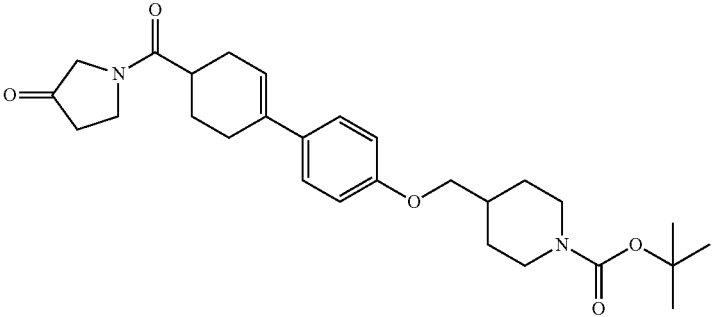 [SMILES: CC(C)(C)OC(=O)N1CCC(COc2ccc(C3=CCC(C(=O)N4CCC(=O)C4)CC3)cc2)CC1] |
| 266 | 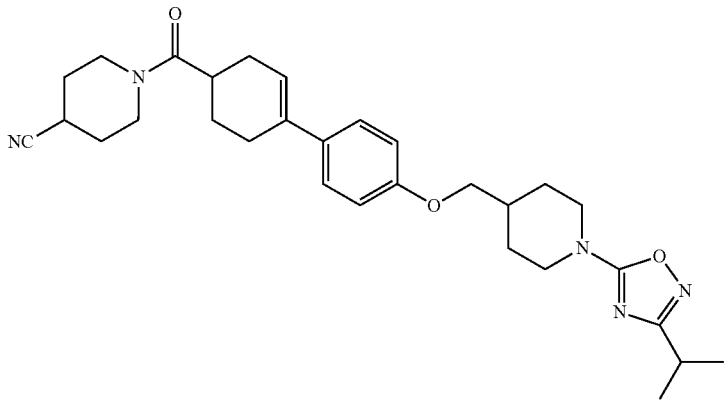 [SMILES: CC(C)c1noc(N2CCC(COc3ccc(C4=CCC(C(=O)N5CCC(C#N)CC5)CC4)cc3)CC2)n1] |

TABLE 1-continued
| Examples | Chemical structures |
|---|---|
| 267 | 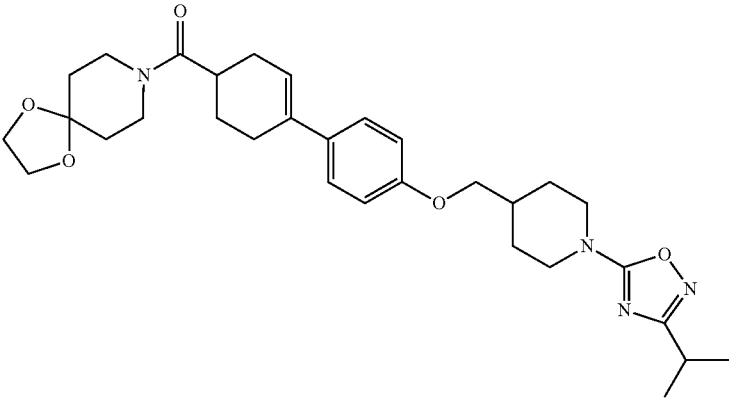 [SMILES: CC(C)c1noc(N2CCC(COc3ccc(C4=CCC(C(=O)N5CCC6(CC5)OCCO6)CC4)cc3)CC2)n1] |
| 268 | 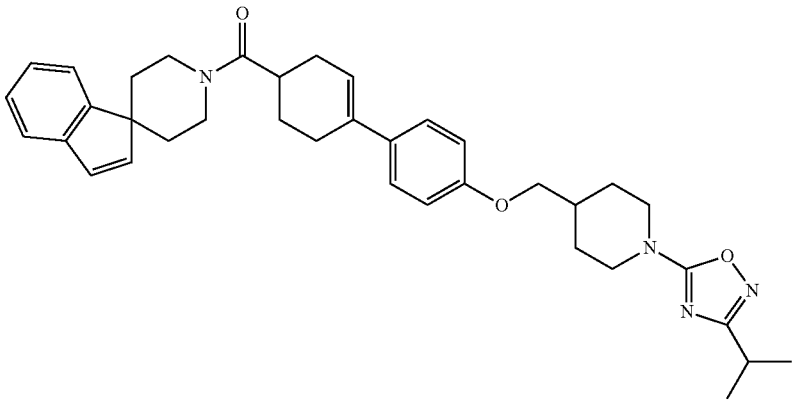 [SMILES: CC(C)c1noc(N2CCC(COc3ccc(C4=CCC(C(=O)N5CCC6(C=Cc7ccccc76)CC5)CC4)cc3)CC2)n1] |
| 269 | 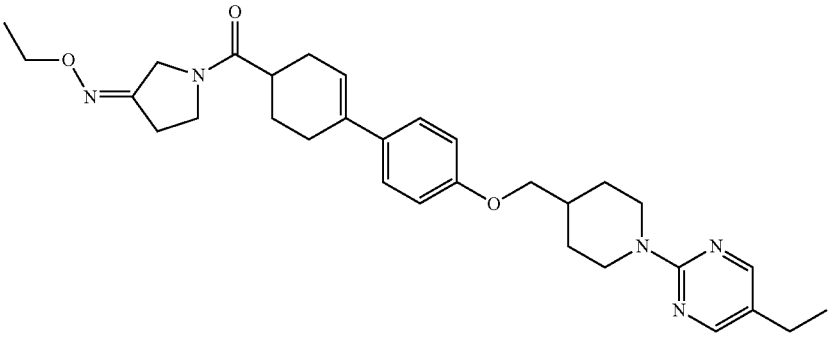 [SMILES: CCO/N=C1/CCN(C(=O)C2CC=C(c3ccc(OCC4CCN(c5ncc(CC)cn5)CC4)cc3)CC2)C1] |
| 270 | 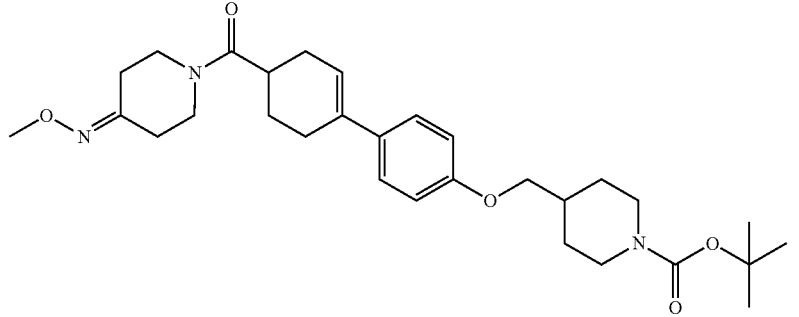 [SMILES: CON=C1CCN(C(=O)C2CC=C(c3ccc(OCC4CCN(C(=O)OC(C)(C)C)CC4)cc3)CC2)CC1] |

TABLE 1-continued
| Examples | Chemical structures |
|---|---|
| 271 | 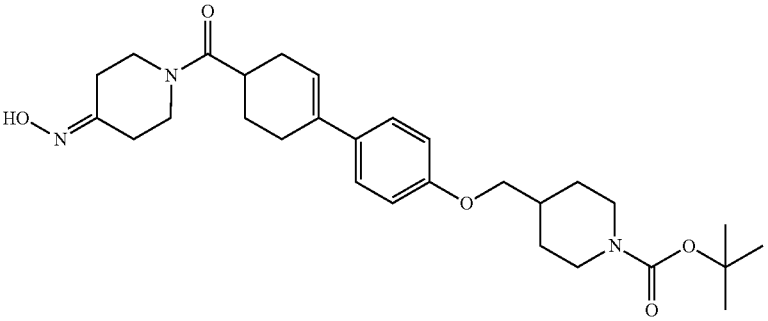 [SMILES: CC(C)(C)OC(=O)N1CCC(COc2ccc(C3=CCC(C(=O)N4CCC(=NO)CC4)CC3)cc2)CC1] |
| 272 | 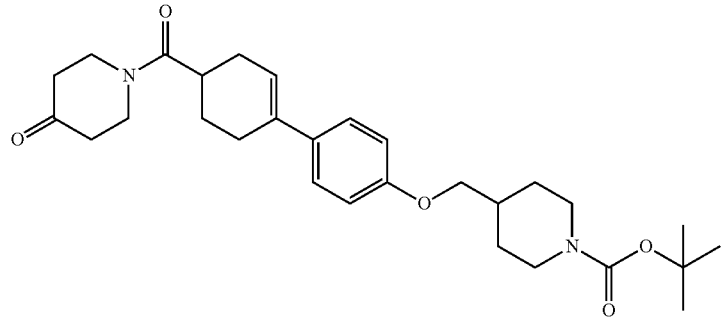 [SMILES: CC(C)(C)OC(=O)N1CCC(COc2ccc(C3=CCC(C(=O)N4CCC(=O)CC4)CC3)cc2)CC1] |
| 273 | 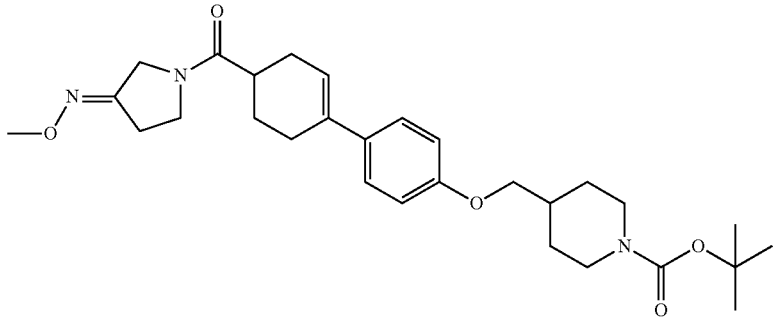 [SMILES: CO/N=C1\CCN(C(=O)C2CC=C(c3ccc(OCC4CCN(C(=O)OC(C)(C)C)CC4)cc3)CC2)C1] |
| 274 | 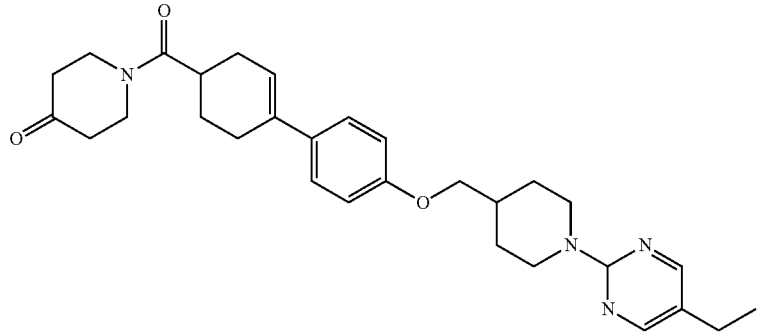 [SMILES: CCC1=CNC(N2CCC(COc3ccc(C4=CCC(C(=O)N5CCC(=O)CC5)CC4)cc3)CC2)N=C1] |

TABLE 1-continued
| Examples | Chemical structures |
|---|---|
| 275 | 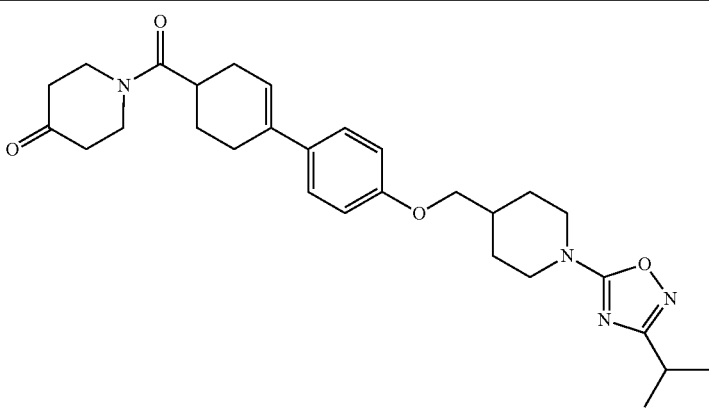 |
| 276 | 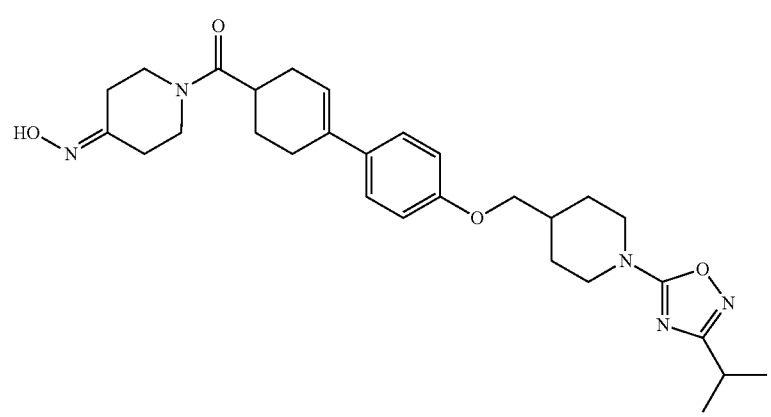 [SMILES: CC(C)c1noc(N2CCC(COc3ccc(C4=CCC(C(=O)N5CCC(=NO)CC5)CC4)cc3)CC2)n1] |
| 277 | 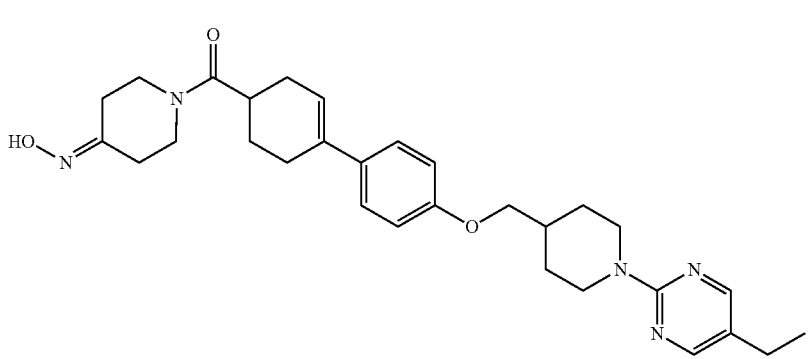 [SMILES: CCc1cnc(N2CCC(COc3ccc(C4=CCC(C(=O)N5CCC(=NO)CC5)CC4)cc3)CC2)nc1] |
| 278 | 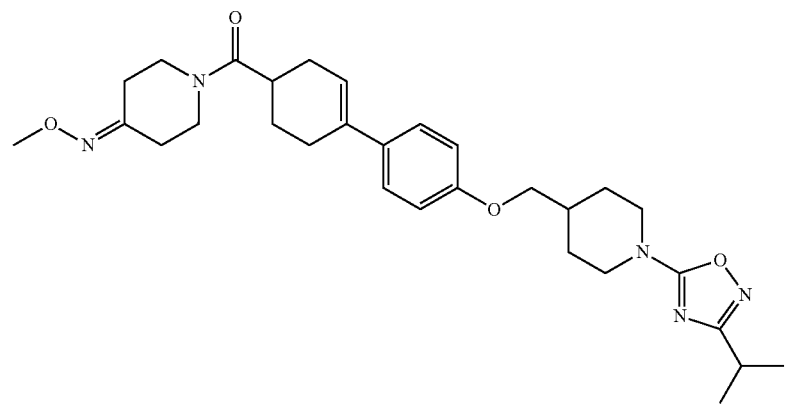 [SMILES: CON=C1CCN(C(=O)C2CC=C(c3ccc(OCC4CCN(c5nc(C(C)C)no5)CC4)cc3)CC2)CC1] |

487 488
TABLE 1-continued
| Examples | Chemical structures |
|---|---|
| 279 | 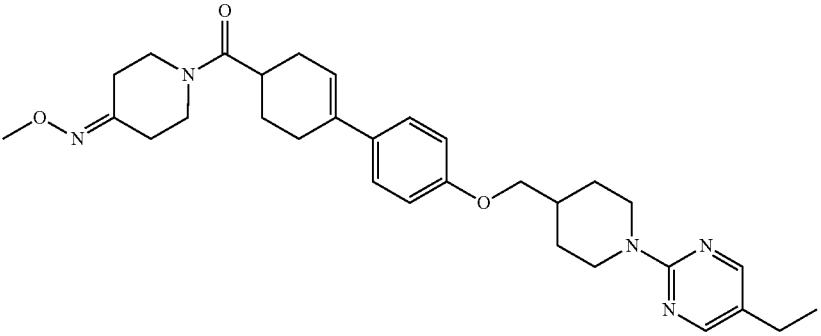 [SMILES: CCc1cnc(N2CCC(COc3ccc(C4=CCC(C(=O)N5CCC(=NOC)CC5)CC4)cc3)CC2)nc1] |
| 280 | 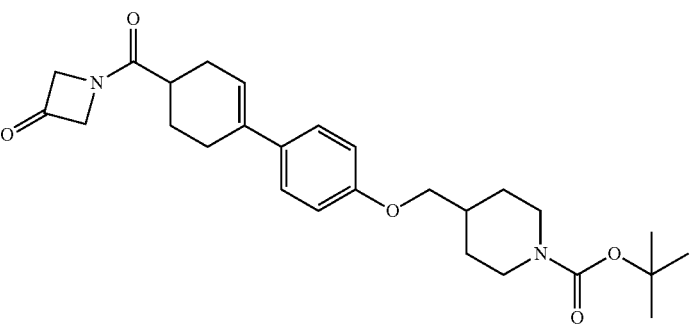 [SMILES: CC(C)(C)OC(=O)N1CCC(COc2ccc(C3=CCC(C(=O)N4CC(=O)C4)CC3)cc2)CC1] |
| 281 | 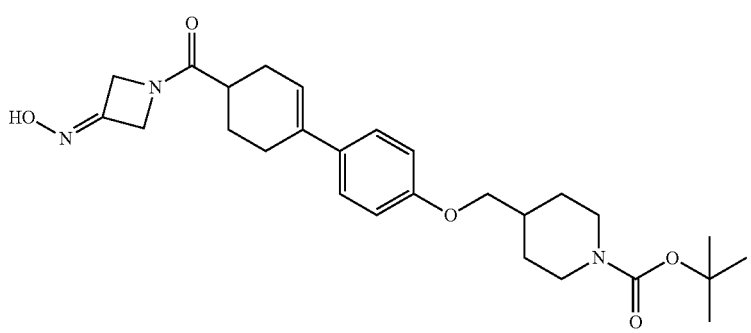 [SMILES: CC(C)(C)OC(=O)N1CCC(COc2ccc(C3=CCC(C(=O)N4CC(=NO)C4)CC3)cc2)CC1] |
| 282 | 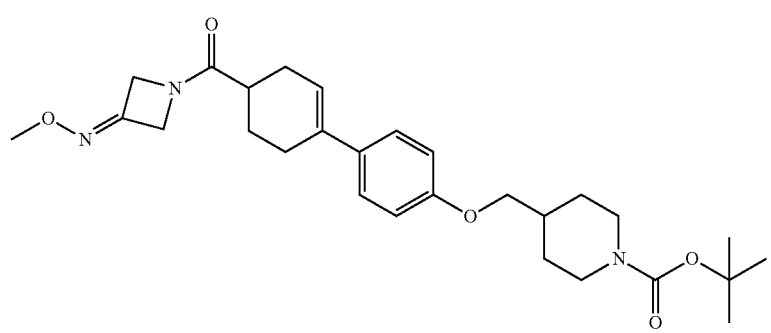 [SMILES: CON=C1CN(C(=O)C2CC=C(c3ccc(OCC4CCN(C(=O)OC(C)(C)C)CC4)cc3)CC2)C1] |

TABLE 1-continued
| Examples | Chemical structures |
|---|---|
| 283 | 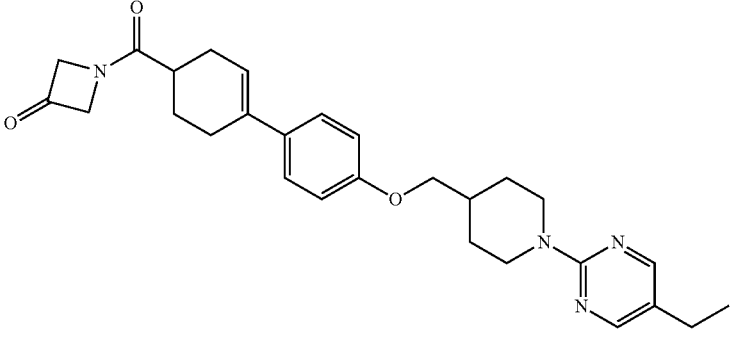 [SMILES: CCc1cnc(N2CCC(COc3ccc(C4=CCC(C(=O)N5CC(=O)C5)CC4)cc3)CC2)nc1] |
| 284 | 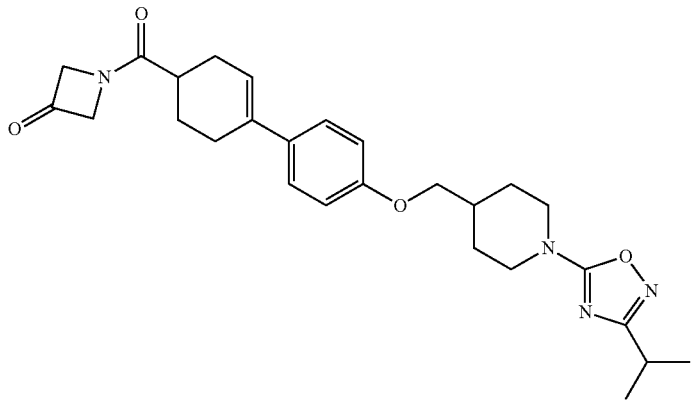 [SMILES: CC(C)c1noc(N2CCC(COc3ccc(C4=CCC(C(=O)N5CC(=O)C5)CC4)cc3)CC2)n1] |
| 285 | 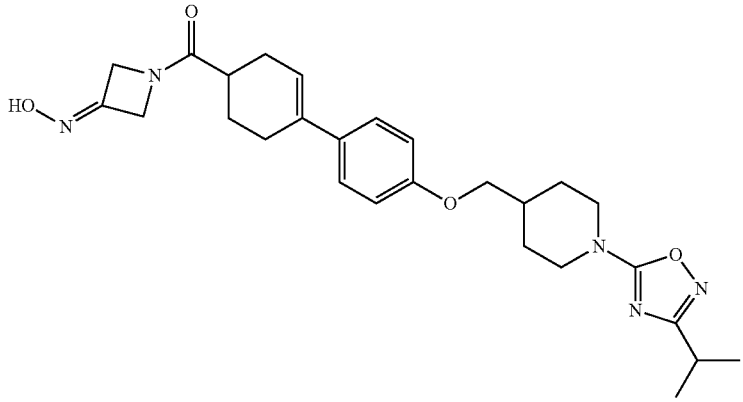 [SMILES: CC(C)c1noc(N2CCC(COc3ccc(C4=CCC(C(=O)N5CC(=NO)C5)CC4)cc3)CC2)n1] |
| 286 | 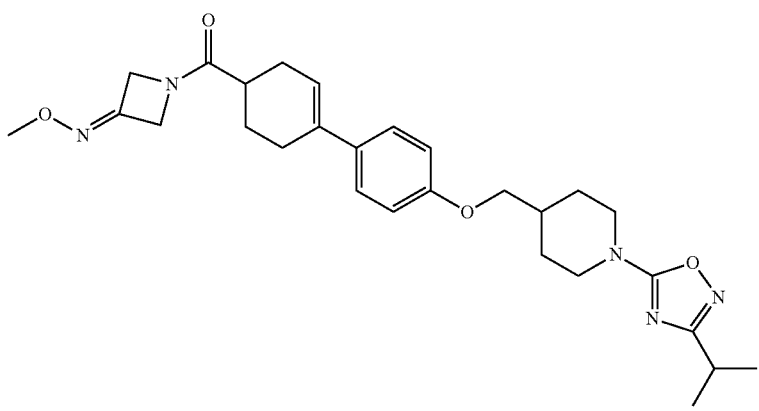 [SMILES: CON=C1CN(C(=O)C2CC=C(c3ccc(OCC4CCN(c5nc(C(C)C)no5)CC4)cc3)CC2)C1] |

TABLE 1-continued
| Examples | Chemical structures |
|---|---|
| 287 | 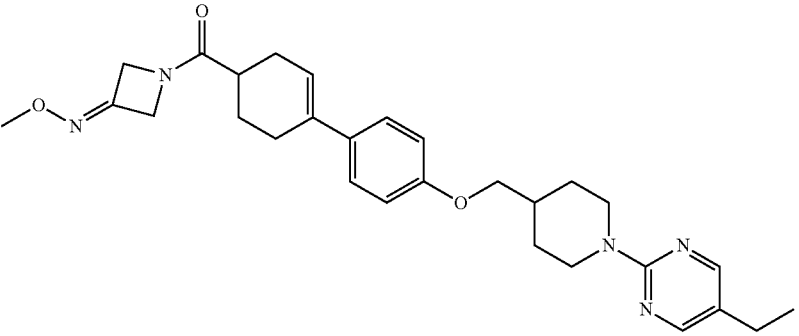 [SMILES: CCc1cnc(N2CCC(COc3ccc(C4=CCC(C(=O)N5CC(=NOC)C5)CC4)cc3)CC2)nc1] |
| 288 | 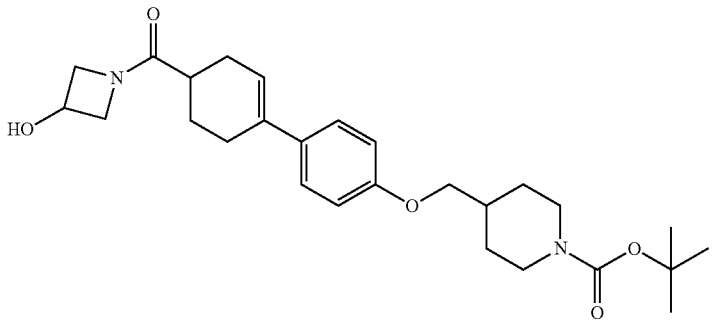 [SMILES: CC(C)(C)OC(=O)N1CCC(COc2ccc(C3=CCC(C(=O)N4CC(O)C4)CC3)cc2)CC1] |
| 289 | 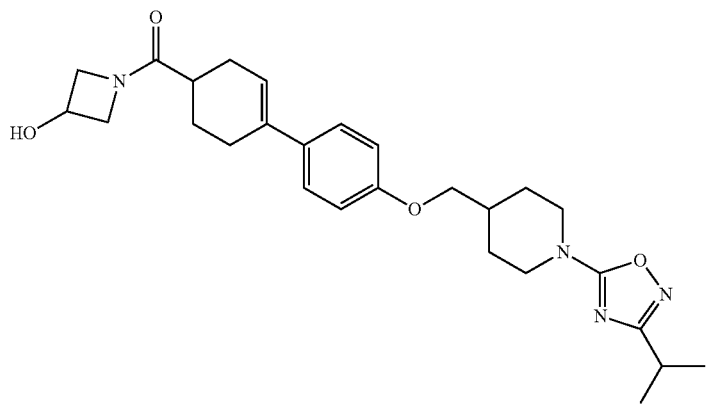 [SMILES: CC(C)c1noc(N2CCC(COc3ccc(C4=CCC(C(=O)N5CC(O)C5)CC4)cc3)CC2)n1] |
| 290 | 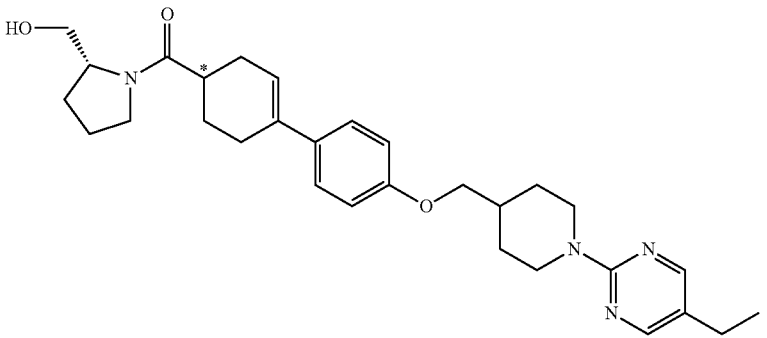 [SMILES: CCc1cnc(N2CCC(COc3ccc(C4=CCC(C(=O)N5CCC[C@@H]5CO)CC4)cc3)CC2)nc1] |

TABLE 1-continued

| Examples | Chemical structures |
|---|---|
| 291 | 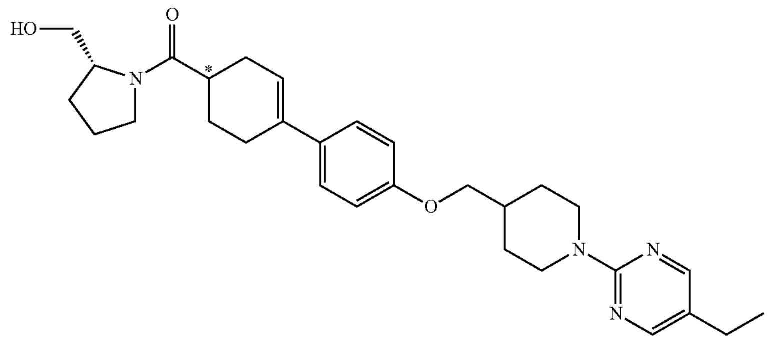 [SMILES: CCc1cnc(N2CCC(COc3ccc(C4=CCC(C(=O)N5CCC[C@@H]5CO)CC4)cc3)CC2)nc1] |
| 292 | 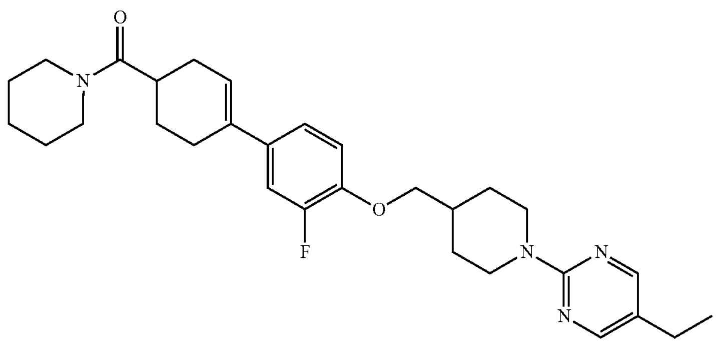 [SMILES: CCc1cnc(N2CCC(COc3ccc(C4=CCC(C(=O)N5CCCCC5)CC4)cc3F)CC2)nc1] |
| 293 | 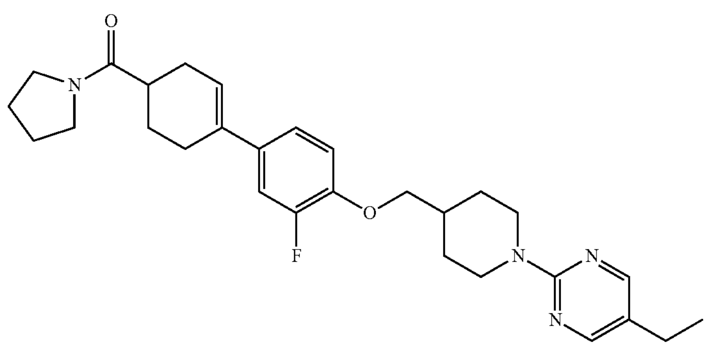 [SMILES: CCc1cnc(N2CCC(COc3ccc(C4=CCC(C(=O)N5CCCC5)CC4)cc3F)CC2)nc1] |
| 294 | 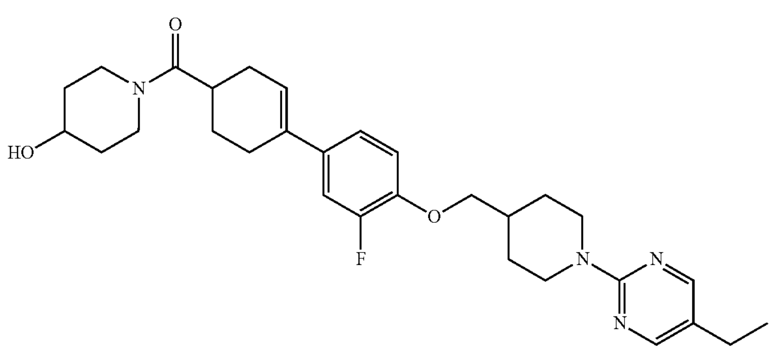 |

TABLE 1-continued
| Examples | Chemical structures |
|---|---|
| 295 | 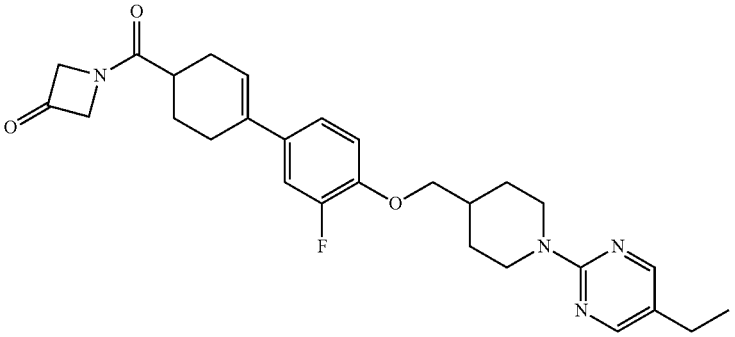 [SMILES: CCc1cnc(N2CCC(COc3ccc(C4=CCC(C(=O)N5CC(=O)C5)CC4)cc3F)CC2)nc1] |
| 296 | 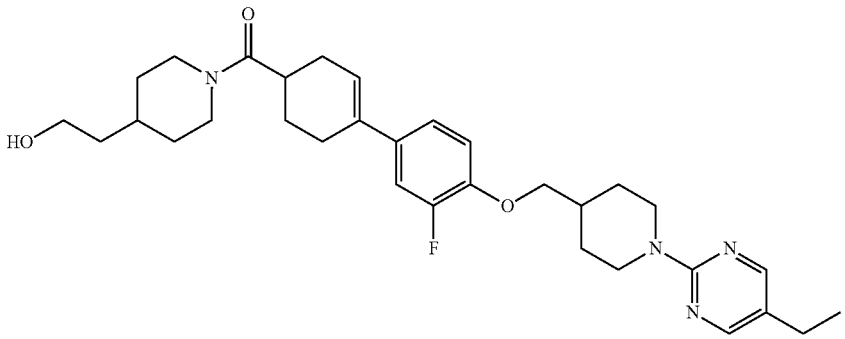 [SMILES: CCc1cnc(N2CCC(COc3ccc(C4=CCC(C(=O)N5CCC(CCO)CC5)CC4)cc3F)CC2)nc1] |
| 297 | 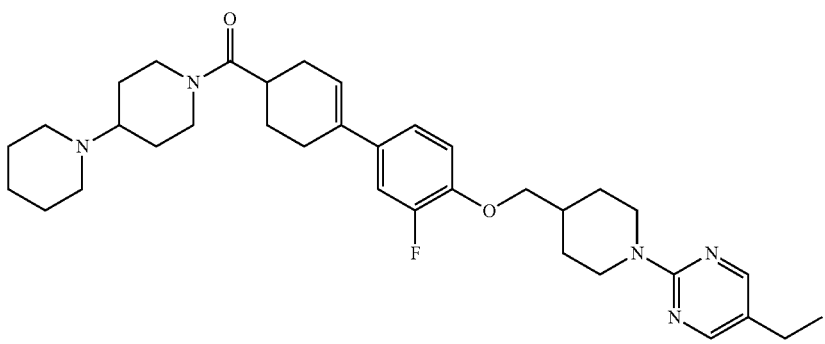 [SMILES: CCc1cnc(N2CCC(COc3ccc(C4=CCC(C(=O)N5CCC(N6CCCCC6)CC5)CC4)cc3F)CC2)nc1] |
| 298 | 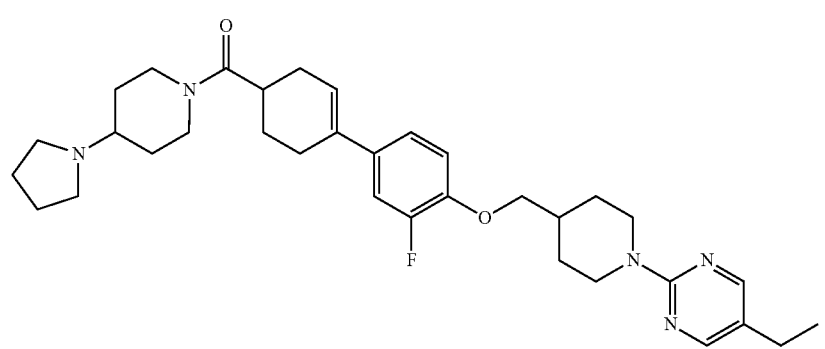 [SMILES: CCc1cnc(N2CCC(COc3ccc(C4=CCC(C(=O)N5CCC(N6CCCC6)CC5)CC4)cc3F)CC2)nc1] |

TABLE 1-continued
| Examples | Chemical structures |
|---|---|
| 299 | 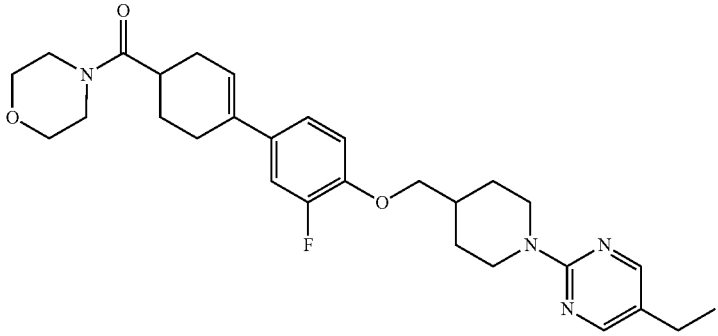 [SMILES: CCc1cnc(N2CCC(COc3ccc(C4=CCC(C(=O)N5CCOCC5)CC4)cc3F)CC2)nc1] |
| 300 | 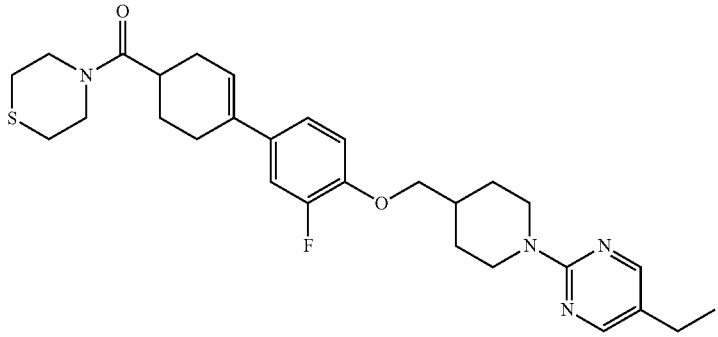 [SMILES: CCc1cnc(N2CCC(COc3ccc(C4=CCC(C(=O)N5CCSCC5)CC4)cc3F)CC2)nc1] |
| 301 | 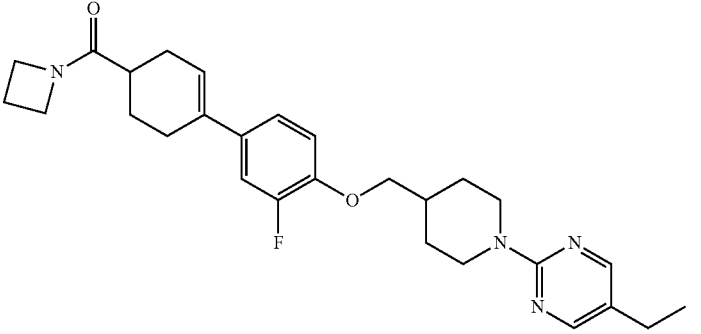 [SMILES: CCc1cnc(N2CCC(COc3ccc(C4=CCC(C(=O)N5CCC5)CC4)cc3F)CC2)nc1] |
| 302 | 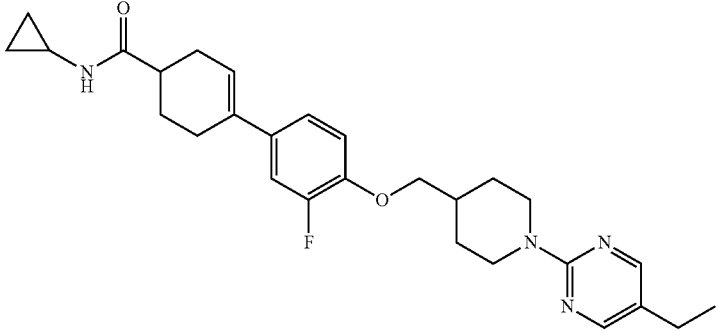 [SMILES: CCc1cnc(N2CCC(COc3ccc(C4=CCC(C(=O)NC5CC5)CC4)cc3F)CC2)nc1] |

TABLE 1-continued
| Examples | Chemical structures |
|---|---|
| 303 | 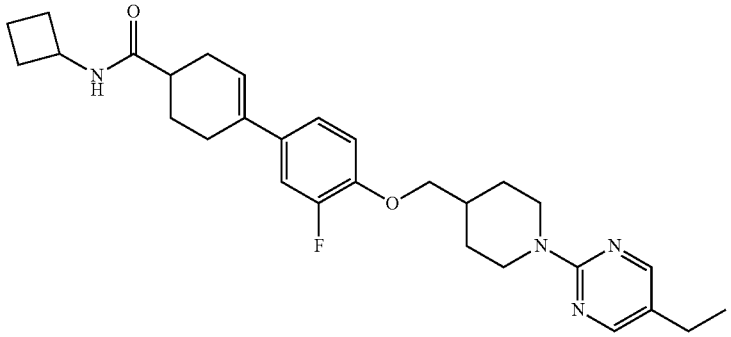 [SMILES: CCc1cnc(N2CCC(COc3ccc(C4=CCC(C(=O)NC5CCC5)CC4)cc3F)CC2)nc1] |
| 304 | 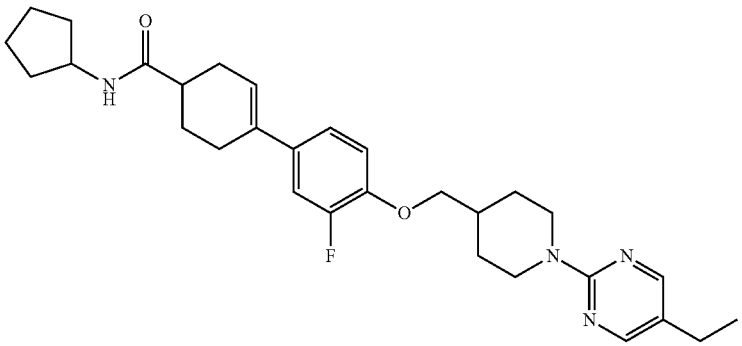 [SMILES: CCc1cnc(N2CCC(COc3ccc(C4=CCC(C(=O)NC5CCCC5)CC4)cc3F)CC2)nc1] |
| 305 | 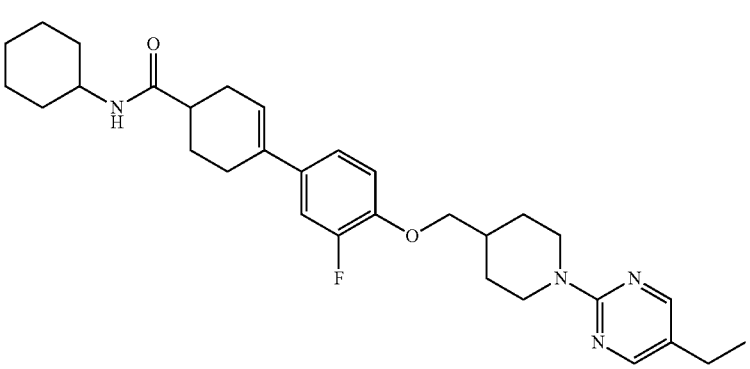 [SMILES: CCc1cnc(N2CCC(COc3ccc(C4=CCC(C(=O)NC5CCCCC5)CC4)cc3F)CC2)nc1] |
| 306 | 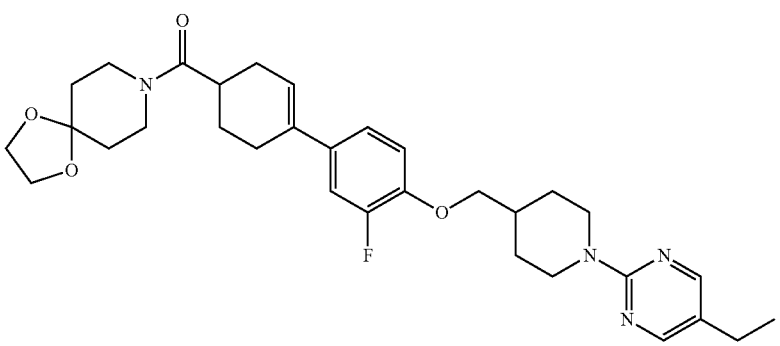 [SMILES: CCc1cnc(N2CCC(COc3ccc(C4=CCC(C(=O)N5CCC6(CC5)OCCO6)CC4)cc3F)CC2)nc1] |

TABLE 1-continued
| Examples | Chemical structures |
|---|---|
| 307 | 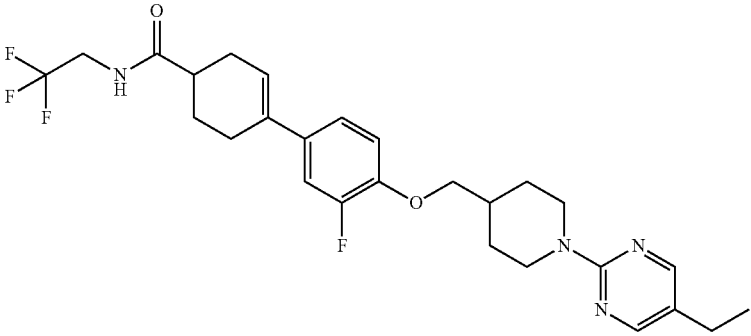 [SMILES: CCc1cnc(N2CCC(COc3ccc(C4=CCC(C(=O)NCC(F)(F)F)CC4)cc3F)CC2)nc1] |
| 308 | 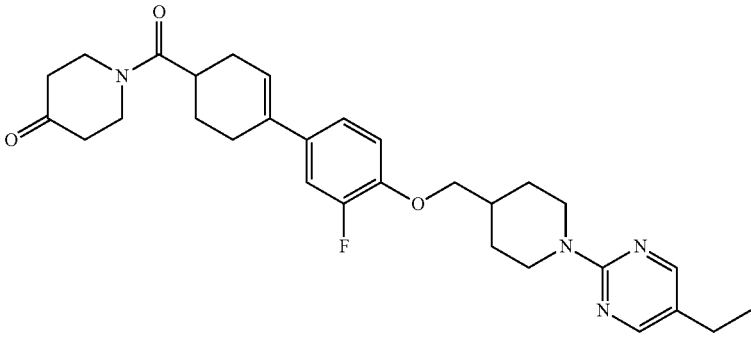 [SMILES: CCc1cnc(N2CCC(COc3ccc(C4=CCC(C(=O)N5CCC(=O)CC5)CC4)cc3F)CC2)nc1] |
| 309 | 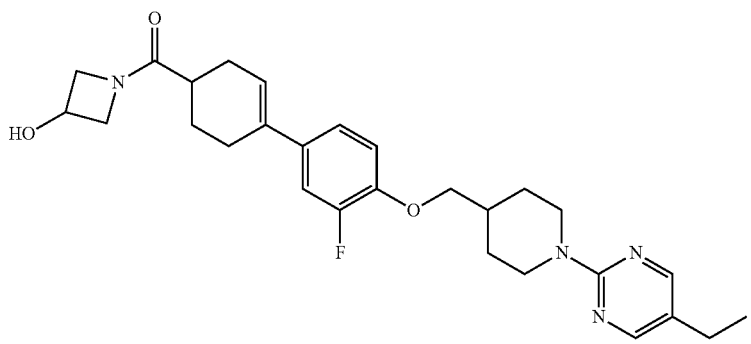 [SMILES: CCc1cnc(N2CCC(COc3ccc(C4=CCC(C(=O)N5CC(O)C5)CC4)cc3F)CC2)nc1] |
| 310 | 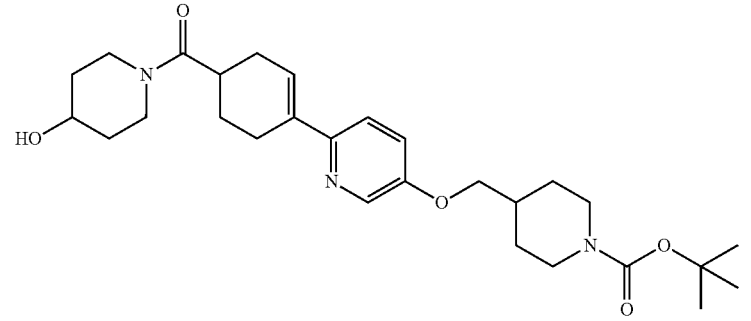 |

TABLE 1-continued
| Examples | Chemical structures |
|---|---|
| 311 | 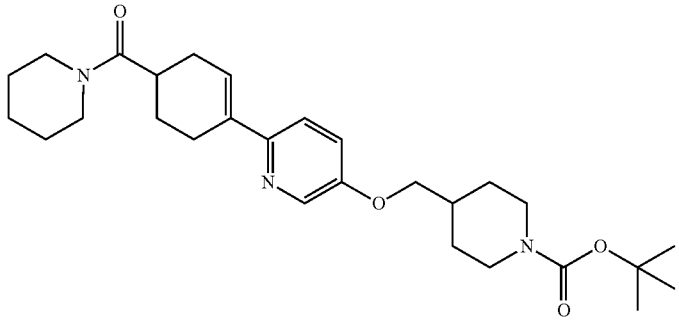 [SMILES: CC(C)(C)OC(=O)N1CCC(COc2ccc(C3=CCC(C(=O)N4CCCCC4)CC3)nc2)CC1] |
| 312 | 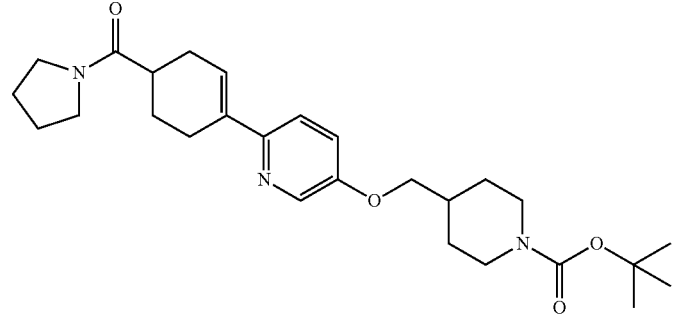 [SMILES: CC(C)(C)OC(=O)N1CCC(COc2ccc(C3=CCC(C(=O)N4CCCC4)CC3)nc2)CC1] |
| 313 | 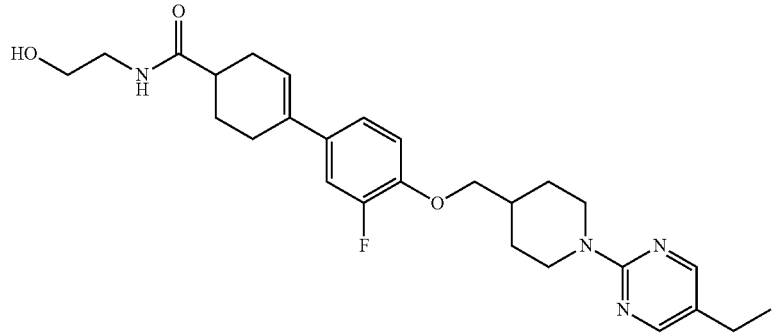 |
| 314 | 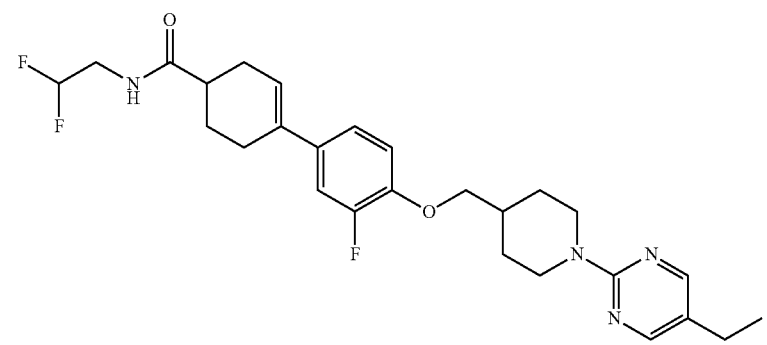 [SMILES: CCc1cnc(N2CCC(COc3ccc(C4=CCC(C(=O)NCC(F)F)CC4)cc3F)CC2)nc1] |

TABLE 1-continued
| Examples | Chemical structures |
|---|---|
| 315 | 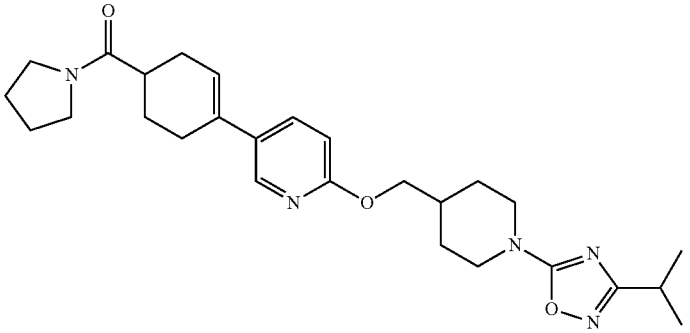 [SMILES: CC(C)c1noc(N2CCC(COc3ccc(C4=CCC(C(=O)N5CCCC5)CC4)cn3)CC2)n1] |
| 316 | 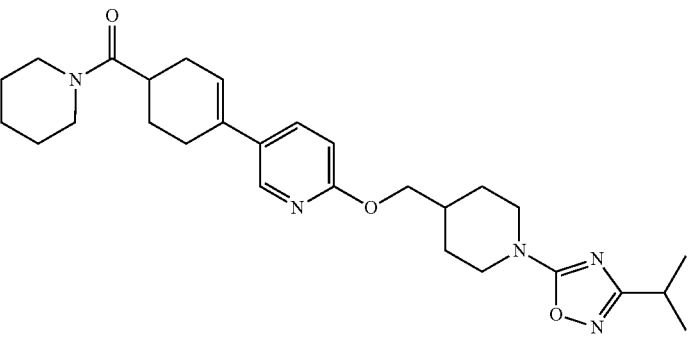 [SMILES: CC(C)c1noc(N2CCC(COc3ccc(C4=CCC(C(=O)N5CCCCC5)CC4)cn3)CC2)n1] |
| 317 | 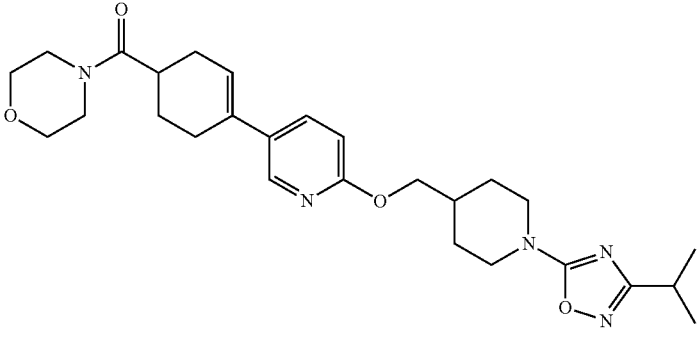 [SMILES: CC(C)c1noc(N2CCC(COc3ccc(C4=CCC(C(=O)N5CCOCC5)CC4)cn3)CC2)n1] |
| 318 | 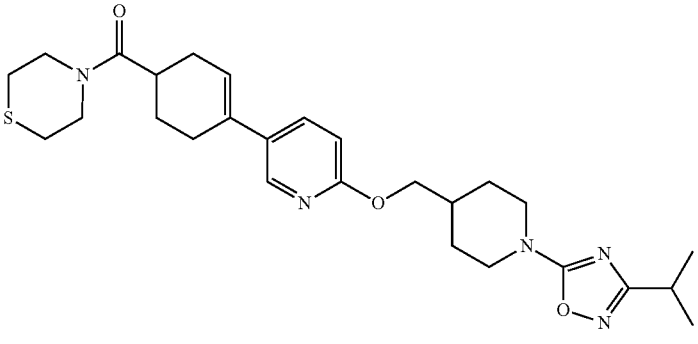 [SMILES: CC(C)c1noc(N2CCC(COc3ccc(C4=CCC(C(=O)N5CCSCC5)CC4)cn3)CC2)n1] |

TABLE 1-continued

| Examples | Chemical structures |
|---|---|
| 319 | 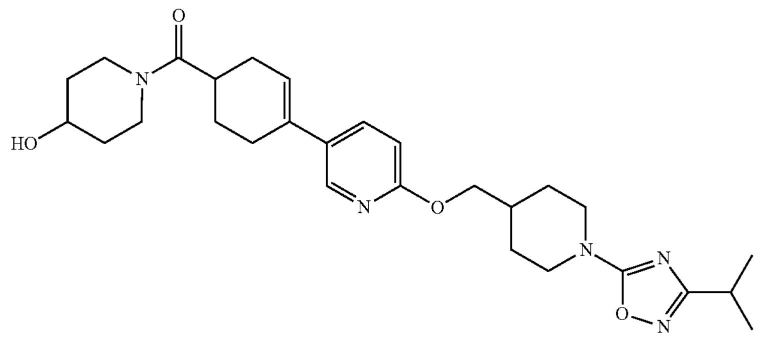 |
| 320 | 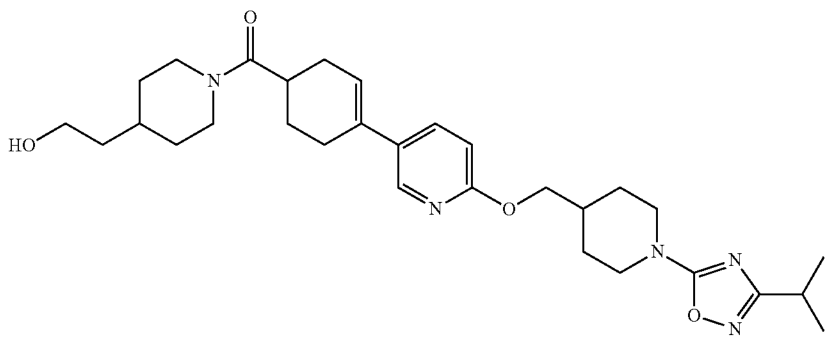 [SMILES: CC(C)c1noc(N2CCC(COc3ccc(C4=CCC(C(=O)N5CCC(CCO)CC5)CC4)cn3)CC2)n1] |
| 321 | 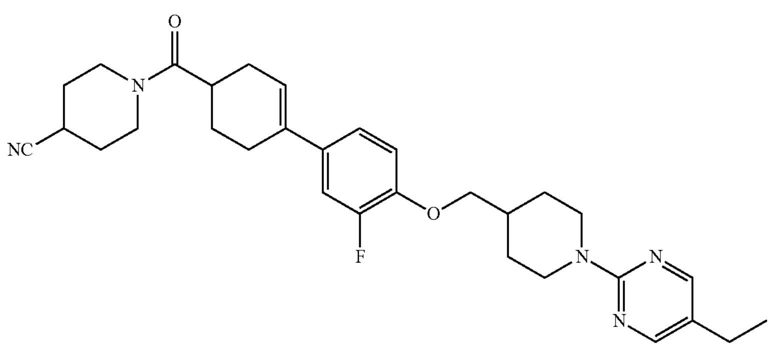 [SMILES: CCc1cnc(N2CCC(COc3ccc(C4=CCC(C(=O)N5CCC(C#N)CC5)CC4)cc3F)CC2)nc1] |
| 322 | 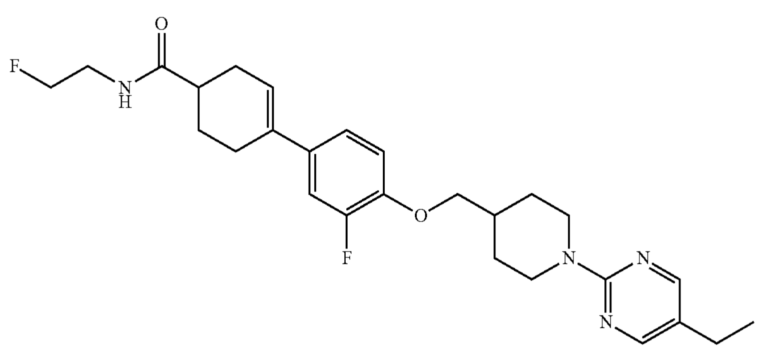 [SMILES: CCc1cnc(N2CCC(COc3ccc(C4=CCC(C(=O)NCCF)CC4)cc3F)CC2)nc1] |

TABLE 1-continued
| Examples | Chemical structures |
|---|---|
| 323 | 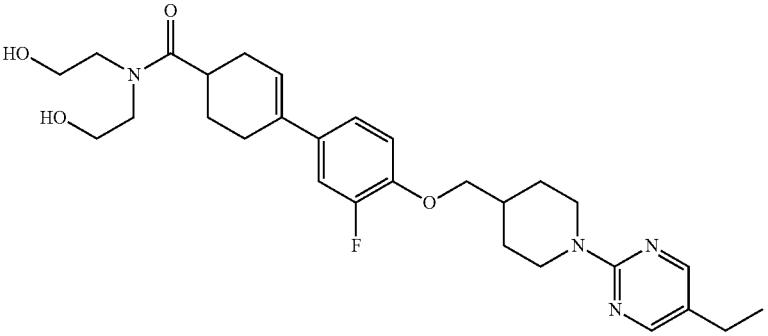 [SMILES: CCc1cnc(N2CCC(COc3ccc(C4=CCC(C(=O)N(CCO)CCO)CC4)cc3F)CC2)nc1] |
| 324 | 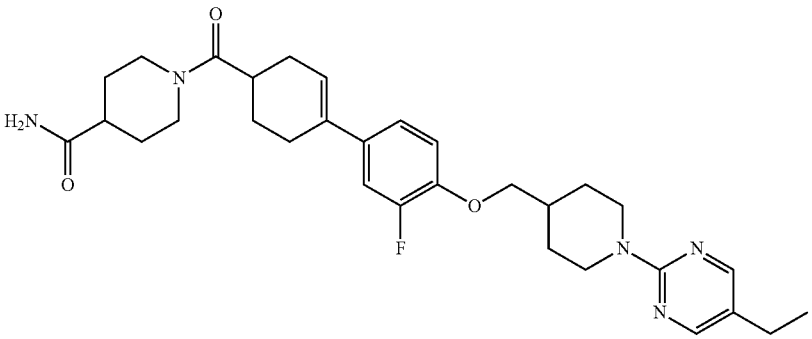 [SMILES: CCc1cnc(N2CCC(COc3ccc(C4=CCC(C(=O)N5CCC(C(N)=O)CC5)CC4)cc3F)CC2)nc1] |
| 325 | 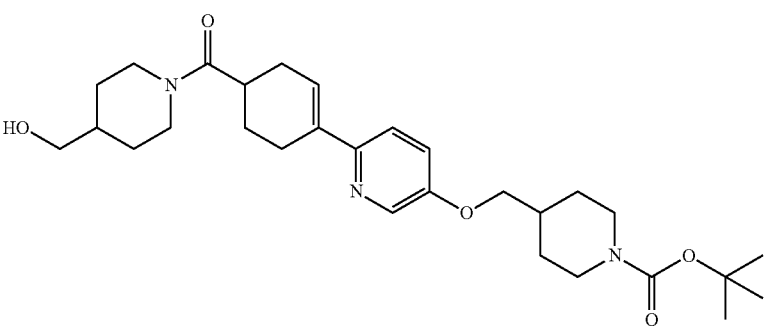 [SMILES: CC(C)(C)OC(=O)N1CCC(COc2ccc(C3=CCC(C(=O)N4CCC(CO)CC4)CC3)nc2)CC1] |
| 326 | 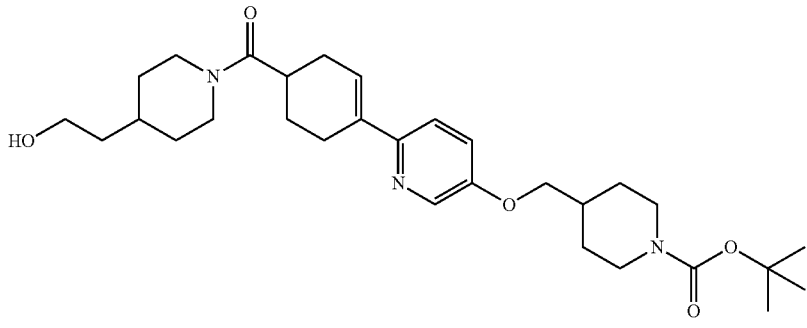 [SMILES: CC(C)(C)OC(=O)N1CCC(COc2ccc(C3=CCC(C(=O)N4CCC(CCO)CC4)CC3)nc2)CC1] |

TABLE 1-continued
| Examples | Chemical structures |
|---|---|
| 327 | 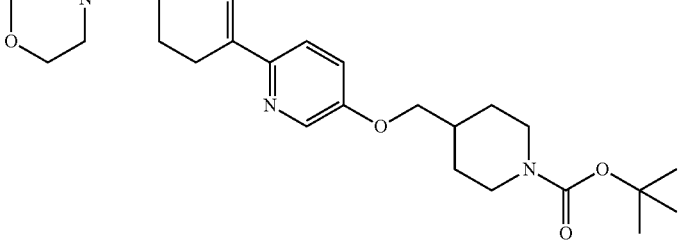 |
| 328 | 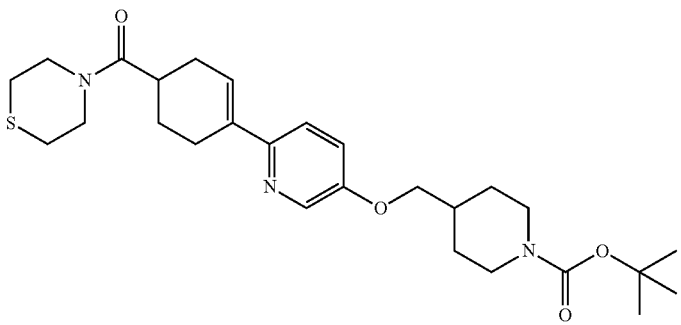 [SMILES: CC(C)(C)OC(=O)N1CCC(COc2ccc(C3=CCC(C(=O)N4CCSCC4)CC3)nc2)CC1] |
| 329 | 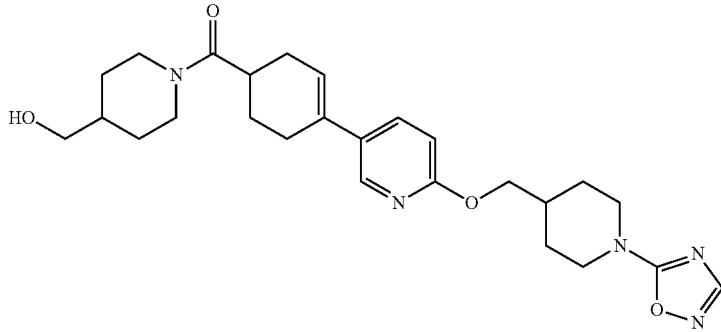 |
| 330 | 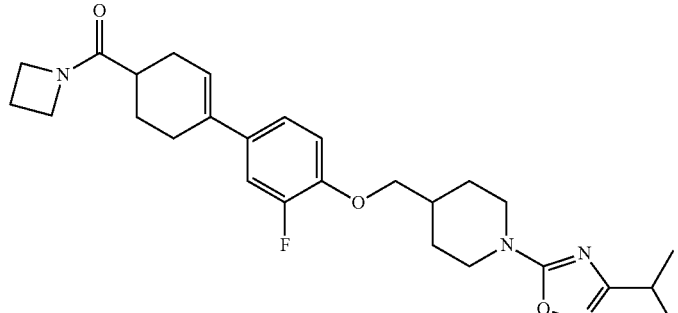 |

TABLE 1-continued
| Examples | Chemical structures |
|---|---|
| 331 | 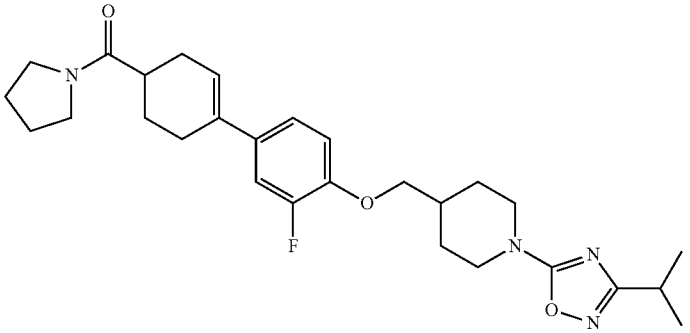 [SMILES: CC(C)c1noc(N2CCC(COc3ccc(C4=CCC(C(=O)N5CCCC5)CC4)cc3F)CC2)n1] |
| 332 | 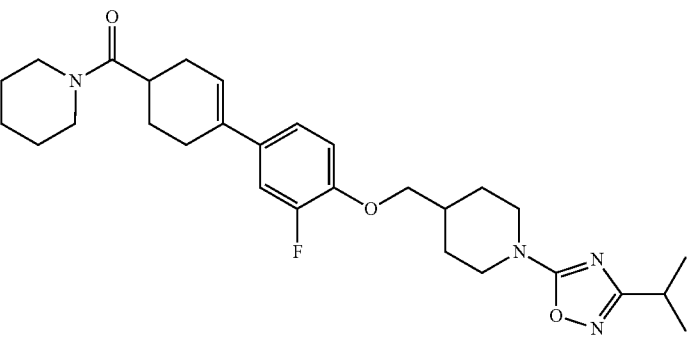 [SMILES: CC(C)c1noc(N2CCC(COc3ccc(C4=CCC(C(=O)N5CCCCC5)CC4)cc3F)CC2)n1] |
| 333 | 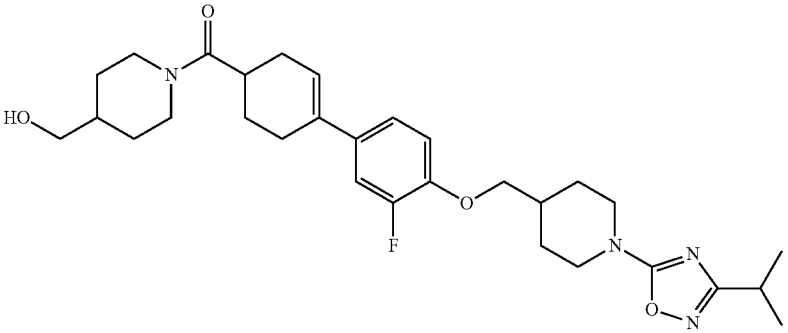 |
| 334 | 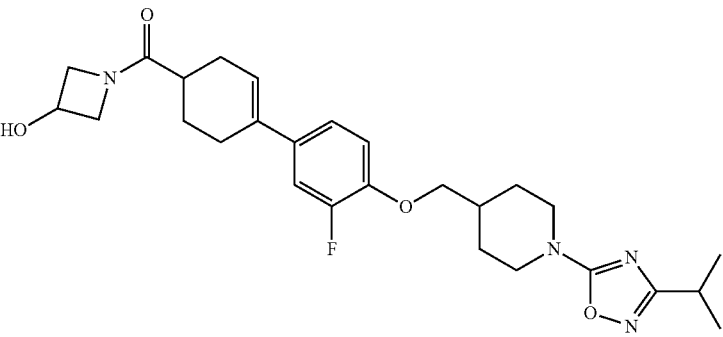 [SMILES: CC(C)c1noc(N2CCC(COc3ccc(C4=CCC(C(=O)N5CC(O)C5)CC4)cc3F)CC2)n1] |

TABLE 1-continued
| Examples | Chemical structures |
|---|---|
| 335 | 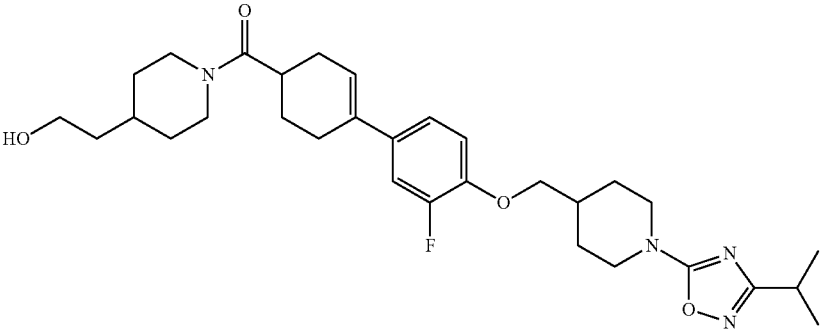 [SMILES: CC(C)c1noc(N2CCC(COc3ccc(C4=CCC(C(=O)N5CCC(CCO)CC5)CC4)cc3F)CC2)n1] |
| 336 | 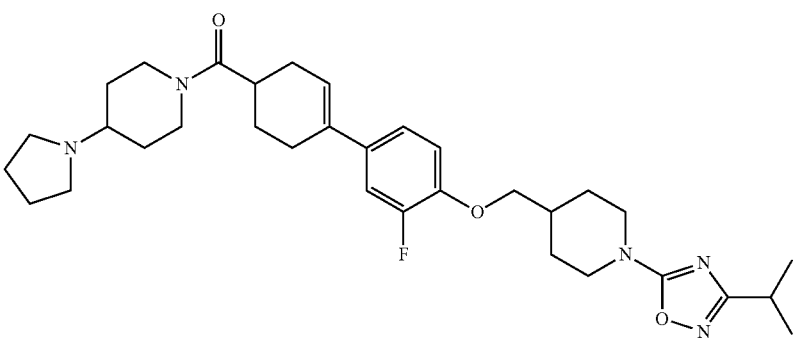 [SMILES: CC(C)c1noc(N2CCC(COc3ccc(C4=CCC(C(=O)N5CCC(N6CCCC6)CC5)CC4)cc3F)CC2)n1] |
| 337 | 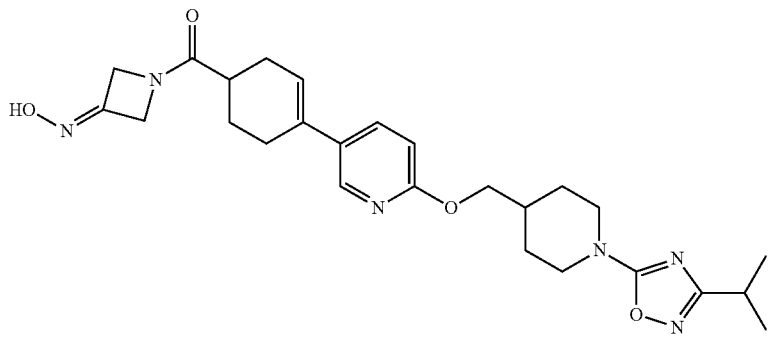 [SMILES: CC(C)c1noc(N2CCC(COc3ccc(C4=CCC(C(=O)N5CC(=NO)C5)CC4)cn3)CC2)n1] |
| 338 | 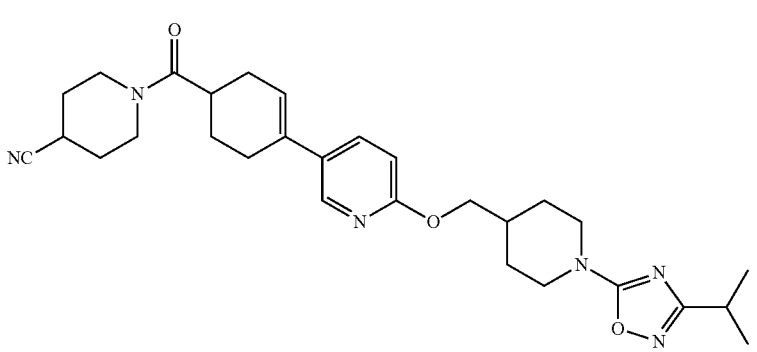 [SMILES: CC(C)c1noc(N2CCC(COc3ccc(C4=CCC(C(=O)N5CCC(C#N)CC5)CC4)cn3)CC2)n1] |

TABLE 1-continued
| Examples | Chemical structures |
|---|---|
| 339 | 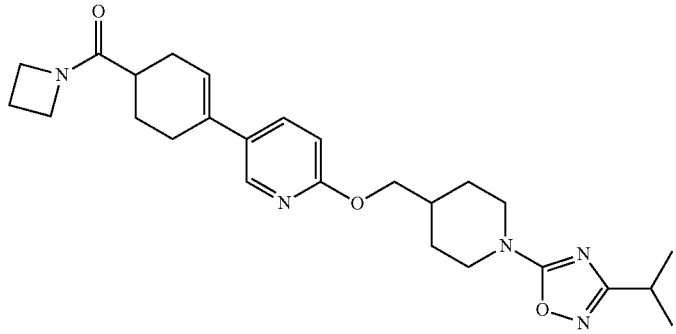 [SMILES: CC(C)c1noc(N2CCC(COc3ccc(C4=CCC(C(=O)N5CCC5)CC4)cn3)CC2)n1] |
| 340 | 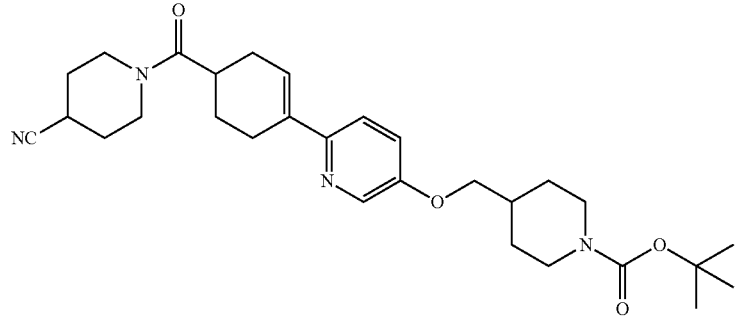 [SMILES: CC(C)(C)OC(=O)N1CCC(COc2ccc(C3=CCC(C(=O)N4CCC(C#N)CC4)CC3)nc2)CC1] |
| 341 | 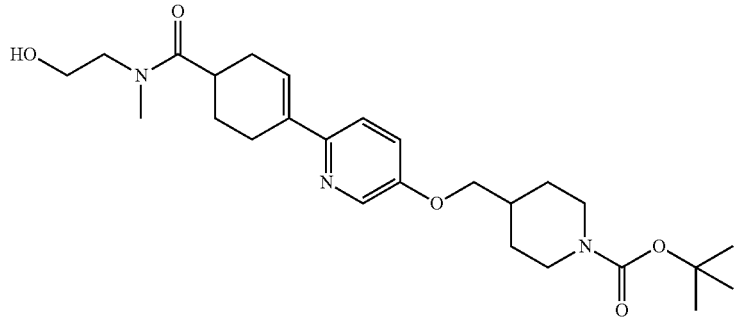 [SMILES: CN(CCO)C(=O)C1CC=C(c2ccc(OCC3CCN(C(=O)OC(C)(C)C)CC3)cn2)CC1] |
| 342 | 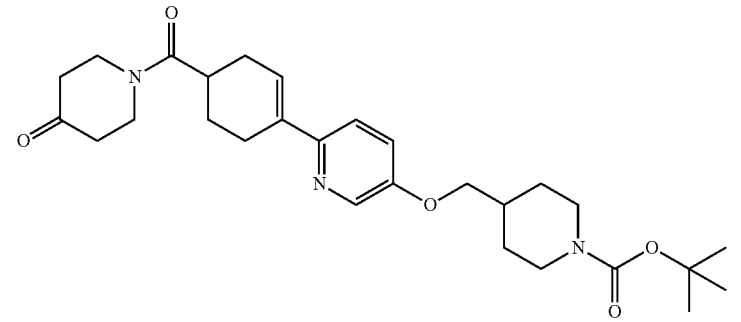 [SMILES: CC(C)(C)OC(=O)N1CCC(COc2ccc(C3=CCC(C(=O)N4CCC(=O)CC4)CC3)nc2)CC1] |

TABLE 1-continued

| Examples | Chemical structures |
|---|---|
| 343 | 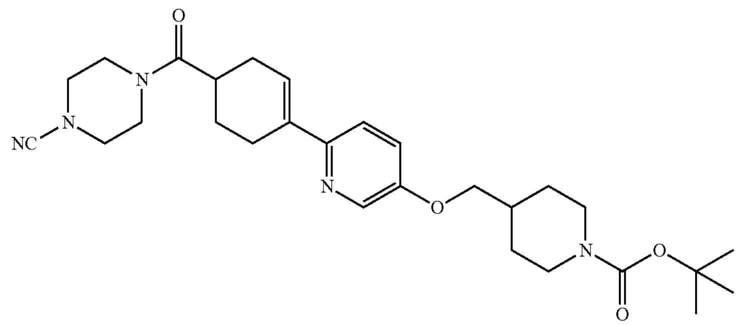 [SMILES: CC(C)(C)OC(=O)N1CCC(COc2ccc(C3=CCC(C(=O)N4CCN(C#N)CC4)CC3)nc2)CC1] |
| 344 | 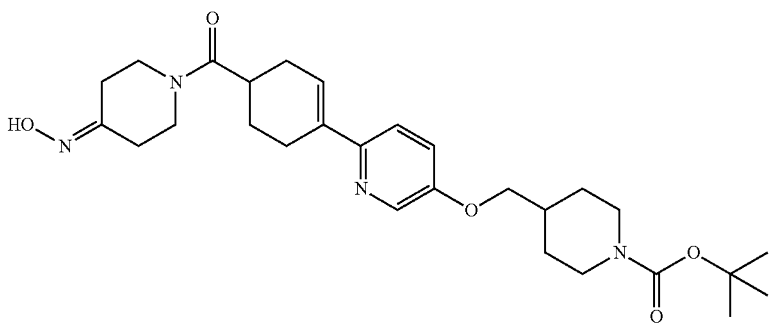 [SMILES: CC(C)(C)OC(=O)N1CCC(COc2ccc(C3=CCC(C(=O)N4CCC(=NO)CC4)CC3)nc2)CC1] |
| 345 | 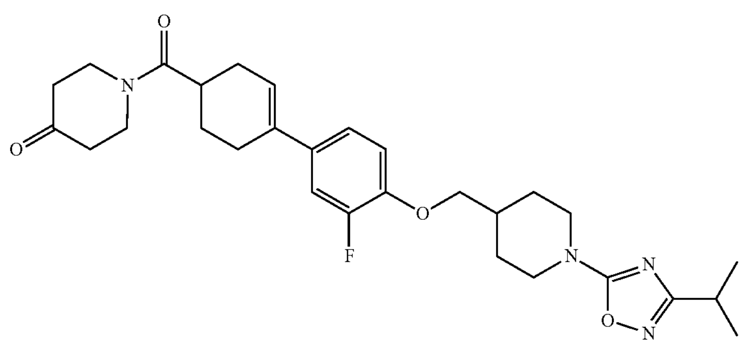 [SMILES: CC(C)c1noc(N2CCC(COc3ccc(C4=CCC(C(=O)N5CCC(=O)CC5)CC4)cc3F)CC2)n1] |
| 346 | 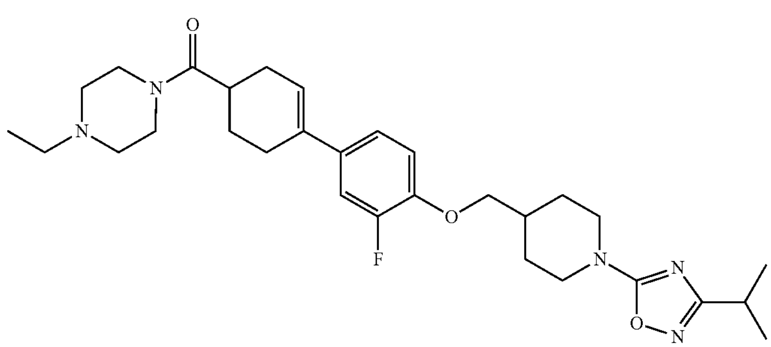 [SMILES: CCN1CCN(C(=O)C2CC=C(c3ccc(OCC4CCN(c5nc(C(C)C)no5)CC4)c(F)c3)CC2)CC1] |

TABLE 1-continued
| Examples | Chemical structures |
|---|---|
| 347 | 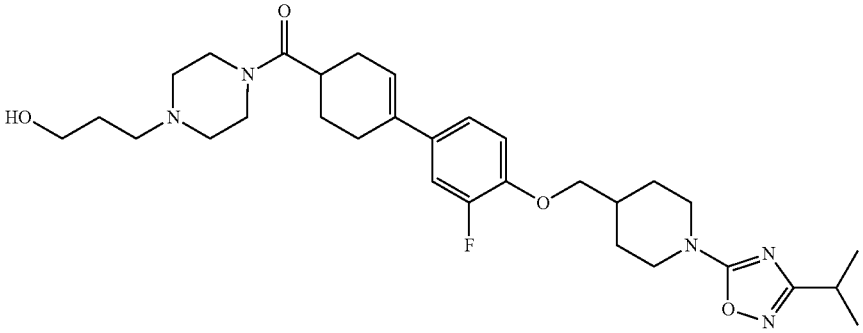 [SMILES: CC(C)c1noc(N2CCC(COc3ccc(C4=CCC(C(=O)N5CCN(CCCO)CC5)CC4)cc3F)CC2)n1] |
| 348 | 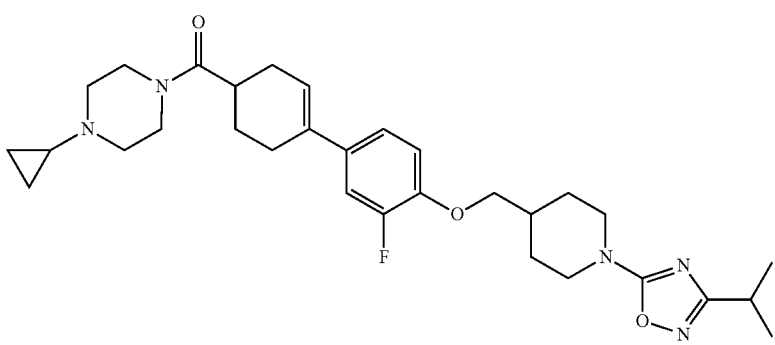 [SMILES: CC(C)c1noc(N2CCC(COc3ccc(C4=CCC(C(=O)N5CCN(C6CC6)CC5)CC4)cc3F)CC2)n1] |
| 349 | 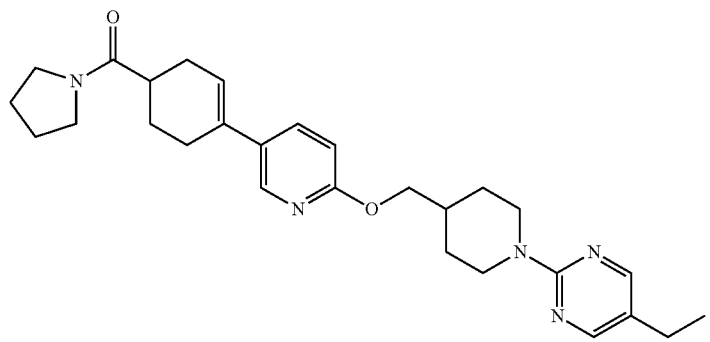 [SMILES: CCc1cnc(N2CCC(COc3ccc(C4=CCC(C(=O)N5CCCC5)CC4)cn3)CC2)nc1] |
| 350 | 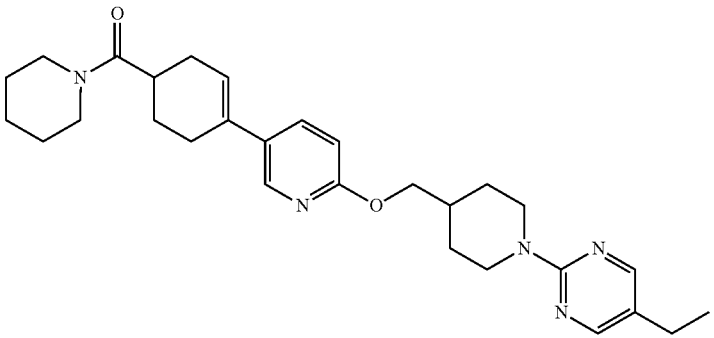 [SMILES: CCc1cnc(N2CCC(COc3ccc(C4=CCC(C(=O)N5CCCCC5)CC4)cn3)CC2)nc1] |

TABLE 1-continued
| Examples | Chemical structures |
|---|---|
| 351 | 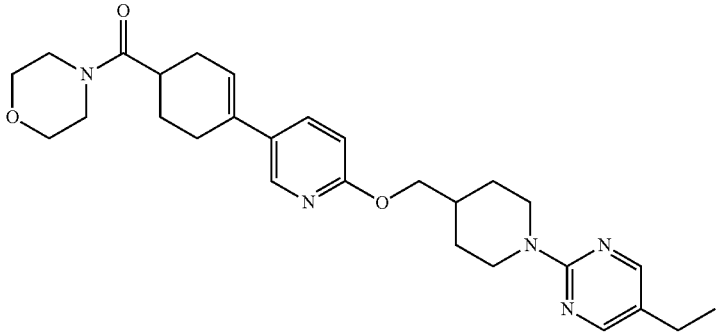 [SMILES: CCc1cnc(N2CCC(COc3ccc(C4=CCC(C(=O)N5CCOCC5)CC4)cn3)CC2)nc1] |
| 352 | 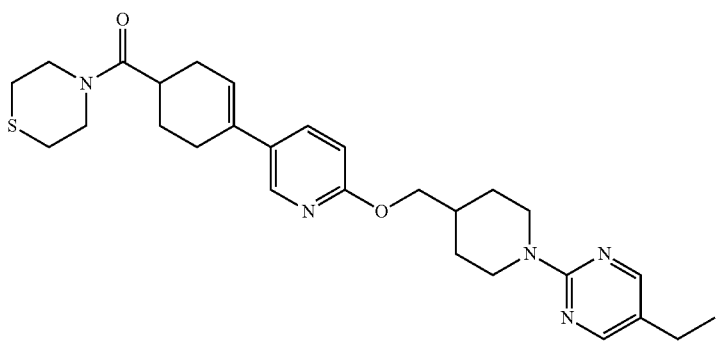 [SMILES: CCc1cnc(N2CCC(COc3ccc(C4=CCC(C(=O)N5CCSCC5)CC4)cn3)CC2)nc1] |
| 353 | 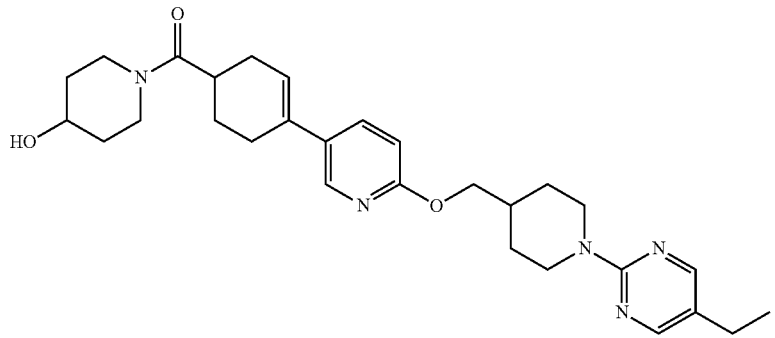 [SMILES: CCc1cnc(N2CCC(COc3ccc(C4=CCC(C(=O)N5CCC(O)CC5)CC4)cn3)CC2)nc1] |
| 354 | 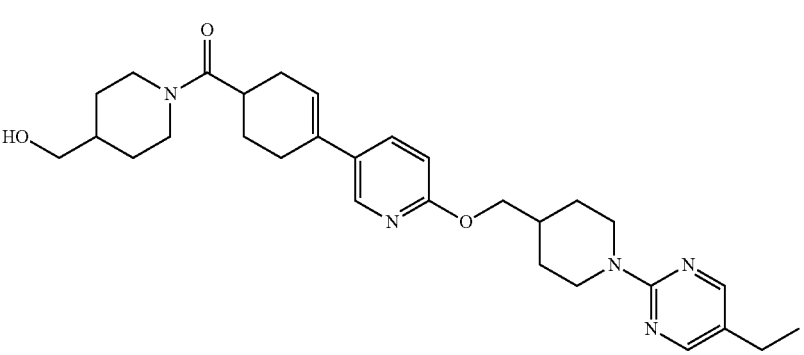 |

TABLE 1-continued
| Examples | Chemical structures |
|---|---|
| 355 | 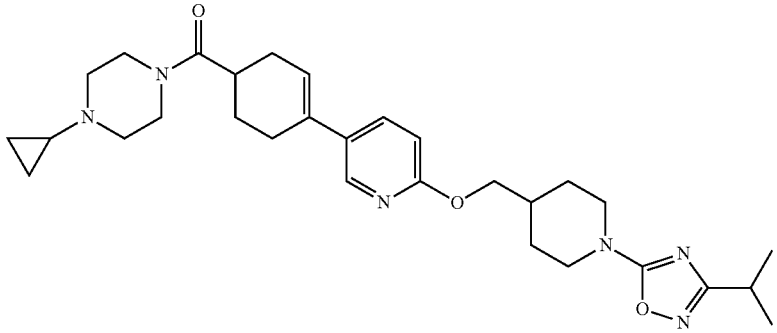 [SMILES: CC(C)c1noc(N2CCC(COc3ccc(C4=CCC(C(=O)N5CCN(C6CC6)CC5)CC4)cn3)CC2)n1] |
| 356 | 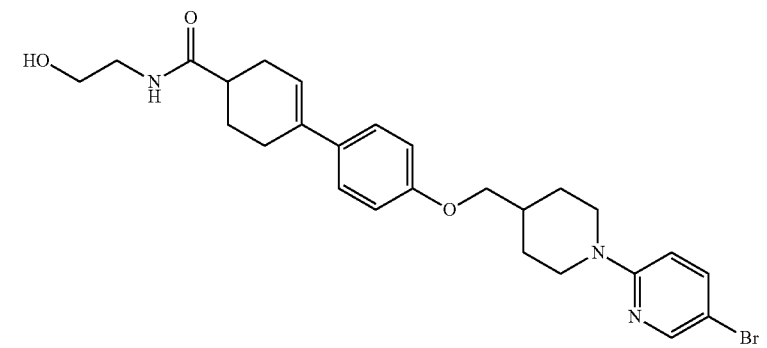 [SMILES: O=C(NCCO)C1CC=C(c2ccc(OCC3CCN(c4ccc(Br)cn4)CC3)cc2)CC1] |
| 357 | 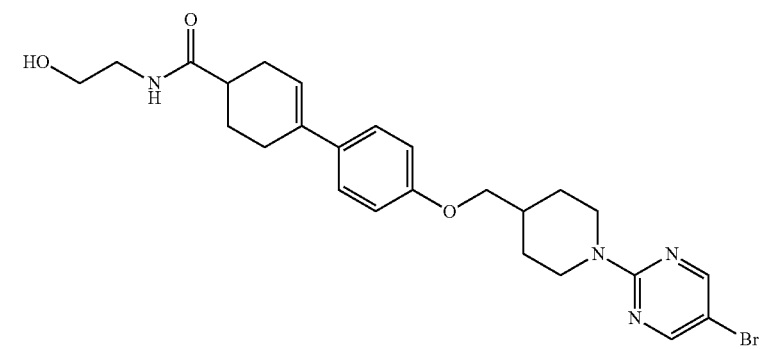 [SMILES: O=C(NCCO)C1CC=C(c2ccc(OCC3CCN(c4ncc(Br)cn4)CC3)cc2)CC1] |
| 358 | 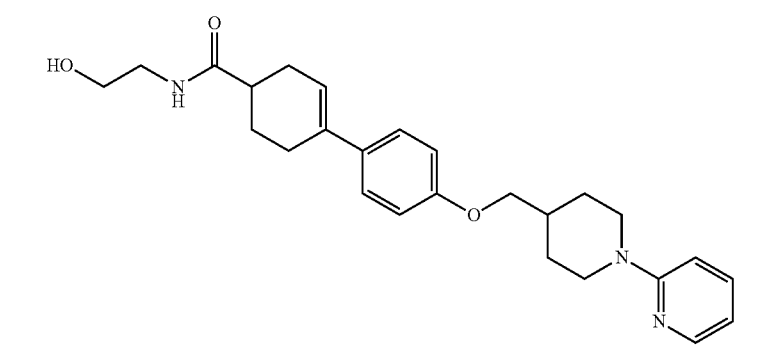 [SMILES: O=C(NCCO)C1CC=C(c2ccc(OCC3CCN(c4ccccn4)CC3)cc2)CC1] |

TABLE 1-continued
| Examples | Chemical structures |
|---|---|
| 359 | 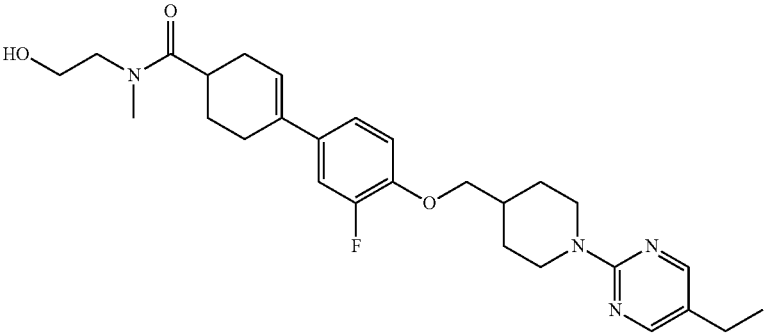 [SMILES: CCc1cnc(N2CCC(COc3ccc(C4=CCC(C(=O)N(C)CCO)CC4)cc3F)CC2)nc1] |
| 360 | 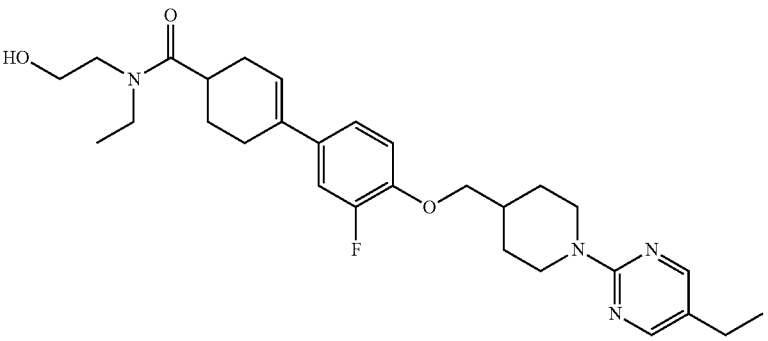 [SMILES: CCc1cnc(N2CCC(COc3ccc(C4=CCC(C(=O)N(CC)CCO)CC4)cc3F)CC2)nc1] |
| 361 | 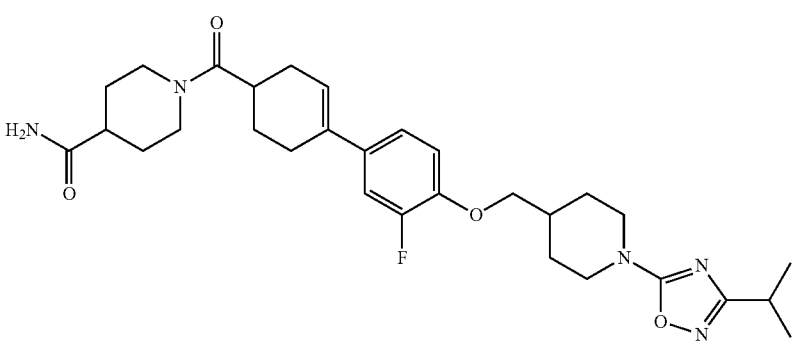 [SMILES: CC(C)c1noc(N2CCC(COc3ccc(C4=CCC(C(=O)N5CCC(C(N)=O)CC5)CC4)cc3F)CC2)n1] |
| 362 | 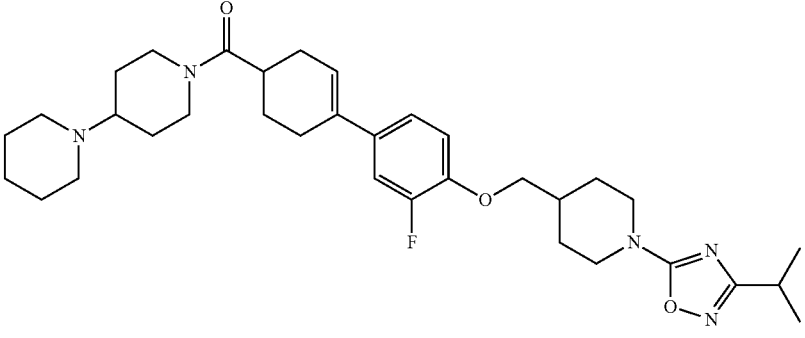 [SMILES: CC(C)c1noc(N2CCC(COc3ccc(C4=CCC(C(=O)N5CCC(N6CCCCC6)CC5)CC4)cc3F)CC2)n1] |

TABLE 1-continued
| Examples | Chemical structures |
|---|---|
| 363 | 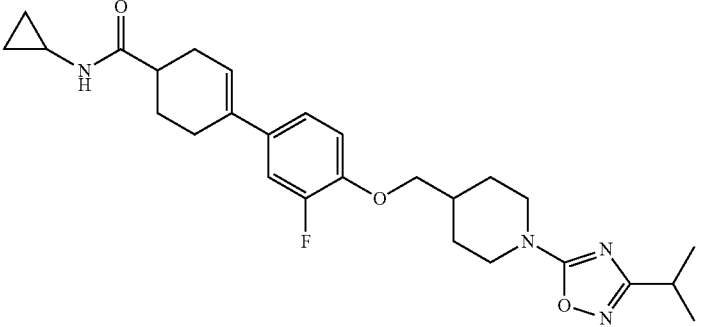 [SMILES: CC(C)c1noc(N2CCC(COc3ccc(C4=CCC(C(=O)NC5CC5)CC4)cc3F)CC2)n1] |
| 364 | 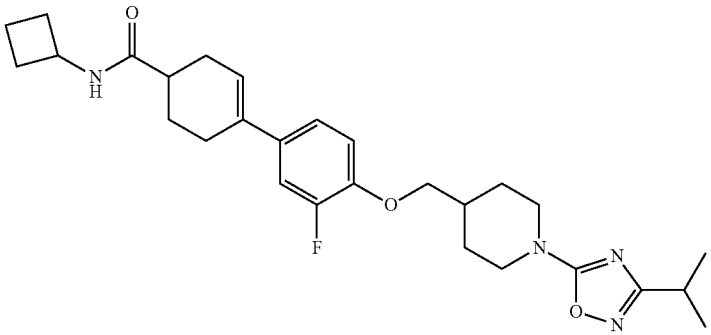 [SMILES: CC(C)c1noc(N2CCC(COc3ccc(C4=CCC(C(=O)NC5CCC5)CC4)cc3F)CC2)n1] |
| 365 | 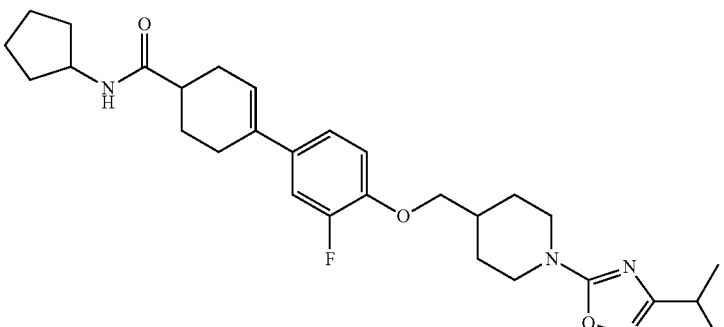 |
| 366 | 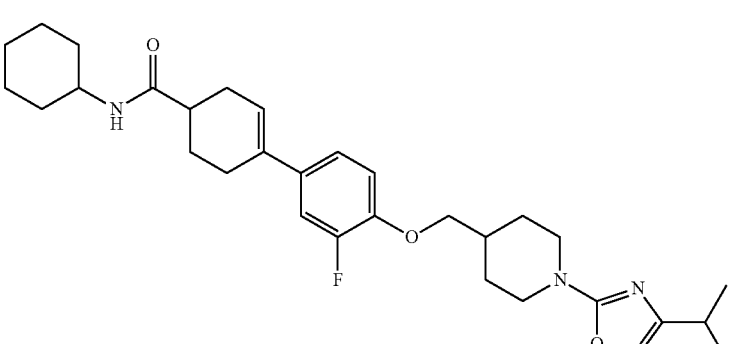 |

TABLE 1-continued
| Examples | Chemical structures |
|---|---|
| 367 | 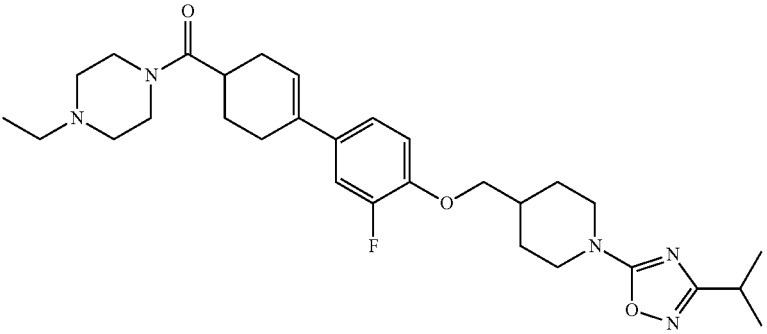 [SMILES: CCN1CCN(C(=O)C2CC=C(c3ccc(OCC4CCN(c5nc(C(C)C)no5)CC4)c(F)c3)CC2)CC1] |
| 368 | 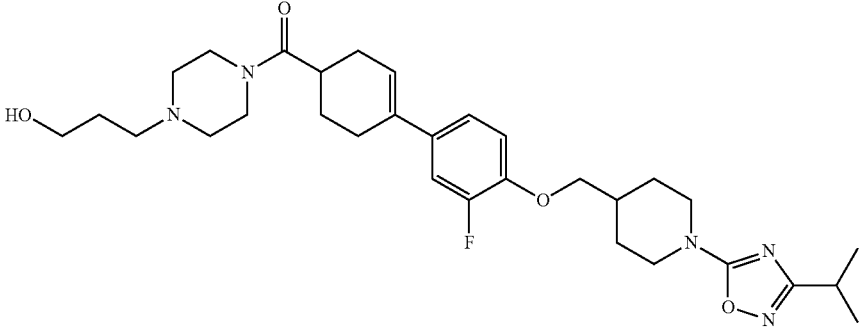 [SMILES: CC(C)c1noc(N2CCC(COc3ccc(C4=CCC(C(=O)N5CCN(CCCO)CC5)CC4)cc3F)CC2)n1] |
| 369 | 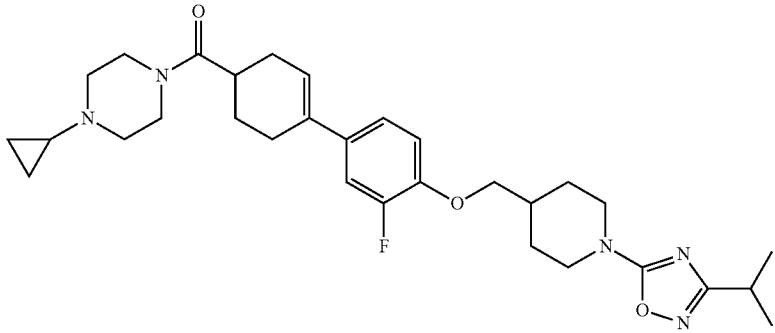 [SMILES: CC(C)c1noc(N2CCC(COc3ccc(C4=CCC(C(=O)N5CCN(C6CC6)CC5)CC4)cc3F)CC2)n1] |
| 370 | 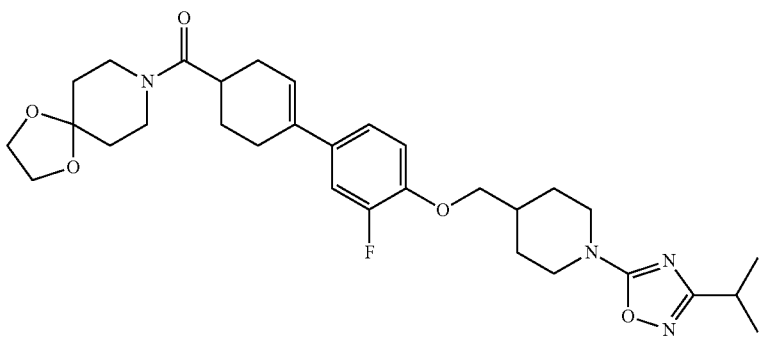 [SMILES: CC(C)c1noc(N2CCC(COc3ccc(C4=CCC(C(=O)N5CCC6(CC5)OCCO6)CC4)cc3F)CC2)n1] |

TABLE 1-continued
| Examples | Chemical structures |
|---|---|
| 371 | 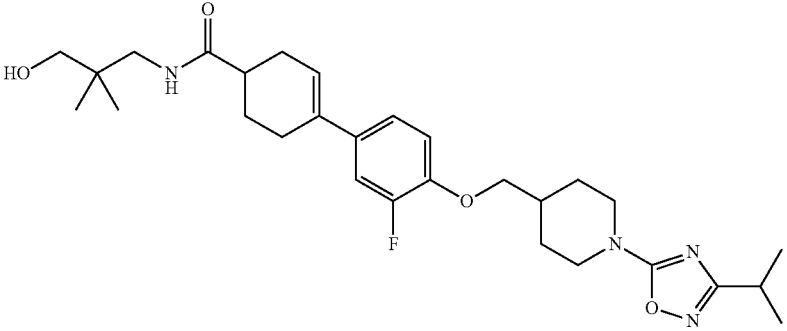 [SMILES: CC(C)c1noc(N2CCC(COc3ccc(C4=CCC(C(=O)NCC(C)(C)CO)CC4)cc3F)CC2)n1] |
| 372 | 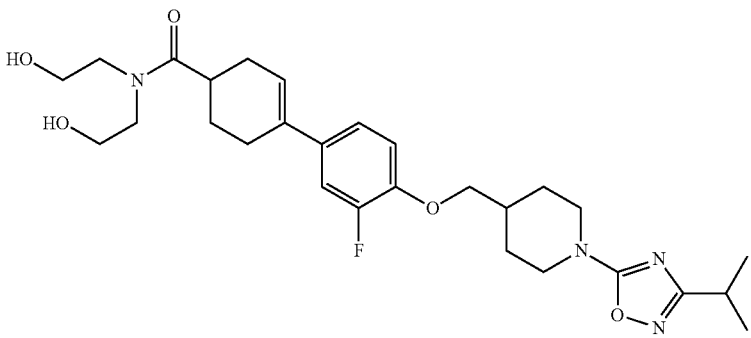 [SMILES: CC(C)c1noc(N2CCC(COc3ccc(C4=CCC(C(=O)N(CCO)CCO)CC4)cc3F)CC2)n1] |
| 373 | 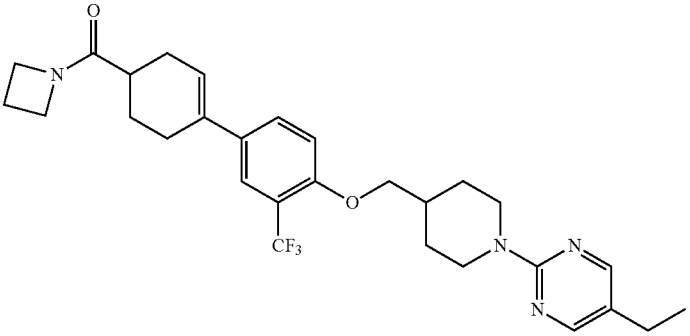 |
| 374 | 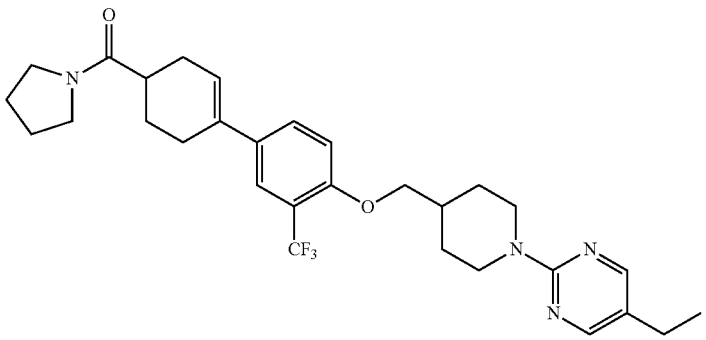 |

TABLE 1-continued
| Examples | Chemical structures |
|---|---|
| 375 | 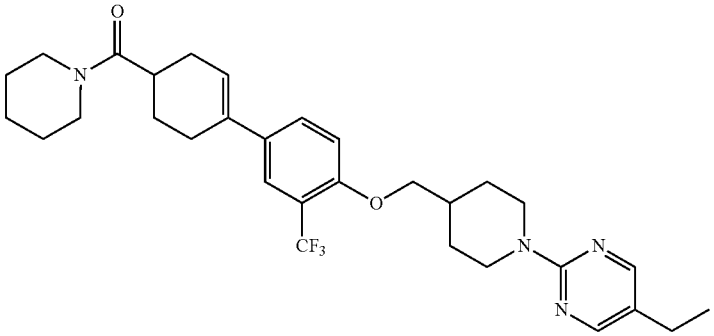 [SMILES: CCc1cnc(N2CCC(COc3ccc(C4=CCC(C(=O)N5CCCCC5)CC4)cc3C(F)(F)F)CC2)nc1] |
| 376 | 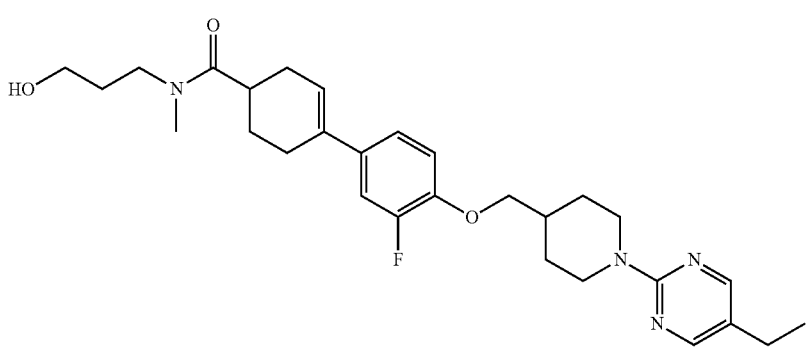 [SMILES: CCc1cnc(N2CCC(COc3ccc(C4=CCC(C(=O)N(C)CCCO)CC4)cc3F)CC2)nc1] |
| 377 | 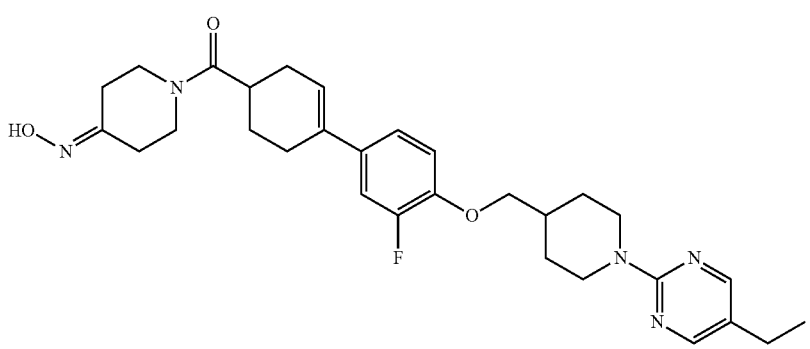 [SMILES: CCc1cnc(N2CCC(COc3ccc(C4=CCC(C(=O)N5CCC(=NO)CC5)CC4)cc3F)CC2)nc1] |
| 378 | 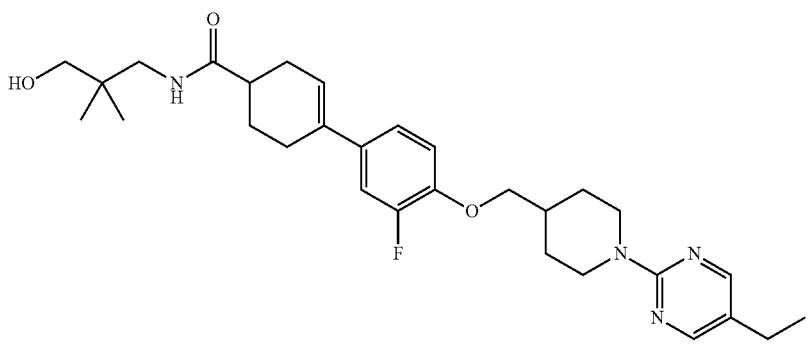 [SMILES: CCc1cnc(N2CCC(COc3ccc(C4=CCC(C(=O)NCC(C)(C)CO)CC4)cc3F)CC2)nc1] |

TABLE 1-continued
| Examples | Chemical structures |
|---|---|
| 379 | 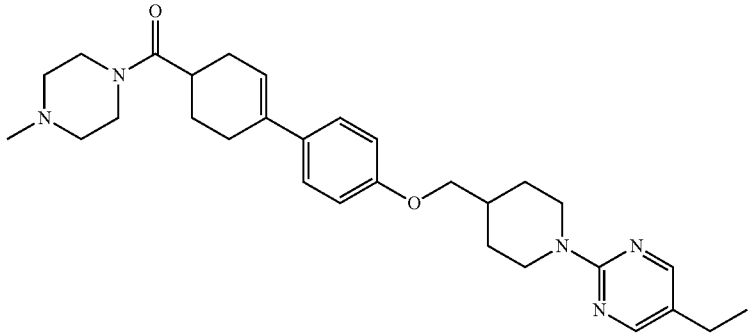 [SMILES: CCc1cnc(N2CCC(COc3ccc(C4=CCC(C(=O)N5CCN(C)CC5)CC4)cc3)CC2)nc1] |
| 380 | 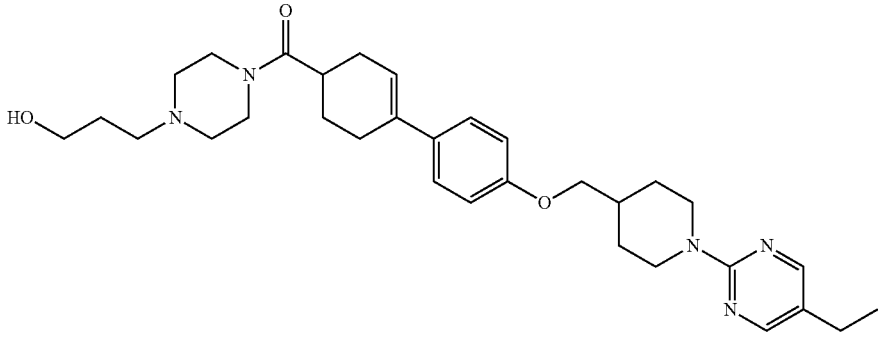 [SMILES: CCc1cnc(N2CCC(COc3ccc(C4=CCC(C(=O)N5CCN(CCCO)CC5)CC4)cc3)CC2)nc1] |
| 381 | 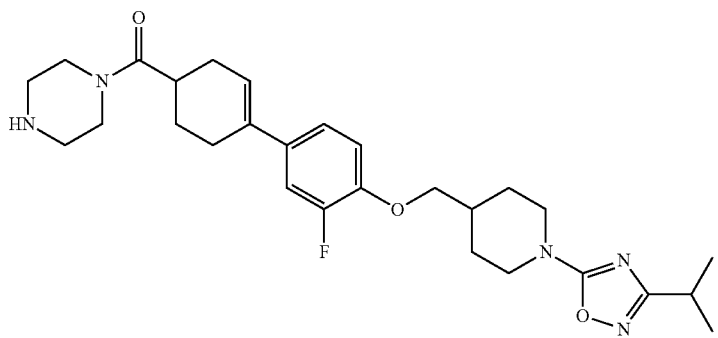 [SMILES: CC(C)c1noc(N2CCC(COc3ccc(C4=CCC(C(=O)N5CCNCC5)CC4)cc3F)CC2)n1] |
| 382 | 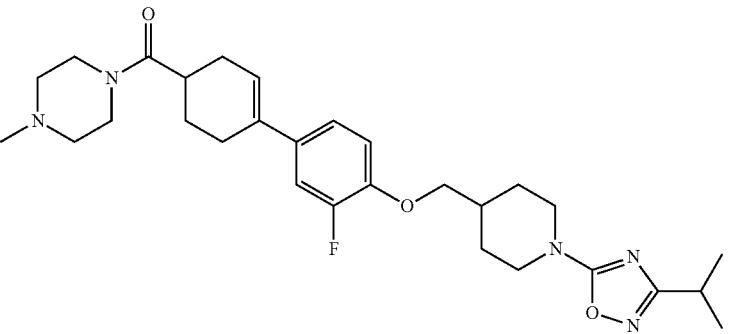 [SMILES: CC(C)c1noc(N2CCC(COc3ccc(C4=CCC(C(=O)N5CCN(C)CC5)CC4)cc3F)CC2)n1] |

TABLE 1-continued
| Examples | Chemical structures |
|---|---|
| 383 | 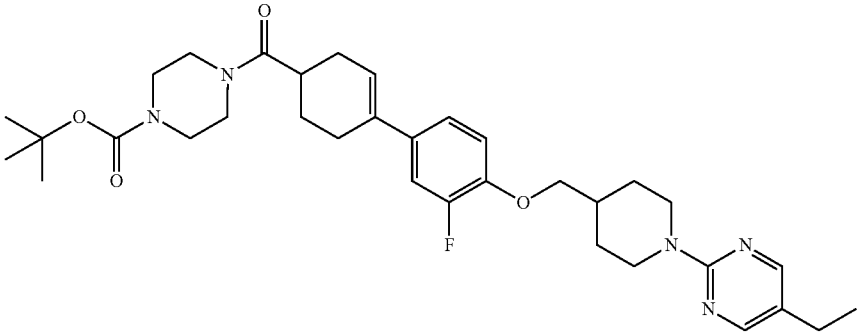 [SMILES: CCc1cnc(N2CCC(COc3ccc(C4=CCC(C(=O)N5CCN(C(=O)OC(C)(C)C)CC5)CC4)cc3F)CC2)nc1] |
| 384 | 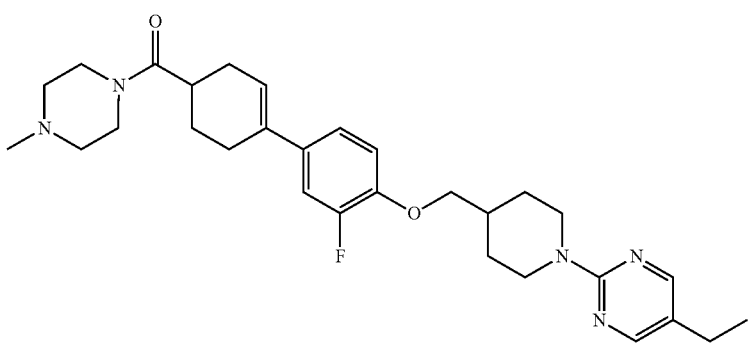 [SMILES: CCc1cnc(N2CCC(COc3ccc(C4=CCC(C(=O)N5CCN(C)CC5)CC4)cc3F)CC2)nc1] |
| 385 | 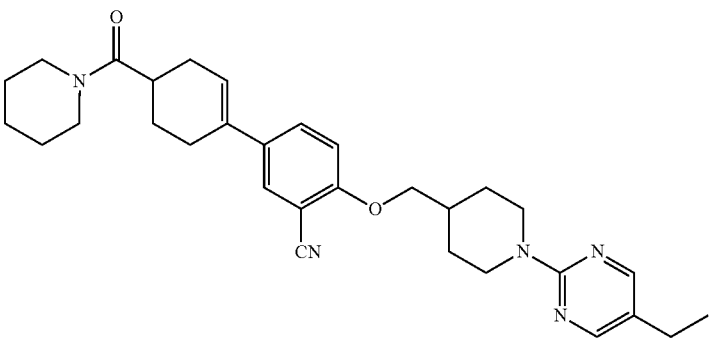 [SMILES: CCc1cnc(N2CCC(COc3ccc(C4=CCC(C(=O)N5CCCCC5)CC4)cc3C#N)CC2)nc1] |
| 386 | 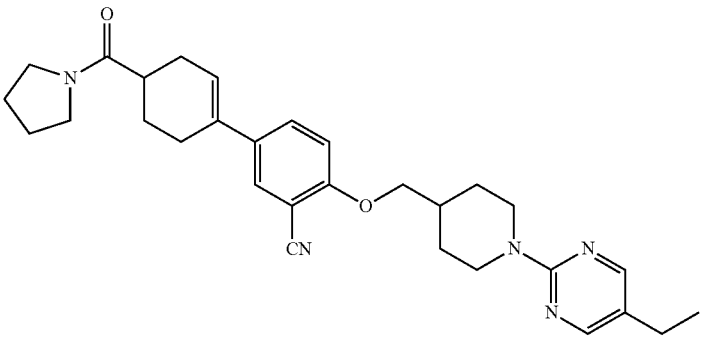 |

TABLE 1-continued
| Examples | Chemical structures |
|---|---|
| 387 | 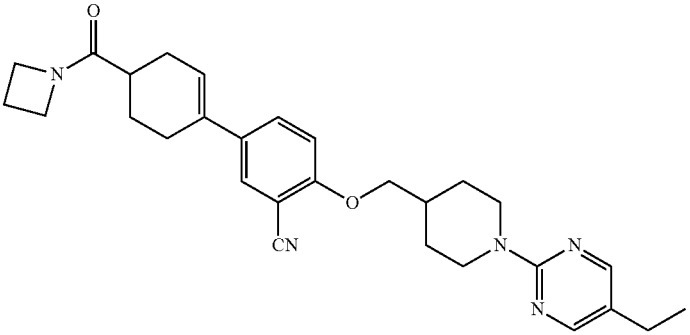 |
| 388 | 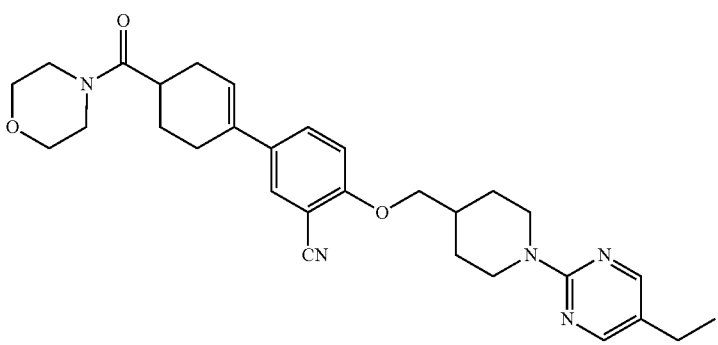 [SMILES: CCc1cnc(N2CCC(COc3ccc(C4=CCC(C(=O)N5CCOCC5)CC4)cc3C#N)CC2)nc1] |
| 389 | 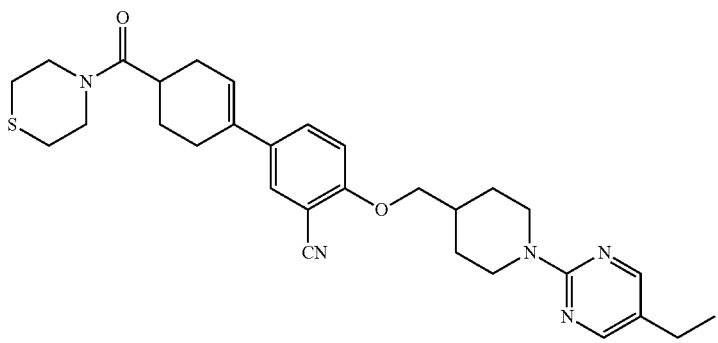 |
| 390 | 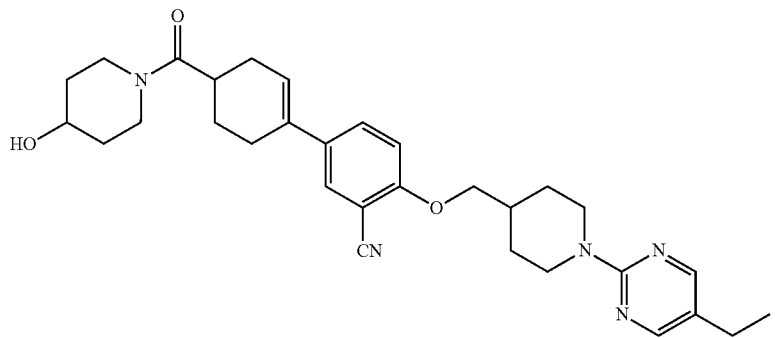 [SMILES: CCc1cnc(N2CCC(COc3ccc(C4=CCC(C(=O)N5CCC(O)CC5)CC4)cc3C#N)CC2)nc1] |

TABLE 1-continued
| Examples | Chemical structures |
|---|---|
| 391 | 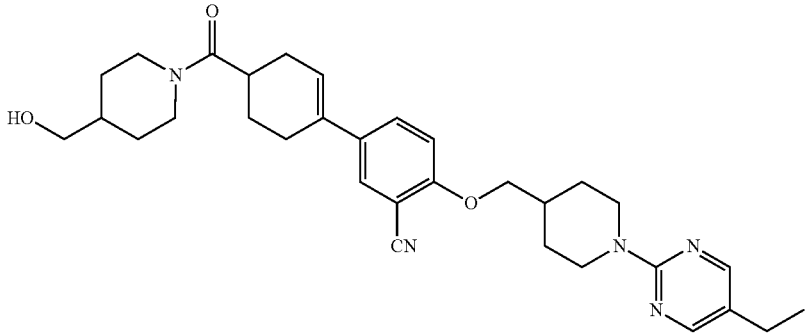 [SMILES: CCc1cnc(N2CCC(COc3ccc(C4=CCC(C(=O)N5CCC(CO)CC5)CC4)cc3C#N)CC2)nc1] |
| 392 | 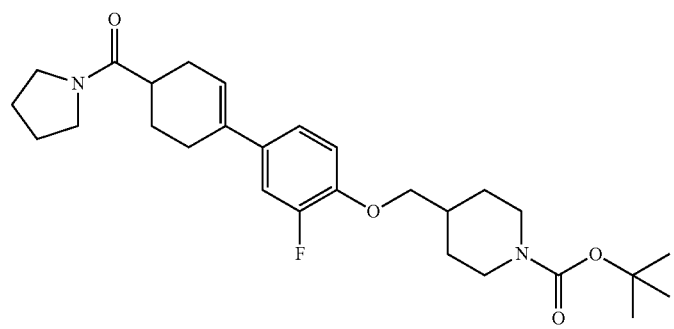 [SMILES: CC(C)(C)OC(=O)N1CCC(COc2ccc(C3=CCC(C(=O)N4CCCC4)CC3)cc2F)CC1] |
| 393 | 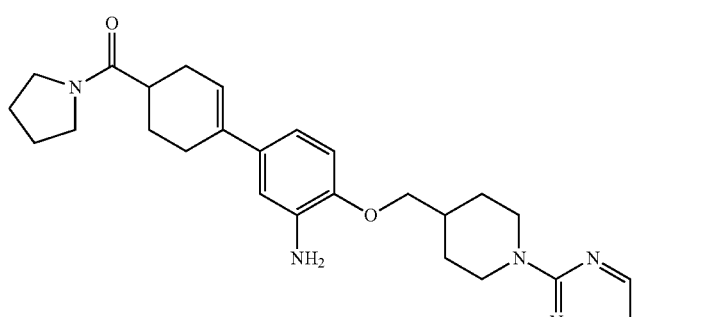 |
| 394 | 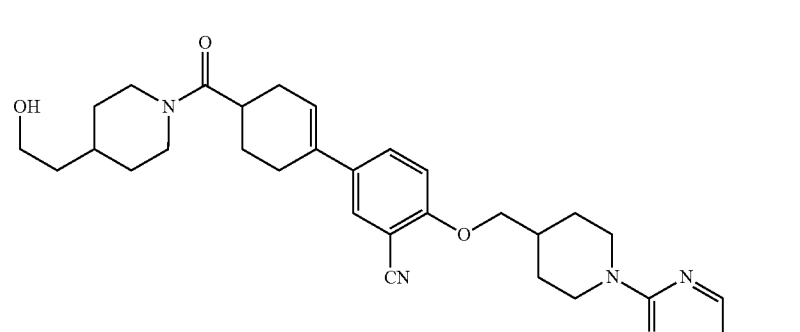 |

TABLE 1-continued

| Examples | Chemical structures |
|---|---|
| 395 | 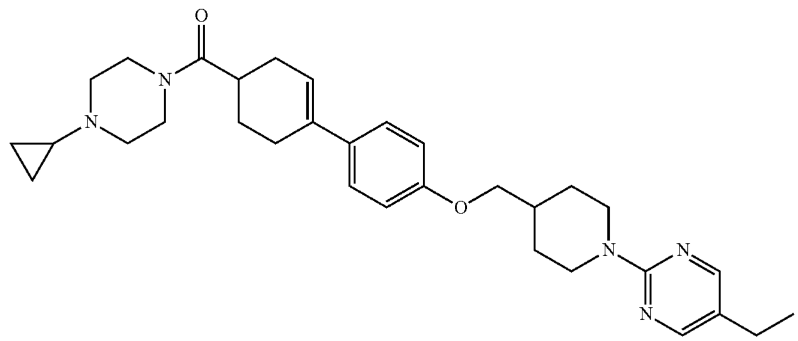 [SMILES: CCc1cnc(N2CCC(COc3ccc(C4=CCC(C(=O)N5CCN(C6CC6)CC5)CC4)cc3)CC2)nc1] |
| 396 | 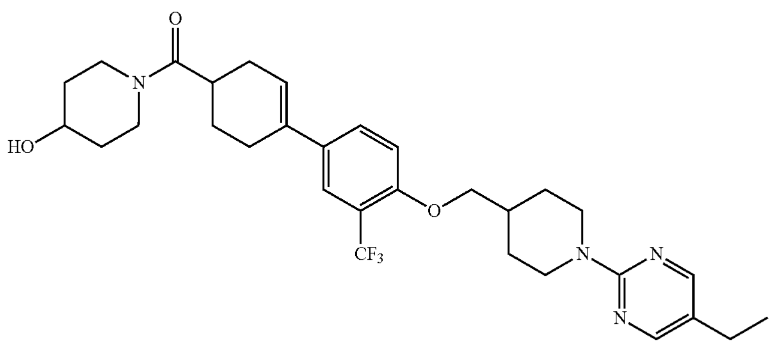 |
| 397 | 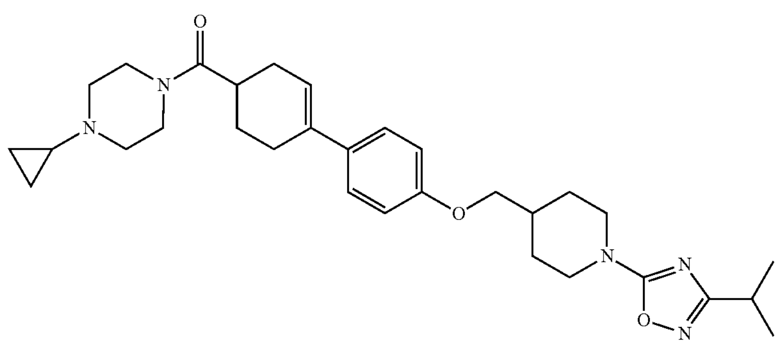 [SMILES: CC(C)c1noc(N2CCC(COc3ccc(C4=CCC(C(=O)N5CCN(C6CC6)CC5)CC4)cc3)CC2)n1] |
| 398 | 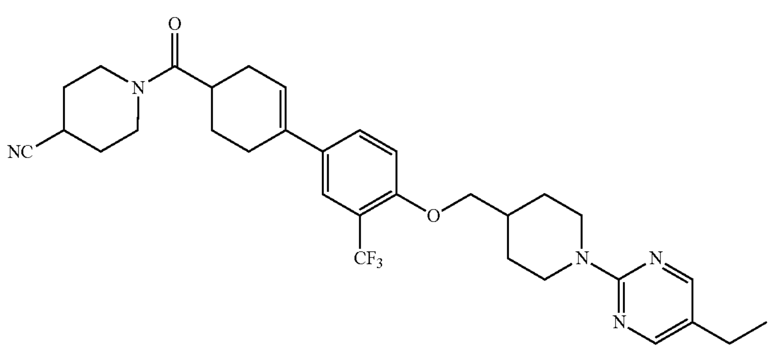 [SMILES: CCc1cnc(N2CCC(COc3ccc(C4=CCC(C(=O)N5CCC(C#N)CC5)CC4)cc3C(F)(F)F)CC2)nc1] |

TABLE 1-continued

| Examples | Chemical structures |
|---|---|
| 399 | 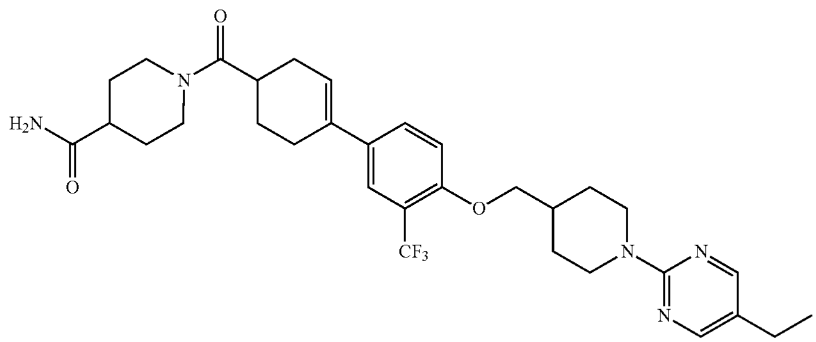 [SMILES: CCc1cnc(N2CCC(COc3ccc(C4=CCC(C(=O)N5CCC(C(N)=O)CC5)CC4)cc3C(F)(F)F)CC2)nc1] |
| 400 | 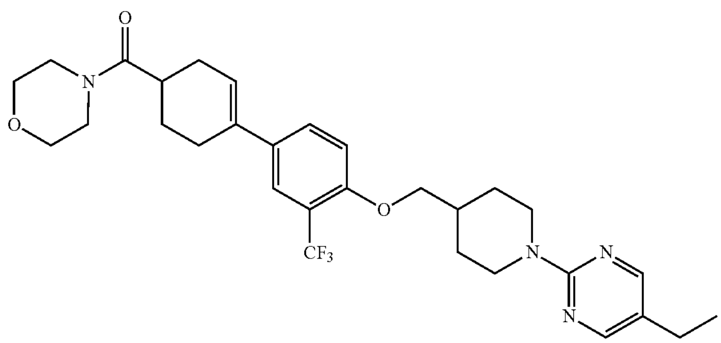 |
| 401 | 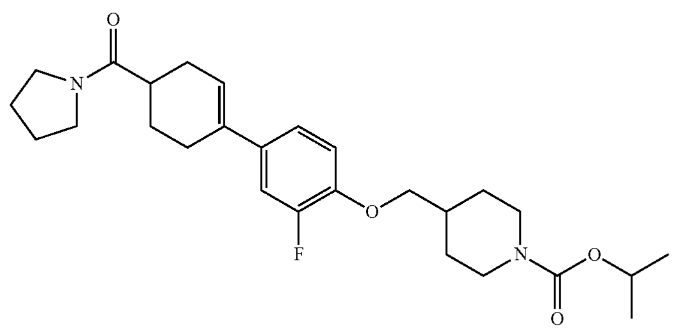 [SMILES: CC(C)OC(=O)N1CCC(COc2ccc(C3=CCC(C(=O)N4CCCC4)CC3)cc2F)CC1] |
| 402 | 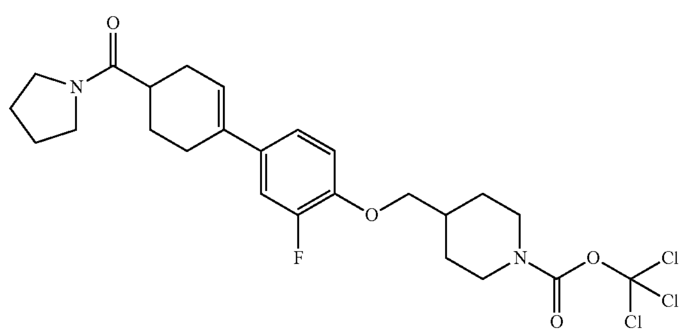 [SMILES: O=C(OC(Cl)(Cl)Cl)N1CCC(COc2ccc(C3=CCC(C(=O)N4CCCC4)CC3)cc2F)CC1] |

TABLE 1-continued
| Examples | Chemical structures |
|---|---|
| 403 | 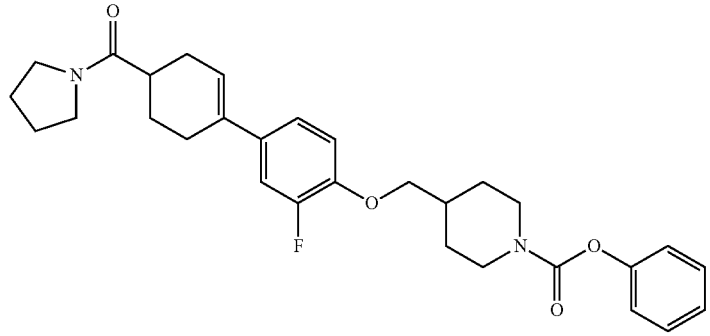 [SMILES: O=C(Oc1ccccc1)N1CCC(COc2ccc(C3=CCC(C(=O)N4CCCC4)CC3)cc2F)CC1] |
| 404 | 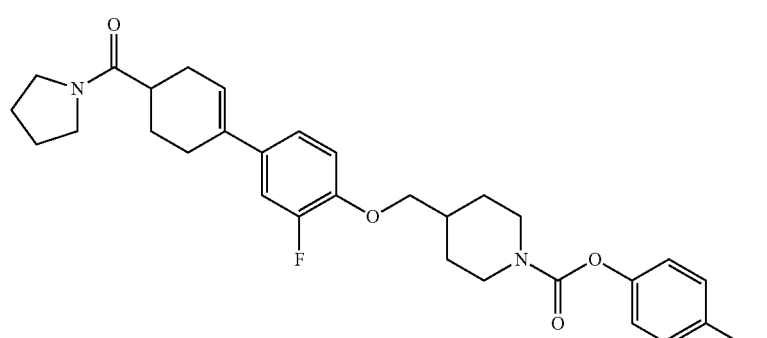 |
| 405 | 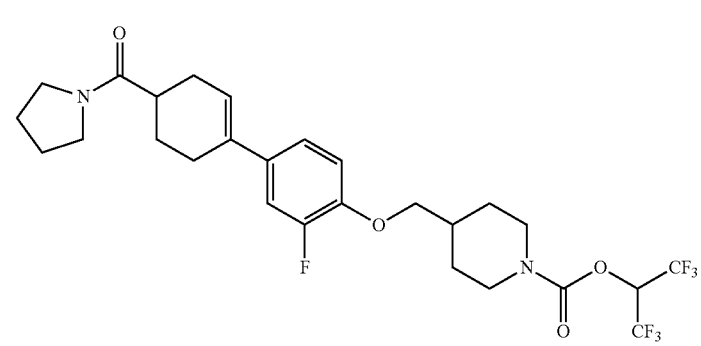 [SMILES: O=C(OC(C(F)(F)F)C(F)(F)F)N1CCC(COc2ccc(C3=CCC(C(=O)N4CCCC4)CC3)cc2F)CC1] |
| 406 | 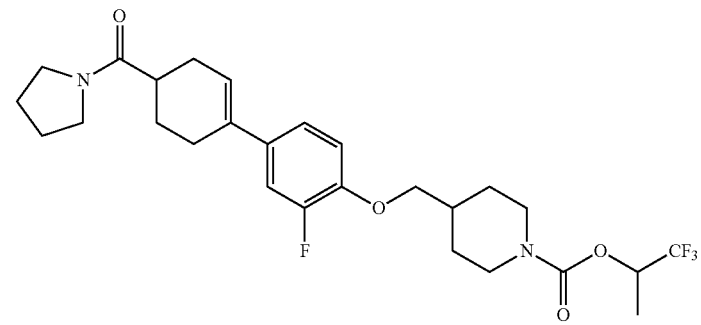 [SMILES: CC(OC(=O)N1CCC(COc2ccc(C3=CCC(C(=O)N4CCCC4)CC3)cc2F)CC1)C(F)(F)F] |

TABLE 1-continued

| Examples | Chemical structures |
|---|---|
| 407 | 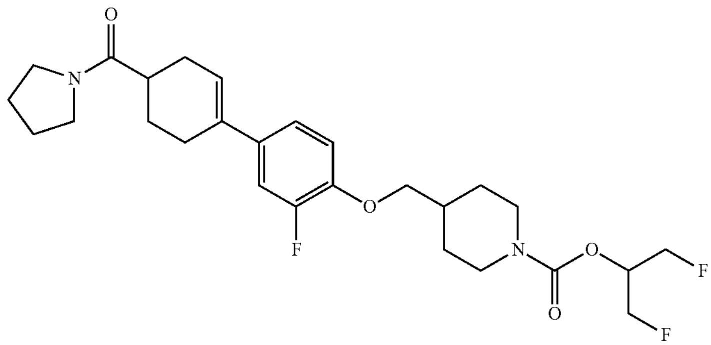 [SMILES: O=C(OC(CF)CF)N1CCC(COc2ccc(C3=CCC(C(=O)N4CCCC4)CC3)cc2F)CC1] |
| 408 | 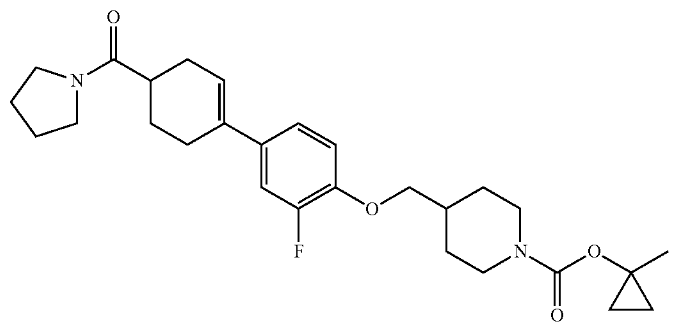 [SMILES: CC1(OC(=O)N2CCC(COc3ccc(C4=CCC(C(=O)N5CCCC5)CC4)cc3F)CC2)CC1] |
| 409 | 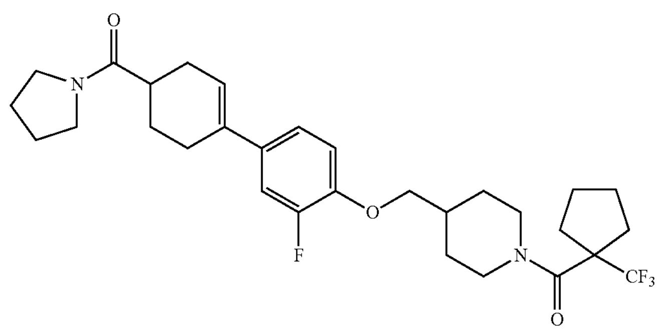 [SMILES: O=C(C1CC=C(c2ccc(OCC3CCN(C(=O)C4(C(F)(F)F)CCCC4)CC3)c(F)c2)CC1)N1CCCC1] |
| 410 | 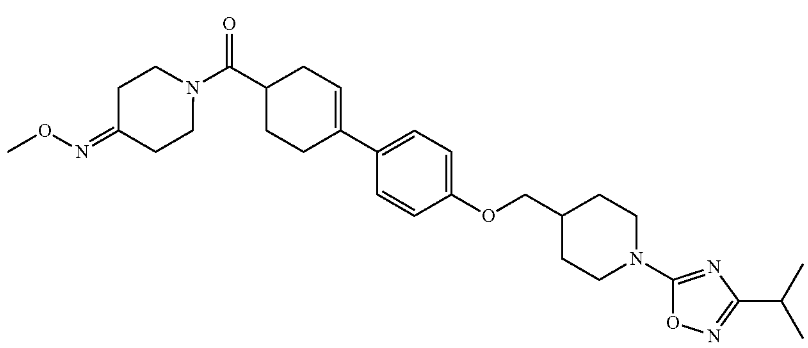 [SMILES: CON=C1CCN(C(=O)C2CC=C(c3ccc(OCC4CCN(c5nc(C(C)C)no5)CC4)cc3)CC2)CC1] |

TABLE 1-continued

| Examples | Chemical structures |
|---|---|
| 411 | 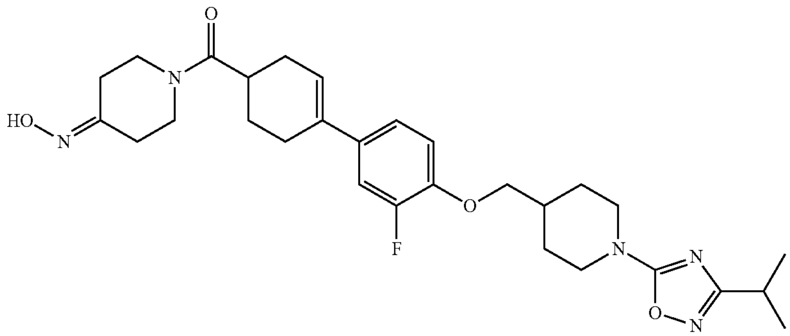 [SMILES: CC(C)c1noc(N2CCC(COc3ccc(C4=CCC(C(=O)N5CCC(=NO)CC5)CC4)cc3F)CC2)n1] |
| 412 | 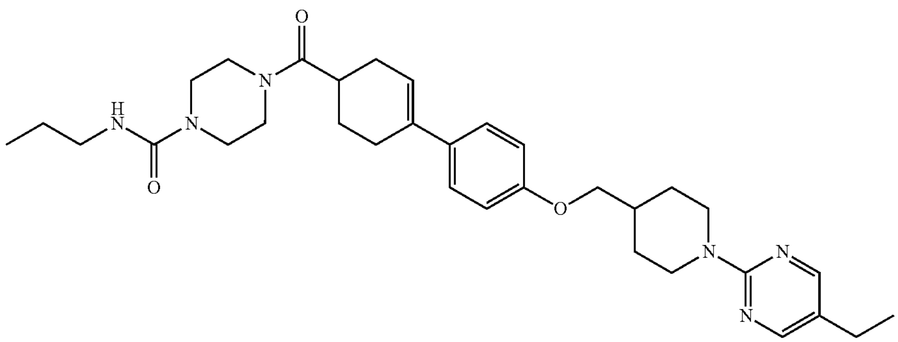 [SMILES: CCCNC(=O)N1CCN(C(=O)C2CC=C(c3ccc(OCC4CCN(c5ncc(CC)cn5)CC4)cc3)CC2)CC1] |
| 413 | 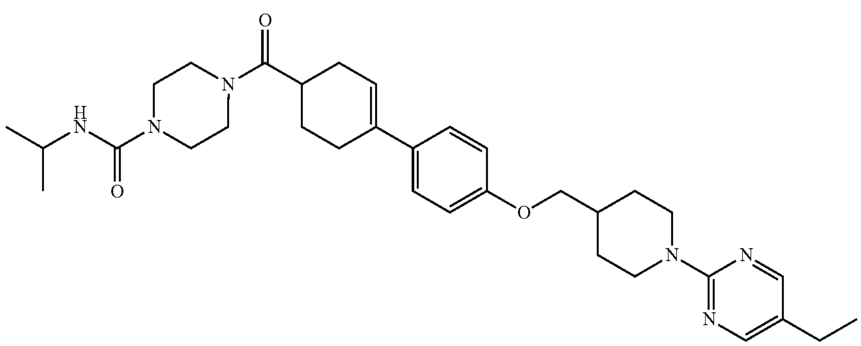 [SMILES: CCc1cnc(N2CCC(COc3ccc(C4=CCC(C(=O)N5CCN(C(=O)NC(C)C)CC5)CC4)cc3)CC2)nc1] |
| 414 | 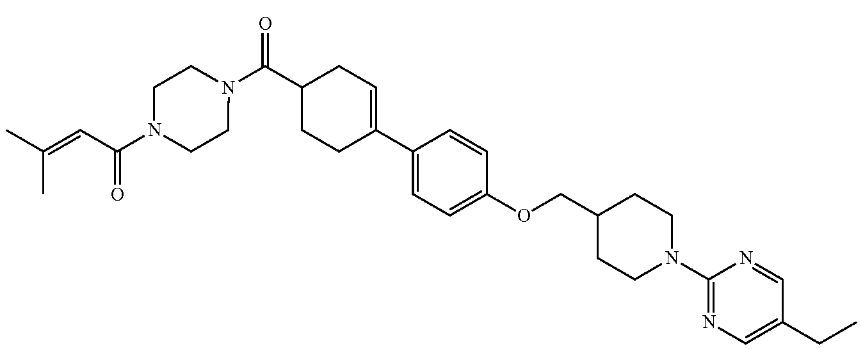 [SMILES: CCc1cnc(N2CCC(COc3ccc(C4=CCC(C(=O)N5CCN(C(=O)C=C(C)C)CC5)CC4)cc3)CC2)nc1] |

TABLE 1-continued
| Examples | Chemical structures |
|---|---|
| 415 | 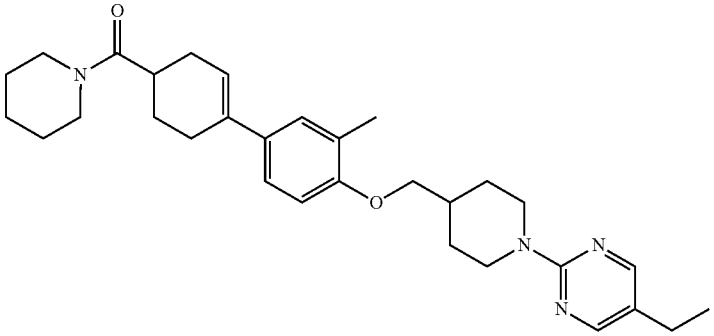 [SMILES: CCc1cnc(N2CCC(COc3ccc(C4=CCC(C(=O)N5CCCCC5)CC4)cc3C)CC2)nc1] |
| 416 | 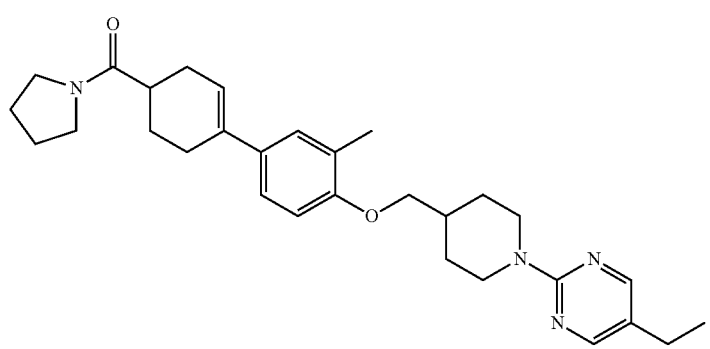 [SMILES: CCc1cnc(N2CCC(COc3ccc(C4=CCC(C(=O)N5CCCC5)CC4)cc3C)CC2)nc1] |
| 417 | 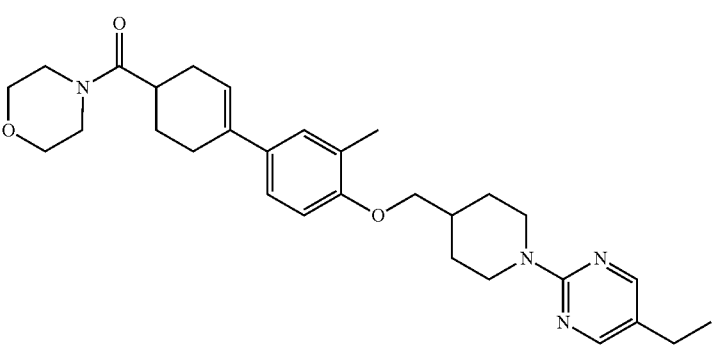 [SMILES: CCc1cnc(N2CCC(COc3ccc(C4=CCC(C(=O)N5CCOCC5)CC4)cc3C)CC2)nc1] |
| 418 | 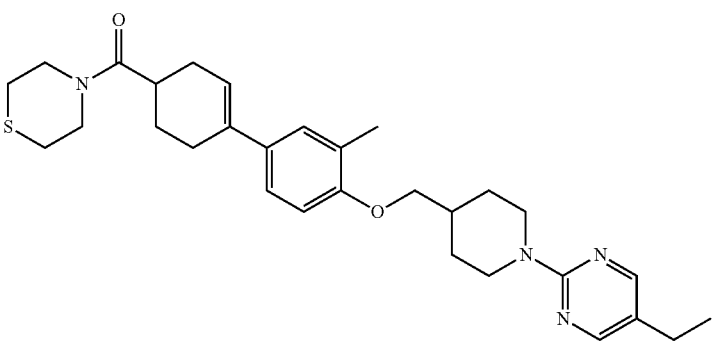 [SMILES: CCc1cnc(N2CCC(COc3ccc(C4=CCC(C(=O)N5CCSCC5)CC4)cc3C)CC2)nc1] |

TABLE 1-continued
| Examples | Chemical structures |
|---|---|
| 419 | 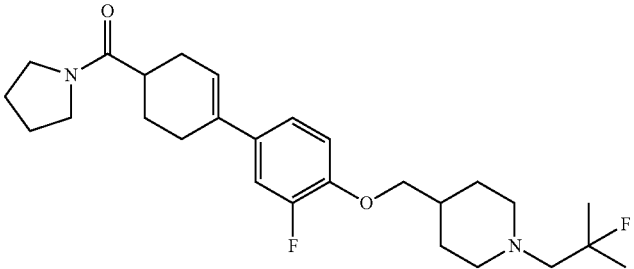 [SMILES: CC(C)(F)CN1CCC(COc2ccc(C3=CCC(C(=O)N4CCCC4)CC3)cc2F)CC1] |
| 420 | 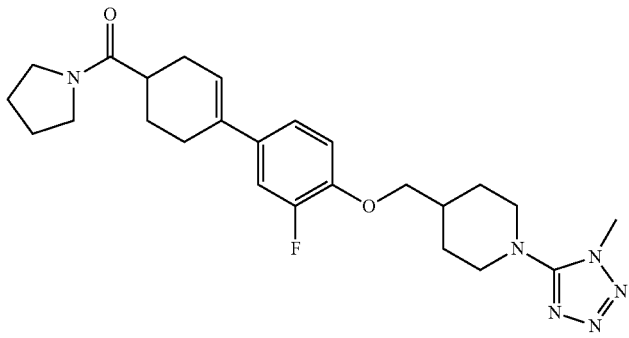 [SMILES: Cn1nnnc1N1CCC(COc2ccc(C3=CCC(C(=O)N4CCCC4)CC3)cc2F)CC1] |
| 421 | 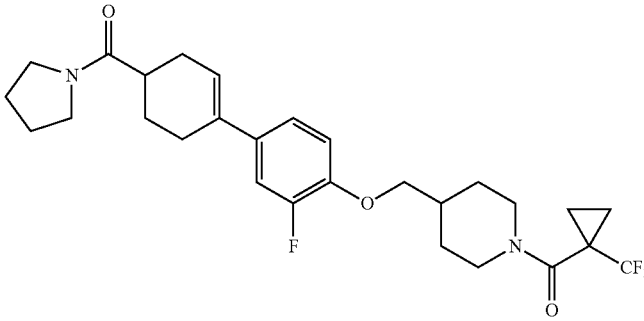 |
| 422 | 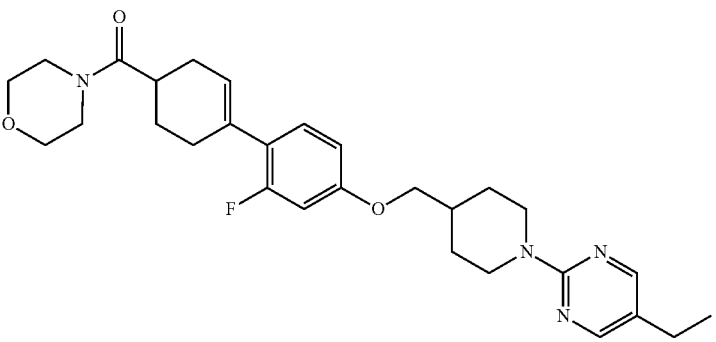 |

TABLE 1-continued
| Examples | Chemical structures |
|---|---|
| 423 | 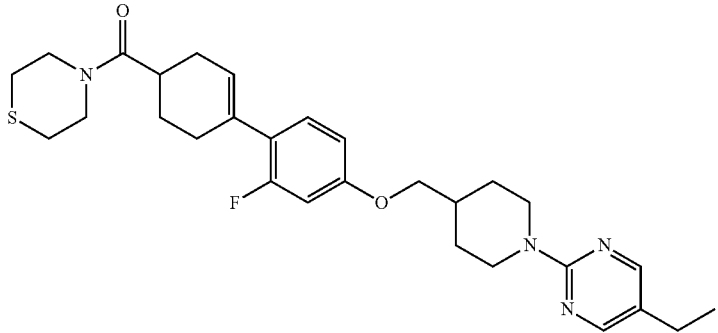 [SMILES: CCc1cnc(N2CCC(COc3ccc(C4=CCC(C(=O)N5CCSCC5)CC4)c(F)c3)CC2)nc1] |
| 424 | 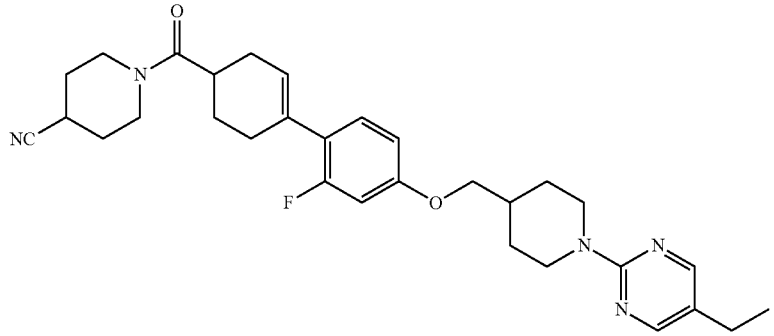 |
| 425 | 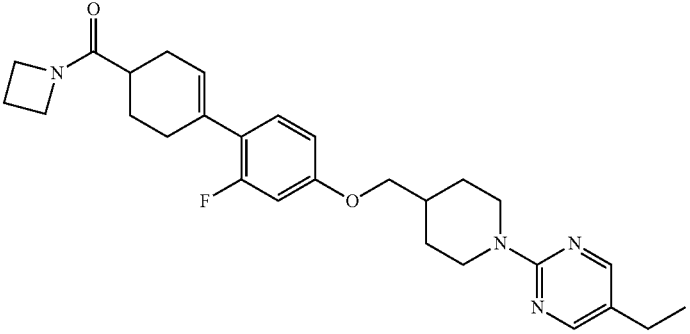 [SMILES: CCc1cnc(N2CCC(COc3ccc(C4=CCC(C(=O)N5CCC5)CC4)c(F)c3)CC2)nc1] |
| 426 | 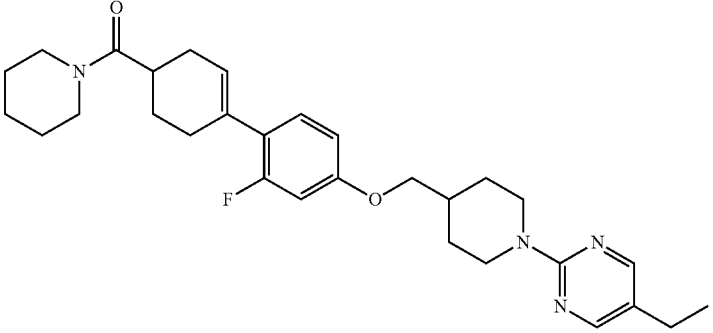 [SMILES: CCc1cnc(N2CCC(COc3ccc(C4=CCC(C(=O)N5CCCCC5)CC4)c(F)c3)CC2)nc1] |

TABLE 1-continued
| Examples | Chemical structures |
|---|---|
| 427 | 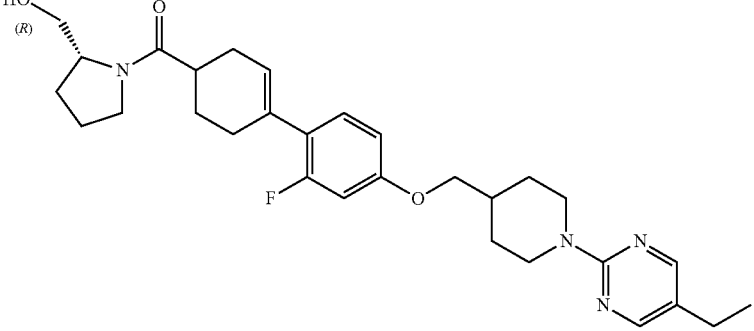 |
| 428 | 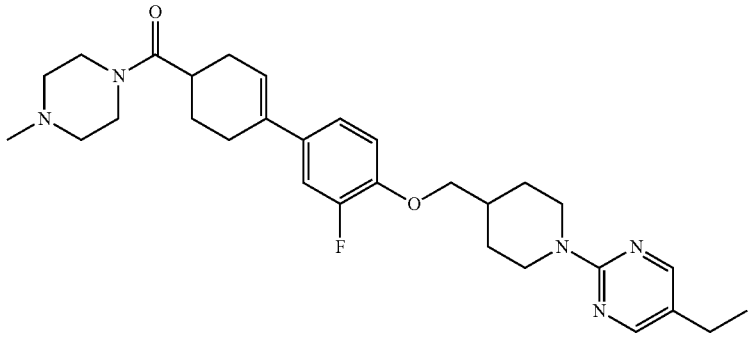 [SMILES: CCc1cnc(N2CCC(COc3ccc(C4=CCC(C(=O)N5CCN(C)CC5)CC4)cc3F)CC2)nc1] |
| 429 | 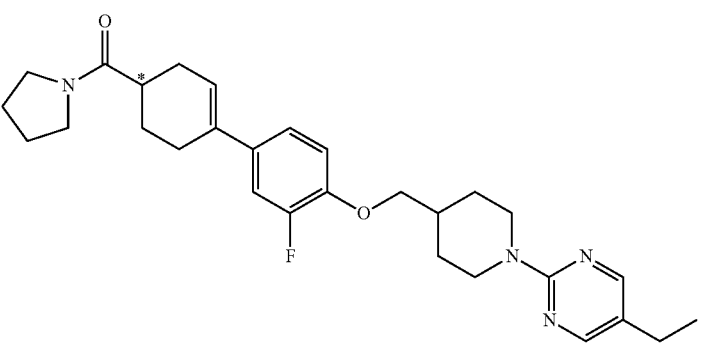 [SMILES: CCc1cnc(N2CCC(COc3ccc(C4=CCC(C(=O)N5CCCC5)CC4)cc3F)CC2)nc1] |
| 430 | 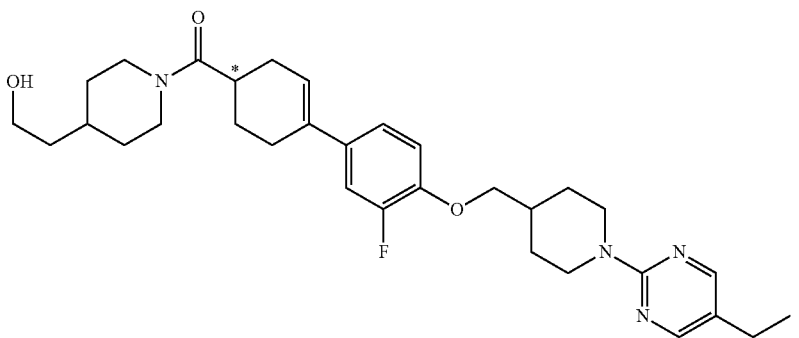 [SMILES: CCc1cnc(N2CCC(COc3ccc(C4=CCC(C(=O)N5CCC(CCO)CC5)CC4)cc3F)CC2)nc1] |

TABLE 1-continued
| Examples | Chemical structures |
|---|---|
| 431 | 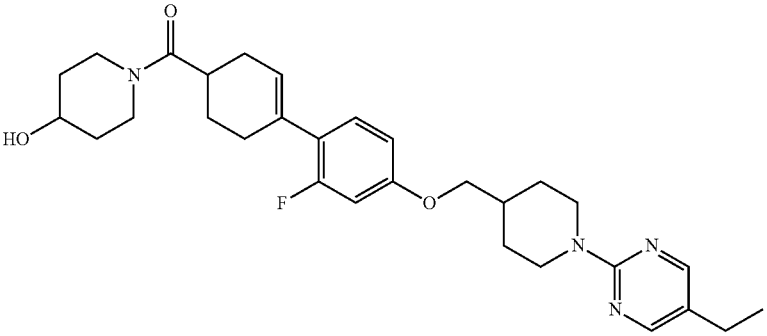 [SMILES: CCc1cnc(N2CCC(COc3ccc(C4=CCC(C(=O)N5CCC(O)CC5)CC4)c(F)c3)CC2)nc1] |
| 432 | 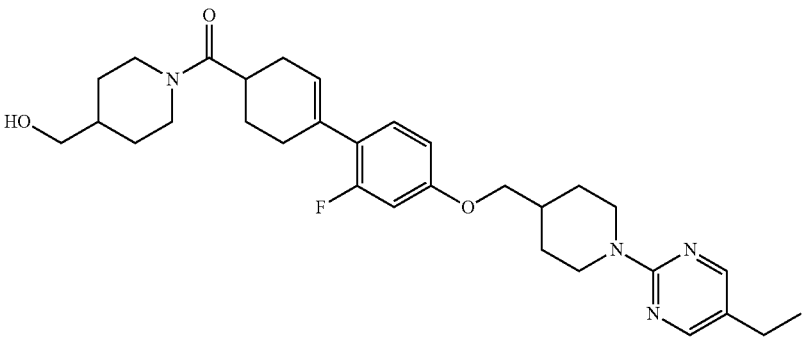 [SMILES: CCc1cnc(N2CCC(COc3ccc(C4=CCC(C(=O)N5CCC(CO)CC5)CC4)c(F)c3)CC2)nc1] |
| 433 | 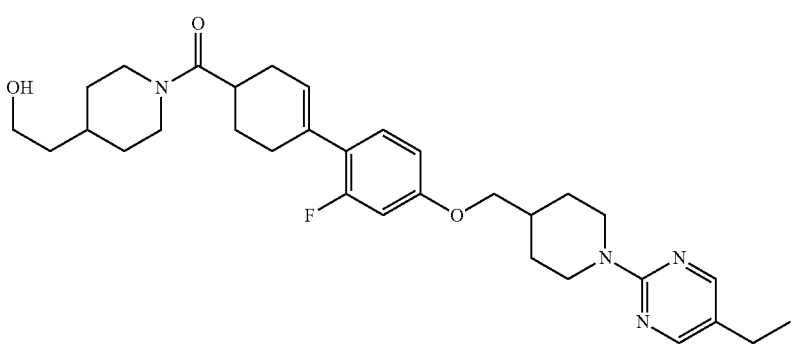 [SMILES: CCc1cnc(N2CCC(COc3ccc(C4=CCC(C(=O)N5CCC(CCO)CC5)CC4)c(F)c3)CC2)nc1] |
| 434 | 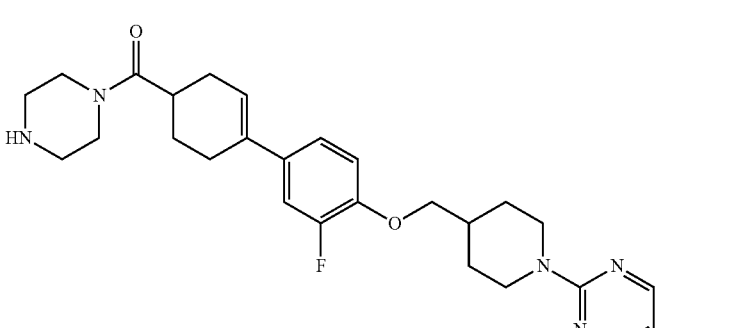 |

TABLE 1-continued
| Examples | Chemical structures |
|---|---|
| 435 | 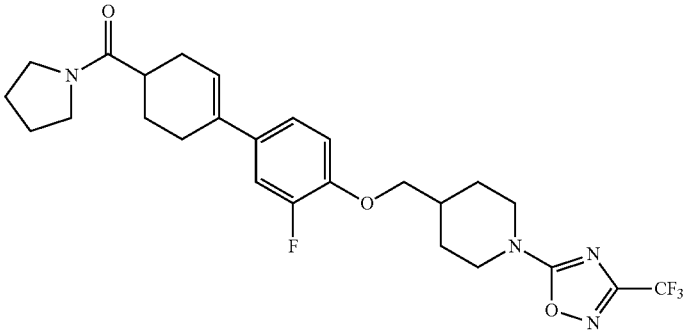 [SMILES: O=C(C1CC=C(c2ccc(OCC3CCN(c4nc(C(F)(F)F)no4)CC3)c(F)c2)CC1)N1CCCC1] |
| 436 | 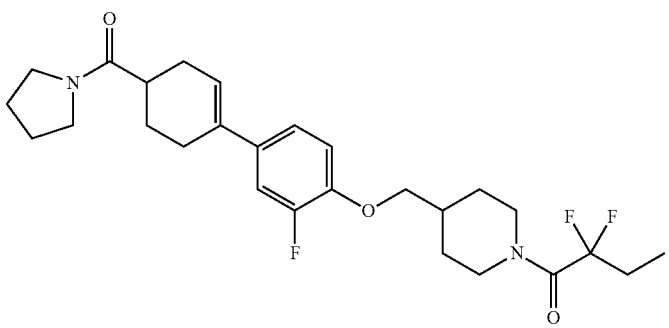 [SMILES: CCC(F)(F)C(=O)N1CCC(COc2ccc(C3=CCC(C(=O)N4CCCC4)CC3)cc2F)CC1] |
| 437 | 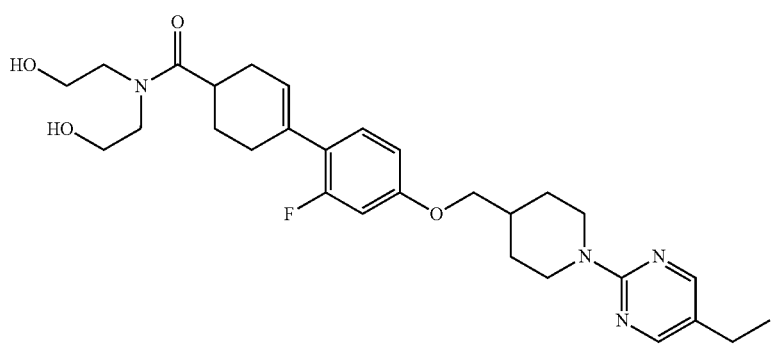 [SMILES: CCc1cnc(N2CCC(COc3ccc(C4=CCC(C(=O)N(CCO)CCO)CC4)c(F)c3)CC2)nc1] |
| 438 | 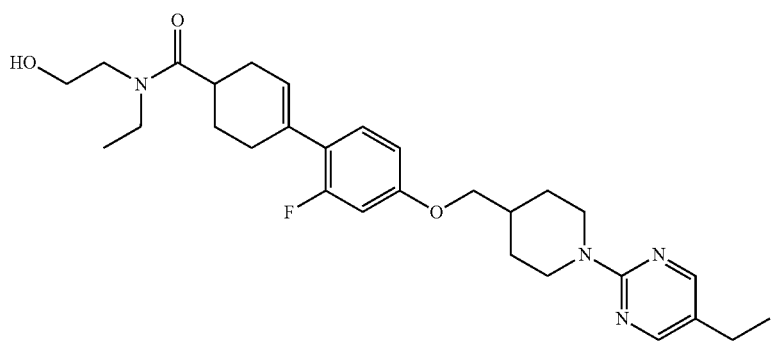 [SMILES: CCc1cnc(N2CCC(COc3ccc(C4=CCC(C(=O)N(CC)CCO)CC4)c(F)c3)CC2)nc1] |

TABLE 1-continued

| Examples | Chemical structures |
|---|---|
| 439 | 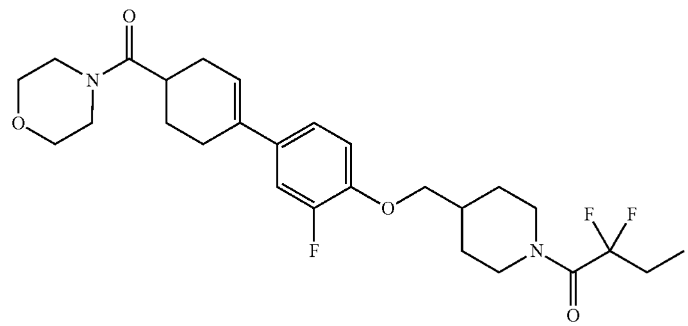 [SMILES: CCC(F)(F)C(=O)N1CCC(COc2ccc(C3=CCC(C(=O)N4CCOCC4)CC3)cc2F)CC1] |
| 440 | 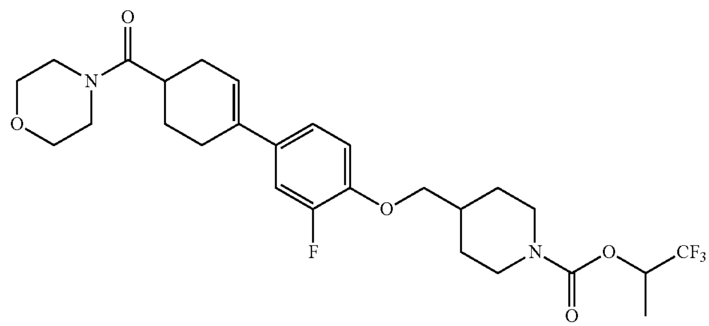 [SMILES: CC(OC(=O)N1CCC(COc2ccc(C3=CCC(C(=O)N4CCOCC4)CC3)cc2F)CC1)C(F)(F)F] |
| 441 | 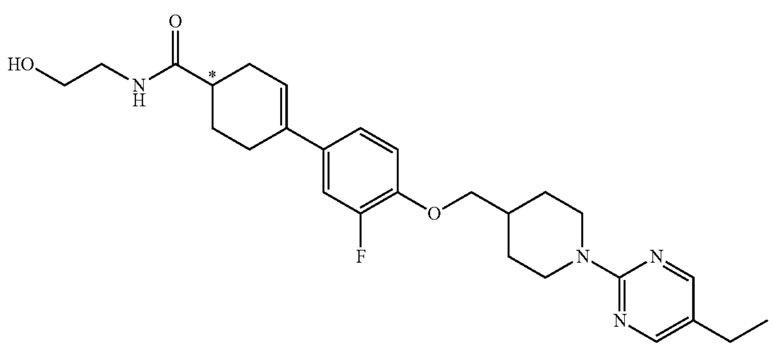 [SMILES: CCc1cnc(N2CCC(COc3ccc(C4=CCC(C(=O)NCCO)CC4)cc3F)CC2)nc1] |
| 442 | 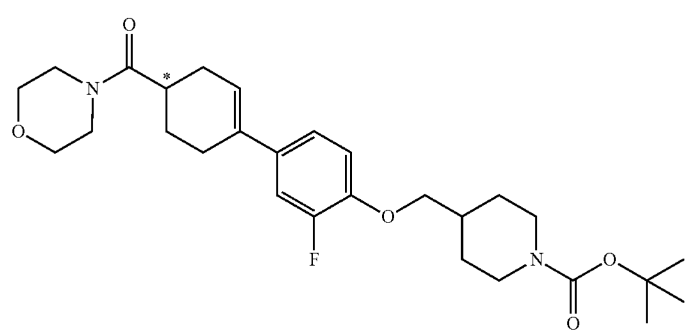 [SMILES: CC(C)(C)OC(=O)N1CCC(COc2ccc(C3=CCC(C(=O)N4CCOCC4)CC3)cc2F)CC1] |

TABLE 1-continued
| Examples | Chemical structures |
|---|---|
| 443 | 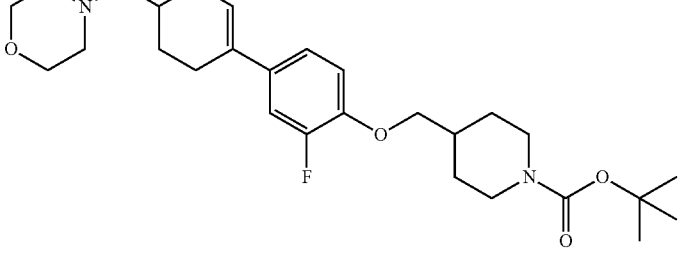 |
| 444 | 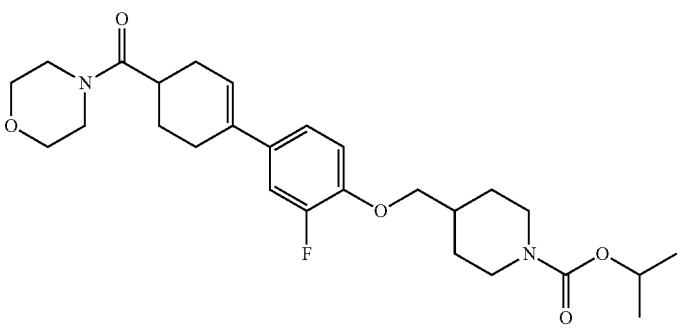 [SMILES: CC(C)OC(=O)N1CCC(COc2ccc(C3=CCC(C(=O)N4CCOCC4)CC3)cc2F)CC1] |
| 445 | 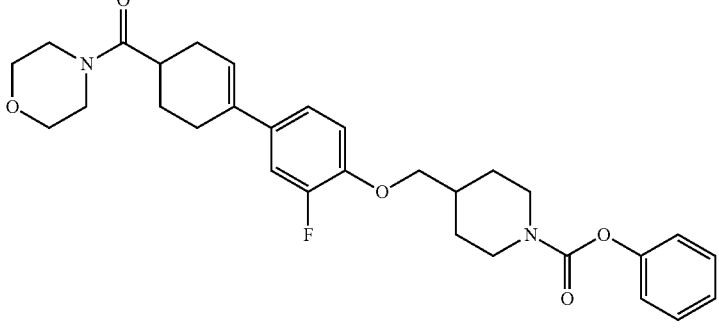 |
| 446 | 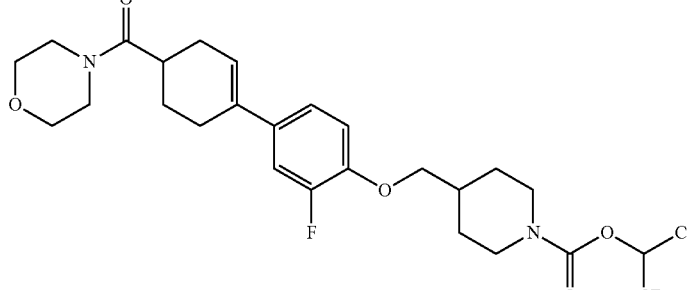 |

TABLE 1-continued

| Examples | Chemical structures |
|---|---|
| 447 | 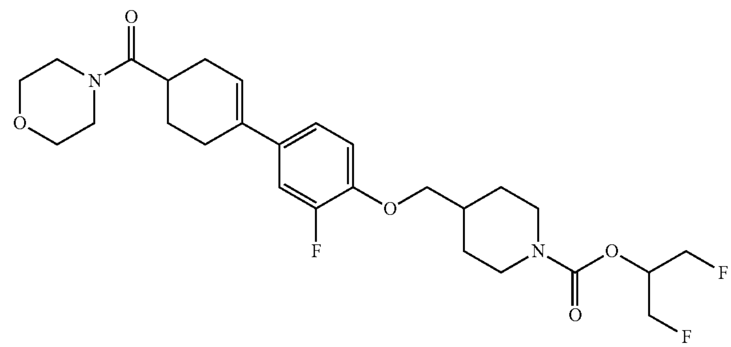 [SMILES: O=C(OC(CF)CF)N1CCC(COc2ccc(C3=CCC(C(=O)N4CCOCC4)CC3)cc2F)CC1] |
| 448 | 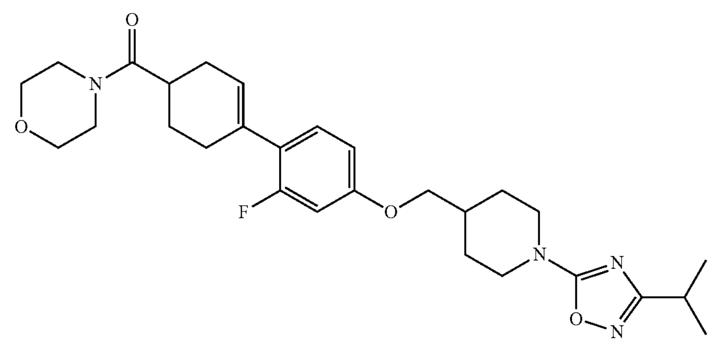 [SMILES: CC(C)c1noc(N2CCC(COc3ccc(C4=CCC(C(=O)N5CCOCC5)CC4)c(F)c3)CC2)n1] |
| 449 | 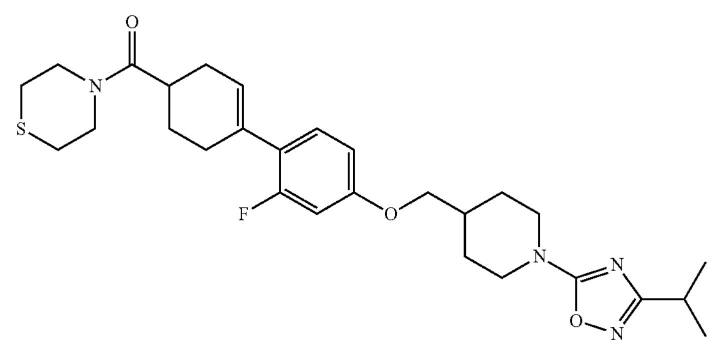 [SMILES: CC(C)c1noc(N2CCC(COc3ccc(C4=CCC(C(=O)N5CCSCC5)CC4)c(F)c3)CC2)n1] |
| 450 | 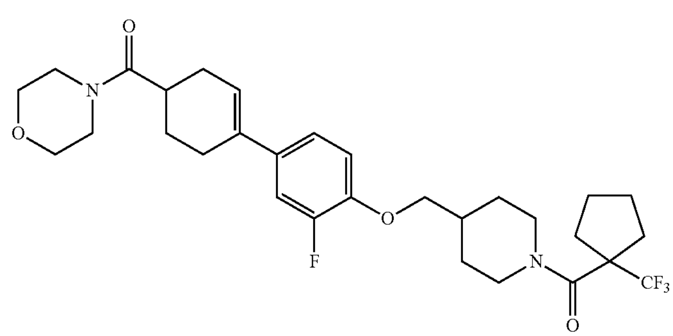 [SMILES: O=C(C1CC=C(c2ccc(OCC3CCN(C(=O)C4(C(F)(F)F)CCCC4)CC3)c(F)c2)CC1)N1CCOCC1] |

TABLE 1-continued
| Examples | Chemical structures |
|---|---|
| 451 | 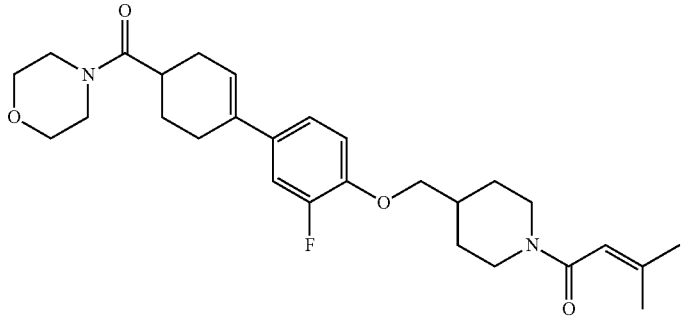 [SMILES: CC(C)=CC(=O)N1CCC(COc2ccc(C3=CCC(C(=O)N4CCOCC4)CC3)cc2F)CC1] |
| 452 | 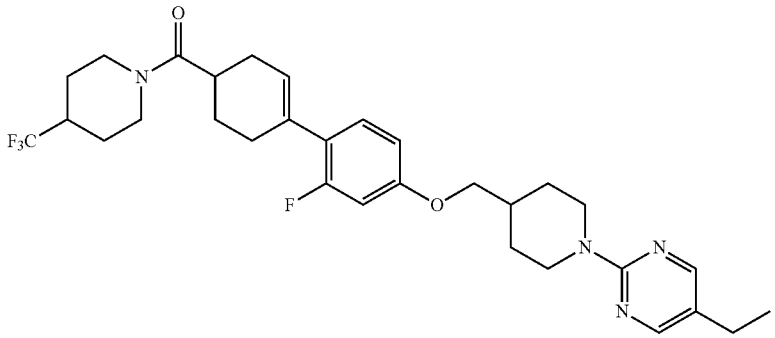 |
| 453 | 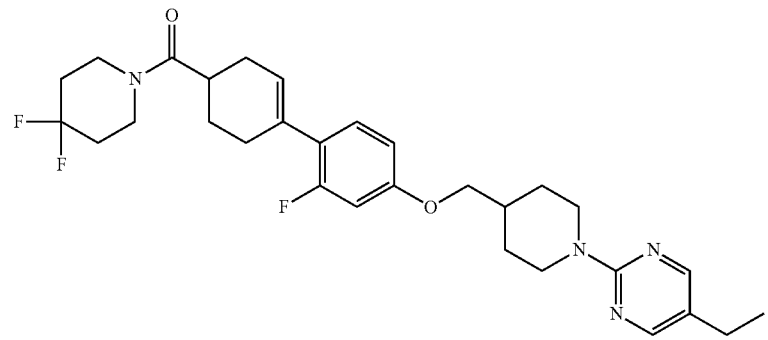 [SMILES: CCc1cnc(N2CCC(COc3ccc(C4=CCC(C(=O)N5CCC(F)(F)CC5)CC4)c(F)c3)CC2)nc1] |
| 454 | 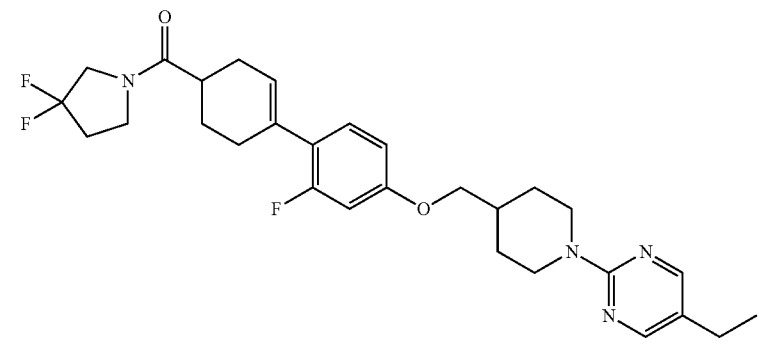 [SMILES: CCc1cnc(N2CCC(COc3ccc(C4=CCC(C(=O)N5CCC(F)(F)C5)CC4)c(F)c3)CC2)nc1] |

TABLE 1-continued
| Examples | Chemical structures |
|---|---|
| 455 | 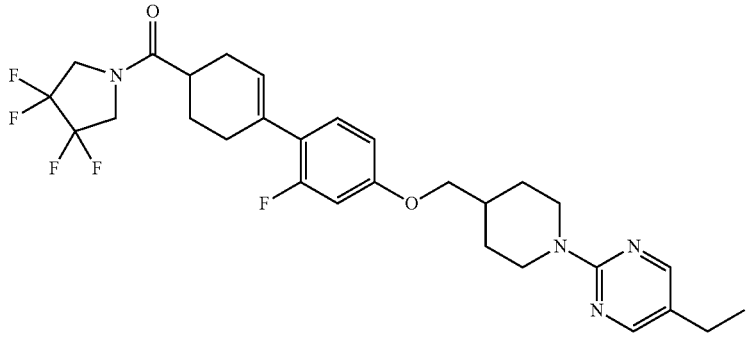 [SMILES: CCc1cnc(N2CCC(COc3ccc(C4=CCC(C(=O)N5CC(F)(F)C(F)(F)C5)CC4)c(F)c3)CC2)nc1] |
| 456 | 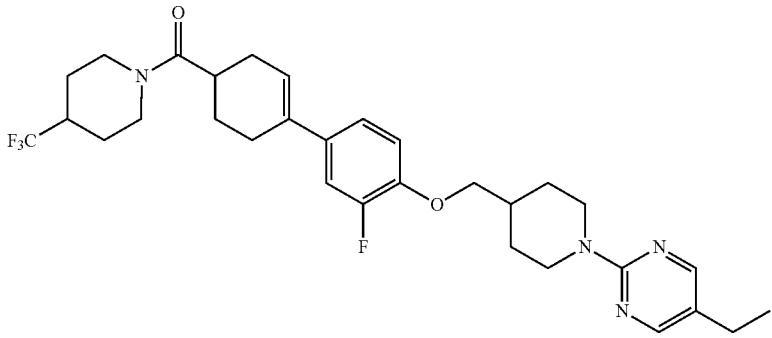 |
| 457 | 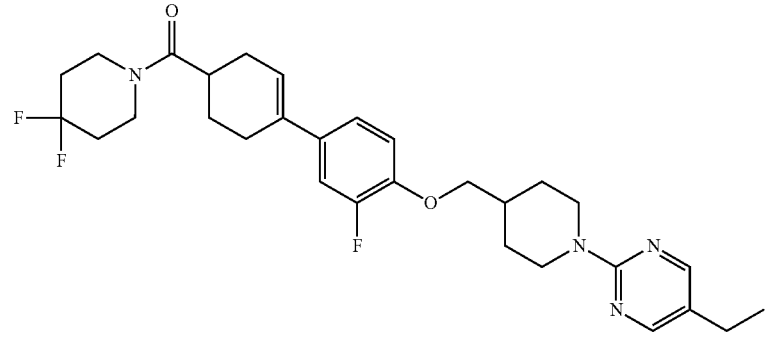 [SMILES: CCc1cnc(N2CCC(COc3ccc(C4=CCC(C(=O)N5CCC(F)(F)CC5)CC4)cc3F)CC2)nc1] |
| 458 | 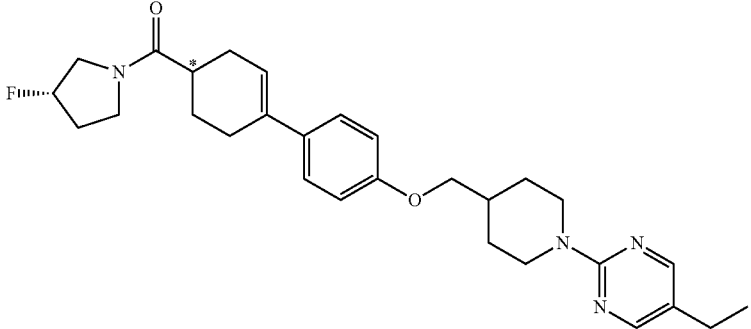 [SMILES: CCc1cnc(N2CCC(COc3ccc(C4=CCC(C(=O)N5CC[C@H](F)C5)CC4)cc3)CC2)nc1] |

TABLE 1-continued
| Examples | Chemical structures |
|---|---|
| 459 | 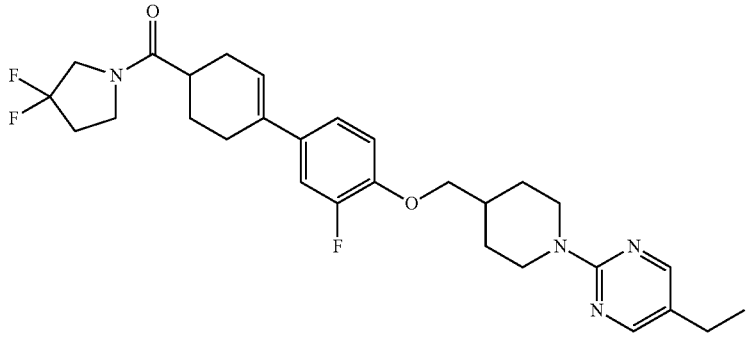 [SMILES: CCc1cnc(N2CCC(COc3ccc(C4=CCC(C(=O)N5CCC(F)(F)C5)CC4)cc3F)CC2)nc1] |
| 460 | 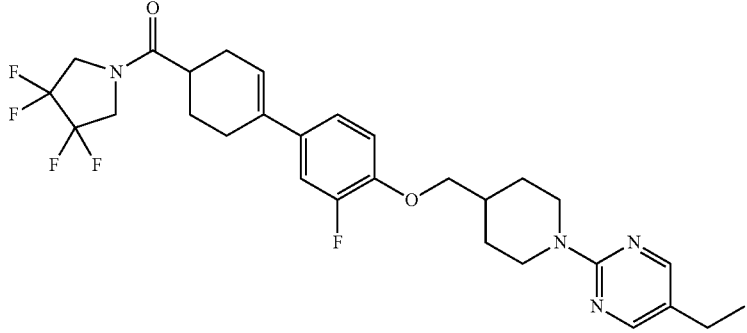 [SMILES: CCc1cnc(N2CCC(COc3ccc(C4=CCC(C(=O)N5CC(F)(F)C(F)(F)C5)CC4)cc3F)CC2)nc1] |
| 461 | 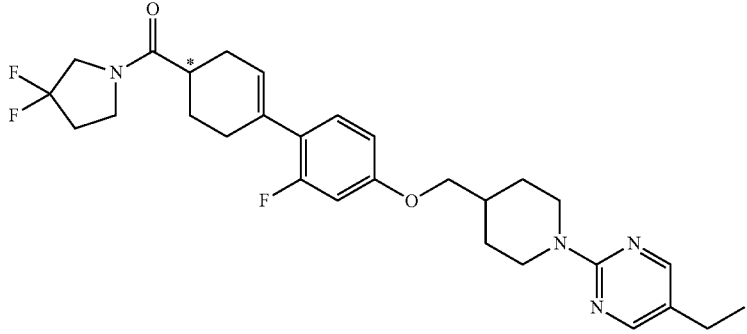 [SMILES: CCc1cnc(N2CCC(COc3ccc(C4=CCC(C(=O)N5CCC(F)(F)C5)CC4)c(F)c3)CC2)nc1] |
| 462 | 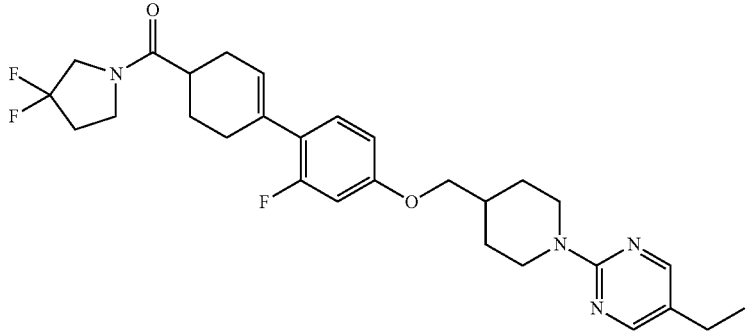 [SMILES: CCc1cnc(N2CCC(COc3ccc(C4=CCC(C(=O)N5CCC(F)(F)C5)CC4)c(F)c3)CC2)nc1] |

TABLE 1-continued

| Examples | Chemical structures |
|---|---|
| 463 | 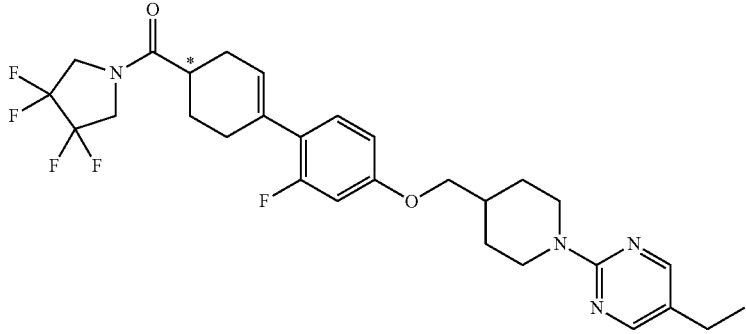 [SMILES: CCc1cnc(N2CCC(COc3ccc(C4=CCC(C(=O)N5CC(F)(F)C(F)(F)C5)CC4)c(F)c3)CC2)nc1] |
| 464 | 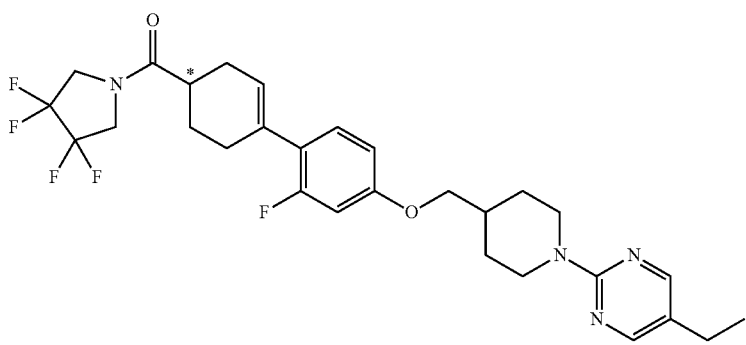 [SMILES: CCc1cnc(N2CCC(COc3ccc(C4=CCC(C(=O)N5CC(F)(F)C(F)(F)C5)CC4)c(F)c3)CC2)nc1] |
| 465 | 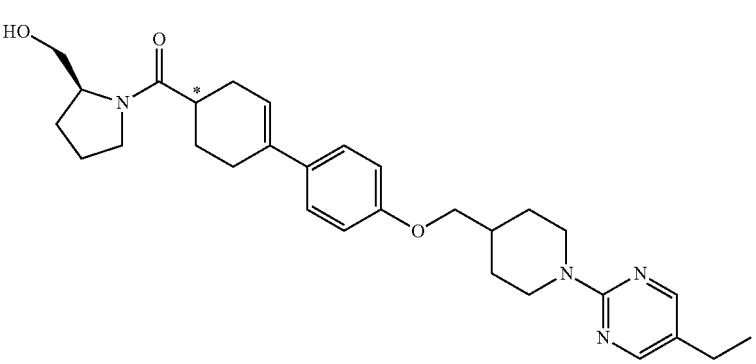 [SMILES: CCc1cnc(N2CCC(COc3ccc(C4=CCC(C(=O)N5CCC[C@H]5CO)CC4)cc3)CC2)nc1] |
| 466 | 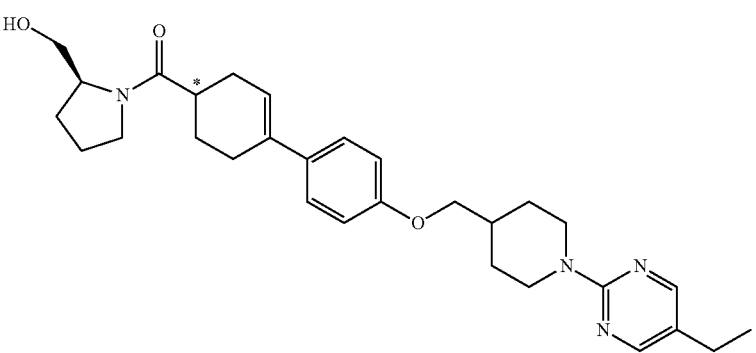 [SMILES: CCc1cnc(N2CCC(COc3ccc(C4=CCC(C(=O)N5CCC[C@H]5CO)CC4)cc3)CC2)nc1] |

Experimental Example 1: Evaluation of cAMP Activity

To check whether the cyclohexene derivatives according to the present invention activate cyclic adenosine monophosphate (cAMP), experiments were carried out, as follows.

Specifically, as hamster-derived β-cells containing G protein-coupled receptor 119 (GPR-119), HIT-T15 cells (Korean Cell Line Bank) were used to determine intracellular activation of cAMP in response to the stimulation of the GPR-119. The HIT-T15 cells were plated on a 96-well plate at 60,000 cells per well. On the next day of plating, the cells were treated with a varying concentration of each of the example compounds according to the present invention, and incubated at 37° C. for an hour. In this case, each of the treated compounds was used at six concentrations, ranging from 0.0032 to 10 μM, to treat the cells.

The cyclic adenosine monophosphate (cAMP) activity was measured according to the manufacturer's instruction using a cAMP dynamic kit commercially available from Cis Bio Inc. (Bedford, Mass.). The cells were lysed, and a level of cAMP was determined by a competitive immunoassay using D2-labeled cAMP and a cryptate-labeled anti-cAMP antibody. Fluorescence was read in Flex Station (Molecular Devices). Fluorescence resonance energy transfer (FRET) was observed when D2 and cryptate were in close proximity, and then measured as a fluorescence ratio of 665 nm/620 nm. Unlabeled cAMP in the cell lysate competed with the D2-labeled cAMP against the cryptate-labeled antibody. Since a decrease in the measured intensity of the FRET signals represents a level of cAMP in the cells, the cAMP activities of the compounds are calculated as a change in FRET signals by adjusting an amount of dimethyl sulfoxide (DMSO). The calculated $EC_{50}$ values are listed in the following Table 2.

[Table 2]

TABLE 2

| Examples | $EC_{50}$ (nM) |
|---|---|
| 1 | 65 |
| 2 | 40 |
| 3 | 34 |
| 4 | 150 |
| 5 | 29 |
| 6 | 38 |
| 7 | 13 |
| 8 | 90 |
| 9 | 75 |
| 10 | 500 |
| 11 | 110 |
| 12 | 80 |
| 13 | 13 |
| 14 | 650 |
| 15 | 370 |
| 16 | 13 |
| 17 | 85 |
| 18 | 170 |
| 19 | 110 |
| 20 | 90 |
| 21 | 16 |
| 22 | 41 |
| 23 | 160 |
| 24 | 260 |
| 25 | 210 |
| 26 | 250 |
| 27 | 310 |
| 28 | 110 |
| 29 | 95 |
| 30 | 105 |
| 31 | 260 |
| 32 | 650 |
| 33 | 600 |
| 34 | 21 |
| 35 | 22 |
| 36 | 170 |
| 37 | 300 |
| 38 | 450 |
| 39 | 350 |
| 40 | 500 |
| 41 | 650 |
| 42 | 82 |
| 43 | 85 |
| 44 | 13 |
| 45 | 25 |
| 46 | 500 |
| 47 | 150 |
| 48 | 35 |
| 49 | 26 |

TABLE 2-continued

| Examples | $EC_{50}$ (nM) |
|---|---|
| 50 | 95 |
| 51 | 66 |
| 52 | 55 |
| 53 | 21 |
| 54 | 42 |
| 55 | 100 |
| 56 | 30 |
| 57 | 8 |
| 58 | 17 |
| 59 | 78 |
| 60 | 40 |
| 61 | 45 |
| 62 | 70 |
| 63 | 110 |
| 64 | 50 |
| 65 | 41 |
| 66 | 18 |
| 67 | 60 |
| 68 | 300 |
| 69 | 7 |
| 70 | 45 |
| 71 | 5.4 |
| 72 | 25 |
| 73 | 11 |
| 74 | 6.2 |
| 75 | 210 |
| 76 | 12 |
| 77 | 12 |
| 78 | 100 |
| 79 | 49 |
| 80 | 89 |
| 81 | 9 |
| 82 | 9 |
| 83 | 75 |
| 84 | 30 |
| 85 | 18 |
| 86 | 130 |
| 87 | 70 |
| 88 | 130 |
| 89 | 21 |
| 90 | 24 |
| 91 | 28 |
| 92 | 64 |
| 93 | 50 |
| 94 | 68 |
| 95 | 16 |
| 96 | 27 |
| 97 | 8.4 |
| 98 | 6.1 |
| 99 | 160 |
| 100 | 95 |
| 101 | 110 |
| 102 | 52 |
| 103 | 75 |
| 104 | 70 |
| 105 | 43 |
| 106 | 22 |
| 107 | 35 |
| 108 | 55 |
| 109 | 190 |
| 110 | 110 |
| 111 | 1,500 |
| 112 | 70 |
| 113 | 68 |
| 114 | 14 |
| 115 | 15 |
| 116 | 28 |
| 117 | 11 |
| 118 | 31 |
| 119 | 6.8 |
| 120 | 80 |
| 121 | 500 |
| 122 | 130 |
| 123 | 35 |
| 124 | 100 |
| 125 | 70 |
| 126 | 130 |
| 127 | 83 |

TABLE 2-continued

| Examples | EC$_{50}$ (nM) |
|---|---|
| 128 | 200 |
| 129 | 140 |
| 130 | 90 |
| 131 | 150 |
| 132 | 210 |
| 133 | 400 |
| 134 | 350 |
| 135 | 30 |
| 136 | 62 |
| 137 | 60 |
| 138 | 100 |
| 139 | 130 |
| 140 | 120 |
| 141 | 75 |
| 142 | 85 |
| 147 | 6.9 |
| 148 | 13 |
| 149 | 23 |
| 150 | 19 |
| 152 | 36 |
| 158 | 25 |
| 159 | 20 |
| 160 | 14 |
| 161 | 6 |
| 162 | 27 |
| 163 | 7 |
| 164 | 16 |
| 165 | 7 |
| 166 | 22 |
| 167 | 14 |
| 168 | 17 |
| 169 | 9 |
| 172 | 38 |
| 173 | 18 |
| 175 | 7 |
| 177 | 38 |
| 181 | 24 |
| 182 | 27 |
| 183 | 12 |
| 186 | 17 |
| 195 | 28 |
| 197 | 18 |
| 199 | 8 |
| 200 | 23 |
| 202 | 24 |
| 203 | 37 |
| 204 | 9 |
| 213 | 24 |
| 217 | 30 |
| 220 | 40 |
| 223 | 25 |
| 224 | 38 |
| 225 | 22 |
| 226 | 14 |
| 227 | 6 |
| 228 | 8 |
| 229 | 11 |
| 235 | 24 |
| 236 | 14 |
| 239 | 22 |
| 242 | 21 |
| 243 | 30 |
| 247 | 16 |
| 250 | 12 |
| 251 | 22 |
| 252 | 17 |
| 253 | 9 |
| 254 | 10 |
| 256 | 32 |
| 257 | 8 |
| 258 | 10 |
| 259 | 10 |
| 262 | 7 |
| 263 | 9 |
| 264 | 18 |
| 265 | 32 |
| 266 | 12 |
| 267 | 21 |
| 268 | 17 |
| 269 | 35 |
| 270 | 12 |
| 271 | 13 |
| 272 | 33 |
| 273 | 11 |
| 274 | 27 |
| 275 | 28 |
| 276 | 29 |
| 277 | 20 |
| 278 | 18 |
| 279 | 29 |
| 286 | 37 |
| 289 | 32 |
| 290 | 3.8 |
| 291 | 32 |
| 292 | 12 |
| 293 | 18 |
| 294 | 23 |
| 295 | 43 |
| 296 | 6.8 |
| 297 | 120 |
| 298 | 150 |
| 299 | 12 |
| 300 | 8.5 |
| 301 | 19 |
| 302 | 110 |
| 303 | 29 |
| 304 | 20 |
| 305 | 24 |
| 306 | 8.9 |
| 307 | 88 |
| 308 | 23 |
| 309 | 11 |
| 310 | 33 |
| 311 | 79 |
| 312 | 120 |
| 313 | 120 |
| 314 | 61 |
| 315 | 68 |
| 316 | 37 |
| 317 | 50 |
| 318 | 38 |
| 319 | 91 |
| 320 | 53 |
| 321 | 28 |
| 322 | 62 |
| 323 | 28 |
| 324 | 27 |
| 325 | 53 |
| 326 | 70 |
| 327 | 80 |
| 328 | 21 |
| 329 | 39 |
| 330 | 35 |
| 331 | 11 |
| 332 | 6.7 |
| 333 | 30 |
| 334 | 52 |
| 335 | 18 |
| 336 | 180 |
| 337 | 160 |
| 338 | 40 |
| 339 | 120 |
| 340 | 28 |
| 341 | 180 |
| 344 | 45 |
| 345 | 36 |
| 346 | 100 |
| 347 | 55 |
| 348 | 14 |
| 349 | 27 |
| 350 | 52 |
| 351 | 41 |
| 352 | 63 |
| 353 | 58 |
| 354 | 22 |
| 355 | 46 |

TABLE 2-continued

| Examples | EC$_{50}$ (nM) |
|---|---|
| 357 | 150 |
| 358 | 190 |
| 359 | 14 |
| 360 | 8.8 |
| 361 | 48 |
| 362 | 180 |
| 363 | 110 |
| 364 | 85 |
| 365 | 38 |
| 366 | 39 |
| 367 | 26 |
| 368 | 48 |
| 369 | 9 |
| 370 | 15 |
| 371 | 39 |
| 372 | 46 |
| 373 | 200 |
| 374 | 150 |
| 375 | 110 |
| 376 | 10.5 |
| 377 | 11 |
| 378 | 20 |
| 379 | 30 |
| 380 | 79 |
| 381 | 110 |
| 382 | 42 |
| 383 | 48 |
| 384 | 100 |
| 385 | 45 |
| 386 | 64 |
| 387 | 79 |
| 388 | 51 |
| 389 | 68 |
| 390 | 70 |
| 391 | 27 |
| 392 | 10 |
| 393 | 130 |
| 395 | 14 |
| 397 | 9.9 |
| 398 | 110 |
| 400 | 140 |
| 401 | 34 |
| 403 | 22 |
| 404 | 55 |
| 405 | 59 |
| 406 | 36 |
| 408 | 25 |
| 409 | 62 |
| 410 | 14 |
| 411 | 15 |
| 412 | 37 |
| 413 | 25 |
| 414 | 27 |
| 415 | 55 |
| 416 | 75 |
| 417 | 50 |
| 418 | 35 |
| 420 | 110 |
| 421 | 53 |
| 422 | 18 |
| 423 | 19 |
| 424 | 21 |
| 425 | 48 |
| 426 | 6.7 |
| 427 | 32 |
| 428 | 70 |
| 429 | 21 |
| 430 | 9 |
| 431 | 27 |
| 432 | 29 |
| 433 | 26 |
| 434 | 180 |
| 435 | 13 |
| 436 | 9.8 |
| 437 | 27 |
| 438 | 23 |
| 439 | 5.9 |
| 440 | 8.7 |
| 441 | 33 |
| 442 | 8 |
| 443 | 38 |
| 444 | 26 |
| 445 | 11 |
| 446 | 20 |
| 447 | 62 |
| 448 | 25 |
| 449 | 33 |
| 450 | 27 |
| 451 | 89 |
| 452 | 18 |
| 453 | 12 |
| 454 | 15 |
| 455 | 18 |
| 456 | 18 |
| 457 | 9.8 |
| 458 | 12 |
| 459 | 36 |
| 460 | 12 |
| 461 | 91 |
| 462 | 14 |
| 463 | 88 |
| 464 | 13 |
| 465 | 110 |
| 466 | 12 |
| Comparative Example 2 | 49 |

As listed in Table 2, it was revealed that the compounds according to the present invention activated cAMP even at a very low concentration. It was revealed that most of the compounds according to the present invention had an EC$_{50}$ value of 200 nM or less. More specifically, it was revealed that the compounds of Examples 2, 3, 5 to 7, 13, 16, 21, 22, 34, 35, 44, 45, 48, 49, 53, 54, 56 to 58, 60, 61, 64 to 66, 69 to 74, 76, 77, 79, 81, 82, 84, 85, 89 to 91, 93, 95 to 98, 105 to 107, 114 to 119, 123, 135, 147 to 150, 152, 158 to 169, 172, 173, 175, 177, 181-183, 186, 195, 197, 199, 200, 202 to 204, 213, 217, 220, 223 to 229, 235, 236, 239, 242, 243, 247, 250 to 254, 256 to 259, 262 to 279, 286, 289 to 296, 299 to 301, 303 to 306, 308 to 310, 316 to 318, 321, 323, 324, 328 to 333, 335, 338, 340, 344, 345, 348, 349, 351, 354, 355, 359 to 361, 365 to 372, 376 to 379, 382, 383, 385, 391, 392, 395, 397, 401, 403, 406, 408, 410 to 414, 417, 418, 422 to 427, 429 to 433, 435 to 446, 448 to 460, 462, 464, and 466 had a high EC$_{50}$ value of 50 nM or less. From these results, it could be seen that the cyclohexene derivative according to the present invention had an excellent effect of activating cAMP by stimulating the GPR-119 receptor.

Therefore, the cyclohexene derivative according to the present invention activated GPR-119 since the cyclohexene derivative had an excellent effect of activating cAMP, and thus was able to be useful for pharmaceutical compositions for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

Experimental Example 2: Oral Glucose Tolerance Test (OGTT)

To evaluate in vivo effective effects of the cyclohexene derivatives according to the present invention, experiments were carried out, as follows.

Specifically, male C57BL/6J (C57 black 6) rats (8 to 10 weeks old) in a high-fat diet model were acclimated for at least 7 days, and only healthy rat populations were selected and subjected to an oral glucose tolerance test (OGTT). The rats were fasted for 12 to 15 hours, and then randomly divided into groups with five rats per group. Thereafter, each of the compounds of Examples 1, 14, 48, 69, 80, 118, 139, 147, 148, 169, 190, 199, 200, 204, 227, 277, 290, 291, 442, 443, and 461 to 466, and Comparative Examples 1 and 2 according to the present invention was administered to the rats at a dose of 20 mg/kg. In this case, a vehicle (0.5%, carboxymethyl cellulose (CMC)) was administered as an untreated group, and the dose of the compound administered together with the vehicle was orally administered at 10 ml/kg. After 30 minutes of administration, glucose (2 g/kg) was orally administered at a dose of 10 ml/kg. A blood glucose level was measured using an Accu-Chek Active Strip (Rosche Diagnostic Co.). In this case, the glucose level in blood collected via caudal venipuncture was measured at time points of −30, 0, 20, 40, 60, and 120 minutes after glucose administration. The results are listed in the following Table 3.

TABLE 3

| Examples | % AUC |
|---|---|
| 1 | 28.5 |
| 14 | 21.9 |
| 48 | 21.2 |
| 69 | 19.1 |
| 80 | 19.7 |
| 118 | 23.5 |
| 139 | 25.4 |
| 147 | 23.3 |
| 148 | 22.6 |
| 169 | 21.7 |
| 190 | 20.9 |
| 199 | 20.9 |
| 200 | 24.0 |
| 204 | 24.0 |
| 227 | 26.8 |
| 277 | 19.8 |
| 290 | 16.5 |
| 291 | 17.0 |
| 462 | 16.7 |
| 464 | 19.9 |
| 465 | 15.8 |
| 466 | 16.6 |
| Comparative Example 1 | 13.5 |
| Comparative Example 2 | 15.3 |

In Table 3, the unit "% AUC (area under the curve)" represents a hypoglycemic level.

As listed in Table 3, it could be seen that the example compounds according to the present invention had an excellent hypoglycemic effect and a high in vivo effective effect, compared to those in the untreated group. Also, it was revealed that the compounds of Comparative Examples 1 and 2 known as the GPR-119 protein activator in the art had a hypoglycemic effect of 13.5% and 15.3%, respectively, but that the example compounds according to the present invention generally had a superior hypoglycemic effect to the compounds of Comparative Examples 1 and 2.

Therefore, the cyclohexene derivative according to the present invention derivative had a very excellent hypoglycemic effect since the cyclohexene derivative had an excellent effect of activating a GPR-119 protein, thereby exhibiting an excellent effect of promoting insulin secretion. Accordingly, a pharmaceutical composition including the cyclohexene derivative as an active ingredient was able to be useful as a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 3: Simultaneous Evaluation of Both Weight-Loss and Hypoglycemic Effects in Diet-Induced Obesity (DIO) Model To simultaneously evaluate both the weight-loss and hypoglycemic effects of the cyclohexene derivative according to the present invention, experiments were carried out, as follows.

Specifically, male Sprague Dawley (SD) rats (approximately 4 weeks old) in a diet-induced obesity model were fed with a high-fat diet (Lab. Diet Co.) for approximately 10 weeks to induce high-fat diet-induced obesity (DIO). The rats undergoing the high-fat diet were randomly selected, and divided into groups (n=8) for respective administrations. The compounds of Comparative Examples 3 and 4 and Examples 48 and 119 were administered to the divided DIO rats each group for 4 weeks.

The weights of the DIO rats were measured twice a week during a period of administration of 4 weeks to record a change in the weights. The results are shown in FIG. 1. At the end of the 4-week period of administration, a hypoglycemic effect was evaluated using an oral glucose tolerance test (OGTT), as follows.

Specifically, each of the compounds of Comparative Example 3 (300 mg/kg) and Examples 48 and 119 (10, 20, 50 mg/kg) was administered, and 2 g/kg of glucose was orally administered after 30 minutes of the administration. A blood glucose level was determined using an Accu-Chek Active Strip (Roche diagnostic Co.). In this case, the glucose level in blood collected via caudal venipuncture was measured at time points of −30, 0, 20, 40, 60, and 120 minutes after glucose administration. Area-under-curve (AUC) values (%) of the respective groups were calculated from the results based on the blood glucose levels measured at the respective time points so as to evaluate the hypoglycemic effect. The results are shown in FIGS. 2A and 2B [FIG. 2A: Example 48, and FIG. 2B: Example 119].

FIG. 1 is a graph determining the changes in weights of rats after compounds of Example 48 and Comparative Examples 3 and 4 according to the present invention are administered to a diet-induced obesity (DIO) rat model for 4 weeks (In FIG. 1, the term "untreated group (Vehicle)" represents an untreated group in a high-fat DIO rat model; and the term "Lean" represents an untreated group in a normal SD rat model rather than a disease model).

FIG. 2A is a graph for evaluating hypoglycemic effects over time when glucose is administered at the end of the 4-week period of administration of the compounds of Example 48 and Comparative Example 3 according to the present invention in the DIO rat model, and after 30 minutes of administration of the compounds of Example 48 and Comparative Example 3.

FIG. 2B is a graph for evaluating hypoglycemic effects over time when glucose is administered at the end of the 4-week period of administration of the compound of Example 119 according to the present invention in the DIO rat model, and after 30 minutes of administration of the compound of Example 119.

As shown in FIG. 1, it was confirmed that the compound of Example 48 according to the present invention had a higher weight-loss effect when administered at a dose of 10, 20, and 50 mg/kg, compared to when the compounds of Comparative Examples 3 and 4 were administered at a dose of 300 mg/kg and 5 mg/kg, respectively. More specifically, it was revealed that the weight loss was observed for 2 weeks after oral administration of the compounds of Comparative Examples 3 and 4 (300 mg/kg and 5 mg/kg, respectively), but the weight rather increased after 2 weeks of the oral administration. On the other hand, it was revealed that the persistent weight loss was observed for 4 weeks after oral administration of the compound of Example 48 (10, 20, and 50 mg/kg) according to the present invention.

As shown in FIG. 2A, it was confirmed that the compound of Example 48 according to the present invention had a hypoglycemic effect of approximately 18 to 25% when administered at a dose of 10, 20, and 50 mg/kg. More specifically, it was revealed that the compound of Comparative Example 3 had a hypoglycemic effect of approximately 22% when orally administered at a dose of 300 mg/kg, and the compound of Example 48 according to the present invention had a hypoglycemic effect of approximately 25% when orally administered at a dose of 50 mg/kg, indicating that the compound of Example 48 had a remarkably superior hypoglycemic effect to that of Comparative Example 3. Also, as shown in FIG. 2B, when it was assumed that the hypoglycemic effect in the untreated group was 0, it was confirmed that the compound of Example 119 according to the present invention had a hypoglycemic effect of approximately 10 to 15% when administered at a dose of 10, 20, and 50 mg/kg.

Therefore, the cyclohexene derivative according to the present invention had excellent weight-loss and hypoglycemic effects during a period of oral administration, and these effects were also expressed at the same time. Accordingly, a pharmaceutical composition including the cyclohexene derivative as an active ingredient was able to be useful as a pharmaceutical composition for treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 4: Evaluation of Promotion of Glucagon-Like Peptide-1 (GLP-1) Secretion To evaluate an effect of the cyclohexene derivative according to the present invention on promotion of glucagon-like peptide-1 (GLP-1) secretion, experiments were carried out, as follows.

NCI-H716 cells that were human enterocytes were plated on 12 wells at $1 \times 10^6$ cells per well. After 48 hours, the cells were starved in serum-free media for 2 hours, and treated with a varying concentration of siptagliptin that was a dipeptidyl peptidase-IV (DPP-IV) inhibitor, and the compounds of Comparative Example 1 (1, 10, 30 µM), Comparative Example 5 (10 µM), Example 48 (1, 10, 30 µM), and Example 291 (1, 10, 30 µM). After an hour, supernatants are recovered to determine an amount of the secreted GLP-1 peptide. The GLP-1 measurement was performed using an enzyme-linked immunosorbant assay (ELISA; Millipore, EGLP-35K), and the amount of the secreted GLP-1 peptide was indicated by the unit "pM". The results are shown in FIG. 3.

FIGS. 3A and 3B are graphs plotted for amounts of secreted GLP-1 when NCI-H716 cells that are human enterocytes are treated with the compounds of Comparative Examples 1 and 5 and Example 48 according to the present invention, and when NCI-H716 cells that are human enterocytes are treated with the compound of Example 291, respectively. As shown in FIGS. 3A and 3B, it was confirmed that the GLP-1 was secreted at approximately 340 to 470 pM when the cells were treated with an increasing concentration (1, 10, and 30 µM) of the compound of Example 48 according to the present invention. More specifically, it was revealed that the compound of Example 48 induced GLP-1 secretion to a higher level than that of Comparative Example 1 in all the 1, 10 and 30 µM-treated groups when comparing the amounts of the GLP-1 secreted in response to the concentrations of the treated compounds of Comparative Example 1 and Example 48. Also, it was revealed that the GLP-1 secretion promoted by the compound of Example 291 according to the present invention was approximately 1.8 times higher than the untreated group.

Therefore, the cyclohexene derivative according to the present invention had an excellent effect of inducing the GLP-1 secretion through activation of GPR-119. Accordingly, a pharmaceutical composition including the cyclohexene derivative as an active ingredient was able to be useful as a pharmaceutical composition for treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 5: Acute Toxicity Test

To evaluate acute toxicity of the cyclohexene derivative according to the present invention, experiments were carried out, as follows.

Five 7-week-old female Ihara's cataract rats (ICRs) were supplied by Nara Biotech Co. Ltd., housed in a breeding farm, and acclimated to new environments while being fed with general solid feeds and water. When the rats were 8 weeks old, experiments were carried out. Environmental conditions were maintained constant: a set temperature of 23±3° C., a humidity of 55±15%, an illuminance of 150 to 300 Lux, a ventilation rate of 10 to 20 times/hour, and a lighting time of 12 hours (light-dark cycle: lighting at 8 a.m. and lights-out at 8 p.m.). As the feeds, solid feeds for laboratory animals (5L79 Lab Diet, Purina Mills, Richmond, Ind., USA), which had been sterilized by exposure to radiation, were provided by Orientbio Inc. so that rats were allowed to freely consume the solid feeds. As the water, running water was disinfected using a UV sterilizer and an ultra-filtration system, and then provided o that rats were allowed to freely drink the water in a water bottle. Analyses of contaminants in the water and feeds were carried out according to the ChemOn Inc.'s standard operating procedure (SOP). Each of the compounds prepared in Examples 48 and 119 of the present invention was diluted to a concentration of 2,000 mg/kg in a vehicle (1% PEG), and the test chemicals were intragastrically administered once daily to each group of five rats using an oral zonde for rats, and the general conditions, toxic symptoms, and mortality of animals were observed twice a day during a test period.

As a result, it was confirmed that the lethal dose 50 percent ($LD_{50}$) values of the female ICR rats were greater than or equal to 2 g/kg. From these result, it could be seen that the cyclohexene derivative according to the present invention had very low toxicity.

Therefore, the cyclohexene derivative according to the present invention had an excellent effect of promoting cAMP by activating GPR-119, and also exhibited very high safety to human bodies due to low cytotoxicity. Accordingly, the cyclohexene derivative according to the present invention activated the GPR-119, and thus was able to be useful for a pharmaceutical composition for preventing or treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.

Experimental Example 6: Measurement of optical rotation

A method of measuring optical rotation was performed according to the USP<781>.
Information on measuring equipment is as follows.
1) Equipment name: Polarimeter
2) Model name: P2000
3) Manufacturer: JASCO
4) Specifications
1. Light source: Sodium Lamp (Na) and Mercury Lamp (Hg)
2. Wavelength: 589, 578, 546, 436, 405, 365 nm
3. Aperture: 1.8, 3 and 8 mm in diameter
4. Angular range: ±85° or better
5. Response speed: 1°/sec. or better
6. Measurement accuracy: ±0.002° (up to 10), ±0.2% (larger than 1°)
7. Reproducibility: 0.002°
8. Resolution: less than 0.0010
9. Integration time: 1 to 100 sec.
10. Detector: Photomultiplier tube Experimental Example 7: Evaluation of Hypoglycemic Effect Using Diet-Induced Obesity (DIO) Model To simultaneously evaluate both the weight-loss and hypoglycemic effects of the cyclohexene derivative according to the present invention, experiments were carried out, as follows.
Specifically, male C57BL/6J mice (approximately 4 weeks old) in a diet-induced obesity model were fed with a high-fat diet (Lab. Diet Co.) for approximately 12 weeks to induce high-fat diet-induced obesity (DIO). The mice undergoing the high-fat diet were randomly selected, and divided into groups (n=8) for respective administrations.
The weights of the DIO mice were measured twice a week during a period of administration of 4 weeks to record a change in the weights. At the end of the 4-week period of administration, a hypoglycemic effect was evaluated using an oral glucose tolerance test (OGTT), as follows.
Specifically, the compound (+)-(4-(4-(4-((1-(5-ethylpyrimidin-2-yl)piperidin-4-yl)methoxy)phenyl)cyclohex-3-enyl) ((R)-2-(hydroxymethyl)pyrrolidin-1-yl)methanone or (−)-(4-(4-((1-(5-ethylpyrimidin-2-yl)piperidin-4-yl)methoxy) phenyl)cyclohex-3-enyl)((R)-2-(hydroxymethyl)pyrrolidin-1-yl)methanone prepared in Example 290 or 291 was orally administered at a dose of 10 to 20 mg/kg. In this case, an equivalent amount of a solution including 1% polyethylene glycol, 1% Tween 80 and 0.25% carboxymethyl cellulose (CMC) (1%/1%/98% (v/v/v) for PEG 400/Tween 80/0.25% CMC) was orally administered to the untreated group (Vehicle). The sample was administered, and glucose (4 g/kg) was orally administered at a dose of 5 ml/kg after 30 minutes of the administration. A blood glucose level was determined using an Accu-Chek Active Strip (Roche diagnostic Co.). In this case, the glucose level in blood collected via caudal venipuncture was measured at time points of −30, 0, 20, 40, 60, and 120 minutes after glucose administration. The area-under-curve (AUC) values (%) of the respective groups were calculated from the results based on the blood glucose levels measured at the respective time points so as to evaluate the hypoglycemic effect. The results are listed in the following Table 4. A significance test on the difference between the untreated group and the experimental groups was carried out by one-way ANOVA (a Dunnett method) using 'GraphPad Prism 4' software (Graphpad Co., La Jolla, Calif., USA). A P value of p<0.05 was considered to have a statistically significant difference.

TABLE 4

|  | % AUC |
| --- | --- |
| Vehicle | 0.0 |
| Compound of Example 291 - 10 mg/kg | 16.2 |
| Compound of Example 291 - 20 mg/kg | 17.6 |

In Table 4, the unit "% AUC" represents a hypoglycemic level.
As listed in Table 4, it was confirmed that the compound of Example 290 or 291 according to the present invention had a hypoglycemic effect of 16% or more in response to its treatment dose, and also had a superior in vivo effective effect, compared to the untreated group.
Therefore, the cyclohexene derivative according to the present invention had excellent hypoglycemic effects during a period of oral administration, and these effects were also expressed at the same time. Accordingly, a pharmaceutical composition including the cyclohexene derivative as an active ingredient was able to be useful as a pharmaceutical composition for treating metabolic diseases such as obesity, type 1 diabetes, type 2 diabetes, inadequate glucose tolerance, insulin resistance, hyperglycemia, hyperlipidemia, hypertriglyceridemia, hypercholesterolemia, dyslipidemia, syndrome X, etc.
Meanwhile, the compound represented by Formula 1 according to the present invention may be prepared into various types according to a purpose. It should be understood that the following methods of preparing a formulation, which includes the compound represented by Formula 1 as an active ingredient according to the present invention are provided by way of illustration of the present invention only, but not intended to limit the scope of the present invention.

Experimental Example 8: CYP Inhibition Assay

CYP enzymes play a major role in the metabolism of drugs. Depending on the inhibition activity of the CYP enzymes, the dose of the drugs and toxicity due to the co-administration of other drugs can be predicted. Therefore, we have measured the inhibitory activity for CYP3A4, CYP2C9, CYP1A2, CYP2D6 and CYP2C19 enzymes present in the body using the compounds of the present invention. Invitrogen P2862 kit was used for CYP2D6 inhibition assay, and BD GENTEST (459100, 459300, 459400, 459500) kits were used for CYP1A2, CYP2C9, CYP2C19 and CYP3A4 inhibition assay. In case of Invitrogen kit, the test materials were diluted in distilled water into 2.5× of the final test concentration.
P450 BACULOSOMES® reagent and regeneration device (100×) provided by the Invitrogen kit were diluted in the Vivid® reaction buffer (2×) into the appropriate concentration for the type of CYP450. After mixing 80 µl of the 2.5× test material and 100 µl of the mixture of the diluted P450 BACULOSOMES® reagent in U-bottom 96-well plate, the resulting mixture was pre-incubated for 20 minutes. Vivid® CYP450 substrate and NADP+ (100×) were diluted in the Vivid® CYP450 reaction buffer (2×) into the appropriate concentration for the types of CYP450 and the substrates. After completion of the pre-incubation, 20/l of the substrate-NADP (nicotinamide adenine dinucleotide phosphate) mixture was added, and then incubated for 1 hour. After completion of the reaction, the reactants were transferred to the white plates, and fluorescence values were measured using a micro-plate reader (Excitation and absorption wavelengths of CYP2D6 were 400 nm and 502 nm, respectively).

In case of BD GENTEST kit, the test materials were diluted in acetonitrile into 50× of the final test concentration. NADPH-cofactor mixture containing cofactor, G6PDH and control protein was prepared in distilled water as per manufacturer's instruction. 4 µl of 50× test materials and 96 µl of NADPH-cofactor mixture were mixed in U-bottom 96-well plate, and the resulting mixture were pre-incubated at 37° C. for 10 minutes. Predetermined concentrations of enzyme/substrate mixture were prepared in distilled water using buffer (0.5M potassium phosphate, pH 7.4) and each of CYP450 enzyme/substrate mixture provided in the kit for the types of CYP450. To the pre-incubated plate, 100 µl of enzyme/substrate mixture was added, and then incubated at 37° C. for 15 minutes (CYP1A2), 30 minutes (CYP3A4 and CYP2C19) or 1.5 hours (CYP2C9). After completion of the reaction, the reactants were transferred to the white plates, and fluorescent values were measured using a micro-plate reader (Excitation and absorption wavelengths of CYP1A2 and CYP2C19 were 410 nm and 460 nm, respectively; and excitation and absorption wavelengths of CYP2C9 and CYP3A4 were 409 nm and 530 nm, respectively).

The measured values were converted into the inhibition percent of the test materials as compared to the value of the untreated control, and the results were summarized in Table 5.

TABLE 5

| Compound | CYP inhibition (% at 10 µM) | | | | |
| --- | --- | --- | --- | --- | --- |
| | 1A2 | 2C9 | 2C19 | 2D6 | 3A4 |
| Comparative Example 1 | 10.37 | 24.06 | NT* | 9.84 | 47.83 |
| Example 118 | 0 | 29.77 | 48.38 | 9.42 | 48.16 |
| Example 290 | 3.82 | 23.97 | 44.86 | 48.97 | 33.15 |
| Example 291 | 0 | 47.32 | 54.06 | 2.49 | 36.36 |

*NT: not tested.

Preparative Examples 1: Preparation of Pharmaceutical Formulations 1-1: Preparation of Powder
Compound of Formula 1 500 mg
Lactose 100 mg
Talc 10 mg
The components are mixed, and filled in an airtight pack to prepare a powder.

1-2: Preparation of Tablet
Compound of Formula 1 500 mg
Corn starch 100 mg
Lactose 100 mg
Magnesium stearate 2 mg
The components were mixed, and tablet-pressed to prepare a tablet according to a conventional method of preparing a tablet.

1-3: Preparation of Capsule
Compound of Formula 1 500 mg
Corn starch 100 mg
Lactose 100 mg
Magnesium stearate 2 mg
The components were mixed, and filled in a gelatin capsule to prepare a capsule according to a conventional method of preparing a capsule.

1-4: Preparation of Injectable Solution
Compound of Formula 1 500 mg
Sterile distilled water for injection Proper amount
pH regulating agent Proper amount
An injectable solution was prepared, according to a conventional method of preparing an injectable solution, so that one ampule (2 ml) contains the above-mentioned contents of the components.

1-5: Preparation of Solution
Compound of Formula 1 100 mg
Isomerized sugar 10 g
Mannitol 5 g
Purified water Proper amount
A solution was prepared according to a conventional method of preparing a solution by dissolving the respective components in purified water, adding a proper amount of a lemon flavor thereto, mixing all the components, adding purified water to the resulting mixture so that a final amount of the mixture was adjusted to 100 ml, putting the mixture into a brown vial, and sterilizing the mixture.

The invention claimed is:
1. A compound selected from the group consisting of:
(290) (+)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;
(291) (−)-(4-(4-((1-(5-ethylpyrimidin-2-yl)piperidin-4-yl)methoxy)phenyl)cyclohex-3-enyl)((R)-2-(hydroxymethyl)pyrrolidin-1-yl)methanone;
(292) (4-(4-((1-(5-ethylpyrimidin-2-yl)piperidin-4-yl)methoxy)-3-fluorophenyl)cyclohex-3-enyl)(piperidin-1-yl)methanone;
(293) (4-(4-((1-(5-ethylpyrimidin-2-yl)piperidin-4-yl)methoxy)-3-fluorophenyl)cyclohex-3-enyl)(pyrrolidin-1-yl)methanone;
(294) (4-(4-((1-(5-ethylpyrimidin-2-yl)piperidin-4-yl)methoxy)-3-fluorophenyl)cyclohex-3-enyl)(4-hydroxypiperidin-1-yl)methanone;
(295) 1-(4-(4-((1-(5-ethylpyrimidin-2-yl)piperidin-4-yl)methoxy)-3-fluorophenyl)cyclohex-3-enecarbonyl)azetidin-3-one;
(296) (4-(4-((1-(5-ethylpyrimidin-2-yl)piperidin-4-yl)methoxy)-3-fluorophenyl)cyclohex-3-enyl)(4-(2-hydroxyethyl)piperidin-1-yl)methanone;
(297) 1,4'-bipiperidin-1'-yl(4-(4-((1-(5-ethylpyrimidin-2-yl)piperidin-4-yl)methoxy)-3-fluorophenyl)cyclohex-3-enyl)methanone;
(298) (4-(4-((1-(5-ethylpyrimidin-2-yl)piperidin-4-yl)methoxy)-3-fluorophenyl)cyclohex-3-enyl)(4-(pyrrolidin-1-yl)piperidin-1-yl)methanone;
(299) (4-(4-((1-(5-ethylpyrimidin-2-yl)piperidin-4-yl)methoxy)-3-fluorophenyl)cyclohex-3-enyl)(morpholino)methanone;
(300) (4-(4-((1-(5-ethylpyrimidin-2-yl)piperidin-4-yl)methoxy)-3-fluorophenyl)cyclohex-3-enyl)(thiomorpholino)methanone;
(301) azetidin-1-yl(4-(4-((1-(5-ethylpyrimidin-2-yl)piperidin-4-yl)methoxy)-3-fluorophenyl)cyclohex-3-enyl)methanone;

(302) N-cyclopropyl-4-(4-((1-(5-ethylpyrimidin-2-yl)piperidin-4-yl)methoxy)-3-fluorophenyl)cyclohex-3-enecarboxamide;
(303) N-cyclobutyl-4-(4-((1-(5-ethylpyrimidin-2-yl)piperidin-4-yl)methoxy)-3-fluorophenyl)cyclohex-3-enecarboxamide;
(304) N-cyclopentyl-4-(4-((1-(5-ethylpyrimidin-2-yl)piperidin-4-yl)methoxy)-3-fluorophenyl)cyclohex-3-enecarboxamide;
(305) N-cyclohexyl-4-(4-((1-(5-ethylpyrimidin-2-yl)piperidin-4-yl)methoxy)-3-fluorophenyl)cyclohex-3-enecarboxamide;
(306) (4-(4-((1-(5-ethylpyrimidin-2-yl)piperidin-4-yl)methoxy)-3-fluorophenyl)cyclohex-3-enyl)(1,4-dioxa-8-azaspiro[4.5]decan-8-yl)methanone;
(307) 4-(4-((1-(5-ethylpyrimidin-2-yl)piperidin-4-yl)methoxy)-3-fluorophenyl)-N-(2,2,2-trifluoroethyl)cyclohex-3-enecarboxamide;
(308) 1-(4-(4-((1-(5-ethylpyrimidin-2-yl)piperidin-4-yl)methoxy)-3-fluorophenyl)cyclohex-3-enecarbonyl)piperidin-4-one;
(309) (4-(4-((1-(5-ethylpyrimidin-2-yl)piperidin-4-yl)methoxy)-3-fluorophenyl)cyclohex-3-enyl)(3-hydroxyazetidin-1-yl)methanone;
(310) tert-butyl 4-((6-(4-(4-hydroxypiperidine-1-carbonyl)cyclohex-1-enyl)pyridin-3-yloxy)methyl)piperidine-1-carboxylate;
(311) tert-butyl 4-((6-(4-(piperidine-1-carbonyl)cyclohex-1-enyl)pyridin-3-yloxy)methyl)piperidine-1-carboxylate;
(312) tert-butyl 4-((6-(4-(pyrrolidine-1-carbonyl)cyclohex-1-enyl)pyridin-3-yloxy)methyl)piperidine-1-carboxylate;
(313) 4-(4-((1-(5-ethylpyrimidin-2-yl)piperidin-4-yl)methoxy)-3-fluorophenyl)-N-(2-hydroxyethyl)cyclohex-3-enecarboxamide;
(314) N-(2,2-difluoroethyl)-4-(4-((1-(5-ethylpyrimidin-2-yl)piperidin-4-yl)methoxy)-3-fluorophenyl)cyclohex-3-enecarboxamide;
(315) (4-(6-((1-(3-isopropyl-1,2,4-oxadiazol-5-yl)piperidin-4-yl)methoxy)pyridin-3-yl)cyclohex-3-enyl)(pyrrolidin-1-yl)methanone;
(316) (4-(6-((1-(3-isopropyl-1,2,4-oxadiazol-5-yl)piperidin-4-yl)methoxy)pyridin-3-yl)cyclohex-3-enyl)(piperidin-1-yl)methanone;
(317) (4-(6-((1-(3-isopropyl-1,2,4-oxadiazol-5-yl)piperidin-4-yl)methoxy)pyridin-3-yl)cyclohex-3-enyl)(morpholino)methanone;
(318) (4-(6-((1-(3-isopropyl-1,2,4-oxadiazol-5-yl)piperidin-4-yl)methoxy)pyridin-3-yl)cyclohex-3-enyl)(thiomorpholino)methanone;
(319) 1-(4-(6-((1-(3-isopropyl-1,2,4-oxadiazol-5-yl)piperidin-4-yl)methoxy)pyridin-3-yl)cyclohex-3-enecarbonyl)piperidine-4-carbonitrile;
(320) (4-(2-hydroxyethyl)piperidin-1-yl)(4-(6-((1-(3-isopropyl-1,2,4-oxadiazol-5-yl)piperidin-4-yl)methoxy)pyridin-3-yl)cyclohex-3-enyl)methanone;
(321) 1-(4-(4-((1-(5-ethylpyrimidin-2-yl)piperidin-4-yl)methoxy)-3-fluorophenyl)cyclohex-3-enecarbonyl)piperidine-4-carbonitrile;
(322) 4-(4-((1-(5-ethylpyrimidin-2-yl)piperidin-4-yl)methoxy)-3-fluorophenyl)-N-(2-fluoroethyl)cyclohex-3-enecarboxamide;
(323) 4-(4-((1-(5-ethylpyrimidin-2-yl)piperidin-4-yl)methoxy)-3-fluorophenyl)-N,N-bis(2-hydroxyethyl)cyclohex-3-enecarboxamide;
(324) 1-(4-(4-((1-(5-ethylpyrimidin-2-yl)piperidin-4-yl)methoxy)-3-fluorophenyl)cyclohex-3-enecarbonyl)piperidine-4-carboxamide;
(325) tert-butyl 4-((6-(4-(4-(hydroxymethyl)piperidine-1-carbonyl)cyclohex-1-enyl)pyridin-3-yloxy)methyl)piperidine-1-carboxylate;
(326) tert-butyl 4-((6-(4-(4-(2-hydroxyethyl)piperidine-1-carbonyl)cyclohex-1-enyl)pyridin-3-yloxy)methyl)piperidine-1-carboxylate;
(327) tert-butyl 4-((6-(4-(morpholine-4-carbonyl)cyclohex-1-enyl)pyridin-3-yloxy)methyl)piperidine-1-carboxylate;
(328) tert-butyl 4-((6-(4-(thiomorpholine-4-carbonyl)cyclohex-1-enyl)pyridin-3-yloxy)methyl)piperidine-1-carboxylate;
(329) (4-(hydroxymethyl)piperidin-1-yl)(4-(5-((1-(3-isopropyl-1,2,4-oxadiazol-5-yl)piperidin-4-yl)methoxy)pyridin-2-yl)cyclohex-3-enyl)methanone;
(330) azetidin-1-yl(4-(3-fluoro-4-((1-(3-isopropyl-1,2,4-oxadiazol-5-yl)piperidin-4-yl)methoxy)phenyl)cyclohex-3-enyl)methanone;
(331) (4-(3-fluoro-4-((1-(3-isopropyl-1,2,4-oxadiazol-5-yl)piperidin-4-yl)methoxy)phenyl)cyclohex-3-enyl)(pyrrolidin-1-yl)methanone;
(332) (4-(3-fluoro-4-((1-(3-isopropyl-1,2,4-oxadiazol-5-yl)piperidin-4-yl)methoxy)phenyl)cyclohex-3-enyl)(piperidin-1-yl)methanone;
(333) (4-(3-fluoro-4-((1-(3-isopropyl-1,2,4-oxadiazol-5-yl)piperidin-4-yl)methoxy)phenyl)cyclohex-3-enyl)(4-(hydroxymethyl)piperidin-1-yl)methanone;
(334) (4-(3-fluoro-4-((1-(3-isopropyl-1,2,4-oxadiazol-5-yl)piperidin-4-yl)methoxy)phenyl)cyclohex-3-enyl)(3-hydroxyazetidin-1-yl)methanone;
(335) (4-(3-fluoro-4-((1-(3-isopropyl-1,2,4-oxadiazol-5-yl)piperidin-4-yl)methoxy)phenyl)cyclohex-3-enyl)(4-(2-hydroxyethyl)piperidin-1-yl)methanone;
(336) (4-(3-fluoro-4-((1-(3-isopropyl-1,2,4-oxadiazol-5-yl)piperidin-4-yl)methoxy)phenyl)cyclohex-3-enyl)(4-(pyrrolidin-1-yl)piperidin-1-yl)methanone;
(337) (3-(hydroxyimino)azetidin-1-yl)(4-(6-((1-(3-isopropyl-1,2,4-oxadiazol-5-yl)piperidin-4-yl)methoxy)pyridin-3-yl)cyclohex-3-enyl)methanone;
(338) 1-(4-(6-((1-(3-isopropyl-1,2,4-oxadiazol-5-yl)piperidin-4-yl)methoxy)pyridin-3-yl)cyclohex-3-enecarbonyl)piperidine-4-carbonitrile;
(339) azetidin-1-yl(4-(6-((1-(3-isopropyl-1,2,4-oxadiazol-5-yl)piperidin-4-yl)methoxy)pyridin-3-yl)cyclohex-3-enyl)methanone;
(340) tert-butyl 4-((6-(4-(4-cyanopiperidine-1-carbonyl)cyclohex-1-enyl)pyridin-3-yloxy)methyl)piperidine-1-carboxylate;
(341) tert-butyl 4-((6-(4-((2-hydroxyethyl)(methyl)carbamoyl)cyclohex-1-enyl)pyridin-3-yloxy)methyl)piperidine-1-carboxylate;
(342) tert-butyl 4-((6-(4-(4-oxopiperidine-1-carbonyl)cyclohex-1-enyl)pyridin-3-yloxy)methyl)piperidine-1-carboxylate;
(343) tert-butyl 4-((6-(4-(4-cyanopiperazine-1-carbonyl)cyclohex-1-enyl)pyridin-3-yloxy)methyl)piperidine-1-carboxylate;
(344) tert-butyl 4-((6-(4-(4-(hydroxyimino)piperidine-1-carbonyl)cyclohex-1-enyl)pyridin-3-yloxy)methyl)piperidine-1-carboxylate;
(345) 1-(4-(3-fluoro-4-((1-(3-isopropyl-1,2,4-oxadiazol-5-yl)piperidin-4-yl)methoxy)phenyl)cyclohex-3-enecarbonyl)piperidin-4-one;

(346) (4-ethylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;

(347) (4-(3-fluoro-4-((1-(3-isopropyl-1,2,4-oxadiazol-5-yl)piperidin-4-yl)methoxy)phenyl)cyclohex-3-enyl)(4-(3-hydroxypropyl)piperazin-1-yl)methanone;

(348) (4-cyclopropylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;

(349) (4-(6-((1-(5-ethylpyrimidin-2-yl)piperidin-4-yl)methoxy)pyridin-3-yl)cyclohex-3-enyl)(pyrrolidin-1-yl)methanone;

(350) (4-(6-((1-(5-ethylpyrimidin-2-yl)piperidin-4-yl)methoxy)pyridin-3-yl)cyclohex-3-enyl)(piperidin-1-yl)methanone;

(351) (4-(6-((1-(5-ethylpyrimidin-2-yl)piperidin-4-yl)methoxy)pyridin-3-yl)cyclohex-3-enyl)(morpholino)methanone;

(352) (4-(6-((1-(5-ethylpyrimidin-2-yl)piperidin-4-yl)methoxy)pyridin-3-yl)cyclohex-3-enyl)(thiomorpholino)methanone;

(353) (4-(6-((1-(5-ethylpyrimidin-2-yl)piperidin-4-yl)methoxy)pyridin-3-yl)cyclohex-3-enyl)(4-hydroxypiperidin-1-yl)methanone;

(354) (4-(6-((1-(5-ethylpyrimidin-2-yl)piperidin-4-yl)methoxy)pyridin-3-yl)cyclohex-3-enyl)(4-(hydroxymethyl)piperidin-1-yl)methanone;

(355) (4-cyclopropylpiperazin-1-yl)(4-(6-((1-(3-isopropyl-1,2,4-oxadiazol-5-yl)piperidin-4-yl)methoxy)pyridin-3-yl)cyclohex-3-enyl)methanone;

(356) 4-(4-((1-(5-bromopyridin-2-yl)piperidin-4-yl)methoxy)phenyl)-N-(2-hydroxyethyl)cyclohex-3-enecarboxamide;

(357) 4-(4-((1-(5-bromopyrimidin-2-yl)piperidin-4-yl)methoxy)phenyl)-N-(2-hydroxyethyl)cyclohex-3-enecarboxamide;

(358) N-(2-hydroxyethyl)-4-(4-((1-(pyridin-2-yl)piperidin-4-yl)methoxy)phenyl)cyclohex-3-enecarboxamide;

(359) 4-(4-((1-(5-ethylpyrimidin-2-yl)piperidin-4-yl)methoxy)-3-fluorophenyl)-N-(2-hydroxyethyl)-N-methylcyclohex-3-enecarboxamide;

(360) N-ethyl-4-(4-((1-(5-ethylpyrimidin-2-yl)piperidin-4-yl)methoxy)-3-fluorophenyl)-N-(2-hydroxyethyl)cyclohex-3-enecarboxamide;

(361) 1-(4-(3-fluoro-4-((1-(3-isopropyl-1,2,4-oxadiazol-5-yl)piperidin-4-yl)methoxy)phenyl)cyclohex-3-enecarbonyl)piperidine-4-carboxamide;

(362) 1,4'-bipiperidin-1'-yl(4-(3-fluoro-4-((1-(3-isopropyl-1,2,4-oxadiazol-5-yl)piperidin-4-yl)methoxy)phenyl)cyclohex-3-enyl)methanone;

(363) N-cyclopropyl-4-(3-fluoro-4-((1-(3-isopropyl-1,2,4-oxadiazol-5-yl)piperidin-4-yl)methoxy)phenyl)cyclohex-3-enecarboxamide;

(364) N-cyclobutyl-4-(3-fluoro-4-((1-(3-isopropyl-1,2,4-oxadiazol-5-yl)piperidin-4-yl)methoxy)phenyl)cyclohex-3-enecarboxamide;

(365) N-cyclopentyl-4-(3-fluoro-4-((1-(3-isopropyl-1,2,4-oxadiazol-5-yl)piperidin-4-yl)methoxy)phenyl)cyclohex-3-enecarboxamide;

(366) N-cyclohexyl-4-(3-fluoro-4-((1-(3-isopropyl-1,2,4-oxadiazol-5-yl)piperidin-4-yl)methoxy)phenyl)cyclohex-3-enecarboxamide;

(367) (4-ethylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;

(368) (4-(3-fluoro-4-((1-(3-isopropyl-1,2,4-oxadiazol-5-yl)piperidin-4-yl)methoxy)phenyl)cyclohex-3-enyl)(4-(3-hydroxypropyl)piperazin-1-yl)methanone;

(369) (4-cyclopropylpiperazin-1-yl)(4-(3-fluoro-4-((1-(3-isopropyl-1,2,4-oxadiazol-5-yl)piperidin-4-yl)methoxy)phenyl)cyclohex-3-enyl)methanone;

(370) (4-(3-fluoro-4-((1-(3-isopropyl-1,2,4-oxadiazol-5-yl)piperidin-4-yl)methoxy)phenyl)cyclohex-3-enyl)(1,4-dioxa-8-azaspiro[4.5]decan-8-yl)methanone;

(371) 4-(3-fluoro-4-((1-(3-isopropyl-1,2,4-oxadiazol-5-yl)piperidin-4-yl)methoxy)phenyl)-N-(3-hydroxy-2,2-dimethylpropyl)cyclohex-3-enecarboxamide;

(372) 4-(3-fluoro-4-((1-(3-isopropyl-1,2,4-oxadiazol-5-yl)piperidin-4-yl)methoxy)phenyl)-N,N-bis(2-hydroxyethyl)cyclohex-3-enecarboxamide;

(373) azetidin-1-yl(4-(4-((1-(3-isopropyl-1,2,4-oxadiazol-5-yl)piperidin-4-yl)methoxy)-3-(trifluoromethyl)phenyl)cyclohex-3-enyl)methanone;

(374) (4-(4-((1-(3-isopropyl-1,2,4-oxadiazol-5-yl)piperidin-4-yl)methoxy)-3-(trifluoromethyl)phenyl)cyclohex-3-enyl)(pyrrolidin-1-yl)methanone;

(375) (4-(4-((1-(5-ethylpyrimidin-2-yl)piperidin-4-yl)methoxy)-3-(trifluoromethyl)phenyl)cyclohex-3-enyl)(piperidin-1-yl)methanone;

(376) 4-(4-((1-(5-ethylpyrimidin-2-yl)piperidin-4-yl)methoxy)-3-fluorophenyl)-N-(3-hydroxypropyl)-N-methylcyclohex-3-enecarboxamide;

(377) (4-(4-((1-(5-ethylpyrimidin-2-yl)piperidin-4-yl)methoxy)-3-fluorophenyl)cyclohex-3-enyl)(4-(hydroxyimino)piperidin-1-yl)methanone;

(378) 4-(4-((1-(5-ethylpyrimidin-2-yl)piperidin-4-yl)methoxy)-3-fluorophenyl)-N-(3-hydroxy-2,2-dimethylpropyl)cyclohex-3-enecarboxamide;

(379) (4-(4-((1-(5-ethylpyrimidin-2-yl)piperidin-4-yl)methoxy)-3-fluorophenyl)cyclohex-3-enyl)(4-methylpiperazin-1-yl)methanone;

(380) (4-(4-((1-(5-ethylpyrimidin-2-yl)piperidin-4-yl)methoxy)phenyl)cyclohex-3-enyl)(4-(3-hydroxypropyl)piperazin-1-yl)methanone;

(381) (4-(3-fluoro-4-((1-(3-isopropyl-1,2,4-oxadiazol-5-yl)piperidin-4-yl)methoxy)phenyl)cyclohex-3-enyl)(piperazin-1-yl)methanone;

(382) (4-(3-fluoro-4-((1-(3-isopropyl-1,2,4-oxadiazol-5-yl)piperidin-4-yl)methoxy)phenyl)cyclohex-3-enyl)(4-methylpiperazin-1-yl)methanone;

(383) tert-butyl 4-(4-(4-((1-(5-ethylpyrimidin-2-yl)piperidin-4-yl)methoxy)-3-fluorophenyl)cyclohex-3-enecarbonyl)piperazine-1-carboxylate;

(384) (4-(4-((1-(5-ethylpyrimidin-2-yl)piperidin-4-yl)methoxy)-3-fluorophenyl)cyclohex-3-enyl)(4-methylpiperazin-1-yl)methanone;

(385) 2-((1-(5-ethylpyrimidin-2-yl)piperidin-4-yl)methoxy)-5-(4-(piperidine-1-carbonyl)cyclohex-1-enyl)benzonitrile;

(386) 2-((1-(5-ethylpyrimidin-2-yl)piperidin-4-yl)methoxy)-5-(4-(pyrrolidine-1-carbonyl)cyclohex-1-enyl)benzonitrile;

(387) 5-(4-(azetidine-1-carbonyl)cyclohex-1-enyl)-2-((1-(5-ethylpyrimidin-2-yl)piperidin-4-yl)methoxy)benzonitrile;

(388) 2-((1-(5-ethylpyrimidin-2-yl)piperidin-4-yl)methoxy)-5-(4-(morpholine-4-carbonyl)cyclohex-1-enyl)benzonitrile;

(389) 2-((1-(5-ethylpyrimidin-2-yl)piperidin-4-yl)methoxy)-5-(4-(thiomorpholine-4-carbonyl)cyclohex-1-enyl)benzonitrile;

(390) 2-((1-(5-ethylpyrimidin-2-yl)piperidin-4-yl)methoxy)-5-(4-(4-hydroxypiperidine-1-carbonyl)cyclohex-1-enyl)benzonitrile;
(391) 2-((1-(5-ethylpyrimidin-2-yl)piperidin-4-yl)methoxy)-5-(4-(4-(hydroxymethyl)piperidine-1-carbonyl)cyclohex-1-enyl)benzonitrile;
(392) tert-butyl 4-((2-fluoro-4-(4-(pyrrolidine-1-carbonyl)cyclohex-1-enyl)phenoxy)methyl)piperidine-1-carboxylate;
(393) (4-(3-amino-4-((1-(5-ethylpyrimidin-2-yl)piperidin-4-yl)methoxy)phenyl)cyclohex-3-enyl)(pyrrolidin-1-yl)methanone;
(394) 2-((1-(5-ethylpyrimidin-2-yl)piperidin-4-yl)methoxy)-5-(4-(4-(2-hydroxyethyl)piperidine-1-carbonyl)cyclohex-1-enyl)benzonitrile;
(395) (4-cyclopropylpiperazin-1-yl)(4-(4-((1-(5-ethylpyrimidin-2-yl)piperidin-4-yl)methoxy)phenyl)cyclohex-3-enyl)methanone;
(396) (4-(4-((1-(5-ethylpyrimidin-2-yl)piperidin-4-yl)methoxy)-3-(trifluoromethyl)phenyl)cyclohex-3-enyl)(4-hydroxypiperidin-1-yl)methanone;
(397) (4-cyclopropylpiperazin-1-yl)(4-(4-((1-(3-isopropyl-1,2,4-oxadiazol-5-yl)piperidin-4-yl)methoxy)phenyl)cyclohex-3-enyl)methanone;
(398) 1-(4-(4-((1-(5-ethylpyrimidin-2-yl)piperidin-4-yl)methoxy)-3-(trifluoromethyl)phenyl)cyclohex-3-enecarbonyl)piperidine-4-carbonitrile;
(399) 1-(4-(4-((1-(5-ethylpyrimidin-2-yl)piperidin-4-yl)methoxy)-3-(trifluoromethyl)phenyl)cyclohex-3-enecarbonyl)piperidine-4-carboxamide;
(400) (4-(4-((1-(5-ethylpyrimidin-2-yl)piperidin-4-yl)methoxy)-3-(trifluoromethyl)phenyl)cyclohex-3-enyl)(morpholino)methanone;
(401) isopropyl 4-((2-fluoro-4-(4-(pyrrolidine-1-carbonyl)cyclohex-1-enyl)phenoxy)methyl)piperidine-1-carboxylate;
(402) trichloromethyl 4-((2-fluoro-4-(4-(pyrrolidine-1-carbonyl)cyclohex-1-enyl)phenoxy)methyl)piperidine-1-carboxylate;
(403) phenyl 4-((2-fluoro-4-(4-(pyrrolidine-1-carbonyl)cyclohex-1-enyl)phenoxy)methyl)piperidine-1-carboxylate;
(404) 4-nitrophenyl 4-((2-fluoro-4-(4-(pyrrolidine-1-carbonyl)cyclohex-1-enyl)phenoxy)methyl)piperidine-1-carboxylate;
(405) 1,1,1,3,3,3-hexafluoropropan-2-yl 4-((2-fluoro-4-(4-(pyrrolidine-1-carbonyl)cyclohex-1-enyl)phenoxy)methyl)piperidine-1-carboxylate;
(406) 1,1,1-trifluoropropan-2-yl 4-((2-fluoro-4-(4-(pyrrolidine-1-carbonyl)cyclohex-1-enyl)phenoxy)methyl)piperidine-1-carboxylate;
(407) 1,3-difluoropropan-2-yl 4-((2-fluoro-4-(4-(pyrrolidine-1-carbonyl)cyclohex-1-enyl)phenoxy)methyl)piperidine-1-carboxylate;
(408) 1-methylcyclopropyl 4-((2-fluoro-4-(4-(pyrrolidine-1-carbonyl)cyclohex-1-enyl)phenoxy)methyl)piperidine-1-carboxylate;
(409) (4-(3-fluoro-4-((1-(1-(trifluoromethyl)cyclopentanecarbonyl)piperidin-4-yl)methoxy)phenyl)cyclohex-3-enyl)(pyrrolidin-1-yl)methanone;
(410) (4-(4-((1-(3-isopropyl-1,2,4-oxadiazol-5-yl)piperidin-4-yl)methoxy)phenyl)cyclohex-3-enyl)(4-(methoxyimino)piperidin-1-yl)methanone;
(411) (4-(3-fluoro-4-((1-(3-isopropyl-1,2,4-oxadiazol-5-yl)piperidin-4-yl)methoxy)phenyl)cyclohex-3-enyl)(4-(hydroxyimino)piperidin-1-yl)methanone;
(412) 4-(4-(4-((1-(5-ethylpyrimidin-2-yl)piperidin-4-yl)methoxy)phenyl)cyclohex-3-enecarbonyl)-N-propylpiperazine-1-carboxamide;
(413) 4-(4-(4-((1-(5-ethylpyrimidin-2-yl)piperidin-4-yl)methoxy)phenyl)cyclohex-3-enecarbonyl)-N-isopropylpiperazine-1-carboxamide;
(414) 1-(4-(4-(4-((1-(5-ethylpyrimidin-2-yl)piperidin-4-yl)methoxy)phenyl)cyclohex-3-enecarbonyl)piperazin-1-yl)-3-methylbut-2-en-1-one;
(415) (4-(4-((1-(5-ethylpyrimidin-2-yl)piperidin-4-yl)methoxy)-3-methylphenyl)cyclohex-3-enyl)(piperidin-1-yl)methanone;
(416) (4-(4-((1-(5-ethylpyrimidin-2-yl)piperidin-4-yl)methoxy)-3-methylphenyl)cyclohex-3-enyl)(pyrrolidin-1-yl)methanone;
(417) (4-(4-((1-(5-ethylpyrimidin-2-yl)piperidin-4-yl)methoxy)-3-methylphenyl)cyclohex-3-enyl)(morpholino)methanone;
(418) (4-(4-((1-(5-ethylpyrimidin-2-yl)piperidin-4-yl)methoxy)-3-methylphenyl)cyclohex-3-enyl)(thiomorpholino)methanone;
(419) (4-(3-fluoro-4-((1-(2-fluoro-2-methylpropyl)piperidin-4-yl)methoxy)phenyl)cyclohex-3-enyl)(pyrrolidin-1-yl)methanone;
(420) (4-(3-fluoro-4-((1-(1-methyl-1H-tetrazol-5-yl)piperidin-4-yl)methoxy)phenyl)cyclohex-3-enyl)(pyrrolidin-1-yl)methanone;
(421) (4-(3-fluoro-4-((1-(1-(trifluoromethyl)cyclopropanecarbonyl)piperidin-4-yl)methoxy)phenyl)cyclohex-3-enyl)(pyrrolidin-1-yl)methanone;
(422) (4-(4-((1-(5-ethylpyrimidin-2-yl)piperidin-4-yl)methoxy)-2-fluorophenyl)cyclohex-3-enyl)(morpholino)methanone;
(423) (4-(4-((1-(5-ethylpyrimidin-2-yl)piperidin-4-yl)methoxy)-2-fluorophenyl)cyclohex-3-enyl)(thiomorpholino)methanone;
(424) 1-(4-(4-((1-(5-ethylpyrimidin-2-yl)piperidin-4-yl)methoxy)-2-fluorophenyl)cyclohex-3-enecarbonyl)piperidine-4-carbonitrile;
(425) azetidin-1-yl(4-(4-((1-(5-ethylpyrimidin-2-yl)piperidin-4-yl)methoxy)-2-fluorophenyl)cyclohex-3-enyl)methanone;
(426) (4-(4-((1-(5-ethylpyrimidin-2-yl)piperidin-4-yl)methoxy)-2-fluorophenyl)cyclohex-3-enyl)(piperidin-1-yl)methanone;
(427) (4-(4-((1-(5-ethylpyrimidin-2-yl)piperidin-4-yl)methoxy)-2-fluorophenyl)cyclohex-3-enyl)((R)-2-(hydroxymethyl)pyrrolidin-1-yl)methanone;
(428) (4-(4-((1-(5-ethylpyrimidin-2-yl)piperidin-4-yl)methoxy)-3-fluorophenyl)cyclohex-3-enyl)(4-methylpiperazin-1-yl)methanone;
(429) (−)-(4-(4-((1-(5-ethylpyrimidin-2-yl)piperidin-4-yl)methoxy)-3-fluorophenyl)cyclohex-3-enyl)(pyrrolidin-1-yl)methanone;
(430) (−)-(4-(4-((1-(5-ethylpyrimidin-2-yl)piperidin-4-yl)methoxy)-3-fluorophenyl)cyclohex-3-enyl)(4-(2-hydroxyethyl)piperidin-1-yl)methanone;
(431) (4-(4-((1-(5-ethylpyrimidin-2-yl)piperidin-4-yl)methoxy)-2-fluorophenyl)cyclohex-3-enyl)(4-hydroxypiperidin-1-yl)methanone;
(432) (4-(4-((1-(5-ethylpyrimidin-2-yl)piperidin-4-yl)methoxy)-2-fluorophenyl)cyclohex-3-enyl)(4-(hydroxymethyl)piperidin-1-yl)methanone;
(433) (4-(4-((1-(5-ethylpyrimidin-2-yl)piperidin-4-yl)methoxy)-2-fluorophenyl)cyclohex-3-enyl)(4-hydroxypiperidin-1-yl)methanone;

(434) (4-(4-((1-(5-ethylpyrimidin-2-yl)piperidin-4-yl)methoxy)-3-fluorophenyl)cyclohex-3-enyl)(piperazin-1-yl)methanone;
(435) (4-(3-fluoro-4-((1-(3-(trifluoromethyl)-1,2,4-oxadiazol-5-yl)piperidin-4-yl)methoxy)phenyl)cyclohex-3-enyl)(pyrrolidin-1-yl)methanone;
(436) 2,2-difluoro-1-(4-((2-fluoro-4-(4-(pyrrolidine-1-carbonyl)cyclohex-1-enyl)phenoxy)methyl)piperidin-1-yl)butan-1-one;
(437) 4-(4-((1-(5-ethylpyrimidin-2-yl)piperidin-4-yl)methoxy)-2-fluorophenyl)-N,N-bis(2-hydroxyethyl)cyclohex-3-enecarboxamide;
(438) N-ethyl-4-(4-((1-(5-ethylpyrimidin-2-yl)piperidin-4-yl)methoxy)-2-fluorophenyl)-N-(2-hydroxyethyl)cyclohex-3-enecarboxamide;
(439) 2,2-difluoro-1-(4-((2-fluoro-4-(4-(morpholine-4-carbonyl)cyclohex-1-enyl)phenoxy)methyl)piperidin-1-yl)butan-1-one;
(440) 1,1,1-trifluoropropan-2-yl 4-((2-fluoro-4-(4-(morpholine-4-carbonyl)cyclohex-1-enyl)phenoxy)methyl)piperidine-1-carboxylate;
(441) (−)-4-(4-((1-(5-ethylpyrimidin-2-yl)piperidin-4-yl)methoxy)-3-fluorophenyl)-N-(2-hydroxyethyl)cyclohex-3-enecarboxamide;
(442) (+)-tert-butyl 4-((2-fluoro-4-(4-(morpholine-4-carbonyl)cyclohex-1-enyl)phenoxy)methyl)piperidine-1-carboxylate;
(443) (−)-tert-butyl 4-((2-fluoro-4-(4-(morpholine-4-carbonyl)cyclohex-1-enyl)phenoxy)methyl)piperidine-1-carboxylate;
(444) isopropyl 4-((2-fluoro-4-(4-(morpholine-4-carbonyl)cyclohex-1-enyl)phenoxy)methyl)piperidine-1-carboxylate;
(445) phenyl 4-((2-fluoro-4-(4-(morpholine-4-carbonyl)cyclohex-1-enyl)phenoxy)methyl)piperidine-1-carboxylate;
(446) 1,1,1,3,3,3-hexafluoropropan-2-yl 4-((2-fluoro-4-(4-(morpholine-4-carbonyl)cyclohex-1-enyl)phenoxy)methyl)piperidine-1-carboxylate;
(447) 1,3-difluoropropan-2-yl 4-((2-fluoro-4-(4-(morpholine-4-carbonyl)cyclohex-1-enyl)phenoxy)methyl)piperidine-1-carboxylate;
(448) (4-(2-fluoro-4-((1-(3-isopropyl-1,2,4-oxadiazol-5-yl)piperidin-4-yl)methoxy)phenyl)cyclohex-3-enyl)(morpholino)methanone;
(449) (4-(2-fluoro-4-((1-(3-isopropyl-1,2,4-oxadiazol-5-yl)piperidin-4-yl)methoxy)phenyl)cyclohex-3-enyl)(thiomorpholino)methanone;
(450) (4-(3-fluoro-4-((1-(1-(trifluoromethyl)cyclopentanecarbonyl)piperidin-4-yl)methoxy)phenyl)cyclohex-3-enyl)(morpholino)methanone;
(451) 1-(4-((2-fluoro-4-(4-(morpholine-4-carbonyl)cyclohex-1-enyl)phenoxy)methyl)piperidin-1-yl)-3-methylbut-2-en-1-one;
(452) (4-(4-((1-(5-ethylpyrimidin-2-yl)piperidin-4-yl)methoxy)-2-fluorophenyl)cyclohex-3-enyl)(4-(trifluoromethyl)piperidin-1-yl)methanone;
(453) (4,4-difluoropiperidin-1-yl)(4-(4-((1-(5-ethylpyrimidin-2-yl)piperidin-4-yl)methoxy)-2-fluorophenyl)cyclohex-3-enyl)methanone;
(454) (3,3-difluoropyrrolidin-1-yl)(4-(4-((1-(5-ethylpyrimidin-2-yl)piperidin-4-yl)methoxy)-2-fluorophenyl)cyclohex-3-enyl)methanone;
(455) (4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone;
(456) (4-(4-((1-(5-ethylpyrimidin-2-yl)piperidin-4-yl)methoxy)-3-fluorophenyl)cyclohex-3-enyl)(4-(trifluoromethyl)piperidin-1-yl)methanone;
(457) (4,4-difluoropiperidin-1-yl)(4-(4-((1-(5-ethylpyrimidin-2-yl)piperidin-4-yl)methoxy)-3-fluorophenyl)cyclohex-3-enyl)methanone;
(458) ((−)-4-(4-((1-(5-ethylpyrimidin-2-yl)piperidin-4-yl)methoxy)phenyl)cyclohex-3-enyl)((S)-3-fluoropyrrolidin-1-yl)methanone;
(459) (3,3-difluoropyrrolidin-1-yl)(4-(4-((1-(5-ethylpyrimidin-2-yl)piperidin-4-yl)methoxy)-3-fluorophenyl)cyclohex-3-enyl)methanone;
(460) (4-(4-((1-(5-ethylpyrimidin-2-yl)piperidin-4-yl)methoxy)-3-fluorophenyl)cyclohex-3-enyl)(3,3,4,4-tetrafluoropyrrolidin-1-yl)methanone;
(461) (−)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone;
(462) (+)-(3,3-difluoropyrrolidin-1-yl)(4-(4-((1-(5-ethylpyrimidin-2-yl)piperidin-4-yl)methoxy)-2-fluorophenyl)cyclohex-3-enyl)methanone;
(463) (−)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone;
(464) (+)-(4-(4-((1-(5-ethylpyrimidin-2-yl)piperidin-4-yl)methoxy)-2-fluorophenyl)cyclohex-3-enyl)(3,3,4,4-tetrafluoropyrrolidin-1-yl)methanone;
(465) ((−)-4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone; and
(466) ((+)-4-(4-((1-(5-ethylpyrimidin-2-yl)piperidin-4-yl)methoxy)phenyl)cyclohex-3-enyl)((S)-2-(hydroxymethyl)pyrrolidin-1-yl)methanone, or a pharmaceutically acceptable salt thereof.

2. A pharmaceutical composition for preventing or treating a metabolic disease comprising the compound of claim 1, or a pharmaceutically acceptable salt thereof.

3. The pharmaceutical composition according to claim 2, wherein the compound activates G protein-coupled receptor 119 (GPR-119) to enhance the intracellular activity of cyclic adenosine monophosphate (cAMP), and induces the release of glucagon-like peptide-1 (GLP-1) that is a neuroendocrine protein.

4. The pharmaceutical composition according to claim 2, wherein the metabolic disease is selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

5. A GPR-119 activator comprising the compound of claim 1, or a pharmaceutically acceptable salt thereof.

6. A health functional food for preventing or improving a metabolic disease comprising the compound of claim 1, or a pharmaceutically acceptable salt thereof.

7. The health functional food according to claim 6, wherein the metabolic disease is selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

8. A method of preventing or treating a metabolic disease, comprising administrating a therapeutically effective amount of a pharmaceutical composition comprising the compound of claim 1 or a pharmaceutically acceptable salt thereof to a patient in need thereof.

9. A method of enhancing the intracellular activity of cyclic adenosine monophosphate (cAMP) in a subject in need thereof, comprising administrating an effective amount of a pharmaceutical composition comprising the compound of claim 1 or a pharmaceutically acceptable salt thereof to the subject.

10. The method according to claim 8, wherein the metabolic disease is selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

11. The method according to claim 9, wherein the subject is in need of a treatment or prevention of a metabolic disease selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

12. A method of inducing the release of glucagon-like peptide-1 (GLP-1) in a subject in need thereof, comprising administrating an effective amount of a pharmaceutical composition comprising the compound of claim 1 or a pharmaceutically acceptable salt thereof to the subject.

13. The method according to claim 12, wherein the subject is in need of a treatment or prevention of a metabolic disease selected from the group consisting of obesity, type 1 diabetes, type 2 diabetes, inadequate glucose tolerance, insulin resistance, hyperglycemia, hyperlipidemia, hypertriglyceridemia, hypercholesterolemia, dyslipidemia, and syndrome X.

* * * * *